US008911734B2

(12) United States Patent
Latham et al.

(10) Patent No.: US 8,911,734 B2
(45) Date of Patent: *Dec. 16, 2014

(54) METHODS OF PREVENTING OR TREATING PAIN USING ANTI-NGF ANTIBODIES THAT SELECTIVELY INHIBIT THE ASSOCIATION OF NGF WITH TRKA, WITHOUT AFFECTING THE ASSOCIATION OF NGF WITH P75

(75) Inventors: John A. Latham, Seattle, WA (US); Ethan W. Ojala, Snohomish, WA (US); Jeffrey T. L. Smith, Bellevue, WA (US); Benjamin H. Dutzar, Seattle, WA (US); Leon F. Garcia-Martinez, Woodinville, WA (US)

(73) Assignee: Alderbio Holdings LLC, Las Vegas, NV (US)

( * ) Notice: Subject to any disclaimer, the term of this patent is extended or adjusted under 35 U.S.C. 154(b) by 30 days.

This patent is subject to a terminal disclaimer.

(21) Appl. No.: 13/308,665

(22) Filed: Dec. 1, 2011

(65) Prior Publication Data

US 2012/0164067 A1 Jun. 28, 2012

Related U.S. Application Data

(60) Provisional application No. 61/418,832, filed on Dec. 1, 2010.

(51) Int. Cl.
*A61K 39/395* (2006.01)
*C07K 16/22* (2006.01)
*C07K 16/28* (2006.01)
*A61K 39/00* (2006.01)

(52) U.S. Cl.
CPC ......... *C07K 16/2875* (2013.01); *C07K 2317/55* (2013.01); *C07K 2317/24* (2013.01); *A61K 2039/505* (2013.01); *C07K 2317/76* (2013.01)
USPC .................. 424/145.1; 424/130.1; 424/133.1; 424/141.1; 530/387.1; 530/387.3; 530/388.23

(58) Field of Classification Search
None
See application file for complete search history.

(56) References Cited

U.S. PATENT DOCUMENTS

| | | | |
|---|---|---|---|
| 5,604,202 A | 2/1997 | Kessler et al. |
| 5,653,975 A | 8/1997 | Baetge et al. |
| 5,656,481 A | 8/1997 | Baetge et al. |
| 5,672,683 A | 9/1997 | Friden et al. |
| 5,683,894 A | 11/1997 | Edwards et al. |
| 5,688,911 A | 11/1997 | Schneider et al. |
| 5,731,284 A | 3/1998 | Williams |
| 5,753,225 A | 5/1998 | Clary et al. |
| 5,795,790 A | 8/1998 | Schinstine et al. |
| 5,830,462 A | 11/1998 | Crabtree et al. |
| 5,844,092 A | 12/1998 | Presta et al. |
| 5,869,337 A | 2/1999 | Crabtree et al. |
| 5,877,016 A | 3/1999 | Presta et al. |
| 5,908,623 A | 6/1999 | Baetge et al. |
| 5,977,307 A | 11/1999 | Friden et al. |
| 5,990,129 A | 11/1999 | Bryant et al. |
| 6,011,004 A | 1/2000 | Kessler et al. |
| 6,017,878 A | 1/2000 | Saragovi et al. |
| 6,024,734 A | 2/2000 | Brewitt |
| 6,043,082 A | 3/2000 | Crabtree et al. |
| 6,046,047 A | 4/2000 | Crabtree et al. |
| 6,063,768 A | 5/2000 | First |
| 6,096,716 A | 8/2000 | Hayes et al. |
| 6,140,120 A | 10/2000 | Crabtree et al. |
| 6,153,189 A | 11/2000 | Presta et al. |
| 6,165,787 A | 12/2000 | Crabtree et al. |
| 6,211,142 B1 | 4/2001 | Hammonds et al. |
| 6,271,205 B1 | 8/2001 | Ross et al. |
| 6,280,732 B1 | 8/2001 | Caras et al. |
| 6,291,247 B1 | 9/2001 | Riopelle et al. |
| 6,299,895 B1 | 10/2001 | Hammang et al. |
| 6,333,310 B1 | 12/2001 | Presta et al. |
| 6,355,858 B1 | 3/2002 | Gibbins |
| 6,365,373 B2 | 4/2002 | Presta et al. |
| 6,417,159 B1 | 7/2002 | Riopelle et al. |
| 6,428,579 B1 | 8/2002 | Valentini |
| 6,440,928 B1 | 8/2002 | Ishii |
| 6,485,480 B1 | 11/2002 | Brewitt |
| 6,503,713 B1 | 1/2003 | Rana |
| 6,503,728 B1 | 1/2003 | Urfer et al. |
| 6,548,062 B2 | 4/2003 | Buchkovich et al. |
| 6,596,269 B1 | 7/2003 | Iadarola et al. |
| 6,630,478 B2 | 10/2003 | Diamond et al. |
| 6,630,490 B2 | 10/2003 | Diamond et al. |
| 6,652,864 B1 | 11/2003 | Webb et al. |
| 6,656,465 B2 | 12/2003 | Clary et al. |
| 6,680,292 B1 | 1/2004 | Guillemin et al. |
| 6,719,970 B1 | 4/2004 | Costantino et al. |
| 6,806,251 B2 | 10/2004 | Lamb |
| 6,887,861 B1 | 5/2005 | Hill et al. |
| 6,919,426 B2 | 7/2005 | Boone et al. |
| 7,144,983 B1 | 12/2006 | Urfer et al. |
| 7,169,568 B2 | 1/2007 | Chao et al. |
| 7,205,387 B2 | 4/2007 | Wang et al. |
| 7,252,822 B2 | 8/2007 | Shelton et al. |
| 7,255,860 B2 | 8/2007 | Shelton et al. |
| 7,282,482 B2 | 10/2007 | Bartke et al. |
| 7,342,146 B2 | 3/2008 | Tsai et al. |
| 7,425,329 B2 | 9/2008 | Shelton et al. |

(Continued)

OTHER PUBLICATIONS

MacCallum et al. (1996). J. Mol. Biol. 262:732-745.*

(Continued)

*Primary Examiner* — Christine J Saoud
*Assistant Examiner* — Jon M Lockard
(74) *Attorney, Agent, or Firm* — LeClairRyan, a Professional Corporation; Robin L. Teskin

(57) ABSTRACT

NGF antagonists including antibodies and antibody fragments thereof having binding specificity to human Nerve Growth Factor ("NGF"), and methods of treating pain. Methods of treating pain or eliciting an analgesic effect in an individual comprising administering an effective amount of an NGF antagonist inhibits the association of NGF with TrkA without inhibiting the association of NGF with p75. The methods may further comprise administering an effective amount of a second anti-human NGF antibody or fragment thereof which inhibits the association of NGF with p75, that may further also inhibit the association of NGF with TrkA.

45 Claims, 96 Drawing Sheets

(56) References Cited

U.S. PATENT DOCUMENTS

| | | |
|---|---|---|
| 7,449,616 B2 | 11/2008 | Pons et al. |
| 7,452,863 B1 | 11/2008 | Presta et al. |
| 7,459,156 B2 | 12/2008 | Clary et al. |
| 7,569,364 B2 | 8/2009 | Rosenthal et al. |
| 7,601,352 B1 | 10/2009 | Novak |
| 7,601,818 B2 | 10/2009 | Wild, Jr. et al. |
| 7,612,181 B2 | 11/2009 | Wu et al. |
| 7,615,383 B2 | 11/2009 | Devaux et al. |
| 7,655,231 B2 | 2/2010 | Shelton et al. |
| 7,655,232 B2 | 2/2010 | Pons et al. |
| 7,678,378 B2 | 3/2010 | Webb et al. |
| 7,718,605 B2 | 5/2010 | Webb et al. |
| 7,727,527 B2 | 6/2010 | Shelton |
| 7,750,122 B2 | 7/2010 | Cho et al. |
| 7,785,588 B2 | 8/2010 | Klein et al. |
| 7,795,413 B2 | 9/2010 | Wild, Jr. et al. |
| 7,846,891 B2 | 12/2010 | Ellis-Behnke et al. |
| 7,922,999 B2 | 4/2011 | Bankiewicz |
| 7,935,671 B2 | 5/2011 | Urfer et al. |
| 7,988,966 B2 | 8/2011 | Pavone et al. |
| 7,988,967 B2 | 8/2011 | MacDonald et al. |
| 8,007,800 B2 | 8/2011 | Shelton et al. |
| 8,034,346 B2 | 10/2011 | Shelton et al. |
| 8,088,384 B2 | 1/2012 | Pons et al. |
| 8,101,571 B2 | 1/2012 | Presta et al. |
| 8,106,167 B2 | 1/2012 | Wild, Jr. et al. |
| 8,124,724 B2 | 2/2012 | Boone et al. |
| 8,148,107 B2 | 4/2012 | Macdonald et al. |
| 8,163,018 B2 | 4/2012 | Trieu |
| 8,168,169 B2 | 5/2012 | Cataldo et al. |
| 8,183,219 B2 | 5/2012 | Burright |
| 8,198,410 B2 | 6/2012 | Wild, Jr. et al. |
| 8,226,951 B2 | 7/2012 | Shelton et al. |
| 8,246,956 B2 | 8/2012 | Cattaneo et al. |
| 8,257,696 B2 | 9/2012 | Steindler et al. |
| 8,257,710 B2 | 9/2012 | Cattaneo et al. |
| 8,258,268 B2 | 9/2012 | Wu et al. |
| 8,296,079 B2 | 10/2012 | Cattaneo et al. |
| 8,309,088 B2 | 11/2012 | MacDonald et al. |
| 8,420,779 B2 | 4/2013 | Walker et al. |
| 8,425,907 B2 | 4/2013 | MacDonald et al. |
| 8,426,673 B2 | 4/2013 | Tanahashi et al. |
| 8,435,523 B2 | 5/2013 | Powell et al. |
| 8,460,657 B2 | 6/2013 | Nykjær et al. |
| 8,461,110 B2 | 6/2013 | Vitagliano et al. |
| 8,475,788 B2 | 7/2013 | Sing et al. |
| 8,481,036 B2 | 7/2013 | Shelton |
| 8,486,401 B2 | 7/2013 | Novak |
| 8,513,241 B2 | 8/2013 | Cervi et al. |
| 8,540,990 B2 | 9/2013 | Rosenthal et al. |
| 8,557,245 B2 | 10/2013 | Shelton et al. |
| 8,591,898 B2 | 11/2013 | Mills et al. |
| 8,598,140 B2 | 12/2013 | Schneider et al. |
| 8,613,927 B2 | 12/2013 | MacDonald et al. |
| 8,637,031 B2 | 1/2014 | MacDonald et al. |
| 8,642,040 B2 | 2/2014 | Mi et al. |
| 8,674,071 B2 | 3/2014 | Chan et al. |
| 8,691,221 B2 | 4/2014 | Pavone et al. |
| 8,715,666 B2 | 5/2014 | Pavone et al. |
| 8,716,450 B2 | 5/2014 | Ghayur et al. |
| 8,722,019 B2 | 5/2014 | Jefferies et al. |
| 8,728,473 B2 | 5/2014 | Garcia-Martinez et al. |
| 2001/0019833 A1 | 9/2001 | Wallach et al. |
| 2001/0046959 A1 | 11/2001 | Buchkovich et al. |
| 2002/0004061 A1 | 1/2002 | Panayotatos |
| 2002/0012914 A1 | 1/2002 | Bureau et al. |
| 2002/0037280 A1 | 3/2002 | Lieber et al. |
| 2002/0045576 A1 | 4/2002 | Rosenthal |
| 2002/0051974 A1 | 5/2002 | Dodge et al. |
| 2002/0061327 A1 | 5/2002 | Hammang et al. |
| 2002/0086015 A1 | 7/2002 | Gold |
| 2002/0090682 A1 | 7/2002 | Willson et al. |
| 2002/0104104 A1 | 8/2002 | Games et al. |
| 2002/0110525 A1 | 8/2002 | Adjei et al. |
| 2002/0110526 A1 | 8/2002 | Zhu et al. |
| 2002/0110527 A1 | 8/2002 | Zhu et al. |
| 2002/0110528 A1 | 8/2002 | Zhu et al. |
| 2002/0110539 A1 | 8/2002 | Zhu et al. |
| 2002/0115173 A1 | 8/2002 | Ben-Sasson |
| 2002/0119117 A1 | 8/2002 | Zhu et al. |
| 2002/0128179 A1 | 9/2002 | Tacon et al. |
| 2002/0137126 A1 | 9/2002 | Cares et al. |
| 2002/0146416 A1 | 10/2002 | Presta et al. |
| 2002/0164333 A1 | 11/2002 | Nemerow et al. |
| 2002/0168338 A1 | 11/2002 | Baird |
| 2002/0177120 A1 | 11/2002 | Elliott et al. |
| 2002/0187551 A1 | 12/2002 | Yoon |
| 2002/0194630 A1 | 12/2002 | Manning, Jr. et al. |
| 2003/0008394 A1 | 1/2003 | Yoon |
| 2003/0008807 A1 | 1/2003 | Levine et al. |
| 2003/0027779 A1 | 2/2003 | Neuman et al. |
| 2003/0059945 A1 | 3/2003 | Dzekunov et al. |
| 2003/0073238 A1 | 4/2003 | Dzekunov et al. |
| 2003/0073653 A1 | 4/2003 | Bureau et al. |
| 2003/0082234 A1 | 5/2003 | Seo et al. |
| 2003/0096753 A1 | 5/2003 | Robertson et al. |
| 2003/0097667 A1 | 5/2003 | Robertson et al. |
| 2003/0143693 A1 | 7/2003 | Silbiger et al. |
| 2003/0152562 A1 | 8/2003 | Mitrani |
| 2003/0157099 A1 | 8/2003 | Presta et al. |
| 2003/0203383 A1 | 10/2003 | Rosenthal |
| 2003/0232419 A1 | 12/2003 | Kolodkin et al. |
| 2003/0235580 A1 | 12/2003 | Zhang |
| 2004/0009149 A1 | 1/2004 | Altman et al. |
| 2004/0009589 A1 | 1/2004 | Levenberg et al. |
| 2004/0029169 A1 | 2/2004 | He et al. |
| 2004/0058393 A1 | 3/2004 | Fukishima et al. |
| 2004/0063610 A1 | 4/2004 | Gold |
| 2004/0071701 A1 | 4/2004 | Delafoy et al. |
| 2004/0077540 A1 | 4/2004 | Quay |
| 2004/0077545 A1 | 4/2004 | Lipps et al. |
| 2004/0097456 A1 | 5/2004 | Paulista et al. |
| 2004/0105840 A1 | 6/2004 | Kinstler et al. |
| 2004/0115671 A1 | 6/2004 | Zlokovic et al. |
| 2004/0131615 A1 | 7/2004 | Shelton et al. |
| 2004/0138155 A1 | 7/2004 | Baird et al. |
| 2004/0142388 A1 | 7/2004 | Lamping et al. |
| 2004/0185113 A1 | 9/2004 | Mizushima et al. |
| 2004/0197883 A1 | 10/2004 | Dzekunov et al. |
| 2004/0209801 A1 | 10/2004 | Brand et al. |
| 2004/0219144 A1 | 11/2004 | Shelton |
| 2004/0228862 A1 | 11/2004 | Shelton et al. |
| 2004/0237124 A1 | 11/2004 | Pons et al. |
| 2004/0242847 A1 | 12/2004 | Fukushima et al. |
| 2004/0253244 A1 | 12/2004 | Shelton et al. |
| 2004/0258684 A1 | 12/2004 | Fukushima et al. |
| 2005/0008624 A1 | 1/2005 | Peled et al. |
| 2005/0027110 A1 | 2/2005 | Russell et al. |
| 2005/0037493 A1 | 2/2005 | Mandalam et al. |
| 2005/0054097 A1 | 3/2005 | Peled et al. |
| 2005/0074435 A1 | 4/2005 | Casper et al. |
| 2005/0074821 A1 | 4/2005 | Wild, Jr. et al. |
| 2005/0074865 A1 | 4/2005 | Afeyan et al. |
| 2005/0079200 A1 | 4/2005 | Rathenow et al. |
| 2005/0085417 A1 | 4/2005 | Wickstrom et al. |
| 2005/0119712 A1 | 6/2005 | Shafer |
| 2005/0123526 A1 | 6/2005 | Shafer |
| 2005/0143336 A1 | 6/2005 | Ramesh et al. |
| 2005/0169882 A1 | 8/2005 | Lowe et al. |
| 2005/0220774 A1 | 10/2005 | Peled et al. |
| 2005/0221368 A1 | 10/2005 | Rana |
| 2005/0226871 A1 | 10/2005 | Gold |
| 2005/0260711 A1 | 11/2005 | Datta et al. |
| 2005/0265994 A1 | 12/2005 | Shelton et al. |
| 2005/0281781 A1 | 12/2005 | Ostroff |
| 2006/0050596 A1 | 3/2006 | Abassi et al. |
| 2006/0051818 A1 | 3/2006 | Adriaenssens et al. |
| 2006/0068469 A1 | 3/2006 | Payne et al. |
| 2006/0088936 A1 | 4/2006 | Warrington et al. |
| 2006/0093589 A1 | 5/2006 | Warrington et al. |
| 2006/0104973 A1 | 5/2006 | He et al. |
| 2006/0106203 A1 | 5/2006 | Winter et al. |
| 2006/0115874 A1 | 6/2006 | Garrard et al. |
| 2006/0140934 A1 | 6/2006 | Gegg et al. |

(56) References Cited

U.S. PATENT DOCUMENTS

| | | |
|---|---|---|
| 2006/0147450 A1 | 7/2006 | Shelton |
| 2006/0147932 A1 | 7/2006 | Davies et al. |
| 2006/0159666 A1 | 7/2006 | Willing et al. |
| 2006/0182724 A1 | 8/2006 | Riordan |
| 2006/0185025 A1 | 8/2006 | Oshimura et al. |
| 2006/0193825 A1 | 8/2006 | Musso et al. |
| 2006/0211619 A1 | 9/2006 | Steward et al. |
| 2006/0216751 A1 | 9/2006 | Boschetti et al. |
| 2006/0240007 A1 | 10/2006 | Sanders |
| 2006/0269478 A1 | 11/2006 | Panayotatos |
| 2006/0275290 A1 | 12/2006 | Barbeito et al. |
| 2006/0292114 A1 | 12/2006 | Klein et al. |
| 2006/0293240 A1 | 12/2006 | Ron |
| 2007/0015248 A1 | 1/2007 | Anton et al. |
| 2007/0020696 A1 | 1/2007 | Zerial et al. |
| 2007/0036751 A1 | 2/2007 | Lode et al. |
| 2007/0036797 A1 | 2/2007 | Kim et al. |
| 2007/0041972 A1 | 2/2007 | Rother et al. |
| 2007/0071675 A1 | 3/2007 | Wu et al. |
| 2007/0081992 A1 | 4/2007 | Pardridge et al. |
| 2007/0086942 A1 | 4/2007 | Chang et al. |
| 2007/0092968 A1 | 4/2007 | Ji et al. |
| 2007/0122904 A1 | 5/2007 | Nordon |
| 2007/0154524 A1 | 7/2007 | Kauper et al. |
| 2007/0160605 A1 | 7/2007 | Shelton et al. |
| 2007/0212357 A1 | 9/2007 | Pons et al. |
| 2007/0243132 A1 | 10/2007 | Russell-Jones et al. |
| 2007/0253907 A1 | 11/2007 | Cattaneo et al. |
| 2007/0264195 A1 | 11/2007 | Nykiaer et al. |
| 2007/0264265 A1 | 11/2007 | Goldenberg et al. |
| 2007/0269369 A1 | 11/2007 | Gegg et al. |
| 2007/0275412 A1 | 11/2007 | Gama et al. |
| 2008/0008999 A1 | 1/2008 | Hankins |
| 2008/0009537 A1 | 1/2008 | Sakai |
| 2008/0019940 A1 | 1/2008 | Papisov |
| 2008/0025968 A1 | 1/2008 | Wallach et al. |
| 2008/0025978 A1 | 1/2008 | Hempstead et al. |
| 2008/0033157 A1 | 2/2008 | Wild, Jr. et al. |
| 2008/0038717 A1 | 2/2008 | Garrard et al. |
| 2008/0044428 A1 | 2/2008 | Schofield |
| 2008/0081040 A1 | 4/2008 | Shelton et al. |
| 2008/0095767 A1 | 4/2008 | Jennings et al. |
| 2008/0107658 A1 | 5/2008 | Franks et al. |
| 2008/0132427 A1 | 6/2008 | Zhuang et al. |
| 2008/0138855 A1 | 6/2008 | Wang |
| 2008/0138877 A1 | 6/2008 | Dzekunov et al. |
| 2008/0139790 A1 | 6/2008 | Jennings et al. |
| 2008/0182978 A1 | 7/2008 | Rosenthal et al. |
| 2008/0187966 A1 | 8/2008 | Simmons |
| 2008/0233088 A1 | 9/2008 | Guha et al. |
| 2008/0233140 A1 | 9/2008 | Banchereau et al. |
| 2008/0241170 A1 | 10/2008 | Zurawski et al. |
| 2008/0254044 A1 | 10/2008 | Zurawski |
| 2008/0254047 A1 | 10/2008 | Banchereau et al. |
| 2008/0255343 A1 | 10/2008 | Jennings et al. |
| 2008/0260757 A1 | 10/2008 | Holt et al. |
| 2008/0274077 A1 | 11/2008 | Benowitz et al. |
| 2008/0311078 A1 | 12/2008 | Gokarn et al. |
| 2008/0313749 A1 | 12/2008 | Timmerman et al. |
| 2008/0318314 A1 | 12/2008 | Fulga et al. |
| 2009/0004742 A1 | 1/2009 | Mitchell et al. |
| 2009/0012272 A1 | 1/2009 | Gegg et al. |
| 2009/0022683 A1 | 1/2009 | Song et al. |
| 2009/0022744 A1 | 1/2009 | Gegg et al. |
| 2009/0023901 A1 | 1/2009 | Steward et al. |
| 2009/0030308 A1 | 1/2009 | Bradford et al. |
| 2009/0030364 A1 | 1/2009 | Harmon et al. |
| 2009/0035257 A1 | 2/2009 | Moseley et al. |
| 2009/0035836 A1 | 2/2009 | Datta et al. |
| 2009/0041717 A1 | 2/2009 | Macdonald et al. |
| 2009/0041768 A1 | 2/2009 | Gegg et al. |
| 2009/0042229 A1 | 2/2009 | Folkman et al. |
| 2009/0047348 A1 | 2/2009 | Song et al. |
| 2009/0053786 A1 | 2/2009 | Kao et al. |
| 2009/0060864 A1 | 3/2009 | Lode et al. |
| 2009/0074779 A1 | 3/2009 | Bock et al. |
| 2009/0123464 A1 | 5/2009 | Pavone et al. |
| 2009/0123468 A1 | 5/2009 | Khan |
| 2009/0148908 A1 | 6/2009 | Paciotti et al. |
| 2009/0155274 A1 | 6/2009 | Wild, Jr. et al. |
| 2009/0162380 A1 | 6/2009 | Glaser et al. |
| 2009/0175847 A1 | 7/2009 | Barghorn et al. |
| 2009/0181088 A1 | 7/2009 | Song et al. |
| 2009/0202433 A1 | 8/2009 | Chang et al. |
| 2009/0208490 A1 | 8/2009 | Pavone et al. |
| 2009/0220466 A1 | 9/2009 | Ratajczak et al. |
| 2009/0226439 A1 | 9/2009 | Sanders |
| 2009/0227655 A1 | 9/2009 | Khan |
| 2009/0232801 A1 | 9/2009 | Hillen et al. |
| 2009/0234104 A1 | 9/2009 | Gegg et al. |
| 2009/0252744 A1 | 10/2009 | Shelton et al. |
| 2009/0269346 A1 | 10/2009 | Starr et al. |
| 2009/0281286 A1 | 11/2009 | Gregg et al. |
| 2009/0286964 A1 | 11/2009 | Gegg et al. |
| 2009/0300780 A1 | 12/2009 | Cattaneo et al. |
| 2009/0304580 A1 | 12/2009 | Goldenberg et al. |
| 2009/0304693 A1 | 12/2009 | Ghayur et al. |
| 2009/0311253 A1 | 12/2009 | Ghayur et al. |
| 2009/0311718 A1 | 12/2009 | Fukushima et al. |
| 2010/0003679 A1 | 1/2010 | Ichii et al. |
| 2010/0009997 A1 | 1/2010 | Oppenheimer et al. |
| 2010/0011454 A1 | 1/2010 | Kakeda et al. |
| 2010/0016836 A1 | 1/2010 | Makower et al. |
| 2010/0034818 A1 | 2/2010 | Wild, Jr. et al. |
| 2010/0035236 A1 | 2/2010 | Garrard et al. |
| 2010/0047239 A1 | 2/2010 | Wu et al. |
| 2010/0048461 A1 | 2/2010 | Saragovi |
| 2010/0055109 A1 | 3/2010 | Barbeito et al. |
| 2010/0068137 A1 | 3/2010 | Chang et al. |
| 2010/0074900 A1 | 3/2010 | Ghayur et al. |
| 2010/0081172 A1 | 4/2010 | Liu et al. |
| 2010/0081794 A1 | 4/2010 | Liu et al. |
| 2010/0104652 A1 | 4/2010 | Biris et al. |
| 2010/0111970 A1 | 5/2010 | Pons et al. |
| 2010/0119492 A1 | 5/2010 | Hans et al. |
| 2010/0143355 A1 | 6/2010 | Shelton et al. |
| 2010/0166700 A1 | 7/2010 | Charles |
| 2010/0168625 A1 | 7/2010 | Swain et al. |
| 2010/0168720 A1 | 7/2010 | Swain et al. |
| 2010/0168870 A1 | 7/2010 | Swain et al. |
| 2010/0172871 A1 | 7/2010 | Flannery et al. |
| 2010/0179515 A1 | 7/2010 | Swain et al. |
| 2010/0189641 A1 | 7/2010 | Chang et al. |
| 2010/0196266 A1 | 8/2010 | Goldenberg et al. |
| 2010/0203044 A1 | 8/2010 | Nikolaev et al. |
| 2010/0209447 A1 | 8/2010 | Kumar-Singh et al. |
| 2010/0210523 A1 | 8/2010 | Andersen et al. |
| 2010/0221250 A1 | 9/2010 | Kim et al. |
| 2010/0254990 A1 | 10/2010 | Shelton |
| 2010/0260775 A1 | 10/2010 | Mills et al. |
| 2010/0260853 A1 | 10/2010 | Basran et al. |
| 2010/0266496 A1 | 10/2010 | Hansen et al. |
| 2010/0267573 A1 | 10/2010 | Keene et al. |
| 2010/0267934 A1 | 10/2010 | Van De Winkel et al. |
| 2010/0272636 A1 | 10/2010 | Byrd et al. |
| 2010/0278839 A1 | 11/2010 | Powell et al. |
| 2010/0291083 A1 | 11/2010 | Pavone et al. |
| 2010/0330115 A1 | 12/2010 | Zurawski et al. |
| 2011/0008251 A1 | 1/2011 | Chang et al. |
| 2011/0014189 A1 | 1/2011 | Soula et al. |
| 2011/0014208 A1 | 1/2011 | Macdonald et al. |
| 2011/0033447 A1 | 2/2011 | Rosenthal et al. |
| 2011/0033463 A1 | 2/2011 | Thakker et al. |
| 2011/0034383 A1 | 2/2011 | Arenzana et al. |
| 2011/0038865 A1 | 2/2011 | Shin et al. |
| 2011/0040076 A1 | 2/2011 | Wild, Jr. et al. |
| 2011/0044901 A1 | 2/2011 | Seed et al. |
| 2011/0053221 A1 | 3/2011 | Chen et al. |
| 2011/0059095 A1 | 3/2011 | Macdonald et al. |
| 2011/0064653 A1 | 3/2011 | Hansen et al. |
| 2011/0070188 A1 | 3/2011 | Fowers et al. |
| 2011/0070607 A1 | 3/2011 | Wang |
| 2011/0071216 A1 | 3/2011 | Fowers et al. |
| 2011/0091463 A1 | 4/2011 | Ghayur et al. |

(56) References Cited

U.S. PATENT DOCUMENTS

| | | |
|---|---|---|
| 2011/0091476 A1 | 4/2011 | Wild, Jr. et al. |
| 2011/0091936 A1 | 4/2011 | Gawlitzek et al. |
| 2011/0097341 A1 | 4/2011 | Shelton |
| 2011/0104164 A1 | 5/2011 | Cattaneo et al. |
| 2011/0105728 A1 | 5/2011 | Cattaneo et al. |
| 2011/0110851 A1 | 5/2011 | Chang et al. |
| 2011/0110852 A1 | 5/2011 | Miller et al. |
| 2011/0123480 A1 | 5/2011 | Wallach |
| 2011/0129462 A1 | 6/2011 | Maggio |
| 2011/0145941 A1 | 6/2011 | Benigni et al. |
| 2011/0151515 A1 | 6/2011 | Heifetz et al. |
| 2011/0158905 A1 | 6/2011 | Goldenberg et al. |
| 2011/0160439 A1 | 6/2011 | Munck Petersen et al. |
| 2011/0171126 A1 | 7/2011 | Burton et al. |
| 2011/0171217 A1 | 7/2011 | Badkar et al. |
| 2011/0182912 A1 | 7/2011 | Evans et al. |
| 2011/0189083 A1 | 8/2011 | Chang et al. |
| 2011/0189206 A1 | 8/2011 | Barbas, III |
| 2011/0191872 A1 | 8/2011 | Cattaneo et al. |
| 2011/0195020 A1 | 8/2011 | Chang et al. |
| 2011/0195124 A1 | 8/2011 | Jin |
| 2011/0198286 A1 | 8/2011 | Niazi |
| 2011/0206682 A1 | 8/2011 | Novak |
| 2011/0212094 A1 | 9/2011 | Ghayur et al. |
| 2011/0243841 A1 | 10/2011 | Chang et al. |
| 2011/0243893 A1 | 10/2011 | Axtell et al. |
| 2011/0243961 A1 | 10/2011 | Shelton et al. |
| 2011/0250130 A1 | 10/2011 | Benatuil et al. |
| 2011/0250206 A1 | 10/2011 | Axtell et al. |
| 2011/0256053 A1 | 10/2011 | Chang et al. |
| 2011/0256135 A1 | 10/2011 | Fraunhofer et al. |
| 2011/0256150 A1 | 10/2011 | Watts et al. |
| 2011/0256587 A1 | 10/2011 | Macdonald et al. |
| 2011/0268725 A1 | 11/2011 | Shelton |
| 2011/0268776 A1 | 11/2011 | Schapira et al. |
| 2011/0293607 A1 | 12/2011 | Labrijn et al. |
| 2012/0004643 A1 | 1/2012 | Zurawski et al. |
| 2012/0009205 A1 | 1/2012 | Gegg et al. |
| 2012/0014957 A1 | 1/2012 | Ghayur et al. |
| 2012/0014968 A1 | 1/2012 | Walsh et al. |
| 2012/0027847 A1 | 2/2012 | Kusk et al. |
| 2012/0087858 A1 | 4/2012 | Ghayur et al. |
| 2012/0093824 A1 | 4/2012 | Macdonald et al. |
| 2012/0095193 A1 | 4/2012 | Burden et al. |
| 2012/0141484 A1 | 6/2012 | Garcia-Martinez et al. |
| 2012/0141485 A1 | 6/2012 | Garcia-Martinez et al. |
| 2012/0148490 A1 | 6/2012 | Dutzar et al. |
| 2012/0164067 A1 | 6/2012 | Latham et al. |
| 2012/0164688 A1 | 6/2012 | Macdonald et al. |
| 2012/0195900 A1 | 8/2012 | Ghayur et al. |
| 2012/0201746 A1 | 8/2012 | Liu et al. |
| 2012/0213784 A1 | 8/2012 | Pavone et al. |
| 2012/0252717 A1 | 10/2012 | Besman et al. |
| 2012/0315271 A1 | 12/2012 | Shelton et al. |
| 2013/0004495 A1 | 1/2013 | Shelton |
| 2013/0028892 A1 | 1/2013 | Macdonald et al. |
| 2013/0058873 A1 | 3/2013 | Jefferies et al. |
| 2013/0101601 A1 | 4/2013 | King et al. |
| 2013/0183311 A1 | 7/2013 | Powell et al. |
| 2013/0295112 A1 | 11/2013 | Powell et al. |
| 2013/0302325 A1 | 11/2013 | Rosenthal et al. |
| 2013/0330348 A1 | 12/2013 | Lacy et al. |
| 2013/0336964 A1 | 12/2013 | Rovati et al. |
| 2013/0336975 A1 | 12/2013 | Dutzar et al. |
| 2013/0344064 A1 | 12/2013 | Blein et al. |
| 2013/0344068 A1 | 12/2013 | Garcia-Martinez et al. |
| 2014/0004115 A1 | 1/2014 | Latham et al. |
| 2014/0004116 A1 | 1/2014 | Garcia-Martinez et al. |
| 2014/0017235 A1 | 1/2014 | Rosenthal et al. |
| 2014/0099254 A1 | 4/2014 | Chang et al. |
| 2014/0147439 A1 | 5/2014 | Gearing |
| 2014/0155582 A1 | 6/2014 | Kamohara et al. |
| 2014/0170136 A1 | 6/2014 | Gearing |

OTHER PUBLICATIONS

De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*

* cited by examiner

Heavy chain full length protein sequence.
QSLEESGGRLVTPGTPLTLTCTVSGFSLSSYAMSWVRQAPGKGLEWIGVITSIGSTVYAS
WAKGRFTISKTSTTVDLKITSPTTEDTATYFCARGYDDYDEMTYFNIWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO:4)

Variable region heavy chain protein sequence.
QSLEESGGRLVTPGTPLTLTCTVSGFSLSSYAMSWVRQAPGKGLEWIGVITSIGSTVYAS
WAKGRFTISKTSTTVDLKITSPTTEDTATYFCARGYDDYDEMTYFNIWGQGTLVTVSS
(SEQ ID NO:3)

Variable region heavy chain protein sequence. CDR1:Bold; CDR2: Underline; CDR3:Italics.
QSLEESGGRLVTPGTPLTLTCTVSGFSLSSYAMSWVRQAPGKGLEWIG<u>VITSIGSTVYAS
WAKGRFTISKTSTTVDLKITS</u>PTTEDTATYFCAR*GYDDYDEMTYFNI*WGQGTLVTVSS
(SEQ ID NOS: 8, 9, 10, respectively)

Variable region heavy chain DNA sequence. CDR1:Bold; CDR2: Underline; CDR3:Italics.
CAGTCGCTGGAGGAGTCCGGGGGTCGCCTGGTCACGCCTGGGACACCCCTGACACTCACC
TGCACAGTCTCTGGCTTCTCCCTCAGTAGCTATGCAATGAGCTGGGTCCGCCAGGCTCCA
GGGAAGGGGCTGGAATGGATCGGA<u>GTCATTACTAGTATTGGTAGCACAGTCTACGCGAGC
TGGGCGAAAGGC</u>CGATTCACCATCTCCAAAACCTCGACCACGGTGGATCTGAAAATCACC
AGTCCGACAACCGAGGACACGGCCACCTATTTCTGTGCCAGAGGCTAC*GATGACTATGAT
GAGATGACCTACTTTAACATCTGGGGCCAGGGGACCCTCGTCACCGTCTCGAGC* (SEQ
ID NO: 203)

Heavy chain Full length DNA sequence.
CAGTCGCTGGAGGAGTCCGGGGGTCGCCTGGTCACGCCTGGGACACCCCTGACACTCACC
TGCACAGTCTCTGGCTTCTCCCTCAGTAGCTATGCAATGAGCTGGGTCCGCCAGGCTCCA
GGGAAGGGGCTGGAATGGATCGGAGTCATTACTAGTATTGGTAGCACAGTCTACGCGAGC
TGGGCGAAAGGCCGATTCACCATCTCCAAAACCTCGACCACGGTGGATCTGAAAATCACC
AGTCCGACAACCGAGGACACGGCCACCTATTTCTGTGCCAGAGGCTACGATGACTATGAT
GAGATGACCTACTTTAACATCTGGGGCCAGGGGACCCTCGTCACCGTCTCGAGCGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG

FIG. 1B

GACGGCGTGGAGGTGCATAATGCCAAGACAAAGCCGCGGGAGGAGCAGTACGCCAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATGA (SEQ ID NO: 204)

Light_chain Full length protein sequence.

ALVMTQTPSSVSAAVGGTVTINCQASQNIYSNLAWYQQRPGQRPKLLIYGASNLDAGVPS
RFRGSGSGTEYTLTISDLECDDVGTYYCQSAFDSDSTENTFGGGTEVVVKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:2)

Variable_region_light_chain protein sequence.

ALVMTQTPSSVSAAVGGTVTINCQASQNIYSNLAWYQQRPGQRPKLLIYGASNLDAGVPS
RFRGSGSGTEYTLTISDLECDDVGTYYCQSAFDSDSTENTFGGGTEVVVKR (SEQ ID NO:1)

Variable_region_light_chain protein sequence. CDR1:Bold; CDR2: Underline; CDR3:Italics.

ALVMTQTPSSVSAAVGGTVTINCQASQNIYSNLAWYQQRPGQRPKLLIY<u>GASNLDAGVPS</u>
RFRGSGSGTEYTLTISDLECDDVGTYYCQ*SAFDSDSTENT*FGGGTEVVVKR (SEQ ID NOS: 5, 6, 7, respectively)

Variable_region_light_chain DNA sequence. CDR1:Bold; CDR2: Underline; CDR3:Italics.

GCCCTTGTGATGACCCAGACTCCATCCTCCGTGTCTGCAGCTGTGGGAGGCACAGTCACC
ATCAATTGCCAGGCCAGTCAGAACATTTACAGCAATTTAGCCTGGTATCAACAGAGACCA
GGGCAGCGTCCCAAGCTCCTGATCTAT<u>GGTGCATCCAATCTGGATGCTGGGGTCCCATCG</u>
CGGTTCAGAGGCAGTGGATCTGGGACAGAGTACACTCTCACCATCAGCGACCTGGAGTGT
GACGATGTTGGCACTTACTACTGT*CAAAGTGCTTTTGATAGTGATAGTACTGAAAATACT*
TTCGGCGGAGGGACCGAGGTGGTGGTCAAACGT (SEQ ID NO: 201)

Light_chain Full length DNA sequence.

GCCCTTGTGATGACCCAGACTCCATCCTCCGTGTCTGCAGCTGTGGGAGGCACAGTCACC
ATCAATTGCCAGGCCAGTCAGAACATTTACAGCAATTTAGCCTGGTATCAACAGAGACCA
GGGCAGCGTCCCAAGCTCCTGATCTATGGTGCATCCAATCTGGATGCTGGGGTCCCATCG
CGGTTCAGAGGCAGTGGATCTGGGACAGAGTACACTCTCACCATCAGCGACCTGGAGTGT
GACGATGTTGGCACTTACTACTGTCAAAGTGCTTTTGATAGTGATAGTACTGAAAATACT
TTCGGCGGAGGGACCGAGGTGGTGGTCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ ID NO: 202)

Heavy chain Full length protein sequence.

EVQLVESGGGLVQPGGSLRLSCAASGFTVSSYAMSWVRQAPGKGLEWVGVITSIGSTVYA
SSAKGRFTISRDNSKNTLYLQMNSLRAEDTAVYYCARGYDDYDEMTYFNIWGQGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCPAPELLG
GPSVFLFPPKPKDTLMISRTPEVTCVVVDVSHEDPEVKFNWYVDGVEVHNAKTKPREEQY
ASTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO:14)

Variable region heavy chain protein sequence.

EVQLVESGGGLVQPGGSLRLSCAASGFTVSSYAMSWVRQAPGKGLEWVGVITSIGSTVYA
SSAKGRFTISRDNSKNTLYLQMNSLRAEDTAVYYCARGYDDYDEMTYFNIWGQGTLVTVS
S (SEQ ID NO:13)

Variable region heavy chain protein sequence. CDR1:Bold; CDR2: Underline; CDR3:Italics.

EVQLVESGGGLVQPGGSLRLSCAASGFTVSSSYAMSWVRQAPGKGLEWVG<u>VITSIGSTVYA
SSAKGRFTI</u>SRDNSKNTLYLQMNSLRAEDTAVYYCAR*GYDDYDEMTYFNI*WGQGTLVTVS
S (SEQ ID NOS: 18, 19, 20, respectively)

Variable region heavy chain DNA sequence. CDR1:Bold; CDR2: Underline; CDR3:Italics.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAGCTATGCAATGAGCTGGGTCCGTCAGGCT
CCAGGGAAGGGGCTGGAGTGGGTCGGA<u>GTCATTACTAGTATTGGTAGCACAGTCTACGCG
AGCAGCGCGAAAGGC</u>CGATTCACCATCTCCAGAGACAATTCCAAGAACACCCTGTATCTT
CAAATGAACAGCCTGAGAGCTGAGGACACTGCTGTGTATTACTGTGCTAGA*GGCTACGAT
GACTATGATGAGATGACCTACTTTAACATCTGGGGCC*AAGGGACCCTCGTCACCGTCTCG
AGC (SEQ ID NO: 213)

Heavy chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAGCTATGCAATGAGCTGGGTCCGTCAGGCT
CCAGGGAAGGGGCTGGAGTGGGTCGGAGTCATTACTAGTATTGGTAGCACAGTCTACGCG
AGCAGCGCGAAAGGCCGATTCACCATCTCCAGAGACAATTCCAAGAACACCCTGTATCTT
CAAATGAACAGCCTGAGAGCTGAGGACACTGCTGTGTATTACTGTGCTAGAGGCTACGAT
GACTATGATGAGATGACCTACTTTAACATCTGGGGCCAAGGGACCCTCGTCACCGTCTCG
AGCGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAG
CCCAAATCTTGTGACAAAACTCACACATGCCCACCGTGCCCAGCACCTGAACTCCTGGGG
GGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAAC

FIG. 2B

TGGTACGTGGACGGCGTGGAGGTGCATAATGCCAAGACAAAGCCGCGGGAGGAGCAGTAC
GCCAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAATGA (SEQ ID NO: 214)

Light chain Full length protein sequence.

DIQMTQSPSTLSASVGDRVTITCQASQNIYSNLAWYQQKPGKAPKLLIYGASNLDAGVPS
RFSGSGSGTEYTLTISSLQPDDFATYYCQSAFDSDSTENTFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:12)

Variable region Light chain protein sequence.

DIQMTQSPSTLSASVGDRVTITCQASQNIYSNLAWYQQKPGKAPKLLIYGASNLDAGVPS
RFSGSGSGTEYTLTISSLQPDDFATYYCQSAFDSDSTENTFGGGTKVEIKR (SEQ ID
NO:11)

**Variable region Light chain protein sequence. CDR1:Bold;
CDR2: Underline; CDR3:Italics.**

DIQMTQSPSTLSASVGDRVTITCQASQNIYSNLAWYQQKPGKAPKLLIY<u>GASNLDAGVPS</u>
RFSGSGSGTEYTLTISSLQPDDFATYYC*QSAFDSDSTENT*FGGGTKVEIKR (SEQ ID
NOS: 15, 16, 17, respectively)

**Variable region Light chain DNA sequence. CDR1:Bold; CDR2:
Underline; CDR3:Italics.**

GACATCCAGATGACCCAGTCTCCTTCCACCCTGTCTGCATCTGTAGGAGACAGAGTCACC
ATCACTTGCCAGGCCAGTCAGAACATTTACAGCAACTTAGCCTGGTATCAGCAGAAACCA
GGAAAAGCCCCTAAGCTCCTGATCTAT<u>GGTGCATCCAATCTGGATGCT</u>GGAGTCCCATCA
AGGTTCTCTGGCAGTGGATCTGGGACAGAGTACACTCTCACCATCAGCAGCCTGCAGCCT
GATGATTTTGCAACTTACTACTGC*CAAAGTGCTTTTGATAGTGATAGTACTGAAAACACT*
TTCGGCGGAGGAACCAAGGTGGAAATCAAACGT (SEQ ID NO: 211)

Light chain Full length DNA sequence.

GACATCCAGATGACCCAGTCTCCTTCCACCCTGTCTGCATCTGTAGGAGACAGAGTCACC
ATCACTTGCCAGGCCAGTCAGAACATTTACAGCAACTTAGCCTGGTATCAGCAGAAACCA
GGAAAAGCCCCTAAGCTCCTGATCTATGGTGCATCCAATCTGGATGCTGGAGTCCCATCA
AGGTTCTCTGGCAGTGGATCTGGGACAGAGTACACTCTCACCATCAGCAGCCTGCAGCCT
GATGATTTTGCAACTTACTACTGCCAAAGTGCTTTTGATAGTGATAGTACTGAAAACACT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 212)

Heavy_chain Full length protein sequence.
QSVEESGGRLVTPGTPLTLTCTVSGFSLSSYVMIWVRQAPGKGLEYIGITWSAGTYYASW
AKGRFTISKTSSTTVDLKITSPTTEDTATYFCAGGGGSIYDIWGPGTLVTVSSASTKGPS
VFPLAPSSKSTSGGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYASTYRVVS
VLTVLHQDWLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSRWQQGNVFS
CSVMHEALHNHYTQKSLSLSPGK (SEQ ID NO:24)

Variable_region_heavy_chain protein sequence.
QSVEESGGRLVTPGTPLTLTCTVSGFSLSSYVMIWVRQAPGKGLEYIGITWSAGTYYASW
AKGRFTISKTSSTTVDLKITSPTTEDTATYFCAGGGGSIYDIWGPGTLVTVSS (SEQ
ID NO:23)

**Variable_region_heavy_chain protein sequence. CDR1:Bold;
CDR2: Underline; CDR3:Italics.**
QSVEESGGRLVTPGTPLTLTCTVSGFSLSSYVMIWVRQAPGKGLEYIG<u>ITWSAGTYYASW
AKG</u>RFTISKTSSTTVDLKITSPTTEDTATYFCAG*GGGSIYDI*WGPGTLVTVSS (SEQ
ID NOS: 28, 29, 30, respectively)

**Variable_region_heavy_chain DNA sequence. CDR1:Bold; CDR2:
Underline; CDR3:Italics.**
CAGTCGGTGGAGGAGTCCGGGGGTCGCCTGGTCACGCCTGGGACACCCCTGACACTCACC
TGCACAGTCTCTGGATTCTCCCTCAGTAGCTATGTAATGATCTGGGTCCGCCAGGCTCCA
GGGAAGGGGCTGGAATACATCGGA<u>ATCACTTGGAGTGCTGGTACATACTACGCGAGCTGG
GCGAAAGGC</u>CGATTCACCATCTCCAAAACCTCGTCGACCACGGTGGATCTGAAAATCACC
AGTCCGACAACCGAGGACACGGCCACCTATTTCTGTGCCGGA*GGTGGTGGTAGTATTTAT
GATATT*GGGGCCCGGGCACCCTGGTCACCGTCTCGAGC (SEQ ID NO: 223)

Heavy_chain Full length DNA sequence.
CAGTCGGTGGAGGAGTCCGGGGGTCGCCTGGTCACGCCTGGGACACCCCTGACACTCACC
TGCACAGTCTCTGGATTCTCCCTCAGTAGCTATGTAATGATCTGGGTCCGCCAGGCTCCA
GGGAAGGGGCTGGAATACATCGGAATCACTTGGAGTGCTGGTACATACTACGCGAGCTGG
GCGAAAGGCCGATTCACCATCTCCAAAACCTCGTCGACCACGGTGGATCTGAAAATCACC
AGTCCGACAACCGAGGACACGGCCACCTATTTCTGTGCCGGAGGTGGTGGTAGTATTTAT
GATATTGGGGCCCGGGCACCCTGGTCACCGTCTCGAGCGCCTCCACCAAGGGCCCATCG
GTCTTCCCCCTGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATCAC
AAGCCCAGCAACACCAAGGTGGACAAGAGAGTTGAGCCCAAATCTTGTGACAAAACTCAC
ACATGCCCACCGTGCCCAGCACCTGAACTCCTGGGGGGACCGTCAGTCTTCCTCTTCCCC
CCAAAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGAGGTG
CATAATGCCAAGACAAAGCCGCGGGAGGAGCAGTACGCCAGCACGTACCGTGTGGTCAGC

FIG. 3B

```
GTCCTCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCCCCGA
GAACCACAGGTGTACACCCTGCCCCCATCCCGGGAGGAGATGACCAAGAACCAGGTCAGC
CTGACCTGCCTGGTCAAAGGCTTCTATCCCAGCGACATCGCCGTGGAGTGGGAGAGCAAT
GGGCAGCCGGAGAACAACTACAAGACCACGCCTCCCGTGCTGGACTCCGACGGCTCCTTC
TTCCTCTACAGCAAGCTCACCGTGGACAAGAGCAGGTGGCAGCAGGGGAACGTCTTCTCA
TGCTCCGTGATGCATGAGGCTCTGCACAACCACTACACGCAGAAGAGCCTCTCCCTGTCT
CCGGGTAAATGA (SEQ ID NO: 224)
```

Light chain Full length protein sequence.

```
AVLTQTPSPVSAAMGDTVTIKCQSSQSVYKNNYLSWYQQKPGQPPRLLIYDASNLPSGVP
SRFSGSGSGTQFTLTISGVQCDDAATYYCLGDYDDDADNAFGGGTEVVVKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:22)
```

Variable region light chain protein sequence.

```
AVLTQTPSPVSAAMGDTVTIKCQSSQSVYKNNYLSWYQQKPGQPPRLLIYDASNLPSGVP
SRFSGSGSGTQFTLTISGVQCDDAATYYCLGDYDDDADNAFGGGTEVVVKR (SEQ ID
NO:21)
```

Variable region light chain protein sequence. CDR1:Bold; CDR2: Underline; CDR3:Italics.

```
AVLTQTPSPVSAAMGDTVTIKCQSSQSVYKNNYLSWYQQKPGQPPRLLIYDASNLPSGVP
SRFSGSGSGTQFTLTISGVQCDDAATYYCLGDYDDDADNAFGGGTEVVVKR (SEQ ID
NOS: 25, 26, 27, respectively)
```

Variable region light chain DNA sequence. CDR1:Bold; CDR2: Underline; CDR3:Italics.

```
GCAGCCGTGCTGACCCAGACACCATCGCCCGTGTCTGCAGCTATGGGAGACACAGTCACC
ATCAAGTGCCAGTCCAGTCAGAGTGTTTATAAGAACAACTACTTATCCTGGTATCAGCAG
AAACCAGGGCAGCCTCCCAGGCTCCTGATCTATGATGCATCCAATCTGCCATCTGGGGTC
CCATCACGGTTCAGCGGCAGTGGATCTGGGACACAGTTCACTCTCACCATCAGCGGCGTG
CAGTGTGACGATGCTGCCACTTACTACTGTCTAGGCGATTATGATGATGATGCTGATAAT
GCTTTCGGCGGAGGGACCGAGGTGGTGGTCAAACGT (SEQ ID NO: 221)
```

Light chain Full length DNA sequence.

```
GCAGCCGTGCTGACCCAGACACCATCGCCCGTGTCTGCAGCTATGGGAGACACAGTCACC
ATCAAGTGCCAGTCCAGTCAGAGTGTTTATAAGAACAACTACTTATCCTGGTATCAGCAG
AAACCAGGGCAGCCTCCCAGGCTCCTGATCTATGATGCATCCAATCTGCCATCTGGGGTC
CCATCACGGTTCAGCGGCAGTGGATCTGGGACACAGTTCACTCTCACCATCAGCGGCGTG
CAGTGTGACGATGCTGCCACTTACTACTGTCTAGGCGATTATGATGATGATGCTGATAAT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 222)
```

Heavy_chain Full length protein sequence.
EVQLVESGGGLVQPGGSLRLSCAASGFTVSSYVMIWVRQAPGKGLEYIGITWSAGTYYAS
SAKGRFTISRDNSKNTLYLQMNSLRAEDTAVYYCAGGGGSIYDIWGQGTLVTVSSASTKG
PSVFPLAPSSKSTSGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO:34)

Variable_region_heavy_chain protein sequence.
EVQLVESGGGLVQPGGSLRLSCAASGFTVSSYVMIWVRQAPGKGLEYIGITWSAGTYYAS
SAKGRFTISRDNSKNTLYLQMNSLRAEDTAVYYCAGGGGSIYDIWGQGTLVTVSS (SEQ
ID NO:33)

Variable_region_heavy_chain protein sequence. CDR1:Bold; CDR2: Underline; CDR3:Italics.
EVQLVESGGGLVQPGGSLRLSCAASGFTVSSYVMIWVRQAPGKGLEYIG<u>ITWSAGTYYAS
SAKG</u>RFTISRDNSKNTLYLQMNSLRAEDTAVYYCAG*GGGSIYDI*WGQGTLVTVSS (SEQ
ID NOS: 38, 39, 40, respectively)

Variable_region_heavy_chain DNA sequence. CDR1:Bold; CDR2: Underline; CDR3:Italics.
GAGGTGCAGCTGGTGGAGTCTGGGGGAGGCTTGGTCCAGCCTGGGGGGTCCCTGAGACTC
TCCTGTGCAGCCTCTGGATTCACCGTCAGTAGCTATGTAATGATCTGGGTCCGTCAGGCT
CCAGGGAAGGGGCTGGAGTACATCGGA<u>ATCACTTGGAGTGCTGGTACATACTACGCGAGC
AGTGCGAAAGGC</u>CGATTCACCATCTCCAGAGACAATTCCAAGAACACCCTGTATCTTCAA
ATGAACAGCCTGAGAGCTGAGGACACTGCTGTGTATTACTGTCTGGAG*GTGGTGGTAGT
ATCTATGATATT*TGGGGCCAAGGGACCCTCGTCACCGTCTCGAGC (SEQ ID NO:
233)

Heavy_chain Full length DNA sequence.
GAGGTGCAGCTGGTGGAGTCTGGGGGAGGCTTGGTCCAGCCTGGGGGGTCCCTGAGACTC
TCCTGTGCAGCCTCTGGATTCACCGTCAGTAGCTATGTAATGATCTGGGTCCGTCAGGCT
CCAGGGAAGGGGCTGGAGTACATCGGAATCACTTGGAGTGCTGGTACATACTACGCGAGC
AGTGCGAAAGGCCGATTCACCATCTCCAGAGACAATTCCAAGAACACCCTGTATCTTCAA
ATGAACAGCCTGAGAGCTGAGGACACTGCTGTGTATTACTGTCTGGAGGTGGTGGTAGT
ATCTATGATATTTGGGGCCAAGGGACCCTCGTCACCGTCTCGAGCGCCTCCACCAAGGGC
CCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAACGTG
AATCACAAGCCCAGCAACACCAAGGTGGACAAGAGAGTTGAGCCCAAATCTTGTGACAAA
ACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTG

FIG. 4B

GAGGTGCATAATGCCAAGACAAAGCCGCGGGAGGAGCAGTACGCCAGCACGTACCGTGTG
GTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAG
CCCCGAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCC
CTGTCTCCGGGTAAATGA (SEQ ID NO: 234)

Light_chain Full length protein sequence.

DIQMTQSPSTLSASVGDRVTITCQSSQSVYKNNYLSWYQQKPGKAPKLLIYDASNLPSGV
PSRFSGSGSGTEFTLTISSLQPDDFATYYCLGDYDDDADNAFGGGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO:32)

Variable_region Light_chain protein sequence.

DIQMTQSPSTLSASVGDRVTITCQSSQSVYKNNYLSWYQQKPGKAPKLLIYDASNLPSGV
PSRFSGSGSGTEFTLTISSLQPDDFATYYCLGDYDDDADNAFGGGTKVEIKR (SEQ ID
NO:31)

Variable_region Light_chain protein sequence. CDR1:Bold; CDR2: Underline; CDR3:Italics.

DIQMTQSPSTLSASVGDRVTITCQSSQSVYKNNYLSWYQQKPGKAPKLLIY<u>DASNLPSGV</u>
PSRFSGSGSGTEFTLTISSLQPDDFATYYC*LGDYDDDADN*AFGGGTKVEIKR (SEQ ID
NOS: 35, 36, 37, respectively)

Variable_region Light_chain DNA sequence. CDR1:Bold; CDR2: Underline; CDR3:Italics.

GACATCCAGATGACCCAGTCTCCTTCCACCCTGTCTGCATCTGTAGGAGACAGAGTCACC
ATCACTTGCAGTCCAGTCAGAGTGTCTATAAGAACAACTACTTATCCTGGTATCAGCAG
AAACCAGGAAAAGCCCCTAAGCTCCTGATCTAT<u>GATGCATCCAATCTGCCATCT</u>GGAGTC
CCATCAAGGTTCAGCGGCAGTGGATCTGGAACAGAATTCACTCTCACCATCAGCAGCCTG
CAGCCTGATGATTTTGCAACTTATTACTGC*CTAGGCGATTATGATGATGATGCTGATAAT
GC*TTTCGGCGGAGGAACCAAGGTGGAAATCAAACGT (SEQ ID NO: 231)

Light_chain Full length DNA sequence.

GACATCCAGATGACCCAGTCTCCTTCCACCCTGTCTGCATCTGTAGGAGACAGAGTCACC
ATCACTTGCCAGTCCAGTCAGAGTGTCTATAAGAACAACTACTTATCCTGGTATCAGCAG
AAACCAGGAAAAGCCCCTAAGCTCCTGATCTATGATGCATCCAATCTGCCATCTGGAGTC
CCATCAAGGTTCAGCGGCAGTGGATCTGGAACAGAATTCACTCTCACCATCAGCAGCCTG
CAGCCTGATGATTTTGCAACTTATTACTGCCTAGGCGATTATGATGATGATGCTGATAAT
GCTTTCGGCGGAGGAACCAAGGTGGAAATCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 232)

Heavy_chain Full length protein sequence.

QSVEESGGRLVTPGTPLTLTCTVSGFSLSNYAVGWVRQAPGKGLEWIGIIGRNGNTWYAS
WARGRFTISKTSTTVDLKITSPTSEDTATYFCARGYGRSVAYYVFNIWGPGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO:44)

Variable_region_heavy_chain protein sequence.

QSVEESGGRLVTPGTPLTLTCTVSGFSLSNYAVGWVRQAPGKGLEWIGIIGRNGNTWYAS
WARGRFTISKTSTTVDLKITSPTSEDTATYFCARGYGRSVAYYVFNIWGPGTLVTVSS
(SEQ ID NO:43)

Variable_region_heavy_chain protein sequence. CDR1:Bold; CDR2: Underline; CDR3:Italics.

QSVEESGGRLVTPGTPLTLTCTVSGFSLSNYAVGWVRQAPGKGLEWIGI<u>IGRNGNTWYAS
WARG</u>RFTISKTSTTVDLKITSPTSEDTATYFCAR*GYGRSVAYYVFNI*WGPGTLVTVSS
(SEQ ID NOS: 48, 49, 50, respectively)

Variable_region_heavy_chain DNA sequence. CDR1:Bold; CDR2: Underline; CDR3:Italics.

CAGTCGGTGGAGGAGTCCGGGGGTCGCCTGGTCACGCCTGGGACACCCCTGACACTCACC
TGCACAGTCTCTGGATTCTCCCTCAGTAACTATGCAGTGGGCTGGGTCCGCCAGGCTCCA
GGGAAGGGGCTGGAATGGATCGGA<u>ATCATTGGTCGTAATGGTAACACATGGTACGCGAGC
TGGGCAAGAGGC</u>CGATTCACCATCTCCAAAACCTCGACCACGGTGGATCTGAAAATCACC
AGTCCGACAAGCGAGGACACGGCCACATATTTCTGTGCCAGAG*GATATGGCCGTAGTGTT
GCTTATTACGTCTTTAACATCT*GGGGCCCAGGCACCCTCGTCACCGTCTCGAGC (SEQ
ID NO: 243)

Heavy_chain Full length DNA sequence.

CAGTCGGTGGAGGAGTCCGGGGGTCGCCTGGTCACGCCTGGGACACCCCTGACACTCACC
TGCACAGTCTCTGGATTCTCCCTCAGTAACTATGCAGTGGGCTGGGTCCGCCAGGCTCCA
GGGAAGGGGCTGGAATGGATCGGAATCATTGGTCGTAATGGTAACACATGGTACGCGAGC
TGGGCAAGAGGCCGATTCACCATCTCCAAAACCTCGACCACGGTGGATCTGAAAATCACC
AGTCCGACAAGCGAGGACACGGCCACATATTTCTGTGCCAGAGGATATGGCCGTAGTGTT
GCTTATTACGTCTTTAACATCTGGGGCCCAGGCACCCTCGTCACCGTCTCGAGCGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG

FIG. 5B

GACGGCGTGGAGGTGCATAATGCCAAGACAAAGCCGCGGGAGGAGCAGTACGCCAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATGA (SEQ ID NO: 244)

Light chain Full length protein sequence.

AYDMTQTPASVEVAVGGTVTIKCQASQSIYSNLAWYQQRPGQPPKLLIYDASTLESGVPS
RFKGSGSGTEYTLTISGVECADAASYYCQQGFTVSDIDNAFGGGTEVVVKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:42)

Variable region light chain protein sequence.

AYDMTQTPASVEVAVGGTVTIKCQASQSIYSNLAWYQQRPGQPPKLLIYDASTLESGVPS
RFKGSGSGTEYTLTISGVECADAASYYCQQGFTVSDIDNAFGGGTEVVVKR (SEQ ID
NO:41)

Variable region light chain protein sequence. CDR1:Bold; CDR2: Underline; CDR3:Italics.

AYDMTQTPASVEVAVGGTVTIKCQASQSIYSNLAWYQQRPGQPPKLLIY<u>DASTLES</u>GVPS
RFKGSGSGTEYTLTISGVECADAASYYC*QQGFTVSDIDN*AFGGGTEVVVKR (SEQ ID
NOS: 45, 46, 47, respectively)

Variable region light chain DNA sequence. CDR1:Bold; CDR2: Underline; CDR3:Italics.

GCCTATGATATGACCCAGACTCCAGCCTCTGTGGAGGTAGCTGTGGGAGGCACAGTCACC
ATCAAGTGCCAGGCCAGTCAGAGCATTTACAGCAATTTAGCCTGGTATCAGCAGAGACCA
GGGCAGCCTCCCAAGCTCCTGATCTAT<u>GATGCATCCACTCTGGAATCTG</u>GGGTCCCATCG
CGGTTCAAAGGCAGTGGATCTGGGACAGAGTACACTCTCACCATCAGCGGCGTGGAGTGT
GCCGATGCTGCCTCTTACTACTGT*CAACAGGGTTTTACTGTTAGTGATATTGATAAT*GCT
TTCGGCGGAGGGACCGAGGTGGTGGTCAAACGT (SEQ ID NO: 241)

Light chain Full length DNA sequence.

GCCTATGATATGACCCAGACTCCAGCCTCTGTGGAGGTAGCTGTGGGAGGCACAGTCACC
ATCAAGTGCCAGGCCAGTCAGAGCATTTACAGCAATTTAGCCTGGTATCAGCAGAGACCA
GGGCAGCCTCCCAAGCTCCTGATCTATGATGCATCCACTCTGGAATCTGGGGTCCCATCG
CGGTTCAAAGGCAGTGGATCTGGGACAGAGTACACTCTCACCATCAGCGGCGTGGAGTGT
GCCGATGCTGCCTCTTACTACTGTCAACAGGGTTTTACTGTTAGTGATATTGATAATGCT
TTCGGCGGAGGGACCGAGGTGGTGGTCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 242)

Heavy_chain Full length protein sequence.
EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCPAPELLG
GPSVFLFPPKPKDTLMISRTPEVTCVVVDVSHEDPEVKFNWYVDGVEVHNAKTKPREEQY
ASTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO:54)

Variable_region_heavy_chain protein sequence.
EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
S (SEQ ID NO:53)

Variable_region_heavy_chain protein sequence. CDR1:Bold; CDR2: Underline; CDR3:Italics.
EVQLVESGGGLVQPGGSLRLSCAASGFTVSNYAVGWVRQAPGKGLEWVGI<u>IGRNGNTWYA
SSARGRFTISRDNSKNTLYLQMNSLRAEDTAVYYCAR</u>*GYGRSVAYYVFN*IWGPGTLVTVS
S (SEQ ID NOS: 58, 59, 60, respectively)

Variable_region_heavy_chain DNA sequence. CDR1:Bold; CDR2: Underline; CDR3:Italics.
GAGGTGCAGCTGGTGGAGTCTGGGGGAGGCTTGGTCCAGCCTGGGGGGTCCCTGAGACTC
TCCTGTGCAGCCTCTGGATTCACCGTCAGTAACTATGCAGTGGGCTGGGTCCGTCAGGCT
CCAGGGAAGGGGCTGGAGTGGGTCGGA<u>ATCATTGGTCGTAATGGTAACACATGGTACGCG
AGCTCTGCAAGAGGC</u>CGATTCACCATCTCCAGAGACAATTCCAAGAACACCTGTATCTT
CAAATGAACAGCCTGAGAGCTGAGGACACTGCTGTGTATTACTGTGCTAGA*GGATATGGC
CGTAGTGTTGCTTATTACGTCTTTAAC*ATCTGGGGCCCAGGGACCCTCGTCACCGTCTCG
AGC (SEQ ID NO: 253)

Heavy_chain Full length DNA sequence.
GAGGTGCAGCTGGTGGAGTCTGGGGGAGGCTTGGTCCAGCCTGGGGGGTCCCTGAGACTC
TCCTGTGCAGCCTCTGGATTCACCGTCAGTAACTATGCAGTGGGCTGGGTCCGTCAGGCT
CCAGGGAAGGGGCTGGAGTGGGTCGGAATCATTGGTCGTAATGGTAACACATGGTACGCG
AGCTCTGCAAGAGGCCGATTCACCATCTCCAGAGACAATTCCAAGAACACCTGTATCTT
CAAATGAACAGCCTGAGAGCTGAGGACACTGCTGTGTATTACTGTGCTAGAGGATATGGC
CGTAGTGTTGCTTATTACGTCTTTAACATCTGGGGCCCAGGGACCCTCGTCACCGTCTCG
AGCGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAG
CCCAAATCTTGTGACAAAACTCACACATGCCCACCGTGCCCAGCACCTGAACTCCTGGGG
GGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAAC

FIG. 6B

TGGTACGTGGACGGCGTGGAGGTGCATAATGCCAAGACAAAGCCGCGGGAGGAGCAGTAC
GCCAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAATGA (SEQ ID NO: 254)

Light chain Full length protein sequence.

DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:52)

Variable_region Light chain protein sequence.

DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKR (SEQ ID
NO:51)

Variable_region Light_chain protein sequence. CDR1:Bold; CDR2: Underline; CDR3:Italics.

DIQMTQSPSTLSASVGDRVTITCQASQSIYSNLAWYQQKPGKAPKLLIY<u>DASTLESGVPS</u>
RFSGSGSGTEYTLTISSLQPDDFATYYC*QQGFTVSDIDN*AFGGGTKVEIKR (SEQ ID
NOS: 55, 56, 57, respectively)

Variable_region Light_chain DNA sequence. CDR1:Bold; CDR2: Underline; CDR3:Italics.

GACATCCAGATGACCCAGTCTCCTTCCACCCTGTCTGCATCTGTAGGAGACAGAGTCACC
ATCACTTGCCAGGCCAGTCAGAGCATTTACAGCAATTTGCCTGGTATCAGCAGAAACCA
GGAAAAGCCCCTAAGCTCCTGATCTAT<u>GATGCATCCACTCTGGAATCTGGAGTCCCATCA</u>
AGGTTCAGCGGCAGTGGATCTGGGACAGAGTACACTCTCACCATCAGCAGCCTGCAGCCT
GATGATTTTGCAACTTACTACTGC*CAACAGGGTTTTACTGTTAGTGATATTGATAATGCT*
TTCGGCGGAGGAACCAAGGTGGAAATCAAACGT (SEQ ID NO: 251)

Light_chain Full length DNA sequence.

GACATCCAGATGACCCAGTCTCCTTCCACCCTGTCTGCATCTGTAGGAGACAGAGTCACC
ATCACTTGCCAGGCCAGTCAGAGCATTTACAGCAATTTGCCTGGTATCAGCAGAAACCA
GGAAAAGCCCCTAAGCTCCTGATCTATGATGCATCCACTCTGGAATCTGGAGTCCCATCA
AGGTTCAGCGGCAGTGGATCTGGGACAGAGTACACTCTCACCATCAGCAGCCTGCAGCCT
GATGATTTTGCAACTTACTACTGCCAACAGGGTTTTACTGTTAGTGATATTGATAATGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 252)

Heavy_chain Full length protein sequence.
QEQLKESGGRLVTPGTPLTLTCTVSGFSLSSYAMIWVRQAPGKGLEYIGYIDTDTSAYYA
SWVKGRFTISRTSTTVDLKITSPTTEDTATYFCARSYAAYGGYPATFDPWGPGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO:64)

Variable_region_heavy_chain protein sequence.
QEQLKESGGRLVTPGTPLTLTCTVSGFSLSSYAMIWVRQAPGKGLEYIGYIDTDTSAYYA
SWVKGRFTISRTSTTVDLKITSPTTEDTATYFCARSYAAYGGYPATFDPWGPGTLVTVSS
(SEQ ID NO:63)

Variable_region_heavy_chain protein sequence. CDR1:Bold; CDR2: Underline; CDR3:Italics.
QEQLKESGGRLVTPGTPLTLTCTVSGFSLSSYAMIWVRQAPGKGLEYIG<u>YIDTDTSAYYA
SWVKG</u>RFTISRTSTTVDLKITSPTTEDTATYFCAR*SYAAYGGYPATFDP*WGPGTLVTVSS
(SEQ ID NOS: 68, 69, 70, respectively)

Variable_region_heavy_chain DNA sequence. CDR1:Bold; CDR2: Underline; CDR3:Italics.
CAGGAGCAGCTGAAGGAGTCCGGGGGTCGCCTGGTCACGCCTGGGACACCCCTGACACTC
ACCTGTACAGTCTCTGGATTCTCCCTCAGTAGCTATGCAATGATCTGGGTCCGCCAGGCT
CCAGGGAAGGGGCTGGAATACATCGGA<u>TACATTGATACTGATACTAGCGCATACTACGCG
AGCTGGGTGAAAGGC</u>CGATTCACCATCTCCAGAACCTCGACCACGGTGGATCTCAAAATC
ACTAGTCCGACAACCGAGGACACGGCCACCTATTTCTGTGCCAGA*TCTTATGCTGCTTAT
GGTGGTTATCCTGCTACTTTTGATCCT*GGGGCCCAGGCACCCTGGTCACCGTCTCGAGC
(SEQ ID NO: 263)

Heavy_chain Full length DNA sequence.
CAGGAGCAGCTGAAGGAGTCCGGGGGTCGCCTGGTCACGCCTGGGACACCCCTGACACTC
ACCTGTACAGTCTCTGGATTCTCCCTCAGTAGCTATGCAATGATCTGGGTCCGCCAGGCT
CCAGGGAAGGGGCTGGAATACATCGGATACATTGATACTGATACTAGCGCATACTACGCG
AGCTGGGTGAAAGGCCGATTCACCATCTCCAGAACCTCGACCACGGTGGATCTCAAAATC
ACTAGTCCGACAACCGAGGACACGGCCACCTATTTCTGTGCCAGATCTTATGCTGCTTAT
GGTGGTTATCCTGCTACTTTTGATCCTGGGGCCCAGGCACCCTGGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 7B

TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 264)

Light chain Full length protein sequence.

ADVVMTQTPASVSQPVGGTVTIKCQASEDIYNLLAWYQQKPGQPPKLLIYSASTLASGVP
SRFKGSGSGTEYTLTISGLECADAATYYCQNNYLVTTYGVAFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO:62)

Variable region light chain protein sequence.

ADVVMTQTPASVSQPVGGTVTIKCQASEDIYNLLAWYQQKPGQPPKLLIYSASTLASGVP
SRFKGSGSGTEYTLTISGLECADAATYYCQNNYLVTTYGVAFGGGTEVVVKR (SEQ ID
NO:61)

Variable region light chain protein sequence. CDR1:Bold; CDR2: Underline; CDR3:Italics.

ADVVMTQTPASVSQPVGGTVTIKCQASEDIYNLLAWYQQKPGQPPKLLIY<u>SASTLAS</u>GVP
SRFKGSGSGTEYTLTISGLECADAATYYC*QNNYLVTTYGVAF*GGGTEVVVKR (SEQ ID
NOS: 65, 66, 67, respectively)

Variable region light chain DNA sequence. CDR1:Bold; CDR2: Underline; CDR3:Italics.

GCCGATGTTGTGATGACCCAGACTCCAGCCTCCGTGTCTCAACCTGTGGGAGGCACAGTC
ACCATCAAGTGCCAGGCCAGTGAGGACATTTATAACTTATGGCCTGGTATCAGCAGAAA
CCAGGGCAGCCTCCCAAGCTCCTGATCTATT<u>CTGCATCCACTCTGGCATCT</u>GGGGTCCCA
TCGCGGTTCAAAGGCAGTGGATCTGGGACAGAGTACACTCTCACCATCAGCGGCCTGGAG
TGTGCCGATGCTGCCACTTACTACTGT*CAAAACAATTATCTTGTTACTACTTATGGTGTT
GCTTTCGGCGGAGGGACCGAGGTGGTGGTCAAACGT* (SEQ ID NO: 261)

Light chain Full length DNA sequence.

GCCGATGTTGTGATGACCCAGACTCCAGCCTCCGTGTCTCAACCTGTGGGAGGCACAGTC
ACCATCAAGTGCCAGGCCAGTGAGGACATTTATAACTTATGGCCTGGTATCAGCAGAAA
CCAGGGCAGCCTCCCAAGCTCCTGATCTATTCTGCATCCACTCTGGCATCTGGGGTCCCA
TCGCGGTTCAAAGGCAGTGGATCTGGGACAGAGTACACTCTCACCATCAGCGGCCTGGAG
TGTGCCGATGCTGCCACTTACTACTGTCAAAACAATTATCTTGTTACTACTTATGGTGTT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 262)

Heavy_chain Full length protein sequence.

QVQLVESGGGVVQPGRSLRLSCAASGFTFSSYAMIWVRQAPGKGLEYIGYIDTDTSAYYA
SSVKGRFTISRDNSKNTLYLQMSSLRAEDTAVYYCARSYAAYGGYPATFDPWGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPELL
GGPSVFLFPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDKS
RWQQGNVFSCSVMHEALHNHYTQKSLSLSPGK (SEQ ID NO:74)

Variable_region_heavy_chain protein sequence.

QVQLVESGGGVVQPGRSLRLSCAASGFTFSSYAMIWVRQAPGKGLEYIGYIDTDTSAYYA
SSVKGRFTISRDNSKNTLYLQMSSLRAEDTAVYYCARSYAAYGGYPATFDPWGQGTLVTV
SS (SEQ ID NO:73)

Variable_region_heavy_chain protein sequence. CDR1:Bold; CDR2: Underline; CDR3:Italics.

QVQLVESGGGVVQPGRSLRLSCAASGFTFSSYAMIWVRQAPGKGLEYIG<u>YIDTDTSAYYA
SSVKG</u>RFTISRDNSKNTLYLQMSSLRAEDTAVYYCAR*SYAAYGGYPATFDP*WGQGTLVTV
SS (SEQ ID NOS: 78, 79, 80, respectively)

Variable_region_heavy_chain DNA sequence. CDR1:Bold; CDR2: Underline; CDR3:Italics.

CAGGTACAGCTGGTGGAGTCTGGTGGAGGCGTGGTCCAGCCTGGGAGGTCCCTGAGACTC
TCCTGTGCAGCTTCTGGATTCACCTTCAGTAGCTATGCAATGATCTGGGTCCGCCAGGCT
CCAGGGAAGGGGCTGGAATACATCGGA<u>TACATTGATACTGATACTAGCGCATACTACGCA
AGCAGTGTGAAAGGC</u>CGATTCACCATCTCCAGAGACAATTCCAAGAACACGCTGTACCTG
CAAATGTCTAGCCTGAGAGCCGAGGACACGGCTGTGTATTACTGTGCTAGA*TCTTATGCT
GCTTATGGTGGTTATCCTGCTACTTTTGATCCT*GGGGCCAAGGTACCCTCGTCACCGTC
TCGAGC (SEQ ID NO: 273)

Heavy_chain Full length DNA sequence.

CAGGTACAGCTGGTGGAGTCTGGTGGAGGCGTGGTCCAGCCTGGGAGGTCCCTGAGACTC
TCCTGTGCAGCTTCTGGATTCACCTTCAGTAGCTATGCAATGATCTGGGTCCGCCAGGCT
CCAGGGAAGGGGCTGGAATACATCGGATACATTGATACTGATACTAGCGCATACTACGCA
AGCAGTGTGAAAGGCCGATTCACCATCTCCAGAGACAATTCCAAGAACACGCTGTACCTG
CAAATGTCTAGCCTGAGAGCCGAGGACACGGCTGTGTATTACTGTGCTAGATCTTATGCT
GCTTATGGTGGTTATCCTGCTACTTTTGATCCTGGGGCCAAGGTACCCTCGTCACCGTC
TCGAGCGCCTCCACCAAGGGCCCATCGGTCTTCCCCCTGGCACCCTCCTCCAAGAGCACC
TCTGGGGGCACAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTGGGCACC
CAGACCTACATCTGCAACGTGAATCACAAGCCCAGCAACACCAAGGTGGACAAGAGAGTT
GAGCCCAAATCTTGTGACAAAACTCACACATGCCCACCGTGCCCAGCACCTGAACTCCTG
GGGGGACCGTCAGTCTTCCTCTTCCCCCCAAAACCCAAGGACACCCTCATGATCTCCCGG
ACCCCTGAGGTCACATGCGTGGTGGTGGACGTGAGCCACGAAGACCCTGAGGTCAAGTTC

FIG. 8B

AACTGGTACGTGGACGGCGTGGAGGTGCATAATGCCAAGACAAAGCCGCGGGAGGAGCAG
TACGCCAGCACGTACCGTGTGGTCAGCGTCCTCACCGTCCTGCACCAGGACTGGCTGAAT
GGCAAGGAGTACAAGTGCAAGGTCTCCAACAAAGCCCTCCCAGCCCCCATCGAGAAAACC
ATCTCCAAAGCCAAAGGGCAGCCCCGAGAACCACAGGTGTACACCCTGCCCCCATCCCGG
GAGGAGATGACCAAGAACCAGGTCAGCCTGACCTGCCTGGTCAAAGGCTTCTATCCCAGC
GACATCGCCGTGGAGTGGGAGAGCAATGGGCAGCCGGAGAACAACTACAAGACCACGCCT
CCCGTGCTGGACTCCGACGGCTCCTTCTTCCTCTACAGCAAGCTCACCGTGGACAAGAGC
AGGTGGCAGCAGGGGAACGTCTTCTCATGCTCCGTGATGCATGAGGCTCTGCACAACCAC
TACACGCAGAAGAGCCTCTCCCTGTCTCCGGGTAAATGA (SEQ ID NO: 274)

Light_chain Full length protein sequence.

DIQMTQSPSSLSASVGDRVTITCQASEDIYNLLAWYQQKPGKVPKLLIYSASTLASGVPS
RFSGSGSGTDYTLTISSLQPEDVATYYCQNNYLVTTYGVAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:72)

Variable_region_Light_chain protein sequence.

DIQMTQSPSSLSASVGDRVTITCQASEDIYNLLAWYQQKPGKVPKLLIYSASTLASGVPS
RFSGSGSGTDYTLTISSLQPEDVATYYCQNNYLVTTYGVAFGGGTKVEIKR (SEQ ID
NO:71)

Variable_region_Light_chain protein sequence. CDR1:Bold; CDR2: Underline; CDR3:Italics.

DIQMTQSPSSLSASVGDRVTITCQASEDIYNLLAWYQQKPGKVPKLLIY<u>SASTLAS</u>GVPS
RFSGSGSGTDYTLTISSLQPEDVATYYC*QNNYLVTTYGVAF*GGGTKVEIKR (SEQ ID
NOS: 75, 76, 77, respectively)

Variable_region_Light_chain DNA sequence. CDR1:Bold; CDR2: Underline; CDR3:Italics.

GACATCCAGATGACCCAGTCTCCATCCTCCCTGTCTGCATCTGTAGGAGACAGAGTCACC
ATCACTTGCCAGGCCAGTGAGGACATTTACAACTTATTGGCCTGGTATCAGCAGAAACCA
GGGAAAGTCCCTAAGCTCCTGATCTAT<u>TCTGCATCCACTCTGGCATCT</u>GGGGTCCCATCT
CGTTTCAGTGGCAGTGGATCTGGGACAGATTACACTCTCACCATCAGCAGCCTGCAGCCT
GAAGATGTTGCAACTTATTACTGT*CAAAACAACTATCTTGTTACTACTTATGGTGTTGCT*
TTCGGCGGAGGAACCAAGGTGGAAATCAAACGT (SEQ ID NO: 271)

Light_chain Full length DNA sequence.

GACATCCAGATGACCCAGTCTCCATCCTCCCTGTCTGCATCTGTAGGAGACAGAGTCACC
ATCACTTGCCAGGCCAGTGAGGACATTTACAACTTATTGGCCTGGTATCAGCAGAAACCA
GGGAAAGTCCCTAAGCTCCTGATCTATTCTGCATCCACTCTGGCATCTGGGGTCCCATCT
CGTTTCAGTGGCAGTGGATCTGGGACAGATTACACTCTCACCATCAGCAGCCTGCAGCCT
GAAGATGTTGCAACTTATTACTGTCAAAACAACTATCTTGTTACTACTTATGGTGTTGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 272)

Heavy_chain Full length protein sequence.
QSVEESGGRLVTPGTPLTLTCTVSGIDLSMYSMGWVRQAPGKGLEYIGWISYGGTAYYAS
WAKGRFTISKTSTTVELKITSPTIEDTATYFCARETPVNYYLDIWGQGTLVTVSSASTKG
PSVFPLAPSSKSTSGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO:84)

Variable_region_heavy_chain protein sequence.
QSVEESGGRLVTPGTPLTLTCTVSGIDLSMYSMGWVRQAPGKGLEYIGWISYGGTAYYAS
WAKGRFTISKTSTTVELKITSPTIEDTATYFCARETPVNYYLDIWGQGTLVTVSS (SEQ
ID NO:83)

Variable_region_heavy_chain protein sequence. CDR1:Bold; CDR2: Underline; CDR3:Italics.
QSVEESGGRLVTPGTPLTLTCTVSGIDLSMYSMGWVRQAPGKGLEYIGWISYGGTAYYAS
WAKGRFTISKTSTTVELKITSPTIEDTATYFCAR*ETPVNYYLD*IWGQGTLVTVSS (SEQ
ID NOS: 88, 89, 90, respectively)

Variable_region_heavy_chain DNA sequence. CDR1:Bold; CDR2: Underline; CDR3:Italics.
CAGTCGGTGGAGGAGTCCGGGGGTCGCCTGGTCACGCCTGGGACACCCCTGACACTCACC
TGCACAGTCTCTGGAATCGACCTCAGTATGTATTCAATGGGCTGGGTCCGCCAGGCTCCA
GGGAAGGGGCTGGAATACATCGGATGGATTAGTTATGGTGGTACTGCATATTACGCGAGC
TGGGCGAAGGGCCGATTCACCATCTCCAAAACCTCGACCACGGTGGAGCTGAAGATCACC
AGTCCGACAATCGAGGACACGGCCACCTATTTCTGTGCCAGA*GAGACTCCTGTTAATTAT
TATTTGGACATT*TGGGGCCAGGGGACCCTCGTCACCGTCTCGAGC (SEQ ID NO:
283)

Heavy_chain Full length DNA sequence.
CAGTCGGTGGAGGAGTCCGGGGGTCGCCTGGTCACGCCTGGGACACCCCTGACACTCACC
TGCACAGTCTCTGGAATCGACCTCAGTATGTATTCAATGGGCTGGGTCCGCCAGGCTCCA
GGGAAGGGGCTGGAATACATCGGATGGATTAGTTATGGTGGTACTGCATATTACGCGAGC
TGGGCGAAGGGCCGATTCACCATCTCCAAAACCTCGACCACGGTGGAGCTGAAGATCACC
AGTCCGACAATCGAGGACACGGCCACCTATTTCTGTGCCAGAGAGACTCCTGTTAATTAT
TATTTGGACATTTGGGGCCAGGGGACCCTCGTCACCGTCTCGAGCGCCTCCACCAAGGGC
CCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAACGTG
AATCACAAGCCCAGCAACACCAAGGTGGACAAGAGAGTTGAGCCCAAATCTTGTGACAAA
ACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTG

FIG. 9B

GAGGTGCATAATGCCAAGACAAAGCCGCGGGAGGAGCAGTACGCCAGCACGTACCGTGTG
GTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAG
CCCCGAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCC
CTGTCTCCGGGTAAATGA (SEQ ID NO: 284)

Light chain Full length protein sequence.

AYDMTQTPASVSAAVGGTVTIKCQASENIGSYLAWYQQKPGQPPELLIYRASTLASGVPS
RFKGSGSGTQFTLTISGVECADAATYYCQQGYNSENLDNAFGGGTEVVVKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO:82)

Variable region light chain protein sequence.

AYDMTQTPASVSAAVGGTVTIKCQASENIGSYLAWYQQKPGQPPELLIYRASTLASGVPS
RFKGSGSGTQFTLTISGVECADAATYYCQQGYNSENLDNAFGGGTEVVVKR (SEQ ID
NO:81)

Variable region light chain protein sequence. CDR1:Bold; CDR2: Underline; CDR3:Italics.

AYDMTQTPASVSAAVGGTVTIKCQASENIGSYLAWYQQKPGQPPELLIY<u>RASTLA</u>SGVPS
RFKGSGSGTQFTLTISGVECADAATYYC*QQGYNSENLDN*AFGGGTEVVVKR (SEQ ID
NOS: 85, 86, 87, respectively)

Variable region light chain DNA sequence. CDR1:Bold; CDR2: Underline; CDR3:Italics.

GCCTATGATATGACCCAGACTCCAGCCTCCGTGTCTGCAGCTGTGGGAGGCACAGTCACC
ATCAAGTGCCAGGCCAGTGAGAACATTGGTAGCTACTTAGCCTGGTATCAGCAGAAACCA
GGGCAGCCTCCCGAACTCCTGATCTAC<u>AGGGCGTCCACTCTGGCATCT</u>GGGGTCCCATCG
CGGTTCAAAGGCAGTGGATCTGGGACACAGTTCACTCTCACCATCAGCGGCGTGGAGTGT
GCCGATGCTGCCACTTACTACTGT*CAACAGGGTTATAATAGTGAGAATCTTGATAAT*GCT
TTCGGCGGAGGGACCGAGGTGGTGGTCAAACGT (SEQ ID NO: 281)

Light chain Full length DNA sequence.

GCCTATGATATGACCCAGACTCCAGCCTCCGTGTCTGCAGCTGTGGGAGGCACAGTCACC
ATCAAGTGCCAGGCCAGTGAGAACATTGGTAGCTACTTAGCCTGGTATCAGCAGAAACCA
GGGCAGCCTCCCGAACTCCTGATCTACAGGGCGTCCACTCTGGCATCTGGGGTCCCATCG
CGGTTCAAAGGCAGTGGATCTGGGACACAGTTCACTCTCACCATCAGCGGCGTGGAGTGT
GCCGATGCTGCCACTTACTACTGTCAACAGGGTTATAATAGTGAGAATCTTGATAATGCT
TTCGGCGGAGGGACCGAGGTGGTGGTCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 282)

Heavy_chain Full length protein sequence.
QVQLVESGGGVVQPGRSLRLSCAASGFTFSMYSMGWVRQAPGKGLEYIGWISYGGTAYYA
SSAKGRFTISRDNSKNTLYLQMSSLRAEDTAVYYCARETPVNYYLDIWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 94)

Variable_region_heavy_chain protein sequence.
QVQLVESGGGVVQPGRSLRLSCAASGFTFSMYSMGWVRQAPGKGLEYIGWISYGGTAYYA
SSAKGRFTISRDNSKNTLYLQMSSLRAEDTAVYYCARETPVNYYLDIWGQGTLVTVSS
(SEQ ID NO: 93)

Variable_region_heavy_chain protein sequence. CDR1:Bold; CDR2: Underline; CDR3:Italics.
QVQLVESGGGVVQPGRSLRLSCAASGFTFSMYSMGWVRQAPGKGLEYIGWISYGGTAYYA
SSAKGRFTISRDNSKNTLYLQMSSLRAEDTAVYYCAR*ETPVNYYLDI*WGQGTLVTVSS
(SEQ ID NOS: 98, 99, 100, respectively)

Variable_region_heavy_chain DNA sequence. CDR1:Bold; CDR2: Underline; CDR3:Italics.
CAGGTACAGCTGGTGGAGTCTGGTGGAGGCGTGGTCCAGCCTGGGAGGTCCCTGAGACTC
TCCTGTGCAGCTTCTGGATTCACCTTCAGTATGTATTCAATGGGCTGGGTCCGCCAGGCT
CCAGGGAAGGGGCTGGAATACATCGGATGGATTAGTTATGGTGGTACTGCATACTACGCT
AGCAGCGCTAAGGGCCGATTCACCATCTCCAGAGACAATTCCAAGAACACGCTGTACCTG
CAAATGTCTAGCCTGAGAGCCGAGGACACGGCTGTGTATTACTGTGCTAGAGAGACTCCT
GTTAATTACTACTTGGACATTTGGGGCCAAGGTACCCTCGTCACCGTCTCGAGC (SEQ
ID NO: 293)

Heavy_chain Full length DNA sequence.
CAGGTACAGCTGGTGGAGTCTGGTGGAGGCGTGGTCCAGCCTGGGAGGTCCCTGAGACTC
TCCTGTGCAGCTTCTGGATTCACCTTCAGTATGTATTCAATGGGCTGGGTCCGCCAGGCT
CCAGGGAAGGGGCTGGAATACATCGGATGGATTAGTTATGGTGGTACTGCATACTACGCT
AGCAGCGCTAAGGGCCGATTCACCATCTCCAGAGACAATTCCAAGAACACGCTGTACCTG
CAAATGTCTAGCCTGAGAGCCGAGGACACGGCTGTGTATTACTGTGCTAGAGAGACTCCT
GTTAATTACTACTTGGACATTTGGGGCCAAGGTACCCTCGTCACCGTCTCGAGCGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG

FIG. 10B

GACGGCGTGGAGGTGCATAATGCCAAGACAAAGCCGCGGGAGGAGCAGTACGCCAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATGA (SEQ ID NO: 294)

Light chain Full length protein sequence.

AYDMTQSPSSLSASVGDRVTITCQASENIGSYLAWYQQKPGKVPKLLIYRASTLASGVPS
RFSGSGSGTDFTLTISSLQPEDVATYYCQQGYNSENLDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 92)

Variable region Light chain protein sequence.

AYDMTQSPSSLSASVGDRVTITCQASENIGSYLAWYQQKPGKVPKLLIYRASTLASGVPS
RFSGSGSGTDFTLTISSLQPEDVATYYCQQGYNSENLDNAFGGGTKVEIKR (SEQ ID
NO: 91)

**Variable region Light chain protein sequence. CDR1:Bold;
CDR2: Underline; CDR3:Italics.**

AYDMTQSPSSLSASVGDRVTITCQASENIGSYLAWYQQKPGKVPKLLIY<u>RASTLAS</u>GVPS
RFSGSGSGTDFTLTISSLQPEDVATYYC*QQGYNSENLDN*AFGGGTKVEIKR (SEQ ID
NOS: 95, 96, 97, respectively)

**Variable region Light chain DNA sequence. CDR1:Bold; CDR2:
Underline; CDR3:Italics.**

GCCTATGATATGACCCAGTCTCCATCCTCCCTGTCTGCATCTGTAGGAGACAGAGTCACC
ATCACTTGCCAGGCCAGTGAGAACATTGGTAGCTACTTAGGTATCAGCAGAAACCA
GGGAAAGTCCCTAAGCTCCTGATCTAT<u>AGGGCTTCCACTCTGGCATCTGGGGTCCCATCT</u>
CGTTTCAGTGGCAGTGGATCTGGGACAGATTTCACTCTCACCATCAGCAGCCTGCAGCCT
GAAGATGTTGCAACTTATTACTGT*CAACAGGGTTACAATAGTGAGAATCTTGATAATGCT*
TTCGGCGGAGGAACCAAGGTGGAAATCAAACGT (SEQ ID NO: 291)

Light chain Full length DNA sequence.

GCCTATGATATGACCCAGTCTCCATCCTCCCTGTCTGCATCTGTAGGAGACAGAGTCACC
ATCACTTGCCAGGCCAGTGAGAACATTGGTAGCTACTTAGGTATCAGCAGAAACCA
GGGAAAGTCCCTAAGCTCCTGATCTATAGGGCTTCCACTCTGGCATCTGGGGTCCCATCT
CGTTTCAGTGGCAGTGGATCTGGGACAGATTTCACTCTCACCATCAGCAGCCTGCAGCCT
GAAGATGTTGCAACTTATTACTGTCAACAGGGTTACAATAGTGAGAATCTTGATAATGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 292)

Heavy_chain Full length protein sequence.
QSLEESGGRLVTPGTPLTLTCTASGFSLSGYDMSWVRQAPGKGLEYIGLISYDGNTYYAT
WAKGRFTISKTSTTVDLKITSPTTEDTATYFCARSLYAGPNAGIGPFNIWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 104)

Variable_region_heavy_chain protein sequence.
QSLEESGGRLVTPGTPLTLTCTASGFSLSGYDMSWVRQAPGKGLEYIGLISYDGNTYYAT
WAKGRFTISKTSTTVDLKITSPTTEDTATYFCARSLYAGPNAGIGPFNIWGQGTLVTVSS
(SEQ ID NO: 103)

Variable_region_heavy_chain protein sequence. CDR1:Bold; CDR2: Underline; CDR3:Italics.
QSLEESGGRLVTPGTPLTLTCTASGFSLSGYDMSWVRQAPGKGLEYIGL<u>ISYDGNTYYAT
WAKG</u>RFTISKTSTTVDLKITSPTTEDTATYFCAR*SLYAGPNAGIGPFNI*WGQGTLVTVSS
(SEQ ID NOS: 108, 109, 110, respectively)

Variable_region_heavy_chain DNA sequence. CDR1:Bold; CDR2: Underline; CDR3:Italics.
CAGTCGCTGGAGGAGTCCGGGGGTCGCCTGGTCACGCCTGGGACACCCCTGACACTCACC
TGCACAGCCTCTGGATTCTCCCTCAGTGGCTACGACATGAGCTGGGTCCGCCAGGCTCCA
GGAAAGGGGCTGGAATACATCGGA<u>CTCATTAGTTATGATGGTAACACATACTACGCGACC
TGGGCGAAAGGC</u>CGATTCACCATCTCCAAAACCTCGACCACGGTGGATCTGAAAATCACC
AGTCCGACAACCGAGGACACGGCCACCTATTTCTGTGCCAGA*AGTCTTTATGCTGGTCCT
AATGCTGGTATCGGACCGTTTAACATC*TGGGGCCAGGGGACCCTCGTCACCGTCTCGAGC
(SEQ ID NO: 303)

Heavy_chain Full length DNA sequence.
CAGTCGCTGGAGGAGTCCGGGGGTCGCCTGGTCACGCCTGGGACACCCCTGACACTCACC
TGCACAGCCTCTGGATTCTCCCTCAGTGGCTACGACATGAGCTGGGTCCGCCAGGCTCCA
GGAAAGGGGCTGGAATACATCGGACTCATTAGTTATGATGGTAACACATACTACGCGACC
TGGGCGAAAGGCCGATTCACCATCTCCAAAACCTCGACCACGGTGGATCTGAAAATCACC
AGTCCGACAACCGAGGACACGGCCACCTATTTCTGTGCCAGAAGTCTTTATGCTGGTCCT
AATGCTGGTATCGGACCGTTTAACATCTGGGGCCAGGGGACCCTCGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 11B

TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 304)

Light chain Full length protein sequence.

AFELTQTPSSVEAAVGGTVTIKCQASQNIVTNLAWYQQKPGQPPKLLIYGASTLASGVSS
RFKGSGSGTQFTLTISDLECADAATYFCQSYDGFNSAGFGGGTEVVVKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC (SEQ ID NO: 102)

Variable region light chain protein sequence.

AFELTQTPSSVEAAVGGTVTIKCQASQNIVTNLAWYQQKPGQPPKLLIYGASTLASGVSS
RFKGSGSGTQFTLTISDLECADAATYFCQSYDGFNSAGFGGGTEVVVKR (SEQ ID
NO: 101)

Variable region light chain protein sequence. CDR1:Bold; CDR2: Underline; CDR3:Italics.

AFELTQTPSSVEAAVGGTVTIKCQASQNIVTNLAWYQQKPGQPPKLLIY<u>GASTLASGVSS</u>
RFKGSGSGTQFTLTISDLECADAATYFC*QSYDGFNSAGFGGGTEVVVKR* (SEQ ID
NOS: 105, 106, 107, respectively)

Variable region light chain DNA sequence. CDR1:Bold; CDR2: Underline; CDR3:Italics.

GCATTCGAATTGACCCAGACTCCATCCTCCGTGGAGGCAGCTGTGGGAGGCACAGTCACC
ATCAAGTGCCAGGCCAGTCAGAACATTGTTACCAATTTAGCCTGGTATCAACAGAAACCA
GGGCAGCCTCCCAAGCTCCTGATCTAT<u>GGTGCATCCACTCTGGCATCTGGGGTCTCATCG</u>
CGGTTCAAAGGCAGTGGATCTGGGACACAGTTCACTCTCACCATCAGCGACCTGGAGTGT
GCCGATGCTGCCACTTATTTCTGT*CAGAGCTATGATGGTTTTAATAGTGCTGGGTTCGGC
GGAGGGACCGAGGTGGTGGTCAAACGT* (SEQ ID NO: 301)

Light chain Full length DNA sequence.

GCATTCGAATTGACCCAGACTCCATCCTCCGTGGAGGCAGCTGTGGGAGGCACAGTCACC
ATCAAGTGCCAGGCCAGTCAGAACATTGTTACCAATTTAGCCTGGTATCAACAGAAACCA
GGGCAGCCTCCCAAGCTCCTGATCTATGGTGCATCCACTCTGGCATCTGGGGTCTCATCG
CGGTTCAAAGGCAGTGGATCTGGGACACAGTTCACTCTCACCATCAGCGACCTGGAGTGT
GCCGATGCTGCCACTTATTTCTGTCAGAGCTATGATGGTTTTAATAGTGCTGGGTTCGGC
GGAGGGACCGAGGTGGTGGTCAAACGTACGGTGGCTGCACCATCTGTCTTCATCTTCCCG
CCATCTGATGAGCAGTTGAAATCTGGAACTGCCTCTGTTGTGTGCCTGCTGAATAACTTC
TATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGTTAG (SEQ ID NO:
302)

Heavy_chain Full length protein sequence.
QVQLVESGGGVVQPGRSLRLSCAASGFSLSGYDMSWVRQAPGKGLEWVGLISYDGNTYYA
TSAKGRFTISRDNSKNTLYLQMSSLRAEDTAVYYCARSLYAGPNAGIGPFNIWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTHTCPPCPAPEL
LGGPSVFLFPPKPKDTLMISRTPEVTCVVVDVSHEDPEVKFNWYVDGVEVHNAKTKPREE
QYASTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 114)

Variable_region_heavy_chain protein sequence.
QVQLVESGGGVVQPGRSLRLSCAASGFSLSGYDMSWVRQAPGKGLEWVGLISYDGNTYYA
TSAKGRFTISRDNSKNTLYLQMSSLRAEDTAVYYCARSLYAGPNAGIGPFNIWGQGTLVT
VSS (SEQ ID NO: 113)

Variable_region_heavy_chain protein sequence. CDR1:Bold; CDR2: Underline; CDR3:Italics.
QVQLVESGGGVVQPGRSLRLSCAASGFSLSGYDMSWVRQAPGKGLEWVGL<u>ISYDGNTYYA
TSAKGRFTI</u>SRDNSKNTLYLQMSSLRAEDTAVYYCAR*SLYAGPNAGIGPFNI*WGQGTLVT
VSS (SEQ ID NOS: 118, 119, 120, respectively)

Variable_region_heavy_chain DNA sequence. CDR1:Bold; CDR2: Underline; CDR3:Italics.
CAGGTACAGCTGGTGGAGTCTGGTGGAGGCGTGGTCCAGCCTGGGAGGTCCCTGAGACTC
TCCTGTGCAGCTTCTGGATTCTCCCTCAGTGGCTACGACATGAGCTGGGTCCGTCAGGCT
CCAGGCAAGGGACTGGAGTGGGTGGGA<u>CTCATTAGTTATGATGGTAACACATACTACGCG
ACCTCCGCGAAAGGCCGATTCACCATCTC</u>CAGAGACAATTCCAAGAACACGCTGTACCTG
CAAATGTCTAGCCTGAGAGCCGAGGACACGGCTGTGTATTACTGTGCTAGA*AGTCTTTAT
GCTGGTCCTAATGCTGGTATCGGACCGTTTAACATC*TGGGGCCAAGGTACCCTCGTCACC
GTCTCGAGC (SEQ ID NO: 313)

Heavy_chain Full length DNA sequence.
CAGGTACAGCTGGTGGAGTCTGGTGGAGGCGTGGTCCAGCCTGGGAGGTCCCTGAGACTC
TCCTGTGCAGCTTCTGGATTCTCCCTCAGTGGCTACGACATGAGCTGGGTCCGTCAGGCT
CCAGGCAAGGGACTGGAGTGGGTGGGACTCATTAGTTATGATGGTAACACATACTACGCG
ACCTCCGCGAAAGGCCGATTCACCATCTCCAGAGACAATTCCAAGAACACGCTGTACCTG
CAAATGTCTAGCCTGAGAGCCGAGGACACGGCTGTGTATTACTGTGCTAGAAGTCTTTAT
GCTGGTCCTAATGCTGGTATCGGACCGTTTAACATCTGGGGCCAAGGTACCCTCGTCACC
GTCTCGAGCGCCTCCACCAAGGGCCCATCGGTCTTCCCCCTGGCACCCTCCTCCAAGAGC
ACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGCAGCTTGGGC
ACCCAGACCTACATCTGCAACGTGAATCACAAGCCCAGCAACACCAAGGTGGACAAGAGA
GTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAGGTCAAG

FIG. 12B

TTCAACTGGTACGTGGACGGCGTGGAGGTGCATAATGCCAAGACAAAGCCGCGGGAGGAG
CAGTACGCCAGCACGTACCGTGTGGTCAGCGTCCTCACCGTCCTGCACCAGGACTGGCTG
AATGGCAAGGAGTACAAGTGCAAGGTCTCCAACAAAGCCCTCCCAGCCCCCATCGAGAAA
ACCATCTCCAAAGCCAAAGGGCAGCCCCGAGAACCACAGGTGTACACCCTGCCCCCATCC
CGGGAGGAGATGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACAAG
AGCAGGTGGCAGCAGGGGAACGTCTTCTCATGCTCCGTGATGCATGAGGCTCTGCACAAC
CACTACACGCAGAAGAGCCTCTCCCTGTCTCCGGGTAAATGA (SEQ ID NO: 314)

Light_chain Full length protein sequence.

AFQMTQSPSSLSASVGDRVTITCQASQNIVTNLAWYQQKPGKVPKLLIYGASTLASGVPS
RFSGSGSGTDFTLTISSLQPEDVATYYCQSYDGFNSAGFGGGTKVEIKRTVAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC (SEQ ID NO: 112)

Variable_region_Light_chain protein sequence.

AFQMTQSPSSLSASVGDRVTITCQASQNIVTNLAWYQQKPGKVPKLLIYGASTLASGVPS
RFSGSGSGTDFTLTISSLQPEDVATYYCQSYDGFNSAGFGGGTKVEIKR (SEQ ID
NO: 111)

Variable_region_Light_chain protein sequence. CDR1:Bold; CDR2: Underline; CDR3:Italics.

AFQMTQSPSSLSASVGDRVTITCQASQNIVTNLAWYQQKPGKVPKLLIY<u>GASTLAS</u>GVPS
RFSGSGSGTDFTLTISSLQPEDVATYYC*QSYDGFNSAG*FGGGTKVEIKR (SEQ ID
NOS: 115, 116, 117, respectively)

Variable_region_Light_chain DNA sequence. CDR1:Bold; CDR2: Underline; CDR3:Italics.

GCATTCCAGATGACCCAGTCTCCATCCTCCCTGTCTGCATCTGTAGGAGACAGAGTCACC
ATCACTTGCCAGGCCAGTCAGAACATTGTTACCAACTTAGCCTGGTATCAGCAGAAACCA
GGGAAAGTCCCTAAGCTCCTGATCTAT<u>GGTGCATCCACTCTGGCATCT</u>GGGGTCCCATCT
CGTTTCAGTGGCAGTGGATCTGGGACAGATTTCACTCTCACCATCAGCAGCCTGCAGCCT
GAAGATGTTGCAACTTATTACTGT*CAGAGCTATGATGGTTTCAATAGTGCTGGT*TTCGGC
GGAGGAACCAAGGTGGAAATCAAACGT (SEQ ID NO: 311)

Light_chain Full length DNA sequence.

GCATTCCAGATGACCCAGTCTCCATCCTCCCTGTCTGCATCTGTAGGAGACAGAGTCACC
ATCACTTGCCAGGCCAGTCAGAACATTGTTACCAACTTAGCCTGGTATCAGCAGAAACCA
GGGAAAGTCCCTAAGCTCCTGATCTATGGTGCATCCACTCTGGCATCTGGGGTCCCATCT
CGTTTCAGTGGCAGTGGATCTGGGACAGATTTCACTCTCACCATCAGCAGCCTGCAGCCT
GAAGATGTTGCAACTTATTACTGTCAGAGCTATGATGGTTTCAATAGTGCTGGTTTCGGC
GGAGGAACCAAGGTGGAAATCAAACGTACGGTGGCTGCACCATCTGTCTTCATCTTCCCG
CCATCTGATGAGCAGTTGAAATCTGGAACTGCCTCTGTTGTGTGCCTGCTGAATAACTTC
TATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGTTAG (SEQ ID NO:
312)

Heavy_chain Full length protein sequence.
QSVEASGGRLVTPGTPLTLTCTASGFSLSTYWMSWVRQAPGKGLEWIGDIYFSNEETNYA
SWAKGRFTISKTSTTVDLNVISPTTEDTATYFCARGSPDVDIGIDMWGPGTLVTVSSAST
KGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYASTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 124)

Variable_region_heavy_chain protein sequence.
QSVEASGGRLVTPGTPLTLTCTASGFSLSTYWMSWVRQAPGKGLEWIGDIYFSNEETNYA
SWAKGRFTISKTSTTVDLNVISPTTEDTATYFCARGSPDVDIGIDMWGPGTLVTVSS
(SEQ ID NO: 123)

Variable_region_heavy_chain protein sequence. CDR1:Bold; CDR2: Underline; CDR3:Italics.
QSVEASGGRLVTPGTPLTLTCTASGFSLSTYWMSWVRQAPGKGLEWIG<u>DIYFSNEETNYA
SWAKG</u>RFTISKTSTTVDLNVISPTTEDTATYFCAR*GSPDVDIGIDM*WGPGTLVTVSS
(SEQ ID NOS: 128, 129, 130, respectively)

Variable_region_heavy_chain DNA sequence. CDR1:Bold; CDR2: Underline; CDR3:Italics.
CAGTCGGTGGAGGCGTCCGGGGGTCGCCTGGTCACGCCTGGGACACCCCTGACACTCACC
TGCACAGCCTCTGGATTCTCCCTCAGTACCTACTGGATGAGCTGGGTCCGCCAGGCTCCA
GGGAAGGGGCTGGAATGGATCGGA<u>GACATTTATTTAGTAATGAAGAAACAAACTACGCG
AGCTGGGCGAAAGGC</u>CGATTTACCATCTCCAAAACCTCGACCACGGTGGATCTGAATGTC
ATCAGTCCGACAACCGAGGACACGGCCACCTATTTCTGTGCCAGA*GGTTCTCCTGATGTT
GATATTGGTATAGATATGTGGGGCCCGGGCACCCTCGTCACCGTCTCGAGC* (SEQ ID
NO: 323)

Heavy_chain Full length DNA sequence.
CAGTCGGTGGAGGCGTCCGGGGGTCGCCTGGTCACGCCTGGGACACCCCTGACACTCACC
TGCACAGCCTCTGGATTCTCCCTCAGTACCTACTGGATGAGCTGGGTCCGCCAGGCTCCA
GGGAAGGGGCTGGAATGGATCGGAGACATTTATTTAGTAATGAAGAAACAAACTACGCG
AGCTGGGCGAAAGGCCGATTTACCATCTCCAAAACCTCGACCACGGTGGATCTGAATGTC
ATCAGTCCGACAACCGAGGACACGGCCACCTATTTCTGTGCCAGAGGTTCTCCTGATGTT
GATATTGGTATAGATATGTGGGGCCCGGGCACCCTCGTCACCGTCTCGAGCGCCTCCACC
AAGGGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTAC
TCCCTCAGCAGCGTGGTGACCGTGCCCTCCAGCAGCTTGGGCACCCAGACCTACATCTGC
AACGTGAATCACAAGCCCAGCAACACCAAGGTGGACAAGAGAGTTGAGCCCAAATCTTGT
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC

FIG. 13B

```
GGCGTGGAGGTGCATAATGCCAAGACAAAGCCGCGGGAGGAGCAGTACGCCAGCACGTAC
CGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAGAGC
CTCTCCCTGTCTCCGGGTAAATGA (SEQ ID NO: 324)
```

Light_chain Full length protein sequence.

```
AAVLTQTPSPVSAAVGGTVSISCQSSQNVYKNNYLSWYQQKPGQPPKLLIYKASTLASGV
PSRFKGGGSGTDFTLTISDVQCDAAATYYCAGGYTSSSDNAFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 122)
```

Variable_region_light_chain protein sequence.

```
AAVLTQTPSPVSAAVGGTVSISCQSSQNVYKNNYLSWYQQKPGQPPKLLIYKASTLASGV
PSRFKGGGSGTDFTLTISDVQCDAAATYYCAGGYTSSSDNAFGGGTEVVVKR (SEQ ID
NO: 121)
```

Variable_region_light_chain protein sequence. CDR1:Bold; CDR2: Underline; CDR3:Italics.

```
AAVLTQTPSPVSAAVGGTVSISCQSSQNVYKNNYLSWYQQKPGQPPKLLIY<u>KASTLASGV</u>
PSRFKGGGSGTDFTLTISDVQCDAAATYYC*AGGYTSSSDNA*FGGGTEVVVKR (SEQ ID
NOS: 125, 126, 127, respectively)
```

Variable_region_light_chain DNA sequence. CDR1:Bold; CDR2: Underline; CDR3:Italics.

```
GCCGCCGTGCTGACCCAGACTCCATCTCCCGTGTCTGCAGCTGTGGGAGGCACAGTCAGC
ATCAGTTGCCAGTCCAGTCAGAATGTTTATAAGAACAACTACTTATCCTGGTATCAGCAG
AAACCAGGGCAGCCTCCCAAGCTCCTGATCTAC<u>AAGGCATCCACTCTGGCATCTGGGGTC</u>
CCATCGCGGTTCAAAGGCGGTGGATCTGGGACAGATTTCACTCTCACCATCAGCGACGTG
CAGTGTGACGCTGCTGCCACTTACTACTGT*CAGGCGGTTATACCAGTAGTAGTGATAAT
GCTTTC*GGCGGAGGGACCGAGGTGGTGGTCAAACGT (SEQ ID NO: 321)
```

Light_chain Full length DNA sequence.

```
GCCGCCGTGCTGACCCAGACTCCATCTCCCGTGTCTGCAGCTGTGGGAGGCACAGTCAGC
ATCAGTTGCCAGTCCAGTCAGAATGTTTATAAGAACAACTACTTATCCTGGTATCAGCAG
AAACCAGGGCAGCCTCCCAAGCTCCTGATCTACAAGGCATCCACTCTGGCATCTGGGGTC
CCATCGCGGTTCAAAGGCGGTGGATCTGGGACAGATTTCACTCTCACCATCAGCGACGTG
CAGTGTGACGCTGCTGCCACTTACTACTGTCAGGCGGTTATACCAGTAGTAGTGATAAT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 322)
```

Heavy_chain Full length protein sequence.

EVQLVESGGGLVQPGGSLRLSCAASGFTVSTYWMSWVRQAPGKGLEWVGDIYFSNEETNY
ASSAKGRFTISRDNSKNTLYLQMNSLRAEDTAVYYCARGSPDVDIGIDMWGPGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 134)

Variable_region_heavy_chain protein sequence.

EVQLVESGGGLVQPGGSLRLSCAASGFTVSTYWMSWVRQAPGKGLEWVGDIYFSNEETNY
ASSAKGRFTISRDNSKNTLYLQMNSLRAEDTAVYYCARGSPDVDIGIDMWGPGTLVTVSS
(SEQ ID NO: 133)

Variable_region_heavy_chain protein sequence. CDR1:Bold; CDR2: Underline; CDR3:Italics.

EVQLVESGGGLVQPGGSLRLSCAASGFTVSTYWMSWVRQAPGKGLEWVGD<u>IYFSNEETNY
ASSAKG</u>RFTISRDNSKNTLYLQMNSLRAEDTAVYYCAR*GSPDVDIGIDM*WGPGTLVTVSS
(SEQ ID NOS: 138, 139, 140, respectively)

Variable_region_heavy_chain DNA sequence. CDR1:Bold; CDR2: Underline; CDR3:Italics.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTACCTACTGGATGAGCTGGGTCCGTCAGGCT
CCAGGGAAGGGGCTGGAGTGGGTCGGA<u>GACATTTACTTTAGTAATGAAGAAACAAACTAC
GCGAGCAGCGCGAAAGGC</u>CGATTCACCATCTCCAGAGACAATTCCAAGAACACCCTGTAT
CTTCAAATGAACAGCCTGAGAGCTGAGGACACTGCTGTGTATTACTGTGCTAGA*GGTTCT
CCTGATGTTGATATTGGTATAGATATGTGGGGCC*CAGGGACCCTCGTCACCGTCTCGAGC
(SEQ ID NO: 333)

Heavy_chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTACCTACTGGATGAGCTGGGTCCGTCAGGCT
CCAGGGAAGGGGCTGGAGTGGGTCGGAGACATTTACTTTAGTAATGAAGAAACAAACTAC
GCGAGCAGCGCGAAAGGCCGATTCACCATCTCCAGAGACAATTCCAAGAACACCCTGTAT
CTTCAAATGAACAGCCTGAGAGCTGAGGACACTGCTGTGTATTACTGTGCTAGAGGTTCT
CCTGATGTTGATATTGGTATAGATATGTGGGGCCCAGGGACCCTCGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 14B

```
TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 334)
```

Light_chain Full length protein sequence.

```
DIQMTQSPSSLSASVGDRVTITCQSSQNVYKNNYLSWYQQKPGKVPKLLIYKASTLASGV
PSRFSGSGSGTDFTLTISSLQPEDVATYYCAGGYTSSSDNAFGGGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 132)
```

Variable_region_Light_chain protein sequence.

```
DIQMTQSPSSLSASVGDRVTITCQSSQNVYKNNYLSWYQQKPGKVPKLLIYKASTLASGV
PSRFSGSGSGTDFTLTISSLQPEDVATYYCAGGYTSSSDNAFGGGTKVEIKR (SEQ ID
NO: 131)
```

Variable_region_Light_chain protein sequence. CDR1:Bold; CDR2: Underline; CDR3:Italics.

```
DIQMTQSPSSLSASVGDRVTITCQSSQNVYKNNYLSWYQQKPGKVPKLLIY<u>KASTLASGV</u>
PSRFSGSGSGTDFTLTISSLQPEDVATYYC*AGGYTSSSDN*AFGGGTKVEIKR (SEQ ID
NOS: 135, 136, 137, respectively)
```

Variable_region_Light_chain DNA sequence. CDR1:Bold; CDR2: Underline; CDR3:Italics.

```
GACATCCAGATGACCCAGTCTCCATCCTCCCTGTCTGCATCTGTAGGAGACAGAGTCACC
ATCACTTGCCAGTCCAGTCAGAATGTTTATAAGAACAACTACTTATCCTGGTATCAGCAG
AAACCAGGGAAAGTCCCTAAGCTCCTGATCTAT<u>AAGGCATCCACTCTGGCATCTGGGGTC</u>
CCATCTCGTTTCAGTGGCAGTGGATCTGGGACAGATTTCACTCTCACCATCAGCAGCCTG
CAGCCTGAAGATGTTGCAACTTATTACTGT*GCAGGCGGTTATACCAGTAGTAGTGATAAT*
*GCTTTC*GGCGGAGGAACCAAGGTGGAAATCAAACGT (SEQ ID NO: 331)
```

Light_chain Full length DNA sequence.

```
GACATCCAGATGACCCAGTCTCCATCCTCCCTGTCTGCATCTGTAGGAGACAGAGTCACC
ATCACTTGCCAGTCCAGTCAGAATGTTTATAAGAACAACTACTTATCCTGGTATCAGCAG
AAACCAGGGAAAGTCCCTAAGCTCCTGATCTATAAGGCATCCACTCTGGCATCTGGGGTC
CCATCTCGTTTCAGTGGCAGTGGATCTGGGACAGATTTCACTCTCACCATCAGCAGCCTG
CAGCCTGAAGATGTTGCAACTTATTACTGTGCAGGCGGTTATACCAGTAGTAGTGATAAT
GCTTTCGGCGGAGGAACCAAGGTGGAAATCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 332)
```

Heavy_chain Full length protein sequence.

QSVEESGGRLVTPGTPLTLTCTVSGIDLSSYAMIWVRQAPGKGLEYIGIIWSGGTYYATW
AKGRFTISKTSTTVDLQITSPTTEDAATYFCAAGGGSIYDVWGPGTLVTVSSASTKGPSV
FPLAPSSKSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREEQYASTYRVVSV
LTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSC
SVMHEALHNHYTQKSLSLSPGK (SEQ ID NO: 144)

Variable_region_heavy_chain protein sequence.

QSVEESGGRLVTPGTPLTLTCTVSGIDLSSYAMIWVRQAPGKGLEYIGIIWSGGTYYATW
AKGRFTISKTSTTVDLQITSPTTEDAATYFCAAGGGSIYDVWGPGTLVTVSS (SEQ ID
NO: 143)

Variable_region_heavy_chain protein sequence. CDR1:Bold; CDR2: Underline; CDR3:Italics.

QSVEESGGRLVTPGTPLTLTCTVSGIDLSSSYAMIWVRQAPGKGLEYIGI<u>IWSGGTYYATW
AKGRFTIS</u>KTSTTVDLQITSPTTEDAATYFCAA*GGGSIYDV*WGPGTLVTVSS (SEQ ID
NOS: 148, 149, 150, respectively)

Variable_region_heavy_chain DNA sequence. CDR1:Bold; CDR2: Underline; CDR3:Italics.

CAGTCGGTGGAGGAGTCCGGGGGTCGCCTGGTCACGCCTGGGACACCCCTGACACTCACC
TGCACAGTCTCTGGAATCGACCTCAGTAGCTATGCAATGATCTGGGTCCGCCAGGCTCCA
GGGAAGGGGCTGGAATACATCGGA<u>ATCATTTGGAGTGGTGGCACCTACTACGCGACCTGG
GCGAAAGGC</u>CGATTCACCATCTCCAAAACCTCGACCACGGTGGATCTGCAAATCACCAGT
CCGACAACCGAGGACGCGGCCACCTATTTCTGTGCCGCAG*GTGGTGGTAGTATTTATGAT
GTT*TGGGGCCCGGGCACCCTGGTCACCGTCTCGAGC (SEQ ID NO: 343)

Heavy_chain Full length DNA sequence.

CAGTCGGTGGAGGAGTCCGGGGGTCGCCTGGTCACGCCTGGGACACCCCTGACACTCACC
TGCACAGTCTCTGGAATCGACCTCAGTAGCTATGCAATGATCTGGGTCCGCCAGGCTCCA
GGGAAGGGGCTGGAATACATCGGAATCATTTGGAGTGGTGGCACCTACTACGCGACCTGG
GCGAAAGGCCGATTCACCATCTCCAAAACCTCGACCACGGTGGATCTGCAAATCACCAGT
CCGACAACCGAGGACGCGGCCACCTATTTCTGTGCCGCAGGTGGTGGTAGTATTTATGAT
GTTTGGGGCCCGGGCACCCTGGTCACCGTCTCGAGCGCCTCCACCAAGGGCCCATCGGTC
TTCCCCCTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTGACCAGC
GGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAG
CCCAGCAACACCAAGGTGGACAAGAGAGTTGAGCCCAAATCTTGTGACAAAACTCACACA
TGCCCACCGTGCCCAGCACCTGAACTCCTGGGGGGACCGTCAGTCTTCCTCTTCCCCCCA
AAACCCAAGGACACCCTCATGATCTCCCGGACCCCTGAGGTCACATGCGTGGTGGTGGAC
GTGAGCCACGAAGACCCTGAGGTCAAGTTCAACTGGTACGTGGACGGCGTGGAGGTGCAT
AATGCCAAGACAAAGCCGCGGGAGGAGCAGTACGCCAGCACGTACCGTGTGGTCAGCGTC

FIG. 15B

CTCACCGTCCTGCACCAGGACTGGCTGAATGGCAAGGAGTACAAGTGCAAGGTCTCCAAC
AAAGCCCTCCCAGCCCCCATCGAGAAACCATCTCCAAAGCCAAAGGGCAGCCCCGAGAA
CCACAGGTGTACACCCTGCCCCCATCCCGGGAGGAGATGACCAAGAACCAGGTCAGCCTG
ACCTGCCTGGTCAAAGGCTTCTATCCCAGCGACATCGCCGTGGAGTGGGAGAGCAATGGG
CAGCCGGAGAACAACTACAAGACCACGCCTCCCGTGCTGGACTCCGACGGCTCCTTCTTC
CTCTACAGCAAGCTCACCGTGGACAAGAGCAGGTGGCAGCAGGGGAACGTCTTCTCATGC
TCCGTGATGCATGAGGCTCTGCACAACCACTACACGCAGAAGAGCCTCTCCCTGTCTCCG
GGTAAATGA (SEQ ID NO: 344)

Light chain Full length protein sequence.

AAVLTQTPSPVSAAVGDTVTIKCQSSQSVYKNNYLSWYQQKPGQPPKLLIYDASNLPSGV
PSRFSGSGSGTQFTLTISGVQCDDAATYYCLGDYDDDTDNGFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 142)

Variable region light chain protein sequence.

AAVLTQTPSPVSAAVGDTVTIKCQSSQSVYKNNYLSWYQQKPGQPPKLLIYDASNLPSGV
PSRFSGSGSGTQFTLTISGVQCDDAATYYCLGDYDDDTDNGFGGGTEVVVKR (SEQ ID NO: 141)

Variable region light chain protein sequence. CDR1:Bold; CDR2: Underline; CDR3:Italics.

AAVLTQTPSPVSAAVGDTVTIKCQSSQSVYKNNYLSWYQQKPGQPPKLLIY<u>DASNLPSGV</u>
PSRFSGSGSGTQFTLTISGVQCDDAATYYC*LGDYDDDTDNGFGGGTEVVVKR* (SEQ ID NOS: 145, 146, 147, respectively)

Variable region light chain DNA sequence. CDR1:Bold; CDR2: Underline; CDR3:Italics.

GCAGCCGTGCTGACCCAGACACCATCGCCCGTGTCTGCAGCTGTGGGAGACACAGTCACC
ATCAAGTGCAGTCCAGTCAGAGTGTTTATAAGAACAACTACTTATCCTGGTATCAGCAG
AAACCAGGGCAGCCTCCCAAGCTCCTGATCTAT<u>GATGCATCCAATCTGCCATCTGGGGTC</u>
CCATCACGGTTCAGCGGCAGTGGATCTGGGACACAGTTCACTCTCACCATCAGCGGCGTG
CAGTGTGACGATGCTGCCACTTACTACTGT*CTAGGCGATTATGATGATGATACTGATAAT*
*GGTTTCGGCGGAGGGACCGAGGTGGTGGTCAAACGT* (SEQ ID NO: 341)

Light chain Full length DNA sequence.

GCAGCCGTGCTGACCCAGACACCATCGCCCGTGTCTGCAGCTGTGGGAGACACAGTCACC
ATCAAGTGCCAGTCCAGTCAGAGTGTTTATAAGAACAACTACTTATCCTGGTATCAGCAG
AAACCAGGGCAGCCTCCCAAGCTCCTGATCTATGATGCATCCAATCTGCCATCTGGGGTC
CCATCACGGTTCAGCGGCAGTGGATCTGGGACACAGTTCACTCTCACCATCAGCGGCGTG
CAGTGTGACGATGCTGCCACTTACTACTGTCTAGGCGATTATGATGATGATACTGATAAT
GGTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 342)

Heavy_chain Full length protein sequence.

QSVEEFGGRLVTPGTPLTLTCTVSGFSLNNYAMTWVRQAPGKGLEWIGIIGSIGTTYYAS
WAKGRFFISKTSTTVDLKIISPTTEDTATYFCARDAGVTVDGYGYYFNIWGPGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 154)

Variable_region_heavy_chain protein sequence.

QSVEEFGGRLVTPGTPLTLTCTVSGFSLNNYAMTWVRQAPGKGLEWIGIIGSIGTTYYAS
WAKGRFFISKTSTTVDLKIISPTTEDTATYFCARDAGVTVDGYGYYFNIWGPGTLVTVSS
(SEQ ID NO: 153)

Variable_region_heavy_chain protein sequence. CDR1:Bold;
CDR2: Underline; CDR3:Italics.

QSVEEFGGRLVTPGTPLTLTCTVSGFSLNNYAMTWVRQAPGKGLEWIGI<u>IGSIGTTYYAS
WAK</u>GRFFISKTSTTVDLKIISPTTEDTATYFCAR*DAGVTVDGYGYYFNI*WGPGTLVTVSS
(SEQ ID NOS: 158, 159, 160, respectively)

Variable_region_heavy_chain DNA sequence. CDR1:Bold; CDR2:
Underline; CDR3:Italics.

CAGTCGGTGGAGGAGTTCGGGGGTCGCCTGGTCACGCCTGGGACACCCCTGACACTCACC
TGCACCGTCTCTGGATTCTCCCTCAATAACTATGCAATGACCTGGGTCCGCCAGGCTCCA
GGGAAGGGGCTGGAGTGGATCGGG<u>ATCATTGGTAGTATTGGTACCACATACTACGCGAGC
TGGGCGAAAGGC</u>CGATTCTTCATCTCCAAAACCTCGACCACTGTGGATCTGAAAATCATT
AGTCCGACAACCGAGGACACGGCCACCTATTTCTGTGCCAGA*GATGCTGGCGTTACTGTT
GATGGTTATGGCTACTACTTTAACATC*TGGGGCCCAGGCACCCTCGTCACCGTCTCGAGC
(SEQ ID NO: 353)

Heavy_chain Full length DNA sequence.

CAGTCGGTGGAGGAGTTCGGGGGTCGCCTGGTCACGCCTGGGACACCCCTGACACTCACC
TGCACCGTCTCTGGATTCTCCCTCAATAACTATGCAATGACCTGGGTCCGCCAGGCTCCA
GGGAAGGGGCTGGAGTGGATCGGGATCATTGGTAGTATTGGTACCACATACTACGCGAGC
TGGGCGAAAGGCCGATTCTTCATCTCCAAAACCTCGACCACTGTGGATCTGAAAATCATT
AGTCCGACAACCGAGGACACGGCCACCTATTTCTGTGCCAGAGATGCTGGCGTTACTGTT
GATGGTTATGGCTACTACTTTAACATCTGGGGCCCAGGCACCCTCGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 16B

TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 354)

Light chain Full length protein sequence.

ALVMTQTPSSTSEPVGGTVTINCQASQNIGNDLSWYQQKPGQPPELLIYSTSKLATGVPK
RFSGSRSGTQFTLTISDLECDDAATYYCLGVYSYISDDGNAFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 152)

Variable region light chain protein sequence.

ALVMTQTPSSTSEPVGGTVTINCQASQNIGNDLSWYQQKPGQPPELLIYSTSKLATGVPK
RFSGSRSGTQFTLTISDLECDDAATYYCLGVYSYISDDGNAFGGGTEVVVKR (SEQ ID
NO: 151)

Variable region light chain protein sequence. CDR1:Bold; CDR2: Underline; CDR3:Italics.

ALVMTQTPSSTSEPVGGTVTINCQASQNIGNDLSWYQQKPGQPPELLIY<u>STSKLATGVPK</u>
RFSGSRSGTQFTLTISDLECDDAATYYC*LGVYSYISDDGN*AFGGGTEVVVKR (SEQ ID
NOS: 155, 156, 157, respectively)

Variable region light chain DNA sequence. CDR1:Bold; CDR2: Underline; CDR3:Italics.

GCCCTGGTGATGACCCAGACTCCATCCTCCACGTCTGAACCAGTGGGAGGCACAGTCACC
ATCAATTGCCAGGCTAGTCAGAATATTGGTAACGACCTATCCTGGTATCAGCAGAAACCA
GGGCAGCCTCCCGAGCTCCTAATCTAT<u>TCTACATCCAAACTGGCAACTGGGGTCCCAAAG</u>
CGGTTCAGTGGCAGCAGATCTGGGACACAGTTCACTCTCACCATCAGCGACCTGGAGTGT
GACGATGCTGCCACTTACTACTGT*CTAGGTGTTTATAGTTATATTAGTGATGATGGTAAT*
GCTTTCGGCGGAGGGACCGAGGTGGTGGTCAAACGT (SEQ ID NO: 351)

Light chain Full length DNA sequence.

GCCCTGGTGATGACCCAGACTCCATCCTCCACGTCTGAACCAGTGGGAGGCACAGTCACC
ATCAATTGCCAGGCTAGTCAGAATATTGGTAACGACCTATCCTGGTATCAGCAGAAACCA
GGGCAGCCTCCCGAGCTCCTAATCTATTCTACATCCAAACTGGCAACTGGGGTCCCAAAG
CGGTTCAGTGGCAGCAGATCTGGGACACAGTTCACTCTCACCATCAGCGACCTGGAGTGT
GACGATGCTGCCACTTACTACTGTCTAGGTGTTTATAGTTATATTAGTGATGATGGTAAT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 352)

Heavy_chain Full length protein sequence.

QSLEESGGRLVTPGGSLTLTCAASGFSLTGYNLVWVRQAPGKGLEWIGFISYGDTTYYAS
WAKGRFTISKTSTTVTLTITDLQPSDTGTYFCARETANTYDYGIWGPGTLVTVSSASTKG
PSVFPLAPSSKSTSGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYASTYRV
VSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO: 164)

Variable_region_heavy_chain protein sequence.

QSLEESGGRLVTPGGSLTLTCAASGFSLTGYNLVWVRQAPGKGLEWIGFISYGDTTYYAS
WAKGRFTISKTSTTVTLTITDLQPSDTGTYFCARETANTYDYGIWGPGTLVTVSS (SEQ
ID NO: 163)

Variable_region_heavy_chain protein sequence. CDR1:Bold; CDR2: Underline; CDR3:Italics.

QSLEESGGRLVTPGGSLTLTCAASGFSLTGYNLVWVRQAPGKGLEWIG<u>FISYGDTTYYAS
WAKG</u>RFTISKTSTTVTLTITDLQPSDTGTYFCAR*ETANTYDYGI*WGPGTLVTVSS (SEQ
ID NOS: 168, 169, 170, respectively)

Variable_region_heavy_chain DNA sequence. CDR1:Bold; CDR2: Underline; CDR3:Italics.

CAGTCGCTGGAGGAGTCCGGGGGTCGCCTGGTCACGCCTGGGGGATCCCTGACACTCACC
TGCGCAGCCTCTGGATTCTCCCTCACTGGCTACAACTTGGTCTGGGTCCGCCAGGCTCCA
GGGAAGGGGCTGGAGTGGATCGGA<u>TTCATTAGTTATGGTGATACCACATACTACGCGAGC
TGGGCGAAAGGC</u>CGATTCACCATCTCCAAAACCTCGACCACGGTGACTCTGACGATCACC
GATCTGCAACCTTCAGACACGGGCACCTATTTCTGTGCCAGAGAG*ACTGCTAATACTTAT
GATTATGGCATC*TGGGGCCCAGGCACCCTCGTCACCGTCTCGAGC (SEQ ID NO:
363)

Heavy_chain Full length DNA sequence.

CAGTCGCTGGAGGAGTCCGGGGGTCGCCTGGTCACGCCTGGGGGATCCCTGACACTCACC
TGCGCAGCCTCTGGATTCTCCCTCACTGGCTACAACTTGGTCTGGGTCCGCCAGGCTCCA
GGGAAGGGGCTGGAGTGGATCGGATTCATTAGTTATGGTGATACCACATACTACGCGAGC
TGGGCGAAAGGCCGATTCACCATCTCCAAAACCTCGACCACGGTGACTCTGACGATCACC
GATCTGCAACCTTCAGACACGGGCACCTATTTCTGTGCCAGAGAGACTGCTAATACTTAT
GATTATGGCATCTGGGGCCCAGGCACCCTCGTCACCGTCTCGAGCGCCTCCACCAAGGGC
CCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAACGTG
AATCACAAGCCCAGCAACACCAAGGTGGACAAGAGAGTTGAGCCCAAATCTTGTGACAAA
ACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTG

FIG. 17B

GAGGTGCATAATGCCAAGACAAAGCCGCGGGAGGAGCAGTACGCCAGCACGTACCGTGTG
GTCAGCGTCCTCACCGTCCTGCACCAGGACTGGCTGAATGGCAAGGAGTACAAGTGCAAG
GTCTCCAACAAAGCCCTCCCAGCCCCCATCGAGAAACCATCTCCAAAGCCAAAGGGCAG
CCCCGAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCC
CTGTCTCCGGGTAAATGA (SEQ ID NO: 364)

<ins>Light_chain Full length protein sequence.</ins>

AIEMTQTPFSVSAAVGGTVTIKCQASQTISNYLAWYQQKPGQPPKLLIYGASNLESGVPS
RFKGSGSGTQFTLTISDLECDDAATYYCQQGYTISNVDNNVFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 162)

<ins>Variable_region_light_chain protein sequence.</ins>

AIEMTQTPFSVSAAVGGTVTIKCQASQTISNYLAWYQQKPGQPPKLLIYGASNLESGVPS
RFKGSGSGTQFTLTISDLECDDAATYYCQQGYTISNVDNNVFGGGTEVVVKR (SEQ ID
NO: 161)

<ins>Variable_region_light_chain protein sequence. CDR1:Bold;
CDR2: Underline; CDR3:Italics.</ins>

AIEMTQTPFSVSAAVGGTVTIKCQASQTISNYLAWYQQKPGQPPKLLIY<ins>GASNLES</ins>GVPS
RFKGSGSGTQFTLTISDLECDDAATYYC*QQGYTISNVDNNV*FGGGTEVVVKR (SEQ ID
NOS: 165, 166, 167, respectively)

<ins>Variable_region_light_chain DNA sequence. CDR1:Bold; CDR2:
Underline; CDR3:Italics.</ins>

GCCATCGAAATGACCCAGACTCCATTCTCCGTGTCTGCAGCTGTGGGAGGCACAGTCACC
ATCAAGTGCCAGGCCAGTCAGACCATTAGCAACTACTTAGCCTGGTATCAGCAGAAACCA
GGGCAGCCTCCCAAGCTCCTGATCTAT<ins>GGTGCATCCAATCTGGAATCT</ins>GGGGTCCCATCG
CGGTTCAAAGGCAGTGGATCTGGGACACAGTTCACTCTCACCATCAGCGACCTGGAGTGT
GACGATGCTGCCACTTACTACTGT*CAACAGGGTTATACTATCAGTAATGTTGATAACAAT
GTTTTC*GGCGGAGGGACCGAGGTGGTGGTCAAACGT (SEQ ID NO: 361)

<ins>Light_chain Full length DNA sequence.</ins>

GCCATCGAAATGACCCAGACTCCATTCTCCGTGTCTGCAGCTGTGGGAGGCACAGTCACC
ATCAAGTGCCAGGCCAGTCAGACCATTAGCAACTACTTAGCCTGGTATCAGCAGAAACCA
GGGCAGCCTCCCAAGCTCCTGATCTATGGTGCATCCAATCTGGAATCTGGGGTCCCATCG
CGGTTCAAAGGCAGTGGATCTGGGACACAGTTCACTCTCACCATCAGCGACCTGGAGTGT
GACGATGCTGCCACTTACTACTGTCAACAGGGTTATACTATCAGTAATGTTGATAACAAT
GTTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 362)

Heavy_chain Full length protein sequence.
EVQLVESGGGLVQPGGSLRLSCAASGFTVSGYNLVWVRQAPGKGLEWVGFISYGDTTYYA
SSAKGRFTISRDNSKNTLYLQMNSLRAEDTAVYYCARETANTYDYGIWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 174)

Variable_region_heavy_chain protein sequence.
EVQLVESGGGLVQPGGSLRLSCAASGFTVSGYNLVWVRQAPGKGLEWVGFISYGDTTYYA
SSAKGRFTISRDNSKNTLYLQMNSLRAEDTAVYYCARETANTYDYGIWGQGTLVTVSS
(SEQ ID NO: 173)

Variable_region_heavy_chain protein sequence. CDR1:Bold; CDR2: Underline; CDR3:Italics.
EVQLVESGGGLVQPGGSLRLSCAASGFTVSGYNLVWVRQAPGKGLEWVGF<u>ISYGDTTYYA
SSAKG</u>RFTISRDNSKNTLYLQMNSLRAEDTAVYYCAR*ETANTYDYGI*WGQGTLVTVSS
(SEQ ID NOS: 178, 179, 180, respectively)

Variable_region_heavy_chain DNA sequence. CDR1:Bold; CDR2: Underline; CDR3:Italics.
GAGGTGCAGCTGGTGGAGTCTGGGGGAGGCTTGGTCCAGCCTGGGGGGTCCCTGAGACTC
TCCTGTGCAGCCTCTGGATTCACCGTCAGTGGCTACAACTTGGTCTGGGTCCGTCAGGCT
CCAGGGAAGGGGCTGGAGTGGGTCGGA<u>TTCATTAGTTATGGTGATACCACATACTACGCT
AGCTCTGCTAAAGGC</u>CGATTCACCATCTCCAGAGACAATTCCAAGAACACCCTGTATCTT
CAAATGAACAGCCTGAGAGCTGAGGACACTGCTGTGTATTACTGTGCTAGA*GAGACTGCT
AATACTTATGATTATGGCATC*TGGGGCCAAGGGACCCTCGTCACCGTCTCGAGC (SEQ
ID NO: 373)

Heavy_chain Full length DNA sequence.
GAGGTGCAGCTGGTGGAGTCTGGGGGAGGCTTGGTCCAGCCTGGGGGGTCCCTGAGACTC
TCCTGTGCAGCCTCTGGATTCACCGTCAGTGGCTACAACTTGGTCTGGGTCCGTCAGGCT
CCAGGGAAGGGGCTGGAGTGGGTCGGATTCATTAGTTATGGTGATACCACATACTACGCT
AGCTCTGCTAAAGGCCGATTCACCATCTCCAGAGACAATTCCAAGAACACCCTGTATCTT
CAAATGAACAGCCTGAGAGCTGAGGACACTGCTGTGTATTACTGTGCTAGAGAGACTGCT
AATACTTATGATTATGGCATCTGGGGCCAAGGGACCCTCGTCACCGTCTCGAGCGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG

FIG. 18B

GACGGCGTGGAGGTGCATAATGCCAAGACAAAGCCGCGGGAGGAGCAGTACGCCAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATGA (SEQ ID NO: 374)

Light chain Full length protein sequence.

DIQMTQSPSTLSASVGDRVTITCQASQTISNYLAWYQQKPGKAPKLLIYGASNLESGVPS
RFSGSGSGTEFTLTISSLQPDDFATYYCQQGYTISNVDNNVFGGGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 172)

Variable region Light chain protein sequence.

DIQMTQSPSTLSASVGDRVTITCQASQTISNYLAWYQQKPGKAPKLLIYGASNLESGVPS
RFSGSGSGTEFTLTISSLQPDDFATYYCQQGYTISNVDNNVFGGGTKVEIKR (SEQ ID
NO: 171)

Variable region Light chain protein sequence. CDR1:Bold; CDR2: Underline; CDR3:Italics.

DIQMTQSPSTLSASVGDRVTITCQASQTISNYLAWYQQKPGKAPKLLIY<u>GASNLESGVPS</u>
RFSGSGSGTEFTLTISSLQPDDFATYYC*QQGYTISNVDNNV*FGGGTKVEIKR (SEQ ID
NOS: 175, 176, 177, respectively)

Variable region Light chain DNA sequence. CDR1:Bold; CDR2: Underline; CDR3:Italics.

GACATCCAGATGACCCAGTCTCCTTCCACCCTGTCTGCATCTGTAGGAGACAGAGTCACC
ATCACTTGTCAGGCTAGTCAGACCATTAGCAACTACTTAGCCTGGTATCAGCAGAAACCA
GGAAAAGCCCCTAAGCTCCTGATCTAT<u>GGTGCATCCAATCTGGAATCTGGAGTCCCATCA</u>
AGGTTCAGCGGCAGTGGATCTGGAACAGAATTCACTCTCACCATCAGCAGCCTGCAGCCT
GATGATTTTGCAACTTACTACTGT*CAACAGGGTTATACTATCAGTAATGTTGATAACAAT
GTTTTC*GGCGGAGGAACCAAGGTGGAAATCAAACGT (SEQ ID NO: 371)

Light chain Full length DNA sequence.

GACATCCAGATGACCCAGTCTCCTTCCACCCTGTCTGCATCTGTAGGAGACAGAGTCACC
ATCACTTGTCAGGCTAGTCAGACCATTAGCAACTACTTAGCCTGGTATCAGCAGAAACCA
GGAAAAGCCCCTAAGCTCCTGATCTATGGTGCATCCAATCTGGAATCTGGAGTCCCATCA
AGGTTCAGCGGCAGTGGATCTGGAACAGAATTCACTCTCACCATCAGCAGCCTGCAGCCT
GATGATTTTGCAACTTACTACTGTCAACAGGGTTATACTATCAGTAATGTTGATAACAAT
GTTTTCGGCGGAGGAACCAAGGTGGAAATCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 372)

Heavy_chain Full length protein sequence.

QSVEASGGRLVMPGGSLTLTCTASGFSLSTYWMSWVRQAPGKGLEWIGDIYFSNEETNYA
TWAKGRFTISKTSTTVDLNVISPTTEDTATYFCARGSPDVEIAIDMWGQGTLVTVSSAST
KGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYASTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 184)

Variable_region_heavy_chain protein sequence.

QSVEASGGRLVMPGGSLTLTCTASGFSLSTYWMSWVRQAPGKGLEWIGDIYFSNEETNYA
TWAKGRFTISKTSTTVDLNVISPTTEDTATYFCARGSPDVEIAIDMWGQGTLVTVSS
(SEQ ID NO: 183)

Variable_region_heavy_chain protein sequence. CDR1:Bold; CDR2: Underline; CDR3:Italics.

QSVEASGGRLVMPGGSLTLTCTASGFSLSTYWMSWVRQAPGKGLEWIG<u>DIYFSNEETNYA
TWAKG</u>RFTISKTSTTVDLNVISPTTEDTATYFCAR*GSPDVEIAIDM*WGQGTLVTVSS
(SEQ ID NOS: 188, 189, 190, respectively)

Variable_region_heavy_chain DNA sequence. CDR1:Bold; CDR2: Underline; CDR3:Italics.

CAGTCGGTGGAGGCGTCCGGGGGTCGTCTGGTCATGCCTGGAGGATCCCTGACACTCACC
TGCACAGCCTCTGGATTCTCCCTCAGTACCTACTGGATGTCCTGGGTCCGCCAGGCTCCA
GGGAAGGGGCTGGAATGGATCGGA<u>GACATTTATTTTAGTAATGAGGAAACAAACTACGCG
ACCTGGGCGAAAGGC</u>CGATTTACCATCTCCAAAACCTCGACCACGGTGGATCTGAATGTC
ATCAGTCCGACAACCGAGGACACGGCCACCTATTTCTGTGCAAGA*GGTTCTCCTGATGTT
GAGATTGCTATAGATATGTGG*GGCCAGGGCACCCTCGTCACCGTCTCGAGC (SEQ ID
NO: 383)

Heavy_chain Full length DNA sequence.

CAGTCGGTGGAGGCGTCCGGGGGTCGTCTGGTCATGCCTGGAGGATCCCTGACACTCACC
TGCACAGCCTCTGGATTCTCCCTCAGTACCTACTGGATGTCCTGGGTCCGCCAGGCTCCA
GGGAAGGGGCTGGAATGGATCGGAGACATTTATTTTAGTAATGAGGAAACAAACTACGCG
ACCTGGGCGAAAGGCCGATTTACCATCTCCAAAACCTCGACCACGGTGGATCTGAATGTC
ATCAGTCCGACAACCGAGGACACGGCCACCTATTTCTGTGCAAGAGGTTCTCCTGATGTT
GAGATTGCTATAGATATGTGGGGCCAGGGCACCCTCGTCACCGTCTCGAGCGCCTCCACC
AAGGGCCCATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTAC
TCCCTCAGCAGCGTGGTGACCGTGCCCTCCAGCAGCTTGGGCACCCAGACCTACATCTGC
AACGTGAATCACAAGCCCAGCAACACCAAGGTGGACAAGAGAGTTGAGCCCAAATCTTGT
GACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGAC

FIG. 19B

GGCGTGGAGGTGCATAATGCCAAGACAAAGCCGCGGGAGGAGCAGTACGCCAGCACGTAC
CGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAGATGACCAAG
AACCAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCAGAAGAGC
CTCTCCCTGTCTCCGGGTAAATGA (SEQ ID NO: 384)

Light_chain Full length protein sequence.

AAVLTQTPSPVSAAVGGTVSISCQSSQNVYKNNYLSWYQQKPGQPPKLLIYKASTLASGV
PSRFKGSGSGTDFTLTISDVQCDAAATYYCAGGYSSSSDNAFGGGTEVVVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 182)

Variable_region light_chain protein sequence.

AAVLTQTPSPVSAAVGGTVSISCQSSQNVYKNNYLSWYQQKPGQPPKLLIYKASTLASGV
PSRFKGSGSGTDFTLTISDVQCDAAATYYCAGGYSSSSDNAFGGGTEVVVKR (SEQ ID
NO: 181)

Variable_region_light_chain protein sequence. CDR1:Bold; CDR2: Underline; CDR3:Italics.

AAVLTQTPSPVSAAVGGTVSISCQSSQNVYKNNYLSWYQQKPGQPPKLLIY<u>KASTLAS</u>GV
PSRFKGSGSGTDFTLTISDVQCDAAATYYC*AGGYSSSSDNA*FGGGTEVVVKR (SEQ ID
NOS: 185, 186, 187, respectively)

Variable_region_light_chain DNA sequence. CDR1:Bold; CDR2: Underline; CDR3:Italics.

GCCGCCGTGCTGACCCAGACTCCATCTCCCGTGTCTGCAGCTGTGGGAGGCACAGTCAGC
ATCAGTTGCAGTCCAGTCAGAATGTTTATAAGAACAACTATTTATCCTGGTATCAGCAG
AAACCAGGGCAGCCTCCCAAGCTCCTGATCTAC<u>AAGGCTTCCACTCTGGCATCT</u>GGGGTC
CCATCGCGGTTCAAAGGCAGTGGATCTGGGACAGATTTCACTCTCACCATCAGCGACGTG
CAGTGTGACGCTGCTGCCACTTACTACTGT*GCAGGCGGTTATAGTAGTAGTAGTGATAAT
GCT*TTCGGCGGAGGGACCGAGGTGGTGGTCAAACGT (SEQ ID NO: 381)

Light_chain Full length DNA sequence.

GCCGCCGTGCTGACCCAGACTCCATCTCCCGTGTCTGCAGCTGTGGGAGGCACAGTCAGC
ATCAGTTGCAGTCCAGTCAGAATGTTTATAAGAACAACTATTTATCCTGGTATCAGCAG
AAACCAGGGCAGCCTCCCAAGCTCCTGATCTACAAGGCTTCCACTCTGGCATCTGGGGTC
CCATCGCGGTTCAAAGGCAGTGGATCTGGGACAGATTTCACTCTCACCATCAGCGACGTG
CAGTGTGACGCTGCTGCCACTTACTACTGTGCAGGCGGTTATAGTAGTAGTAGTGATAAT
GCTTTCGGCGGAGGGACCGAGGTGGTGGTCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 382)

Heavy_chain Full length protein sequence.

EVQLVESGGGLVQPGGSLRLSCAASGFTVSTYWMSWVRQAPGKGLEWVGDIYFSNEETNY
ATSAKGRFTISRDNSKNTLYLQMNSLRAEDTAVYYCARGSPDVEIAIDMWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 194)

Variable_region_heavy_chain protein sequence.

EVQLVESGGGLVQPGGSLRLSCAASGFTVSTYWMSWVRQAPGKGLEWVGDIYFSNEETNY
ATSAKGRFTISRDNSKNTLYLQMNSLRAEDTAVYYCARGSPDVEIAIDMWGQGTLVTVSS
(SEQ ID NO: 193)

Variable_region_heavy_chain protein sequence. CDR1:Bold; CDR2: Underline; CDR3:Italics.

EVQLVESGGGLVQPGGSLRLSCAASGFTVSTYWMSWVRQAPGKGLEWVG<u>DIYFSNEETNY
ATSAKGRFTISRDNSKNTLYLQMNSLRAEDTAVYYCAR</u>*GSPDVEIAIDM*WGQGTLVTVSS
(SEQ ID NOS: 198, 199, 200, respectively)

Variable_region_heavy_chain DNA sequence. CDR1:Bold; CDR2: Underline; CDR3:Italics.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTACCTACTGGATGAGCTGGGTCCGTCAGGCT
CCAGGGAAGGGGCTGGAGTGGGTCGGA<u>GACATTTACTTTAGTAATGAAGAAACAAACTAC
GCGACCAGCGCGAAAGGC</u>CGATTCACCATCTCCAGAGACAATTCCAAGAACACCCTGTAT
CTTCAAATGAACAGCCTGAGAGCTGAGGACACTGCTGTGTATTACTGTGCTAGA*GGTTCT
CCTGATGTTGAGATTGCTATAGATATGT*GGGGCCAAGGGACCCTCGTCACCGTCTCGAGC
(SEQ ID NO: 393)

Heavy_chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTACCTACTGGATGAGCTGGGTCCGTCAGGCT
CCAGGGAAGGGGCTGGAGTGGGTCGGAGACATTTACTTTAGTAATGAAGAAACAAACTAC
GCGACCAGCGCGAAAGGCCGATTCACCATCTCCAGAGACAATTCCAAGAACACCCTGTAT
CTTCAAATGAACAGCCTGAGAGCTGAGGACACTGCTGTGTATTACTGTGCTAGAGGTTCT
CCTGATGTTGAGATTGCTATAGATATGTGGGGCCAAGGGACCCTCGTCACCGTCTCGAGC
GCCTCCACCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGG

FIG. 20B

```
TACGTGGACGGCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCC
AAAGCCAAAGGGCAGCCCCGAGAACCACAGGTGTACACCCTGCCCCATCCCGGGAGGAG
ATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACACG
CAGAAGAGCCTCTCCCTGTCTCCGGGTAAATGA (SEQ ID NO: 394)
```

Light_chain Full length protein sequence.

```
DIQMTQSPSSLSASVGDRVTITCQSSQNVYKNNYLSWYQQKPGKVPKLLIYKASTLASGV
PSRFSGSGSGTDFTLTISSLQPEDVATYYCAGGYTSSSDNAFGGGTKVEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 192)
```

Variable_region Light chain protein sequence.

```
DIQMTQSPSSLSASVGDRVTITCQSSQNVYKNNYLSWYQQKPGKVPKLLIYKASTLASGV
PSRFSGSGSGTDFTLTISSLQPEDVATYYCAGGYTSSSDNAFGGGTKVEIKR (SEQ ID
NO: 191)
```

Variable_region Light chain protein sequence. CDR1:Bold; CDR2: Underline; CDR3:Italics.

```
DIQMTQSPSSLSASVGDRVTITCQSSQNVYKNNYLSWYQQKPGKVPKLLIYKASTLASGV
PSRFSGSGSGTDFTLTISSLQPEDVATYYCAGGYTSSSDNAFGGGTKVEIKR (SEQ ID
NOS: 195, 196, 197, respectively)
```

Variable_region Light chain DNA sequence. CDR1:Bold; CDR2: Underline; CDR3:Italics.

```
GACATCCAGATGACCCAGTCTCCATCCTCCCTGTCTGCATCTGTAGGAGACAGAGTCACC
ATCACTTGCCAGTCCAGTCAGAATGTTTATAAGAACAACTACTTATCCTGGTATCAGCAG
AAACCAGGGAAAGTCCCTAAGCTCCTGATCTATAAGGCATCCACTCTGGCATCTGGGGTC
CCATCTCGTTTCAGTGGCAGTGGATCTGGGACAGATTTCACTCTCACCATCAGCAGCCTG
CAGCCTGAAGATGTTGCAACTTATTACTGTGCAGGCGGTTATACCAGTAGTAGTGATAAT
GCTTTCGGCGGAGGAACCAAGGTGGAAATCAAACGT (SEQ ID NO: 391)
```

Light_chain Full length DNA sequence.

```
GACATCCAGATGACCCAGTCTCCATCCTCCCTGTCTGCATCTGTAGGAGACAGAGTCACC
ATCACTTGCCAGTCCAGTCAGAATGTTTATAAGAACAACTACTTATCCTGGTATCAGCAG
AAACCAGGGAAAGTCCCTAAGCTCCTGATCTATAAGGCATCCACTCTGGCATCTGGGGTC
CCATCTCGTTTCAGTGGCAGTGGATCTGGGACAGATTTCACTCTCACCATCAGCAGCCTG
CAGCCTGAAGATGTTGCAACTTATTACTGTGCAGGCGGTTATACCAGTAGTAGTGATAAT
GCTTTCGGCGGAGGAACCAAGGTGGAAATCAAACGTACGGTGGCTGCACCATCTGTCTTC
ATCTTCCCGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG
(SEQ ID NO: 392)
```

Heavy_chain Full length protein sequence.

EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDARVEPKSCDKTHTCPPCPAPELLG
GPSVFLFPPKPKDTLMISRTPEVTCVVVDVSHEDPEVKFNWYVDGVEVHNAKTKPREEQY
ASTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 402)

Heavy_chain Full length DNA sequence.

GAGGTGCAGCTGGTGGAGTCTGGGGGAGGCTTGGTCCAGCCTGGGGGGTCCCTGAGACTC
TCCTGTGCAGCCTCTGGATTCACCGTCAGTAACTATGCAGTGGGCTGGGTCCGTCAGGCT
CCAGGGAAGGGGCTGGAGTGGGTCGGAATCATTGGTCGTAATGGTAACACATGGTACGCG
AGCTCTGCAAGAGGCCGATTCACCATCTCCAGAGACAATTCCAAGAACACCCTGTATCTT
CAAATGAACAGCCTGAGAGCTGAGGACACTGCTGTGTATTACTGTGCTAGAGGATATGGC
CGTAGTGTTGCTTACTACGTCTTTAACATCTGGGGCCCAGGGACCCTCGTCACCGTCTCG
AGCGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACGCGAGAGTTGAG
CCCAAATCTTGTGACAAAACTCACACATGCCCACCGTGCCCAGCACCTGAACTCCTGGGG
GGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGAGGAGCAGTAC
GCCAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTAC
ACGCAGAAGAGCCTCTCCCTGTCTCCGGGTAAATGA (SEQ ID NO: 404)

Light_chain Full length protein sequence.

DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 401)

Light_chain Full length DNA sequence.

GACATCCAGATGACCCAGTCTCCTTCCACCCTGTCTGCATCTGTAGGAGACAGAGTCACC
ATCACTTGCCAGGCCAGTCAGAGCATTTACAGCAATCTTGCCTGGTATCAGCAGAAACCA
GGGAAAGCCCCTAAGCTCCTGATCTATGATGCATCCACTCTGGAATCTGGAGTCCCATCA

FIG. 21B

AGGTTCAGCGGCAGTGGATCTGGGACAGAGTACACTCTCACCATCAGCAGCCTGCAGCCT
GATGATTTTGCAACTTACTACTGCCAACAGGGTTTTACTGTTAGTGATATTGATAATGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 403)

Figure 22

Fab1 Sequences

Heavy chain Fab protein sequence.

EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDARVEPKSCDKTH (SEQ ID NO: 406)

Light chain Fab protein sequence.

DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 405)

Figure 23

Fab2 Sequences

<ins>Heavy chain Fab protein sequence.</ins>
EVQLVESGGGLVQPGGSLRLSCAASGFTVSNYAVGWVRQAPGKGLEWVGIIGRNGNTWYA
SSARGRFTISRDNSKNTLYLQMNSLRAEDTAVYYCARGYGRSVAYYVFNIWGPGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDARVEPKSCDKTH (SEQ ID NO:
408)

<ins>Heavy chain Fab DNA sequence.</ins>
GAGGTGCAGCTGGTGGAGTCTGGGGGAGGCTTGGTCCAGCCTGGGGGGTCCCTGAGACTC
TCCTGTGCAGCCTCTGGATTCACCGTCAGTAACTATGCAGTGGGCTGGGTCCGTCAGGCT
CCAGGGAAGGGGCTGGAGTGGGTCGGAATCATTGGTCGTAATGGTAACACATGGTACGCG
AGCTCTGCAAGAGGCCGATTCACCATCTCCAGAGACAATTCCAAGAACACCCTGTATCTT
CAAATGAACAGCCTGAGAGCTGAGGACACTGCTGTGTATTACTGTGCTAGAGGATATGGC
CGTAGTGTTGCTTACTACGTCTTTAACATCTGGGGCCCAGGGACCCTCGTCACCGTCTCG
AGCGCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACGCGAGAGTTGAG
CCCAAATCTTGTGACAAAACTCACTAG (SEQ ID NO: 410)

<ins>Light chain Fab protein sequence.</ins>
DIQMTQSPSTLSASVGDRVTITCQASQSIYSNLAWYQQKPGKAPKLLIYDASTLESGVPS
RFSGSGSGTEYTLTISSLQPDDFATYYCQQGFTVSDIDNAFGGGTKVEIKRTVAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC (SEQ ID NO: 407)

<ins>Light chain Fab DNA sequence.</ins>
GACATCCAGATGACCCAGTCTCCTTCCACCCTGTCTGCATCTGTAGGAGACAGAGTCACC
ATCACTTGCCAGGCCAGTCAGAGCATTTACAGCAATCTTGCCTGGTATCAGCAGAAACCA
GGAAAAGCCCCTAAGCTCCTGATCTATGATGCATCCACTCTGGAATCTGGAGTCCCATCA
AGGTTCAGCGGCAGTGGATCTGGACAGAGTACACTCTCACCATCAGCAGCCTGCAGCCT
GATGATTTTGCAACTTACTACTGCCAACAGGGTTTTACTGTTAGTGATATTGATAATGCT
TTCGGCGGAGGAACCAAGGTGGAAATCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTAG (SEQ
ID NO: 409)

Inhibition of NGF induced TF1 cells proliferation

Inhibition of NGF induced TF1 cells proliferation

Inhibition of NGF induced TF1 cells proliferation

Inhibition of NGF induced TF1 cells proliferation

Inhibition of NGF induced TF1 cells proliferation

Inhibition of NGF induced TF1 cells proliferation

Inhibition of NGF induced TF1 cells proliferation

Inhibition of NGF induced TF1 cells proliferation

Inhibition of NGF induced TF1 cells proliferation

Inhibition of NGF induced TF1 cells proliferation

Inhibition of NGF induced TF1 cells proliferation

Inhibition of NGF induced TF1 cells proliferation

Figure 53
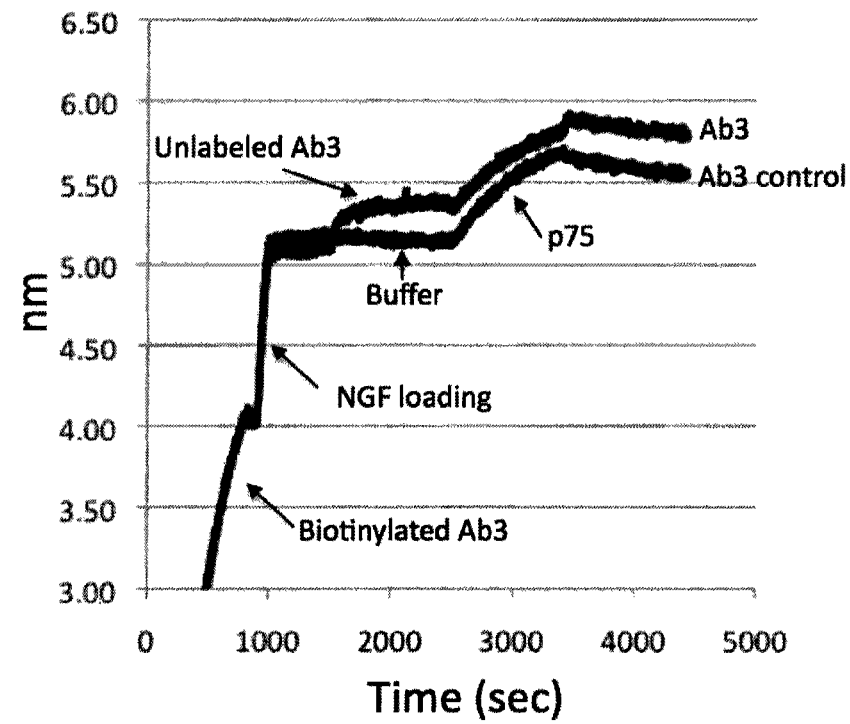
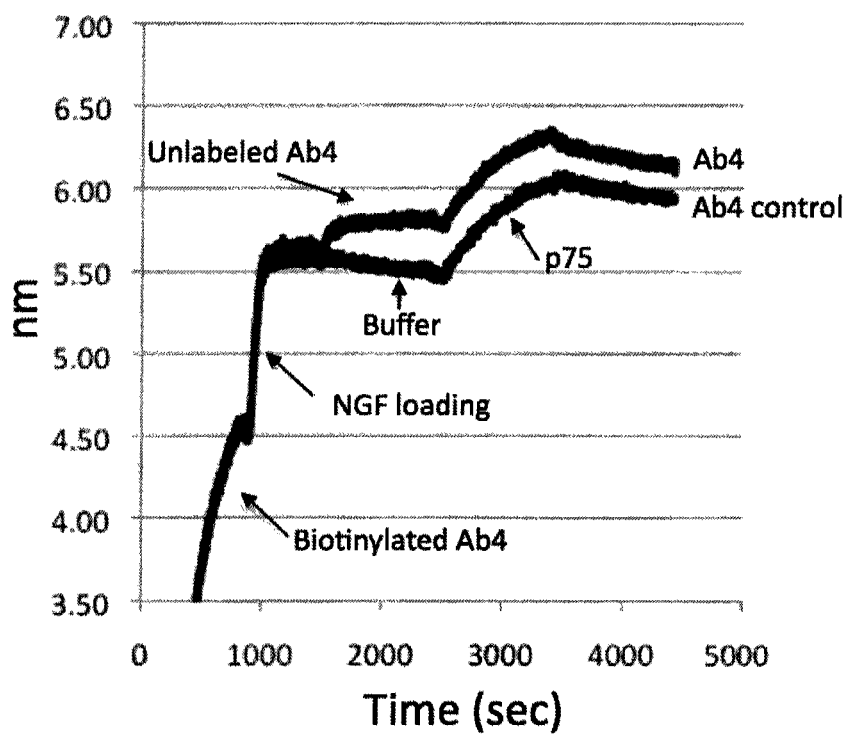

PC-12 Neurite Outgrowth

Ab1

Figure 57
PC-12 Neurite Outgrowth
Ab2
Control-NGF only
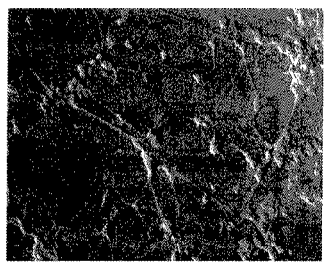
0.1X Ab2
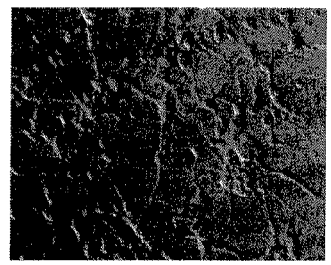
0.3X Ab2
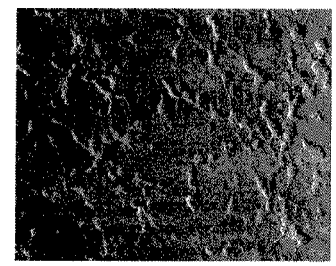
1X Ab2
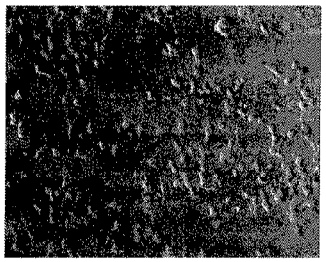
3X Ab2
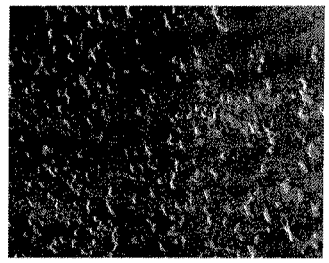
10X Ab2
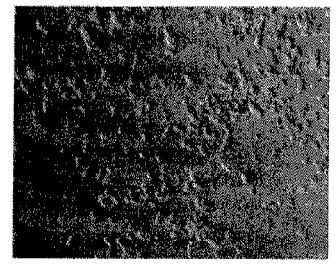

PC-12 Neurite Outgrowth

Ab3

PC-12 Neurite Outgrowth

Ab5

PC-12 Neurite Outgrowth

Ab6

PC-12 Neurite Outgrowth

Ab7

PC-12 Neurite Outgrowth

Ab8

PC-12 Neurite Outgrowth

Ab9

PC-12 Neurite Outgrowth

Ab10

PC-12 Neurite Outgrowth

Ab11

Figure 66
PC-12 Neurite Outgrowth
Ab13
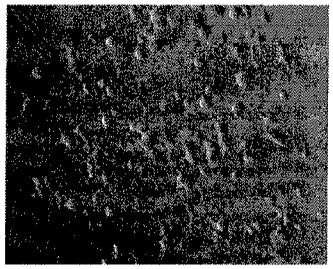
Control 1
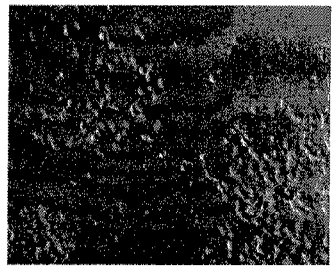
1X Ab13
10X Ab13

PC-12 Neurite Outgrowth

Ab17

PC-12 Neurite Outgrowth

Ab18

Figure 69
PC-12 Neurite Outgrowth
Ab19
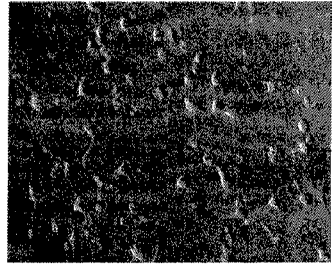
Control-NGF Only
1X Ab19
10X Ab19

Figure 78
PC-12 Neurite Outgrowth
Ab16
Control-NGF only          1X Ab16          10X Ab16
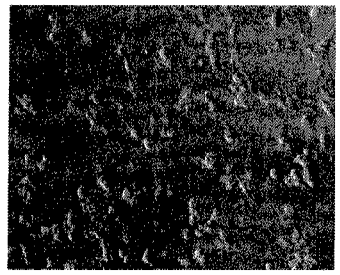 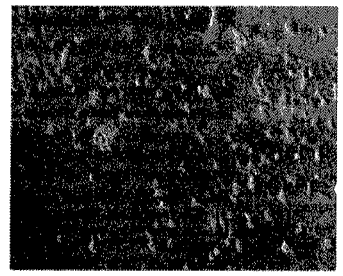 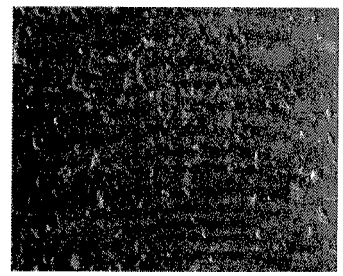

Figure 79
PC-12 Neurite Outgrowth
Ab15
Control-NGF only         1X Ab15         10X Ab15
  

METHODS OF PREVENTING OR TREATING PAIN USING ANTI-NGF ANTIBODIES THAT SELECTIVELY INHIBIT THE ASSOCIATION OF NGF WITH TRKA, WITHOUT AFFECTING THE ASSOCIATION OF NGF WITH P75

CROSS-REFERENCE TO RELATED APPLICATIONS

This application claims the benefit of priority to U.S. provisional patent application No. 61/418,832, filed Dec. 1, 2010, the contents of which are incorporated herein by reference in its entirety. In addition this application relates to U.S. application Ser. No. 13/308,831, entitled "METHODS OF PREVENTING INFLAMMATION AND TREATING PAIN USING ANTI-NGF COMPOSITIONS"; U.S. application Ser. No. 13/309,153, now U.S. Pat. No. 8,728,473, entitled "METHODS OF PREVENTING OR TREATING PAIN USING ANTI-NGF ANTIBODIES", and U.S. application Ser. No. 13/309,295 entitled "ANTI-NGF COMPOSITIONS AND USE THEREOF", all assigned to Alder Biopharmaceuticals, and all filed on Dec. 1, 2011, the contents of which are all incorporated by reference in their entireties.

BACKGROUND OF THE INVENTION

1. Field of the Invention

This invention pertains to anti-pain medicaments comprising at least one NGF antagonist compound that selectively inhibits the association of NGF with TrkA, without appreciably inhibiting the association of NGF with p75 Preferably, these NGF antagonist compounds will comprise an antibody or fragment thereof (including Fab fragments and other monovalent agents identified infra) having binding specificity to human Nerve Growth Factor (hereinafter "NGF"), and methods of using one or more of said NGF antagonist compounds, e.g., antibodies and fragments thereof to treat pain in an individual. While antibodies and fragments are exemplified, it is anticipated that other NGF antagonists may be selected using appropriate binding and/or functional assays which possess similar antagonist properties, e.g., polypeptide fragments of NGF or TrkA, small molecules, antisense RNA's and silencing RNA's. and the like that selectively inhibit the association of NGF with TrkA, without appreciably inhibiting the association of NGF with p75 These compounds, e.g., antibodies and antibody fragments may be used as a monotherapy to treat or prevent different types of pain in a subject in need thereof when administered alone or in association with another active agent, e.g., a NSAID or opioid analgesic. More specifically the invention pertains to anti-human NGF antibodies or fragments thereof including monovalent agents that inhibit the association of NGF with TrkA, without appreciably inhibiting the association of NGF with p75. These antibodies and fragments, e.g., monovalent agents, may be modified to affect circulation half-life, such as via the attachment of PEG or other polymers or by attachment of other moieties such as detectable agents or functional agents. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

In addition, and related thereto the invention pertains to novel methods of treating pain or eliciting an analgesic effect in an individual, comprising administering an effective amount of any NGF antagonist compound that selectively inhibits the association of NGF with TrkA, without appreciably inhibiting the association of NGF with p75 Preferably, these antagonist compounds will comprise an anti-human NGF antibody or fragment thereof which inhibits the association of NGF with TrkA, without appreciably inhibiting the association of NGF with p75. The present invention further optionally includes methods of treating pain further including the administration of a second anti-NGF antibody or fragment that inhibits the association of NGF with p75, that may in addition inhibits the association of NGF with TrkA.

2. Description of Related Art

Nerve Growth Factor (NGF) (also known as beta nerve growth factor (Beta-NGF)) is produced as a mature protein of 222 amino acids in length, following cleavage of a 18 amino acid signal peptide. The gene encoding NGF is located on chromosome 1p13.1. A biologically active form of NGF is a secreted protein which homodimerizes and is incorporated into a larger complex. NGF is a member of the neurotrophins (NTs), which are a group of structurally-related proteins further including brain-derived neurotrophic factor (BDNF), NT-3, and NT-4/5. (Wyman et al., Gene Therapy (1999), 6:1648-1660). NTs support the survival of specific types of neurons and neurotransmitter systems, being produced by cells that are targeted by innervating neurons. Id. Basal forebrain, substantia nigra, brain stem, cortex, and spinal cord are nervous system regions having demonstrated responsiveness to NGF. Id.

All NTs bind to a low-affinity receptor identified as p75. (Sarchielli et al., Expert Rev. Neurotherapeutics (2004), 4(1): 115-127). NGF selectively binds to, and displays a high affinity for, the high affinity neurotrophin receptor TrkA. Id. It has recently been demonstrated that NGF acts through its low-affinity receptor p75 in a developmentally-regulated signaling pathway necessary for myogenic differentiation and muscle repair in vivo. (Deponti et al., Mol. Biol. Cell (2009), 20:3620-3627).

NGF has also been demonstrated to interact with pain-signalling systems in adult animals, and is responsible for hyperalgesia when administered either locally or systemically in many species. (Sarchielli et al., Expert Rev. Neurotherapeutics (2004), 4(1):115-127). NGF has been shown to induce a pain-like response when infused into the CSF in rats, and has been demonstrated to maintain chronic pain. Furthermore, NGF has been demonstrated to contribute to the development of mechanical allodynia occurring 8-12 hours later, and to the secondary pain response. Id.

Pain may often be addressed through the administration of certain narcotics or non-steroidal anti-inflammatory drugs (NSAIDs). However, the administration of these treatments may occur at the cost of certain negative consequences. NSAIDs have the potential to cause kidney failure, intestinal bleeding, and liver dysfunction. Narcotics have the potential to cause nausea, vomiting, impaired mental functioning, and addiction. Therefore, it is desirable to identify alternative treatments for pain in order to avoid certain of these negative consequences.

NGF is believed to play a role in a multitude of diseases and disorders, including but not limited to pain associated with a broad range of diseases and disorders, such as pain associated with cancers, neuropathic pain, and neurogenic pain. Due to the perceived involvement of NGF in a wide range of pain-related diseases and disorders, there remains a need in the art for compositions and methods useful for preventing or treating diseases and disorders associated with NGF, and particularly those associated with pain. Particularly preferred anti-NGF compositions are those having minimal or minimizing adverse reactions, such as inflammation when administered to the patient. Compositions or methods that reduce or inhibit diseases or disorders associated with NGF, such as pain, are beneficial to the patient in need thereof.

BRIEF SUMMARY OF THE INVENTION

The present invention is directed to methods of treating pain and compositions for use therein including antibodies and fragments thereof having binding specificity for NGF, in particular antibodies having desired epitopic specificity, high affinity or avidity and/or functional properties in the treatment of pain. More specifically the invention pertains to NGF antagonists, e.g. small molecules, polypeptides, nucleic acids, and preferably anti-human NGF antibodies or fragments thereof, including monovalent and bivalent antibody fragments that inhibit the association of NGF with TrkA, without appreciably inhibiting the association of NGF with p75. These antibodies and fragments, e.g., monovalent agents may be modified to affect circulation half-life, such as via the attachment of PEG or other polymers or by attachment of other moieties such as detectable agents or functional agents. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

The present invention includes in particular monovalent antibody molecules that bind NGF, which are analogous to MetMab molecules. MetMab is a monovalent antibody specific to Met. (Met is a protein encoded by the nucleotide sequence set forth in Park et al., Proc. Natl. Acad. Sci. 84, 7479-(1987), or fragments thereof, as well as related polypeptides, which include, but are not limited to, allelic variants, splice variants, derivative variants, substitution variants, deletion variants, and/or insertion variants, fusion polypeptides, and interspecies homologs). The MetMab antibody, is a monovalent antibody known by different names including OA-5d5 (Genentech) and is also called One Armed 5d5, 5d5, MetMab, PRO143966, among others). Antibody OA-5d5, including its structure and properties, and methods for making and using it, are described in U.S. Publication No. 2007/0092520. In one embodiment, an anti-NGF antibody according to the invention may comprise a single Fab region linked to an Fc region. In such embodiment, an antibody of the invention may comprise light and heavy chain variable domains as described herein. In such an embodiment, the antibody is monovalent and may comprise an intact Fc region. In another such embodiment, the Fc region may comprise at least one protuberance (knob) and at least one cavity (hole), wherein the presence of the protuberance and cavity enhances formation of a complex between an Fc polypeptide comprising the protuberance and an Fc polypeptide comprising the cavity, for example as described in WO 2005/063816. In one embodiment, the Fc region of an antibody of the invention may comprise a first and a second Fc polypeptide, wherein the first and second polypeptide each comprises one or more mutations with respect to wild type human Fc. In one embodiment, a cavity mutation is T366S, L368A and/or Y407V. In another embodiment, a protuberance mutation is T366W. In a specific embodiment, a monovalent antibody according to the subject invention may comprise a one-armed antibody synthesized as described in WO2005/063816. In such embodiment, the one-armed antibody may comprise Fc mutations constituting "knobs" and "holes" as described in WO2005/063816. For example, a hole mutation can be one or more of T366A, L368A and/or Y407V in an Fc polypeptide, and a cavity mutation can be T366W.

The invention is also directed to an anti-human NGF monovalent agent that binds with the same NGF epitope and/or competes with an anti-NGF antibody for binding to NGF as an antibody or antibody fragment disclosed herein, including but not limited to an anti-NGF antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20 or Ab21.

In addition, and related thereto the invention is directed to novel methods of treating pain or eliciting an analgesic effect in an individual, comprising administering an effective amount of an NGF antagonist, e.g., an anti-human NGF antibody or fragment thereof which inhibits the association of NGF with TrkA, without appreciably inhibiting the association of NGF with p75. The subject invention provides a plurality of novel anti-human NGF antibodies and fragments thereof that inhibit the association of NGF with TrkA, without appreciably inhibiting the association of NGF with p75. These antibodies and fragments may be used as a monotherapy or may be used in conjunctions with other actives including other analgesics and other anti-NGF antibodies and antibody fragments including those that inhibit the interaction of NGF with p75. In addition the invention provides methods for producing, identifying and isolating other anti-human NGF antibodies or fragments thereof, including bivalent and monovalent fragments such as Fab, Fab', F(ab')$_2$, Fv, scFv fragments, SMIPs (small molecule immunopharmaceuticals), camelbodies, nanobodies, and IgNAR, which inhibit the association of NGF with TrkA, without appreciably inhibiting the association of NGF with p75. Another embodiment of this invention relates to methods of using the antibodies described herein, comprising the sequences of the $V_H$, $V_L$ and CDR polypeptides described herein, and the polynucleotides encoding them to treat or prevent pain by selectively inhibiting the association of NGF with TrkA and not its association with p75. This invention provides novel human monoclonal antibodies and fragments and conjugates thereof that are therapeutically useful for managing pain. Preferably, the invention provides monoclonal antibodies that bind to nerve growth factor (NGF) which inhibit the association of NGF with TrkA, without appreciably inhibiting the association of NGF with p75 that are useful in treating or preventing pain, e.g., associated with cancer, migraine, pre or post surgery associated pain and other pain related conditions. Preferably, the monoclonal antibodies or fragments are human or chimeric or humanized monoclonal antibodies or fragments or conjugates thereof which neutralize biological activities of NGF and are useful for ameliorating the effects of NGF-mediated pain responses, i.e., those involving the TrkA pathway. Also provided by the invention are vectors containing nucleic acids that encode for such NGF antibodies and fragments, and cells containing such as bacterial, yeast, mammalian, insect, or avian cells that express these nucleic acids, and most preferably, secrete into cell culture media the monoclonal antibodies and fragments of the invention. In addition to their use for treating and managing pain, the antibodies and antibody fragments and other NGF antagonists of the invention are useful for treating neuropathic and inflammatory pain-related responses that involve the use of NGF antagonists, e.g., antibodies or antibody fragments or other compounds that bind to nerve growth factor (NGF), which inhibit the association of NGF with TrkA, without appreciably inhibiting the association of NGF with p75.

In addition the application describes monoclonal antibodies and fragments that bind to nerve growth factor (NGF) which inhibit the association of NGF with TrkA, as well as the association of NGF with p75, and which antibodies are also useful in treating or preventing pain disorders as well as other disorders such as inflammation. These antibodies and fragments, e.g., monovalent or bivalent agents, may be modified to affect circulation half-life, such as via the attachment of PEG or other polymers or by attachment of other moieties such as detectable agents or functional agents. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof.

These antibodies are the subject of applications filed on the same date as this application, the contents of which are incorporated by reference herein. These antibodies are disclosed herein as they corroborate the distinct binding properties of the antibodies of the present invention relative to other anti-NGF antibodies. In addition, these other anti-NGF antibodies and fragments are provided herein as the present invention contemplates the use of these antibodies and fragments thereof, or other antibodies or fragments having similar binding properties, in association with the antibodies of the present invention which inhibit the association of NGF with TrkA, without appreciably inhibiting the association of NGF with p75.

In one aspect, the invention features a method for preventing or treating post-surgical pain (referred to interchangeably as "post-incisional" or "post-traumatic pain") by administering an antibody or antibody fragment specific to NGF or other NGF antagonist according to the invention that binds to nerve growth factor (NGF), which inhibits the association of NGF with TrkA, without appreciably inhibiting the association of NGF with p75. This includes inhibiting or blocking the pain resulting from post-surgical pain, including pain from surgery or from an incisional or traumatic wound. In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

In another aspect, the invention provides methods for reducing incidence of post-surgical pain, ameliorating post-surgical pain, palliating post-surgical pain; and/or delaying the development or progression of post-surgical pain in an individual, said method comprising administering an effective amount of an NGF antagonist according to the invention, e.g., an anti-NGF antibody or antibody fragment according to the invention that binds to nerve growth factor (NGF), which inhibits the association of NGF with TrkA, without appreciably inhibiting the association of NGF with p75. In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. These antibodies and fragments, e.g., monovalent agents, may be modified to affect circulation half-life, such as via the attachment of PEG or other polymers or by attachment of other moieties such as detectable agents or functional agents. These monovalent agents include by way of example Fab, Fab', Fv, scFv fragments, SMIPs (small molecule immunopharmaceuticals), camelbodies, nanobodies, IgNAR, a monovalent antibody molecule analogous to MetMab, or one or more combinations thereof. As discussed infra, these compositions may be administrable by different routes and dosage regimens.

In another aspect, the invention provides methods for increasing pain threshold in an individual comprising administering an effective amount of an NGF antagonist, e.g., an anti-NGF antibody or antibody fragment according to the invention that binds to nerve growth factor (NGF), which inhibits the association of NGF with TrkA, without appreciably inhibiting the association of NGF with p75. In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

In another aspect, the invention provides methods for enhancing recovery from surgery and/or injury-induced traumatic wound in an individual comprising administering an effective amount of an NGF antagonist, e.g., an anti-NGF antibody or antibody fragment according to the invention that binds to nerve growth factor (NGF), which inhibits the association of NGF with TrkA, without appreciably inhibiting the association of NGF with p75. In some embodiments, resting pain is suppressed, ameliorated and/or prevented, in some embodiments, mechanically-induced pain (including pain resulting from movement) is suppressed, ameliorated and/or prevented, and in some embodiment, thermally-induced pain is suppressed, ameliorated and/or prevented. In some embodiments, mechanically-induced pain is suppressed, ameliorated and/or prevented by administering an anti-NGF antibody or fragment according to the invention that binds to nerve growth factor (NGF), which inhibits the association of NGF with TrkA, without appreciably inhibiting the association of NGF with p75. In some embodiments, resting pain is suppressed, ameliorated and/or prevented by administering an NGF antagonist according to the invention, e.g., an anti-NGF antibody or fragment according to the invention that binds to nerve growth factor (NGF), which inhibits the association of NGF with TrkA, without appreciably inhibiting the association of NGF with p75. In some embodiment, thermally-induced pain is suppressed, ameliorated and/or prevented by administering an NGF antagonist according to the invention, e.g., an anti-NGF antibody or fragment according to the invention that binds to nerve growth factor (NGF), which inhibits the association of NGF with TrkA, without appreciably inhibiting the association of NGF with p75. In some embodiments, allodynia (i.e., increased response (i.e., increased noxious sensation) to a normally non-noxious stimulus)) is suppressed, ameliorated and/or prevented, and/or hyperalgesia (i.e., increased response to a normally noxious or unpleasant stimulus) is suppressed, ameliorated and/or prevented. In still further embodiments, allodynia and/or hyperalgesia is thermal or mechanical (tactile) in nature, or resting pain. In some embodiments, the pain is chronic pain. In other embodiments, the pain is associated with site of incision, wound or trauma, and/or proximal, at or near the site of incision, wound, and/or trauma. In addition the invention provides pharmaceutical compositions suitable for use in treating or preventing said pain indications, preferably for human therapy, comprising an effective amount of at least one an NGF antagonist according to the inventing, e.g., an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

Another aspect of the invention consists in using the capacity of an NGF antagonist according to the invention, e.g., an antibody or antibody fragment according to the invention that binds to nerve growth factor (NGF), or another polypeptide, such as a fragment of NGF or TrkA or a nucleic acid which selectively inhibits the association of NGF with TrkA, without appreciably inhibiting the association of NGF with p75 to bring relief to the patient suffering from chronic visceral pain. The subject NGF antagonists according to the invention, e.g., antibodies or antibody fragments, are capable of inhibiting or blocking the visceral hypersensitivity present in the pathophysiology of visceral functional disorders, in the case of chronic pain. Herein, the expression chronic visceral functional disorders is understood to include by way of example disorders of the sensitivity of the viscera having a nervous origin, also known by the name visceralgia. The viscera include the digestive, respiratory and urogenital organs and the endocrine systems, as well as the spleen, the heart and the large vessels. From the medical point of view, a chronic visceralgia is characterized by a threshold of sensitivity to pain which is lowered compared with the normal threshold, in response to external mechanical stimuli. Chronic visceral pain is in addition characterized by the absence of an inflammatory situation concomitant with the functional disorders. More specifically, chronic visceral pain includes the following chronic disorders: chronic dyspepsia, a functional digestion disorder occurring in the absence of a detectable organic lesion and which may be symptomatic of other diseases or other disorders; chronic dysmenorrhea, characterized by pain associated with menstruation; chronic pancreatitis, which is characterized by rapid loss of weight, asthenia, pain at the pancreatic point, a jaundice with distension of the gall bladder and digestive disorders due to pancreatic insufficiency, including hereditary chronic pancreatitis, a dominant autosomally transmitted disease which manifests itself from childhood by abdominal and recidivous painful attacks and which is characterized in adults by signs of insufficiency as well as by calcifications of the pancreas; chronic gastroesophageal reflux, which is characterized by a return into the esophagus of the acidic gastric content and which causes, generally after a meal, ascending retrosternal burns, sometimes accompanied by acidic regurgitations; IBS (irritable bowel syndrome), which is a non-inflammatory chronic disease characterized by abdominal pain and diarrhea and/or constipation, with no detectable biochemical and histological modification. In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

The criteria for the diagnosis of IBS are (1) abdominal pain or discomfort which is relieved by defecation and which is associated with a modification of the frequency and of the consistency of the stools and (2) an irregular defecation profile characterized by at least three of the following phenomena: (a) frequency of the stools affected, (b) form of the stools altered, (c) passing of the stool affected, (d) passing of mucus, and (e) sensation of abdominal distension.

Chronic visceral pain, in particular gastrointestinal pain, is characterized by an abnormal perception of various external stimuli in the patients or in the animal. This abnormal perception of external stimuli may be defined as a decrease in the sensitivity threshold of the patient or of the animal to these external stimuli, compared with a control subject. This physiopathological condition in which a stimulus which is not painful under normal conditions is perceived as being painful and which corresponds to a decrease in the sensitivity threshold is called allodynia. The administration of a an antibody or antibody fragment according to the invention to a subject suffering from chronic visceral pain made it possible to abolish the lowering of the sensitivity threshold of this subject to external stimuli, with a return to a sensitivity threshold comparable to that observed in a control healthy subject. The subject antibodies or fragments according to the invention may be used for the manufacture of a medicament intended for the prevention or treatment of chronic visceral pain.

In another embodiment, the invention provides methods for enhancing opioid analgesic pain treatment comprising administering an effective amount of an opioid analgesic in conjunction with an effective amount of an NGF antagonist according to the invention, e.g., an anti-NGF antibody or antibody fragment according to the invention that binds to nerve growth factor (NGF), which inhibits the association of NGF with TrkA, without appreciably inhibiting the association of NGF with p75. Administration in conjunction, as used herein, comprises simultaneous administration and/or administration at different times. Administration in conjunction also encompasses administration as a co-formulation (i.e., the NGF antibody or fragment according to the invention and opioid analgesic are present (combined) in the same composition) and/or administration as separate compositions. As used herein, "administration in conjunction" is meant to encompass any circumstance wherein an NGF antagonist according to the invention, e.g., an NGF antibody or fragment according to the invention that binds to nerve growth factor (NGF), which inhibits the association of NGF with TrkA, without appreciably inhibiting the association of NGF with p75 and another active, e.g. another analgesic agent are administered in an effective amount to an individual. In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

As further discussed herein, it is understood that the NGF antagonist according to the invention, e.g., an anti-NGF antibody or fragment and other active, e.g., opioid analgesic can be administered at different dosing frequencies and/or intervals. For example, an anti-NGF antibody or fragment can be administered weekly, while an opioid analgesic can be administered more frequently. It is understood that the NGF antibody or fragment and the opioid analgesic can be administered using the same route of administration or different routes of administration, and that different dosing regimens may change over the course of administration(s). Administration may be before the onset of pain.

In another aspect, the invention provides methods for reducing incidence of pain, ameliorating pain, palliating pain; and/or delaying the development or progression of pain in an individual, said methods comprising administering an effective amount of an opioid analgesic in conjunction with an effective amount of an NGF antagonist according to the invention, e.g., an NGF antibody or fragment according to the invention that binds to nerve growth factor (NGF), which inhibits the association of NGF with TrkA, without appreciably inhibiting the association of NGF with p75. The methods of the invention are suitable for treating or preventing any pain of any etiology, including pain where the use of an opioid analgesic is generally prescribed, for example, pancreatitis, kidney stone, headache, dysmenorrhea, musculoskeletal pain (e.g., lower back pain), sprain, visceral pain, ovarian cysts, prostatitis, cystitis, chemical or thermal burns, or cancer (such as prostate cancer metastasized to bone, breast cancer that has metastasized to bone, lung cancer that has metastasized to bone, pancreatic cancer). In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

In another aspect, the present invention features a method for treating (or, in other embodiments, preventing) pain comprising administering an amount of an NGF antagonist according to the invention, e.g., an anti-NGF antibody or fragment according to the invention in association with another active, e.g., an NSAID in order to provide effective pain relief In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

In another aspect, the invention provides methods for enhancing NSAID pain treatment comprising administering an effective amount of an NSAID in conjunction with an effective amount of an NGF antagonist according to the invention, e.g., an anti-anti-NGF antibody or antibody fragment according to the invention that binds to nerve growth factor (NGF), which inhibits the association of NGF with TrkA, without appreciably inhibiting the association of NGF with p75. Administration in conjunction, as used herein, comprises simultaneous administration and/or administration at different times. Administration in conjunction also encompasses administration as a co-formulation (i.e., the NGF antibody and NSAID are present (combined) in the same composition) and/or administration as separate compositions. As used herein, "administration in conjunction" is meant to encompass any circumstance wherein an NSAID and anti-NGF antibody are administered in an effective amount to an individual. As further discussed herein, it is understood that the NGF antibody or fragment and NSAID can be administered at different dosing frequencies and/or intervals. For example, an NGF antagonist according to the invention, e.g., an anti-NGF antibody can be administered weekly, while an NSAID can be administered more frequently. It is understood that the NGF antibody and the NSAID can be administered using the same route of administration or different routes of administration, and that different dosing regimens may change over the course of administration(s). Administration may be before the onset of pain. In addition the invention provides pharmaceutical compositions suitable for use in treating or preventing said pain indications, preferably for human therapy, comprising an effective amount of at least one NGF antagonist according to the invention, e.g., an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

In another aspect, the invention provides methods for reducing incidence of pain, ameliorating pain, palliating pain, and/or delaying the development or progression of pain in an individual, said methods comprising administering an effective amount of an NGF antagonist according to the invention, e.g., an NGF antibody or antibody fragment according to the invention that binds to nerve growth factor (NGF), which inhibits the association of NGF with TrkA, without appreciably inhibiting the association of NGF with p75 in conjunction with an effective amount of an NSAID. The methods of the invention are suitable for treating or preventing any pain of any etiology, including pain where the use of an NSAID is generally prescribed. In some embodiments, the pain is post-surgical pain. In some embodiments, the pain is pain associated with burn. In other embodiments, the pain is pain associated with rheumatoid arthritis. In other embodiments, the pain is pain associated with osteoarthritis. In addition the invention provides pharmaceutical compositions suitable for use in treating or preventing said pain indications, preferably for human therapy, comprising an effective amount of at least one NGF antagonist according to the invention, e.g., an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

In another aspect, the invention features a method for preventing or treating bone cancer pain including cancer pain associated with bone metastasis (also termed "bone metastasis pain") by administering an NGF antagonist according to the invention, e.g., an anti-NGF antibody or antibody fragment according to the invention that binds to nerve growth factor (NGF), which inhibits the association of NGF with TrkA, without appreciably inhibiting the association of NGF with p75. In some embodiments, the NGF antagonist according to the invention, e.g., an NGF antibody or fragment is co-administered with an opioid analgesic. In some embodiments, the NGF antibody or antibody fragment according to the invention is co-administered with an NSAID. In some embodiments, the NGF antagonist is co-administered with an opioid analgesic and an NSAID. In some embodiments, the NGF antagonist is not co-administered with an opioid analgesic. In some embodiments, the NGF antagonist is not co-administered with an NSAID. In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

In another aspect, the invention provides methods for reducing incidence of bone cancer pain including cancer pain associated with bone metastasis, ameliorating bone cancer pain including cancer pain associated with bone metastasis, palliating bone cancer pain including cancer pain associated with bone metastasis; and/or delaying the development or progression of bone cancer pain including cancer pain associated with bone metastasis in an individual, said methods comprising administering an effective amount of an NGF antagonist according to the invention, e.g., an NGF antibody or fragment according to the invention that binds to nerve growth factor (NGF), which inhibits the association of NGF with TrkA, without appreciably inhibiting the association of NGF with p75. In some embodiments, the NGF antagonist according to the invention, e.g., an NGF antibody or fragment is co-administered with an opioid analgesic. In some embodiments, the NGF antibody or fragment is co-administered with an NSAID. In some embodiments, the NGF antagonist according to the invention, e.g., an NGF antibody or fragment is co-administered with an opioid analgesic and an NSAID. In some embodiments, the NGF antagonist according to the invention, e.g., an NGF antibody or fragment is not co-administered with an opioid analgesic. In some embodiments, the NGF antagonist according to the invention, e.g., an NGF antibody or fragment is not co-administered with an NSAID. In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

In some embodiments, the bone cancer pain is from cancer originated in bone. In some embodiments, the bone cancer pain is from osteosarcoma. In some embodiments, the bone cancer pain is from cancer metastasized to bone. In some embodiments, the bone metastasis is prostate cancer metastasized to bone. In some embodiments, the bone metastasis is breast cancer metastasized to bone. In some embodiments, the bone metastasis is lung cancer metastasized to bone. In some embodiments, the bone metastasis is sarcoma metastasized to bone. In some embodiments, the bone metastasis is kidney cancer metastasized to bone. In some embodiments, the bone metastasis is multiple myeloma metastasized to bone. In some embodiments, the cancer pain treated is mild to moderate. In some embodiments, the cancer pain treated is moderate to severe. In some embodiments, the cancer pain treated is severe.

In preferred embodiments of the invention methods of treating pain are provided using chimeric or humanized antibodies and fragments thereof capable of binding to NGF and selectively inhibiting the biological activities mediated by the binding of NGF to the TrkA receptor, while not inhibiting the biological activities mediated by the binding of NGF to the p75 receptor. In another preferred embodiment of the invention, full length antibodies and Fab fragments thereof are provided which bind to nerve growth factor (NGF), which inhibit the association of NGF with TrkA, without appreciably inhibiting the association of NGF with p75, and that are capable of significantly reducing pain in vivo in murine models, as measured by Gait analysis (as described in the examples herein) or that inhibit PC12 neurite outgrowth as described infra. As noted these antibodies and antibody fragments may be administered alone or in association with other actives such as NSAIDs or opioid analgesics. In addition the invention provides pharmaceutical compositions suitable for use in treating or preventing said pain indications, preferably for human therapy, comprising an effective amount of at least one an antibody or antibody fragment specific to NGF according to the invention that binds to nerve growth factor (NGF), which inhibits the association of NGF with TrkA, without appreciably inhibiting the association of NGF with p75. As discussed infra, these compositions may be administrable by different routes and dosage regimens.

In another embodiment of the invention, chimeric or humanized antibodies and fragments thereof (including Fab fragments) are provided which are capable of binding to NGF that inhibit the association of NGF with TrkA, without appreciably inhibiting the association of NGF with p75 and which further inhibit TF1 cell proliferation. In another embodiment of the invention, chimeric or humanized antibodies and fragments thereof (including Fab fragments) capable of binding to NGF, which inhibits the association of NGF with TrkA, without appreciably inhibiting the association of NGF with p75 and which inhibit PC12 neurite outgrowth. In addition the invention provides pharmaceutical compositions suitable for use in treating or preventing said pain indications, preferably for human therapy, comprising an effective amount of said chimeric or humanized antibodies and fragments thereof (including Fab fragments) are provided which are capable of binding to NGF that inhibit the association of NGF with TrkA, without appreciably inhibiting the association of NGF with p75 and which further inhibit TF1 cell proliferation. As discussed infra, these compositions may be administrable by different routes and dosage regimens.

In another embodiment of the invention these antibodies and humanized versions may be derived from rabbit immune cells (B lymphocytes) and may be selected based on their homology (sequence identity) to human germ line sequences. These antibodies may require minimal or no sequence modifications, thereby facilitating retention of functional properties after humanization. A further embodiment of the invention is directed to fragments from anti-NGF antibodies encompassing $V_H$, $V_L$ and CDR polypeptides, e.g., derived from rabbit immune cells and the polynucleotides encoding the same, as well as methods of using these antibody fragments and the polynucleotides encoding them in the creation of novel antibodies and polypeptide compositions capable of binding to NGF and/or NGF/p75 and NGF/TrkA complexes.

The invention also contemplates conjugates of NGF antagonist according to the invention, e.g., an anti-NGF antibodies and binding fragments thereof that bind to nerve growth factor, which inhibit the association of NGF with TrkA, without appreciably inhibiting the association of NGF with p75, which are conjugated to one or more functional or detectable moieties. In addition, these compounds may be attached to moieties that affect (enhance or inhibit) in vivo half-life or which promote targeting to desired cells. The invention also contemplates methods of making said chimeric or humanized anti-NGF, anti-NGF/p75 complex or anti-NGF/TrkA complex antibodies and binding fragments thereof. In one embodiment, binding fragments include, but are not limited to, Fab, Fab', F(ab')$_2$, Fv, scFv fragments, SMIPs (small molecule immunopharmaceuticals), camelbodies, nanobodies, MetMab like monovalent antibody fragments, and IgNAR. In addition the invention provides pharmaceutical compositions suitable for use in treating or preventing said pain indications, preferably for human therapy, comprising an effective amount of said conjugates of anti-NGF antibodies and binding fragments thereof that bind to nerve growth factor, which inhibit the association of NGF with TrkA, without appreciably inhibiting the association of NGF with p75, which are conjugated to one or more functional or detectable moieties.

Embodiments of the invention pertain to the use of NGF antagonist according to the invention, e.g., an anti-NGF antibodies and binding fragments thereof which inhibit the association of NGF with TrkA, without appreciably inhibiting the association of NGF with p75, for the diagnosis, assessment and treatment of diseases and disorders associated with NGF or aberrant expression thereof, especially pain associated disorders. The invention also contemplates the use of fragments of anti-NGF antibodies which inhibit the association of NGF with TrkA, without appreciably inhibiting the association of NGF with p75, for the diagnosis, assessment and treatment of diseases and disorders associated with NGF or aberrant expression thereof. Other embodiments of the invention relate to the production of anti-NGF antibodies or fragments thereof and nucleic acids encoding said antibodies or fragments, which antibodies or fragments inhibit the association of NGF with TrkA, without appreciably inhibiting the association of NGF with p75, by the expression of these nucleic acids in recombinant host cells, for example mammalian cells such as CHO, NSO or HEK 293 cells, or yeast cells (for example diploid yeast such as diploid *Pichia*) and other yeast strains. In addition the invention provides pharmaceutically acceptable compositions for use in said methods.

BRIEF DESCRIPTION OF THE SEVERAL VIEWS OF THE DRAWINGS

FIG. 1 provides polynucleotide and polypeptide sequences corresponding to the full-length Antibody Ab1.

FIG. 2 provides polynucleotide and polypeptide sequences corresponding to the full-length Antibody Ab2.

FIG. 3 provides polynucleotide and polypeptide sequences corresponding to the full-length Antibody Ab3.

FIG. 4 provides polynucleotide and polypeptide sequences corresponding to the full-length Antibody Ab4.

FIG. 5 provides polynucleotide and polypeptide sequences corresponding to the full-length Antibody Ab5.

FIG. 6 provides polynucleotide and polypeptide sequences corresponding to the full-length Antibody Ab6.

FIG. 7 provides polynucleotide and polypeptide sequences corresponding to the full-length Antibody Ab7.

FIG. 8 provides polynucleotide and polypeptide sequences corresponding to the full-length Antibody Ab8.

FIG. 9 provides polynucleotide and polypeptide sequences corresponding to the full-length Antibody Ab9.

FIG. 10 provides polynucleotide and polypeptide sequences corresponding to the full-length Antibody Ab10.

FIG. 11 provides polynucleotide and polypeptide sequences corresponding to the full-length Antibody Ab11.

FIG. 12 provides polynucleotide and polypeptide sequences corresponding to the full-length Antibody Ab12.

FIG. 13 provides polynucleotide and polypeptide sequences corresponding to the full-length Antibody Ab13.

FIG. 14 provides polynucleotide and polypeptide sequences corresponding to the full-length Antibody Ab14.

FIG. 15 provides polynucleotide and polypeptide sequences corresponding to the full-length Antibody Ab15.

FIG. 16 provides polynucleotide and polypeptide sequences corresponding to the full-length Antibody Ab16.

FIG. 17 provides polynucleotide and polypeptide sequences corresponding to the full-length Antibody Ab17.

FIG. 18 provides polynucleotide and polypeptide sequences corresponding to the full-length Antibody Ab18.

FIG. 19 provides polynucleotide and polypeptide sequences corresponding to the full-length Antibody Ab19.

FIG. 20 provides polynucleotide and polypeptide sequences corresponding to the full-length Antibody Ab20.

FIG. 21 provides polynucleotide and polypeptide sequences corresponding to the full-length Antibody Ab21, produced by expression in *Pichia pastoris*.

FIG. 22 provides the heavy and light chain polypeptide sequences of Fab1.

FIG. 23 provides the heavy and light chain polypeptide sequences of Fab2.

FIG. 53 provides the inhibition of NGF-p75 interaction data obtained following example 5 for antibodies Ab3 and Ab4. Antibodies Ab3 and Ab4 do not demonstrate the ability to inhibit the interaction of NGF and p75.

FIG. 57 demonstrates the inhibition of PC-12 neurite outgrowth in the presence of increasing concentrations of antibody Ab2 obtained following example 6.

FIG. 66 demonstrates the inhibition of PC-12 neurite outgrowth in the presence of increasing concentrations of antibody Ab13 obtained following example 6.

FIG. 69 demonstrates the inhibition of PC-12 neurite outgrowth in the presence of increasing concentrations of antibody Ab19 obtained following example 6.

FIG. 78 demonstrates the inhibition of PC-12 neurite outgrowth in the presence of increasing concentrations of antibody Ab16 obtained following example 6. The results further demonstrate that the inhibition of PC-12 neurite outgrowth at the same concentrations of antibody is less than that seen with anti-NGF antibodies which exhibit different NGF binding selectivity.

FIG. 79 demonstrates the inhibition of PC-12 neurite outgrowth in the presence of increasing concentrations of antibody Ab15 obtained following example 6. The results further demonstrate that the inhibition of PC-12 neurite outgrowth at the same concentrations of antibody is less than that seen with anti-NGF antibodies which exhibit different NGF binding selectivity.

DETAILED DESCRIPTION OF PREFERRED EMBODIMENTS

Definitions

Figure 24:
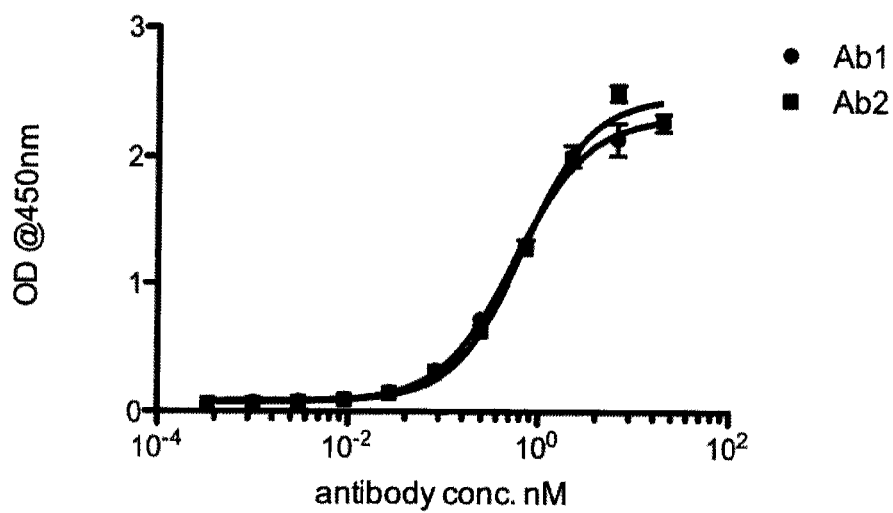
FIG. 24 provides the NGF ELISA binding data obtained following the protocol described infra for antibodies Ab1 and Ab2.
Figure 25:
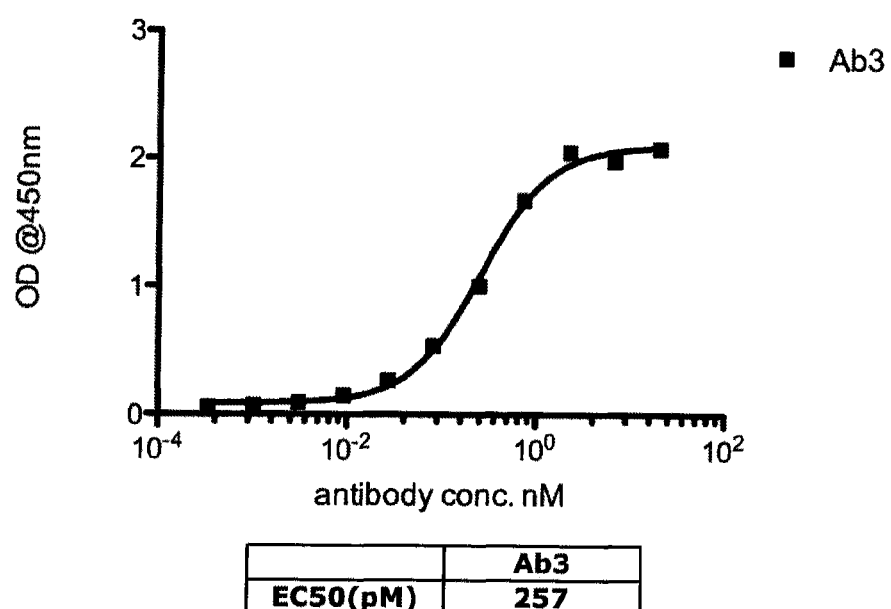
FIG. 25 provides the NGF ELISA binding data obtained following the protocol described infra for antibody Ab3.
Figure 26:
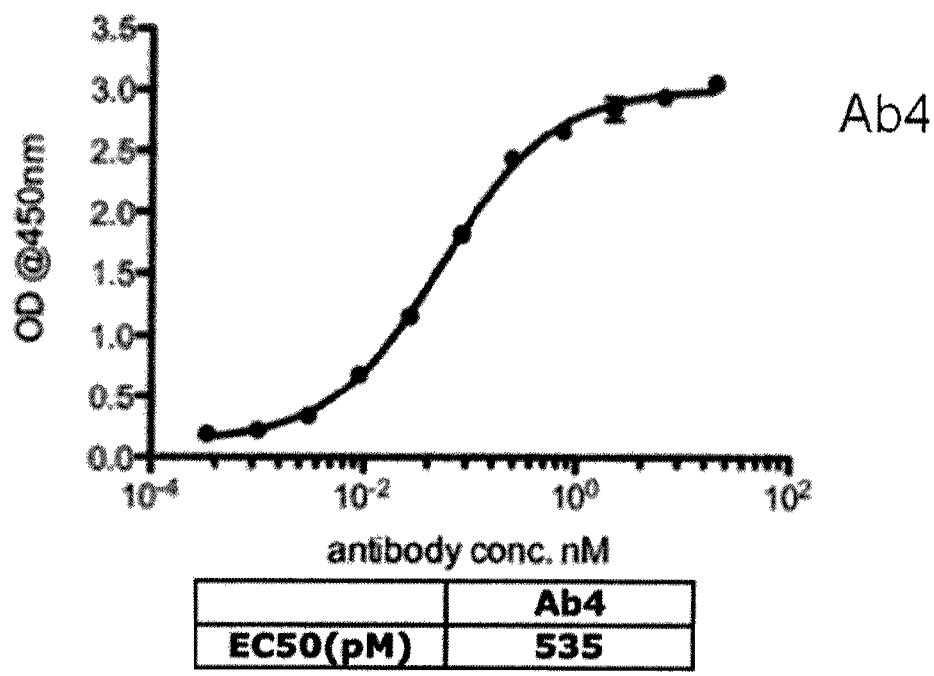
FIG. 26 provides the NGF ELISA binding data obtained following the protocol described infra for antibody Ab4.
Figure 27:
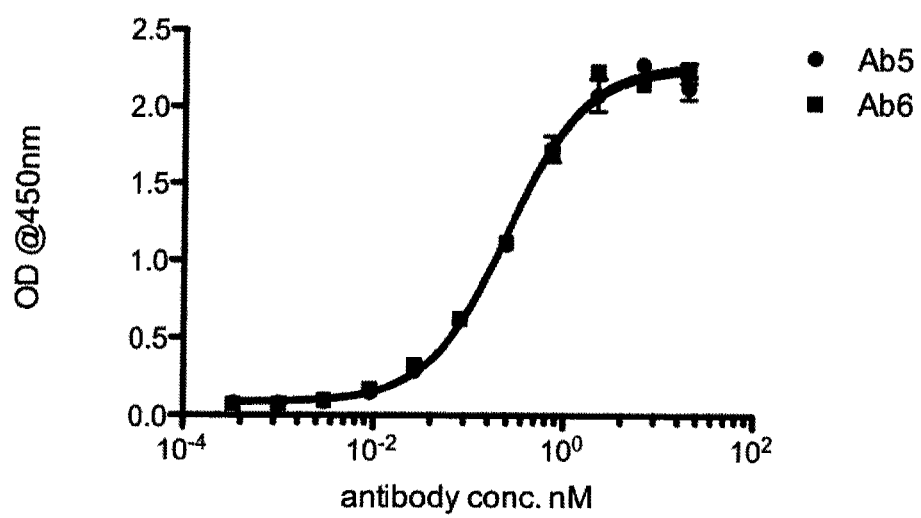
FIG. 27 provides the NGF ELISA binding data obtained following the protocol described infra for antibodies Ab5 and Ab6.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims. As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Nerve Growth Factor (NGF): As used herein, NGF (also referred to as Beta-NGF; HSAN5; and NGFB) encompasses not only the following mature amino acid sequence available from R&D Systems (Minneapolis, Minn.) as *Homo sapiens* Beta-Nerve Growth Factor (β-NGF):

ssshpifhrgefsvcdsysvwvgdkt-tatdikgkevmvlgevninnsvfkqyffetkcrdpnpvdsgcrgids khwnsycttthtfvkaltmdgkqaawrfiridtacvcvlsrkavrra (SEQ ID NO: 411), but also any pro-, mature, soluble, and/or membrane-bound forms of this NGF amino acid sequence, as well as mutants (mutiens), splice variants, isoforms, orthologues, homologues and variants of this sequence.

"Nerve Growth Factor antagonist" as used refers to any compound that antagonizes at least one biological activity elicited by NGF. In the preferred embodiment the NGF antagonist according to the invention will comprise an NGF antibody or fragment according to the invention, or another compound, that binds to nerve growth factor (NGF), and which inhibits the association of NGF with TrkA, without appreciably inhibiting the association of NGF with p75. These compounds may include fragments of NGF or TrkA, antisense or silencing RNAs, small molecules or other compounds identified in suitable binding and/or functional assays that binds to nerve growth factor (NGF), and which inhibits the association of NGF with TrkA, without appreciably inhibiting the association of NGF with p75.

"Pain" as used herein refers to pain of any etiology, including acute and chronic pain, and any pain with an inflammatory component. As used herein, "pain" includes nociception and the sensation of pain, and pain can be assessed objectively and subjectively, using pain scores and other methods well-known in the art. The pain can be primary or secondary pain, as is well-known in the art. Deagle's Law of the Multilevel Pain Gate states, "Changes at one level of the multilevel gate cause pathway and molecular neurotransmitter and inflammatory mediator changes at all other levels." Pain can arise at any level of the gating process, with different molecules responsible, and different genetic, pharmaceutical, immunopharmaceutical and technical challenges to block the gate mediators. Pain of all types arises through the multilevel gate, with changes in molecular upregulation at all other continuous levels. Thus levels of molecules that open the gate in the skin are increased in fibromyalgia and skin levels of cytokines and excitatory neurotransmitters are increased in the brain and skin in spinal cord and peripheral nerve injuries. Pain is a neurologic signal disease and may or may not be associated with tissue inflammation. Lack of structural disease or tissue inflammation in conditions such as fibromyalgia or other non-inflammatory pain disorders such as non-inflammatory neuropathy, are primarily due to molecular increased pain signal transmission. Irrespective of the type of pain, whether it is acute pain as in a sprain, sports injury or jellyfish sting, or whether it is chronic pain as in arthritis, migraine pain, back or neck pain from herniated disks, RSD/CRPS pain, migraine, fibromyalgia, interstitial cystitis, neuropathic pain, post-stroke pain, etc., the underlying basis is the opening of the pain gate to allow the transmission of the pain signal from the primary or higher gates to the cortex at gate levels six and seven, where higher receptive, motor and behavioral responses occur. This model differs substantially from the model that inflammation is the sole cause of pain and that other molecular modulators of pain signal transmission or inhibition are not primary in the cause of chronic or acute pain disorders. In fibromyalgia, non-inflammatory neuromodulatory molecules are increased in the skin as well as in other disorders at the pain gates inflammatory molecules and pro-facilatory pain signal modulators are increased. Receptor density on the nerve fibers increases due to increased nerve traffic transmitting painful stimuli. Blockade of facilitative neurotransmitters and inflammatory gate controlling molecules narrows the twelve-lane superhighway facilitated for pain in the chronic pain state down to a two lane normal pathway, and reduces the receptor density for neurotransmitters as well.

This process involves pain gate facilitatory molecules. In other tissues and circumstances, these may be proinflammatory, or neutral, or anti-inflammatory. Irrespective of the characteristic of the pain, whether it is sharp, dull, aching, burning, stabbing, numbing or tingling, all pain arises with the allowance of increased signal of pain at one of the seven pain gate levels at the specific site of the structures that comprise the gates. In the skin this structure is the Langerhans dermal structures, next the dorsal root ganglion, the dorsal horn substantia gelatinosa, ascending spinothalamic tracts, subthalamic nuclei, sensory receptive cortex, and anterior motor and behavioral response cortex. Pain gate facilatatory molecules such as in the condition of fibromyalgia can be identified in the skin with increased frequency in this condition. Lack of pain gate inhibitory molecules may also be identified at all seven levels of the gate, with upregulation of genes, proteins, enzymes and glial cell transformation to open the gate in pain and down-regulation of genes, proteins, enzymes and blockade of glial cell transformation molecules in the pain state. Thus pain can be viewed as a signal disease and a neurological informational disorder, with excessive transmission to higher levels from one gate to another gate of pain signal increasingly processed, with lack of signal inhibition until there is a cortical response. According to a study on neuropharmaceutical multilevel neural pain gate and transduction-transmission blockades, the neural process of pain requires multilevel hierarchical integrated gating and requires the pain gate to be opened by inflammatory molecules. These include interleukin 1 Beta, IL1B; necrosis factor alpha, TNF-Alpha; interleukin 6, IL-6; interleukin 8, IL-8; interleukin 2, IL-2; and vanilloid receptor 1, VR1; and granulocyte inhibitor factor, GIF; iNO, glial cell activation, and free radical molecules such as hydroxyl OH, and nitric oxide or nitroperoxyl radicals NO, and NOOH. These may be blocked with pharmaceuticals that bind to the receptor.

Pain may be present in inflammatory or non-inflammatory conditions and therefore the presence of molecules that are found to cause or propagate pain if these molecules are not found at the pain gate. Non-inflammatory conditions such as fibromyalgia, myofascial pain, and non-inflammatory metabolic neuritic pain syndromes are excellent examples.

For example, "pain associated with chronic prostatitis and/or chronic pelvic pain syndrome" as used herein refers to lower abdominal (pelvic) pain; lower stomach pain; bladder pain; suprapubic pain; pain in the penis, testicles, scrotum and perineum; urethral pain; dyspareunia; pain, pressure or discomfort that may increase as the bladder fills; dysuria; and ejaculatory pain.

Although analgesia in the strictest sense is an absence of pain, as used herein, "analgesia" refers to reduction in pain perceived by an individual.

"Analgesia agent", "analgesic agent" or "analgesic" refers to any biomolecule, drug or active agent that alleviates or prevents pain. This includes in particular the subject NGF antibodies and fragments as well as other actives such as opioids and NSAIDs.

"Acute pain" refers to sudden pain from a specific cause (injury, infection, inflammation, etc.) that has lasted for a limited period of time (as opposed to chronic pain).

"Chronic pain" refers to a persistent state of pain. Chronic pain is often associated with long-term incurable or intractable medical conditions or diseases.

"Procedural pain" refers to pain arising from a medical, dental surgical or other procedure wherein the procedure may be planned or associated with acute trauma.

"Headache disorder" includes migraine, tension headache, cluster headache, trigeminal neuralgia, secondary headaches, and miscellaneous-type headaches.

"Migraine" includes migraine headache, migraine without aura, migraine with aura, and migraine with aura but without headache.

"Systemic side effects" sometimes associated with pain include, but are not limited to, cardiovascular including peripheral vasodilatation and inhibition of baroreceptors; dermatologic including pruritus (itching), flushing and red eyes; gastrointestinal including nausea and vomiting, decreased gastric motility, decreased biliary, pancreatic and intestinal secretions and delays in food digestion, diminished peristaltic waves in large intestine contributing to constipation, epigastric distress or biliary colic in biliary tract; respiratory including depressed respiratory effort; and urinary including urinary urgency and difficulty with urination; and peripheral limb heaviness.

"Central nervous system side effects" or "CNS side effects" associated with pain sometimes include, but are not limited to, narcosis, euphoria, drowsiness, apathy, psychotic ideation, mental confusion, alteration in mood, reduction in body temperature, feelings of relaxation, dysphoria (an emotional state characterized by anxiety, depression, or unease), and nausea and vomiting (caused by direct stimulation of chemoreceptors in the medulla).

As used herein, "treatment" is an approach for obtaining beneficial or desired clinical results. For purposes of this invention, beneficial or desired clinical results include, but are not limited to, one or more of the following: improvement or alleviation of any aspect of pain, including acute, chronic, inflammatory, neuropathic, or post-surgical pain. For purposes of this invention, beneficial or desired clinical results include, but are not limited to, one or more of the following: including lessening severity, alleviation of one or more symptoms associated with pain including any aspect of pain (such as shortening duration of pain, and/or reduction of pain sensitivity or sensation).

"Reducing incidence" of pain means any of reducing severity (which can include reducing need for and/or amount of (e.g., exposure to) other drugs and/or therapies generally used for this conditions), duration, and/or frequency (including, for example, delaying or increasing time to pain in an individual). As is understood by those skilled in the art, individuals may vary in terms of their response to treatment, and, as such, for example, a "method of reducing incidence of pain in an individual" reflects administering the NGF antibodies or fragments described herein alone or in association with another active such as an NSAID or opioid as described herein, based on a reasonable expectation that such administration may likely cause such a reduction in incidence in that particular individual.

"Ameliorating" pain or one or more symptoms of pain means a lessening or improvement of one or more symptoms of a pain as compared to not administering an NGF antibody or fragment alone or in association with another active agonist such as an NSA/D or opioid.

"Ameliorating" also includes shortening or reduction in duration of a symptom.

"Palliating" pain or one or more symptoms of pain means lessening the extent of one or more undesirable clinical manifestations of pain in an individual or population of individuals treated with an NGF antibody or fragment in accordance with the invention.

As used therein, "delaying" the development of pain means to defer, hinder, slow, retard, stabilize, and/or postpone progression of pain. This delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

For example, palliating" bone cancer pain (such as cancer pain associated with bone metastasis) or one or more symptoms of a bone cancer pain means lessening the extent of one or more undesirable clinical manifestations of bone cancer pain in an individual or population of individuals treated with an NGF antibody or fragment in accordance with the invention.

As used therein, "delaying" the development of pain, e.g., bone cancer pain including cancer pain associated with bone metastasis means to defer, hinder, slow, retard, stabilize, and/or postpone progression of bone cancer pain including cancer pain associated with bone metastasis. This delay can be of varying lengths of time, depending on the history of the disease and/or individuals being treated. As is evident to one skilled in the art, a sufficient or significant delay can, in effect, encompass prevention, in that the individual does not develop bone cancer pain including cancer pain associated with bone metastasis. A method that "delays" development of the symptom is a method that reduces probability of developing the symptom in a given time frame and/or reduces extent of the symptoms in a given time frame, when compared to not using the method. Such comparisons are typically based on clinical studies, using a number of subjects sufficient to give a statistically significant result.

"Development" or "progression" of pain, e.g., bone cancer pain including cancer pain associated with bone metastasis means initial manifestations and/or ensuing progression of the pain related disorder. Development of bone cancer pain including cancer pain associated with bone metastasis can be detectable and assessed using standard clinical techniques as well known in the art. However, development also refers to progression that may be undetectable. For purpose of this invention, development or progression refers to the biological course of the symptoms.

"Development" includes occurrence, recurrence, and onset. As used herein "onset" or "occurrence" of pain, e.g., bone cancer pain (such as cancer pain associated with bone metastasis) includes initial onset and/or recurrence.

As used herein, "co-administration" includes simultaneous administration and/or administration at different times. Co-administration also encompasses administration as a co-formulation (i.e., the NGF antibody or fragment and another agent are present in the same composition) or administration as separate compositions. As used herein, co-administration is meant to encompass any circumstance wherein an agent and NGF antibody or fragment are administered to an individual, which can occur simultaneously and/or separately. As further discussed herein, it is understood that the NGF antibody or fragment and an agent can be administered at different dosing frequencies or intervals. For example, an anti-NGF antibody can be administered weekly, while the agent can be administered more frequently. It is understood that the NGF antagonist and the agent can be administered using the same route of administration or different routes of administration.

Preferably the anti-NGF antibody or fragment is one that elicits an effective analgesic response alone, i.e., palliates or prevents pain in subjects where this is needed. Such conditions are identified infra and include any condition where pain is to be alleviated or prevented by antagonizing NGF, e.g., via the interaction of NGF with TrkA while not appreciably affecting the interaction of NGF with p75. These conditions include in particular conditions involving acute and/or chronic pain such as associated with cancer, rheumatoid arthritis, migraine, and the like.

The term "opioid analgesic" refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Exemplary opioid analgesics include codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine or pharmaceutically acceptable salts thereof.

The term "NSAID" refers to a non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and slindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam. Another class of NSAID has been described which selectively inhibit cyclooxygenase 2. Cox-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), DUP-697, flosulide (CGP-28238), meloxicam, 6-methoxy-2 naphthylacetic acid (6-MNA), rofecoxib, MK-966, nabumetone (prodrug for 6-MNA), nimesulide, NS-398, SC-5766, SC-58215, T-614; or combinations thereof.

In some embodiments, aspirin and/or acetominophen are taken in conjunction with NGF antibody or fragment. Aspirin is another type of non-steroidal anti-inflammatory compound.

"Host cell" herein refers to any cell, e.g., a bacterial, yeast, mammalian, avian, plant or insect cell that contains and/or expresses an NGF antagonist according to the invention, e.g., an NGF antibody or fragment thereof as disclosed herein. In the exemplary embodiment the host cell is a mating competent yeast cell.

"Transgenic animal or plant" refers to a non-human animal or a plant which is genetically engineered to introduce or delete a specific gene or gene sequence. Herein this typically refers to a non-human animal such as a rodent, bovine, or a plant engineered to express a NGF antagonist according to the invention, e.g., an antibody or antibody fragment that specifically binds NGF and preferably one that antagonizes the interaction of NGF with TrkA and which does not appreciably affect the interaction of NGF with p75, or alternatively is an antibody or antibody fragment that specifically binds NGF and is one that antagonizes the interaction of NGF with TrkA and the interaction of NGF with p75. expr Mating competent yeast species: In the present invention this is intended to broadly encompass any diploid or tetraploid yeast which can be grown in culture. Such species of yeast may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or spheroplast fusion.

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia; Rhodosporidium; Candida; Hansenula; Filobasium; Sporidiobolus; Bullera; Leucosporidium* and *Filobasidella*.

In a preferred embodiment of the invention, the mating competent yeast is a member of the genus *Pichia*. In a further preferred embodiment of the invention, the mating competent yeast of the genus *Pichia* is one of the following species: *Pichia pastoris, Pichia methanolica*, and *Hansenula polymorpha* (*Pichia angusta*). In a particularly preferred embodiment of the invention, the mating competent yeast of the genus *Pichia* is the species *Pichia pastoris*. In an even more preferred embodiment expression will be effected using the diploid expression system disclosed in U.S. Pat. No. 7,927,863, issued on Apr. 19, 2011, assigned to Alder Biopharmaceuticals and the Keck Graduate Institute.

Selectable Marker: A selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two ts mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

Expression Vector: These DNA vectors contain elements that facilitate manipulation for the expression of a foreign protein within the target host cell. Often, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual. Plainview, N.Y.: Cold Spring Harbor Laboratory Press.

Expression vectors for use in the methods of the invention will further typically include host cell specific sequences, including a selectable auxotrophic or drug marker for identifying transformed host cells, e.g., yeast strains. A drug marker may further be used to amplify copy number of the vector in a host cell or in a transgenic animal.

The polypeptide coding sequence of interest is operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e.g. a signal sequence, and the like. A host specific origin of replication is optional, as expression vectors are often integrated into the host cell genome. In one embodiment of the invention, the polypeptide of interest is operably linked, or fused, to sequences providing for optimized secretion of the polypeptide from host cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (GatewayR Technology; Invitrogen, Carlsbad Calif.). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The promoter fragment may also serve as the site for homologous recombination and integration of the expression vector into the same site in the host cell genome; alternatively a selectable marker is used as the site for homologous recombination.

The inventive antibody polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The S. cerevisiae alpha factor pre-pro signal has proven effective in the secretion of a variety of recombinant proteins from P. pastoris. Other yeast signal sequences include the alpha mating factor signal sequence, the invertase signal sequence, and signal sequences derived from other secreted yeast polypeptides. Additionally, these signal peptide sequences may be engineered to provide for enhanced secretion in the chosen expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) Ann. Rev. Biochem. 58:913-949; and are known to those of skill in the art. Such methods utilize intermolecular DNA recombination that is mediated by a mixture of lambda and E. coli—encoded recombination proteins. Recombination occurs between specific attachment (att) sites on the interacting DNA molecules. For a description of att sites see Weisberg and Landy (1983) Site-Specific Recombination in Phage Lambda, in Lambda II, Weisberg, ed. (Cold Spring Harbor, N.Y.:Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, each of the haploid parental strains expresses a distinct folding enzyme, e.g. one strain may express BIP, and the other strain may express PDI or combinations thereof.

The terms "desired protein" or "desired antibody" are used interchangeably and refer generally to a NGF antagonist polypeptide, e.g., a parent antibody specific to a target, i.e., NGF or a chimeric or humanized antibody or a binding portion thereof derived therefrom as described herein. In some instances the NGF antagonist may be a moiety, e.g., a polypeptide or nucleic acid that selectively antagonizes the interaction of NGF with TrkA while not appreciably affecting the interaction of NGF with p75. Examples thereof include fragments of NGF, TrkA, small molecules, nucleic acids, and the like which may be identified in appropriate screening assays, e.g., NGF binding assays, including competitive binding assays.

The term "antibody" is intended to include any polypeptide chain-containing molecular structure with a specific shape that fits to and recognizes an epitope, where one or more non-covalent binding interactions stabilize the complex between the molecular structure and the epitope. This includes intact antibodies and antibody fragments. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies (such as scFvs), camelbodies, nanobodies, IgNAR (single-chain antibodies derived from sharks), small-modular immunopharmaceuticals (SMIPs), and antibody fragments such as Fabs, Fab', F(ab')$_2$ and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al., A new antigen receptor gene family that undergoes rearrangement and extensive somatic diversification in sharks, Nature. 1995 Mar. 9; 374(6518):168-73; Nuttall S D, et al., Isolation of the new antigen receptor from wobbegong sharks, and use as a scaffold for the display of protein loop libraries, Mol Immunol. 2001 August; 38(4):313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6):653-8. Epub 2006 Oct. 19.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions (VL and $V_H$), obtained from antibody producing cells of one species with the constant light and heavy chain regions from another. Herein chimeric antibodies are also intended to broadly encompass any antibody that contains amino acid residues derived from different antibodies, of the same or different species origin. Therefore, chimeric antibodies encompasses humanized antibodies. Accordingly, in some instances in this application these terms are used interchangeably. Typically herein chimeric antibodies are obtained by combining non-human variable regions, e.g., rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

Humanized antibodies, a species of chimeric antibodies, are antibodies containing residues of human and non-human antibody or antibodies, which typically are engineered to avoid immunogenicity in a human subject, while retaining desired antibody characteristics such as antigen binding and in some instances desired antibody effector functions. Typically, humanized antibodies are engineered to contain even more human-like immunoglobulin domains, and incorporate the complementarity-determining regions of the animal-derived antibody and no or few framework residues from the non-human animal antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', $F(ab')_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291-294). Polymerase chain reaction or PCR is a prototype of nucleic acid amplification, and use of PCR herein should be considered exemplary of other suitable amplification techniques.

The general structure of antibodies in vertebrates now is well understood (Edelman, G. M., Ann. N.Y. Acad. Sci., 190: 5 (1971)). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the Fab region; the stem portion of the "Y" configuration is designated the Fc region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to γ, μ, α, δ, and ε (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)).

The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

Anti-NGF Antibodies and Binding Fragments Thereof Having Binding Activity for NGF Antibody Ab1

The invention contemplates methods of treating pain and the specific pain associated disorders using antibody Ab1 or fragments thereof, or an antibody or antibody fragment that binds to the same or overlapping epitope as Ab1, for example as set forth below, alone or is association with another active agent, e.g., an NSAID or opioid analgesic, in a therapeutically effective amount which inhibits the association of NGF with TrkA and the association of NGF with p75 and/or inhibits or prevents pain. In one embodiment, the invention includes chimeric antibodies having binding specificity to NGF and possessing a variable light chain sequence comprising the sequence set forth below:

```
                                          (SEQ ID NO: 1)
ALVMTQTPSSVSAAVGGTVTINCQASQNIYSNLAWYQQRPGQRPKLLIY

GASNLDAGVPSRFRGSGSGTEYTLTISDLECDDVGTYYCQSAFDSDSTE

NTFGGGTEVVVKR.
```

The invention optionally contemplates methods of treating pain and the specific pain associated disorders alone or is association with another active agent, e.g., an NSAID or opioid analgesic, wherein the antibodies include chimeric antibodies having binding specificity to NGF and possessing a light chain sequence comprising the sequence set forth below:

```
                                          (SEQ ID NO: 2)
ALVMTQTPSSVSAAVGGTVTINCQASQNIYSNLAWYQQRPGQRPKLLIY

GASNLDAGVPSRFRGSGSGTEYTLTISDLECDDVGTYYCQSAFDSDSTE

NTFGGGTEVVVKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.
```

The invention optionally contemplates methods of treating pain and the specific pain associated disorders alone or is association with another active agent, e.g., an NSAID or opioid analgesic, wherein the antibodies include chimeric antibodies having binding specificity to NGF and possessing a variable heavy chain sequence comprising the sequence set forth below:

```
                                          (SEQ ID NO: 3)
QSLEESGGRLVTPGTPLTLTCTVSGFSLSSYAMSWVRQAPGKGLEWIGV

TISIGSTVYASWAKGRFTISKTSTTVDLKITSPTTEDTATYFCARGYDD

YDEMTYFNIWGQGTLVTVSS.
```

The invention optionally contemplates methods of treating pain and the specific pain associated disorders alone or is association with another active agent, e.g., an NSAID or opioid analgesic, wherein the antibodies include chimeric antibodies having binding specificity to NGF and possessing a heavy chain sequence comprising the sequence set forth below:

(SEQ ID NO: 4)
QSLEESGGRLVTPGTPLTLTCTVSGFSLSSYAMSWVRQAPGKGLEWIGV

ITSIGSTVYASWAKGRFTISKTSTTVDLKITSPTTEDTATYFCARGYDD

YDEMTYFNIWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK.

The invention optionally contemplates methods of treating pain and the specific pain associated disorders alone or is association with another active agent, e.g., an NSAID or opioid analgesic, wherein the antibodies comprise one or more of the polypeptide sequences of SEQ ID NO: 5; SEQ ID NO: 6; and SEQ ID NO: 7 which correspond to the complementarity-determining regions (CDRs, or hypervariable regions) of the variable light chain sequence of SEQ ID NO: 1 or the light chain sequence of SEQ ID NO: 2, and/or one or more of the polypeptide sequences of SEQ ID NO: 8; SEQ ID NO: 9; and SEQ ID NO: 10 which correspond to the complementarity-determining regions (CDRs, or hypervariable regions) of the variable heavy chain sequence of SEQ ID NO: 3 or the heavy chain sequence of SEQ ID NO: 4, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention optionally contemplates methods of treating pain and the specific pain associated disorders alone or is association with another active agent, e.g., an NSAID or opioid analgesic, wherein the antibody is a fragment having binding specificity to NGF. In one embodiment of the invention, antibody fragments of the invention comprise, or alternatively consist of, the polypeptide sequence of SEQ ID NO: 1 or SEQ ID NO: 2. In another embodiment of the invention, antibody fragments of the invention comprise, or alternatively consist of, the polypeptide sequence of SEQ ID NO: 3 or SEQ ID NO: 4.

In a further embodiment of the invention, fragments of the antibody having binding specificity to NGF for treatment or prevention of pain comprise, or alternatively consist of, one or more of the polypeptide sequences of SEQ ID NO: 5; SEQ ID NO: 6; and SEQ ID NO: 7 which correspond to the complementarity-determining regions (CDRs, or hypervariable regions) of the variable light chain sequence of SEQ ID NO: 1 or the light chain sequence of SEQ ID NO: 2.

The invention optionally contemplates methods of treating pain and the specific pain associated disorders alone or is association with another active agent, e.g., an NSAID or opioid analgesic, wherein the antibodies include fragments having binding specificity to NGF comprise, or alternatively consist of, one or more of the polypeptide sequences of SEQ ID NO: 8; SEQ ID NO: 9; and SEQ ID NO: 10 which correspond to the complementarity-determining regions (CDRs, or hypervariable regions) of the variable heavy chain sequence of SEQ ID NO: 3 or the heavy chain sequence of SEQ ID NO: 4.

The invention also optionally contemplates antibody fragments which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 1; the variable heavy chain region of SEQ ID NO: 3; the complementarity-determining regions (SEQ ID NO: 5; SEQ ID NO: 6; and SEQ ID NO: 7) of the variable light chain region of SEQ ID NO: 1; and the complementarity-determining regions (SEQ ID NO: 8; SEQ ID NO: 9; and SEQ ID NO: 10) of the variable heavy chain region of SEQ ID NO: 3.

In a particularly preferred optional embodiment of the invention, the chimeric anti-NGF antibody is Ab1, comprising, or alternatively consisting of, SEQ ID NO: 2 and SEQ ID NO: 4, and having at least one of the biological activities set forth herein.

In a further particularly preferred optional embodiment of the invention, antibody fragments for use herein comprise, or alternatively consist of, Fab (fragment antigen binding) fragments having binding specificity for NGF or another Fab or monovalent antibody fragment that binds to the same or overlapping epitope as Ab1. With respect to antibody Ab1, the Fab fragment includes the variable light chain sequence of SEQ ID NO: 1 and the variable heavy chain sequence of SEQ ID NO: 3. This embodiment of the invention further contemplates additions, deletions, and variants of SEQ ID NO: 1 and/or SEQ ID NO: 3 in said Fab while retaining binding specificity for NGF.

In one optional embodiment of the invention described herein (infra), Fab fragments may be produced by enzymatic digestion (e.g., papain) of Ab1. In another embodiment of the invention, anti-NGF antibodies such as Ab1 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab2

The invention optionally contemplates methods of treating pain and the specific pain associated disorders alone or is association with another active agent, e.g., an NSAID or opioid analgesic, wherein the antibodies include chimeric or humanized antibodies having binding specificity to NGF wherein the antibody is antibody Ab2 or fragments thereof, or an antibody or antibody fragment that binds to the same or overlapping epitope as Ab2, for example as set forth below, in a therapeutically effective amount which inhibits the association of NGF with TrkA and the association of NGF with p75. In one embodiment, the invention includes chimeric or humanized antibodies having binding specificity to NGF and possessing a variable light chain sequence comprising the sequence set forth below:

(SEQ ID NO: 11)
DIQMTQSPSTLSASVGDRVTITCQASQNIYSNLAWYQQKPGKAPKLLIY

GASNLDAGVPSRFSGSGSGTEYTLTISSLQPDDFATYYCQSAFDSDSTE

NTFGGGTKVEIKR.

The invention also optionally includes chimeric or humanized antibodies for treatment or prevention of pain and pain associated conditions having binding specificity to NGF and possessing a light chain sequence comprising the sequence set forth below:

(SEQ ID NO: 12)
DIQMTQSPSTLSASVGDRVTITCQASQNIYSNLAWYQQKPGKAPKLLIY

GASNLDAGVPSRFSGSGSGTEYTLTISSLQPDDFATYYCQSAFDSDSTE

NTFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.

The invention further optionally includes chimeric or humanized antibodies having binding specificity to NGF for treatment or prevention of pain and pain associated conditions and possessing a variable heavy chain sequence comprising the sequence set forth below:

(SEQ ID NO: 13)
EVQLVESGGGLVQPGGSLRLSCAASGFTVSSYAMSWVRQAPGKGLEWVG

VITSIGSTVYASSAKGRFTISRDNSKNTLYLQMNSLRAEDTAVYYCARG

YDDYDEMTYFNIWGQGTLVTVSS.

The invention also optionally includes chimeric or humanized antibodies having binding specificity to NGF for treatment or prevention of pain and pain associated conditions and possessing a heavy chain sequence comprising the sequence set forth below:

(SEQ ID NO: 14)
EVQLVESGGGLVQPGGSLRLSCAASGFTVSSYAMSWVRQAPGKGLEWVG

VITSIGSTVYASSAKGRFTISRDNSKNTLYLQMNSLRAEDTAVYYCARG

YDDYDEMTYFNIWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKP

REEQYASTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK.

The invention further optionally contemplates antibodies for treatment or prevention of pain and pain associated conditions comprising one or more of the polypeptide sequences of SEQ ID NO: 15; SEQ ID NO: 16; and SEQ ID NO: 17 which correspond to the complementarity-determining regions (CDRs, or hypervariable regions) of the variable light chain sequence of SEQ ID NO: 11 or the light chain sequence of SEQ ID NO: 12, and/or one or more of the polypeptide sequences of SEQ ID NO: 18; SEQ ID NO: 19; and SEQ ID NO: 20 which correspond to the complementarity-determining regions (CDRs, or hypervariable regions) of the variable heavy chain sequence of SEQ ID NO: 13 or the heavy chain sequence of SEQ ID NO: 14, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 11 or SEQ ID NO: 12. In another embodiment of the invention, antibody fragments of the invention comprise, or alternatively consist of, the polypeptide sequence of SEQ ID NO: 13 or SEQ ID NO: 14.

In a further embodiment of the invention, fragments of the antibody having binding specificity to NGF for treatment or prevention of pain and pain associated conditions optionally comprise, or alternatively consist of, one or more of the polypeptide sequences of SEQ ID NO: 15; SEQ ID NO: 16; and SEQ ID NO: 17 which correspond to the complementarity-determining regions (CDRs, or hypervariable regions) of the variable light chain sequence of SEQ ID NO: 11 or the light chain sequence of SEQ ID NO: 12.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 18; SEQ ID NO: 19; and SEQ ID NO: 20 which correspond to the complementarity-determining regions (CDRs, or hypervariable regions) of the variable heavy chain sequence of SEQ ID NO: 13 or the heavy chain sequence of SEQ ID NO: 14.

The invention also optionally contemplates antibody fragments which include one or more of the antibody fragments described herein. In one embodiment of the invention, fragments of the antibodies having binding specificity to NGF for treatment or prevention of pain and pain associated conditions comprise, or alternatively consist of, one, two, three or more, including all of the following antibody fragments: the variable light chain region of SEQ ID NO: 11; the variable heavy chain region of SEQ ID NO: 13; the complementarity-determining regions (SEQ ID NO: 15; SEQ ID NO: 16; and SEQ ID NO: 17) of the variable light chain region of SEQ ID NO: 11; and the complementarity-determining regions (SEQ ID NO: 18; SEQ ID NO: 19; and SEQ ID NO: 20) of the variable heavy chain region of SEQ ID NO: 13.

In a particularly preferred optional embodiment of the invention, the chimeric or humanized anti-NGF antibody for treatment or prevention of pain and pain associated conditions optionally is Ab2, comprising, or alternatively consisting of, SEQ ID NO: 12 and SEQ ID NO: 14, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF or a Fab or other monovalent antibody fragment that binds to the same or overlapping epitope as Ab2. With respect to antibody Ab2, the Fab fragment includes the variable light chain sequence of SEQ ID NO: 11 and the variable heavy chain sequence of SEQ ID NO: 13. This embodiment of the invention further contemplates additions, deletions, and variants of SEQ ID NO: 11 and/or SEQ ID NO: 13 in said Fab while retaining binding specificity for NGF.

In one optional embodiment of the invention described herein (infra), Fab fragments may be produced by enzymatic digestion (e.g., papain) of Ab2. In another embodiment of the invention, anti-NGF antibodies such as Ab2 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab3

The invention contemplates methods of treating pain and the specific pain associated disorders alone or is association with another active agent, e.g., an NSAID or opioid analgesic, wherein the antibodies include chimeric or humanized antibodies having binding specificity to NGF wherein the antibody is Ab3 or fragments thereof, or another antibody or antibody fragment that binds to the same or overlapping epitope as Ab3, for example as set forth below, in a therapeutically effective amount which inhibits the association of NGF with TrkA without appreciably inhibiting the association of NGF with p75. In one embodiment, the invention includes chimeric antibodies having binding specificity to NGF and possessing a variable light chain sequence comprising the sequence set forth below:

```
                                              (SEQ ID NO: 21)
AVLTQTPSPVSAAMGDTVTIKCQSSQSVYKNNYLSWYQQKPGQPPRLLI

YDASNLPSGVPSRFSGSGSGTQFTLTISGVQCDDAATYYCLGDYDDDAD

NAFGGGTEVVVKR.
```

The invention also includes chimeric antibodies or treatment or prevention of pain and pain associated conditions having binding specificity to NGF and possessing a light chain sequence comprising the sequence set forth below:

```
                                              (SEQ ID NO: 22)
AVLTQTPSPVSAAMGDTVTIKCQSSQSVYKNNYLSWYQQKPGQPPRLLI

YDASNLPSGVPSRFSGSGSGTQFTLTISGVQCDDAATYYCLGDYDDDAD

NAFGGGTEVVVKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.
```

The invention further includes chimeric antibodies for treatment or prevention of pain and pain associated conditions having binding specificity to NGF and possessing a variable heavy chain sequence comprising the sequence set forth below:

```
                                              (SEQ ID NO: 23)
QSVEESGGRLVTPGTPLTLTCTVSGFSLSSYVMIWVRQAPGKGLEYIGI

TWSAGTYYASWAKGRFTISKTSSTTVDLKITSPTTEDTATYFCAGGGGS

IYDIWGPGTLVTVSS.
```

The invention also includes chimeric antibodies for treatment or prevention of pain and pain associated conditions having binding specificity to NGF and possessing a heavy chain sequence comprising the sequence set forth below:

```
                                              (SEQ ID NO: 24)
QSVEESGGRLVTPGTPLTLTCTVSGFSLSSYVMIWVRQAPGKGLEYIGIT

WSAGTYYASWAKGRFTISKTSSTTVDLKITSPTTEDTATYFCAGGGGSIY

DIWGPGTLVTVSSASTKGPSVFPLAPSSKSTSGGTAALGCLVKDYFPEPV

-continued
TVSWNSGALTSGVHTFPAVLQSSGLYSLSSVVTVPSSSLGTQTYICNVNH

KPSNTKVDKRVEPKSCDKTHTCPPCPAPELLGGPSVFLFPPKPKDTLMIS

RTPEVTCVVVDVSHEDPEVKFNWYVDGVEVHNAKTKPREEQYASTYRVVS

VLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSF

FLYSKLTVDKSRWQQGNVFSCSVMHEALHNHYTQKSLSLSPGK.
```

The invention further contemplates antibodies for treatment or prevention of pain and pain associated conditions comprising one or more of the polypeptide sequences of SEQ ID NO: 25; SEQ ID NO: 26; and SEQ ID NO: 27 which correspond to the complementarity-determining regions (CDRs, or hypervariable regions) of the variable light chain sequence of SEQ ID NO: 21 or the light chain sequence of SEQ ID NO: 22, and/or one or more of the polypeptide sequences of SEQ ID NO: 28; SEQ ID NO: 29; and SEQ ID NO: 30 which correspond to the complementarity-determining regions (CDRs, or hypervariable regions) of the variable heavy chain sequence of SEQ ID NO: 23 or the heavy chain sequence of SEQ ID NO: 24, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody for treatment or prevention of pain and pain associated conditions having binding specificity to NGF. In one embodiment of the invention, antibody fragments of the invention comprise, or alternatively consist of, the polypeptide sequence of SEQ ID NO: 21 or SEQ ID NO: 22. In another embodiment of the invention, antibody fragments of the invention comprise, or alternatively consist of, the polypeptide sequence of SEQ ID NO: 23 or SEQ ID NO: 24.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 25; SEQ ID NO: 26; and SEQ ID NO: 27 which correspond to the complementarity-determining regions (CDRs, or hypervariable regions) of the variable light chain sequence of SEQ ID NO: 21 or the light chain sequence of SEQ ID NO: 22.

In a further embodiment of the invention, fragments of the antibody having binding specificity to NGF for treatment or prevention of pain and pain associated conditions comprise, or alternatively consist of, one or more of the polypeptide sequences of SEQ ID NO: 28; SEQ ID NO: 29; and SEQ ID NO: 30 which correspond to the complementarity-determining regions (CDRs, or hypervariable regions) of the variable heavy chain sequence of SEQ ID NO: 23 or the heavy chain sequence of SEQ ID NO: 24.

The invention also optionally contemplates antibody fragments which include one or more of the antibody fragments described herein for treatment or prevention of pain and pain associated conditions. In one embodiment of the invention, fragments of the antibodies having binding specificity to NGF comprise, or alternatively consist of, one, two, three or more, including all of the following antibody fragments: the variable light chain region of SEQ ID NO: 21; the variable heavy chain region of SEQ ID NO: 23; the complementarity-determining regions (SEQ ID NO: 25; SEQ ID NO: 26; and SEQ ID NO: 27) of the variable light chain region of SEQ ID NO: 21; and the complementarity-determining regions (SEQ ID NO: 28; SEQ ID NO: 29; and SEQ ID NO: 30) of the variable heavy chain region of SEQ ID NO: 23.

In a particularly preferred optional embodiment of the invention, the chimeric anti-NGF antibody for treatment or prevention of pain and pain associated conditions is Ab3, comprising, or alternatively consisting of, SEQ ID NO: 22 and SEQ ID NO: 24, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF or another Fab or monovalent antibody fragment that binds to the same or overlapping epitope as Ab3. With respect to antibody Ab3, the Fab fragment includes the variable light chain sequence of SEQ ID NO: 21 and the variable heavy chain sequence of SEQ ID NO: 23. This embodiment of the invention further contemplates additions, deletions, and variants of SEQ ID NO: 21 and/or SEQ ID NO: 23 in said Fab while retaining binding specificity for NGF.

In one optional embodiment of the invention described herein (infra), Fab fragments may be produced by enzymatic digestion (e.g., papain) of Ab3. In another embodiment of the invention, anti-NGF antibodies such as Ab3 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab4

The invention contemplates methods of treating pain and the specific pain associated disorders alone or is association with another active agent, e.g., an NSAID or opioid analgesic, wherein the antibodies include chimeric or humanized antibodies having binding specificity to NGF wherein the antibody is antibody Ab4 or fragments thereof, or another antibody or antibody fragment that binds to the same or overlapping epitope as Ab4, for example as set forth below, in a therapeutically effective amount which inhibits the association of NGF with TrkA without appreciably inhibiting the association of NGF with p75 and/or for preventing or effectively treating pain. In one embodiment, the invention includes humanized antibodies for treatment or prevention of pain and pain associated conditions having binding specificity to NGF and possessing a variable light chain sequence comprising the sequence set forth below:

(SEQ ID NO: 31)
DIQMTQSPSTLSASVGDRVTITCQSSQSVYKNNYLSWYQQKPGKAPKLLI

YDASNLPSGVPSRFSGSGSGTEFTLTISSLQPDDFATYYCLGDYDDDADN

AFGGGTKVEIKR.

The invention also includes chimeric or humanized antibodies for treatment or prevention of pain and pain associated conditions having binding specificity to NGF and possessing a light chain sequence comprising the sequence set forth below:

(SEQ ID NO: 32)
DIQMTQSPSTLSASVGDRVTITCQSSQSVYKNNYLSWYQQKPGKAPKLLI

YDASNLPSGVPSRFSGSGSGTEFTLTISSLQPDDFATYYCLGDYDDDADN

-continued
AFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

The invention further includes humanized antibodies for treatment or prevention of pain and pain associated conditions having binding specificity to NGF and possessing a variable heavy chain sequence comprising the sequence set forth below:

(SEQ ID NO: 33)
EVQLVESGGGLVQPGGSLRLSCAASGFTVSSYVMIWVRQAPGKGLEYIGI

TWSAGTYYASSAKGRFTISRDNSKNTLYLQMNSLRAEDTAVYYCAGGGGS

IYDIWGQGTLVTVSS.

The invention also includes chimeric or humanized antibodies for treatment or prevention of pain and pain associated conditions having binding specificity to NGF and possessing a heavy chain sequence comprising the sequence set forth below:

(SEQ ID NO: 34)
EVQLVESGGGLVQPGGSLRLSCAASGFTVSSYVMIWVRQAPGKGLEYIGI

TWSAGTYYASSAKGRFTISRDNSKNTLYLQMNSLRAEDTAVYYCAGGGGS

IYDIWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLM

ISRTPEVTCVVVDVSHEDPEVKFNWYVDGVEVHNAKTKPREEQYASTYRV

VSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK.

The invention further contemplates antibodies for treatment or prevention of pain and pain associated conditions comprising one or more of the polypeptide sequences of SEQ ID NO: 35; SEQ ID NO: 36; and SEQ ID NO: 37 which correspond to the complementarity-determining regions (CDRs, or hypervariable regions) of the variable light chain sequence of SEQ ID NO: 31 or the light chain sequence of SEQ ID NO: 32, and/or one or more of the polypeptide sequences of SEQ ID NO: 38; SEQ ID NO: 39; and SEQ ID NO: 40 which correspond to the complementarity-determining regions (CDRs, or hypervariable regions) of the variable heavy chain sequence of SEQ ID NO: 33 or the heavy chain sequence of SEQ ID NO: 34, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 31 or SEQ ID NO: 32. In another embodiment of the invention, antibody fragments of the invention comprise, or alternatively consist of, the polypeptide sequence of SEQ ID NO: 33 or SEQ ID NO: 34.

In a further embodiment of the invention, fragments of the antibody having binding specificity to NGF for treatment or prevention of pain and pain associated conditions comprise, or alternatively consist of, one or more of the polypeptide sequences of SEQ ID NO: 35; SEQ ID NO: 36; and SEQ ID NO: 37 which correspond to the complementarity-determining regions (CDRs, or hypervariable regions) of the variable light chain sequence of SEQ ID NO: 31 or the light chain sequence of SEQ ID NO: 32.

In a further embodiment of the invention, fragments of the antibody having binding specificity to NGF for treatment or prevention of pain and pain associated conditions comprise, or alternatively consist of, one or more of the polypeptide sequences of SEQ ID NO: 38; SEQ ID NO: 39; and SEQ ID NO: 40 which correspond to the complementarity-determining regions (CDRs, or hypervariable regions) of the variable heavy chain sequence of SEQ ID NO: 33 or the heavy chain sequence of SEQ ID NO: 34.

The invention also optional contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 31; the variable heavy chain region of SEQ ID NO: 33; the complementarity-determining regions (SEQ ID NO: 35; SEQ ID NO: 36; and SEQ ID NO: 37) of the variable light chain region of SEQ ID NO: 31; and the complementarity-determining regions (SEQ ID NO: 38; SEQ ID NO: 39; and SEQ ID NO: 40) of the variable heavy chain region of SEQ ID NO: 33.

In a particularly preferred embodiment of the invention, the chimeric or humanized anti-NGF antibody for treatment or prevention of pain and pain associated conditions is Ab4, comprising, or alternatively consisting of, SEQ ID NO: 32 and SEQ ID NO: 34, and having at least one of the biological activities set forth herein.

In a further particularly preferred embodiment of the invention, antibody fragments for treatment or prevention of pain and pain associated conditions comprise, or alternatively consist of, Fab (fragment antigen binding) fragments having binding specificity for NGF or another Fab or monovalent antibody fragment that binds to the same or overlapping epitope as Ab14. With respect to antibody Ab4, the Fab fragment includes the variable light chain sequence of SEQ ID NO: 31 and the variable heavy chain sequence of SEQ ID NO: 33. This embodiment of the invention further contemplates additions, deletions, and variants of SEQ ID NO: 31 and/or SEQ ID NO: 33 in said Fab while retaining binding specificity for NGF.

In one embodiment of the invention described herein (infra), Fab fragments for treatment or prevention of pain and pain associated conditions may be produced by enzymatic digestion (e.g., papain) of Ab4. In another embodiment of the invention, anti-NGF antibodies such as Ab4 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.
Antibody Ab5

The invention contemplates methods of treating pain and the specific pain associated disorders alone or is association with another active agent, e.g., an NSAID or opioid analgesic, wherein the antibodies optionally include Ab5 or fragments thereof, or another antibody or antibody fragment that binds to the same or overlapping epitope as Ab5, for example as set forth below, in a therapeutically effective amount which inhibits the association of NGF with TrkA and the association of NGF with p75. In one embodiment, the invention includes chimeric antibodies having binding specificity to NGF and possessing a variable light chain sequence comprising the sequence set forth below:

```
                                          (SEQ ID NO: 41)
AYDMTQTPASVEVAVGGTVTIKCQASQSIYSNLAWYQQRPGQPPKLLIYD

ASTLESGVPSRFKGSGSGTEYTLTISGVECADAASYYCQQGFTVSDIDNA

FGGGTEVVVKR.
```

The invention also optionally includes chimeric antibodies for treatment or prevention of pain and pain associated conditions having binding specificity to NGF and possessing a light chain sequence comprising the sequence set forth below:

```
                                          (SEQ ID NO: 42)
AYDMTQTPASVEVAVGGTVTIKCQASQSIYSNLAWYQQRPGQPPKLLIYD

ASTLESGVPSRFKGSGSGTEYTLTISGVECADAASYYCQQGFTVSDIDNA

FGGGTEVVVKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC.
```

The invention further optionally includes chimeric antibodies for treatment or prevention of pain and pain associated conditions having binding specificity to NGF and possessing a variable heavy chain sequence comprising the sequence set forth below:

```
                                          (SEQ ID NO: 43)
QSVEESGGRLVTPGTPLTLTCTVSGFSLSNYAVGWVRQAPGKGLEWIGII

GRNGNTWYASWARGRFTISKTSTTVDLKITSPTSEDTATYFCARGYGRSV

AYYVFNIWGPGTLVTVSS.
```

The invention also optionally includes chimeric antibodies for treatment or prevention of pain and pain associated conditions having binding specificity to NGF and possessing a heavy chain sequence comprising the sequence set forth below:

```
                                          (SEQ ID NO: 44)
QSVEESGGRLVTPGTPLTLTCTVSGFSLSNYAVGWVRQAPGKGLEWIGII

GRNGNTWYASWARGRFTISKTSTTVDLKITSPTSEDTATYFCARGYGRSV

AYYVFNIWGPGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK.
```

The invention further optionally contemplates antibodies for treatment or prevention of pain and pain associated conditions comprising one or more of the polypeptide sequences of SEQ ID NO: 45; SEQ ID NO: 46; and SEQ ID NO: 47 which correspond to the complementarity-determining regions (CDRs, or hypervariable regions) of the variable light chain sequence of SEQ ID NO: 41 or the light chain sequence of SEQ ID NO: 42, and/or one or more of the polypeptide sequences of SEQ ID NO: 48; SEQ ID NO: 49; and SEQ ID NO: 50 which correspond to the complementarity-determining regions (CDRs, or hypervariable regions) of the variable heavy chain sequence of SEQ ID NO: 43 or the heavy chain sequence of SEQ ID NO: 44, or combinations of these polypeptide sequences. In another embodiment of the invention, the antibodies of the invention or fragments thereof optionally comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 41 or SEQ ID NO: 42. In another optional embodiment of the invention, antibody fragments of the invention for treatment or prevention of pain and pain associated conditions comprise, or alternatively consist of, the polypeptide sequence of SEQ ID NO: 43 or SEQ ID NO: 44.

In a further embodiment of the invention, fragments of the antibody having binding specificity to NGF comprise, or alternatively consist of, one or more of the polypeptide sequences of SEQ ID NO: 45; SEQ ID NO: 46; and SEQ ID NO: 47 which correspond to the complementarity-determining regions (CDRs, or hypervariable regions) of the variable light chain sequence of SEQ ID NO: 41 or the light chain sequence of SEQ ID NO: 42.

In a further optional embodiment of the invention, fragments of the antibody having binding specificity to NGF for treatment or prevention of pain and pain associated conditions optionally comprise, or alternatively consist of, one or more of the polypeptide sequences of SEQ ID NO: 48; SEQ ID NO: 49; and SEQ ID NO: 50 which correspond to the complementarity-determining regions (CDRs, or hypervariable regions) of the variable heavy chain sequence of SEQ ID NO: 43 or the heavy chain sequence of SEQ ID NO: 44.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 41; the variable heavy chain region of SEQ ID NO: 43; the complementarity-determining regions (SEQ ID NO: 45; SEQ ID NO: 46; and SEQ ID NO: 47) of the variable light chain region of SEQ ID NO: 41; and the complementarity-determining regions (SEQ ID NO: 48; SEQ ID NO: 49; and SEQ ID NO: 50) of the variable heavy chain region of SEQ ID NO: 43.

In a particularly preferred optional embodiment of the invention, the optionally included chimeric anti-NGF antibody for treatment or prevention of pain and pain associated conditions is Ab5, comprising, or alternatively consisting of, SEQ ID NO: 42 and SEQ ID NO: 44, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF or another Fab or antibody fragment that binds to the same or overlapping epitope as Ab5. With respect to antibody Ab5, the Fab fragment includes the variable light chain sequence of SEQ ID NO: 41 and the variable heavy chain sequence of SEQ ID NO: 43. This embodiment of the invention further contemplates additions, deletions, and variants of SEQ ID NO: 41 and/or SEQ ID NO: 43 in said Fab while retaining binding specificity for NGF.

In one embodiment of the invention described herein (infra), Fab fragments for treatment or prevention of pain and pain associated conditions may be produced by enzymatic digestion (e.g., papain) of Ab5. In another embodiment of the invention, anti-NGF antibodies such as Ab5 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab6

The invention optionally contemplates methods of treating pain and the specific pain associated disorders alone or is association with another active agent, e.g., an NSAID or opioid analgesic, wherein the antibodies include Ab6 or fragments thereof, or another antibody or antibody fragment that binds to the same or overlapping epitope as Ab6, for example as set forth below, in a therapeutically effective amount which inhibits the association of NGF with TrkA and the association of NGF with p75. In one embodiment, the invention includes chimeric or humanized antibodies having binding specificity to NGF and possessing a variable light chain sequence comprising the sequence set forth below:

```
                                          (SEQ ID NO: 51)
DIQMTQSPSTLSASVGDRVTITCQASQSIYSNLAWYQQKPGKAPKLLIYD

ASTLESGVPSRFSGSGSGTEYTLTISSLQPDDFATYYCQQGFTVSDIDNA

FGGGTKVEIKR.
```

The invention also optionally includes chimeric or humanized antibodies for treatment or prevention of pain and pain associated conditions having binding specificity to NGF and possessing a light chain sequence comprising the sequence set forth below:

```
                                          (SEQ ID NO: 52)
DIQMTQSPSTLSASVGDRVTITCQASQSIYSNLAWYQQKPGKAPKLLIYD

ASTLESGVPSRFSGSGSGTEYTLTISSLQPDDFATYYCQQGFTVSDIDNA

FGGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC.
```

The invention further optionally includes chimeric or humanized antibodies for treatment or prevention of pain and pain associated conditions having binding specificity to NGF and possessing a variable heavy chain sequence comprising the sequence set forth below:

(SEQ ID NO: 53)
EVQLVESGGGLVQPGGSLRLSCAASGFTVSNYAVGWVRQAPGKGLEWVGI

IGRNGNTWYASSARGRFTISRDNSKNTLYLQMNSLRAEDTAVYYCARGYG

RSVAYYVFNIWGPGTLVTVSS.

The invention also optionally includes chimeric or humanized antibodies for treatment or prevention of pain and pain associated conditions having binding specificity to NGF and possessing a heavy chain sequence comprising the sequence set forth below:

(SEQ ID NO: 54)
EVQLVESGGGLVQPGGSLRLSCAASGFTVSNYAVGWVRQAPGKGLEWVGI

IGRNGNTWYASSARGRFTISRDNSKNTLYLQMNSLRAEDTAVYYCARGYG

RSVAYYVFNIWGPGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

ASTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K.

The invention further optionally contemplates antibodies for treatment or prevention of pain and pain associated conditions comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 52, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 54, or combinations of these polypeptide sequences. In another optional embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody for treatment or prevention of pain and pain associated conditions having binding specificity to NGF. In one embodiment of the invention, antibody fragments of the invention comprise, or alternatively consist of, the polypeptide sequence of SEQ ID NO: 51 or SEQ ID NO: 52. In another embodiment of the invention, antibody fragments of the invention comprise, or alternatively consist of, the polypeptide sequence of SEQ ID NO: 53 or SEQ ID NO: 54.

In a further optional embodiment of the invention, fragments of the antibody having binding specificity to NGF comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 52.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 54.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 51; the variable heavy chain region of SEQ ID NO: 53; the complementarity-determining regions (SEQ ID NO: 55; SEQ ID NO: 56; and SEQ ID NO: 57) of the variable light chain region of SEQ ID NO: 51; and the complementarity-determining regions (SEQ ID NO: 58; SEQ ID NO: 59; and SEQ ID NO: 60) of the variable heavy chain region of SEQ ID NO: 53.

In a particularly preferred optional embodiment of the invention, the chimeric or humanized anti-NGF antibody for treatment or prevention of pain and pain associated conditions is Ab6, comprising, or alternatively consisting of, SEQ ID NO: 52 and SEQ ID NO: 54, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF or another Fab or monovalent antibody fragment that binds to the same or overlapping epitope as Ab6. With respect to antibody Ab6, the Fab fragment includes the variable light chain sequence of SEQ ID NO: 51 and the variable heavy chain sequence of SEQ ID NO: 53. This optional embodiment of the invention further contemplates additions, deletions, and variants of SEQ ID NO: 51 and/or SEQ ID NO: 53 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab6. In another embodiment of the invention, anti-NGF antibodies such as Ab6 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab7

The invention optionally contemplates methods of treating pain and the specific pain associated disorders alone or is association with another active agent, e.g., an NSAID or opioid analgesic, wherein the antibodies include Ab7 or fragments thereof, or another antibody or antibody fragment that binds to the same or overlapping epitope as Ab7, for example as set forth below, in a therapeutically effective amount which inhibits the association of NGF with TrkA and the association of NGF with p75. In one embodiment, the invention includes chimeric antibodies for treatment or prevention of pain and pain associated conditions having binding specificity to NGF and possessing a variable light chain sequence comprising the sequence set forth below:

```
                                                     (SEQ ID NO: 61)
ADVVMTQTPASVSQPVGGTVTIKCQASEDIYNLLAWYQQKPGQPPKLLIY

SASTLASGVPSRFKGSGSGTEYTLTISGLECADAATYYCQNNYLVTTYGV

AFGGGTEVVVKR.
```

The invention also optionally includes chimeric antibodies for treatment or prevention of pain and pain associated conditions having binding specificity to NGF and possessing a light chain sequence comprising the sequence set forth below:

```
                                                     (SEQ ID NO: 62)
ADVVMTQTPASVSQPVGGTVTIKCQASEDIYNLLAWYQQKPGQPPKLLIY

SASTLASGVPSRFKGSGSGTEYTLTISGLECADAATYYCQNNYLVTTYGV

AFGGGTEVVVKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

The invention further optionally includes chimeric antibodies for treatment or prevention of pain and pain associated conditions having binding specificity to NGF and possessing a variable heavy chain sequence comprising the sequence set forth below:

```
                                                     (SEQ ID NO: 63)
QEQLKESGGRLVTPGTPLTLTCTVSGFSLSSYAMIWVRQAPGKGLEYIG

YIDTDTSAYYASWVKGRFTISRTSTTVDLKITSPTTEDTATYFCARSYA

AYGGYPATFDPWGPGTLVTVSS.
```

The invention also optionally includes chimeric antibodies for treatment or prevention of pain and pain associated conditions having binding specificity to NGF and possessing a heavy chain sequence comprising the sequence set forth below:

```
                                                     (SEQ ID NO: 64)
QEQLKESGGRLVTPGTPLTLTCTVSGFSLSSYAMIWVRQAPGKGLEYIG

YIDTDTSAYYASWVKGRFTISRTSTTVDLKITSPTTEDTATYFCARSYA

AYGGYPATFDPWGPGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKP

REEQYASTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK.
```

The invention further optionally contemplates antibodies for treatment or prevention of pain and pain associated conditions comprising one or more of the polypeptide sequences of SEQ ID NO: 65; SEQ ID NO: 66; and SEQ ID NO: 67 which correspond to the complementarity-determining regions (CDRs, or hypervariable regions) of the variable light chain sequence of SEQ ID NO: 61 or the light chain sequence of SEQ ID NO: 62, and/or one or more of the polypeptide sequences of SEQ ID NO: 68; SEQ ID NO: 69; and SEQ ID NO: 70 which correspond to the complementarity-determining regions (CDRs, or hypervariable regions) of the variable heavy chain sequence of SEQ ID NO: 63 or the heavy chain sequence of SEQ ID NO: 64, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody for treatment or prevention of pain and pain associated conditions having binding specificity to NGF. In one embodiment of the invention, antibody fragments of the invention comprise, or alternatively consist of, the polypeptide sequence of SEQ ID NO: 61 or SEQ ID NO: 62. In another embodiment of the invention, antibody fragments of the invention comprise, or alternatively consist of, the polypeptide sequence of SEQ ID NO: 63 or SEQ ID NO: 64.

In a further optional embodiment of the invention, fragments of the antibody for treatment or prevention of pain and pain associated conditions having binding specificity to NGF comprise, or alternatively consist of, one or more of the polypeptide sequences of SEQ ID NO: 65; SEQ ID NO: 66; and SEQ ID NO: 67 which correspond to the complementarity-determining regions (CDRs, or hypervariable regions) of the variable light chain sequence of SEQ ID NO: 61 or the light chain sequence of SEQ ID NO: 62.

In a further optional embodiment of the invention, fragments of the antibody for treatment or prevention of pain and pain associated conditions having binding specificity to NGF comprise, or alternatively consist of, one or more of the polypeptide sequences of SEQ ID NO: 68; SEQ ID NO: 69; and SEQ ID NO: 70 which correspond to the complementarity-determining regions (CDRs, or hypervariable regions) of the variable heavy chain sequence of SEQ ID NO: 63 or the heavy chain sequence of SEQ ID NO: 64.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 61; the variable heavy chain region of SEQ ID NO: 63; the complementarity-determining regions (SEQ ID NO: 65; SEQ ID NO: 66; and SEQ ID NO: 67) of the variable light chain region of SEQ ID NO: 61; and the complementarity-determining regions (SEQ ID NO: 68; SEQ ID NO: 69; and SEQ ID NO: 70) of the variable heavy chain region of SEQ ID NO: 63.

In a particularly preferred optional embodiment of the invention, the chimeric anti-NGF antibody for treatment or prevention of pain and pain associated conditions is Ab7, comprising, or alternatively consisting of, SEQ ID NO: 62 and SEQ ID NO: 64, and having at least one of the biological activities set forth herein.

In a further particularly optionally preferred embodiment of the invention, antibody fragments for treatment or prevention of pain and pain associated conditions comprise, or alternatively consist of, Fab (fragment antigen binding) fragments having binding specificity for NGF or another Fab or monovalent antibody fragment that binds to the same or overlapping epitope as Ab7. With respect to antibody Ab7, the Fab fragment includes the variable light chain sequence of SEQ ID NO: 61 and the variable heavy chain sequence of SEQ ID NO: 63. This embodiment of the invention further contemplates additions, deletions, and variants of SEQ ID NO: 61 and/or SEQ ID NO: 63 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab7. In another embodiment of the invention, anti-NGF antibodies such as Ab7 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab8

The invention optionally contemplates methods of treating pain and the specific pain associated disorders alone or is association with another active agent, e.g., an NSAID or opioid analgesic, wherein the antibodies include Ab8 or fragments thereof, or another antibody or fragment that binds to the same or overlapping epitope as Ab8, for example as set forth below, in a therapeutically effective amount which inhibits the association of NGF with TrkA and the association of NGF with p75. In one embodiment, the invention includes chimeric or humanized antibodies having binding specificity to NGF and possessing a variable light chain sequence comprising the sequence set forth below:

```
                                              (SEQ ID NO: 71)
DIQMTQSPSSLSASVGDRVTITCQASEDIYNLLAWYQQKPGKVPKLLIY

SASTLASGVPSRFSGSGSGTDYTLTISSLQPEDVATYYCQNNYLVTTYG

VAFGGGTKVEIKR.
```

The invention also optionally includes chimeric or humanized antibodies for treatment or prevention of pain and pain associated conditions having binding specificity to NGF and possessing a light chain sequence comprising the sequence set forth below:

```
                                              (SEQ ID NO: 72)
DIQMTQSPSSLSASVGDRVTITCQASEDIYNLLAWYQQKPGKVPKLLIY

SASTLASGVPSRFSGSGSGTDYTLTISSLQPEDVATYYCQNNYLVTTYG

VAFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.
```

The invention further optionally includes chimeric or humanized antibodies for treatment or prevention of pain and pain associated conditions having binding specificity to NGF and possessing a variable heavy chain sequence comprising the sequence set forth below:

```
                                              (SEQ ID NO: 73)
QVQLVESGGGVVQPGRSLRLSCAASGFTFSSYAMIWVRQAPGKGLEYIG

YIDTDTSAYYASSVKGRFTISRDNSKNTLYLQMSSLRAEDTAVYYCARS

YAAYGGYPATFDPWGQGTLVTVSS.
```

The invention also optionally includes chimeric or humanized antibodies for treatment or prevention of pain and pain associated conditions having binding specificity to NGF and possessing a heavy chain sequence comprising the sequence set forth below:

```
                                              (SEQ ID NO: 74)
QVQLVESGGGVVQPGRSLRLSCAASGFTFSSYAMIWVRQAPGKGLEYIG

YIDTDTSAYYASSVKGRFTISRDNSKNTLYLQMSSLRAEDTAVYYCARS

YAAYGGYPATFDPWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSV

FLFPPKPKDTLMISRTPEVTCVVVDVSHEDPEVKFNWYVDGVEVHNAKT

KPREEQYASTYRVVSVLTVLHQDWLNGKEYKCKVSNKALPAPIEKTISK

AKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHY

TQKSLSLSPGK.
```

The invention further optionally contemplates antibodies for treatment or prevention of pain and pain associated conditions comprising one or more of the polypeptide sequences of SEQ ID NO: 75; SEQ ID NO: 76; and SEQ ID NO: 77 which correspond to the complementarity-determining regions (CDRs, or hypervariable regions) of the variable light chain sequence of SEQ ID NO: 71 or the light chain sequence of SEQ ID NO: 72, and/or one or more of the polypeptide sequences of SEQ ID NO: 78; SEQ ID NO: 79; and SEQ ID NO: 80 which correspond to the complementarity-determining regions (CDRs, or hypervariable regions) of the variable heavy chain sequence of SEQ ID NO: 73 or the heavy chain sequence of SEQ ID NO: 74, or combinations of these polypeptide sequences. In another optional embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody for treatment or prevention of pain and pain associated conditions having binding specificity to NGF. In one embodiment of the invention, antibody fragments of the invention comprise, or alternatively consist of, the polypeptide sequence of SEQ ID NO: 71 or SEQ ID NO: 72. In another embodiment of the invention, antibody fragments of the invention comprise, or alternatively consist of, the polypeptide sequence of SEQ ID NO: 73 or SEQ ID NO: 74.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 75; SEQ ID NO: 76; and SEQ ID NO: 77 which correspond to the complementarity-determining regions (CDRs, or hypervariable regions) of the variable light chain sequence of SEQ ID NO: 71 or the light chain sequence of SEQ ID NO: 72.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 78; SEQ ID NO: 79; and SEQ ID NO: 80 which correspond to the complementarity-determining regions (CDRs, or hypervariable regions) of the variable heavy chain sequence of SEQ ID NO: 73 or the heavy chain sequence of SEQ ID NO: 74.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 71; the variable heavy chain region of SEQ ID NO: 73; the complementarity-determining regions (SEQ ID NO: 75; SEQ ID NO: 76; and SEQ ID NO: 77) of the variable light chain region of SEQ ID NO: 71; and the complementarity-determining regions (SEQ ID NO: 78; SEQ ID NO: 79; and SEQ ID NO: 80) of the variable heavy chain region of SEQ ID NO: 73.

In a particularly preferred optional embodiment of the invention, the chimeric or humanized anti-NGF antibody for treatment or prevention of pain and pain associated conditions is Ab8, comprising, or alternatively consisting of, SEQ ID NO: 72 and SEQ ID NO: 74, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab8, the Fab fragment includes the variable light chain sequence of SEQ ID NO: 71 and the variable heavy chain sequence of SEQ ID NO: 73 or another Fab or monovalent antibody fragment that binds to the same or overlapping epitope as Ab8. This embodiment of the invention further contemplates additions, deletions, and variants of SEQ ID NO: 71 and/or SEQ ID NO: 73 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab8. In another embodiment of the invention, anti-NGF antibodies such as Ab8 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab9

The invention optionally contemplates methods of treating pain and the specific pain associated disorders alone or is association with another active agent, e.g., an NSAID or opioid analgesic, wherein the antibodies include Ab9 or fragments thereof, or another antibody or antibody fragment that binds to the same or overlapping epitope as Ab9, for example as set forth below, in a therapeutically effective amount which inhibits the association of NGF with TrkA and the association of NGF with p75. In one optional embodiment, the invention includes chimeric antibodies for treatment or prevention of pain and pain associated conditions having binding specificity to NGF and possessing a variable light chain sequence comprising the sequence set forth below:

(SEQ ID NO: 81)
AYDMTQTPASVSAAVGGTVTIKCQASENIGSYLAWYQQKPGQPPELLIY

RASTLASGVPSRFKGSGSGTQFTLTISGVECADAATYYCQQGYNSENLD

NAFGGGTEVVVKR.

The invention also optionally includes chimeric antibodies for treatment or prevention of pain and pain associated conditions having binding specificity to NGF and possessing a light chain sequence comprising the sequence set forth below:

(SEQ ID NO: 82)
AYDMTQTPASVSAAVGGTVTIKCQASENIGSYLAWYQQKPGQPPELLIY

RASTLASGVPSRFKGSGSGTQFTLTISGVECADAATYYCQQGYNSENLD

NAFGGGTEVVVKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.

The invention further optionally includes chimeric antibodies for treatment or prevention of pain and pain associated conditions having binding specificity to NGF and possessing a variable heavy chain sequence comprising the sequence set forth below:

(SEQ ID NO: 83)
QSVEESGGRLVTPGTPLTLTCTVSGIDLSMYSMGWVRQAPGKGLEYIGW

ISYGGTAYYASWAKGRFTISKTSTTVELKITSPTIEDTATYFCARETPV

NYYLDIWGQGTLVTVSS.

The invention also optionally includes chimeric antibodies for treatment or prevention of pain and pain associated conditions having binding specificity to NGF and possessing a heavy chain sequence comprising the sequence set forth below:

(SEQ ID NO: 84)
QSVEESGGRLVTPGTPLTLTCTVSGIDLSMYSMGWVRQAPGKGLEYIGW

ISYGGTAYYASWAKGRFTISKTSTTVELKITSPTIEDTATYFCARETPV

NYYLDIWGQGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQY

ASTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSL

SPGK.

The invention further optionally contemplates antibodies for treatment or prevention of pain and pain associated conditions comprising one or more of the polypeptide sequences of SEQ ID NO: 85; SEQ ID NO: 86; and SEQ ID NO: 87 which correspond to the complementarity-determining regions (CDRs, or hypervariable regions) of the variable light chain sequence of SEQ ID NO: 81 or the light chain sequence of SEQ ID NO: 82, and/or one or more of the polypeptide sequences of SEQ ID NO: 88; SEQ ID NO: 89; and SEQ ID NO: 90 which correspond to the complementarity-determining regions (CDRs, or hypervariable regions) of the variable heavy chain sequence of SEQ ID NO: 83 or the heavy chain sequence of SEQ ID NO: 84, or combinations of these polypeptide sequences. In another optional embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody for treatment or prevention of pain and pain associated conditions having binding specificity to NGF. In one embodiment of the invention, antibody fragments of the invention comprise, or alternatively consist of, the polypeptide sequence of SEQ ID NO: 81 or SEQ ID NO: 82. In another embodiment of the invention, antibody fragments of the invention comprise, or alternatively consist of, the polypeptide sequence of SEQ ID NO: 83 or SEQ ID NO: 84.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 85; SEQ ID NO: 86; and SEQ ID NO: 87 which correspond to the complementarity-determining regions (CDRs, or hypervariable regions) of the variable light chain sequence of SEQ ID NO: 81 or the light chain sequence of SEQ ID NO: 82.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 88; SEQ ID NO: 89; and SEQ ID NO: 90 which correspond to the complementarity-determining regions (CDRs, or hypervariable regions) of the variable heavy chain sequence of SEQ ID NO: 83 or the heavy chain sequence of SEQ ID NO: 84.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 81; the variable heavy chain region of SEQ ID NO: 83; the complementarity-determining regions (SEQ ID NO: 85; SEQ ID NO: 86; and SEQ ID NO: 87) of the variable light chain region of SEQ ID NO: 81; and the complementarity-determining regions (SEQ ID NO: 88; SEQ ID NO: 89; and SEQ ID NO: 90) of the variable heavy chain region of SEQ ID NO: 83.

In a particularly preferred optional embodiment of the invention, the chimeric anti-NGF antibody for treatment or prevention of pain and pain associated conditions is Ab9, comprising, or alternatively consisting of, SEQ ID NO: 82 and SEQ ID NO: 84, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab9, the Fab fragment includes the variable light chain sequence of SEQ ID NO: 81 and the variable heavy chain sequence of SEQ ID NO: 83 or another Fab or monovalent antibody fragment that binds to the same or overlapping epitope as Ab9. This embodiment of the invention further contemplates additions, deletions, and variants of SEQ ID NO: 81 and/or SEQ ID NO: 83 in said Fab while retaining binding specificity for NGF.

In one embodiment of the invention described herein (infra), Fab fragments for treatment or prevention of pain and pain associated conditions may be produced by enzymatic digestion (e.g., papain) of Ab9. In another optional embodiment of the invention, anti-NGF antibodies such as Ab9 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab10

The invention optionally contemplates methods of treating pain and the specific pain associated disorders alone or is association with another active agent, e.g., an NSAID or opioid analgesic, wherein the antibodies include Ab10 or fragments thereof, or another antibody or antibody fragment that binds to the same or overlapping epitope as Ab10, for example as set forth below, in a therapeutically effective amount which inhibits the association of NGF with TrkA and the association of NGF with p75. In one embodiment, the invention includes chimeric or humanized antibodies for treatment or prevention of pain and pain associated conditions having binding specificity to NGF and possessing a variable light chain sequence comprising the sequence set forth below:

```
                                           (SEQ ID NO: 91)
AYDMTQSPSSLSASVGDRVTITCQASENIGSYLAWYQQKPGKVPKLLIY

RASTLASGVPSRFSGSGSGTDFTLTISSLQPEDVATYYCQQGYNSENLD

NAFGGGTKVEIKR.
```

The invention also optionally includes chimeric or humanized antibodies for treatment or prevention of pain and pain associated conditions having binding specificity to NGF and possessing a light chain sequence comprising the sequence set forth below:

```
                                           (SEQ ID NO: 92)
AYDMTQSPSSLSASVGDRVTITCQASENIGSYLAWYQQKPGKVPKLLIY

RASTLASGVPSRFSGSGSGTDFTLTISSLQPEDVATYYCQQGYNSENLD

NAFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.
```

The invention further optionally includes chimeric or humanized antibodies for treatment or prevention of pain and pain associated conditions having binding specificity to NGF and possessing a variable heavy chain sequence comprising the sequence set forth below:

```
                                           (SEQ ID NO: 93)
QVQLVESGGGVVQPGRSLRLSCAASGFTFSMYSMGWVRQAPGKGLEYIG

WISYGGTAYYASSAKGRFTISRDNSKNTLYLQMSSLRAEDTAVYYCARE

TPVNYYLDIWGQGTLVTVSS.
```

The invention also optionally includes chimeric or humanized antibodies for treatment or prevention of pain and pain associated conditions having binding specificity to NGF and possessing a heavy chain sequence comprising the sequence set forth below:

```
                                           (SEQ ID NO: 94)
QVQLVESGGGVVQPGRSLRLSCAASGFTFSMYSMGWVRQAPGKGLEYIG

WISYGGTAYYASSAKGRFTISRDNSKNTLYLQMSSLRAEDTAVYYCARE

TPVNYYLDIWGQGTLVTVSSASTKGPSVFPLAPSSKSTSGGTAALGCLV
```

```
KDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK.
```

The invention further optionally contemplates antibodies for treatment or prevention of pain and pain associated conditions comprising one or more of the polypeptide sequences of SEQ ID NO: 95; SEQ ID NO: 96; and SEQ ID NO: 97 which correspond to the complementarity-determining regions (CDRs, or hypervariable regions) of the variable light chain sequence of SEQ ID NO: 91 or the light chain sequence of SEQ ID NO: 92, and/or one or more of the polypeptide sequences of SEQ ID NO: 98; SEQ ID NO: 99; and SEQ ID NO: 100 which correspond to the complementarity-determining regions (CDRs, or hypervariable regions) of the variable heavy chain sequence of SEQ ID NO: 93 or the heavy chain sequence of SEQ ID NO: 94, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody for treatment or prevention of pain and pain associated conditions having binding specificity to NGF. In one embodiment of the invention, antibody fragments of the invention comprise, or alternatively consist of, the polypeptide sequence of SEQ ID NO: 91 or SEQ ID NO: 92. In another embodiment of the invention, antibody fragments of the invention comprise, or alternatively consist of, the polypeptide sequence of SEQ ID NO: 93 or SEQ ID NO: 94.

In a further embodiment of the invention, fragments of the antibody having binding specificity to NGF for treatment or prevention of pain and pain associated conditions optionally comprise, or alternatively consist of, one or more of the polypeptide sequences of SEQ ID NO: 95; SEQ ID NO: 96; and SEQ ID NO: 97 which correspond to the complementarity-determining regions (CDRs, or hypervariable regions) of the variable light chain sequence of SEQ ID NO: 91 or the light chain sequence of SEQ ID NO: 92.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 98; SEQ ID NO: 99; and SEQ ID NO: 100 which correspond to the complementarity-determining regions (CDRs, or hypervariable regions) of the variable heavy chain sequence of SEQ ID NO: 93 or the heavy chain sequence of SEQ ID NO: 94.

The invention also optionally contemplates antibody fragments for treatment or prevention of pain and pain associated conditions which include one or more of the antibody fragments described herein. In one embodiment of the invention, fragments of the antibodies for treatment or prevention of pain and pain associated conditions having binding specificity to NGF comprise, or alternatively consist of, one, two, three or more, including all of the following antibody fragments: the variable light chain region of SEQ ID NO: 91; the variable heavy chain region of SEQ ID NO: 93; the complementarity-determining regions (SEQ ID NO: 95; SEQ ID NO: 96; and SEQ ID NO: 97) of the variable light chain region of SEQ ID NO: 91; and the complementarity-determining regions (SEQ ID NO: 98; SEQ ID NO: 99; and SEQ ID NO: 100) of the variable heavy chain region of SEQ ID NO: 93.

In a particularly preferred optional embodiment of the invention, the chimeric or humanized anti-NGF antibody for treatment or prevention of pain and pain associated conditions is Ab10, comprising, or alternatively consisting of, SEQ ID NO: 92 and SEQ ID NO: 94, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab10, the Fab fragment for treatment or prevention of pain and pain associated conditions includes the variable light chain sequence of SEQ ID NO: 91 and the variable heavy chain sequence of SEQ ID NO: 93 or another Fab or monovalent antibody fragment that binds to the same or overlapping epitope as Ab10. This embodiment of the invention further optionally contemplates additions, deletions, and variants of SEQ ID NO: 91 and/or SEQ ID NO: 93 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab10. In another embodiment of the invention, anti-NGF antibodies such as Ab10 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab11

The invention optionally contemplates methods of treating pain and the specific pain associated disorders alone or is association with another active agent, e.g., an NSAID or opioid analgesic, wherein the antibodies include Ab11 or fragments thereof, or another antibody or antibody fragment that binds to the same or overlapping epitope as Ab11, for example as set forth below, in a therapeutically effective amount which inhibits the association of NGF with TrkA and the association of NGF with p75. In one optional embodiment, the invention includes chimeric antibodies having binding specificity to NGF and possessing a variable light chain sequence comprising the sequence set forth below:

```
                                           (SEQ ID NO: 101)
AFELTQTPSSVEAAVGGTVTIKCQASQNIVTNLAWYQQKPGQPPKLLIY

GASTLASGVSSRFKGSGSGTQFTLTISDLECADAATYFCQSYDGFNSAG

FGGGTEVVVKR.
```

The invention also optionally includes chimeric antibodies for treatment or prevention of pain and pain associated conditions having binding specificity to NGF and possessing a light chain sequence comprising the sequence set forth below:

```
                                                    (SEQ ID NO: 102)
AFELTQTPSSVEAAVGGTVTIKCQASQNIVTNLAWYQQKPGQPPKLLIYG

ASTLASGVSSRFKGSGSGTQFTLTISDLECADAATYFCQSYDGFNSAGFG

GGTEVVVKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC.
```

The invention further optionally includes chimeric antibodies for treatment or prevention of pain and pain associated conditions having binding specificity to NGF and possessing a variable heavy chain sequence comprising the sequence set forth below:

```
                                                    (SEQ ID NO: 103)
QSLEESGGRLVTPGTPLTLTCTASGFSLSGYDMSWVRQAPGKGLEYIGLI

SYDGNTYYATWAKGRFTISKTSTTVDLKITSPTTEDTATYFCARSLYAGP

NAGIGPFNIWGQGTLVTVSS.
```

The invention also optionally includes chimeric antibodies for treatment or prevention of pain and pain associated conditions having binding specificity to NGF and possessing a heavy chain sequence comprising the sequence set forth below:

```
                                                    (SEQ ID NO: 104)
QSLEESGGRLVTPGTPLTLTCTASGFSLSGYDMSWVRQAPGKGLEYIGLI

SYDGNTYYATWAKGRFTISKTSTTVDLKITSPTTEDTATYFCARSLYAGP

NAGIGPFNIWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYA

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG

K.
```

The invention further optionally contemplates antibodies for treatment or prevention of pain and pain associated conditions comprising one or more of the polypeptide sequences of SEQ ID NO: 105; SEQ ID NO: 106; and SEQ ID NO: 107 which correspond to the complementarity-determining regions (CDRs, or hypervariable regions) of the variable light chain sequence of SEQ ID NO: 101 or the light chain sequence of SEQ ID NO: 102, and/or one or more of the polypeptide sequences of SEQ ID NO: 108; SEQ ID NO: 109; and SEQ ID NO: 110 which correspond to the complementarity-determining regions (CDRs, or hypervariable regions) of the variable heavy chain sequence of SEQ ID NO: 103 or the heavy chain sequence of SEQ ID NO: 104, or combinations of these polypeptide sequences. In another optional embodiment of the invention, the antibodies of the invention or fragments thereof optionally comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 101 or SEQ ID NO: 102. In another optional embodiment of the invention, antibody fragments of the invention comprise, or alternatively consist of, the polypeptide sequence of SEQ ID NO: 103 or SEQ ID NO: 104.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 105; SEQ ID NO: 106; and SEQ ID NO: 107 which correspond to the complementarity-determining regions (CDRs, or hypervariable regions) of the variable light chain sequence of SEQ ID NO: 101 or the light chain sequence of SEQ ID NO: 102.

In a further optional embodiment of the invention, fragments of the antibody for treatment or prevention of pain and pain associated conditions having binding specificity to NGF comprise, or alternatively consist of, one or more of the polypeptide sequences of SEQ ID NO: 108; SEQ ID NO: 109; and SEQ ID NO: 110 which correspond to the complementarity-determining regions (CDRs, or hypervariable regions) of the variable heavy chain sequence of SEQ ID NO: 103 or the heavy chain sequence of SEQ ID NO: 104.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 101; the variable heavy chain region of SEQ ID NO: 103; the complementarity-determining regions (SEQ ID NO: 105; SEQ ID NO: 106; and SEQ ID NO: 107) of the variable light chain region of SEQ ID NO: 101; and the complementarity-determining regions (SEQ ID NO: 108; SEQ ID NO: 109; and SEQ ID NO: 110) of the variable heavy chain region of SEQ ID NO: 103.

In a particularly preferred optional embodiment of the invention, the chimeric anti-NGF antibody for treatment or prevention of pain and pain associated conditions is Ab11, comprising, or alternatively consisting of, SEQ ID NO: 102 and SEQ ID NO: 104, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab11, the Fab fragment includes the variable light chain sequence of SEQ ID NO: 101 and the variable heavy chain sequence of SEQ ID NO: 103 or comprises another Fab or monovalent antibody fragment that binds to the same or overlapping epitope as Ab11. This embodiment of the invention further contemplates additions, deletions, and variants of SEQ ID NO: 101 and/or SEQ ID NO: 103 in said Fab while retaining binding specificity for NGF.

In one optional embodiment of the invention described herein (infra), Fab fragments may for treatment or prevention of pain and pain associated conditions be produced by enzymatic digestion (e.g., papain) of Ab11. In another optional embodiment of the invention, anti-NGF antibodies such as Ab11 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab12

The invention optionally contemplates methods of treating pain and the specific pain associated disorders alone or is association with another active agent, e.g., an NSAID or opioid analgesic, wherein the antibodies include Ab12 or fragments thereof, for another antibody or antibody fragment that binds to the same or overlapping epitope as Ab12, or example as set forth below, in a therapeutically effective amount which inhibits the association of NGF with TrkA and the association of NGF with p75. In one embodiment, the invention includes chimeric or humanized antibodies for treatment or prevention of pain and pain associated conditions having binding specificity to NGF and possessing a variable light chain sequence comprising the sequence set forth below:

(SEQ ID NO: 111)
AFQMTQSPSSLSASVGDRVTITCQASQNIVTNLAWYQQKPGKVPKLLIYG

ASTLASGVPSRFSGSGSGTDFTLTISSLQPEDVATYYCQSYDGFNSAGFG

GGTKVEIKR.

The invention also optionally includes chimeric or humanized antibodies for treatment or prevention of pain and pain associated conditions having binding specificity to NGF and possessing a light chain sequence comprising the sequence set forth below:

(SEQ ID NO: 112)
AFQMTQSPSSLSASVGDRVTITCQASQNIVTNLAWYQQKPGKVPKLLIYG

ASTLASGVPSRFSGSGSGTDFTLTISSLQPEDVATYYCQSYDGFNSAGFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC.

The invention further optionally includes chimeric or humanized antibodies for treatment or prevention of pain and pain associated conditions having binding specificity to NGF and possessing a variable heavy chain sequence comprising the sequence set forth below:

(SEQ ID NO: 113)
QVQLVESGGGVVQPGRSLRLSCAASGFSLSGYDMSWVRQAPGKGLEWVGL

ISYDGNTYYATSAKGRFTISRDNSKNTLYLQMSSLRAEDTAVYYCARSLY

AGPNAGIGPFNIWGQGTLVTVSS.

The invention also optionally includes chimeric or humanized antibodies for treatment or prevention of pain and pain associated conditions having binding specificity to NGF and possessing a heavy chain sequence comprising the sequence set forth below:

(SEQ ID NO: 114)
QVQLVESGGGVVQPGRSLRLSCAASGFSLSGYDMSWVRQAPGKGLEWVGL

ISYDGNTYYATSAKGRFTISRDNSKNTLYLQMSSLRAEDTAVYYCARSLY

AGPNAGIGPFNIWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPREE

QYASTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGK.

The invention further optionally contemplates antibodies for treatment or prevention of pain and pain associated conditions comprising one or more of the polypeptide sequences of SEQ ID NO: 115; SEQ ID NO: 116; and SEQ ID NO: 117 which correspond to the complementarity-determining regions (CDRs, or hypervariable regions) of the variable light chain sequence of SEQ ID NO: 111 or the light chain sequence of SEQ ID NO: 112, and/or one or more of the polypeptide sequences of SEQ ID NO: 118; SEQ ID NO: 119; and SEQ ID NO: 120 which correspond to the complementarity-determining regions (CDRs, or hypervariable regions) of the variable heavy chain sequence of SEQ ID NO: 113 or the heavy chain sequence of SEQ ID NO: 114, or combinations of these polypeptide sequences. In another optional embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF for treatment or prevention of pain and pain associated conditions. In one optional embodiment of the invention, antibody fragments of the invention comprise, or alternatively consist of, the polypeptide sequence of SEQ ID NO: 111 or SEQ ID NO: 112. In another embodiment of the invention, antibody fragments of the invention comprise, or alternatively consist of, the polypeptide sequence of SEQ ID NO: 113 or SEQ ID NO: 114.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 115; SEQ ID NO: 116; and SEQ ID NO: 117 which correspond to the complementarity-determining regions (CDRs, or hypervariable regions) of the variable light chain sequence of SEQ ID NO: 111 or the light chain sequence of SEQ ID NO: 112.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 118; SEQ ID NO: 119; and SEQ ID NO: 120 which correspond to the complementarity-determining regions (CDRs, or hypervariable regions) of the variable heavy chain sequence of SEQ ID NO: 113 or the heavy chain sequence of SEQ ID NO: 114.

The invention also optionally contemplates antibody fragments which include one or more of the antibody fragments described herein. In one optional embodiment of the invention, fragments of the antibodies having binding specificity to NGF for treatment or prevention of pain and pain associated conditions comprise, or alternatively consist of, one, two, three or more, including all of the following antibody fragments: the variable light chain region of SEQ ID NO: 111; the variable heavy chain region of SEQ ID NO: 113; the complementarity-determining regions (SEQ ID NO: 115; SEQ ID NO: 116; and SEQ ID NO: 117) of the variable light chain region of SEQ ID NO: 111; and the complementarity-determining regions (SEQ ID NO: 118; SEQ ID NO: 119; and SEQ ID NO: 120) of the variable heavy chain region of SEQ ID NO: 113.

In a particularly preferred optional embodiment of the invention, the chimeric or humanized anti-NGF antibody for treatment or prevention of pain and pain associated conditions is Ab12, comprising, or alternatively consisting of, SEQ ID NO: 112 and SEQ ID NO: 114, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab12, the Fab fragment includes the variable light chain sequence of SEQ ID NO: 111 and the variable heavy chain sequence of SEQ ID NO: 113 or comprises another Fab or monovalent antibody fragment that binds to the same or overlapping epitope as Ab12. This optional embodiment of the invention further contemplates additions, deletions, and variants of SEQ ID NO: 111 and/or SEQ ID NO: 113 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab12. In another embodiment of the invention, anti-NGF antibodies such as Ab12 or Fab fragments thereof for treatment or prevention of pain and pain associated conditions may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab13

The invention optionally contemplates methods of treating pain and the specific pain associated disorders alone or is association with another active agent, e.g., an NSAID or opioid analgesic, wherein the antibodies include Ab13 or fragments thereof, or another antibody or antibody fragment that binds to the same or overlapping epitope as Ab13, for example as set forth below, in a therapeutically effective amount which inhibits the association of NGF with TrkA and the association of NGF with p75. In one embodiment, the invention includes chimeric antibodies for treatment or prevention of pain and pain associated conditions having binding specificity to NGF and possessing a variable light chain sequence comprising the sequence set forth below:

```
                                          (SEQ ID NO: 121)
AAVLTQTPSPVSAAVGGTVSISCQSSQNVYKNNYLSWYQQKPGQPPKLLI

YKASTLASGVPSRFKGGGSGTDFTLTISDVQCDAAATYYCAGGYTSSSDN

AFGGGTEVVVKR.
```

The invention also optionally includes chimeric antibodies for treatment or prevention of pain and pain associated conditions having binding specificity to NGF and possessing a light chain sequence comprising the sequence set forth below:

```
                                          (SEQ ID NO: 122)
AAVLTQTPSPVSAAVGGTVSISCQSSQNVYKNNYLSWYQQKPGQPPKLLI

YKASTLASGVPSRFKGGGSGTDFTLTISDVQCDAAATYYCAGGYTSSSDN

AFGGGTEVVVKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

The invention further optionally includes chimeric antibodies for treatment or prevention of pain and pain associated conditions having binding specificity to NGF and possessing a variable heavy chain sequence comprising the sequence set forth below:

```
                                          (SEQ ID NO: 123)
QSVEASGGRLVTPGTPLTLTCTASGFSLSTYWMSWVRQAPGKGLEWIGDI

YFSNEETNYASWAKGRFTISKTSTTVDLNVISPTTEDTATYFCARGSPDV

DIGIDMWGPGTLVTVSS.
```

The invention also optionally includes chimeric antibodies for treatment or prevention of pain and pain associated conditions having binding specificity to NGF and possessing a heavy chain sequence comprising the sequence set forth below:

```
                                          (SEQ ID NO: 124)
QSVEASGGRLVTPGTPLTLTCTASGFSLSTYWMSWVRQAPGKGLEWIGDI

YFSNEETNYASWAKGRFTISKTSTTVDLNVISPTTEDTATYFCARGSPDV

DIGIDMWGPGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSCDKTHTCPPCPAPELLGGPSVFLFPPKPKDT

LMISRTPEVTCVVVDVSHEDPEVKFNWYVDGVEVHNAKTKPREEQYASTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK.
```

The invention further optionally contemplates antibodies for treatment or prevention of pain and pain associated conditions comprising one or more of the polypeptide sequences of SEQ ID NO: 125; SEQ ID NO: 126; and SEQ ID NO: 127 which correspond to the complementarity-determining regions (CDRs, or hypervariable regions) of the variable light chain sequence of SEQ ID NO: 121 or the light chain sequence of SEQ ID NO: 122, and/or one or more of the polypeptide sequences of SEQ ID NO: 128; SEQ ID NO: 129; and SEQ ID NO: 130 which correspond to the complementarity-determining regions (CDRs, or hypervariable regions) of the variable heavy chain sequence of SEQ ID NO: 123 or the heavy chain sequence of SEQ ID NO: 124, or combinations of these polypeptide sequences. In another optional embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 121 or SEQ ID NO: 122. In another embodiment of the invention, antibody fragments of the invention comprise, or alternatively consist of, the polypeptide sequence of SEQ ID NO: 123 or SEQ ID NO: 124.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 125; SEQ ID NO: 126; and SEQ ID NO: 127 which correspond to the complementarity-determining regions (CDRs, or hypervariable regions) of the variable light chain sequence of SEQ ID NO: 121 or the light chain sequence of SEQ ID NO: 122.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 128; SEQ ID NO: 129; and SEQ ID NO: 130 which correspond to the complementarity-determining regions (CDRs, or hypervariable regions) of the variable heavy chain sequence of SEQ ID NO: 123 or the heavy chain sequence of SEQ ID NO: 124.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 121; the variable heavy chain region of SEQ ID NO: 123; the complementarity-determining regions (SEQ ID NO: 125; SEQ ID NO: 126; and SEQ ID NO: 127) of the variable light chain region of SEQ ID NO: 121; and the complementarity-determining regions (SEQ ID NO: 128; SEQ ID NO: 129; and SEQ ID NO: 130) of the variable heavy chain region of SEQ ID NO: 123.

In a particularly preferred optional embodiment of the invention, the chimeric anti-NGF antibody for treatment or prevention of pain and pain associated conditions is Ab13, comprising, or alternatively consisting of, SEQ ID NO: 122 and SEQ ID NO: 124, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab13, the Fab fragment includes the variable light chain sequence of SEQ ID NO: 121 and the variable heavy chain sequence of SEQ ID NO: 123 or comprises another Fab or monovalent antibody fragment that binds to the same or overlapping epitope as Ab13. This optional embodiment of the invention further contemplates additions, deletions, and variants of SEQ ID NO: 121 and/or SEQ ID NO: 123 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab13. In another embodiment of the invention, anti-NGF antibodies such as Ab13 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab14

The invention optionally contemplates methods of treating pain and the specific pain associated disorders alone or is association with another active agent, e.g., an NSAID or opioid analgesic, wherein the antibodies include chimeric antibodies having binding specificity to NGF wherein the antibody is Ab14 or fragments thereof, or another antibody or fragment that binds to the same or overlapping epitope as Ab14, for example as set forth below, in a therapeutically effective amount which inhibits the association of NGF with TrkA and the association of NGF with p75. In one optional embodiment, the invention includes chimeric or humanized antibodies having binding specificity to NGF and possessing a variable light chain sequence comprising the sequence set forth below:

(SEQ ID NO: 131)
DIQMTQSPSSLSASVGDRVTITCQSSQNVYKNNYLSWYQQKPGKVPKLLI

YKASTLASGVPSRFSGSGSGTDFTLTISSLQPEDVATYYCAGGYTSSSDN

AFGGGTKVEIKR.

The invention also optionally includes chimeric or humanized antibodies for treatment or prevention of pain and pain associated conditions having binding specificity to NGF and possessing a light chain sequence comprising the sequence set forth below:

(SEQ ID NO: 132)
DIQMTQSPSSLSASVGDRVTITCQSSQNVYKNNYLSWYQQKPGKVPKLLI

YKASTLASGVPSRFSGSGSGTDFTLTISSLQPEDVATYYCAGGYTSSSDN

AFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

The invention further optionally includes chimeric or humanized antibodies for treatment or prevention of pain and pain associated conditions having binding specificity to NGF and possessing a variable heavy chain sequence comprising the sequence set forth below:

(SEQ ID NO: 133)
EVQLVESGGGLVQPGGSLRLSCAASGFTVSTYWMSWVRQAPGKGLEWVGD

IYFSNEETNYASSAKGRFTISRDNSKNTLYLQMNSLRAEDTAVYYCARGS

PDVDIGIDMWGPGTLVTVSS.

The invention also optionally includes chimeric or humanized antibodies for treatment or prevention of pain and pain associated conditions having binding specificity to NGF and possessing a heavy chain sequence comprising the sequence set forth below:

(SEQ ID NO: 134)
EVQLVESGGGLVQPGGSLRLSCAASGFTVSTYWMSWVRQAPGKGLEWVGD

IYFSNEETNYASSAKGRFTISRDNSKNTLYLQMNSLRAEDTAVYYCARGS

-continued

```
PDVDIGIDMWGPGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYA

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG

K.
```

The invention further optionally contemplates antibodies for treatment or prevention of pain and pain associated conditions comprising one or more of the polypeptide sequences of SEQ ID NO: 135; SEQ ID NO: 136; and SEQ ID NO: 137 which correspond to the complementarity-determining regions (CDRs, or hypervariable regions) of the variable light chain sequence of SEQ ID NO: 131 or the light chain sequence of SEQ ID NO: 132, and/or one or more of the polypeptide sequences of SEQ ID NO: 138; SEQ ID NO: 139; and SEQ ID NO: 140 which correspond to the complementarity-determining regions (CDRs, or hypervariable regions) of the variable heavy chain sequence of SEQ ID NO: 133 or the heavy chain sequence of SEQ ID NO: 134, or combinations of these polypeptide sequences. In another optional embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 131 or SEQ ID NO: 132. In another embodiment of the invention, antibody fragments of the invention comprise, or alternatively consist of, the polypeptide sequence of SEQ ID NO: 133 or SEQ ID NO: 134.

In a further optional embodiment of the invention, fragments of the antibody having binding specificity to NGF for treatment or prevention of pain and pain associated conditions optionally comprise, or alternatively consist of, one or more of the polypeptide sequences of SEQ ID NO: 135; SEQ ID NO: 136; and SEQ ID NO: 137 which correspond to the complementarity-determining regions (CDRs, or hypervariable regions) of the variable light chain sequence of SEQ ID NO: 131 or the light chain sequence of SEQ ID NO: 132.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 138; SEQ ID NO: 139; and SEQ ID NO: 140 which correspond to the complementarity-determining regions (CDRs, or hypervariable regions) of the variable heavy chain sequence of SEQ ID NO: 133 or the heavy chain sequence of SEQ ID NO: 134.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 131; the variable heavy chain region of SEQ ID NO: 133; the complementarity-determining regions (SEQ ID NO: 135; SEQ ID NO: 136; and SEQ ID NO: 137) of the variable light chain region of SEQ ID NO: 131; and the complementarity-determining regions (SEQ ID NO: 138; SEQ ID NO: 139; and SEQ ID NO: 140) of the variable heavy chain region of SEQ ID NO: 133.

In a particularly preferred optional embodiment of the invention, the chimeric or humanized anti-NGF antibody for treatment or prevention of pain and pain associated conditions is Ab14, comprising, or alternatively consisting of, SEQ ID NO: 132 and SEQ ID NO: 134, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab14, the Fab fragment includes the variable light chain sequence of SEQ ID NO: 131 and the variable heavy chain sequence of SEQ ID NO: 133 or another Fab or monovalent antibody fragment that binds to the same or overlapping epitope as Ab14. This embodiment of the invention further contemplates additions, deletions, and variants of SEQ ID NO: 131 and/or SEQ ID NO: 133 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab14. In another embodiment of the invention, anti-NGF antibodies such as Ab14 or Fab fragments thereof for treatment or prevention of pain and pain associated conditions may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab15

The invention contemplates methods of treating pain and the specific pain associated disorders alone or is association with another active agent, e.g., an NSAID or opioid analgesic, wherein the antibodies include chimeric antibodies having binding specificity to NGF wherein the antibody is Ab15 or fragments thereof, for example as set forth below, or comprises another antibody or antibody fragment that binds to the same or overlapping epitope as Ab15, in a therapeutically effective amount which inhibits the association of NGF with TrkA without appreciably inhibiting the association of NGF with p75. In one embodiment, the invention includes chimeric antibodies for treatment or prevention of pain and pain associated conditions having binding specificity to NGF and possessing a variable light chain sequence comprising the sequence set forth below:

```
                                         (SEQ ID NO: 141)
AAVLTQTPSPVSAAVGDTVTIKCQSSQSVYKNNYLSWYQQKPGQPPKLLI

YDASNLPSGVPSRFSGSGSGTQFTLTISGVQCDDAATYYCLGDYDDDTDN

GFGGGTEVVVKR.
```

The invention also includes chimeric antibodies for treatment or prevention of pain and pain associated conditions having binding specificity to NGF and possessing a light chain sequence comprising the sequence set forth below:

```
                                              (SEQ ID NO: 142)
AAVLTQTPSPVSAAVGDTVTIKCQSSQSVYKNNYLSWYQQKPGQPPKLLI

YDASNLPSGVPSRFSGSGSGTQFTLTISGVQCDDAATYYCLGDYDDDTDN

GFGGGTEVVVKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

The invention further includes chimeric antibodies for treatment or prevention of pain and pain associated conditions having binding specificity to NGF and possessing a variable heavy chain sequence comprising the sequence set forth below:

```
                                              (SEQ ID NO: 143)
QSVEESGGRLVTPGTPLTLTCTVSGIDLSSYAMIWVRQAPGKGLEYIGII

WSGGTYYATWAKGRFTISKTSTTVDLQITSPTTEDAATYFCAAGGGSIYD

VWGPGTLVTVSS.
```

The invention also includes chimeric antibodies for treatment or prevention of pain and pain associated conditions having binding specificity to NGF and possessing a heavy chain sequence comprising the sequence set forth below:

```
                                              (SEQ ID NO: 144)
QSVEESGGRLVTPGTPLTLTCTVSGIDLSSYAMIWVRQAPGKGLEYIGII

WSGGTYYATWAKGRFTISKTSTTVDLQITSPTTEDAATYFCAAGGGSIYD

VWGPGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHK

PSNTKVDKRVEPKSCDKTHTCPPCPAPELLGGPSVFLFPPKPKDTLMISR

TPEVTCVVVDVSHEDPEVKFNWYVDGVEVHNAKTKPREEQYASTYRVVSV

LTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFF

LYSKLTVDKSRWQQGNVFSCSVMHEALHNHYTQKSLSLSPGK.
```

The invention further contemplates antibodies for treatment or prevention of pain and pain associated conditions comprising one or more of the polypeptide sequences of SEQ ID NO: 145; SEQ ID NO: 146; and SEQ ID NO: 147 which correspond to the complementarity-determining regions (CDRs, or hypervariable regions) of the variable light chain sequence of SEQ ID NO: 141 or the light chain sequence of SEQ ID NO: 142, and/or one or more of the polypeptide sequences of SEQ ID NO: 148; SEQ ID NO: 149; and SEQ ID NO: 150 which correspond to the complementarity-determining regions (CDRs, or hypervariable regions) of the variable heavy chain sequence of SEQ ID NO: 143 or the heavy chain sequence of SEQ ID NO: 144, or combinations of these polypeptide sequences. In another embodiment of the invention, the antibodies of the invention or fragments thereof for treatment or prevention of pain and pain associated conditions comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 141 or SEQ ID NO: 142. In another embodiment of the invention, antibody fragments of the invention comprise, or alternatively consist of, the polypeptide sequence of SEQ ID NO: 143 or SEQ ID NO: 144.

In a further embodiment of the invention, fragments of the antibody having binding specificity to NGF for treatment or prevention of pain and pain associated conditions comprise, or alternatively consist of, one or more of the polypeptide sequences of SEQ ID NO: 145; SEQ ID NO: 146; and SEQ ID NO: 147 which correspond to the complementarity-determining regions (CDRs, or hypervariable regions) of the variable light chain sequence of SEQ ID NO: 141 or the light chain sequence of SEQ ID NO: 142.

In a further embodiment of the invention, fragments of the antibody having binding specificity to NGF for treatment or prevention of pain and pain associated conditions comprise, or alternatively consist of, one or more of the polypeptide sequences of SEQ ID NO: 148; SEQ ID NO: 149; and SEQ ID NO: 150 which correspond to the complementarity-determining regions (CDRs, or hypervariable regions) of the variable heavy chain sequence of SEQ ID NO: 143 or the heavy chain sequence of SEQ ID NO: 144.

The invention also contemplates antibody fragments for treatment or prevention of pain and pain associated conditions which include one or more of the antibody fragments described herein. In one embodiment of the invention, fragments of the antibodies having binding specificity to NGF for treatment or prevention of pain and pain associated conditions comprise, or alternatively consist of, one, two, three or more, including all of the following antibody fragments: the variable light chain region of SEQ ID NO: 141; the variable heavy chain region of SEQ ID NO: 143; the complementarity-determining regions (SEQ ID NO: 145; SEQ ID NO: 146; and SEQ ID NO: 147) of the variable light chain region of SEQ ID NO: 141; and the complementarity-determining regions (SEQ ID NO: 148; SEQ ID NO: 149; and SEQ ID NO: 150) of the variable heavy chain region of SEQ ID NO: 143.

In a particularly preferred embodiment of the invention, the chimeric anti-NGF antibody for treatment or prevention of pain and pain associated conditions is Ab15, comprising, or alternatively consisting of, SEQ ID NO: 142 and SEQ ID NO: 144, and having at least one of the biological activities set forth herein.

In a further particularly preferred embodiment of the invention, antibody fragments for treatment or prevention of pain and pain associated conditions comprise, or alternatively consist of, Fab (fragment antigen binding) fragments having binding specificity for NGF. With respect to antibody Ab15, the Fab fragment includes the variable light chain sequence of SEQ ID NO: 141 and the variable heavy chain sequence of SEQ ID NO: 143 or comprises another Fab that binds to the same or overlapping epitope as Ab15. This embodiment of the invention further contemplates additions, deletions, and variants of SEQ ID NO: 141 and/or SEQ ID NO: 143 in said Fab while retaining binding specificity for NGF.

In one embodiment of the invention described herein (infra), Fab fragments for treatment or prevention of pain and pain associated conditions may be produced by enzymatic digestion (e.g., papain) of Ab15. In another embodiment of the invention, anti-NGF antibodies for treatment or prevention of pain and pain associated conditions such as Ab15 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab16

The invention contemplates methods of treating pain and the specific pain associated disorders alone or is association with another active agent, e.g., an NSAID or opioid analgesic, wherein the antibodies include chimeric antibodies having binding specificity to NGF wherein the antibody is Ab16 or fragments thereof, for example as set forth below, or comprises another antibody or antibody fragment that binds to the same or overlapping epitope as Ab16, in a therapeutically effective amount which inhibits the association of NGF with TrkA without appreciably inhibiting the association of NGF with p75. In one embodiment, the invention includes chimeric or humanized antibodies for treatment or prevention of pain and pain associated conditions having binding specificity to NGF and possessing a variable light chain sequence comprising the sequence set forth below:

```
                                           (SEQ ID NO: 151)
ALVMTQTPSSTSEPVGGTVTINCQASQNIGNDLSWYQQKPGQPPELLIYS

TSKLATGVPKRFSGSRSGTQFTLTISDLECDDAATYYCLGVYSYISDDGN

AFGGGTEVVVKR.
```

The invention also includes chimeric or humanized antibodies for treatment or prevention of pain and pain associated conditions having binding specificity to NGF and possessing a light chain sequence comprising the sequence set forth below:

```
                                           (SEQ ID NO: 152)
ALVMTQTPSSTSEPVGGTVTINCQASQNIGNDLSWYQQKPGQPPELLIYS

TSKLATGVPKRFSGSRSGTQFTLTISDLECDDAATYYCLGVYSYISDDGN

AFGGGTEVVVKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

The invention further includes chimeric or humanized antibodies for treatment or prevention of pain and pain associated conditions having binding specificity to NGF and possessing a variable heavy chain sequence comprising the sequence set forth below:

```
                                           (SEQ ID NO: 153)
QSVEEFGGRLVTPGTPLTLTCTVSGFSLNNYAMTWVRQAPGKGLEWIGII

GSIGTTYYASWAKGRFFISKTSTTVDLKIISPTTEDTATYFCARDAGVTV

DGYGYYFNIWGPGTLVTVSS.
```

The invention also includes chimeric or humanized antibodies for treatment or prevention of pain and pain associated conditions having binding specificity to NGF and possessing a heavy chain sequence comprising the sequence set forth below:

```
                                           (SEQ ID NO: 154)
QSVEEFGGRLVTPGTPLTLTCTVSGFSLNNYAMTWVRQAPGKGLEWIGII

GSIGTTYYASWAKGRFFISKTSTTVDLKIISPTTEDTATYFCARDAGVTV

DGYGYYFNIWGPGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYA

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLS

PGK.
```

The invention further contemplates antibodies for treatment or prevention of pain and pain associated conditions comprising one or more of the polypeptide sequences of SEQ ID NO: 155; SEQ ID NO: 156; and SEQ ID NO: 157 which correspond to the complementarity-determining regions (CDRs, or hypervariable regions) of the variable light chain sequence of SEQ ID NO: 151 or the light chain sequence of SEQ ID NO: 152, and/or one or more of the polypeptide sequences of SEQ ID NO: 158; SEQ ID NO: 159; and SEQ ID NO: 160 which correspond to the complementarity-determining regions (CDRs, or hypervariable regions) of the variable heavy chain sequence of SEQ ID NO: 153 or the heavy chain sequence of SEQ ID NO: 154, or combinations of these polypeptide sequences. In another embodiment of the invention, the antibodies of the invention or fragments thereof for treatment or prevention of pain and pain associated conditions comprise, or alternatively consist of, combinations of one or more of the CDRs, the variable heavy and variable light chain sequences, and the heavy and light chain sequences set forth above, including all of them.

The invention also contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 151 or SEQ ID NO: 152. In another embodiment of the invention, antibody fragments of the invention for treatment or prevention of pain and pain associated conditions comprise, or alternatively consist of, the polypeptide sequence of SEQ ID NO: 153 or SEQ ID NO: 154.

In a further embodiment of the invention, fragments of the antibody having binding specificity to NGF for treatment or prevention of pain and pain associated conditions comprise, or alternatively consist of, one or more of the polypeptide sequences of SEQ ID NO: 155; SEQ ID NO: 156; and SEQ ID NO: 157 which correspond to the complementarity-determining regions (CDRs, or hypervariable regions) of the variable light chain sequence of SEQ ID NO: 151 or the light chain sequence of SEQ ID NO: 152.

In a further embodiment of the invention, fragments of the antibody having binding specificity to NGF for treatment or prevention of pain and pain associated conditions comprise, or alternatively consist of, one or more of the polypeptide sequences of SEQ ID NO: 158; SEQ ID NO: 159; and SEQ ID NO: 160 which correspond to the complementarity-determining regions (CDRs, or hypervariable regions) of the variable heavy chain sequence of SEQ ID NO: 153 or the heavy chain sequence of SEQ ID NO: 154.

The invention also contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 151; the variable heavy chain region of SEQ ID NO: 153; the complementarity-determining regions (SEQ ID NO: 155; SEQ ID NO: 156; and SEQ ID NO: 157) of the variable light chain region of SEQ ID NO: 151; and the complementarity-determining regions (SEQ ID NO: 158; SEQ ID NO: 159; and SEQ ID NO: 160) of the variable heavy chain region of SEQ ID NO: 153.

In a particularly preferred embodiment of the invention, the chimeric or humanized anti-NGF antibody for treatment or prevention of pain and pain associated conditions is Ab16, comprising, or alternatively consisting of, SEQ ID NO: 152 and SEQ ID NO: 154, and having at least one of the biological activities set forth herein.

In a further particularly preferred embodiment of the invention, antibody fragments for treatment or prevention of pain and pain associated conditions comprise, or alternatively consist of, Fab (fragment antigen binding) fragments having binding specificity for NGF. With respect to antibody Ab16, the Fab fragment includes the variable light chain sequence of SEQ ID NO: 151 and the variable heavy chain sequence of SEQ ID NO: 153 or comprises another Fab or another bivalent or monovalent antibody fragment that binds to the same or overlapping epitope as Ab16. This embodiment of the invention further contemplates additions, deletions, and variants of SEQ ID NO: 151 and/or SEQ ID NO: 153 in said Fab while retaining binding specificity for NGF.

In one embodiment of the invention described herein (infra), Fab fragments for treatment or prevention of pain and pain associated conditions may be produced by enzymatic digestion (e.g., papain) of Ab16. In another embodiment of the invention, anti-NGF antibodies for treatment or prevention of pain and pain associated conditions such as Ab16 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab17

The invention optionally contemplates methods of treating pain and the specific pain associated disorders alone or is association with another active agent, e.g., an NSAID or opioid analgesic, wherein the antibodies include chimeric antibodies having binding specificity to NGF wherein the antibody is Ab17 or fragments thereof, for example as set forth below, or comprises another antibody or antibody fragment that binds to the same or overlapping epitope as Ab17, in a therapeutically effective amount which inhibits the association of NGF with TrkA and the association of NGF with p75. In one embodiment, the invention includes chimeric antibodies for treatment or prevention of pain and pain associated conditions having binding specificity to NGF and possessing a variable light chain sequence comprising the sequence set forth below:

```
                                        (SEQ ID NO: 161)
AIEMTQTPFSVSAAVGGTVTIKCQASQTISNYLAWYQQKPGQPPKLLIYG

ASNLESGVPSRFKGSGSGTQFTLTISDLECDDAATYYCQQGYTISNVDNN

VFGGGTEVVVKR.
```

The invention also optionally includes chimeric antibodies for treatment or prevention of pain and pain associated conditions having binding specificity to NGF and possessing a light chain sequence comprising the sequence set forth below:

```
                                        (SEQ ID NO: 162)
AIEMTQTPFSVSAAVGGTVTIKCQASQTISNYLAWYQQKPGQPPKLLIYG

ASNLESGVPSRFKGSGSGTQFTLTISDLECDDAATYYCQQGYTISNVDNN

VFGGGTEVVVKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

The invention further optionally includes chimeric antibodies for treatment or prevention of pain and pain associated conditions having binding specificity to NGF and possessing a variable heavy chain sequence comprising the sequence set forth below:

```
                                        (SEQ ID NO: 163)
QSLEESGGRLVTPGGSLTLTCAASGFSLTGYNLVWVRQAPGKGLEWIGFI

SYGDTTYYASWAKGRFTISKTSTTVTLTITDLQPSDTGTYFCARETANTY

DYGIWGPGTLVTVSS.
```

The invention also optionally includes chimeric antibodies for treatment or prevention of pain and pain associated conditions having binding specificity to NGF and possessing a heavy chain sequence comprising the sequence set forth below:

```
                                        (SEQ ID NO: 164)
QSLEESGGRLVTPGGSLTLTCAASGFSLTGYNLVWVRQAPGKGLEWIGFI

SYGDTTYYASWAKGRFTISKTSTTVTLTITDLQPSDTGTYFCARETANTY

DYGIWGPGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLM

ISRTPEVTCVVVDVSHEDPEVKFNWYVDGVEVHNAKTKPREEQYASTYRV

VSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK.
```

The invention further optionally contemplates antibodies for treatment or prevention of pain and pain associated conditions comprising one or more of the polypeptide sequences of SEQ ID NO: 165; SEQ ID NO: 166; and SEQ ID NO: 167 which correspond to the complementarity-determining regions (CDRs, or hypervariable regions) of the variable light chain sequence of SEQ ID NO: 161 or the light chain sequence of SEQ ID NO: 162, and/or one or more of the polypeptide sequences of SEQ ID NO: 168; SEQ ID NO: 169; and SEQ ID NO: 170 which correspond to the complementarity-determining regions (CDRs, or hypervariable regions) of the variable heavy chain sequence of SEQ ID NO: 163 or the heavy chain sequence of SEQ ID NO: 164, or combinations of these polypeptide sequences. In another optional embodiment of the invention, the antibodies of the invention or fragments thereof for treatment or prevention of pain and pain associated conditions comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 161 or SEQ ID NO: 162. In another optional embodiment of the invention, antibody fragments of the invention comprise, or alternatively consist of, the polypeptide sequence of SEQ ID NO: 163 or SEQ ID NO: 164.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 165; SEQ ID NO: 166; and SEQ ID NO: 167 which correspond to the complementarity-determining regions (CDRs, or hypervariable regions) of the variable light chain sequence of SEQ ID NO: 161 or the light chain sequence of SEQ ID NO: 162.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 168; SEQ ID NO: 169; and SEQ ID NO: 170 which correspond to the complementarity-determining regions (CDRs, or hypervariable regions) of the variable heavy chain sequence of SEQ ID NO: 163 or the heavy chain sequence of SEQ ID NO: 164.

The invention also optionally contemplates antibody fragments for treatment or prevention of pain and pain associated conditions which include one or more of the antibody fragments described herein. In one embodiment of the invention, fragments of the antibodies for treatment or prevention of pain and pain associated conditions having binding specificity to NGF comprise, or alternatively consist of, one, two, three or more, including all of the following antibody fragments: the variable light chain region of SEQ ID NO: 161; the variable heavy chain region of SEQ ID NO: 163; the complementarity-determining regions (SEQ ID NO: 165; SEQ ID NO: 166; and SEQ ID NO: 167) of the variable light chain region of SEQ ID NO: 161; and the complementarity-determining regions (SEQ ID NO: 168; SEQ ID NO: 169; and SEQ ID NO: 170) of the variable heavy chain region of SEQ ID NO: 163.

In a particularly preferred optional embodiment of the invention, the chimeric anti-NGF antibody for treatment or prevention of pain and pain associated conditions is Ab17, comprising, or alternatively consisting of, SEQ ID NO: 162 and SEQ ID NO: 164, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab17, the Fab fragment includes the variable light chain sequence of SEQ ID NO: 161 and the variable heavy chain sequence of SEQ ID NO: 163 or comprises another Fab or monovalent or bivalent antibody fragment that binds to the same or overlapping epitope as Ab15. This embodiment of the invention further contemplates additions, deletions, and variants of SEQ ID NO: 161 and/or SEQ ID NO: 163 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab17. In another embodiment of the invention, anti-NGF antibodies such as Ab17 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab18

The invention optionally contemplates methods of treating pain and the specific pain associated disorders alone or is association with another active agent, e.g., an NSAID or opioid analgesic, wherein the antibodies include chimeric antibodies having binding specificity to NGF wherein the antibody is Ab18 or fragments thereof, for example as set forth below, or comprises another antibody or antibody fragment that binds to the same or overlapping epitope as Ab18, in a therapeutically effective amount which inhibits the association of NGF with TrkA and the association of NGF with p75. In one embodiment, the invention includes chimeric or humanized antibodies for treatment or prevention of pain and pain associated conditions having binding specificity to NGF and possessing a variable light chain sequence comprising the sequence set forth below:

(SEQ ID NO: 171)
DIQMTQSPSTLSASVGDRVTITCQASQTISNYLAWYQQKPGKAPKLLIYG

ASNLESGVPSRFSGSGSGTEFTLTISSLQPDDFATYYCQQGYTISNVDNN

VFGGGTKVEIKR.

The invention also optionally includes chimeric or humanized antibodies for treatment or prevention of pain and pain associated conditions having binding specificity to NGF and possessing a light chain sequence comprising the sequence set forth below:

(SEQ ID NO: 172)
DIQMTQSPSTLSASVGDRVTITCQASQTISNYLAWYQQKPGKAPKLLIYG

ASNLESGVPSRFSGSGSGTEFTLTISSLQPDDFATYYCQQGYTISNVDNN

VFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

The invention further optionally includes chimeric or humanized antibodies for treatment or prevention of pain and pain associated conditions having binding specificity to NGF and possessing a variable heavy chain sequence comprising the sequence set forth below:

(SEQ ID NO: 173)
EVQLVESGGGLVQPGGSLRLSCAASGFTVSGYNLVWVRQAPGKGLEWVGF

ISYGDTTYYASSAKGRFTISRDNSKNTLYLQMNSLRAEDTAVYYCARETA

NTYDYGIWGQGTLVTVSS.

The invention also optionally includes chimeric or humanized antibodies for treatment or prevention of pain and pain associated conditions having binding specificity to NGF and possessing a heavy chain sequence comprising the sequence set forth below:

(SEQ ID NO: 174)
EVQLVESGGGLVQPGGSLRLSCAASGFTVSGYNLVWVRQAPGKGLEWVG

FISYGDTTYYASSAKGRFTISRDNSKNTLYLQMNSLRAEDTAVYYCARE

TANTYDYGIWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQK

SLSLSPGK.

The invention further optionally contemplates antibodies for treatment or prevention of pain and pain associated conditions comprising one or more of the polypeptide sequences of SEQ ID NO: 175; SEQ ID NO: 176; and SEQ ID NO: 177 which correspond to the complementarity-determining regions (CDRs, or hypervariable regions) of the variable light chain sequence of SEQ ID NO: 171 or the light chain sequence of SEQ ID NO: 172, and/or one or more of the polypeptide sequences of SEQ ID NO: 178; SEQ ID NO: 179; and SEQ ID NO: 180 which correspond to the complementarity-determining regions (CDRs, or hypervariable regions) of the variable heavy chain sequence of SEQ ID NO: 173 or the heavy chain sequence of SEQ ID NO: 174, or combinations of these polypeptide sequences. In another embodiment of the invention, the antibodies of the invention or fragments thereof for treatment or prevention of pain and pain associated conditions comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 171 or SEQ ID NO: 172. In another embodiment of the invention, antibody fragments of the invention comprise, or alternatively consist of, the polypeptide sequence of SEQ ID NO: 173 or SEQ ID NO: 174.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 175; SEQ ID NO: 176; and SEQ ID NO: 177 which correspond to the complementarity-determining regions (CDRs, or hypervariable regions) of the variable light chain sequence of SEQ ID NO: 171 or the light chain sequence of SEQ ID NO: 172.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 178; SEQ ID NO: 179; and SEQ ID NO: 180 which correspond to the complementarity-determining regions (CDRs, or hypervariable regions) of the variable heavy chain sequence of SEQ ID NO: 173 or the heavy chain sequence of SEQ ID NO: 174.

The invention also optional contemplates antibody fragments for treatment or prevention of pain and pain associated conditions which include one or more of the antibody fragments described herein. In one embodiment of the invention, fragments of the antibodies having binding specificity to NGF for treatment or prevention of pain and pain associated conditions comprise, or alternatively consist of, one, two, three or more, including all of the following antibody fragments: the variable light chain region of SEQ ID NO: 171; the variable heavy chain region of SEQ ID NO: 173; the complementarity-determining regions (SEQ ID NO: 175; SEQ ID NO: 176; and SEQ ID NO: 177) of the variable light chain region of SEQ ID NO: 171; and the complementarity-determining regions (SEQ ID NO: 178; SEQ ID NO: 179; and SEQ ID NO: 180) of the variable heavy chain region of SEQ ID NO: 173.

In a particularly preferred optional embodiment of the invention, the chimeric or humanized anti-NGF antibody for treatment or prevention of pain and pain associated conditions is Ab18, comprising, or alternatively consisting of, SEQ ID NO: 172 and SEQ ID NO: 174, and having at least one of the biological activities set forth herein.

In a further particularly preferred optional embodiment of the invention, antibody fragments comprise, or alternatively consist of, Fab (fragment antigen binding) fragments having binding specificity for NGF. With respect to antibody Ab18, the Fab fragment includes the variable light chain sequence of SEQ ID NO: 171 and the variable heavy chain sequence of SEQ ID NO: 173 or comprise another Fab or antibody fragment that binds to the same or overlapping epitope as Ab18. This embodiment of the invention further contemplates additions, deletions, and variants of SEQ ID NO: 171 and/or SEQ ID NO: 173 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab18. In another embodiment of the invention, anti-NGF antibodies such as Ab18 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab19

The invention optionally contemplates methods of treating pain and the specific pain associated disorders alone or is association with another active agent, e.g., an NSAID or opioid analgesic, wherein the antibodies include chimeric antibodies having binding specificity to NGF wherein the antibody is Ab19 or fragments thereof, for example as set forth below, or comprises another antibody or antibody fragment that binds to the same or overlapping epitope as Ab19, in a therapeutically effective amount which inhibits the association of NGF with TrkA and the association of NGF with p75. In one embodiment, the invention includes chimeric antibodies for treatment or prevention of pain and pain associated conditions having binding specificity to NGF and possessing a variable light chain sequence comprising the sequence set forth below:

(SEQ ID NO: 181)
AAVLTQTPSPVSAAVGGTVSISCQSSQNVYKNNYLSWYQQKPGQPPKLL

IYKASTLASGVPSRFKGSGSGTDFTLTISDVQCDAAATYYCAGGYSSSS

DNAFGGGTEVVVKR.

The invention also optionally includes chimeric antibodies for treatment or prevention of pain and pain associated conditions having binding specificity to NGF and possessing a light chain sequence comprising the sequence set forth below:

```
                                         (SEQ ID NO: 182)
AAVLTQTPSPVSAAVGGTVSISCQSSQNVYKNNYLSWYQQKPGQPPKLL

IYKASTLASGVPSRFKGSGSGTDFTLTISDVQCDAAATYYCAGGYSSSS

DNAFGGGTEVVVKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC.
```

The invention further optionally includes chimeric antibodies for treatment or prevention of pain and pain associated conditions having binding specificity to NGF and possessing a variable heavy chain sequence comprising the sequence set forth below:

```
                                         (SEQ ID NO: 183)
QSVEASGGRLVMPGGSLTLTCTASGFSLSTYWMSWVRQAPGKGLEWIGD

IYFSNEETNYATWAKGRFTISKTSTTVDLNVISPTTEDTATYFCARGSP

DVEIAIDMWGQGTLVTVSS.
```

The invention also optionally includes chimeric antibodies for treatment or prevention of pain and pain associated conditions having binding specificity to NGF and possessing a heavy chain sequence comprising the sequence set forth below:

```
                                         (SEQ ID NO: 184)
QSVEASGGRLVMPGGSLTLTCTASGFSLSTYWMSWVRQAPGKGLEWIGD

IYFSNEETNYATWAKGRFTISKTSTTVDLNVISPTTEDTATYFCARGSP

DVEIAIDMWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREE

QYASTYRVVSVLTVLHQDWLNGKEYKCKVSNKALPAPIEKTISKAKGQP

REPQVYTLPPSREEMTKNQVSLTCLVKGFYPSDIAVEWESNGQPENNYK

TTPPVLDSDGSFFLYSKLTVDKSRWQQGNVFSCSVMHEALHNHYTQKSL

SLSPGK.
```

The invention further optionally contemplates antibodies for treatment or prevention of pain and pain associated conditions comprising one or more of the polypeptide sequences of SEQ ID NO: 185; SEQ ID NO: 186; and SEQ ID NO: 187 which correspond to the complementarity-determining regions (CDRs, or hypervariable regions) of the variable light chain sequence of SEQ ID NO: 181 or the light chain sequence of SEQ ID NO: 182, and/or one or more of the polypeptide sequences of SEQ ID NO: 188; SEQ ID NO: 189; and SEQ ID NO: 190 which correspond to the complementarity-determining regions (CDRs, or hypervariable regions) of the variable heavy chain sequence of SEQ ID NO: 183 or the heavy chain sequence of SEQ ID NO: 184, or combinations of these polypeptide sequences. In another embodiment of the invention, the antibodies of the invention or fragments thereof for treatment or prevention of pain and pain associated conditions comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF for treatment or prevention of pain and pain associated conditions. In one embodiment of the invention, antibody fragments of the invention comprise, or alternatively consist of, the polypeptide sequence of SEQ ID NO: 181 or SEQ ID NO: 182. In another embodiment of the invention, antibody fragments of the invention comprise, or alternatively consist of, the polypeptide sequence of SEQ ID NO: 183 or SEQ ID NO: 184.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 185; SEQ ID NO: 186; and SEQ ID NO: 187 which correspond to the complementarity-determining regions (CDRs, or hypervariable regions) of the variable light chain sequence of SEQ ID NO: 181 or the light chain sequence of SEQ ID NO: 182.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 188; SEQ ID NO: 189; and SEQ ID NO: 190 which correspond to the complementarity-determining regions (CDRs, or hypervariable regions) of the variable heavy chain sequence of SEQ ID NO: 183 or the heavy chain sequence of SEQ ID NO: 184.

The invention also optionally contemplates antibody fragments which include one or more of the antibody fragments described herein for treatment or prevention of pain and pain associated conditions. In one optional embodiment of the invention, fragments of the antibodies having binding specificity to NGF comprise, or alternatively consist of, one, two, three or more, including all of the following antibody fragments: the variable light chain region of SEQ ID NO: 181; the variable heavy chain region of SEQ ID NO: 183; the complementarity-determining regions (SEQ ID NO: 185; SEQ ID NO: 186; and SEQ ID NO: 187) of the variable light chain region of SEQ ID NO: 181; and the complementarity-determining regions (SEQ ID NO: 188; SEQ ID NO: 189; and SEQ ID NO: 190) of the variable heavy chain region of SEQ ID NO: 183.

In a particularly preferred optional embodiment of the invention, the chimeric anti-NGF antibody for treatment or prevention of pain and pain associated conditions is Ab19, comprising, or alternatively consisting of, SEQ ID NO: 182 and SEQ ID NO: 184, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab19, the Fab fragment includes the variable light chain sequence of SEQ ID NO: 181 and the variable heavy chain sequence of SEQ ID NO: 183 or comprises another Fab or antibody fragment that binds to the same or overlapping epitope as Ab19. This optional embodiment of the invention further contemplates additions, deletions, and variants of SEQ ID NO: 181 and/or SEQ ID NO: 183 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab19. In another embodiment of the invention, anti-NGF antibodies such as Ab19 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab20

The invention optionally contemplates methods of treating pain and the specific pain associated disorders alone or is association with another active agent, e.g., an NSAID or opioid analgesic, wherein the antibodies include chimeric antibodies having binding specificity to NGF wherein the antibody is Ab20 or fragments thereof, for example as set forth below, or comprises another antibody or antibody fragment that binds to the same or overlapping epitope as Ab20, in a therapeutically effective amount which inhibits the association of NGF with TrkA and the association of NGF with p75. In one embodiment, the invention includes chimeric or humanized antibodies for treatment or prevention of pain and pain associated conditions having binding specificity to NGF and possessing a variable light chain sequence comprising the sequence set forth below:

(SEQ ID NO: 191)
DIQMTQSPSSLSASVGDRVTITCQSSQNVYKNNYLSWYQQKPGKVPKLL

IYKASTLASGVPSRFSGSGSGTDFTLTISSLQPEDVATYYCAGGYTSSS

DNAFGGGTKVEIKR.

The invention also optionally includes chimeric or humanized antibodies for treatment or prevention of pain and pain associated conditions having binding specificity to NGF and possessing a light chain sequence comprising the sequence set forth below:

(SEQ ID NO: 192)
DIQMTQSPSSLSASVGDRVTITCQSSQNVYKNNYLSWYQQKPGKVPKLL

IYKASTLASGVPSRFSGSGSGTDFTLTISSLQPEDVATYYCAGGYTSSS

DNAFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC.

The invention further optionally includes chimeric or humanized antibodies for treatment or prevention of pain and pain associated conditions having binding specificity to NGF and possessing a variable heavy chain sequence comprising the sequence set forth below:

(SEQ ID NO: 193)
EVQLVESGGGLVQPGGSLRLSCAASGFTVSTYWMSWVRQAPGKGLEWVG

DIYFSNEETNYATSAKGRFTISRDNSKNTLYLQMNSLRAEDTAVYYCAR

GSPDVEIAIDMWGQGTLVTVSS.

The invention also optionally includes chimeric or humanized antibodies for treatment or prevention of pain and pain associated conditions having binding specificity to NGF and possessing a heavy chain sequence comprising the sequence set forth below:

(SEQ ID NO: 194)
EVQLVESGGGLVQPGGSLRLSCAASGFTVSTYWMSWVRQAPGKGLEWVG

DIYFSNEETNYATSAKGRFTISRDNSKNTLYLQMNSLRAEDTAVYYCAR

GSPDVEIAIDMWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKP

REEQYASTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK.

The invention further optionally contemplates antibodies for treatment or prevention of pain and pain associated conditions comprising one or more of the polypeptide sequences of SEQ ID NO: 195; SEQ ID NO: 196; and SEQ ID NO: 197 which correspond to the complementarity-determining regions (CDRs, or hypervariable regions) of the variable light chain sequence of SEQ ID NO: 191 or the light chain sequence of SEQ ID NO: 192, and/or one or more of the polypeptide sequences of SEQ ID NO: 198; SEQ ID NO: 199; and SEQ ID NO: 200 which correspond to the complementarity-determining regions (CDRs, or hypervariable regions) of the variable heavy chain sequence of SEQ ID NO: 193 or the heavy chain sequence of SEQ ID NO: 194, or combinations of these polypeptide sequences. In another embodiment of the invention, the antibodies of the invention or fragments thereof for treatment or prevention of pain and pain associated conditions comprise, or alternatively consist of, combinations of one or more of the CDRs, the variable heavy and variable light chain sequences, and the heavy and light chain sequences set forth above, including all of them.

The invention also optionally contemplates fragments of the antibody having binding specificity to NGF. In one embodiment of the invention, antibody fragments of the invention for treatment or prevention of pain and pain associated conditions comprise, or alternatively consist of, the polypeptide sequence of SEQ ID NO: 191 or SEQ ID NO: 192. In another embodiment of the invention, antibody fragments of the invention comprise, or alternatively consist of, the polypeptide sequence of SEQ ID NO: 193 or SEQ ID NO: 194.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 195; SEQ ID NO: 196; and SEQ ID NO: 197 which correspond to the complementarity-determining regions (CDRs, or hypervariable regions) of the variable light chain sequence of SEQ ID NO: 191 or the light chain sequence of SEQ ID NO: 192.

In a further optional embodiment of the invention, fragments of the antibody having binding specificity to NGF comprise, or alternatively consist of, one or more of the polypeptide sequences of SEQ ID NO: 198; SEQ ID NO: 199; and SEQ ID NO: 200 which correspond to the complementarity-determining regions (CDRs, or hypervariable regions) of the variable heavy chain sequence of SEQ ID NO: 193 or the heavy chain sequence of SEQ ID NO: 194.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 191; the variable heavy chain region of SEQ ID NO: 193; the complementarity-determining regions (SEQ ID NO: 195; SEQ ID NO: 196; and SEQ ID NO: 197) of the variable light chain region of SEQ ID NO: 191; and the complementarity-determining regions (SEQ ID NO: 198; SEQ ID NO: 199; and SEQ ID NO: 200) of the variable heavy chain region of SEQ ID NO: 193.

In a particularly preferred optional embodiment of the invention, the chimeric or humanized anti-NGF antibody for treatment or prevention of pain and pain associated conditions is Ab20, comprising, or alternatively consisting of, SEQ ID NO: 192 and SEQ ID NO: 194, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab20, the Fab fragment includes the variable light chain sequence of SEQ ID NO: 191 and the variable heavy chain sequence of SEQ ID NO: 193. This embodiment of the invention further contemplates additions, deletions, and variants of SEQ ID NO: 191 and/or SEQ ID NO: 193 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab20. In another embodiment of the invention, anti-NGF antibodies for treatment or prevention of pain and pain associated conditions such as Ab20 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab21

The invention optionally contemplates methods of treating pain and the specific pain associated disorders alone or is association with another active agent, e.g., an NSAID or opioid analgesic, wherein the antibodies include chimeric antibodies having binding specificity to NGF wherein the antibody is Ab21 or fragments thereof, or another antibody or antibody fragment that binds to the same or overlapping epitope as Ab5, for example as set forth below, in a therapeutically effective amount which inhibits the association of NGF with TrkA and the association of NGF with p75. In one embodiment, the invention includes chimeric or humanized antibodies having binding specificity to NGF and possessing a variable light chain sequence comprising the sequence set forth below:

(SEQ ID NO: 51)
DIQMTQSPSTLSASVGDRVTITCQASQSIYSNLAWYQQKPGKAPKLLIY

DASTLESGVPSRFSGSGSGTEYTLTISSLQPDDFATYYCQQGFTVSDID

NAFGGGTKVEIKR.

The invention also optionally includes chimeric or humanized antibodies for treatment or prevention of pain and pain associated conditions having binding specificity to NGF and possessing a light chain sequence comprising the sequence set forth below:

(SEQ ID NO: 401)
DIQMTQSPSTLSASVGDRVTITCQASQSIYSNLAWYQQKPGKAPKLLIY

DASTLESGVPSRFSGSGSGTEYTLTISSLQPDDFATYYCQQGFTVSDID

NAFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.

The invention further optionally includes chimeric or humanized antibodies for treatment or prevention of pain and pain associated conditions having binding specificity to NGF and possessing a variable heavy chain sequence comprising the sequence set forth below:

(SEQ ID NO: 53)
EVQLVESGGGLVQPGGSLRLSCAASGFTVSNYAVGWVRQAPGKGLEWVG

IIGRNGNTWYASSARGRFTISRDNSKNTLYLQMNSLRAEDTAVYYCARG

YGRSVAYYVFNIWGPGTLVTVSS.

The invention also optionally includes chimeric or humanized antibodies for treatment or prevention of pain and pain associated conditions having binding specificity to NGF and possessing a heavy chain sequence comprising the sequence set forth below:

(SEQ ID NO: 402)
EVQLVESGGGLVQPGGSLRLSCAASGFTVSNYAVGWVRQAPGKGLEWVG

IIGRNGNTWYASSARGRFTISRDNSKNTLYLQMNSLRAEDTAVYYCARG

YGRSVAYYVFNIWGPGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDARVEPKSCDKTHTCPPCPAPELLGGPSVF

LFPPKPKDTLMISRTPEVTCVVVDVSHEDPEVKFNWYVDGVEVHNAKTK

PREEQYASTYRVVSVLTVLHQDWLNGKEYKCKVSNKALPAPIEKTISKA

KGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYT

QKSLSLSPGK.

The invention further optionally contemplates antibodies for treatment or prevention of pain and pain associated conditions comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 401, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 402, or combinations of these polypeptide sequences. In another optional embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also optionally contemplates fragments of the antibody for treatment or prevention of pain and pain associated conditions having binding specificity to NGF. In one embodiment of the invention, antibody fragments of the invention for treatment or prevention of pain and pain associated conditions comprise, or alternatively consist of, the polypeptide sequence of SEQ ID NO: 51 or SEQ ID NO: 401. In another embodiment of the invention, antibody fragments of the invention for treatment or prevention of pain and pain associated conditions comprise, or alternatively consist of, the polypeptide sequence of SEQ ID NO: 53 or SEQ ID NO: 402.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 401.

In a further optional embodiment of the invention, fragments of the antibody having binding specificity to NGF for treatment or prevention of pain and pain associated conditions comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 402.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 51; the variable heavy chain region of SEQ ID NO: 53; the complementarity-determining regions (SEQ ID NO: 55; SEQ ID NO: 56; and SEQ ID NO: 57) of the variable light chain region of SEQ ID NO: 51; and the complementarity-determining regions (SEQ ID NO: 58; SEQ ID NO: 59; and SEQ ID NO: 60) of the variable heavy chain region of SEQ ID NO: 53.

In a particularly preferred optional embodiment of the invention, the chimeric or humanized anti-NGF antibody for treatment or prevention of pain and pain associated conditions is Ab21, comprising, or alternatively consisting of, SEQ ID NO: 401 and SEQ ID NO: 402, and having at least one of the biological activities set forth herein.

In a further particularly preferred optional embodiment of the invention, antibody fragments for treatment or prevention of pain and pain associated conditions comprise, or alternatively consist of, Fab (fragment antigen binding) fragments having binding specificity for NGF. With respect to antibody Ab21, the Fab fragment includes the variable light chain sequence of SEQ ID NO: 51 and the variable heavy chain sequence of SEQ ID NO: 53 or another Fab or monovalent antibody fragment that binds to the same or overlapping epitope as Ab5. This embodiment of the invention further contemplates additions, deletions, and variants of SEQ ID NO: 51 and/or SEQ ID NO: 53 in said Fab while retaining binding specificity for NGF.

In one optional embodiment of the invention described herein (infra), Fab fragments for treatment or prevention of pain and pain associated conditions may be produced by enzymatic digestion (e.g., papain) of Ab21. In another embodiment of the invention, anti-NGF antibodies for treatment or prevention of pain and pain associated conditions such as Ab21 or Fab fragments thereof may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Fragment Fab1

The invention optionally contemplates methods of treating pain using antibody fragment Fab1 or fragments thereof, for example as set forth below, in a therapeutically effective amount which inhibits the association of NGF with TrkA and the association of NGF with p75. In one embodiment, the invention optionally includes Fab antibody fragments for treatment or prevention of pain and pain associated conditions having binding specificity to NGF and possessing a light chain sequence comprising the sequence set forth below:

```
                                        (SEQ ID NO: 405)
DIQMTQSPSTLSASVGDRVTITCQASQSIYSNLAWYQQKPGKAPKLLIY

DASTLESGVPSRFSGSGSGTEYTLTISSLQPDDFATYYCQQGFTVSDID

NAFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC.
```

The invention further optionally includes Fab antibody fragments for treatment or prevention of pain and pain associated conditions having binding specificity to NGF and possessing a heavy chain sequence comprising the sequence set forth below:

```
                                        (SEQ ID NO: 406)
EVQLVESGGGLVQPGGSLRLSCAASGFTVSNYAVGWVRQAPGKGLEWVG

IIGRNGNTWYASSARGRFTISRDNSKNTLYLQMNSLRAEDTAVYYCARG

YGRSVAYYVFNIWGPGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDARVEPKSCDKTH.
```

The invention further optionally contemplates antibody fragments for treatment or prevention of pain and pain associated conditions comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 405, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 406, or combinations of these polypeptide sequences. In another optional embodiment of the invention, antibody fragments of the invention for treatment or prevention of pain and pain associated conditions comprise, or alternatively consist of, combinations of one or more of the CDRs, the variable heavy and variable light chain sequences, and the heavy and light chain sequences set forth above, including all of them.

The invention also optionally contemplates fragments of the antibody for treatment or prevention of pain and pain associated conditions having binding specificity to NGF. In one embodiment of the invention, antibody fragments of the invention comprise, or alternatively consist of, the polypeptide sequence of SEQ ID NO: 51 or SEQ ID NO: 405. In another embodiment of the invention, antibody fragments of the invention comprise, or alternatively consist of, the polypeptide sequence of SEQ ID NO: 53 or SEQ ID NO: 406.

In a further optional embodiment of the invention, antibody fragments for treatment or prevention of pain and pain associated conditions having binding specificity to NGF comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 405.

In a further optional embodiment of the invention, antibody fragments for treatment or prevention of pain and pain associated conditions having binding specificity to NGF comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 406.

The invention also optionally contemplates antibody fragments for treatment or prevention of pain and pain associated conditions which include one or more of the antibody fragments described herein. In one embodiment of the invention, fragments of the antibodies having binding specificity to NGF comprise, or alternatively consist of, one, two, three or more, including all of the following antibody fragments: the variable light chain region of SEQ ID NO: 51; the variable heavy chain region of SEQ ID NO: 53; the complementarity-determining regions (SEQ ID NO: 55; SEQ ID NO: 56; and SEQ ID NO: 57) of the variable light chain region of SEQ ID NO: 51; and the complementarity-determining regions (SEQ ID NO: 58; SEQ ID NO: 59; and SEQ ID NO: 60) of the variable heavy chain region of SEQ ID NO: 53.

In a particularly preferred optional embodiment of the invention, the anti-NGF antibody fragment for treatment or prevention of pain and pain associated conditions is Fab1, comprising SEQ ID NO: 405 and SEQ ID NO: 406, or another Fab or antibody fragment that binds to the same or overlapping epitope as Fab1, and having at least one of the biological activities set forth herein. In one embodiment of the invention, antibody fragment Fab1 may be produced by enzymatic digestion (e.g., papain) of Ab21.

Antibody Fragment Fab2

The invention optionally contemplates methods of treating pain using antibody fragment Fab2 or fragments thereof, for example as set forth below, in a therapeutically effective amount which inhibits the association of NGF with TrkA and the association of NGF with p75. In one embodiment, the invention includes Fab antibody fragments for treatment or prevention of pain and pain associated conditions having binding specificity to NGF and possessing a light chain sequence comprising the sequence set forth below:

(SEQ ID NO: 407)
DIQMTQSPSTLSASVGDRVTITCQASQSIYSNLAWYQQKPGKAPKLLIYD

ASTLESGVPSRFSGSGSGTEYTLTISSLQPDDFATYYCQQGFTVSDIDNA

FGGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC.

The invention further optionally includes Fab antibody fragments for treatment or prevention of pain and pain associated conditions having binding specificity to NGF and possessing a heavy chain sequence comprising the sequence set forth below:

(SEQ ID NO: 408)
EVQLVESGGGLVQPGGSLRLSCAASGFTVSNYAVGWVRQAPGKGLEWVGI

IGRNGNTWYASSARGRFTISRDNSKNTLYLQMNSLRAEDTAVYYCARGYG

RSVAYYVFNIWGPGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDARVEPKSCDKTH.

The invention further optionally contemplates antibody fragments for treatment or prevention of pain and pain associated conditions comprising one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 407, and/or one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 408, or combinations of these polypeptide sequences. In another embodiment of the invention, antibody fragments of the invention comprise, or alternatively consist of, combinations of one or more of the CDRs, the variable heavy and variable light chain sequences, and the heavy and light chain sequences set forth above, including all of them.

The invention also optionally contemplates fragments of the antibody for treatment or prevention of pain and pain associated conditions having binding specificity to NGF. In one embodiment of the invention, antibody fragments of the invention for treatment or prevention of pain and pain associated conditions comprise, or alternatively consist of, the polypeptide sequence of SEQ ID NO: 51 or SEQ ID NO: 407. In another embodiment of the invention, antibody fragments of the invention for treatment or prevention of pain and pain associated conditions comprise, or alternatively consist of, the polypeptide sequence of SEQ ID NO: 53 or SEQ ID NO: 408.

In a further optional embodiment of the invention, antibody fragments for treatment or prevention of pain and pain associated conditions having binding specificity to NGF comprise, or alternatively consist of, one or more of the polypeptide sequences of SEQ ID NO: 55; SEQ ID NO: 56; and SEQ ID NO: 57 which correspond to the complementarity-determining regions (CDRs, or hypervariable regions) of the variable light chain sequence of SEQ ID NO: 51 or the light chain sequence of SEQ ID NO: 407.

In a further optional embodiment of the invention, antibody fragments for treatment or prevention of pain and pain associated conditions having binding specificity to NGF comprise, or alternatively consist of, one or more of the polypeptide sequences of SEQ ID NO: 58; SEQ ID NO: 59; and SEQ ID NO: 60 which correspond to the complementarity-determining regions (CDRs, or hypervariable regions) of the variable heavy chain sequence of SEQ ID NO: 53 or the heavy chain sequence of SEQ ID NO: 408.

The invention also optionally contemplates antibody fragments for treatment or prevention of pain and pain associated conditions which include one or more of the antibody fragments described herein. In one embodiment of the invention, fragments of the antibodies having binding specificity to NGF for treatment or prevention of pain and pain associated conditions comprise, or alternatively consist of, one, two, three or more, including all of the following antibody fragments: the variable light chain region of SEQ ID NO: 51; the variable heavy chain region of SEQ ID NO: 53; the complementarity-determining regions (SEQ ID NO: 55; SEQ ID NO: 56; and SEQ ID NO: 57) of the variable light chain region of SEQ ID NO: 51; and the complementarity-determining regions (SEQ ID NO: 58; SEQ ID NO: 59; and SEQ ID NO: 60) of the variable heavy chain region of SEQ ID NO: 53.

In a particularly preferred optional embodiment of the invention, the anti-NGF antibody fragment for treatment or prevention of pain and pain associated conditions is Fab2, comprising SEQ ID NO: 407 and SEQ ID NO: 408, or another Fab or antibody fragment that binds to the same or overlapping epitope as Fab2, and having at least one of the biological activities set forth herein.

In another optional embodiment of the invention described herein (infra), Fab fragments for treatment or prevention of pain and pain associated conditions may be produced via expression in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*. In one embodiment of the invention, antibody fragment Fab2 may be produced by expression in *Pichia pastoris* using protocols set forth herein in the examples.

In another embodiment, antibody fragments may be present in one or more of the following non-limiting forms: Fab, Fab', F(ab')$_2$, Fv and single chain Fv antibody forms. In a preferred embodiment, the anti-NGF antibodies described herein further comprises the kappa constant light chain sequence comprising the sequence set forth below:

(SEQ ID NO: 412)
VAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTK

SFNRGEC.

In another preferred optional embodiment, the anti-NGF antibodies described herein for treatment or prevention of pain and pain associated conditions further comprises the gamma-1 constant heavy chain polypeptide sequence comprising the sequence set forth below:

(SEQ ID NO: 413)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

-continued
EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In another optional embodiment, the invention contemplates an isolated anti-NGF antibody for treatment or prevention of pain and pain associated conditions comprising a V$_H$ polypeptide sequence selected from: SEQ ID NO: 3, 13, 23, 33, 43, 53, 63, 73, 83, 93, 103, 113, 123, 133, 143, 153, 163, 173, 183, 193, or 402, or a variant thereof; and further comprising a V$_L$ polypeptide sequence selected from: SEQ ID NO: 1, 11, 21, 31, 41, 51, 61, 71, 81, 91, 101, 111, 121, 131, 141, 151, 161, 171, 181, 191, or 401, or a variant thereof, wherein one or more of the framework residues (FR residues) in said V$_H$ or V$_L$ polypeptide has been substituted with another amino acid residue resulting in an anti-NGF antibody that specifically binds NGF. The invention contemplates humanized and chimeric forms of these antibodies for treatment or prevention of pain and pain associated conditions. The chimeric antibodies may include an Fc derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

In one embodiment of the invention, the antibodies or V$_H$ or V$_L$ polypeptides originate or are selected from one or more rabbit B cell populations prior to initiation of the humanization process referenced herein.

In another embodiment of the invention, the anti-NGF antibodies and fragments thereof for treatment or prevention of pain and pain associated conditions do not have binding specificity for p75 or TrkA. In a further embodiment of the invention, there is contemplated methods for treating pain comprising using the anti-NGF antibodies and fragments thereof to inhibit the association of NGF with p75 and/or TrkA. In another embodiment of the invention, there is contemplated methods for treating pain comprising using anti-NGF antibodies and fragments thereof to inhibit the association of NGF with TrkA and/or multimers thereof and/or antagonizes the biological effects thereof. In another embodiment of the invention, there is contemplated methods for treating pain comprising using anti-NGF antibodies and fragments thereof to inhibit the association of NGF with p75 and/or multimers thereof and the association of NGF with TrkA and/or multimers thereof, and antagonizes the biological effects of p75 and TrkA.

As stated supra, antibodies and fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Regarding detectable moieties, further exemplary enzymes include, but are not limited to, horseradish peroxidase, acetylcholinesterase, alkaline phosphatase, beta-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}$I), Carbon 14 ($^{14}$C), Sulfur 35 ($^{35}$S), Tritium ($^{3}$H) and Phosphorus 32 ($^{32}$P).

Regarding functional moieties, exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, caminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine and bleomycin. Toxic enzymes from plants and bacteria such as ricin, diphtheria toxin and *Pseudomonas* toxin may be conjugated to the humanized or chimeric antibodies, or binding fragments thereof, to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32 ($^{32}$P), Scandium-47 ($^{47}$Sc), Copper-67 ($^{67}$Cu), Gallium-67 ($^{67}$Ga), Yttrium-88 ($^{88}$Y), Yttrium-90 ($^{90}$Y), Iodine-125 ($^{125}$I), Iodine-131 ($^{131}$I), Samarium-153 ($^{153}$Sm), Lutetium-177 ($^{177}$Lu), Rhenium-186 ($^{186}$Re) or Rhenium-188 ($^{188}$Re), and alpha-emitters such as Astatine-211 ($^{211}$At), Lead-212 ($^{212}$Pb), Bismuth-212 or -213 ($^{213}$Bi) or Actinium-225 ($^{225}$Ac).

Further exemplary radioactive materials include, but are not limited to, Iodine 125 ($^{125}$I), Carbon 14 ($^{14}$C), Sulfur 35 ($^{35}$S), Tritium ($^{3}$H) and Phosphorus 32 ($^{32}$P).

Regarding functional moieties, exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, caminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine and bleomycin. Toxic enzymes from plants and bacteria such as ricin, diphtheria toxin and *Pseudomonas* toxin may be conjugated to the humanized or chimeric antibodies, or binding fragments thereof, to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32 ($^{32}$P), Scandium-47 ($^{47}$Sc), Copper-67 ($^{67}$Cu), Gallium-67 ($^{67}$Ga), Yttrium-88 ($^{88}$Y), Yttrium-90 ($^{90}$Y), Iodine-125 ($^{125}$I), Iodine-131 ($^{131}$I), Samarium-153 ($^{153}$Sm), Lutetium-177 ($^{177}$Lu), Rhenium-186 ($^{186}$Re) or Rhenium-188 ($^{188}$Re), and alpha emitters such as Astatine-211 ($^{211}$At), Lead-212 ($^{212}$Pb), Bismuth-212 or -213 ($^{213}$Bi) or Actinium-225 ($^{225}$Ac).

Methods are known in the art for conjugating an antibody or binding fragment thereof to a detectable moiety and the like, such as for example those methods described by Hunter et al, Nature 144:945 (1962); David et al, Biochemistry 13:1014 (1974); Pain et al, J. Immunol. Meth. 40:219 (1981); and Nygren, J., Histochem. and Cytochem. 30:407 (1982).

Embodiments described herein further include variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antibody fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antibody fragments, variable regions and CDRs set forth herein. Methods for determining homology between nucleic acid and amino acid sequences are well known to those of ordinary skill in the art.

In another embodiment, the invention further contemplates the above-recited polypeptide homologs of the antibody fragments, variable regions and CDRs set forth herein further having anti-NGF activity. Non-limiting examples of anti-NGF activity are set forth herein.

In another embodiment, the invention further contemplates the generation and use of anti-idiotypic antibodies that bind any of the foregoing sequences. In an exemplary embodiment, such an anti-idiotypic antibody could be administered to a subject who has received an anti-NGF antibody to modulate, reduce, or neutralize, the effect of the anti-NGF antibody. Such anti-idiotypic antibodies could also be useful for treatment of an autoimmune disease characterized by the presence of anti-NGF antibodies. A further exemplary use of such anti-idiotypic antibodies is for detection of the anti-NGF antibodies of the present invention, for example to monitor the levels of the anti-NGF antibodies present in a subject's blood or other bodily fluids.

The present invention also contemplates anti-NGF antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Additional Exemplary Embodiments of the Invention

In another embodiment, the invention contemplates methods of treating pain in an individual comprising administering to said individual one or more anti-human NGF antibodies or antibody fragments thereof that inhibit the association of NGF with TrkA, without appreciably inhibiting the association of NGF with p75, that specifically bind to the same or overlappingor conformational epitope(s) and/or compete for binding to the same or overlappingor conformational epitope(s) on an intact human NGF polypeptide or fragment thereof as an anti-human NGF antibody selected from Ab3, Ab4, Ab5, Ab6, Ab15, or Ab16; optionally in association with another antibody or antibody fragment that inhibits the association of NGF with TrkA, and further inhibits the association of NGF with p75, that specifically bind to the same or overlappingor conformational epitope(s) and/or compete for binding to the same or overlappingor conformational epitope(s) on an intact human NGF polypeptide or fragment thereof as an anti-human NGF antibody selected from Ab1, Ab2, Ab5, Ab6, Ab7, Ab8, Ab9, Ab10, Ab11, Ab12, Ab13, Ab14, Ab17, Ab18, Ab19, Ab20, or Ab21. In a preferred embodiment, the anti-human NGF antibody or fragment thereof specifically binds to the same or overlappingor conformational epitope(s) as an intact human NGF polypeptide or a fragment thereof as Ab3, Ab4, Ab5, Ab6, Ab15, or Ab16.

A preferred optional embodiment of the invention is directed to methods of treating pain in an individual comprising administering to said individual chimeric or humanized antibodies and fragments thereof (including Fab fragments) having binding specificity for NGF that inhibits the association of NGF with TrkA, without appreciably inhibiting the association of NGF with p75 in association with another anti-NGF antibody that further inhibits biological activities mediated by the binding of NGF to the p75 and TrkA receptors. In a particularly preferred embodiment of the invention, the chimeric or humanized anti-NGF antibodies are selected from Ab1, Ab2, Ab5-Ab14, or Ab17-Ab21.

Another preferred embodiment of the invention is directed to methods of treating pain in an individual comprising administering to said individual chimeric or humanized antibodies and fragments thereof capable of binding to NGF and selectively inhibiting biological activities mediated by the binding of NGF to the TrkA receptor, while not inhibiting biological activities mediated by the binding of NGF to the p75 receptor. In a particularly preferred embodiment of the invention, the chimeric or humanized anti-NGF antibodies that inhibit the association of NGF with TrkA, without appreciably inhibiting the association of NGF with p75 are selected from Ab3, Ab4, Ab15, or Ab16. In a preferred embodiment of the invention is contemplated a method of treating diseases or disorders associated with NGF by affecting those biological activities mediated only via TrkA, thereby avoiding the biological activities mediated via binding of NGF to p75. In one embodiment, the disease or disorder associated with NGF is pain. A further listing of diseases and disorders associated with NGF is provided herein.

In another embodiment of the invention, one or more of the chimeric or humanized anti-NGF antibodies Ab3, Ab4, Ab15, or Ab16, or fragments thereof (including Fab fragments) that inhibit the association of NGF with TrkA, without appreciably inhibiting the association of NGF with p75, are utilized in methods of treating pain associated with pre- and post-operative surgery, and pain associated with trauma or injury to the musculoskeletal system. Because the chimeric or humanized anti-NGF antibodies Ab3, Ab4, Ab15, or Ab16 are not believed to interfere with the NGF/p75 signaling pathway, these antibodies (and fragments thereof) are particularly useful in addressing pain in individuals in need to myogenic differentiation and muscle repair.

In another preferred embodiment of the invention, full length antibodies and Fab fragments thereof are capable of significantly reducing pain in vivo in murine models as assessed by using Gait analysis (as described in Example 7 herein), compared to results obtained with controls, and are therefore useful in methods comprising administering said antibodies to an individual to treat pain.

A particularly preferred embodiment of the invention contemplates the use of Fab polypeptide sequences for the treatment of pain in a patient that inhibit the association of NGF with TrkA, without appreciably inhibiting the association of NGF with p75. Non-limiting types of pain that may be treated using Fab polypeptide sequences are provided elsewhere in this disclosure.

In another embodiment of the invention, chimeric or humanized anti-NGF antibodies and fragments thereof (including Fab fragments) having binding specificity for NGF inhibit TF1 cell proliferation. In another embodiment of the invention, chimeric or humanized anti-NGF antibodies and fragments thereof (including Fab fragments) having binding specificity for NGF inhibit PC-12 neurite outgrowth and preferably inhibit the association of NGF with TrkA, without appreciably inhibiting the association of NGF with p75.

In another embodiment of the invention, the invention is directed to methods of treating pain using anti-human NGF antibodies and/or fragments thereof which inhibit the association of NGF with TrkA, without appreciably inhibiting the association of NGF with p75, and which specifically binds to the same or overlappingor conformational epitopes on an intact NGF polypeptide or fragment thereof that is (are) specifically bound by Ab3, Ab4, Ab15, or Ab16 as ascertained by epitopic mapping using overlapping linear peptide fragments which span the full length of the native human NGF polypeptide.

The invention is also directed to methods of treating pain using an anti-NGF antibody that binds with the same NGF epitope and/or competes with an anti-NGF antibody for binding to NGF as an antibody or antibody fragment disclosed herein, that inhibits the association of NGF with TrkA, without appreciably inhibiting the association of NGF with p75, including but not limited to an anti-NGF antibody selected from Ab3, Ab4, Ab15 and Ab16, optionally in association with another antibody that inhibits the association of NGF with TrkA, and which also inhibits the association of NGF with p75, selected from Ab1, Ab2, Ab5, Ab6, Ab7, Ab8, Ab9, Ab10, Ab11, Ab12, Ab13, Ab14, Ab17, Ab18, Ab19, or Ab20.

In another embodiment, the invention is also directed to methods of treating or preventing pain using an isolated anti-NGF antibody and/or antibody fragment comprising one or more of the CDRs contained in the $V_H$ polypeptide sequences selected from: 3, 13, 23, 33, 43, 53, 63, 73, 83, 93, 103, 113, 123, 133, 143, 153, 163, 173, 183, 193, or 402, or a variant thereof, and/or one or more of the CDRs contained in the $V_L$ polypeptide sequences selected from: 1, 11, 21, 31, 41, 51, 61, 71, 81, 91, 101, 111, 121, 131, 141, 151, 161, 171, 181, 191, or 401, or a variant thereof.

In one embodiment of the invention, the anti-human NGF antibody discussed in the two prior paragraphs comprises at least 2 complementarity determining regions (CDRs) in each the variable light and the variable heavy regions which are identical to those contained in an anti-human NGF antibody selected from the group consisting of Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20 or Ab21.

In a preferred embodiment, the anti-human NGF antibody discussed above for treatment or prevention of pain and pain associated conditions comprises at least 2 complementarity determining regions (CDRs) in each the variable light and the variable heavy regions which are identical to those contained in Ab3, Ab4, Ab5, or Ab6. In another embodiment, all of the CDRs of the anti-human NGF antibody discussed above are identical to the CDRs contained in an anti-human NGF antibody selected from Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20 or Ab21. In a preferred embodiment of the invention, all of the CDRs of the anti-human NGF antibody discussed above are identical to the CDRs contained in an anti-human NGF antibody selected from Ab3, Ab4, Ab15, or Ab16 that inhibits the association of NGF with TrkA, without appreciably inhibiting the association of NGF with p75.

The invention further contemplates that the one or more anti-human NGF antibodies discussed above are aglycosylated; that contain an Fc region that has been modified to alter effector function, half-life, proteolysis, and/or glycosylation; are human, humanized, single chain or chimeric; and are a humanized antibody derived from a rabbit (parent) anti-human NGF antibody for treatment or prevention of pain and pain associated conditions.

The invention further contemplates one or more anti-human NGF antibodies for treatment or prevention of pain and pain associated conditions wherein the framework regions (FRs) in the variable light region and the variable heavy regions of said antibody respectively are human FRs which are unmodified or which have been modified by the substitution of at most 2 or 3 human FR residues in the variable light or heavy chain region with the corresponding FR residues of the parent rabbit antibody, and wherein said human FRs have been derived from human variable heavy and light chain antibody sequences which have been selected from a library of human germline antibody sequences based on their high level of homology to the corresponding rabbit variable heavy or light chain regions relative to other human germline antibody sequences contained in the library.

In one embodiment of the invention, the anti-human NGF antibody or fragment for treatment or prevention of pain and pain associated conditions specifically binds to NGF expressing human cells and/or to circulating soluble NGF molecules in vivo, including NGF expressed on or by human cells in a patient with a disease associated with cells that express NGF and inhibits the association of NGF with TrkA, without appreciably inhibiting the association of NGF with p75.

In another embodiment, the disease is selected from inflammatory pain, post-operative incision pain, complex regional pain syndrome, cancer pain, primary or metastatic bone cancer pain, fracture pain, osteoporotic fracture pain, pain resulting from burn, osteoporosis, gout joint pain, pain associated with sickle cell crises, and other nociceptive pain, as well as hepatocellular carcinoma, breast cancer, liver cirrhosis, neurogenic pain, neuropathic pain, nociceptive pain, trigeminal neuralgia, post-herpetic neuralgia, phantom limb pain, fibromyalgia, menstrual pain, ovarialgia, reflex sympathetic dystrophy, neurogenic pain, osteoarthritis or rheumatoid arthritis pain, lower back pain, diabetic neuropathy, sciatica, or migraine.

The invention further contemplates anti-human NGF antibodies or fragments for treatment or prevention of pain and pain associated conditions directly or indirectly attached to a detectable label or therapeutic agent that preferably inhibit the association of NGF with TrkA, without appreciably inhibiting the association of NGF with p75.

The invention also contemplates one or more nucleic acid sequences which result in the expression of an anti-human NGF antibody or antibody fragment for treatment or prevention of pain and pain associated conditions as set forth above that preferably inhibit the association of NGF with TrkA, without appreciably inhibiting the association of NGF with p75, including those comprising, or alternatively consisting of, yeast or human preferred codons. The invention also contemplates vectors (including plasmids or recombinant viral vectors) comprising said nucleic acid sequence(s). The invention also contemplates host cells or recombinant host cells expressing at least one of the antibodies set forth above, including a mammalian, yeast, bacterial, and insect cells. In a preferred embodiment, the host cell is a yeast cell. In a further preferred embodiment, the yeast cell is a diploidal yeast cell. In a more preferred embodiment, the yeast cell is a *Pichia* yeast.

The invention also contemplates a method of treatment comprising administering to a patient with a disease or condition associated with NGF expressing cells a therapeutically effective amount of at least one anti-human NGF antibody or fragment described herein that inhibits the association of NGF with TrkA, without appreciably inhibiting the association of NGF with p75. The invention also contemplates that the treatment method for treatment or prevention of pain and pain associated conditions may involve the administration of two or more anti-NGF antibodies or fragments thereof and disclosed herein. If more than one antibody is administered to the patient, the multiple antibodies may be administered simultaneously or concurrently, or may be staggered in their administration. The diseases that may be treated are presented in the non-limiting list set forth above and elsewhere herein. In a preferred embodiment, the disease is selected from cancer pain or neuropathic pain. In a particularly preferred embodiment, the disease is cancer pain. In another embodiment the treatment further includes the administration of another therapeutic agent or regimen selected from chemotherapy, radiotherapy, cytokine administration or gene therapy.

In a non-limiting embodiment of the invention, another therapeutic agent or regimen includes Taxol (paclitaxel) or its derivatives, platinum compounds such as carboplatin or cisplatin, anthrocyclines such as doxorubicin, alkylating agents such as cyclophosphamide, anti-metabolites such as 5-fluorouracil, or etoposide.

The invention further contemplates a method of in vivo imaging which detects the presence of cells which express NGF comprising administering a diagnostically effective amount of at least one anti-human NGF antibody, preferably one that inhibits the association of NGF with TrkA, without appreciably inhibiting the association of NGF with p75. In one embodiment, said administration further includes the administration of a radionuclide or fluorophore that facilitates detection of the antibody at NGF expressing disease sites. In another embodiment of the invention, the method of in vivo imaging is used to detect NGF expressing tumors or metastases, or tumors or metastases expressing TrkA and/or p75 capable of binding to NGF. In a further embodiment, the results of said in vivo imaging method are used to facilitate the design of an appropriate therapeutic regimen, including therapeutic regimens including radiotherapy, chemotherapy or a combination thereof.

Polynucleotides Encoding Anti-NGF Antibody Polypeptides Antibody Ab1

The invention is further optionally directed to the use of polynucleotides set forth below to produce antibody Ab1 polypeptides for treatment or prevention of pain and pain associated conditions having binding specificity to NGF, which inhibit the association of NGF with TrkA and the association of NGF with p75, in methods of treating pain in an individual comprising administering to said individual antibody Ab1 polypeptides. In one embodiment of the invention, polynucleotides of the invention comprise, or alternatively consist of, the following polynucleotide sequence encoding the variable light chain polypeptide sequence of SEQ ID NO: 1:

```
                                        (SEQ ID NO: 201)
GCCCTTGTGATGACCCAGACTCCATCCTCCGTGTCTGCAGCTGTGGGAGG

CACAGTCACCATCAATTGCCAGGCCAGTCAGAACATTTACAGCAATTTAG

CCTGGTATCAACAGAGACCAGGGCAGCGTCCCAAGCTCCTGATCTATGGT

GCATCCAATCTGGATGCTGGGGTCCCATCGCGGTTCAGAGGCAGTGGATC

TGGGACAGAGTACACTCTCACCATCAGCGACCTGGAGTGTGACGATGTTG

GCACTTACTACTGTCAAAGTGCTTTTGATAGTGATAGTACTGAAAATACT

TTCGGCGGAGGGACCGAGGTGGTGGTCAAACGT.
```

In one optional embodiment of the invention, polynucleotides of the invention comprise, or alternatively consist of, the following polynucleotide sequence encoding the light chain polypeptide sequence of SEQ ID NO: 2:

```
                                        (SEQ ID NO: 202)
GCCCTTGTGATGACCCAGACTCCATCCTCCGTGTCTGCAGCTGTGGGAGG

CACAGTCACCATCAATTGCCAGGCCAGTCAGAACATTTACAGCAATTTAG

CCTGGTATCAACAGAGACCAGGGCAGCGTCCCAAGCTCCTGATCTATGGT

GCATCCAATCTGGATGCTGGGGTCCCATCGCGGTTCAGAGGCAGTGGATC

TGGGACAGAGTACACTCTCACCATCAGCGACCTGGAGTGTGACGATGTTG

GCACTTACTACTGTCAAAGTGCTTTTGATAGTGATAGTACTGAAAATACT

TTCGGCGGAGGGACCGAGGTGGTGGTCAAACGTACGGTAGCGGCCCCATC

TGTCTTCATCTTCCCGCCATCTGATGAGCAGTTGAAATCTGGAACTGCCT

CTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCAC

AGAGCAGGACAGCAAGGACAGCACCTACAGCCTCAGCAGCACCCTGACGC

TGAGCAAAGCAGACTACGAGAAACACAAAGTCTACGCCTGCGAAGTCACC

CATCAGGGCCTGAGCTCGCCCGTCACAAAGAGCTTCAACAGGGGAGAGTG

TTAG.
```

In another optional embodiment of the invention, polynucleotides of the invention comprise, or alternatively consist of, the following polynucleotide sequence encoding the variable heavy chain polypeptide sequence of SEQ ID NO: 3:

```
                                        (SEQ ID NO: 203)
CAGTCGCTGGAGGAGTCCGGGGGTCGCCTGGTCACGCCTGGGACACCCCT

GACACTCACCTGCACAGTCTCTGGCTTCTCCCTCAGTAGCTATGCAATGA

GCTGGGTCCGCCAGGCTCCAGGGAAGGGGCTGGAATGGATCGGAGTCATT

ACTAGTATTGGTAGCACAGTCTACGCGAGCTGGGCGAAAGGCCGATTCAC

CATCTCCAAAACCTCGACCACGGTGGATCTGAAAATCACCAGTCCGACAA

CCGAGGACACGGCCACCTATTTCTGTGCCAGAGGCTACGATGACTATGAT

GAGATGACCTACTTTAACATCTGGGGCCAGGGGACCCTCGTCACCGTCTC

GAGC.
```

In one optional embodiment of the invention, polynucleotides of the invention comprise, or alternatively consist of, the following polynucleotide sequence encoding the heavy chain polypeptide sequence of SEQ ID NO: 4:

```
                                        (SEQ ID NO: 204)
CAGTCGCTGGAGGAGTCCGGGGGTCGCCTGGTCACGCCTGGGACACCCCT

GACACTCACCTGCACAGTCTCTGGCTTCTCCCTCAGTAGCTATGCAATGA

GCTGGGTCCGCCAGGCTCCAGGGAAGGGGCTGGAATGGATCGGAGTCATT

ACTAGTATTGGTAGCACAGTCTACGCGAGCTGGGCGAAAGGCCGATTCAC

CATCTCCAAAACCTCGACCACGGTGGATCTGAAAATCACCAGTCCGACAA

CCGAGGACACGGCCACCTATTTCTGTGCCAGAGGCTACGATGACTATGAT

GAGATGACCTACTTTAACATCTGGGGCCAGGGGACCCTCGTCACCGTCTC

GAGCGCCTCCACCAAGGGCCCATCGGTCTTCCCCCTGGCACCCTCCTCCA

AGAGCACCTCTGGGGGCACAGCGGCCCTGGGCTGCCTGGTCAAGGACTAC

TTCCCCGAACCGGTGACGGTGTCGTGGAACTCAGGCGCCCTGACCAGCGG

CGTGCACACCTTCCCGGCTGTCCTACAGTCCTCAGGACTCTACTCCCTCA

GCAGCGTGGTGACCGTGCCCTCCAGCAGCTTGGGCACCCAGACCTACATC

TGCAACGTGAATCACAAGCCCAGCAACACCAAGGTGGACAAGAGAGTTGA
```

-continued

```
GCCCAAATCTTGTGACAAAACTCACACATGCCCACCGTGCCCAGCACCTG

AACTCCTGGGGGACCGTCAGTCTTCCTCTTCCCCCCAAAACCCAAGGAC

ACCCTCATGATCTCCCGGACCCCTGAGGTCACATGCGTGGTGGTGGACGT

GAGCCACGAAGACCCTGAGGTCAAGTTCAACTGGTACGTGGACGGCGTGG

AGGTGCATAATGCCAAGACAAAGCCGCGGGAGGAGCAGTACGCCAGCACG

TACCGTGTGGTCAGCGTCCTCACCGTCCTGCACCAGGACTGGCTGAATGG

CAAGGAGTACAAGTGCAAGGTCTCCAACAAAGCCCTCCCAGCCCCCATCG

AGAAAACCATCTCCAAAGCCAAAGGGCAGCCCCGAGAACCACAGGTGTAC

ACCCTGCCCCCATCCCGGGAGGAGATGACCAAGAACCAGGTCAGCCTGAC

CTGCCTGGTCAAAGGCTTCTATCCCAGCGACATCGCCGTGGAGTGGGAGA

GCAATGGGCAGCCGGAGAACAACTACAAGACCACGCCTCCCGTGCTGGAC

TCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGC

ACAACCACTACACGCAGAAGAGCCTCTCCCTGTCTCCGGGTAAATGA.
```

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 205; SEQ ID NO: 206; and SEQ ID NO: 207 which correspond to polynucleotides encoding the complementarity-determining regions (CDRs, or hypervariable regions) of the light chain variable sequence of SEQ ID NO: 1 or the light chain sequence of SEQ ID NO: 2.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 208; SEQ ID NO: 209; and SEQ ID NO: 210 which correspond to polynucleotides encoding the complementarity-determining regions (CDRs, or hypervariable regions) of the heavy chain variable sequence of SEQ ID NO: 3 or the heavy chain sequence of SEQ ID NO: 4.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 201 encoding the light chain variable sequence of SEQ ID NO: 1; the polynucleotide SEQ ID NO: 202 encoding the light chain sequence of SEQ ID NO: 2; the polynucleotide SEQ ID NO: 203 encoding the heavy chain variable sequence of SEQ ID NO: 3; the polynucleotide SEQ ID NO: 204 encoding the heavy chain sequence of SEQ ID NO: 4; polynucleotides encoding the complementarity-determining regions (SEQ ID NO: 205; SEQ ID NO: 206; and SEQ ID NO: 207) of the light chain variable sequence of SEQ ID NO: 1 or the light chain sequence of SEQ ID NO: 2; and polynucleotides encoding the complementarity-determining regions (SEQ ID NO: 208; SEQ ID NO: 209; and SEQ ID NO: 210) of the heavy chain variable sequence of SEQ ID NO: 3 or the heavy chain sequence of SEQ ID NO: 4.

In a preferred optional embodiment of the invention, polynucleotides of the invention comprise, or alternatively consist of, polynucleotides encoding Fab (fragment antigen binding) fragments for treatment or prevention of pain and pain associated conditions having binding specificity for NGF. With respect to antibody Ab1, the polynucleotides encoding the full length Ab1 antibody comprise, or alternatively consist of, the polynucleotide SEQ ID NO: 202 encoding the light chain sequence of SEQ ID NO: 2 and the polynucleotide SEQ ID NO: 204 encoding the heavy chain sequence of SEQ ID NO: 4.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments for treatment or prevention of pain and pain associated conditions may be produced by enzymatic digestion (e.g., papain) of Ab1 following expression of the full-length polynucleotides in a suitable host. In another embodiment of the invention, anti-NGF antibodies such as Ab1 or Fab fragments thereof may be produced via expression of Ab1 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab2

The invention is further optionally directed to the use of polynucleotides set forth below to produce antibody Ab2 polypeptides which inhibit the association of NGF with TrkA and the association of NGF with p75, for treatment or prevention of pain and pain associated conditions having binding specificity to NGF in methods of treating pain in an individual comprising administering to said individual antibody Ab2 polypeptides. The invention is further directed to polynucleotides encoding antibody polypeptides having binding specificity to NGF for treatment or prevention of pain and pain associated conditions. In one embodiment of the invention, polynucleotides of the invention comprise, or alternatively consist of, the following polynucleotide sequence encoding the variable light chain polypeptide sequence of SEQ ID NO: 11:

```
                                        (SEQ ID NO: 211)
GACATCCAGATGACCCAGTCTCCTTCCACCCTGTCTGCATCTGTAGGAGA

CAGAGTCACCATCACTTGCCAGGCCAGTCAGAACATTTACAGCAACTTAG

CCTGGTATCAGCAGAAACCAGGAAAAGCCCCTAAGCTCCTGATCTATGGT

GCATCCAATCTGGATGCTGGAGTCCCATCAAGGTTCTCTGGCAGTGGATC

TGGGACAGAGTACACTCTCACCATCAGCAGCCTGCAGCCTGATGATTTTG

CAACTTACTACTGCCAAAGTGCTTTTGATAGTGATAGTACTGAAAACACT

TTCGGCGGAGGAACCAAGGTGGAAATCAAACGT.
```

In one optional embodiment of the invention, polynucleotides of the invention comprise, or alternatively consist of, the following polynucleotide sequence encoding the light chain polypeptide sequence of SEQ ID NO: 12:

(SEQ ID NO: 212)
GACATCCAGATGACCCAGTCTCCTTCCACCCTGTCTGCATCTGTAGGAGA

CAGAGTCACCATCACTTGCCAGGCCAGTCAGAACATTTACAGCAACTTAG

CCTGGTATCAGCAGAAACCAGGAAAAGCCCCTAAGCTCCTGATCTATGGT

GCATCCAATCTGGATGCTGGAGTCCCATCAAGGTTCTCTGGCAGTGGATC

TGGGACAGAGTACACTCTCACCATCAGCAGCCTGCAGCCTGATGATTTTG

CAACTTACTACTGCCAAAGTGCTTTTGATAGTGATAGTACTGAAAACACT

TTCGGCGGAGGAACCAAGGTGGAAATCAAACGTACGGTAGCGGCCCCATC

TGTCTTCATCTTCCCGCCATCTGATGAGCAGTTGAAATCTGGAACTGCCT

CTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCAC

AGAGCAGGACAGCAAGGACAGCACCTACAGCCTCAGCAGCACCCTGACGC

TGAGCAAAGCAGACTACGAGAAACACAAAGTCTACGCCTGCGAAGTCACC

CATCAGGGCCTGAGCTCGCCCGTCACAAAGAGCTTCAACAGGGGAGAGTG

TTAG.

In another optional embodiment of the invention, polynucleotides of the invention comprise, or alternatively consist of, the following polynucleotide sequence encoding the variable heavy chain polypeptide sequence of SEQ ID NO: 13:

(SEQ ID NO: 213)
GAGGTGCAGCTGGTGGAGTCTGGGGGAGGCTTGGTCCAGCCTGGGGGGTC

CCTGAGACTCTCCTGTGCAGCCTCTGGATTCACCGTCAGTAGCTATGCAA

TGAGCTGGGTCCGTCAGGCTCCAGGGAAGGGGCTGGAGTGGGTCGGAGTC

ATTACTAGTATTGGTAGCACAGTCTACGCGAGCAGCGCGAAAGGCCGATT

CACCATCTCCAGAGACAATTCCAAGAACACCCTGTATCTTCAAATGAACA

GCCTGAGAGCTGAGGACACTGCTGTGTATTACTGTGCTAGAGGCTACGAT

GACTATGATGAGATGACCTACTTTAACATCTGGGGCCAAGGGACCCTCGT

CACCGTCTCGAGC.

In one optional embodiment of the invention, polynucleotides of the invention comprise, or alternatively consist of, the following polynucleotide sequence encoding the heavy chain polypeptide sequence of SEQ ID NO: 14:

(SEQ ID NO: 214)
GAGGTGCAGCTGGTGGAGTCTGGGGGAGGCTTGGTCCAGCCTGGGGGGTC

CCTGAGACTCTCCTGTGCAGCCTCTGGATTCACCGTCAGTAGCTATGCAA

TGAGCTGGGTCCGTCAGGCTCCAGGGAAGGGGCTGGAGTGGGTCGGAGTC

ATTACTAGTATTGGTAGCACAGTCTACGCGAGCAGCGCGAAAGGCCGATT

CACCATCTCCAGAGACAATTCCAAGAACACCCTGTATCTTCAAATGAACA

GCCTGAGAGCTGAGGACACTGCTGTGTATTACTGTGCTAGAGGCTACGAT

GACTATGATGAGATGACCTACTTTAACATCTGGGGCCAAGGGACCCTCGT

CACCGTCTCGAGCGCCTCCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCTTGGGCACCCAG

ACCTACATCTGCAACGTGAATCACAAGCCCAGCAACACCAAGGTGGACAA

GAGAGTTGAGCCCAAATCTTGTGACAAAACTCACACATGCCCACCGTGCC

CAGCACCTGAACTCCTGGGGGGACCGTCAGTCTTCCTCTTCCCCCCAAAA

CCCAAGGACACCCTCATGATCTCCCGGACCCCTGAGGTCACATGCGTGGT

GGTGGACGTGAGCCACGAAGACCCTGAGGTCAAGTTCAACTGGTACGTGG

ACGGCGTGGAGGTGCATAATGCCAAGACAAAGCCGCGGGAGGAGCAGTAC

GCCAGCACGTACCGTGTGGTCAGCGTCCTCACCGTCCTGCACCAGGACTG

GCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCA

CAGGTGTACACCCTGCCCCCATCCCGGGAGGAGATGACCAAGAACCAGGT

CAGCCTGACCTGCCTGGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTACAGCAAGCTCACCGTGGA

CAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGT

AAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 215; SEQ ID NO: 216; and SEQ ID NO: 217 which correspond to polynucleotides encoding the complementarity-determining regions (CDRs, or hypervariable regions) of the light chain variable sequence of SEQ ID NO: 11 or the light chain sequence of SEQ ID NO: 12.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 218; SEQ ID NO: 219; and SEQ ID NO: 220 which correspond to polynucleotides encoding the complementarity-determining regions (CDRs, or hypervariable regions) of the heavy chain variable sequence of SEQ ID NO: 13 or the heavy chain sequence of SEQ ID NO: 14.

The invention also optional contemplates polynucleotide sequences including one or more of the polynucleotide sequences encoding antibody fragments for treatment or prevention of pain and pain associated conditions described herein. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 211 encoding the light chain variable sequence of SEQ ID NO: 11; the polynucleotide SEQ ID NO: 212 encoding the light chain sequence of SEQ ID NO: 12; the polynucleotide SEQ ID NO: 213 encoding the heavy chain variable sequence of SEQ ID NO: 13; the polynucleotide SEQ ID NO: 214 encoding the heavy chain sequence of SEQ ID NO: 14; polynucleotides encoding the complementarity-determining regions (SEQ ID NO: 215; SEQ ID NO: 216; and SEQ ID NO: 217) of the light chain variable sequence of SEQ ID NO: 11 or the light chain sequence of SEQ ID NO: 12; and polynucleotides encoding the complementarity-determining regions (SEQ ID NO: 218; SEQ ID NO: 219; and SEQ ID NO: 220) of the heavy chain variable sequence of SEQ ID NO: 13 or the heavy chain sequence of SEQ ID NO: 14.

In a preferred optional embodiment of the invention, polynucleotides of the invention comprise, or alternatively consist of, polynucleotides encoding Fab (fragment antigen binding) fragments for treatment or prevention of pain and pain associated conditions having binding specificity for NGF. With respect to antibody Ab2, the polynucleotides encoding the full length Ab2 antibody comprise, or alternatively consist of, the polynucleotide SEQ ID NO: 212 encoding the light chain sequence of SEQ ID NO: 12 and the polynucleotide SEQ ID NO: 214 encoding the heavy chain sequence of SEQ ID NO: 14.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab2 following expression of the full-length polynucleotides in a suitable host. In another embodiment of the invention, anti-NGF antibodies such as Ab2 or Fab fragments thereof may be produced via expression of Ab2 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab3

The invention is further directed to the use of polynucleotides set forth below to produce antibody Ab3 polypeptides having binding specificity to NGF, which inhibit the association of NGF with TrkA without appreciably inhibiting the association of NGF with p75, in methods of treating pain in an individual comprising administering to said individual antibody Ab3 polypeptides. The invention is further directed to polynucleotides encoding antibody polypeptides having binding specificity to NGF. In one embodiment of the invention, polynucleotides of the invention comprise, or alternatively consist of, the following polynucleotide sequence encoding the variable light chain polypeptide sequence of SEQ ID NO: 21:

(SEQ ID NO: 221)
GCAGCCGTGCTGACCCAGACACCATCGCCCGTGTCTGCAGCTATGGGAGA

CACAGTCACCATCAAGTGCCAGTCCAGTCAGAGTGTTTATAAGAACAACT

ACTTATCCTGGTATCAGCAGAAACCAGGGCAGCCTCCCAGGCTCCTGATC

TATGATGCATCCAATCTGCCATCTGGGGTCCCATCACGGTTCAGCGGCAG

TGGATCTGGGACACAGTTCACTCTCACCATCAGCGGCGTGCAGTGTGACG

ATGCTGCCACTTACTACTGTCTAGGCGATTATGATGATGATGCTGATAAT

GCTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 22:

(SEQ ID NO: 222)
GCAGCCGTGCTGACCCAGACACCATCGCCCGTGTCTGCAGCTATGGGAGA

CACAGTCACCATCAAGTGCCAGTCCAGTCAGAGTGTTTATAAGAACAACT

ACTTATCCTGGTATCAGCAGAAACCAGGGCAGCCTCCCAGGCTCCTGATC

TATGATGCATCCAATCTGCCATCTGGGGTCCCATCACGGTTCAGCGGCAG

TGGATCTGGGACACAGTTCACTCTCACCATCAGCGGCGTGCAGTGTGACG

ATGCTGCCACTTACTACTGTCTAGGCGATTATGATGATGATGCTGATAAT

GCTTTCGGCGGAGGGACCGAGGTGGTGGTCAAACGTACGGTAGCGGCCCC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAG.

In another embodiment of the invention, polynucleotides of the invention comprise, or alternatively consist of, the following polynucleotide sequence encoding the variable heavy chain polypeptide sequence of SEQ ID NO: 23:

(SEQ ID NO: 223)
CAGTCGGTGGAGGAGTCCGGGGGTCGCCTGGTCACGCCTGGGACACCCCT

GACACTCACCTGCACAGTCTCTGGATTCTCCCTCAGTAGCTATGTAATGA

TCTGGGTCCGCCAGGCTCCAGGGAAGGGGCTGGAATACATCGGAATCACT

TGGAGTGCTGGTACATACTACGCGAGCTGGGCGAAAGGCCGATTCACCAT

CTCCAAAACCTCGTCGACCACGGTGGATCTGAAAATCACCAGTCCGACAA

CCGAGGACACGGCCACCTATTTCTGTGCCGGAGGTGGTGGTAGTATTTAT

GATATTTGGGGCCCGGGCACCCTGGTCACCGTCTCGAGC.

In one embodiment of the invention, polynucleotides of the invention comprise, or alternatively consist of, the following polynucleotide sequence encoding the heavy chain polypeptide sequence of SEQ ID NO: 24:

(SEQ ID NO: 224)
CAGTCGGTGGAGGAGTCCGGGGGTCGCCTGGTCACGCCTGGGACACCCC

TGACACTCACCTGCACAGTCTCTGGATTCTCCCTCAGTAGCTATGTAAT

GATCTGGGTCCGCCAGGCTCCAGGGAAGGGGCTGGAATACATCGGAATC

ACTTGGAGTGCTGGTACATACTACGCGAGCTGGGCGAAAGGCCGATTCA

CCATCTCCAAAACCTCGTCGACCACGGTGGATCTGAAAATCACCAGTCC

GACAACCGAGGACACGGCCACCTATTTCTGTGCCGGAGGTGGTGGTAGT

ATTTATGATATTTGGGGCCCGGGCACCCTGGTCACCGTCTCGAGCGCCT

CCACCAAGGGCCCATCGGTCTTCCCCCTGGCACCCTCCTCCAAGAGCAC

CTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGC

ACACCTTCCCGGCTGTCCTACAGTCCTCAGGACTCTACTCCCTCAGCAG

-continued

```
CGTGGTGACCGTGCCCTCCAGCAGCTTGGGCACCCAGACCTACATCTGC

AACGTGAATCACAAGCCCAGCAACACCAAGGTGGACAAGAGAGTTGAGC

CCAAATCTTGTGACAAAACTCACACATGCCCACCGTGCCCAGCACCTGA

ACTCCTGGGGGACCGTCAGTCTTCCTCTTCCCCCCAAAACCCAAGGAC

ACCCTCATGATCTCCCGGACCCCTGAGGTCACATGCGTGGTGGTGGACG

TGAGCCACGAAGACCCTGAGGTCAAGTTCAACTGGTACGTGGACGGCGT

GGAGGTGCATAATGCCAAGACAAAGCCGCGGGAGGAGCAGTACGCCAGC

ACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCC

CATCGAGAAAACCATCTCCAAAGCCAAAGGGCAGCCCCGAGAACCACAG

GTGTACACCCTGCCCCCATCCCGGGAGGAGATGACCAAGAACCAGGTCA

GCCTGACCTGCCTGGTCAAAGGCTTCTATCCCAGCGACATCGCCGTGGA

GTGGGAGAGCAATGGGCAGCCGGAGAACAACTACAAGACCACGCCTCCC

GTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCA

TGAGGCTCTGCACAACCACTACACGCAGAAGAGCCTCTCCCTGTCTCCG

GGTAAATGA.
```

In a further embodiment of the invention, polynucleotides encoding antibody fragments having binding specificity to NGF comprise, or alternatively consist of, one or more of the polynucleotide sequences of SEQ ID NO: 225; SEQ ID NO: 226; and SEQ ID NO: 227 which correspond to polynucleotides encoding the complementarity-determining regions (CDRs, or hypervariable regions) of the light chain variable sequence of SEQ ID NO: 21 or the light chain sequence of SEQ ID NO: 22.

In a further embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 228; SEQ ID NO: 229; and SEQ ID NO: 230 which correspond to polynucleotides encoding the complementarity-determining regions (CDRs, or hypervariable regions) of the heavy chain variable sequence of SEQ ID NO: 23 or the heavy chain sequence of SEQ ID NO: 24.

The invention also contemplates polynucleotide sequences including one or more of the polynucleotide sequences encoding antibody fragments described herein for treatment or prevention of pain and pain associated conditions. In one embodiment of the invention, polynucleotides encoding antibody fragments having binding specificity to NGF comprise, or alternatively consist of, one, two, three or more, including all of the following polynucleotides encoding antibody fragments: the polynucleotide SEQ ID NO: 221 encoding the light chain variable sequence of SEQ ID NO: 21; the polynucleotide SEQ ID NO: 222 encoding the light chain sequence of SEQ ID NO: 22; the polynucleotide SEQ ID NO: 223 encoding the heavy chain variable sequence of SEQ ID NO: 23; the polynucleotide SEQ ID NO: 224 encoding the heavy chain sequence of SEQ ID NO: 24; polynucleotides encoding the complementarity-determining regions (SEQ ID NO: 225; SEQ ID NO: 226; and SEQ ID NO: 227) of the light chain variable sequence of SEQ ID NO: 21 or the light chain sequence of SEQ ID NO: 22; and polynucleotides encoding the complementarity-determining regions (SEQ ID NO: 228; SEQ ID NO: 229; and SEQ ID NO: 230) of the heavy chain variable sequence of SEQ ID NO: 23 or the heavy chain sequence of SEQ ID NO: 24.

In a preferred embodiment of the invention, polynucleotides of the invention comprise, or alternatively consist of, polynucleotides encoding Fab (fragment antigen binding) fragments for treatment or prevention of pain and pain associated conditions having binding specificity for NGF. With respect to antibody Ab3, the polynucleotides encoding the full length Ab3 antibody comprise, or alternatively consist of, the polynucleotide SEQ ID NO: 222 encoding the light chain sequence of SEQ ID NO: 22 and the polynucleotide SEQ ID NO: 224 encoding the heavy chain sequence of SEQ ID NO: 24.

Another embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab3 following expression of the full-length polynucleotides in a suitable host. In another embodiment of the invention, anti-NGF antibodies such as Ab3 or Fab fragments thereof may be produced via expression of Ab3 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab4

The invention is further directed to the use of polynucleotides set forth below to produce antibody Ab4 polypeptides having binding specificity to NGF, which inhibit the association of NGF with TrkA without appreciably inhibiting the association of NGF with p75, in methods of treating pain in an individual comprising administering to said individual antibody Ab4 polypeptides. The invention is further directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 31:

```
                                        (SEQ ID NO: 231)
GACATCCAGATGACCCAGTCTCCTTCCACCCTGTCTGCATCTGTAGGA

GACAGAGTCACCATCACTTGCCAGTCCAGTCAGAGTGTCTATAAGAACA

ACTACTTATCCTGGTATCAGCAGAAACCAGGAAAAGCCCCTAAGCTCCT

GATCTATGATGCATCCAATCTGCCATCTGGAGTCCCATCAAGGTTCAGC

GGCAGTGGATCTGGAACAGAATTCACTCTCACCATCAGCAGCCTGCAGC

CTGATGATTTTGCAACTTATTACTGCCTAGGCGATTATGATGATGATGC

TGATAATGCTTTCGGCGGAGGAACCAAGGTGGAAATCAAACGT.
```

In one embodiment of the invention, polynucleotides of the invention comprise, or alternatively consist of, the following polynucleotide sequence encoding the light chain polypeptide sequence of SEQ ID NO: 32:

(SEQ ID NO: 232)
GACATCCAGATGACCCAGTCTCCTTCCACCCTGTCTGCATCTGTAGGA

GACAGAGTCACCATCACTTGCCAGTCCAGTCAGAGTGTCTATAAGAACA

ACTACTTATCCTGGTATCAGCAGAAACCAGGAAAAGCCCCTAAGCTCCT

GATCTATGATGCATCCAATCTGCCATCTGGAGTCCCATCAAGGTTCAGC

GGCAGTGGATCTGGAACAGAATTCACTCTCACCATCAGCAGCCTGCAGC

CTGATGATTTTGCAACTTATTACTGCCTAGGCGATTATGATGATGATGC

TGATAATGCTTTCGGCGGAGGAACCAAGGTGGAAATCAAACGTACGGTA

GCGGCCCCATCTGTCTTCATCTTCCCGCCATCTGATGAGCAGTTGAAAT

CTGGAACTGCCTCTGTTGTGTGCCTGCTGAATAACTTCTATCCCAGAGA

GGCCAAAGTACAGTGGAAGGTGGATAACGCCCTCCAATCGGGTAACTCC

CAGGAGAGTGTCACAGAGCAGGACAGCAAGGACAGCACCTACAGCCTCA

GCAGCACCCTGACGCTGAGCAAAGCAGACTACGAGAAACACAAAGTCTA

CGCCTGCGAAGTCACCCATCAGGGCCTGAGCTCGCCCGTCACAAAGAGC

TTCAACAGGGGAGAGTGTTAG.

In another embodiment of the invention, polynucleotides of the invention comprise, or alternatively consist of, the following polynucleotide sequence encoding the variable heavy chain polypeptide sequence of SEQ ID NO: 33:

(SEQ ID NO: 233)
GAGGTGCAGCTGGTGGAGTCTGGGGGAGGCTTGGTCCAGCCTGGGGGGT

CCCTGAGACTCTCCTGTGCAGCCTCTGGATTCACCGTCAGTAGCTATGT

AATGATCTGGGTCCGTCAGGCTCCAGGGAAGGGGCTGGAGTACATCGGA

ATCACTTGGAGTGCTGGTACATACTACGCGAGCAGTGCGAAAGGCCGAT

TCACCATCTCCAGAGACAATTCCAAGAACACCCTGTATCTTCAAATGAAC

AGCCTGAGAGCTGAGGACACTGCTGTGTATTACTGTGCTGGAGGTGGTGG

TAGTATCTATGATATTTGGGGCCAAGGGACCCTCGTCACCGTCTCGAGC.

In one embodiment of the invention, polynucleotides of the invention comprise, or alternatively consist of, the following polynucleotide sequence encoding the heavy chain polypeptide sequence of SEQ ID NO: 34:

(SEQ ID NO: 234)
GAGGTGCAGCTGGTGGAGTCTGGGGGAGGCTTGGTCCAGCCTGGGGGGT

CCCTGAGACTCTCCTGTGCAGCCTCTGGATTCACCGTCAGTAGCTATGT

AATGATCTGGGTCCGTCAGGCTCCAGGGAAGGGGCTGGAGTACATCGGA

ATCACTTGGAGTGCTGGTACATACTACGCGAGCAGTGCGAAAGGCCGAT

TCACCATCTCCAGAGACAATTCCAAGAACACCCTGTATCTTCAAATGAA

CAGCCTGAGAGCTGAGGACACTGCTGTGTATTACTGTGCTGGAGGTGGT

GGTAGTATCTATGATATTTGGGGCCAAGGGACCCTCGTCACCGTCTCGA

GCGCCTCCACCAAGGGCCCATCGGTCTTCCCCCTGGCACCCTCCTCCAA

GAGCACCTCTGGGGGCACAGCGGCCCTGGGCTGCCTGGTCAAGGACTAC

TTCCCCGAACCGGTGACGGTGTCGTGGAACTCAGGCGCCCTGACCAGCG

GCGTGCACACCTTCCCGGCTGTCCTACAGTCCTCAGGACTCTACTCCCT

CAGCAGCGTGGTGACCGTGCCCTCCAGCAGCTTGGGCACCCAGACCTAC

ATCTGCAACGTGAATCACAAGCCCAGCAACACCAAGGTGGACAAGAGAG

TTGAGCCCAAATCTTGTGACAAAACTCACACATGCCCACCGTGCCCAGC

ACCTGAACTCCTGGGGGGACCGTCAGTCTTCCTCTTCCCCCCAAAACCC

AAGGACACCCTCATGATCTCCCGGACCCCTGAGGTCACATGCGTGGTGG

TGGACGTGAGCCACGAAGACCCTGAGGTCAAGTTCAACTGGTACGTGGA

CGGCGTGGAGGTGCATAATGCCAAGACAAAGCCGCGGGAGGAGCAGTAC

GCCAGCACGTACCGTGTGGTCAGCGTCCTCACCGTCCTGCACCAGGACT

GGCTGAATGGCAAGGAGTACAAGTGCAAGGTCTCCAACAAAGCCCTCCC

AGCCCCCATCGAGAAAACCATCTCCAAAGCCAAAGGGCAGCCCCGAGAA

CCACAGGTGTACACCCTGCCCCCATCCCGGGAGGAGATGACCAAGAACC

AGGTCAGCCTGACCTGCCTGGTCAAAGGCTTCTATCCCAGCGACATCGC

CGTGGAGTGGGAGAGCAATGGGCAGCCGGAGAACAACTACAAGACCACG

CCTCCCGTGCTGGACTCCGACGGCTCCTTCTTCCTCTACAGCAAGCTCA

CCGTGGACAAGAGCAGGTGGCAGCAGGGGAACGTCTTCTCATGCTCCGT

GATGCATGAGGCTCTGCACAACCACTACACGCAGAAGAGCCTCTCCCTG

TCTCCGGGTAAATGA.

In a further embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 235; SEQ ID NO: 236; and SEQ ID NO: 237 which correspond to polynucleotides encoding the complementarity-determining regions (CDRs, or hypervariable regions) of the light chain variable sequence of SEQ ID NO: 31 or the light chain sequence of SEQ ID NO: 32.

In a further embodiment of the invention, polynucleotides encoding antibody fragments h for treatment or prevention of pain and pain associated conditions having binding specificity to NGF comprise, or alternatively consist of, one or more of the polynucleotide sequences of SEQ ID NO: 238; SEQ ID NO: 239; and SEQ ID NO: 240 which correspond to polynucleotides encoding the complementarity-determining regions (CDRs, or hypervariable regions) of the heavy chain variable sequence of SEQ ID NO: 33 or the heavy chain sequence of SEQ ID NO: 34.

The invention also contemplates polynucleotide sequences including one or more of the polynucleotide sequences encoding antibody fragments described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 231 encoding the light chain variable sequence of SEQ ID NO: 31; the polynucleotide SEQ ID NO: 232 encoding the light chain sequence of SEQ ID NO: 32; the polynucleotide SEQ ID NO: 233 encoding the heavy chain variable sequence of SEQ ID NO: 33; the polynucleotide SEQ ID NO: 234 encoding the heavy chain sequence of SEQ ID NO: 34; polynucleotides encoding the complementarity-determining regions (SEQ ID NO: 235; SEQ ID NO: 236; and SEQ ID NO: 237) of the light chain variable sequence of SEQ ID NO: 31 or the light chain sequence of SEQ ID NO: 32; and polynucleotides encoding the complementarity-determining regions (SEQ ID NO: 238; SEQ ID NO: 239; and SEQ ID NO: 240) of the heavy chain variable sequence of SEQ ID NO: 33 or the heavy chain sequence of SEQ ID NO: 34.

In a preferred embodiment of the invention, polynucleotides of the invention comprise, or alternatively consist of, polynucleotides encoding Fab (fragment antigen binding) fragments for treatment or prevention of pain and pain associated conditions having binding specificity for NGF. With respect to antibody Ab4, the polynucleotides encoding the full length Ab4 antibody comprise, or alternatively consist of, the polynucleotide SEQ ID NO: 232 encoding the light chain sequence of SEQ ID NO: 32 and the polynucleotide SEQ ID NO: 234 encoding the heavy chain sequence of SEQ ID NO: 34.

Another embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab4 following expression of the full-length polynucleotides in a suitable host. In another embodiment of the invention, anti-NGF antibodies for treatment or prevention of pain and pain associated conditions such as Ab4 or Fab fragments thereof may be produced via expression of Ab4 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab5

The invention is further optionally directed to the use of polynucleotides set forth below to produce antibody Ab5 polypeptides for treatment or prevention of pain and pain associated conditions having binding specificity to NGF, which inhibit the association of NGF with TrkA and the association of NGF with p75, in methods of treating pain in an individual comprising administering to said individual antibody Ab5 polypeptides. The invention is further directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 41:

(SEQ ID NO: 241)
GCCTATGATATGACCCAGACTCCAGCCTCTGTGGAGGTAGCTGTGGGAG

GCACAGTCACCATCAAGTGCCAGGCCAGTCAGAGCATTTACAGCAATTT

AGCCTGGTATCAGCAGAGACCAGGGCAGCCTCCCAAGCTCCTGATCTAT

GATGCATCCACTCTGGAATCTGGGGTCCCATCGCGGTTCAAAGGCAGTG

GATCTGGGACAGAGTACACTCTCACCATCAGCGGCGTGGAGTGTGCCGA

TGCTGCCTCTTACTACTGTCAACAGGGTTTTACTGTTAGTGATATTGAT

AATGCTTTCGGCGGAGGGACCGAGGTGGTGGTCAAACGT.

In one optional embodiment of the invention, polynucleotides of the invention comprise, or alternatively consist of, the following polynucleotide sequence encoding the light chain polypeptide sequence of SEQ ID NO: 42:

(SEQ ID NO: 242)
GCCTATGATATGACCCAGACTCCAGCCTCTGTGGAGGTAGCTGTGGGAG

GCACAGTCACCATCAAGTGCCAGGCCAGTCAGAGCATTTACAGCAATTT

AGCCTGGTATCAGCAGAGACCAGGGCAGCCTCCCAAGCTCCTGATCTAT

GATGCATCCACTCTGGAATCTGGGGTCCCATCGCGGTTCAAAGGCAGTG

GATCTGGGACAGAGTACACTCTCACCATCAGCGGCGTGGAGTGTGCCGA

TGCTGCCTCTTACTACTGTCAACAGGGTTTTACTGTTAGTGATATTGAT

AATGCTTTCGGCGGAGGGACCGAGGTGGTGGTCAAACGTACGGTAGCGG

CCCCATCTGTCTTCATCTTCCCGCCATCTGATGAGCAGTTGAAATCTGG

AACTGCCTCTGTTGTGTGCCTGCTGAATAACTTCTATCCCAGAGAGGCC

AAAGTACAGTGGAAGGTGGATAACGCCCTCCAATCGGGTAACTCCCAGG

AGAGTGTCACAGAGCAGGACAGCAAGGACAGCACCTACAGCCTCAGCAG

CACCCTGACGCTGAGCAAAGCAGACTACGAGAAACACAAAGTCTACGCC

TGCGAAGTCACCCATCAGGGCCTGAGCTCGCCCGTCACAAAGAGCTTCA

ACAGGGGAGAGTGTTAG.

In another optional embodiment of the invention, polynucleotides of the invention comprise, or alternatively consist of, the following polynucleotide sequence encoding the variable heavy chain polypeptide sequence of SEQ ID NO: 43:

(SEQ ID NO: 243)
CAGTCGGTGGAGGAGTCCGGGGGTCGCCTGGTCACGCCTGGGACACCCCT

GACACTCACCTGCACAGTCTCTGGATTCTCCCTCAGTAACTATGCAGTG

GGCTGGGTCCGCCAGGCTCCAGGGAAGGGGCTGGAATGGATCGGAATCA

TTGGTCGTAATGGTAACACATGGTACGCGAGCTGGGCAAGAGGCCGATT

CACCATCTCCAAAACCTCGACCACGGTGGATCTGAAAATCACCAGTCCG

ACAAGCGAGGACACGGCCACATATTTCTGTGCCAGAGGATATGGCCGTA

GTGTTGCTTATTACGTCTTTAACATCTGGGGCCCAGGCACCCTCGTCAC

CGTCTCGAGC.

In one optional embodiment of the invention, polynucleotides of the invention comprise, or alternatively consist of, the following polynucleotide sequence encoding the heavy chain polypeptide sequence of SEQ ID NO: 44:

(SEQ ID NO: 244)
CAGTCGGTGGAGGAGTCCGGGGGTCGCCTGGTCACGCCTGGGACACCCC

TGACACTCACCTGCACAGTCTCTGGATTCTCCCTCAGTAACTATGCAGT

GGGCTGGGTCCGCCAGGCTCCAGGGAAGGGGCTGGAATGGATCGGAATC

ATTGGTCGTAATGGTAACACATGGTACGCGAGCTGGGCAAGAGGCCGAT

TCACCATCTCCAAAACCTCGACCACGGTGGATCTGAAAATCACCAGTCC

GACAAGCGAGGACACGGCCACATATTTCTGTGCCAGAGGATATGGCCGT

AGTGTTGCTTATTACGTCTTTAACATCTGGGGCCCAGGCACCCTCGTCA

CCGTCTCGAGCGCCTCCACCAAGGGCCCATCGGTCTTCCCCCTGGCACC

```
-continued
CTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCC

TGACCAGCGGCGTGCACACCTTCCCGGCTGTCCTACAGTCCTCAGGACT

CTACTCCCTCAGCAGCGTGGTGACCGTGCCCTCCAGCAGCTTGGGCACC

CAGACCTACATCTGCAACGTGAATCACAAGCCCAGCAACACCAAGGTGG

ACAAGAGAGTTGAGCCCAAATCTTGTGACAAAACTCACACATGCCCACC

GTGCCCAGCACCTGAACTCCTGGGGGACCGTCAGTCTTCCTCTTCCCC

CCAAAACCCAAGGACACCCTCATGATCTCCCGGACCCCTGAGGTCACAT

GCGTGGTGGTGGACGTGAGCCACGAAGACCCTGAGGTCAAGTTCAACTG

GTACGTGGACGGCGTGGAGGTGCATAATGCCAAGACAAAGCCGCGGGAG

GAGCAGTACGCCAGCACGTACCGTGTGGTCAGCGTCCTCACCGTCCTGC

ACCAGGACTGGCTGAATGGCAAGGAGTACAAGTGCAAGGTCTCCAACAA

AGCCCTCCCAGCCCCCATCGAGAAAACCATCTCCAAAGCCAAAGGGCAG

CCCCGAGAACCACAGGTGTACACCCTGCCCCCATCCCGGGAGGAGATGA

CCAAGAACCAGGTCAGCCTGACCTGCCTGGTCAAAGGCTTCTATCCCAG

CGACATCGCCGTGGAGTGGGAGAGCAATGGGCAGCCGGAGAACAACTAC

AAGACCACGCCTCCCGTGCTGGACTCCGACGGCTCCTTCTTCCTCTACA

GCAAGCTCACCGTGGACAAGAGCAGGTGGCAGCAGGGGAACGTCTTCTC

ATGCTCCGTGATGCATGAGGCTCTGCACAACCACTACACGCAGAAGAGC

CTCTCCCTGTCTCCGGGTAAATGA.
```

In a further optional embodiment of the invention, polynucleotides encoding for treatment or prevention of pain and pain associated conditions fragments having binding specificity to NGF comprise, or alternatively consist of, one or more of the polynucleotide sequences of SEQ ID NO: 245; SEQ ID NO: 246; and SEQ ID NO: 247 which correspond to polynucleotides encoding the complementarity-determining regions (CDRs, or hypervariable regions) of the light chain variable sequence of SEQ ID NO: 41 or the light chain sequence of SEQ ID NO: 42.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 248; SEQ ID NO: 249; and SEQ ID NO: 250 which correspond to polynucleotides encoding the complementarity-determining regions (CDRs, or hypervariable regions) of the heavy chain variable sequence of SEQ ID NO: 43 or the heavy chain sequence of SEQ ID NO: 44.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 241 encoding the light chain variable sequence of SEQ ID NO: 41; the polynucleotide SEQ ID NO: 242 encoding the light chain sequence of SEQ ID NO: 42; the polynucleotide SEQ ID NO: 243 encoding the heavy chain variable sequence of SEQ ID NO: 43; the polynucleotide SEQ ID NO: 244 encoding the heavy chain sequence of SEQ ID NO: 44; polynucleotides encoding the complementarity-determining regions (SEQ ID NO: 245; SEQ ID NO: 246; and SEQ ID NO: 247) of the light chain variable sequence of SEQ ID NO: 41 or the light chain sequence of SEQ ID NO: 42; and polynucleotides encoding the complementarity-determining regions (SEQ ID NO: 248; SEQ ID NO: 249; and SEQ ID NO: 250) of the heavy chain variable sequence of SEQ ID NO: 43 or the heavy chain sequence of SEQ ID NO: 44.

In a preferred optional embodiment of the invention, polynucleotides of the invention comprise, or alternatively consist of, polynucleotides encoding Fab (fragment antigen binding) fragments having binding specificity for NGF. With respect to antibody Ab5, the polynucleotides encoding the full length Ab5 antibody comprise, or alternatively consist of, the polynucleotide SEQ ID NO: 242 encoding the light chain sequence of SEQ ID NO: 42 and the polynucleotide SEQ ID NO: 244 encoding the heavy chain sequence of SEQ ID NO: 44.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab5 following expression of the full-length polynucleotides in a suitable host. In another optional embodiment of the invention, anti-NGF antibodies such as Ab5 or Fab fragments thereof may be produced via expression of Ab5 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab6

The invention is further optionally directed to the use of polynucleotides set forth below to produce antibody Ab6 polypeptides having binding specificity to NGF, which inhibits the association of NGF with TrkA and the association of NGF with p75, in methods of treating pain in an individual comprising administering to said individual antibody Ab6 polypeptides. The invention is further directed to polynucleotides encoding for treatment or prevention of pain and pain associated conditions polypeptides having binding specificity to NGF. In one embodiment of the invention, polynucleotides of the invention comprise, or alternatively consist of, the following polynucleotide sequence encoding the variable light chain polypeptide sequence of SEQ ID NO: 51:

```
                                          (SEQ ID NO: 251)
GACATCCAGATGACCCAGTCTCCTTCCACCCTGTCTGCATCTGTAGGAG

ACAGAGTCACCATCACTTGCCAGGCCAGTCAGAGCATTTACAGCAATCT

TGCCTGGTATCAGCAGAAACCAGGAAAAGCCCCTAAGCTCCTGATCTAT

GATGCATCCACTCTGGAATCTGGAGTCCCATCAAGGTTCAGCGGCAGTG

GATCTGGGACAGAGTACACTCTCACCATCAGCAGCCTGCAGCCTGATGAT

TTTGCAACTTACTACTGCCAACAGGGTTTTACTGTTAGTGATATTGATA

ATGCTTTCGGCGGAGGAACCAAGGTGGAAATCAAACGT.
```

In one optional embodiment of the invention, polynucleotides of the invention comprise, or alternatively consist of, the following polynucleotide sequence encoding the light chain polypeptide sequence of SEQ ID NO: 52:

(SEQ ID NO: 252)
GACATCCAGATGACCCAGTCTCCTTCCACCCTGTCTGCATCTGTAGGAG

ACAGAGTCACCATCACTTGCCAGGCCAGTCAGAGCATTTACAGCAATCT

TGCCTGGTATCAGCAGAAACCAGGAAAAGCCCCTAAGCTCCTGATCTAT

GATGCATCCACTCTGGAATCTGGAGTCCCATCAAGGTTCAGCGGCAGTG

GATCTGGGACAGAGTACACTCTCACCATCAGCAGCCTGCAGCCTGATGA

TTTTGCAACTTACTACTGCCAACAGGGTTTTACTGTTAGTGATATTGAT

AATGCTTTCGGCGGAGGAACCAAGGTGGAAATCAAACGTACGGTAGCGG

CCCCATCTGTCTTCATCTTCCCGCCATCTGATGAGCAGTTGAAATCTGG

AACTGCCTCTGTTGTGTGCCTGCTGAATAACTTCTATCCCAGAGAGGCC

AAAGTACAGTGGAAGGTGGATAACGCCCTCCAATCGGGTAACTCCCAGG

AGAGTGTCACAGAGCAGGACAGCAAGGACAGCACCTACAGCCTCAGCAG

CACCCTGACGCTGAGCAAAGCAGACTACGAGAAACACAAAGTCTACGCC

TGCGAAGTCACCCATCAGGGCCTGAGCTCGCCCGTCACAAAGAGCTTCA

ACAGGGGAGAGTGTTAG.

In another optional embodiment of the invention, polynucleotides of the invention comprise, or alternatively consist of, the following polynucleotide sequence encoding the variable heavy chain polypeptide sequence of SEQ ID NO: 53:

(SEQ ID NO: 253)
GAGGTGCAGCTGGTGGAGTCTGGGGGAGGCTTGGTCCAGCCTGGGGGGT

CCCTGAGACTCTCCTGTGCAGCCTCTGGATTCACCGTCAGTAACTATGC

AGTGGGCTGGGTCCGTCAGGCTCCAGGGAAGGGGCTGGAGTGGGTCGGA

ATCATTGGTCGTAATGGTAACACATGGTACGCGAGCTCTGCAAGAGGCC

GATTCACCATCTCCAGAGACAATTCCAAGAACACCCTGTATCTTCAAAT

GAACAGCCTGAGAGCTGAGGACACTGCTGTGTATTACTGTGCTAGAGGA

TATGGCCGTAGTGTTGCTTATTACGTCTTTAACATCTGGGGCCCAGGGA

CCCTCGTCACCGTCTCGAGC.

In one optional embodiment of the invention, polynucleotides of the invention comprise, or alternatively consist of, the following polynucleotide sequence encoding the heavy chain polypeptide sequence of SEQ ID NO: 54:

(SEQ ID NO: 254)
GAGGTGCAGCTGGTGGAGTCTGGGGGAGGCTTGGTCCAGCCTGGGGGGT

CCCTGAGACTCTCCTGTGCAGCCTCTGGATTCACCGTCAGTAACTATGC

AGTGGGCTGGGTCCGTCAGGCTCCAGGGAAGGGGCTGGAGTGGGTCGGA

ATCATTGGTCGTAATGGTAACACATGGTACGCGAGCTCTGCAAGAGGCC

GATTCACCATCTCCAGAGACAATTCCAAGAACACCCTGTATCTTCAAAT

GAACAGCCTGAGAGCTGAGGACACTGCTGTGTATTACTGTGCTAGAGGA

TATGGCCGTAGTGTTGCTTATTACGTCTTTAACATCTGGGGCCCAGGGA

CCCTCGTCACCGTCTCGAGCGCCTCCACCAAGGGCCCATCGGTCTTCCC

CCTGGCACCCTCCTCCAAGAGCACCTCTGGGGGCACAGCGGCCCTGGGC

TGCCTGGTCAAGGACTACTTCCCCGAACCGGTGACGGTGTCGTGGAACT

CAGGCGCCCTGACCAGCGGCGTGCACACCTTCCCGGCTGTCCTACAGTC

CTCAGGACTCTACTCCCTCAGCAGCGTGGTGACCGTGCCCTCCAGCAGC

TTGGGCACCCAGACCTACATCTGCAACGTGAATCACAAGCCCAGCAACA

CCAAGGTGGACAAGAGAGTTGAGCCCAAATCTTGTGACAAAACTCACAC

ATGCCCACCGTGCCCAGCACCTGAACTCCTGGGGGGACCGTCAGTCTTC

CTCTTCCCCCCAAAACCCAAGGACACCCTCATGATCTCCCGGACCCCTG

AGGTCACATGCGTGGTGGTGGACGTGAGCCACGAAGACCCTGAGGTCAA

GTTCAACTGGTACGTGGACGGCGTGGAGGTGCATAATGCCAAGACAAAG

CCGCGGGAGGAGCAGTACGCCAGCACGTACCGTGTGGTCAGCGTCCTCA

CCGTCCTGCACCAGGACTGGCTGAATGGCAAGGAGTACAAGTGCAAGGT

CTCCAACAAAGCCCTCCCAGCCCCCATCGAGAAAACCATCTCCAAAGCC

AAAGGGCAGCCCCGAGAACCACAGGTGTACACCCTGCCCCCATCCCGGG

AGGAGATGACCAAGAACCAGGTCAGCCTGACCTGCCTGGTCAAAGGCTT

CTATCCCAGCGACATCGCCGTGGAGTGGGAGAGCAATGGGCAGCCGGAG

AACAACTACAAGACCACGCCTCCCGTGCTGGACTCCGACGGCTCCTTCT

TCCTCTACAGCAAGCTCACCGTGGACAAGAGCAGGTGGCAGCAGGGGAA

CGTCTTCTCATGCTCCGTGATGCATGAGGCTCTGCACAACCACTACACG

CAGAAGAGCCTCTCCCTGTCTCCGGGTAAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 255; SEQ ID NO: 256; and SEQ ID NO: 257 which correspond to polynucleotides encoding the complementarity-determining regions (CDRs, or hypervariable regions) of the light chain variable sequence of SEQ ID NO: 51 or the light chain sequence of SEQ ID NO: 52.

In a further optional embodiment of the invention, polynucleotides encoding for treatment or prevention of pain and pain associated conditions fragments having binding specificity to NGF comprise, or alternatively consist of, one or more of the polynucleotide sequences of SEQ ID NO: 258; SEQ ID NO: 259; and SEQ ID NO: 260 which correspond to polynucleotides encoding the complementarity-determining regions (CDRs, or hypervariable regions) of the heavy chain variable sequence of SEQ ID NO: 53 or the heavy chain sequence of SEQ ID NO: 54.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 251 encoding the light chain variable sequence of SEQ ID NO: 51; the polynucleotide SEQ ID NO: 252 encoding the light chain sequence of SEQ ID NO: 52; the polynucleotide SEQ ID NO: 253 encoding the heavy chain variable sequence of SEQ ID NO: 53; the polynucleotide SEQ ID NO: 254 encoding the heavy chain sequence of SEQ ID NO: 54; polynucleotides encoding the complementarity-determining regions (SEQ ID NO: 255; SEQ ID NO: 256; and SEQ ID NO: 257) of the light chain variable sequence of SEQ ID NO: 51 or the light chain sequence of SEQ ID NO: 52; and polynucleotides encoding the complementarity-determining regions (SEQ ID NO: 258; SEQ ID NO: 259; and SEQ ID NO: 260) of the heavy chain variable sequence of SEQ ID NO: 53 or the heavy chain sequence of SEQ ID NO: 54.

In a preferred optional embodiment of the invention, polynucleotides of the invention comprise, or alternatively consist of, polynucleotides encoding Fab (fragment antigen binding) fragments having binding specificity for NGF. With respect to antibody Ab6, the polynucleotides encoding the full length Ab6 antibody comprise, or alternatively consist of, the polynucleotide SEQ ID NO: 252 encoding the light chain sequence of SEQ ID NO: 52 and the polynucleotide SEQ ID NO: 254 encoding the heavy chain sequence of SEQ ID NO: 54.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab6 following expression of the full-length polynucleotides in a suitable host. In another embodiment of the invention, anti-NGF antibodies such as Ab6 or Fab fragments thereof may be produced via expression of Ab6 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab7

The invention optionally is further directed to the use of polynucleotides set forth below to produce antibody Ab7 polypeptides having binding specificity to NGF, which inhibit the association of NGF with TrkA and the association of NGF with p75. in methods of treating pain in an individual comprising administering to said individual antibody Ab7 polypeptides. The invention is further directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 61:

(SEQ ID NO: 261)
GCCGATGTTGTGATGACCCAGACTCCAGCCTCCGTGTCTCAACCTGTGGG

AGGCACAGTCACCATCAAGTGCCAGGCCAGTGAGGACATTTATAACTTAT

TGGCCTGGTATCAGCAGAAACCAGGGCAGCCTCCCAAGCTCCTGATCTA

TTCTGCATCCACTCTGGCATCTGGGGTCCCATCGCGGTTCAAAGGCAGT

GGATCTGGGACAGAGTACACTCTCACCATCAGCGGCCTGGAGTGTGCCG

ATGCTGCCACTTACTACTGTCAAAACAATTATCTTGTTACTACTTATGG

TGTTGCTTTCGGCGGAGGGACCGAGGTGGTGGTCAAACGT.

In one optional embodiment of the invention, polynucleotides of the invention comprise, or alternatively consist of, the following polynucleotide sequence encoding the light chain polypeptide sequence of SEQ ID NO: 62:

(SEQ ID NO: 262)
GCCGATGTTGTGATGACCCAGACTCCAGCCTCCGTGTCTCAACCTGTG

GGAGGCACAGTCACCATCAAGTGCCAGGCCAGTGAGGACATTTATAACT

TATTGGCCTGGTATCAGCAGAAACCAGGGCAGCCTCCCAAGCTCCTGAT

CTATTCTGCATCCACTCTGGCATCTGGGGTCCCATCGCGGTTCAAAGGC

AGTGGATCTGGGACAGAGTACACTCTCACCATCAGCGGCCTGGAGTGTG

CCGATGCTGCCACTTACTACTGTCAAAACAATTATCTTGTTACTACTTA

TGGTGTTGCTTTCGGCGGAGGGACCGAGGTGGTGGTCAAACGTACGGTA

GCGGCCCCATCTGTCTTCATCTTCCCGCCATCTGATGAGCAGTTGAAAT

CTGGAACTGCCTCTGTTGTGTGCCTGCTGAATAACTTCTATCCCAGAGA

GGCCAAAGTACAGTGGAAGGTGGATAACGCCCTCCAATCGGGTAACTCC

CAGGAGAGTGTCACAGAGCAGGACAGCAAGGACAGCACCTACAGCCTCA

GCAGCACCCTGACGCTGAGCAAAGCAGACTACGAGAAACACAAAGTCTA

CGCCTGCGAAGTCACCCATCAGGGCCTGAGCTCGCCCGTCACAAAGAGC

TTCAACAGGGGAGAGTGTTAG.

In another optional embodiment of the invention, polynucleotides of the invention comprise, or alternatively consist of, the following polynucleotide sequence encoding the variable heavy chain polypeptide sequence of SEQ ID NO: 63:

(SEQ ID NO: 263)
CAGGAGCAGCTGAAGGAGTCCGGGGGTCGCCTGGTCACGCCTGGGACAC

CCCTGACACTCACCTGTACAGTCTCTGGATTCTCCCTCAGTAGCTATGC

AATGATCTGGGTCCGCCAGGCTCCAGGGAAGGGGCTGGAATACATCGGA

TACATTGATACTGATACTAGCGCATACTACGCGAGCTGGGTGAAAGGCC

GATTCACCATCTCCAGAACCTCGACCACGGTGGATCTCAAAATCACTAG

TCCGACAACCGAGGACACGGCCACCTATTTCTGTGCCAGATCTTATGCT

GCTTATGGTGGTTATCCTGCTACTTTTGATCCCTGGGGCCCAGGCACCC

TGGTCACCGTCTCGAGC.

In one optional embodiment of the invention, polynucleotides of the invention comprise, or alternatively consist of, the following polynucleotide sequence encoding the heavy chain polypeptide sequence of SEQ ID NO: 64:

(SEQ ID NO: 264)
CAGGAGCAGCTGAAGGAGTCCGGGGGTCGCCTGGTCACGCCTGGGACAC

CCCTGACACTCACCTGTACAGTCTCTGGATTCTCCCTCAGTAGCTATGC

AATGATCTGGGTCCGCCAGGCTCCAGGGAAGGGGCTGGAATACATCGGA

TACATTGATACTGATACTAGCGCATACTACGCGAGCTGGGTGAAAGGCC

GATTCACCATCTCCAGAACCTCGACCACGGTGGATCTCAAAATCACTAG

TCCGACAACCGAGGACACGGCCACCTATTTCTGTGCCAGATCTTATGCT

GCTTATGGTGGTTATCCTGCTACTTTTGATCCCTGGGGCCCAGGCACCC

TGGTCACCGTCTCGAGCGCCTCCACCAAGGGCCCATCGGTCTTCCCCCT

```
GGCACCCTCCTCCAAGAGCACCTCTGGGGGCACAGCGGCCCTGGGCTGC

CTGGTCAAGGACTACTTCCCCGAACCGGTGACGGTGTCGTGGAACTCAG

GCGCCCTGACCAGCGGCGTGCACACCTTCCCGGCTGTCCTACAGTCCTC

AGGACTCTACTCCCTCAGCAGCGTGGTGACCGTGCCCTCCAGCAGCTTG

GGCACCCAGACCTACATCTGCAACGTGAATCACAAGCCCAGCAACACCA

AGGTGGACAAGAGAGTTGAGCCCAAATCTTGTGACAAAACTCACACATG

CCCACCGTGCCCAGCACCTGAACTCCTGGGGGACCGTCAGTCTTCCTC

TTCCCCCCAAAACCCAAGGACACCCTCATGATCTCCCGGACCCCTGAGG

TCACATGCGTGGTGGTGGACGTGAGCCACGAAGACCCTGAGGTCAAGTT

CAACTGGTACGTGGACGGCGTGGAGGTGCATAATGCCAAGACAAAGCCG

CGGGAGGAGCAGTACGCCAGCACGTACCGTGTGGTCAGCGTCCTCACCG

TCCTGCACCAGGACTGGCTGAATGGCAAGGAGTACAAGTGCAAGGTCTC

CAACAAAGCCCTCCCAGCCCCCATCGAGAAAACCATCTCCAAAGCCAAA

GGGCAGCCCCGAGAACCACAGGTGTACACCCTGCCCCCATCCCGGGAGG

AGATGACCAAGAACCAGGTCAGCCTGACCTGCCTGGTCAAAGGCTTCTA

TCCCAGCGACATCGCCGTGGAGTGGGAGAGCAATGGGCAGCCGGAGAAC

AACTACAAGACCACGCCTCCCGTGCTGGACTCCGACGGCTCCTTCTTCC

TCTACAGCAAGCTCACCGTGGACAAGAGCAGGTGGCAGCAGGGGAACGT

CTTCTCATGCTCCGTGATGCATGAGGCTCTGCACAACCACTACACGCAG

AAGAGCCTCTCCCTGTCTCCGGGTAAATGA.
```

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 265; SEQ ID NO: 266; and SEQ ID NO: 267 which correspond to polynucleotides encoding the complementarity-determining regions (CDRs, or hypervariable regions) of the light chain variable sequence of SEQ ID NO: 61 or the light chain sequence of SEQ ID NO: 62.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 268; SEQ ID NO: 269; and SEQ ID NO: 270 which correspond to polynucleotides encoding the complementarity-determining regions (CDRs, or hypervariable regions) of the heavy chain variable sequence of SEQ ID NO: 63 or the heavy chain sequence of SEQ ID NO: 64.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 261 encoding the light chain variable sequence of SEQ ID NO: 61; the polynucleotide SEQ ID NO: 262 encoding the light chain sequence of SEQ ID NO: 62; the polynucleotide SEQ ID NO: 263 encoding the heavy chain variable sequence of SEQ ID NO: 63; the polynucleotide SEQ ID NO: 264 encoding the heavy chain sequence of SEQ ID NO: 64; polynucleotides encoding the complementarity-determining regions (SEQ ID NO: 265; SEQ ID NO: 266; and SEQ ID NO: 267) of the light chain variable sequence of SEQ ID NO: 61 or the light chain sequence of SEQ ID NO: 62; and polynucleotides encoding the complementarity-determining regions (SEQ ID NO: 268; SEQ ID NO: 269; and SEQ ID NO: 270) of the heavy chain variable sequence of SEQ ID NO: 63 or the heavy chain sequence of SEQ ID NO: 64.

In a preferred optional embodiment of the invention, polynucleotides of the invention comprise, or alternatively consist of, polynucleotides encoding Fab (fragment antigen binding) fragments having binding specificity for NGF. With respect to antibody Ab7, the polynucleotides encoding the full length Ab7 antibody comprise, or alternatively consist of, the polynucleotide SEQ ID NO: 262 encoding the light chain sequence of SEQ ID NO: 62 and the polynucleotide SEQ ID NO: 264 encoding the heavy chain sequence of SEQ ID NO: 64.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab7 following expression of the full-length polynucleotides in a suitable host. In another embodiment of the invention, anti-NGF antibodies such as Ab7 or Fab fragments thereof may be produced via expression of Ab7 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab8

The invention is further optionally directed to the use of polynucleotides set forth below to produce antibody Ab8 polypeptides having binding specificity to NGF, which inhibits the association of NGF with TrkA and the association of NGF with p'75, in methods of treating pain in an individual comprising administering to said individual antibody Ab8 polypeptides. The invention is further optionally directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 71:

```
                                          (SEQ ID NO: 271)
GACATCCAGATGACCCAGTCTCCATCCTCCCTGTCTGCATCTGTAGGA

GACAGAGTCACCATCACTTGCCAGGCCAGTGAGGACATTTACAACTTAT

TGGCCTGGTATCAGCAGAAACCAGGGAAAGTCCCTAAGCTCCTGATCTA

TTCTGCATCCACTCTGGCATCTGGGGTCCCATCTCGTTTCAGTGGCAGT

GGATCTGGGACAGATTACACTCTCACCATCAGCAGCCTGCAGCCTGAAG

ATGTTGCAACTTATTACTGTCAAAACAACTATCTTGTTACTACTTATGG

TGTTGCTTTCGGCGGAGGAACCAAGGTGGAAATCAAACGT.
```

In one optional embodiment of the invention, polynucleotides of the invention comprise, or alternatively consist of, the following polynucleotide sequence encoding the light chain polypeptide sequence of SEQ ID NO: 72:

(SEQ ID NO: 272)
GACATCCAGATGACCCAGTCTCCATCCTCCCTGTCTGCATCTGTAGGA

GACAGAGTCACCATCACTTGCCAGGCCAGTGAGGACATTTACAACTTAT

TGGCCTGGTATCAGCAGAAACCAGGGAAAGTCCCTAAGCTCCTGATCTA

TTCTGCATCCACTCTGGCATCTGGGGTCCCATCTCGTTTCAGTGGCAGT

GGATCTGGGACAGATTACACTCTCACCATCAGCAGCCTGCAGCCTGAAG

ATGTTGCAACTTATTACTGTCAAAACAACTATCTTGTTACTACTTATGG

TGTTGCTTTCGGCGGAGGAACCAAGGTGGAAATCAAACGTACGGTAGCG

GCCCCATCTGTCTTCATCTTCCCGCCATCTGATGAGCAGTTGAAATCTG

GAACTGCCTCTGTTGTGTGCCTGCTGAATAACTTCTATCCCAGAGAGGC

CAAAGTACAGTGGAAGGTGGATAACGCCCTCCAATCGGGTAACTCCCAG

GAGAGTGTCACAGAGCAGGACAGCAAGGACAGCACCTACAGCCTCAGCA

GCACCCTGACGCTGAGCAAAGCAGACTACGAGAAACACAAAGTCTACGC

CTGCGAAGTCACCCATCAGGGCCTGAGCTCGCCCGTCACAAAGAGCTTC

AACAGGGGAGAGTGTTAG.

In another optional embodiment of the invention, polynucleotides of the invention comprise, or alternatively consist of, the following polynucleotide sequence encoding the variable heavy chain polypeptide sequence of SEQ ID NO: 73:

(SEQ ID NO: 273)
CAGGTACAGCTGGTGGAGTCTGGTGGAGGCGTGGTCCAGCCTGGGAGGT

CCCTGAGACTCTCCTGTGCAGCTTCTGGATTCACCTTCAGTAGCTATGC

AATGATCTGGGTCCGCCAGGCTCCAGGGAAGGGGCTGGAATACATCGGA

TACATTGATACTGATACTAGCGCATACTACGCAAGCAGTGTGAAAGGCC

GATTCACCATCTCCAGAGACAATTCCAAGAACACGCTGTACCTGCAAAT

GTCTAGCCTGAGAGCCGAGGACACGGCTGTGTATTACTGTGCTAGATCT

TATGCTGCTTATGGTGGTTATCCTGCTACTTTTGATCCCTGGGGCCAAG

GTACCCTCGTCACCGTCTCGAGC.

In one optional embodiment of the invention, polynucleotides of the invention comprise, or alternatively consist of, the following polynucleotide sequence encoding the heavy chain polypeptide sequence of SEQ ID NO: 74:

(SEQ ID NO: 274)
CAGGTACAGCTGGTGGAGTCTGGTGGAGGCGTGGTCCAGCCTGGGAGGT

CCCTGAGACTCTCCTGTGCAGCTTCTGGATTCACCTTCAGTAGCTATGC

AATGATCTGGGTCCGCCAGGCTCCAGGGAAGGGGCTGGAATACATCGGA

TACATTGATACTGATACTAGCGCATACTACGCAAGCAGTGTGAAAGGCC

GATTCACCATCTCCAGAGACAATTCCAAGAACACGCTGTACCTGCAAAT

GTCTAGCCTGAGAGCCGAGGACACGGCTGTGTATTACTGTGCTAGATCT

TATGCTGCTTATGGTGGTTATCCTGCTACTTTTGATCCCTGGGGCCAAG

GTACCCTCGTCACCGTCTCGAGCGCCTCCACCAAGGGCCCATCGGTCTT

CCCCCTGGCACCCTCCTCCAAGAGCACCTCTGGGGGCACAGCGGCCCTG

GGCTGCCTGGTCAAGGACTACTTCCCCGAACCGGTGACGGTGTCGTGGA

ACTCAGGCGCCCTGACCAGCGGCGTGCACACCTTCCCGGCTGTCCTACA

GTCCTCAGGACTCTACTCCCTCAGCAGCGTGGTGACCGTGCCCTCCAGC

AGCTTGGGCACCCAGACCTACATCTGCAACGTGAATCACAAGCCCAGCA

ACACCAAGGTGGACAAGAGAGTTGAGCCCAAATCTTGTGACAAAACTCAC

ACATGCCCACCGTGCCCAGCACCTGAACTCCTGGGGGGACCGTCAGTCT

TCCTCTTCCCCCCAAAACCCAAGGACACCCTCATGATCTCCCGGACCCC

TGAGGTCACATGCGTGGTGGTGGACGTGAGCCACGAAGACCCTGAGGTC

AAGTTCAACTGGTACGTGGACGGCGTGGAGGTGCATAATGCCAAGACAA

AGCCGCGGGAGGAGCAGTACGCCAGCACGTACCGTGTGGTCAGCGTCCT

CACCGTCCTGCACCAGGACTGGCTGAATGGCAAGGAGTACAAGTGCAAG

GTCTCCAACAAAGCCCTCCCAGCCCCCATCGAGAAAACCATCTCCAAAG

CCAAAGGGCAGCCCCGAGAACCACAGGTGTACACCCTGCCCCCATCCCG

GGAGGAGATGACCAAGAACCAGGTCAGCCTGACCTGCCTGGTCAAAGGC

TTCTATCCCAGCGACATCGCCGTGGAGTGGGAGAGCAATGGGCAGCCGG

AGAACAACTACAAGACCACGCCTCCCGTGCTGGACTCCGACGGCTCCTT

CTTCCTCTACAGCAAGCTCACCGTGGACAAGAGCAGGTGGCAGCAGGGG

AACGTCTTCTCATGCTCCGTGATGCATGAGGCTCTGCACAACCACTACA

CGCAGAAGAGCCTCTCCCTGTCTCCGGGTAAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 275; SEQ ID NO: 276; and SEQ ID NO: 277 which correspond to polynucleotides encoding the complementarity-determining regions (CDRs, or hypervariable regions) of the light chain variable sequence of SEQ ID NO: 71 or the light chain sequence of SEQ ID NO: 72.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 278; SEQ ID NO: 279; and SEQ ID NO: 280 which correspond to polynucleotides encoding the complementarity-determining regions (CDRs, or hypervariable regions) of the heavy chain variable sequence of SEQ ID NO: 73 or the heavy chain sequence of SEQ ID NO: 74.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 271 encoding the light chain variable sequence of SEQ ID NO: 71; the polynucleotide SEQ ID NO: 272 encoding the light chain sequence of SEQ ID NO: 72; the polynucleotide SEQ ID NO: 273 encoding the heavy chain variable sequence of SEQ ID NO: 73; the polynucleotide SEQ ID NO: 274 encoding the heavy chain sequence of SEQ ID NO: 74; polynucleotides encoding the complementarity-determining regions (SEQ ID NO: 275; SEQ ID NO: 276; and SEQ ID NO: 277) of the light chain variable sequence of SEQ ID NO: 71 or the light chain sequence of SEQ ID NO: 72; and polynucleotides encoding the complementarity-determining regions (SEQ ID NO: 278; SEQ ID NO: 279; and SEQ ID NO: 280) of the heavy chain variable sequence of SEQ ID NO: 73 or the heavy chain sequence of SEQ ID NO: 74.

In a preferred optional embodiment of the invention, polynucleotides of the invention comprise, or alternatively consist of, polynucleotides encoding Fab (fragment antigen binding) fragments having binding specificity for NGF. With respect to antibody Ab8, the polynucleotides encoding the full length Ab8 antibody comprise, or alternatively consist of, the polynucleotide SEQ ID NO: 272 encoding the light chain sequence of SEQ ID NO: 72 and the polynucleotide SEQ ID NO: 274 encoding the heavy chain sequence of SEQ ID NO: 74.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab8 following expression of the full-length polynucleotides in a suitable host. In another embodiment of the invention, anti-NGF antibodies such as Ab8 or Fab fragments thereof may be produced via expression of Ab8 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab9

The invention is further optionally directed to the use of polynucleotides set forth below to produce antibody Ab9 polypeptides having binding specificity to NGF, which inhibit the association of NGF with TrkA and the association of NGF with p75, in methods of treating pain in an individual comprising administering to said individual antibody Ab9 polypeptides. The invention is further optionally directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 81:

(SEQ ID NO: 281)
GCCTATGATATGACCCAGACTCCAGCCTCCGTGTCTGCAGCTGTGGGAG

GCACAGTCACCATCAAGTGCCAGGCCAGTGAGAACATTGGTAGCTACTT

AGCCTGGTATCAGCAGAAACCAGGGCAGCCTCCCGAACTCCTGATCTAC

AGGGCGTCCACTCTGGCATCTGGGGTCCCATCGCGGTTCAAAGGCAGTG

GATCTGGGACACAGTTCACTCTCACCATCAGCGGCGTGGAGTGTGCCGA

TGCTGCCACTTACTACTGTCAACAGGGTTATAATAGTGAGAATCTTGAT

AATGCTTTCGGCGGAGGGACCGAGGTGGTGGTCAAACGT.

In one optional embodiment of the invention, polynucleotides of the invention comprise, or alternatively consist of, the following polynucleotide sequence encoding the light chain polypeptide sequence of SEQ ID NO: 82:

(SEQ ID NO: 282)
GCCTATGATATGACCCAGACTCCAGCCTCCGTGTCTGCAGCTGTGGGAG

GCACAGTCACCATCAAGTGCCAGGCCAGTGAGAACATTGGTAGCTACTT

AGCCTGGTATCAGCAGAAACCAGGGCAGCCTCCCGAACTCCTGATCTAC

AGGGCGTCCACTCTGGCATCTGGGGTCCCATCGCGGTTCAAAGGCAGTG

GATCTGGGACACAGTTCACTCTCACCATCAGCGGCGTGGAGTGTGCCGA

TGCTGCCACTTACTACTGTCAACAGGGTTATAATAGTGAGAATCTTGAT

AATGCTTTCGGCGGAGGGACCGAGGTGGTGGTCAAACGTACGGTAGCGG

CCCCATCTGTCTTCATCTTCCCGCCATCTGATGAGCAGTTGAAATCTGG

AACTGCCTCTGTTGTGTGCCTGCTGAATAACTTCTATCCCAGAGAGGCC

AAAGTACAGTGGAAGGTGGATAACGCCCTCCAATCGGGTAACTCCCAGG

AGAGTGTCACAGAGCAGGACAGCAAGGACAGCACCTACAGCCTCAGCAG

CACCCTGACGCTGAGCAAAGCAGACTACGAGAAACACAAAGTCTACGCC

TGCGAAGTCACCCATCAGGGCCTGAGCTCGCCCGTCACAAAGAGCTTCA

ACAGGGGAGAGTGTTAG.

In another optional embodiment of the invention, polynucleotides of the invention comprise, or alternatively consist of, the following polynucleotide sequence encoding the variable heavy chain polypeptide sequence of SEQ ID NO: 83:

(SEQ ID NO: 283)
CAGTCGGTGGAGGAGTCCGGGGGTCGCCTGGTCACGCCTGGGACACCCC

TGACACTCACCTGCACAGTCTCTGGAATCGACCTCAGTATGTATTCAAT

GGGCTGGGTCCGCCAGGCTCCAGGGAAGGGGCTGGAATACATCGGATGG

ATTAGTTATGGTGGTACTGCATATTACGCGAGCTGGGCGAAGGGCCGAT

TCACCATCTCCAAAACCTCGACCACGGTGGAGCTGAAGATCACCAGTCCG

ACAATCGAGGACACGGCCACCTATTTCTGTGCCAGAGAGACTCCTGTTAA

TTATTATTTGGACATTTGGGGCCAGGGGACCCTCGTCACCGTCTCGAGC.

In one optional embodiment of the invention, polynucleotides of the invention comprise, or alternatively consist of, the following polynucleotide sequence encoding the heavy chain polypeptide sequence of SEQ ID NO: 84:

(SEQ ID NO: 284)
CAGTCGGTGGAGGAGTCCGGGGGTCGCCTGGTCACGCCTGGGACACCCC

TGACACTCACCTGCACAGTCTCTGGAATCGACCTCAGTATGTATTCAAT

GGGCTGGGTCCGCCAGGCTCCAGGGAAGGGGCTGGAATACATCGGATGG

ATTAGTTATGGTGGTACTGCATATTACGCGAGCTGGGCGAAGGGCCGAT

TCACCATCTCCAAAACCTCGACCACGGTGGAGCTGAAGATCACCAGTCC

-continued
```
GACAATCGAGGACACGGCCACCTATTTCTGTGCCAGAGAGACTCCTGTT

AATTATTATTTGGACATTTGGGGCCAGGGGACCCTCGTCACCGTCTCGA

GCGCCTCCACCAAGGGCCCATCGGTCTTCCCCCTGGCACCCTCCTCCAA

GAGCACCTCTGGGGGCACAGCGGCCCTGGGCTGCCTGGTCAAGGACTAC

TTCCCCGAACCGGTGACGGTGTCGTGGAACTCAGGCGCCCTGACCAGCG

GCGTGCACACCTTCCCGGCTGTCCTACAGTCCTCAGGACTCTACTCCCT

CAGCAGCGTGGTGACCGTGCCCTCCAGCAGCTTGGGCACCCAGACCTAC

ATCTGCAACGTGAATCACAAGCCCAGCAACACCAAGGTGGACAAGAGAG

TTGAGCCCAAATCTTGTGACAAAACTCACACATGCCCACCGTGCCCAGC

ACCTGAACTCCTGGGGGACCGTCAGTCTTCCTCTTCCCCCCAAAACCC

AAGGACACCCTCATGATCTCCCGGACCCCTGAGGTCACATGCGTGGTGG

TGGACGTGAGCCACGAAGACCCTGAGGTCAAGTTCAACTGGTACGTGGA

CGGCGTGGAGGTGCATAATGCCAAGACAAAGCCGCGGGAGGAGCAGTAC

GCCAGCACGTACCGTGTGGTCAGCGTCCTCACCGTCCTGCACCAGGACT

GGCTGAATGGCAAGGAGTACAAGTGCAAGGTCTCCAACAAAGCCCTCCC

AGCCCCATCGAGAAACCATCTCCAAAGCCAAAGGGCAGCCCCGAGAA

CCACAGGTGTACACCCTGCCCCCATCCCGGGAGGAGATGACCAAGAACC

AGGTCAGCCTGACCTGCCTGGTCAAAGGCTTCTATCCCAGCGACATCGC

CGTGGAGTGGGAGAGCAATGGGCAGCCGGAGAACAACTACAAGACCACG

CCTCCCGTGCTGGACTCCGACGGCTCCTTCTTCCTCTACAGCAAGCTCA

CCGTGGACAAGAGCAGGTGGCAGCAGGGGAACGTCTTCTCATGCTCCGT

GATGCATGAGGCTCTGCACAACCACTACACGCAGAAGAGCCTCTCCCTG

TCTCCGGGTAAATGA.
```

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 285; SEQ ID NO: 286; and SEQ ID NO: 287 which correspond to polynucleotides encoding the complementarity-determining regions (CDRs, or hypervariable regions) of the light chain variable sequence of SEQ ID NO: 81 or the light chain sequence of SEQ ID NO: 82.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 288; SEQ ID NO: 289; and SEQ ID NO: 290 which correspond to polynucleotides encoding the complementarity-determining regions (CDRs, or hypervariable regions) of the heavy chain variable sequence of SEQ ID NO: 83 or the heavy chain sequence of SEQ ID NO: 84.

The invention also optionally contemplates polynucleotide sequences including one or more of the polynucleotide sequences encoding antibody fragments for treatment or prevention of pain and pain associated conditions described herein. In one optional embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 281 encoding the light chain variable sequence of SEQ ID NO: 81; the polynucleotide SEQ ID NO: 282 encoding the light chain sequence of SEQ ID NO: 82; the polynucleotide SEQ ID NO: 283 encoding the heavy chain variable sequence of SEQ ID NO: 83; the polynucleotide SEQ ID NO: 284 encoding the heavy chain sequence of SEQ ID NO: 84; polynucleotides encoding the complementarity-determining regions (SEQ ID NO: 285; SEQ ID NO: 286; and SEQ ID NO: 287) of the light chain variable sequence of SEQ ID NO: 81 or the light chain sequence of SEQ ID NO: 82; and polynucleotides encoding the complementarity-determining regions (SEQ ID NO: 288; SEQ ID NO: 289; and SEQ ID NO: 290) of the heavy chain variable sequence of SEQ ID NO: 83 or the heavy chain sequence of SEQ ID NO: 84.

In a preferred optional embodiment of the invention, polynucleotides of the invention comprise, or alternatively consist of, polynucleotides encoding Fab (fragment antigen binding) fragments having binding specificity for NGF. With respect to antibody Ab9, the polynucleotides encoding the full length Ab9 antibody comprise, or alternatively consist of, the polynucleotide SEQ ID NO: 282 encoding the light chain sequence of SEQ ID NO: 82 and the polynucleotide SEQ ID NO: 284 encoding the heavy chain sequence of SEQ ID NO: 84.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab9 following expression of the full-length polynucleotides in a suitable host. In another embodiment of the invention, anti-NGF antibodies such as Ab9 or Fab fragments thereof may be produced via expression of Ab9 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab10

The invention is further optionally directed to the use of polynucleotides set forth below to produce antibody Ab10 polypeptides having binding specificity to NGF, which inhibit the association of NGF with TrkA and the association of NGF with p75, in methods of treating pain in an individual comprising administering to said individual antibody Ab10 polypeptides. The invention is further optionally directed to polynucleotides encoding antibody polypeptides having binding specificity to NGF. In one embodiment of the invention, polynucleotides of the invention comprise, or alternatively consist of, the following polynucleotide sequence encoding the variable light chain polypeptide sequence of SEQ ID NO: 91:

```
                                          (SEQ ID NO: 291)
GCCTATGATATGACCCAGTCTCCATCCTCCCTGTCTGCATCTGTAGGA

GACAGAGTCACCATCACTTGCCAGGCCAGTGAGAACATTGGTAGCTACT

TAGCCTGGTATCAGCAGAAACCAGGGAAAGTCCCTAAGCTCCTGATCTA

TAGGGCTTCCACTCTGGCATCTGGGGTCCCATCTCGTTTCAGTGGCAGT

GGATCTGGGACAGATTTCACTCTCACCATCAGCAGCCTGCAGCCTGAAG
```

In one optional embodiment of the invention, polynucleotides of the invention comprise, or alternatively consist of, the following polynucleotide sequence encoding the light chain polypeptide sequence of SEQ ID NO: 92:

(SEQ ID NO: 292)
GCCTATGATATGACCCAGTCTCCATCCTCCCTGTCTGCATCTGTAGGA

GACAGAGTCACCATCACTTGCCAGGCCAGTGAGAACATTGGTAGCTACT

TAGCCTGGTATCAGCAGAAACCAGGGAAAGTCCCTAAGCTCCTGATCTA

TAGGGCTTCCACTCTGGCATCTGGGGTCCCATCTCGTTTCAGTGGCAGT

GGATCTGGGACAGATTTCACTCTCACCATCAGCAGCCTGCAGCCTGAAG

ATGTTGCAACTTATTACTGTCAACAGGGTTACAATAGTGAGAATCTTGA

TAATGCTTTCGGCGGAGGAACCAAGGTGGAAATCAAACGTACGGTAGCG

GCCCCATCTGTCTTCATCTTCCCGCCATCTGATGAGCAGTTGAAATCTG

GAACTGCCTCTGTTGTGTGCCTGCTGAATAACTTCTATCCCAGAGAGGC

CAAAGTACAGTGGAAGGTGGATAACGCCCTCCAATCGGGTAACTCCCAG

GAGAGTGTCACAGAGCAGGACAGCAAGGACAGCACCTACAGCCTCAGCA

GCACCCTGACGCTGAGCAAAGCAGACTACGAGAAACACAAAGTCTACGC

CTGCGAAGTCACCCATCAGGGCCTGAGCTCGCCCGTCACAAAGAGCTTC

AACAGGGGAGAGTGTTAG.

In another optional embodiment of the invention, polynucleotides of the invention comprise, or alternatively consist of, the following polynucleotide sequence encoding the variable heavy chain polypeptide sequence of SEQ ID NO: 93:

(SEQ ID NO: 293)
CAGGTACAGCTGGTGGAGTCTGGTGGAGGCGTGGTCCAGCCTGGGAGGT

CCCTGAGACTCTCCTGTGCAGCTTCTGGATTCACCTTCAGTATGTATTC

AATGGGCTGGGTCCGCCAGGCTCCAGGGAAGGGGCTGGAATACATCGGA

TGGATTAGTTATGGTGGTACTGCATACTACGCTAGCAGCGCTAAGGGCC

GATTCACCATCTCCAGAGACAATTCCAAGAACACGCTGTACCTGCAAAT

GTCTAGCCTGAGAGCCGAGGACACGGCTGTGTATTACTGTGCTAGAGAG

ACTCCTGTTAATTACTACTTGGACATTTGGGGCCAAGGTACCCTCGTCA

CCGTCTCGAGC.

In one optional embodiment of the invention, polynucleotides of the invention comprise, or alternatively consist of, the following polynucleotide sequence encoding the heavy chain polypeptide sequence of SEQ ID NO: 94:

(SEQ ID NO: 294)
CAGGTACAGCTGGTGGAGTCTGGTGGAGGCGTGGTCCAGCCTGGGAG

GTCCCTGAGACTCTCCTGTGCAGCTTCTGGATTCACCTTCAGTATGTAT

TCAATGGGCTGGGTCCGCCAGGCTCCAGGGAAGGGGCTGGAATACATCG

GATGGATTAGTTATGGTGGTACTGCATACTACGCTAGCAGCGCTAAGGG

CCGATTCACCATCTCCAGAGACAATTCCAAGAACACGCTGTACCTGCAA

ATGTCTAGCCTGAGAGCCGAGGACACGGCTGTGTATTACTGTGCTAGAG

AGACTCCTGTTAATTACTACTTGGACATTTGGGGCCAAGGTACCCTCGT

CACCGTCTCGAGCGCCTCCACCAAGGGCCCATCGGTCTTCCCCCTGGCA

CCCTCCTCCAAGAGCACCTCTGGGGGCACAGCGGCCCTGGGCTGCCTGG

TCAAGGACTACTTCCCCGAACCGGTGACGGTGTCGTGGAACTCAGGCGC

CCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCA

CCCAGACCTACATCTGCAACGTGAATCACAAGCCCAGCAACACCAAGGT

GGACAAGAGAGTTGAGCCCAAATCTTGTGACAAAACTCACACATGCCCA

CCGTGCCCAGCACCTGAACTCCTGGGGGGACCGTCAGTCTTCCTCTTCC

CCCCAAAACCCAAGGACACCCTCATGATCTCCCGGACCCCTGAGGTCAC

ATGCGTGGTGGTGGACGTGAGCCACGAAGACCCTGAGGTCAAGTTCAAC

TGGTACGTGGACGGCGTGGAGGTGCATAATGCCAAGACAAAGCCGCGGG

AGGAGCAGTACGCCAGCACGTACCGTGTGGTCAGCGTCCTCACCGTCCT

GCACCAGGACTGGCTGAATGGCAAGGAGTACAAGTGCAAGGTCTCCAAC

AAAGCCCTCCCAGCCCCCATCGAGAAAACCATCTCCAAAGCCAAAGGGC

AGCCCCGAGAACCACAGGTGTACACCCTGCCCCCATCCCGGGAGGAGAT

GACCAAGAACCAGGTCAGCCTGACCTGCCTGGTCAAAGGCTTCTATCCC

AGCGACATCGCCGTGGAGTGGGAGAGCAATGGGCAGCCGGAGAACAACT

ACAAGACCACGCCTCCCGTGCTGGACTCCGACGGCTCCTTCTTCCTCTA

CAGCAAGCTCACCGTGGACAAGAGCAGGTGGCAGCAGGGGAACGTCTTC

TCATGCTCCGTGATGCATGAGGCTCTGCACAACCACTACACGCAGAAGA

GCCTCTCCCTGTCTCCGGGTAAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 295; SEQ ID NO: 296; and SEQ ID NO: 297 which correspond to polynucleotides encoding the complementarity-determining regions (CDRs, or hypervariable regions) of the light chain variable sequence of SEQ ID NO: 91 or the light chain sequence of SEQ ID NO: 92.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 298; SEQ ID NO: 299; and SEQ ID NO: 300 which correspond to polynucleotides encoding the complementarity-determining regions (CDRs, or hypervariable regions) of the heavy chain variable sequence of SEQ ID NO: 93 or the heavy chain sequence of SEQ ID NO: 94.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 291 encoding the light chain variable sequence of SEQ ID NO: 91; the polynucleotide SEQ ID NO: 292 encoding the light chain sequence of SEQ ID NO: 92; the polynucleotide SEQ ID NO: 293 encoding the heavy chain variable sequence of SEQ ID NO: 93; the polynucleotide SEQ ID NO: 294 encoding the heavy chain sequence of SEQ ID NO: 94; polynucleotides encoding the complementarity-determining regions (SEQ ID NO: 295; SEQ ID NO: 296; and SEQ ID NO: 297) of the light chain variable sequence of SEQ ID NO: 91 or the light chain sequence of SEQ ID NO: 92; and polynucleotides encoding the complementarity-determining regions (SEQ ID NO: 298; SEQ ID NO: 299; and SEQ ID NO: 300) of the heavy chain variable sequence of SEQ ID NO: 93 or the heavy chain sequence of SEQ ID NO: 94.

In a preferred optional embodiment of the invention, polynucleotides of the invention comprise, or alternatively consist of, polynucleotides encoding Fab (fragment antigen binding) fragments having binding specificity for NGF. With respect to antibody Ab10, the polynucleotides encoding the full length Ab10 antibody comprise, or alternatively consist of, the polynucleotide SEQ ID NO: 292 encoding the light chain sequence of SEQ ID NO: 92 and the polynucleotide SEQ ID NO: 294 encoding the heavy chain sequence of SEQ ID NO: 94.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab10 following expression of the full-length polynucleotides in a suitable host. In another embodiment of the invention, anti-NGF antibodies such as Ab10 or Fab fragments thereof may be produced via expression of Ab10 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab11

The invention is further optionally directed to the use of polynucleotides set forth below to produce antibody Ab11 polypeptides having binding specificity to NGF, which inhibits the association of NGF with TrkA and the association of NGF with p75, in methods of treating pain in an individual comprising administering to said individual antibody Ab11 polypeptides. The invention is further directed to polynucleotides encoding antibody polypeptides having binding specificity to NGF. In one embodiment of the invention, polynucleotides of the invention comprise, or alternatively consist of, the following polynucleotide sequence encoding the variable light chain polypeptide sequence of SEQ ID NO: 101:

(SEQ ID NO: 301)
GCATTCGAATTGACCCAGACTCCATCCTCCGTGGAGGCAGCTGTGGGAG

GCACAGTCACCATCAAGTGCCAGGCCAGTCAGAACATTGTTACCAATTT

AGCCTGGTATCAACAGAAACCAGGGCAGCCTCCCAAGCTCCTGATCTAT

-continued
GGTGCATCCACTCTGGCATCTGGGGTCTCATCGCGGTTCAAAGGCAGTG

GATCTGGGACACAGTTCACTCTCACCATCAGCGACCTGGAGTGTGCCGA

TGCTGCCACTTATTTCTGTCAGAGCTATGATGGTTTTAATAGTGCTGGG

TTCGGCGGAGGGACCGAGGTGGTGGTCAAACGT.

In one optional embodiment of the invention, polynucleotides of the invention comprise, or alternatively consist of, the following polynucleotide sequence encoding the light chain polypeptide sequence of SEQ ID NO: 102:

(SEQ ID NO: 302)
GCATTCGAATTGACCCAGACTCCATCCTCCGTGGAGGCAGCTGTGGGAGG

CACAGTCACCATCAAGTGCCAGGCCAGTCAGAACATTGTTACCAATTTAG

CCTGGTATCAACAGAAACCAGGGCAGCCTCCCAAGCTCCTGATCTATGGT

GCATCCACTCTGGCATCTGGGGTCTCATCGCGGTTCAAAGGCAGTGGATC

TGGGACACAGTTCACTCTCACCATCAGCGACCTGGAGTGTGCCGATGCTG

CCACTTATTTCTGTCAGAGCTATGATGGTTTTAATAGTGCTGGGTTCGGC

GGAGGGACCGAGGTGGTGGTCAAACGTACGGTAGCGGCCCCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAG.

In another optional embodiment of the invention, polynucleotides of the invention comprise, or alternatively consist of, the following polynucleotide sequence encoding the variable heavy chain polypeptide sequence of SEQ ID NO: 103:

(SEQ ID NO: 303)
CAGTCGCTGGAGGAGTCCGGGGGTCGCCTGGTCACGCCTGGGACACCCCT

GACACTCACCTGCACAGCCTCTGGATTCTCCCTCAGTGGCTACGACATGA

GCTGGGTCCGCCAGGCTCCAGGAAAGGGGCTGGAATACATCGGACTCATT

AGTTATGATGGTAACATACTACGCGACCTGGGCGAAAGGCCGATTCAC

CATCTCCAAAACCTCGACCACGGTGGATCTGAAAATCACCAGTCCGACAA

CCGAGGACACGGCCACCTATTTCTGTGCCAGAAGTCTTTATGCTGGTCCT

AATGCTGGTATCGGACCGTTTAACATCTGGGGCCAGGGGACCCTCGTCAC

CGTCTCGAGC.

In one optional embodiment of the invention, polynucleotides of the invention comprise, or alternatively consist of, the following polynucleotide sequence encoding the heavy chain polypeptide sequence of SEQ ID NO: 104:

(SEQ ID NO: 304)
CAGTCGCTGGAGGAGTCCGGGGGTCGCCTGGTCACGCCTGGGACACCCCT

GACACTCACCTGCACAGCCTCTGGATTCTCCCTCAGTGGCTACGACATGA

GCTGGGTCCGCCAGGCTCCAGGAAAGGGGCTGGAATACATCGGACTCATT

-continued
```
AGTTATGATGGTAACACATACTACGCGACCTGGGCGAAAGGCCGATTCAC

CATCTCCAAAACCTCGACCACGGTGGATCTGAAAATCACCAGTCCGACAA

CCGAGGACACGGCCACCTATTTCTGTGCCAGAAGTCTTTATGCTGGTCCT

AATGCTGGTATCGGACCGTTTAACATCTGGGGCCAGGGGACCCTCGTCAC

CGTCTCGAGCGCCTCCACCAAGGGCCCATCGGTCTTCCCCCTGGCACCCT

CCTCCaAGAGCACCTCTGGGGGCACAGCGGCCCTGGGCTGCCTGGTCAAG

GACTACTTCCCCGAACCGGTGACGGTGTCGTGGAACTCAGGCGCCCTGAC

CAGCGGCGTGCACACCTTCCCGGCTGTCCTACAGTCCTCAGGACTCTACT

CCCTCAGCAGCGTGGTGACCGTGCCCTCCAGCAGCTTGGGCACCCAGACC

TACATCTGCAACGTGAATCACAAGCCCAGCAACACCAAGGTGGACAAGAG

AGTTGAGCCCAAATCTTGTGACAAAACTCACACATGCCCACCGTGCCCAG

CACCTGAACTCCTGGGGGACCGTCAGTCTTCCTCTTCCCCCCAAAACCC

AAGGACACCCTCATGATCTCCCGGACCCCTGAGGTCACATGCGTGGTGGT

GGACGTGAGCCACGAAGACCCTGAGGTCAAGTTCAACTGGTACGTGGACG

GCGTGGAGGTGCATAATGCCAAGACAAAGCCGCGGGAGGAGCAGTACGCC

AGCACGTACCGTGTGGTCAGCGTCCTCACCGTCCTGCACCAGGACTGGCT

GAATGGCAAGGAGTACAAGTGCAAGGTCTCCAACAAAGCCCTCCCAGCCC

CCATCGAGAAACCATCTCCAAAGCCAAAGGGCAGCCCCGAGAACCACAG

GTGTACACCCTGCCCCCATCCCGGGAGGAGATGACCAAGAACCAGGTCAG

CCTGACCTGCCTGGTCAAAGGCTTCTATCCCAGCGACATCGCCGTGGAGT

GGGAGAGCAATGGGCAGCCGGAGAACAACTACAAGACCACGCCTCCCGTG

CTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

TGA.
```

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 305; SEQ ID NO: 306; and SEQ ID NO: 307 which correspond to polynucleotides encoding the complementarity-determining regions (CDRs, or hypervariable regions) of the light chain variable sequence of SEQ ID NO: 101 or the light chain sequence of SEQ ID NO: 102.

In a further optional embodiment of the invention, polynucleotides encoding for treatment or prevention of pain and pain associated conditions fragments having binding specificity to NGF comprise, or alternatively consist of, one or more of the polynucleotide sequences of SEQ ID NO: 308; SEQ ID NO: 309; and SEQ ID NO: 310 which correspond to polynucleotides encoding the complementarity-determining regions (CDRs, or hypervariable regions) of the heavy chain variable sequence of SEQ ID NO: 103 or the heavy chain sequence of SEQ ID NO: 104.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 301 encoding the light chain variable sequence of SEQ ID NO: 101; the polynucleotide SEQ ID NO: 302 encoding the light chain sequence of SEQ ID NO: 102; the polynucleotide SEQ ID NO: 303 encoding the heavy chain variable sequence of SEQ ID NO: 103; the polynucleotide SEQ ID NO: 304 encoding the heavy chain sequence of SEQ ID NO: 104; polynucleotides encoding the complementarity-determining regions (SEQ ID NO: 305; SEQ ID NO: 306; and SEQ ID NO: 307) of the light chain variable sequence of SEQ ID NO: 101 or the light chain sequence of SEQ ID NO: 102; and polynucleotides encoding the complementarity-determining regions (SEQ ID NO: 308; SEQ ID NO: 309; and SEQ ID NO: 310) of the heavy chain variable sequence of SEQ ID NO: 103 or the heavy chain sequence of SEQ ID NO: 104.

In a preferred optional embodiment of the invention, polynucleotides of the invention comprise, or alternatively consist of, polynucleotides encoding Fab (fragment antigen binding) fragments having binding specificity for NGF. With respect to antibody Ab11, the polynucleotides encoding the full length Ab11 antibody comprise, or alternatively consist of, the polynucleotide SEQ ID NO: 302 encoding the light chain sequence of SEQ ID NO: 102 and the polynucleotide SEQ ID NO: 304 encoding the heavy chain sequence of SEQ ID NO: 104.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab11 following expression of the full-length polynucleotides in a suitable host. In another optional embodiment of the invention, anti-NGF antibodies such as Ab11 or Fab fragments thereof may be produced via expression of Ab11 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab12

The invention is further optionally directed to the use of polynucleotides set forth below to produce antibody Ab12 polypeptides having binding specificity to NGF, which inhibit the association of NGF with TrkA and the association of NGF with p75, in methods of treating pain in an individual comprising administering to said individual antibody Ab12 polypeptides. The invention is further optionally directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 111:

(SEQ ID NO: 311)
```
GCATTCCAGATGACCCAGTCTCCATCCTCCCTGTCTGCATCTGTAGGAGA

CAGAGTCACCATCACTTGCCAGGCCAGTCAGAACATTGTTACCAACTTAG

CCTGGTATCAGCAGAAACCAGGGAAAGTCCCTAAGCTCCTGATCTATGG

TGCATCCACTCTGGCATCTGGGGTCCCATCTCGTTTCAGTGGCAGTGGA
```

-continued

TCTGGGACAGATTTCACTCTCACCATCAGCAGCCTGCAGCCTGAAGATGT

TGCAACTTATTACTGTCAGAGCTATGATGGTTTCAATAGTGCTGGTTTCG

GCGGAGGAACCAAGGTGGAAATCAAACGT.

In one optional embodiment of the invention, polynucleotides of the invention comprise, or alternatively consist of, the following polynucleotide sequence encoding the light chain polypeptide sequence of SEQ ID NO: 112:

(SEQ ID NO: 312)
GCATTCCAGATGACCCAGTCTCCATCCTCCCTGTCTGCATCTGTAGGAGA

CAGAGTCACCATCACTTGCCAGGCCAGTCAGAACATTGTTACCAACTTAG

CCTGGTATCAGCAGAAACCAGGGAAAGTCCCTAAGCTCCTGATCTATG

GTGCATCCACTCTGGCATCTGGGGTCCCATCTCGTTTCAGTGGCAGTG

GATCTGGGACAGATTTCACTCTCACCATCAGCAGCCTGCAGCCTGAAGA

TGTTGCAACTTATTACTGTCAGAGCTATGATGGTTTCAATAGTGCTGGTT

TCGGCGGAGGAACCAAGGTGGAAATCAAACGTACGGTAGCGGCCCCATCT

GTCTTCATCTTCCCGCCATCTGATGAGCAGTTGAAATCTGGAACTGCCTC

TGTTGTGTGCCTGCTGAATAACTTCTATCCCAGAGAGGCCAAAGTACAGT

GGAAGGTGGATAACGCCCTCCAATCGGGTAACTCCCAGGAGAGTGTCAC

AGAGCAGGACAGCAAGGACAGCACCTACAGCCTCAGCAGCACCCTGACGC

TGAGCAAAGCAGACTACGAGAAACACAAAGTCTACGCCTGCGAAGTCACC

CATCAGGGCCTGAGCTCGCCCGTCACAAAGAGCTTCAACAGGGGAGAG

TGTTAG.

In another optional embodiment of the invention, polynucleotides of the invention comprise, or alternatively consist of, the following polynucleotide sequence encoding the variable heavy chain polypeptide sequence of SEQ ID NO: 113:

(SEQ ID NO: 313)
CAGGTACAGCTGGTGGAGTCTGGTGGAGGCGTGGTCCAGCCTGGGAGGTC

CCTGAGACTCTCCTGTGCAGCTTCTGGATTCTCCCTCAGTGGCTACGACA

TGAGCTGGGTCCGTCAGGCTCCAGGCAAGGGACTGGAGTGGGTGGGACTC

ATTAGTTATGATGGTAACACATACTACGCGACCTCCGCGAAAGGCCGATT

CACCATCTCCAGAGACAATTCCAAGAACACGCTGTACCTGCAAATGTCTA

GCCTGAGAGCCGAGGACACGGCTGTGTATTACTGTGCTAGAAGTCTTTAT

GCTGGTCCTAATGCTGGTATCGGACCGTTTAACATCTGGGGCCAAGGTAC

CCTCGTCACCGTCTCGAGC.

In one optional embodiment of the invention, polynucleotides of the invention comprise, or alternatively consist of, the following polynucleotide sequence encoding the heavy chain polypeptide sequence of SEQ ID NO: 114:

(SEQ ID NO: 314)
CAGGTACAGCTGGTGGAGTCTGGTGGAGGCGTGGTCCAGCCTGGGAGGTC

CCTGAGACTCTCCTGTGCAGCTTCTGGATTCTCCCTCAGTGGCTACGACA

TGAGCTGGGTCCGTCAGGCTCCAGGCAAGGGACTGGAGTGGGTGGGACTC

ATTAGTTATGATGGTAACACATACTACGCGACCTCCGCGAAAGGCCGATT

CACCATCTCCAGAGACAATTCCAAGAACACGCTGTACCTGCAAATGTCTA

GCCTGAGAGCCGAGGACACGGCTGTGTATTACTGTGCTAGAAGTCTTTAT

GCTGGTCCTAATGCTGGTATCGGACCGTTTAACATCTGGGGCCAAGGTAC

CCTCGTCACCGTCTCGAGCGCCTCCACCAAGGGCCCATCGGTCTTCCCCC

TGGCACCCTCCTCCAAGAGCACCTCTGGGGGCACAGCGGCCCTGGGCTGC

CTGGTCAAGGACTACTTCCCCGAACCGGTGACGGTGTCGTGGAACTCAGG

CGCCCTGACCAGCGGCGTGCACACCTTCCCGGCTGTCCTACAGTCCTCAG

GACTCTACTCCCTCAGCAGCGTGGTGACCGTGCCCTCCAGCAGCTTGGGC

ACCCAGACCTACATCTGCAACGTGAATCACAAGCCCAGCAACACCAAGGT

GGACAAGAGAGTTGAGCCCAAATCTTGTGACAAAACTCACACATGCCCAC

CGTGCCCAGCACCTGAACTCCTGGGGGGACCGTCAGTCTTCCTCTTCCCC

CCAAAACCCAAGGACACCCTCATGATCTCCCGGACCCCTGAGGTCACATG

CGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAG

CAGTACGCCAGCACGTACCGTGTGGTCAGCGTCCTCACCGTCCTGCACCA

GGACTGGCTGAATGGCAAGGAGTACAAGTGCAAGGTCTCCAACAAAGCCC

TCCCAGCCCCCATCGAGAAAACCATCTCCAAAGCCAAAGGGCAGCCCCGA

GAACCACAGGTGTACACCCTGCCCCCATCCCGGGAGGAGATGACCAAGAA

CCAGGTCAGCCTGACCTGCCTGGTCAAAGGCTTCTATCCCAGCGACATCG

CCGTGGAGTGGGAGAGCAATGGGCAGCCGGAGAACAACTACAAGACCACG

CCTCCCGTGCTGGACTCCGACGGCTCCTTCTTCCTCTACAGCAAGCTCAC

CGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCT

CCGGGTAAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 315; SEQ ID NO: 316; and SEQ ID NO: 317 which correspond to polynucleotides encoding the complementarity-determining regions (CDRs, or hypervariable regions) of the light chain variable sequence of SEQ ID NO: 111 or the light chain sequence of SEQ ID NO: 112.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 318; SEQ ID NO: 319; and SEQ ID NO: 320 which correspond to polynucleotides encoding the complementarity-determining regions (CDRs, or hypervariable regions) of the heavy chain variable sequence of SEQ ID NO: 113 or the heavy chain sequence of SEQ ID NO: 114.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 311 encoding the light chain variable sequence of SEQ ID NO: 111; the polynucleotide SEQ ID NO: 312 encoding the light chain sequence of SEQ ID NO: 112; the polynucleotide SEQ ID NO: 313 encoding the heavy chain variable sequence of SEQ ID NO: 113; the polynucleotide SEQ ID NO: 314 encoding the heavy chain sequence of SEQ ID NO: 114; polynucleotides encoding the complementarity-determining regions (SEQ ID NO: 315; SEQ ID NO: 316; and SEQ ID NO: 317) of the light chain variable sequence of SEQ ID NO: 111 or the light chain sequence of SEQ ID NO: 112; and polynucleotides encoding the complementarity-determining regions (SEQ ID NO: 318; SEQ ID NO: 319; and SEQ ID NO: 320) of the heavy chain variable sequence of SEQ ID NO: 113 or the heavy chain sequence of SEQ ID NO: 114.

In a preferred optional embodiment of the invention, polynucleotides of the invention comprise, or alternatively consist of, polynucleotides encoding Fab (fragment antigen binding) fragments having binding specificity for NGF. With respect to antibody Ab12, the polynucleotides encoding the full length Ab12 antibody comprise, or alternatively consist of, the polynucleotide SEQ ID NO: 312 encoding the light chain sequence of SEQ ID NO: 112 and the polynucleotide SEQ ID NO: 314 encoding the heavy chain sequence of SEQ ID NO: 114.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab12 following expression of the full-length polynucleotides in a suitable host. In another embodiment of the invention, anti-NGF antibodies such as Ab12 or Fab fragments thereof may be produced via expression of Ab12 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab13

The invention is further optionally directed to the use of polynucleotides set forth below to produce antibody Ab13 polypeptides having binding specificity to NGF, which inhibit the association of NGF with TrkA and the association of NGF with p75, in methods of treating pain in an individual comprising administering to said individual antibody Ab13 polypeptides. The invention is further optionally directed to polynucleotides encoding antibody polypeptides having binding specificity to NGF. In one embodiment of the invention, polynucleotides of the invention comprise, or alternatively consist of, the following polynucleotide sequence encoding the variable light chain polypeptide sequence of SEQ ID NO: 121:

(SEQ ID NO: 321)
GCCGCCGTGCTGACCCAGACTCCATCTCCCGTGTCTGCAGCTGTGGGAGG

CACAGTCAGCATCAGTTGCCAGTCCAGTCAGAATGTTTATAAGAACAACT

ACTTATCCTGGTATCAGCAGAAACCAGGGCAGCCTCCCAAGCTCCTGATC

TACAAGGCATCCACTCTGGCATCTGGGGTCCCATCGCGGTTCAAAGGCGG

TGGATCTGGGACAGATTTCACTCTCACCATCAGCGACGTGCAGTGTGACG

CTGCTGCCACTTACTACTGTGCAGGCGGTTATACCAGTAGTAGTGATAAT

GCTTTCGGCGGAGGGACCGAGGTGGTGGTCAAACGT.

In one optional embodiment of the invention, polynucleotides of the invention comprise, or alternatively consist of, the following polynucleotide sequence encoding the light chain polypeptide sequence of SEQ ID NO: 122:

(SEQ ID NO: 322)
GCCGCCGTGCTGACCCAGACTCCATCTCCCGTGTCTGCAGCTGTGGGAGG

CACAGTCAGCATCAGTTGCCAGTCCAGTCAGAATGTTTATAAGAACAACT

ACTTATCCTGGTATCAGCAGAAACCAGGGCAGCCTCCCAAGCTCCTGATC

TACAAGGCATCCACTCTGGCATCTGGGGTCCCATCGCGGTTCAAAGGCGG

TGGATCTGGGACAGATTTCACTCTCACCATCAGCGACGTGCAGTGTGACG

CTGCTGCCACTTACTACTGTGCAGGCGGTTATACCAGTAGTAGTGATAAT

GCTTTCGGCGGAGGGACCGAGGTGGTGGTCAAACGTACGGTAGCGGCCCC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTA.

In another optional embodiment of the invention, polynucleotides of the invention comprise, or alternatively consist of, the following polynucleotide sequence encoding the variable heavy chain polypeptide sequence of SEQ ID NO: 123:

(SEQ ID NO: 323)
CAGTCGGTGGAGGCGTCCGGGGGTCGCCTGGTCACGCCTGGGACACCCCT

GACACTCACCTGCACAGCCTCTGGATTCTCCCTCAGTACCTACTGGATGA

GCTGGGTCCGCCAGGCTCCAGGGAAGGGGCTGGAATGGATCGGAGACATT

TATTTTAGTAATGAAGAAACAAACTACGCGAGCTGGGCGAAAGGCCGATT

TACCATCTCCAAAACCTCGACCACGGTGGATCTGAATGTCATCAGTCCGA

CAACCGAGGACACGGCCACCTATTTCTGTGCCAGAGGTTCTCCTGATGTT

GATATTGGTATAGATATGTGGGGCCCGGGCACCCTCGTCACCGTCTCG

AGC.

In one optional embodiment of the invention, polynucleotides of the invention comprise, or alternatively consist of, the following polynucleotide sequence encoding the heavy chain polypeptide sequence of SEQ ID NO: 124:

(SEQ ID NO: 324)
CAGTCGGTGGAGGCGTCCGGGGGTCGCCTGGTCACGCCTGGGACACCCCT

GACACTCACCTGCACAGCCTCTGGATTCTCCCTCAGTACCTACTGGATGA

-continued
```
GCTGGGTCCGCCAGGCTCCAGGGAAGGGGCTGGAATGGATCGGAGACATT

TATTTTAGTAATGAAGAAACAAACTACGCGAGCTGGGCGAAAGGCCGATT

TACCATCTCCAAAACCTCGACCACGGTGGATCTGAATGTCATCAGTCCGA

CAACCGAGGACACGGCCACCTATTTCTGTGCCAGAGGTTCTCCTGATGTT

GATATTGGTATAGATATGTGGGCCCGGGCACCCTCGTCACCGTCTCGAG

CGCCTCCACCAAGGGCCCATCGGTCTTCCCCCTGGCACCCTCCTCCAAGA

GCACCTCTGGGGGCACAGCGGCCCTGGGCTGCCTGGTCAAGGACTACTTC

CCCGAACCGGTGACGGTGTCGTGGAACTCAGGCGCCCTGACCAGCGGCGT

GCACACCTTCCCGGCTGTCCTACAGTCCTCAGGACTCTACTCCCTCAGCA

GCGTGGTGACCGTGCCCTCCAGCAGCTTGGGCACCCAGACCTACATCTGC

AACGTGAATCACAAGCCCAGCAACACCAAGGTGGACAAGAGAGTTGAGCC

CAAATCTTGTGACAAAACTCACACATGCCCACCGTGCCCAGCACCTGAAC

TCCTGGGGGACCGTCAGTCTTCCTCTTCCCCCCAAAACCCAAGGACACC

CTCATGATCTCCCGGACCCCTGAGGTCACATGCGTGGTGGTGGACGTGAG

CCACGAAGACCCTGAGGTCAAGTTCAACTGGTACGTGGACGGCGTGGAGG

TGCATAATGCCAAGACAAAGCCGCGGGAGGAGCAGTACGCCAGCACGTAC

CGTGTGGTCAGCGTCCTCACCGTCCTGCACCAGGACTGGCTGAATGGCAA

GGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACC

CTGCCCCCATCCCGGGAGGAGATGACCAAGAACCAGGTCAGCCTGACCTG

CCTGGTCAAAGGCTTCTATCCCAGCGACATCGCCGTGGAGTGGGAGAGCA

ATGGGCAGCCGGAGAACAACTACAAGACCACGCCTCCCGTGCTGGACTCC

GACGGCTCCTTCTTCCTCTACAGCAAGCTCACCGTGGACAAGAGCAGGTG

GCAGCAGGGGAACGTCTTCTCATGCTCCGTGATGCATGAGGCTCTGCACA

ACCACTACACGCAGAAGAGCCTCTCCCTGTCTCCGGGTAAATGA.
```

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 325; SEQ ID NO: 326; and SEQ ID NO: 327 which correspond to polynucleotides encoding the complementarity-determining regions (CDRs, or hypervariable regions) of the light chain variable sequence of SEQ ID NO: 121 or the light chain sequence of SEQ ID NO: 122.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 328; SEQ ID NO: 329; and SEQ ID NO: 330 which correspond to polynucleotides encoding the complementarity-determining regions (CDRs, or hypervariable regions) of the heavy chain variable sequence of SEQ ID NO: 123 or the heavy chain sequence of SEQ ID NO: 124.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 321 encoding the light chain variable sequence of SEQ ID NO: 121; the polynucleotide SEQ ID NO: 322 encoding the light chain sequence of SEQ ID NO: 122; the polynucleotide SEQ ID NO: 323 encoding the heavy chain variable sequence of SEQ ID NO: 123; the polynucleotide SEQ ID NO: 324 encoding the heavy chain sequence of SEQ ID NO: 124; polynucleotides encoding the complementarity-determining regions (SEQ ID NO: 325; SEQ ID NO: 326; and SEQ ID NO: 327) of the light chain variable sequence of SEQ ID NO: 121 or the light chain sequence of SEQ ID NO: 122; and polynucleotides encoding the complementarity-determining regions (SEQ ID NO: 328; SEQ ID NO: 329; and SEQ ID NO: 330) of the heavy chain variable sequence of SEQ ID NO: 123 or the heavy chain sequence of SEQ ID NO: 124.

In a preferred optional embodiment of the invention, polynucleotides of the invention comprise, or alternatively consist of, polynucleotides encoding Fab (fragment antigen binding) fragments having binding specificity for NGF. With respect to antibody Ab13, the polynucleotides encoding the full length Ab13 antibody comprise, or alternatively consist of, the polynucleotide SEQ ID NO: 322 encoding the light chain sequence of SEQ ID NO: 122 and the polynucleotide SEQ ID NO: 324 encoding the heavy chain sequence of SEQ ID NO: 124.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab13 following expression of the full-length polynucleotides in a suitable host. In another embodiment of the invention, anti-NGF antibodies such as Ab13 or Fab fragments thereof may be produced via expression of Ab13 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab14

The invention is further optionally directed to the use of polynucleotides set forth below to produce antibody Ab14 polypeptides having binding specificity to NGF, which inhibit the association of NGF with TrkA and the association of NGF with p75, in methods of treating pain in an individual comprising administering to said individual antibody Ab14 polypeptides. The invention is further optionally directed to polynucleotides encoding antibody polypeptides having binding specificity to NGF. In one embodiment of the invention, polynucleotides of the invention comprise, or alternatively consist of, the following polynucleotide sequence encoding the variable light chain polypeptide sequence of SEQ ID NO: 131:

(SEQ ID NO: 331)
```
GACATCCAGATGACCCAGTCTCCATCCTCCCTGTCTGCATCTGTAGGAGA

CAGAGTCACCATCACTTGCCAGTCCAGTCAGAATGTTTATAAGAACAACT
```

ACTTATCCTGGTATCAGCAGAAACCAGGGAAAGTCCCTAAGCTCCTGATC

TATAAGGCATCCACTCTGGCATCTGGGGTCCCATCTCGTTTCAGTGGCAG

TGGATCTGGGACAGATTTCACTCTCACCATCAGCAGCCTGCAGCCTGAAG

ATGTTGCAACTTATTACTGTGCAGGCGGTTATACCAGTAGTAGTGATAAT

GCTTTCGGCGGAGGAACCAAGGTGGAAATCAAACGT.

In one optional embodiment of the invention, polynucleotides of the invention comprise, or alternatively consist of, the following polynucleotide sequence encoding the light chain polypeptide sequence of SEQ ID NO: 132:

(SEQ ID NO: 332)
GACATCCAGATGACCCAGTCTCCATCCTCCCTGTCTGCATCTGTAGGAGA

CAGAGTCACCATCACTTGCCAGTCCAGTCAGAATGTTTATAAGAACAACT

ACTTATCCTGGTATCAGCAGAAACCAGGGAAAGTCCCTAAGCTCCTGATC

TATAAGGCATCCACTCTGGCATCTGGGGTCCCATCTCGTTTCAGTGGCAG

TGGATCTGGGACAGATTTCACTCTCACCATCAGCAGCCTGCAGCCTGAAG

ATGTTGCAACTTATTACTGTGCAGGCGGTTATACCAGTAGTAGTGATAAT

GCTTTCGGCGGAGGAACCAAGGTGGAAATCAAACGTACGGTAGCGGCCCC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTG

TCACAGAGCAGGACAGCAAGGACAGCACCTACAGCCTCAGCAGCACCC

TGACGCTGAGCAAAGCAGACTACGAGAAACACAAAGTCTACGCCTGCGA

AGTCACCCATCAGGGCCTGAGCTCGCCCGTCACAAAGAGCTTCAACA

GGGGAGAGTGTTAG.

In another optional embodiment of the invention, polynucleotides of the invention comprise, or alternatively consist of, the following polynucleotide sequence encoding the variable heavy chain polypeptide sequence of SEQ ID NO: 133:

(SEQ ID NO: 333)
GAGGTGCAGCTGGTGGAGTCTGGGGGAGGCTTGGTCCAGCCTGGGGGGTC

CCTGAGACTCTCCTGTGCAGCCTCTGGATTCACCGTCAGTACCTACTGGA

TGAGCTGGGTCCGTCAGGCTCCAGGGAAGGGGCTGGAGTGGGTCGGAGAC

ATTTACTTTAGTAATGAAGAAACAAACTACGCGAGCAGCGCGAAAGGCCG

ATTCACCATCTCCAGAGACAATTCCAAGAACACCCTGTATCTTCAAATGA

ACAGCCTGAGAGCTGAGGACACTGCTGTGTATTACTGTGCTAGAGGTTCT

CCTGATGTTGATATTGGTATAGATATGTGGGGCCCAGGGACCCTCGTCAC

CGTCTCGAGC.

In one optional embodiment of the invention, polynucleotides of the invention comprise, or alternatively consist of, the following polynucleotide sequence encoding the heavy chain polypeptide sequence of SEQ ID NO: 134:

(SEQ ID NO: 334)
GAGGTGCAGCTGGTGGAGTCTGGGGGAGGCTTGGTCCAGCCTGGGGGGTC

CCTGAGACTCTCCTGTGCAGCCTCTGGATTCACCGTCAGTACCTACTGGA

TGAGCTGGGTCCGTCAGGCTCCAGGGAAGGGGCTGGAGTGGGTCGGAGAC

ATTTACTTTAGTAATGAAGAAACAAACTACGCGAGCAGCGCGAAAGGCCG

ATTCACCATCTCCAGAGACAATTCCAAGAACACCCTGTATCTTCAAATGA

ACAGCCTGAGAGCTGAGGACACTGCTGTGTATTACTGTGCTAGAGGTTCT

CCTGATGTTGATATTGGTATAGATATGTGGGGCCCAGGGACCCTCGTCAC

CGTCTCGAGCGCCTCCACCAAGGGCCCATCGGTCTTCCCCCTGGCACCCT

CCTCCAAGAGCACCTCTGGGGGCACAGCGGCCCTGGGCTGCCTGGTCAAG

GACTACTTCCCCGAACCGGTGACGGTGTCGTGGAACTCAGGCGCCCTGAC

CAGCGGCGTGCACACCTTCCCGGCTGTCCTACAGTCCTCAGGACTCTACT

CCCTCAGCAGCGTGGTGACCGTGCCCTCCAGCAGCTTGGGCACCCAGACC

TACATCTGCAACGTGAATCACAAGCCCAGCAACACCAAGGTGGACAAGAG

AGTTGAGCCCAAATCTTGTGACAAAACTCACACATGCCCACCGTGCCCAG

CACCTGAACTCCTGGGGGGACCGTCAGTCTTCCTCTTCCCCCCAAAACCC

AAGGACACCCTCATGATCTCCCGGACCCCTGAGGTCACATGCGTGGTGGT

GGACGTGAGCCACGAAGACCCTGAGGTCAAGTTCAACTGGTACGTGGACG

GCGTGGAGGTGCATAATGCCAAGACAAAGCCGCGGGAGGAGCAGTACGCC

AGCACGTACCGTGTGGTCAGCGTCCTCACCGTCCTGCACCAGGACTGGCT

GAATGGCAAGGAGTACAAGTGCAAGGTCTCCAACAAAGCCCTCCCAGCCC

CCATCGAGAAAACCATCTCCAAAGCCAAAGGGCAGCCCCGAGAACCACAG

GTGTACACCCTGCCCCCATCCCGGGAGGAGATGACCAAGAACCAGGTCAG

CCTGACCTGCCTGGTCAAAGGCTTCTATCCCAGCGACATCGCCGTGGAGT

GGGAGAGCAATGGGCAGCCGGAGAACAACTACAAGACCACGCCTCCCGTG

CTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGG

CTCTGCACAACCACTACACGCAGAAGAGCCTCTCCCTGTCTCCGGGTAA

ATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 335; SEQ ID NO: 336; and SEQ ID NO: 337 which correspond to polynucleotides encoding the complementarity-determining regions (CDRs, or hypervariable regions) of the light chain variable sequence of SEQ ID NO: 131 or the light chain sequence of SEQ ID NO: 132.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 338; SEQ ID NO: 339; and SEQ ID NO: 340 which correspond to polynucleotides encoding the complementarity-determining regions (CDRs, or hypervariable regions) of the heavy chain variable sequence of SEQ ID NO: 133 or the heavy chain sequence of SEQ ID NO: 134.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 331 encoding the light chain variable sequence of SEQ ID NO: 131; the polynucleotide SEQ ID NO: 332 encoding the light chain sequence of SEQ ID NO: 132; the polynucleotide SEQ ID NO: 333 encoding the heavy chain variable sequence of SEQ ID NO: 133; the polynucleotide SEQ ID NO: 334 encoding the heavy chain sequence of SEQ ID NO: 134; polynucleotides encoding the complementarity-determining regions (SEQ ID NO: 335; SEQ ID NO: 336; and SEQ ID NO: 337) of the light chain variable sequence of SEQ ID NO: 131 or the light chain sequence of SEQ ID NO: 132; and polynucleotides encoding the complementarity-determining regions (SEQ ID NO: 338; SEQ ID NO: 339; and SEQ ID NO: 340) of the heavy chain variable sequence of SEQ ID NO: 133 or the heavy chain sequence of SEQ ID NO: 134.

In a preferred optional embodiment of the invention, polynucleotides of the invention comprise, or alternatively consist of, polynucleotides encoding Fab (fragment antigen binding) fragments having binding specificity for NGF. With respect to antibody Ab14, the polynucleotides encoding the full length Ab14 antibody comprise, or alternatively consist of, the polynucleotide SEQ ID NO: 332 encoding the light chain sequence of SEQ ID NO: 132 and the polynucleotide SEQ ID NO: 334 encoding the heavy chain sequence of SEQ ID NO: 134.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab14 following expression of the full-length polynucleotides in a suitable host. In another embodiment of the invention, anti-NGF antibodies such as Ab14 or Fab fragments thereof may be produced via expression of Ab14 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab15

The invention is further directed to the use of polynucleotides set forth below to produce antibody Ab15 polypeptides having binding specificity to NGF, which inhibit the association of NGF with TrkA without appreciably inhibiting the association of NGF with p75, in methods of treating pain in an individual comprising administering to said individual antibody Ab15 polypeptides. The invention is further directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 141:

```
                                       (SEQ ID NO: 341)
GCAGCCGTGCTGACCCAGACACCATCGCCCGTGTCTGCAGCTGTGGGAGA

CACAGTCACCATCAAGTGCCAGTCCAGTCAGAGTGTTTATAAGAACAACT

ACTTATCCTGGTATCAGCAGAAACCAGGGCAGCCTCCCAAGCTCCTGATC

TATGATGCATCCAATCTGCCATCTGGGGTCCCATCACGGTTCAGCGGCAG

TGGATCTGGGACACAGTTCACTCTCACCATCAGCGGCGTGCAGTGTGACG

ATGCTGCCACTTACTACTGTCTAGGCGATTATGATGATGATACTGATAAT

GGTTTCGGCGGAGGGACCGAGGTGGTGGTCAAACGT.
```

In one embodiment of the invention, polynucleotides of the invention comprise, or alternatively consist of, the following polynucleotide sequence encoding the light chain polypeptide sequence of SEQ ID NO: 142:

```
                                       (SEQ ID NO: 342)
GCAGCCGTGCTGACCCAGACACCATCGCCCGTGTCTGCAGCTGTGGGAGA

CACAGTCACCATCAAGTGCCAGTCCAGTCAGAGTGTTTATAAGAACAACT

ACTTATCCTGGTATCAGCAGAAACCAGGGCAGCCTCCCAAGCTCCTGATC

TATGATGCATCCAATCTGCCATCTGGGGTCCCATCACGGTTCAGCGGCAG

TGGATCTGGGACACAGTTCACTCTCACCATCAGCGGCGTGCAGTGTGACG

ATGCTGCCACTTACTACTGTCTAGGCGATTATGATGATGATACTGATAAT

GGTTTCGGCGGAGGGACCGAGGTGGTGGTCAAACGTACGGTAGCGGCCCC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAG.
```

In another embodiment of the invention, polynucleotides of the invention comprise, or alternatively consist of, the following polynucleotide sequence encoding the variable heavy chain polypeptide sequence of SEQ ID NO: 143:

```
                                       (SEQ ID NO: 343)
CAGTCGGTGGAGGAGTCCGGGGGTCGCCTGGTCACGCCTGGGACACCCCT

GACACTCACCTGCACAGTCTCTGGAATCGACCTCAGTAGCTATGCAATGA

TCTGGGTCCGCCAGGCTCCAGGGAAGGGGCTGGAATACATCGGAATCATT

TGGAGTGGTGGCACCTACTACGCGACCTGGGCGAAAGGCCGATTCACCAT

CTCCAAAACCTCGACCACGGTGGATCTGCAAATCACCAGTCCGACAACCG

AGGACGCGGCCACCTATTTCTGTGCCGCAGGTGGTGGTAGTATTTATGAT

GTTTGGGGCCCGGGCACCCTGGTCACCGTCTCGAGC.
```

In one embodiment of the invention, polynucleotides of the invention comprise, or alternatively consist of, the following polynucleotide sequence encoding the heavy chain polypeptide sequence of SEQ ID NO: 144:

(SEQ ID NO: 344)
```
CAGTCGGTGGAGGAGTCCGGGGGTCGCCTGGTCACGCCTGGGACACCCT

GACACTCACCTGCACAGTCTCTGGAATCGACCTCAGTAGCTATGCAATGA

TCTGGGTCCGCCAGGCTCCAGGGAAGGGGCTGGAATACATCGGAATCATT

TGGAGTGGTGGCACCTACTACGCGACCTGGGCGAAAGGCCGATTCACCAT

CTCCAAAACCTCGACCACGGTGGATCTGCAAATCACCAGTCCGACAACCG

AGGACGCGGCCACCTATTTCTGTGCCGCAGGTGGTGGTAGTATTTATGAT

GTTTGGGGCCCGGGCACCCTGGTCACCGTCTCGAGCGCCTCCACCAAGGG

CCCATCGGTCTTCCCCCTGGCACCCTCCTCCAAGAGCACCTCTGGGGGCA

CAGCGGCCCTGGGCTGCCTGGTCAAGGACTACTTCCCCGAACCGGTGACG

GTGTCGTGGAACTCAGGCGCCCTGACCAGCGGCGTGCACACCTTCCCGGC

TGTCCTACAGTCCTCAGGACTCTACTCCCTCAGCAGCGTGGTGACCGTGC

CCTCCAGCAGCTTGGGCACCCAGACCTACATCTGCAACGTGAATCACAAG

CCCAGCAACACCAAGGTGGACAAGAGAGTTGAGCCCAAATCTTGTGACAA

AACTCACACATGCCCACCGTGCCCAGCACCTGAACTCCTGGGGGGACCGT

CAGTCTTCCTCTTCCCCCCAAAACCCAAGGACACCCTCATGATCTCCCGG

ACCCCTGAGGTCACATGCGTGGTGGTGGACGTGAGCCACGAAGACCCTGA

GGTCAAGTTCAACTGGTACGTGGACGGCGTGGAGGTGCATAATGCCAAGA

CAAAGCCGCGGGAGGAGCAGTACGCCAGCACGTACCGTGTGGTCAGCGTC

CTCACCGTCCTGCACCAGGACTGGCTGAATGGCAAGGAGTACAAGTGCAA

GGTCTCCAACAAAGCCCTCCCAGCCCCCATCGAGAAAACCATCTCCAAAG

CCAAAGGGCAGCCCCGAGAACCACAGGTGTACACCCTGCCCCCATCCCGG

GAGGAGATGACCAAGAACCAGGTCAGCCTGACCTGCCTGGTCAAAGGCTT

CTATCCCAGCGACATCGCCGTGGAGTGGGAGAGCAATGGGCAGCCGGAGA

ACAACTACAAGACCACGCCTCCCGTGCTGGACTCCGACGGCTCCTTCTTC

CTCTACAGCAAGCTCACCGTGGACAAGAGCAGGTGGCAGCAGGGGAACGT

CTTCTCATGCTCCGTGATGCATGAGGCTCTGCACAACCACTACACGCAGA

AGAGCCTCTCCCTGTCTCCGGGTAAATGA.
```

In a further embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 345; SEQ ID NO: 346; and SEQ ID NO: 347 which correspond to polynucleotides encoding the complementarity-determining regions (CDRs, or hypervariable regions) of the light chain variable sequence of SEQ ID NO: 141 or the light chain sequence of SEQ ID NO: 142.

In a further embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 348; SEQ ID NO: 349; and SEQ ID NO: 350 which correspond to polynucleotides encoding the complementarity-determining regions (CDRs, or hypervariable regions) of the heavy chain variable sequence of SEQ ID NO: 143 or the heavy chain sequence of SEQ ID NO: 144.

The invention also contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 341 encoding the light chain variable sequence of SEQ ID NO: 141; the polynucleotide SEQ ID NO: 342 encoding the light chain sequence of SEQ ID NO: 142; the polynucleotide SEQ ID NO: 343 encoding the heavy chain variable sequence of SEQ ID NO: 143; the polynucleotide SEQ ID NO: 344 encoding the heavy chain sequence of SEQ ID NO: 144; polynucleotides encoding the complementarity-determining regions (SEQ ID NO: 345; SEQ ID NO: 346; and SEQ ID NO: 347) of the light chain variable sequence of SEQ ID NO: 141 or the light chain sequence of SEQ ID NO: 142; and polynucleotides encoding the complementarity-determining regions (SEQ ID NO: 348; SEQ ID NO: 349; and SEQ ID NO: 350) of the heavy chain variable sequence of SEQ ID NO: 143 or the heavy chain sequence of SEQ ID NO: 144.

In a preferred embodiment of the invention, polynucleotides of the invention comprise, or alternatively consist of, polynucleotides encoding Fab (fragment antigen binding) fragments having binding specificity for NGF. With respect to antibody Ab15, the polynucleotides encoding the full length Ab15 antibody comprise, or alternatively consist of, the polynucleotide SEQ ID NO: 342 encoding the light chain sequence of SEQ ID NO: 142 and the polynucleotide SEQ ID NO: 344 encoding the heavy chain sequence of SEQ ID NO: 144.

Another embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab15 following expression of the full-length polynucleotides in a suitable host. In another embodiment of the invention, anti-NGF antibodies such as Ab15 or Fab fragments thereof may be produced via expression of Ab15 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab16

The invention is further directed to the use of polynucleotides set forth below to produce antibody Ab16 polypeptides for treatment or prevention of pain and pain associated conditions having binding specificity to NGF, which inhibit the association of NGF with TrkA without appreciably inhibiting the association of NGF with p75, in methods of treating pain in an individual comprising administering to said individual antibody Ab16 polypeptides. The invention is further directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 151:

(SEQ ID NO: 351)
GCCCTGGTGATGACCCAGACTCCATCCTCCACGTCTGAACCAGTGGGAGG
CACAGTCACCATCAATTGCCAGGCTAGTCAGAATATTGGTAACGACCTAT
CCTGGTATCAGCAGAAACCAGGGCAGCCTCCCGAGCTCCTAATCTATTCT
ACATCCAAACTGGCAACTGGGGTCCCAAAGCGGTTCAGTGGCAGCAGATC
TGGGACACAGTTCACTCTCACCATCAGCGACCTGGAGTGTGACGATGCTG
CCACTTACTACTGTCTAGGTGTTTATAGTTATATTAGTGATGATGGTAAT
GCTTTCGGCGGAGGGACCGAGGTGGTGGTCAAACGT.

In one embodiment of the invention, polynucleotides of the invention comprise, or alternatively consist of, the following polynucleotide sequence encoding the light chain polypeptide sequence of SEQ ID NO: 152:

(SEQ ID NO: 352)
GCCCTGGTGATGACCCAGACTCCATCCTCCACGTCTGAACCAGTGGGAGG
CACAGTCACCATCAATTGCCAGGCTAGTCAGAATATTGGTAACGACCTAT
CCTGGTATCAGCAGAAACCAGGGCAGCCTCCCGAGCTCCTAATCTATTCT
ACATCCAAACTGGCAACTGGGGTCCCAAAGCGGTTCAGTGGCAGCAGATC
TGGGACACAGTTCACTCTCACCATCAGCGACCTGGAGTGTGACGATGCTG
CCACTTACTACTGTCTAGGTGTTTATAGTTATATTAGTGATGATGGTAAT
GCTTTCGGCGGAGGGACCGAGGTGGTGGTCAAACGTACGGTAGCGGCCC
ATCTGTCTTCATCTTCCCGCCATCTGATGAGCAGTTGAAATCTGGAACTG
CCTCTGTTGTGTGCCTGCTGAATAACTTCTATCCCAGAGAGGCCAAAGTA
CAGTGGAAGGTGGATAACGCCCTCCAATCGGGTAACTCCCAGGAGAGTGT
CACAGAGCAGGACAGCAAGGACAGCACCTACAGCCTCAGCAGCACCCTGA
CGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGA
GTGTTAG.

In another embodiment of the invention, polynucleotides of the invention comprise, or alternatively consist of, the following polynucleotide sequence encoding the variable heavy chain polypeptide sequence of SEQ ID NO: 153:

(SEQ ID NO: 353)
CAGTCGGTGGAGGAGTTCGGGGGTCGCCTGGTCACGCCTGGGACACCCCT
GACACTCACCTGCACCGTCTCTGGATTCTCCCTCAATAACTATGCAATGA
CCTGGGTCCGCCAGGCTCCAGGGAAGGGGCTGGAGTGGATCGGGATCATT
GGTAGTATTGGTACCACATACTACGCGAGCTGGGCGAAAGGCCGATTCTT
CATCTCCAAAACCTCGACCACTGTGGATCTGAAAATCATTAGTCCGACAA
CCGAGGACACGGCCACCTATTTCTGTGCCAGAGATGCTGGCGTTACTGTT
GATGGTTATGGCTACTACTTTAACATCTGGGGCCCAGGCACCCTCGTCAC
CGTCTCGAGC.

In one embodiment of the invention, polynucleotides of the invention comprise, or alternatively consist of, the following polynucleotide sequence encoding the heavy chain polypeptide sequence of SEQ ID NO: 154:

(SEQ ID NO: 354)
CAGTCGGTGGAGGAGTTCGGGGGTCGCCTGGTCACGCCTGGGACACCCCT
GACACTCACCTGCACCGTCTCTGGATTCTCCCTCAATAACTATGCAATGA
CCTGGGTCCGCCAGGCTCCAGGGAAGGGGCTGGAGTGGATCGGGATCATT
GGTAGTATTGGTACCACATACTACGCGAGCTGGGCGAAAGGCCGATTCTT
CATCTCCAAAACCTCGACCACTGTGGATCTGAAAATCATTAGTCCGACAA
CCGAGGACACGGCCACCTATTTCTGTGCCAGAGATGCTGGCGTTACTGTT
GATGGTTATGGCTACTACTTTAACATCTGGGGCCCAGGCACCCTCGTCAC
CGTCTCGAGCGCCTCCACCAAGGGCCCATCGGTCTTCCCCCTGGCACCCT
CCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGAC
CAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACC
TACATCTGCAACGTGAATCACAAGCCCAGCAACACCAAGGTGGACAAGAG
AGTTGAGCCCAAATCTTGTGACAAAACTCACACATGCCCACCGTGCCCAG
CACCTGAACTCCTGGGGGGACCGTCAGTCTTCCTCTTCCCCCCAAAACCC
AAGGACACCCTCATGATCTCCCGGACCCCTGAGGTCACATGCGTGGTGGT
GGACGTGAGCCACGAAGACCCTGAGGTCAAGTTCAACTGGTACGTGGACG
GCGTGGAGGTGCATAATGCCAAGACAAAGCCGCGGGAGGAGCAGTACGCC
AGCACGTACCGTGTGGTCAGCGTCCTCACCGTCCTGCACCAGGACTGGCT
GAATGGCAAGGAGTACAAGTGCAAGGTCTCCAACAAAGCCCTCCCAGCCC
CCATCGAGAAAACCATCTCCAAAGCCAAAGGGCAGCCCCGAGAACCACAG
GTGTACACCCTGCCCCCATCCCGGGAGGAGATGACCAAGAACCAGGTCAG
CCTGACCTGCCTGGTCAAAGGCTTCTATCCCAGCGACATCGCCGTGGAGT
GGGAGAGCAATGGGCAGCCGGAGAACAACTACAAGACCACGCCTCCCGTG
CTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCTCCGGGTAAA
TGA.

In a further embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 355; SEQ ID NO: 356; and SEQ ID NO: 357 which correspond to polynucleotides encoding the complementarity-determining regions (CDRs, or hypervariable regions) of the light chain variable sequence of SEQ ID NO: 151 or the light chain sequence of SEQ ID NO: 152.

In a further embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 358; SEQ ID NO: 359; and SEQ ID NO: 360 which correspond to polynucleotides encoding the complementarity-determining regions (CDRs, or hypervariable regions) of the heavy chain variable sequence of SEQ ID NO: 153 or the heavy chain sequence of SEQ ID NO: 154.

The invention also contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 351 encoding the light chain variable sequence of SEQ ID NO: 151; the polynucleotide SEQ ID NO: 352 encoding the light chain sequence of SEQ ID NO: 152; the polynucleotide SEQ ID NO: 353 encoding the heavy chain variable sequence of SEQ ID NO: 153; the polynucleotide SEQ ID NO: 354 encoding the heavy chain sequence of SEQ ID NO: 154; polynucleotides encoding the complementarity-determining regions (SEQ ID NO: 355; SEQ ID NO: 356; and SEQ ID NO: 357) of the light chain variable sequence of SEQ ID NO: 151 or the light chain sequence of SEQ ID NO: 152; and polynucleotides encoding the complementarity-determining regions (SEQ ID NO: 358; SEQ ID NO: 359; and SEQ ID NO: 360) of the heavy chain variable sequence of SEQ ID NO: 153 or the heavy chain sequence of SEQ ID NO: 154.

In a preferred embodiment of the invention, polynucleotides of the invention comprise, or alternatively consist of, polynucleotides encoding Fab (fragment antigen binding) fragments having binding specificity for NGF. With respect to antibody Ab16, the polynucleotides encoding the full length Ab16 antibody comprise, or alternatively consist of, the polynucleotide SEQ ID NO: 352 encoding the light chain sequence of SEQ ID NO: 152 and the polynucleotide SEQ ID NO: 354 encoding the heavy chain sequence of SEQ ID NO: 154.

Another embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab16 following expression of the full-length polynucleotides in a suitable host. In another embodiment of the invention, anti-NGF antibodies such as Ab16 or Fab fragments thereof may be produced via expression of Ab16 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab17

The invention is further optionally directed to the use of polynucleotides set forth below to produce antibody Ab17 polypeptides having binding specificity to NGF, which inhibit the association of NGF with TrkA without appreciably inhibiting the association of NGF with p75, in methods of treating pain in an individual comprising administering to said individual antibody Ab17 polypeptides. The invention is further optionally directed to polynucleotides encoding antibody polypeptides for treatment or prevention of pain and pain associated conditions having binding specificity to NGF. In one optional embodiment of the invention, polynucleotides of the invention comprise, or alternatively consist of, the following polynucleotide sequence encoding the variable light chain polypeptide sequence of SEQ ID NO: 161:

(SEQ ID NO: 361)
GCCATCGAAATGACCCAGACTCCATTCTCCGTGTCTGCAGCTGTGGGAGG

CACAGTCACCATCAAGTGCCAGGCCAGTCAGACCATTAGCAACTACTTAG

CCTGGTATCAGCAGAAACCAGGGCAGCCTCCCAAGCTCCTGATCTATGGT

GCATCCAATCTGGAATCTGGGGTCCCATCGCGGTTCAAAGGCAGTGGATC

TGGGACACAGTTCACTCTCACCATCAGCGACCTGGAGTGTGACGATGCTG

CCACTTACTACTGTCAACAGGGTTATACTATCAGTAATGTTGATAACAAT

GTTTTCGGCGGAGGGACCGAGGTGGTGGTCAAACGT.

In one optional embodiment of the invention, polynucleotides of the invention comprise, or alternatively consist of, the following polynucleotide sequence encoding the light chain polypeptide sequence of SEQ ID NO: 162:

(SEQ ID NO: 362)
GCCATCGAAATGACCCAGACTCCATTCTCCGTGTCTGCAGCTGTGGGAGG

CACAGTCACCATCAAGTGCCAGGCCAGTCAGACCATTAGCAACTACTTAG

CCTGGTATCAGCAGAAACCAGGGCAGCCTCCCAAGCTCCTGATCTATGGT

GCATCCAATCTGGAATCTGGGGTCCCATCGCGGTTCAAAGGCAGTGGATC

TGGGACACAGTTCACTCTCACCATCAGCGACCTGGAGTGTGACGATGCTG

CCACTTACTACTGTCAACAGGGTTATACTATCAGTAATGTTGATAACAAT

GTTTTCGGCGGAGGGACCGAGGTGGTGGTCAAACGTACGGTAGCGGCCCC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAG.

In another optional embodiment of the invention, polynucleotides of the invention comprise, or alternatively consist of, the following polynucleotide sequence encoding the variable heavy chain polypeptide sequence of SEQ ID NO: 163:

(SEQ ID NO: 363)
CAGTCGCTGGAGGAGTCCGGGGGTCGCCTGGTCACGCCTGGGGGATCCCT

GACACTCACCTGCGCAGCCTCTGGATTCTCCCTCACTGGCTACAACTTGG

TCTGGGTCCGCCAGGCTCCAGGGAAGGGGCTGGAGTGGATCGGATTCATT

AGTTATGGTGATACCACATACTACGCGAGCTGGGCGAAAGGCCGATTCAC

CATCTCCAAAACCTCGACCACGGTGACTCTGACGATCACCGATCTGCAAC

CTTCAGACACGGGCACCTATTTCTGTGCCAGAGAGACTGCTAATACTTAT

GATTATGGCATCTGGGGCCCAGGCACCCTCGTCACCGTCTCGAGC.

In one optional embodiment of the invention, polynucleotides of the invention comprise, or alternatively consist of, the following polynucleotide sequence encoding the heavy chain polypeptide sequence of SEQ ID NO: 164:

(SEQ ID NO: 364)
CAGTCGCTGGAGGAGTCCGGGGGTCGCCTGGTCACGCCTGGGGATCCCT

GACACTCACCTGCGCAGCCTCTGGATTCTCCCTCACTGGCTACAACTTGG

TCTGGGTCCGCCAGGCTCCAGGGAAGGGGCTGGAGTGGATCGGATTCATT

AGTTATGGTGATACCACATACTACGCGAGCTGGGCGAAAGGCCGATTCAC

CATCTCCAAAACCTCGACCACGGTGACTCTGACGATCACCGATCTGCAAC

CTTCAGACACGGGCACCTATTTCTGTGCCAGAGAGACTGCTAATACTTAT

GATTATGGCATCTGGGGCCCAGGCACCCTCGTCACCGTCTCGAGCGCCTC

CACCAAGGGCCCATCGGTCTTCCCCCTGGCACCCTCCTCCAAGAGCACCT

CTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACAC

CTTCCCGGCTGTCCTACAGTCCTCAGGACTCTACTCCCTCAGCAGCGTGG

TGACCGTGCCCTCCAGCAGCTTGGGCACCCAGACCTACATCTGCAACGTG

AATCACAAGCCCAGCAACACCAAGGTGGACAAGAGAGTTGAGCCCAAATC

TTGTGACAAAACTCACACATGCCCACCGTGCCCAGCACCTGAACTCCTGG

GGGGACCGTCAGTCTTCCTCTTCCCCCCAAAACCCAAGGACACCCTCATG

ATCTCCCGGACCCCTGAGGTCACATGCGTGGTGGTGGACGTGAGCCACGA

AGACCCTGAGGTCAAGTTCAACTGGTACGTGGACGGCGTGGAGGTGCATA

ATGCCAAGACAAAGCCGCGGGAGGAGCAGTACGCCAGCACGTACCGTGTG

GTCAGCGTCCTCACCGTCCTGCACCAGGACTGGCTGAATGGCAAGGAGTA

CAAGTGCAAGGTCTCCAACAAAGCCCTCCCAGCCCCCATCGAGAAAACCA

TCTCCAAAGCCAAAGGGCAGCCCCGAGAACCACAGGTGTACACCCTGCCC

CCATCCCGGGAGGAGATGACCAAGAACCAGGTCAGCCTGACCTGCCTGGT

CAAAGGCTTCTATCCCAGCGACATCGCCGTGGAGTGGGAGAGCAATGGGC

AGCCGGAGAACAACTACAAGACCACGCCTCCCGTGCTGGACTCCGACGGC

TCCTTCTTCCTCTACAGCAAGCTCACCGTGGACAAGAGCAGGTGGCAGCA

GGGGAACGTCTTCTCATGCTCCGTGATGCATGAGGCTCTGCACAACCACT

ACACGCAGAAGAGCCTCTCCCTGTCTCCGGGTAAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 365; SEQ ID NO: 366; and SEQ ID NO: 367 which correspond to polynucleotides encoding the complementarity-determining regions (CDRs, or hypervariable regions) of the light chain variable sequence of SEQ ID NO: 161 or the light chain sequence of SEQ ID NO: 162.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 368; SEQ ID NO: 369; and SEQ ID NO: 370 which correspond to polynucleotides encoding the complementarity-determining regions (CDRs, or hypervariable regions) of the heavy chain variable sequence of SEQ ID NO: 163 or the heavy chain sequence of SEQ ID NO: 164.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 361 encoding the light chain variable sequence of SEQ ID NO: 161; the polynucleotide SEQ ID NO: 362 encoding the light chain sequence of SEQ ID NO: 162; the polynucleotide SEQ ID NO: 363 encoding the heavy chain variable sequence of SEQ ID NO: 163; the polynucleotide SEQ ID NO: 364 encoding the heavy chain sequence of SEQ ID NO: 164; polynucleotides encoding the complementarity-determining regions (SEQ ID NO: 365; SEQ ID NO: 366; and SEQ ID NO: 367) of the light chain variable sequence of SEQ ID NO: 161 or the light chain sequence of SEQ ID NO: 162; and polynucleotides encoding the complementarity-determining regions (SEQ ID NO: 368; SEQ ID NO: 369; and SEQ ID NO: 370) of the heavy chain variable sequence of SEQ ID NO: 163 or the heavy chain sequence of SEQ ID NO: 164.

In a preferred optional embodiment of the invention, polynucleotides of the invention comprise, or alternatively consist of, polynucleotides encoding Fab (fragment antigen binding) fragments having binding specificity for NGF. With respect to antibody Ab17, the polynucleotides encoding the full length Ab17 antibody comprise, or alternatively consist of, the polynucleotide SEQ ID NO: 362 encoding the light chain sequence of SEQ ID NO: 162 and the polynucleotide SEQ ID NO: 364 encoding the heavy chain sequence of SEQ ID NO: 164.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one optional embodiment of the invention described herein (infra), Fab fragments may be produced by enzymatic digestion (e.g., papain) of Ab17 following expression of the full-length polynucleotides in a suitable host. In another embodiment of the invention, anti-NGF antibodies such as Ab17 or Fab fragments thereof may be produced via expression of Ab17 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab18

The invention is further optionally directed to the use of polynucleotides set forth below to produce antibody Ab18 polypeptides having binding specificity to NGF, which inhibit the association of NGF with TrkA and the association of NGF with p75, in methods of treating pain in an individual comprising administering to said individual antibody Ab18 polypeptides. The invention is further directed to polynucleotides encoding antibody polypeptides for treatment or prevention of pain and pain associated conditions having binding specificity to NGF. In one optional embodiment of the invention, polynucleotides of the invention comprise, or alternatively consist of, the following polynucleotide sequence encoding the variable light chain polypeptide sequence of SEQ ID NO: 171:

(SEQ ID NO: 371)
GACATCCAGATGACCCAGTCTCCTTCCACCCTGTCTGCATCTGTAGGAGACAGAGTCACCATCACTTGTCAGGCTAGTCAGACCATTAGCAACTACTTAGCCTGGTATCAGCAGAAACCAGGAAAAGCCCCTAAGCTCCTGATCTATGGTGCATCCAATCTGGAATCTGGAGTCCCATCAAGGTTCAGCGGCAGTGGATCTGGAACAGAATTCACTCTCACCATCAGCAGCCTGCAGCCTGATGATTTTGCAACTTACTACTGTCAACAGGGTTATACTATCAGTAATGTTGATAACAATGTTTTCGGCGGAGGAACCAAGGTGGAAATCAAACGT.

In one optional embodiment of the invention, polynucleotides of the invention comprise, or alternatively consist of, the following polynucleotide sequence encoding the light chain polypeptide sequence of SEQ ID NO: 172:

(SEQ ID NO: 372)
GACATCCAGATGACCCAGTCTCCTTCCACCCTGTCTGCATCTGTAGGAGACAGAGTCACCATCACTTGTCAGGCTAGTCAGACCATTAGCAACTACTTAGCCTGGTATCAGCAGAAACCAGGAAAAGCCCCTAAGCTCCTGATCTATGGTGCATCCAATCTGGAATCTGGAGTCCCATCAAGGTTCAGCGGCAGTGGATCTGGAACAGAATTCACTCTCACCATCAGCAGCCTGCAGCCTGATGATTTTGCAACTTACTACTGTCAACAGGGTTATACTATCAGTAATGTTGATAACAATGTTTTCGGCGGAGGAACCAAGGTGGAAATCAAACGTACGGTAGCGGCCCCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTAG.

In another optional embodiment of the invention, polynucleotides of the invention comprise, or alternatively consist of, the following polynucleotide sequence encoding the variable heavy chain polypeptide sequence of SEQ ID NO: 173:

(SEQ ID NO: 373)
GAGGTGCAGCTGGTGGAGTCTGGGGGAGGCTTGGTCCAGCCTGGGGGTCCCTGAGACTCTCCTGTGCAGCCTCTGGATTCACCGTCAGTGGCTACAACTTGGTCTGGGTCCGTCAGGCTCCAGGGAAGGGGCTGGAGTGGGTCGGATTCATTAGTTATGGTGATACCACATACTACGCTAGCTCTGCTAAAGGCCGATTCACCATCTCCAGAGACAATTCCAAGAACACCCTGTATCTTCAAATGAACAGCCTGAGAGCTGAGGACACTGCTGTGTATTACTGTGCTAGAGAGACTGCTAATACTTATGATTATGGCATCTGGGGCCAAGGGACCCTCGTCACCGTCTCGAGC.

In one optional embodiment of the invention, polynucleotides of the invention comprise, or alternatively consist of, the following polynucleotide sequence encoding the heavy chain polypeptide sequence of SEQ ID NO: 174:

(SEQ ID NO: 374)
GAGGTGCAGCTGGTGGAGTCTGGGGGAGGCTTGGTCCAGCCTGGGGGGTCCCTGAGACTCTCCTGTGCAGCCTCTGGATTCACCGTCAGTGGCTACAACTTGGTCTGGGTCCGTCAGGCTCCAGGGAAGGGGCTGGAGTGGGTCGGATTCATTAGTTATGGTGATACCACATACTACGCTAGCTCTGCTAAAGGCCGATTCACCATCTCCAGAGACAATTCCAAGAACACCCTGTATCTTCAAATGAACAGCCTGAGAGCTGAGGACACTGCTGTGTATTACTGTGCTAGAGAGACTGCTAATACTTATGATTATGGCATCTGGGGCCAAGGGACCCTCGTCACCGTCTCGAGCGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAGAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACGCCAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 375; SEQ ID NO: 376; and SEQ ID NO: 377 which correspond to polynucleotides encoding the complementarity-determining regions (CDRs, or hypervariable regions) of the light chain variable sequence of SEQ ID NO: 171 or the light chain sequence of SEQ ID NO: 172.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 378; SEQ ID NO: 379; and SEQ ID NO: 380 which correspond to polynucleotides encoding the complementarity-determining regions (CDRs, or hypervariable regions) of the heavy chain variable sequence of SEQ ID NO: 173 or the heavy chain sequence of SEQ ID NO: 174.

The invention also optionally contemplates polynucleotide sequences including one or more of the polynucleotide sequences encoding antibody fragments for treatment or prevention of pain and pain associated conditions described herein. In one optional embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 371 encoding the light chain variable sequence of SEQ ID NO: 171; the polynucleotide SEQ ID NO: 372 encoding the light chain sequence of SEQ ID NO: 172; the polynucleotide SEQ ID NO: 373 encoding the heavy chain variable sequence of SEQ ID NO: 173; the polynucleotide SEQ ID NO: 374 encoding the heavy chain sequence of SEQ ID NO: 174; polynucleotides encoding the complementarity-determining regions (SEQ ID NO: 375; SEQ ID NO: 376; and SEQ ID NO: 377) of the light chain variable sequence of SEQ ID NO: 171 or the light chain sequence of SEQ ID NO: 172; and polynucleotides encoding the complementarity-determining regions (SEQ ID NO: 378; SEQ ID NO: 379; and SEQ ID NO: 380) of the heavy chain variable sequence of SEQ ID NO: 173 or the heavy chain sequence of SEQ ID NO: 174.

In a preferred optional embodiment of the invention, polynucleotides of the invention comprise, or alternatively consist of, polynucleotides encoding Fab (fragment antigen binding) fragments for treatment or prevention of pain and pain associated conditions having binding specificity for NGF. With respect to antibody Ab18, the polynucleotides encoding the full length Ab18 antibody comprise, or alternatively consist of, the polynucleotide SEQ ID NO: 372 encoding the light chain sequence of SEQ ID NO: 172 and the polynucleotide SEQ ID NO: 374 encoding the heavy chain sequence of SEQ ID NO: 174.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab18 following expression of the full-length polynucleotides in a suitable host. In another embodiment of the invention, anti-NGF antibodies such as Ab18 or Fab fragments thereof may be produced via expression of Ab18 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab19

The invention is further optionally directed to the use of polynucleotides set forth below to produce antibody Ab19 polypeptides having binding specificity to NGF, which inhibit the association of NGF with TrkA and the association of NGF with p75. in methods of treating pain in an individual comprising administering to said individual antibody Ab19 polypeptides. The invention is further optionally directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 181:

(SEQ ID NO: 381)
GCCGCCGTGCTGACCCAGACTCCATCTCCCGTGTCTGCAGCTGTGGG

AGGCACAGTCAGCATCAGTTGCCAGTCCAGTCAGAATGTTTATAAGAACA

ACTATTTATCCTGGTATCAGCAGAAACCAGGGCAGCCTCCCAAGCTCCTG

ATCTACAAGGCTTCCACTCTGGCATCTGGGGTCCCATCGCGGTTCAAAGG

CAGTGGATCTGGGACAGATTTCACTCTCACCATCAGCGACGTGCAGTGTG

ACGCTGCTGCCACTTACTACTGTGCAGGCGGTTATAGTAGTAGTAGTGAT

AATGCTTTCGGCGGAGGGACCGAGGTGGTGGTCAAACGT.

In one optional embodiment of the invention, polynucleotides of the invention comprise, or alternatively consist of, the following polynucleotide sequence encoding the light chain polypeptide sequence of SEQ ID NO: 182:

(SEQ ID NO: 382)
GCCGCCGTGCTGACCCAGACTCCATCTCCCGTGTCTGCAGCTGTGGG

AGGCACAGTCAGCATCAGTTGCCAGTCCAGTCAGAATGTTTATAAGAACA

ACTATTTATCCTGGTATCAGCAGAAACCAGGGCAGCCTCCCAAGCTCCTG

ATCTACAAGGCTTCCACTCTGGCATCTGGGGTCCCATCGCGGTTCAAAGG

CAGTGGATCTGGGACAGATTTCACTCTCACCATCAGCGACGTGCAGTGTG

ACGCTGCTGCCACTTACTACTGTGCAGGCGGTTATAGTAGTAGTAGTGAT

AATGCTTTCGGCGGAGGGACCGAGGTGGTGGTCAAACGTACGGTAGCGGC

CCCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTAG.

In another optional embodiment of the invention, polynucleotides of the invention comprise, or alternatively consist of, the following polynucleotide sequence encoding the variable heavy chain polypeptide sequence of SEQ ID NO: 183:

(SEQ ID NO: 383)
CAGTCGGTGGAGGCGTCCGGGGGTCGTCTGGTCATGCCTGGAGGATC

CCTGACACTCACCTGCACAGCCTCTGGATTCTCCCTCAGTACCTACTGGA

TGTCCTGGGTCCGCCAGGCTCCAGGGAAGGGGCTGGAATGGATCGGAGAC

ATTTATTTTAGTAATGAGGAAACAAACTACGCGACCTGGGCGAAAGGCCG

ATTTACCATCTCCAAAACCTCGACCACGGTGGATCTGAATGTCATCAGTC

CGACAACCGAGGACACGGCCACCTATTTCTGTGCAAGAGGTTCTCCTGAT

GTTGAGATTGCTATAGATATGTGGGGCCAGGGCACCCTCGTCACCGTCTC

GAGC.

In one optional embodiment of the invention, polynucleotides of the invention comprise, or alternatively consist of, the following polynucleotide sequence encoding the heavy chain polypeptide sequence of SEQ ID NO: 184:

(SEQ ID NO: 384)
CAGTCGGTGGAGGCGTCCGGGGGTCGTCTGGTCATGCCTGGAGGATC

CCTGACACTCACCTGCACAGCCTCTGGATTCTCCCTCAGTACCTACTGGA

TGTCCTGGGTCCGCCAGGCTCCAGGGAAGGGGCTGGAATGGATCGGAGAC

ATTTATTTTAGTAATGAGGAAACAAACTACGCGACCTGGGCGAAAGGCCG

ATTTACCATCTCCAAAACCTCGACCACGGTGGATCTGAATGTCATCAGTC

CGACAACCGAGGACACGGCCACCTATTTCTGTGCAAGAGGTTCTCCTGAT

GTTGAGATTGCTATAGATATGTGGGGCCAGGGCACCCTCGTCACCGTCTC

GAGCGCCTCCACCAAGGGCCCATCGGTCTTCCCCCTGGCACCCTCCTCCA

AGAGCACCTCTGGGGGCACAGCGGCCCTGGGCTGCCTGGTCAAGGACTAC

TTCCCCGAACCGGTGACGGTGTCGTGGAACTCAGGCGCCCTGACCAGCGG

CGTGCACACCTTCCCGGCTGTCCTACAGTCCTCAGGACTCTACTCCCTCA

GCAGCGTGGTGACCGTGCCCTCCAGCAGCTTGGGCACCCAGACCTACATC

TGCAACGTGAATCACAAGCCCAGCAACACCAAGGTGGACAAGAGAGTTGA

GCCCAAATCTTGTGACAAAACTCACACATGCCCACCGTGCCCAGCACCTG

AACTCCTGGGGGACCGTCAGTCTTCCTCTTCCCCCCAAAACCCAAGGAC

ACCCTCATGATCTCCCGGACCCCTGAGGTCACATGCGTGGTGGTGGACGT

GAGCCACGAAGACCCTGAGGTCAAGTTCAACTGGTACGTGGACGGCGTGG

AGGTGCATAATGCCAAGACAAAGCCGCGGGAGGAGCAGTACGCCAGCACG

TACCGTGTGGTCAGCGTCCTCACCGTCCTGCACCAGGACTGGCTGAATGG

CAAGGAGTACAAGTGCAAGGTCTCCAACAAAGCCCTCCCAGCCCCCATCG

AGAAAACCATCTCCAAAGCCAAAGGGCAGCCCCGAGAACCACAGGTGTAC

ACCCTGCCCCCATCCCGGGAGGAGATGACCAAGAACCAGGTCAGCCTGAC

CTGCCTGGTCAAAGGCTTCTATCCCAGCGACATCGCCGTGGAGTGGGAGA

GCAATGGGCAGCCGGAGAACAACTACAAGACCACGCCTCCCGTGCTGGAC

TCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGC

ACAACCACTACACGCAGAAGAGCCTCTCCCTGTCTCCGGGTAAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 385; SEQ ID NO: 386; and SEQ ID NO: 387 which correspond to polynucleotides encoding the complementarity-determining regions (CDRs, or hypervariable regions) of the light chain variable sequence of SEQ ID NO: 181 or the light chain sequence of SEQ ID NO: 182.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 388; SEQ ID NO: 389; and SEQ ID NO: 390 which correspond to polynucleotides encoding the complementarity-determining regions (CDRs, or hypervariable regions) of the heavy chain variable sequence of SEQ ID NO: 183 or the heavy chain sequence of SEQ ID NO: 184.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 381 encoding the light chain variable sequence of SEQ ID NO: 181; the polynucleotide SEQ ID NO: 382 encoding the light chain sequence of SEQ ID NO: 182; the polynucleotide SEQ ID NO: 383 encoding the heavy chain variable sequence of SEQ ID NO: 183; the polynucleotide SEQ ID NO: 384 encoding the heavy chain sequence of SEQ ID NO: 184; polynucleotides encoding the complementarity-determining regions (SEQ ID NO: 385; SEQ ID NO: 386; and SEQ ID NO: 387) of the light chain variable sequence of SEQ ID NO: 181 or the light chain sequence of SEQ ID NO: 182; and polynucleotides encoding the complementarity-determining regions (SEQ ID NO: 388; SEQ ID NO: 389; and SEQ ID NO: 390) of the heavy chain variable sequence of SEQ ID NO: 183 or the heavy chain sequence of SEQ ID NO: 184.

In a preferred optional embodiment of the invention, polynucleotides of the invention comprise, or alternatively consist of, polynucleotides encoding Fab (fragment antigen binding) fragments having binding specificity for NGF. With respect to antibody Ab19, the polynucleotides encoding the full length Ab19 antibody comprise, or alternatively consist of, the polynucleotide SEQ ID NO: 382 encoding the light chain sequence of SEQ ID NO: 182 and the polynucleotide SEQ ID NO: 384 encoding the heavy chain sequence of SEQ ID NO: 184.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one optional embodiment of the invention described herein (infra), Fab fragments may be produced by enzymatic digestion (e.g., papain) of Ab19 following expression of the full-length polynucleotides in a suitable host. In another embodiment of the invention, anti-NGF antibodies such as Ab19 or Fab fragments thereof may be produced via expression of Ab19 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab20

The invention is further optionally directed to the use of polynucleotides set forth below to produce antibody Ab20 polypeptides for treatment or prevention of pain and pain associated conditions having binding specificity to NGF, which inhibits the association of NGF with TrkA and the association of NGF with p75, in methods of treating pain in an individual comprising administering to said individual antibody Ab20 polypeptides. The invention is further directed to polynucleotides encoding antibody polypeptides having binding specificity to NGF. In one optional embodiment of the invention, polynucleotides of the invention comprise, or alternatively consist of, the following polynucleotide sequence encoding the variable light chain polypeptide sequence of SEQ ID NO: 191:

(SEQ ID NO: 391)
GACATCCAGATGACCCAGTCTCCATCCTCCCTGTCTGCATCTGTAGGA

GACAGAGTCACCATCACTTGCCAGTCCAGTCAGAATGTTTATAAGAACAA

CTACTTATCCTGGTATCAGCAGAAACCAGGGAAAGTCCCTAAGCTCCTGA

TCTATAAGGCATCCACTCTGGCATCTGGGGTCCCATCTCGTTTCAGTGGC

AGTGGATCTGGGACAGATTTCACTCTCACCATCAGCAGCCTGCAGCCTGA

AGATGTTGCAACTTATTACTGTGCAGGCGGTTATACCAGTAGTAGTGATA

ATGCTTTCGGCGGAGGAACCAAGGTGGAAATCAAACGT.

In one optional embodiment of the invention, polynucleotides of the invention comprise, or alternatively consist of, the following polynucleotide sequence encoding the light chain polypeptide sequence of SEQ ID NO: 192:

(SEQ ID NO: 392)
GACATCCAGATGACCCAGTCTCCATCCTCCCTGTCTGCATCTGTAGGA

GACAGAGTCACCATCACTTGCCAGTCCAGTCAGAATGTTTATAAGAACAA

CTACTTATCCTGGTATCAGCAGAAACCAGGGAAAGTCCCTAAGCTCCTGA

TCTATAAGGCATCCACTCTGGCATCTGGGGTCCCATCTCGTTTCAGTGGC

AGTGGATCTGGGACAGATTTCACTCTCACCATCAGCAGCCTGCAGCCTGA

AGATGTTGCAACTTATTACTGTGCAGGCGGTTATACCAGTAGTAGTGATA

ATGCTTTCGGCGGAGGAACCAAGGTGGAAATCAAACGTACGGTAGCGGCC

CCATCTGTCTTCATCTTCCCGCCATCTGATGAGCAGTTGAAATCTGGAAC

TGCCTCTGTTGTGTGCCTGCTGAATAACTTCTATCCCAGAGAGGCCAAAG

TACAGTGGAAGGTGGATAACGCCCTCCAATCGGGTAACTCCCAGGAGAGT

GTCACAGAGCAGGACAGCAAGGACAGCACCTACAGCCTCAGCAGCACCCT

GACGCTGAGCAAAGCAGACTACGAGAAACACAAAGTCTACGCCTGCGAAG

TCACCCATCAGGGCCTGAGCTCGCCCGTCACAAAGAGCTTCAACAGGGGA

GAGTGTTAG.

In another optional embodiment of the invention, polynucleotides of the invention comprise, or alternatively consist of, the following polynucleotide sequence encoding the variable heavy chain polypeptide sequence of SEQ ID NO: 193:

(SEQ ID NO: 393)
GAGGTGCAGCTGGTGGAGTCTGGGGGAGGCTTGGTCCAGCCTGGGGG

GTCCCTGAGACTCTCCTGTGCAGCCTCTGGATTCACCGTCAGTACCTACT

GGATGAGCTGGGTCCGTCAGGCTCCAGGGAAGGGGCTGGAGTGGGTCGGA

GACATTTACTTTAGTAATGAAGAAACAAACTACGCGACCAGCGCGAAAGG

CCGATTCACCATCTCCAGAGACAATTCCAAGAACACCCTGTATCTTCAAA

TGAACAGCCTGAGAGCTGAGGACACTGCTGTGTATTACTGTGCTAGAGGT

TCTCCTGATGTTGAGATTGCTATAGATATGTGGGGCCAAGGGACCCTCGT

CACCGTCTCGAGC.

In one optional embodiment of the invention, polynucleotides of the invention comprise, or alternatively consist of, the following polynucleotide sequence encoding the heavy chain polypeptide sequence of SEQ ID NO: 194:

(SEQ ID NO: 394)
GAGGTGCAGCTGGTGGAGTCTGGGGGAGGCTTGGTCCAGCCTGGGGG

GTCCCTGAGACTCTCCTGTGCAGCCTCTGGATTCACCGTCAGTACCTACT

GGATGAGCTGGGTCCGTCAGGCTCCAGGGAAGGGGCTGGAGTGGGTCGGA

GACATTTACTTTAGTAATGAAGAAACAAACTACGCGACCAGCGCGAAAGG

CCGATTCACCATCTCCAGAGACAATTCCAAGAACACCCTGTATCTTCAAA

TGAACAGCCTGAGAGCTGAGGACACTGCTGTGTATTACTGTGCTAGAGGT

TCTCCTGATGTTGAGATTGCTATAGATATGTGGGGCCAAGGGACCCTCGT

CACCGTCTCGAGCGCCTCCACCAAGGGCCCATCGGTCTTCCCCCTGGCAC

CCTCCTCCAAGAGCACCTCTGGGGGCACAGCGGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCTTGGGCACCCAG

ACCTACATCTGCAACGTGAATCACAAGCCCAGCAACACCAAGGTGGACAA

GAGAGTTGAGCCCAAATCTTGTGACAAAACTCACACATGCCCACCGTGCC

CAGCACCTGAACTCCTGGGGGGACCGTCAGTCTTCCTCTTCCCCCCAAAA

CCCAAGGACACCCTCATGATCTCCCGGACCCCTGAGGTCACATGCGTGGT

GGTGGACGTGAGCCACGAAGACCCTGAGGTCAAGTTCAACTGGTACGTGG

ACGGCGTGGAGGTGCATAATGCCAAGACAAAGCCGCGGGAGGAGCAGTAC

GCCAGCACGTACCGTGTGGTCAGCGTCCTCACCGTCCTGCACCAGGACTG

GCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCA

CAGGTGTACACCCTGCCCCCATCCCGGGAGGAGATGACCAAGAACCAGGT

CAGCCTGACCTGCCTGGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTACAGCAAGCTCACCGTGGA

CAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGT

AAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 395; SEQ ID NO: 396; and SEQ ID NO: 397 which correspond to polynucleotides encoding the complementarity-determining regions (CDRs, or hypervariable regions) of the light chain variable sequence of SEQ ID NO: 191 or the light chain sequence of SEQ ID NO: 192.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 398; SEQ ID NO: 399; and SEQ ID NO: 400 which correspond to polynucleotides encoding the complementarity-determining regions (CDRs, or hypervariable regions) of the heavy chain variable sequence of SEQ ID NO: 193 or the heavy chain sequence of SEQ ID NO: 194.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 391 encoding the light chain variable sequence of SEQ ID NO: 191; the polynucleotide SEQ ID NO: 392 encoding the light chain sequence of SEQ ID NO: 192; the polynucleotide SEQ ID NO: 393 encoding the heavy chain variable sequence of SEQ ID NO: 193; the polynucleotide SEQ ID NO: 394 encoding the heavy chain sequence of SEQ ID NO: 194; polynucleotides encoding the complementarity-determining regions (SEQ ID NO: 395; SEQ ID NO: 396; and SEQ ID NO: 397) of the light chain variable sequence of SEQ ID NO: 191 or the light chain sequence of SEQ ID NO: 192; and polynucleotides encoding the complementarity-determining regions (SEQ ID NO: 398; SEQ ID NO: 399; and SEQ ID NO: 400) of the heavy chain variable sequence of SEQ ID NO: 193 or the heavy chain sequence of SEQ ID NO: 194.

In a preferred optional embodiment of the invention, polynucleotides of the invention comprise, or alternatively consist of, polynucleotides encoding Fab (fragment antigen binding) fragments having binding specificity for NGF. With respect to antibody Ab20, the polynucleotides encoding the full length Ab20 antibody comprise, or alternatively consist of, the polynucleotide SEQ ID NO: 392 encoding the light chain sequence of SEQ ID NO: 192 and the polynucleotide SEQ ID NO: 394 encoding the heavy chain sequence of SEQ ID NO: 194.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced by enzymatic digestion (e.g., papain) of Ab20 following expression of the full-length polynucleotides in a suitable host. In another embodiment of the invention, anti-NGF antibodies such as Ab20 or Fab fragments thereof may be produced via expression of Ab20 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Ab21

The invention is further optionally directed to the use of polynucleotides set forth below to produce antibody Ab21 polypeptides having binding specificity to NGF, which inhibit the association of NGF with TrkA and the association of NGF with p75 in methods of treating pain in an individual comprising administering to said individual antibody Ab21 polypeptides. The invention is further optionally directed to polynucleotides encoding antibody polypeptides for treatment or prevention of pain and pain associated conditions having binding specificity to NGF. In one embodiment of the invention, polynucleotides of the invention comprise, or alternatively consist of, the following polynucleotide sequence encoding the variable light chain polypeptide sequence of SEQ ID NO: 251:

(SEQ ID NO: 251)
GACATCCAGATGACCCAGTCTCCTTCCACCCTGTCTGCATCTGTAGGA

GACAGAGTCACCATCACTTGCCAGGCCAGTCAGAGCATTTACAGCAATCT

TGCCTGGTATCAGCAGAAACCAGGAAAAGCCCCTAAGCTCCTGATCTATG

ATGCATCCACTCTGGAATCTGGAGTCCCATCAAGGTTCAGCGGCAGTGGA

TCTGGGACAGAGTACACTCTCACCATCAGCAGCCTGCAGCCTGATGATTT

TGCAACTTACTACTGCCAACAGGGTTTTACTGTTAGTGATATTGATAATG

CTTTCGGCGGAGGAACCAAGGTGGAAATCAAACGT.

In one embodiment of the invention, polynucleotides of the invention optionally comprise, or alternatively consist of, the following polynucleotide sequence encoding the light chain polypeptide sequence of SEQ ID NO: 401:

(SEQ ID NO: 403)
GACATCCAGATGACCCAGTCTCCTTCCACCCTGTCTGCATCTGTAGGA

GACAGAGTCACCATCACTTGCCAGGCCAGTCAGAGCATTTACAGCAATCT

TGCCTGGTATCAGCAGAAACCAGGAAAAGCCCCTAAGCTCCTGATCTATG

ATGCATCCACTCTGGAATCTGGAGTCCCATCAAGGTTCAGCGGCAGTGGA

TCTGGGACAGAGTACACTCTCACCATCAGCAGCCTGCAGCCTGATGATTT

TGCAACTTACTACTGCCAACAGGGTTTTACTGTTAGTGATATTGATAATG

CTTTCGGCGGAGGAACCAAGGTGGAAATCAAACGTACGGTAGCGGCCCCA

TCTGTCTTCATCTTCCCGCCATCTGATGAGCAGTTGAAATCTGGAACTGC

CTCTGTTGTGTGCCTGCTGAATAACTTCTATCCCAGAGAGGCCAAAGTAC

AGTGGAAGGTGGATAACGCCCTCCAATCGGGTAACTCCCAGGAGAGTGTC

ACAGAGCAGGACAGCAAGGACAGCACCTACAGCCTCAGCAGCACCCTGAC

GCTGAGCAAAGCAGACTACGAGAAACACAAAGTCTACGCCTGCGAAGTCA

CCCATCAGGGCCTGAGCTCGCCCGTCACAAAGAGCTTCAACAGGGGAGAG

TGTTAG.

In another optional embodiment of the invention, polynucleotides of the invention comprise, or alternatively consist of, the following polynucleotide sequence encoding the variable heavy chain polypeptide sequence of SEQ ID NO: 253:

(SEQ ID NO: 253)
GAGGTGCAGCTGGTGGAGTCTGGGGGAGGCTTGGTCCAGCCTGGGGG

GTCCCTGAGACTCTCCTGTGCAGCCTCTGGATTCACCGTCAGTAACTATG

CAGTGGGCTGGGTCCGTCAGGCTCCAGGGAAGGGGCTGGAGTGGGTCGGA

ATCATTGGTCGTAATGGTAACACATGGTACGCGAGCTCTGCAAGAGGCCG

ATTCACCATCTCCAGAGACAATTCCAAGAACACCCTGTATCTTCAAATGA

ACAGCCTGAGAGCTGAGGACACTGCTGTGTATTACTGTGCTAGAGGATAT

GGCCGTAGTGTTGCTTATTACGTCTTTAACATCTGGGGCCCAGGGACCCT

CGTCACCGTCTCGAGC.

In one optional embodiment of the invention, polynucleotides of the invention comprise, or alternatively consist of, the following polynucleotide sequence encoding the heavy chain polypeptide sequence of SEQ ID NO: 402:

(SEQ ID NO: 404)
GAGGTGCAGCTGGTGGAGTCTGGGGGAGGCTTGGTCCAGCCTGGGGG

GTCCCTGAGACTCTCCTGTGCAGCCTCTGGATTCACCGTCAGTAACTATG

CAGTGGGCTGGGTCCGTCAGGCTCCAGGGAAGGGGCTGGAGTGGGTCGGA

ATCATTGGTCGTAATGGTAACACATGGTACGCGAGCTCTGCAAGAGGCCG

ATTCACCATCTCCAGAGACAATTCCAAGAACACCCTGTATCTTCAAATGA

ACAGCCTGAGAGCTGAGGACACTGCTGTGTATTACTGTGCTAGAGGATAT

GGCCGTAGTGTTGCTTACTACGTCTTTAACATCTGGGGCCCAGGGACCCT

CGTCACCGTCTCGAGCGCCTCCACCAAGGGCCCATCGGTCTTCCCCCTGG

CACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGC

CCTGACCAGCGGCGTGCACACCTTCCCGGCTGTCCTACAGTCCTCAGGAC

TCTACTCCCTCAGCAGCGTGGTGACCGTGCCCTCCAGCAGCTTGGGCACC

CAGACCTACATCTGCAACGTGAATCACAAGCCCAGCAACACCAAGGTGGA

CGCGAGAGTTGAGCCCAAATCTTGTGACAAAACTCACACATGCCCACCGT

GCCCAGCACCTGAACTCCTGGGGGACCGTCAGTCTTCCTCTTCCCCCCA

AAACCCAAGGACACCCTCATGATCTCCCGGACCCCTGAGGTCACATGCGT

GGTGGTGGACGTGAGCCACGAAGACCCTGAGGTCAAGTTCAACTGGTACG

TGGACGGCGTGGAGGTGCATAATGCCAAGACAAAGCCGCGGGAGGAGCAG

TACGCCAGCACGTACCGTGTGGTCAGCGTCCTCACCGTCCTGCACCAGGA

CTGGCTGAATGGCAAGGAGTACAAGTGCAAGGTCTCCAACAAAGCCCTCC

CAGCCCCCATCGAGAAAACCATCTCCAAAGCCAAAGGGCAGCCCCGAGAA

CCACAGGTGTACACCCTGCCCCCATCCCGGGAGGAGATGACCAAGAACCA

GGTCAGCCTGACCTGCCTGGTCAAAGGCTTCTATCCCAGCGACATCGCCG

TGGAGTGGGAGAGCAATGGGCAGCCGGAGAACAACTACAAGACCACGCCT

CCCGTGCTGGACTCCGACGGCTCCTTCTTCCTCTACAGCAAGCTCACCGT

GGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCG

GGTAAATGA.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 255; SEQ ID NO: 256; and SEQ ID NO: 257 which correspond to polynucleotides encoding the complementarity-determining regions (CDRs, or hypervariable regions) of the light chain variable sequence of SEQ ID NO: 51 or the light chain sequence of SEQ ID NO: 401.

In a further optional embodiment of the invention, polynucleotides encoding antibody fragments for treatment or prevention of pain and pain associated conditions having binding specificity to NGF comprise, or alternatively consist of, one or more of the polynucleotide sequences of SEQ ID NO: 258; SEQ ID NO: 259; and SEQ ID NO: 260 which correspond to polynucleotides encoding the complementarity-determining regions (CDRs, or hypervariable regions) of the heavy chain variable sequence of SEQ ID NO: 53 or the heavy chain sequence of SEQ ID NO: 402.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 251 encoding the light chain variable sequence of SEQ ID NO: 51; the polynucleotide SEQ ID NO: 403 encoding the light chain sequence of SEQ ID NO: 401; the polynucleotide SEQ ID NO: 253 encoding the heavy chain variable sequence of SEQ ID NO: 53; the polynucleotide SEQ ID NO: 404 encoding the heavy chain sequence of SEQ ID NO: 402; polynucleotides encoding the complementarity-determining regions (SEQ ID NO: 255; SEQ ID NO: 256; and SEQ ID NO: 257) of the light chain variable sequence of SEQ ID NO: 51 or the light chain sequence of SEQ ID NO: 401; and polynucleotides encoding the complementarity-determining regions (SEQ ID NO: 258; SEQ ID NO: 259; and SEQ ID NO: 260) of the heavy chain variable sequence of SEQ ID NO: 53 or the heavy chain sequence of SEQ ID NO: 402.

In a preferred optional embodiment of the invention, polynucleotides of the invention comprise, or alternatively consist of, polynucleotides encoding Fab (fragment antigen binding) fragments having binding specificity for NGF. With respect to antibody Ab21, the polynucleotides encoding the full length Ab21 antibody comprise, or alternatively consist of, the polynucleotide SEQ ID NO: 403 encoding the light chain sequence of SEQ ID NO: 401 and the polynucleotide SEQ ID NO: 404 encoding the heavy chain sequence of SEQ ID NO: 402.

Another optional embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one optional embodiment of the invention described herein (infra), Fab fragments may be produced by enzymatic digestion (e.g., papain) of Ab21 following expression of the full-length polynucleotides in a suitable host. In another embodiment of the invention, anti-NGF antibodies such as Ab21 or Fab fragments thereof may be produced via expression of Ab21 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

Antibody Fragment Fab2

The invention is further optionally directed to the use of polynucleotides set forth below to produce antibody fragment Fab2 polypeptides that inhibit the association of NGF with TrkA and p75 for treatment or prevention of pain and pain associated conditions having binding specificity to NGF in methods of treating pain in an individual comprising administering to said individual antibody Ab1 polypeptides. The invention is further directed to polynucleotides encoding antibody fragment polypeptides for treatment or prevention of pain and pain associated conditions having binding specificity to NGF. In one embodiment of the invention, Fab polynucleotides of the invention comprise, or alternatively consist of, the following polynucleotide sequence encoding the light chain polypeptide sequence of SEQ ID NO: 407:

(SEQ ID NO: 409)
GACATCCAGATGACCCAGTCTCCTTCCACCCTGTCTGCATCTGTAGGA

GACAGAGTCACCATCACTTGCCAGGCCAGTCAGAGCATTTACAGCAATCT

TGCCTGGTATCAGCAGAAACCAGGAAAAGCCCCTAAGCTCCTGATCTATG

ATGCATCCACTCTGGAATCTGGAGTCCCATCAAGGTTCAGCGGCAGTGGA

TCTGGGACAGAGTACACTCTCACCATCAGCAGCCTGCAGCCTGATGATTT

TGCAACTTACTACTGCCAACAGGGTTTTACTGTTAGTGATATTGATAATG

CTTTCGGCGGAGGAACCAAGGTGGAAATCAAACGTACGGTAGCGGCCCCA

TCTGTCTTCATCTTCCCGCCATCTGATGAGCAGTTGAAATCTGGAACTGC

CTCTGTTGTGTGCCTGCTGAATAACTTCTATCCCAGAGAGGCCAAAGTAC

AGTGGAAGGTGGATAACGCCCTCCAATCGGGTAACTCCCAGGAGAGTGTC

ACAGAGCAGGACAGCAAGGACAGCACCTACAGCCTCAGCAGCACCCTGAC

GCTGAGCAAAGCAGACTACGAGAAACACAAAGTCTACGCCTGCGAAGTCA

CCCATCAGGGCCTGAGCTCGCCCGTCACAAAGAGCTTCAACAGGGGAGAG

TGTTAG.

In another optional embodiment of the invention, polynucleotides of the invention comprise, or alternatively consist of, the following polynucleotide sequence encoding the heavy chain polypeptide sequence of SEQ ID NO: 408:

(SEQ ID NO: 410)
GAGGTGCAGCTGGTGGAGTCTGGGGGAGGCTTGGTCCAGCCTGGGGG

GTCCCTGAGACTCTCCTGTGCAGCCTCTGGATTCACCGTCAGTAACTATG

CAGTGGGCTGGGTCCGTCAGGCTCCAGGGAAGGGGCTGGAGTGGGTCGGA

ATCATTGGTCGTAATGGTAACACATGGTACGCGAGCTCTGCAAGAGGCCG

ATTCACCATCTCCAGAGACAATTCCAAGAACACCCTGTATCTTCAAATGA

ACAGCCTGAGAGCTGAGGACACTGCTGTGTATTACTGTGCTAGAGGATAT

GGCCGTAGTGTTGCTTACTACGTCTTTAACATCTGGGGCCCAGGGACCCT

CGTCACCGTCTCGAGCGCCTCCACCAAGGGCCCATCGGTCTTCCCCCTGG

CACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGC

CCTGACCAGCGGCGTGCACACCTTCCCGGCTGTCCTACAGTCCTCAGGAC

TCTACTCCCTCAGCAGCGTGGTGACCGTGCCCTCCAGCAGCTTGGGCACC

CAGACCTACATCTGCAACGTGAATCACAAGCCCAGCAACACCAAGGTGGA

CGCGAGAGTTGAGCCCAAATCTTGTGACAAAACTCACTAG.

In a further optional embodiment of the invention, polynucleotides encoding Fab antibody fragments having binding specificity to NGF comprise one or more of the polynucleotide sequences of SEQ ID NO: 255; SEQ ID NO: 256; and SEQ ID NO: 257 which correspond to polynucleotides encoding the complementarity-determining regions (CDRs, or hypervariable regions) of the light chain variable sequence of SEQ ID NO: 51 or the light chain sequence of SEQ ID NO: 409.

In a further optional embodiment of the invention, polynucleotides encoding Fab antibody fragments for treatment or prevention of pain and pain associated conditions having binding specificity to NGF comprise one or more of the polynucleotide sequences of SEQ ID NO: 258; SEQ ID NO: 259; and SEQ ID NO: 260 which correspond to polynucleotides encoding the complementarity-determining regions (CDRs, or hypervariable regions) of the heavy chain variable sequence of SEQ ID NO: 53 or the heavy chain sequence of SEQ ID NO: 410.

The invention also optionally contemplates polynucleotide sequences including one or more of the polynucleotide sequences encoding antibody fragments for treatment or prevention of pain and pain associated conditions described herein. In one embodiment of the invention, polynucleotides encoding antibody fragments for treatment or prevention of pain and pain associated conditions having binding specificity to NGF comprise, or alternatively consist of, one, two, three or more, including all of the following polynucleotides encoding antibody fragments: the polynucleotide SEQ ID NO: 251 encoding the light chain variable sequence of SEQ ID NO: 51; the polynucleotide SEQ ID NO: 409 encoding the light chain sequence of SEQ ID NO: 407; the polynucleotide SEQ ID NO: 253 encoding the heavy chain variable sequence of SEQ ID NO: 53; the polynucleotide SEQ ID NO: 410 encoding the heavy chain sequence of SEQ ID NO: 408; polynucleotides encoding the complementarity-determining regions (SEQ ID NO: 255; SEQ ID NO: 256; and SEQ ID NO: 257) of the light chain variable sequence of SEQ ID NO: 51 or the light chain sequence of SEQ ID NO: 407; and polynucleotides encoding the complementarity-determining regions (SEQ ID NO: 258; SEQ ID NO: 259; and SEQ ID NO: 260) of the heavy chain variable sequence of SEQ ID NO: 53 or the heavy chain sequence of SEQ ID NO: 408.

In a preferred optional embodiment of the invention, polynucleotides of the invention comprise, or alternatively consist of, polynucleotides encoding Fab (fragment antigen binding) fragments having binding specificity for NGF. With respect to antibody fragment Fab2, the polynucleotides encoding the Fab fragment include the polynucleotide SEQ ID NO: 409 encoding the light chain sequence of SEQ ID NO: 407 and the polynucleotide SEQ ID NO: 410 encoding the heavy chain sequence of SEQ ID NO: 408.

Another embodiment of the invention contemplates these polynucleotides incorporated into an expression vector for expression in mammalian cells such as CHO, NSO, HEK-293, or in fungal, insect, plant or microbial systems such as yeast cells such as the yeast *Pichia*. Suitable *Pichia* species include, but are not limited to, *Pichia pastoris*. In one embodiment of the invention described herein (infra), Fab fragments may be produced via expression of Fab2 polynucleotides in mammalian cells such as CHO, NSO or HEK 293 cells, fungal, insect, plant or microbial systems such as yeast cells (for example diploid yeast such as diploid *Pichia*) and other yeast strains. Suitable *Pichia* species include, but are not limited to, *Pichia pastoris*.

In one embodiment, the invention is optionally directed to an isolated polynucleotide comprising a polynucleotide encoding an anti-NGF $V_H$ antibody amino acid sequence selected from SEQ ID NO: 3, 13, 23, 33, 43, 53, 63, 73, 83, 93, 103, 113, 123, 133, 143, 153, 163, 173, 183, 193, or 402, or encoding a variant thereof wherein at least one framework residue (FR residue) has been substituted with an amino acid present at the corresponding position in a rabbit anti-NGF antibody $V_H$ polypeptide or a conservative amino acid substitution.

In another optional embodiment, the invention is directed to an isolated polynucleotide comprising the polynucleotide sequence encoding an anti-NGF $V_L$ antibody amino acid sequence of 1, 11, 21, 31, 41, 51, 61, 71, 81, 91, 101, 111, 121, 131, 141, 151, 161, 171, 181, 191, or 401, or encoding a variant thereof wherein at least one framework residue (FR residue) has been substituted with an amino acid present at the corresponding position in a rabbit anti-NGF antibody $V_L$ polypeptide or a conservative amino acid substitution.

In yet another optional embodiment, the invention is directed to one or more heterologous polynucleotides comprising a sequence encoding the polypeptides contained in SEQ ID NO:1 and SEQ ID NO:3; SEQ ID NO:11 and SEQ ID NO:13; SEQ ID NO:21 and SEQ ID NO:23; SEQ ID NO:31 and SEQ ID NO:33; SEQ ID NO:411 and SEQ ID NO:43; SEQ ID NO:51 and SEQ ID NO:53, SEQ ID NO:61 and SEQ ID NO:63; SEQ ID NO:71 and SEQ ID NO:73; SEQ ID NO:81 and SEQ ID NO:83; SEQ ID NO:91 and SEQ ID NO:93; SEQ ID NO:101 and SEQ ID NO:103; SEQ ID NO:111 and SEQ ID NO:113; SEQ ID NO:121 and SEQ ID NO:123; SEQ ID NO:131 and SEQ ID NO:133; SEQ ID NO:141 and SEQ ID NO:143; SEQ ID NO:151 and SEQ ID NO:153; SEQ ID NO:161 and SEQ ID NO:163; SEQ ID NO:171 and SEQ ID NO:173; SEQ ID NO:181 and SEQ ID NO:183; SEQ ID NO:191 and SEQ ID NO:193; or SEQ ID NO:401 and SEQ ID NO:403.

In another embodiment, the invention is optionally directed to an isolated polynucleotide that expresses a polypeptide containing at least one CDR polypeptide derived from an anti-NGF antibody wherein said expressed polypeptide alone specifically binds NGF or specifically binds NGF when expressed in association with another polynucleotide sequence that expresses a polypeptide containing at least one CDR polypeptide derived from an anti-NGF antibody for treatment or prevention of pain and pain associated conditions wherein said at least one CDR is selected from those contained in the $V_L$ or $V_H$ polypeptides of SEQ ID NO: 1, 3, 11, 13, 21, 23, 31, 33, 41, 43, 51, 53, 61, 63, 71, 73, 81, 83, 91, 93, 101, 103, 111, 113, 121, 123, 131, 133, 141, 143, 151, 153, 161, 163, 171, 173, 181, 183, 191, 193, 401 or SEQ ID NO:403.

Host cells and vectors comprising said polynucleotides are also contemplated.

The invention further optionally contemplates vectors comprising the polynucleotide sequences encoding the variable heavy and light chain polypeptide sequences, as well as the individual complementarity-determining regions (CDRs, or hypervariable regions), as set forth herein, as well as host cells comprising said vector sequences. In one embodiment of the invention, the host cell is a yeast cell. In another embodiment of the invention, the yeast host cell belongs to the genus *Pichia*.

Anti-NGF Activity

The anti-NGF activity of the anti-NGF antibodies of the present invention, and fragments thereof having binding specificity to NGF, preferably which inhibit the association of NGF with TrkA without appreciably inhibiting the association of NGF with p75, may also be described by their strength of binding or their affinity for NGF. In one embodiment of the invention, the anti-NGF antibodies of the present invention, and fragments thereof having binding specificity to NGF, bind to NGF with a dissociation constant ($K_D$) of less than or equal to $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M. Preferably, the anti-NGF antibodies and fragments thereof bind NGF with a dissociation constant of less than or equal to $5\times10^{-10}$ M. In another embodiment of the invention, the anti-NGF antibodies of the present invention, and fragments thereof having binding specificity to NGF, bind to a linear or conformational NGF epitope.

In another embodiment of the invention, the anti-NGF activity of the anti-NGF antibodies of the present invention, and fragments thereof, which inhibit the association of NGF with TrkA without appreciably inhibiting the association of NGF with p75, and further having binding specificity to NGF, bind to NGF with an off-rate of less than or equal to $10^{-4}$ S$^{-1}$, $5\times10^{-5}$ S$^1$, $10^{-5}$ S$^{-1}$, $5\times10^{-6}$ S$^{-1}$, $10^{-6}$ S$^{-1}$, $5\times10^{-7}$ S$^{-1}$, or $10^{-7}$ S$^{-1}$.

In a further embodiment of the invention, the anti-NGF activity of the anti-NGF antibodies of the present invention, and fragments thereof having binding specificity to NGF, exhibit anti-NGF activity by preventing, ameliorating or reducing the symptoms of, or alternatively treating, diseases and disorders associated with NGF, and in preferred embodiments pain-related diseases and disorders, and selectively inhibit the association of NGF with TrkA without appreciably inhibiting the association of NGF with p75. Non-limiting examples of diseases and disorders associated with NGF are set forth infra.

The invention is especially directed to methods of treating pain using chimeric or humanized antibodies and fragments thereof (including Fab fragments) capable of binding to NGF which inhibit the association of NGF with TrkA without appreciably inhibiting the association of NGF with p75. However, the invention further encompasses using chimeric or humanized antibodies and fragments thereof (including Fab fragments) capable of binding and/or inhibiting the biological activities mediated by the binding of NGF to both the p75 and TrkA receptors. Another preferred embodiment of the invention is directed to methods of treating pain using chimeric or humanized antibodies and fragments thereof capable of binding to NGF and selectively inhibiting the biological activities mediated by the binding of NGF to the TrkA receptor, while not inhibiting the biological activities mediated by the binding of NGF to the p75 receptor. In another preferred embodiment of the invention, full length antibodies and Fab fragments thereof are capable of significantly reducing pain in vivo in murine models, as measured by Gait analysis (as described in the examples herein) that further which inhibit the association of NGF with TrkA without appreciably inhibiting the association of NGF with p75.

B-Cell Screening and Isolation

In one embodiment, the present invention contemplates the preparation and isolation of a clonal population of antigen-specific B cells that may be used for isolating at least one NGF antigen-specific cell, which can be used to produce a monoclonal antibody against NGF, which is specific to a desired NGF antigen, or a nucleic acid sequence corresponding to such an antibody. Methods of preparing and isolating said clonal population of antigen-specific B cells are taught, for example, in U.S. patent publication no. US 2007/0269868 to Carvalho-Jensen et al., the disclosure of which is herein incorporated by reference in its entirety. Methods of preparing and isolating said clonal population of antigen-specific B cells are also taught herein in the examples. Methods of "enriching" a cell population by size or density are known in the art. See, e.g., U.S. Pat. No. 5,627,052. These steps can be used in addition to enriching the cell population by antigen-specificity.

Methods of Humanizing Antibodies

In another embodiment, the present invention contemplates methods for humanizing antibody heavy and light chains. Methods for humanizing antibody heavy and light chains which may be applied to anti-NGF antibodies are taught, for example, in U.S. patent application publication no. US 2009/0022659 to Olson et al., and in U.S. patent application publication no. US 2009/0028784 to Garcia-Martinez et al., the disclosures of each of which are herein incorporated by reference in their entireties.

Methods of Producing Antibodies and Fragments Thereof

In another embodiment, the present invention contemplates methods for producing anti-NGF antibodies and fragments thereof. Methods for producing anti-NGF antibodies and fragments thereof secreted from polyploidal, preferably diploid or tetraploid strains of mating competent yeast are taught, for example, in U.S. patent application publication no. US 2009/0022659 to Olson et al., and in U.S. patent application publication no. US 2009/0028784 to Garcia-Martinez et al., the disclosures of each of which are herein incorporated by reference in their entireties.

Other methods of producing antibodies are well known to those of ordinary skill in the art. For example, methods of producing chimeric antibodies are now well known in the art (See, for example, U.S. Pat. No. 4,816,567 to Cabilly et al.; Morrison et al., P.N.A.S. USA, 81:8651-55 (1984); Neuberger, M. S. et al., Nature, 314:268-270 (1985); Boulianne, G. L. et al., Nature, 312:643-46 (1984), the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al, Nature, 321:522-525 (1986); Reichmann, L., et al, Nature, 332:323-327 (1988); Verhoeyen, M, et al, Science, 239:1534-36 (1988), the disclosures of each of which are herein incorporated by reference in their entireties).

Antibody polypeptides of the invention having NGF binding specificity may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibody polypeptides may be either a bacterial cell such as E. coli, or a eukaryotic cell. In a particularly preferred embodiment of the invention, a mammalian cell of a well-defined type for this purpose, such as a myeloma cell, a Chinese hamster ovary (CHO) cell line, a NSO cell line, or a HEK293 cell line may be used.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an E. coli-derived bacterial strain, or a yeast cell line, may alternatively be used.

Similarly, once produced the antibody polypeptides may be purified according to standard procedures in the art, such as for example cross-flow filtration, ammonium sulphate precipitation, affinity column chromatography and the like.

The antibody polypeptides described herein may also be used for the design and synthesis of either peptide or non-peptide mimetics that would be useful for the same therapeutic applications as the antibody polypeptides of the invention. See, for example, Saragobi et al, Science, 253:792-795 (1991), the contents of which is herein incorporated by reference in its entirety.

Screening Assays

The invention also includes screening assays designed to assist in the identification of diseases and disorders associated with NGF in patients exhibiting symptoms of an NGF associated disease or disorder.

In one embodiment of the invention, the anti-NGF antibodies of the invention, or NGF binding fragments thereof, are used to detect the presence of NGF in a biological sample obtained from a patient exhibiting symptoms of a disease or disorder associated with NGF. The presence of NGF, or elevated levels thereof when compared to pre-disease levels of NGF in a comparable biological sample, may be beneficial in diagnosing a disease or disorder associated with NGF.

Another embodiment of the invention provides a diagnostic or screening assay to assist in diagnosis of diseases or disorders associated with NGF in patients exhibiting symptoms of an NGF associated disease or disorder identified herein, comprising assaying the level of NGF expression in a biological sample from said patient using a post-translationally modified anti-NGF antibody or binding fragment thereof. The anti-NGF antibody or binding fragment thereof may be post-translationally modified to include a detectable moiety such as set forth previously in the disclosure.

The NGF level in the biological sample is determined using a modified anti-NGF antibody or binding fragment thereof as set forth herein, and comparing the level of NGF in the biological sample against a standard level of NGF (e.g., the level in normal biological samples). The skilled clinician would understand that some variability may exist between normal biological samples, and would take that into consideration when evaluating results. In one embodiment of the invention, the anti-NGF antibodies of the invention may be used to correlate NGF expression levels with a particular stage of cancerous development. One skilled in the art would be able to measure NGF in numerous subjects in order to establish ranges of NGF expression that correspond to clinically defined stages of cancerous development. These ranges will allow the skilled practitioner to measure NGF in a subject diagnosed with a cancer and correlate the levels in each subject with a range that corresponds to a stage of said cancer.

One skilled in the art would understand that by measuring NGF in the patient at different intervals, the progression of the cancer can be determined.

The above-recited assay may also be useful in monitoring a disease or disorder, where the level of NGF obtained in a biological sample from a patient believed to have a NGF associated disease or disorder is compared with the level of NGF in prior biological samples from the same patient, in order to ascertain whether the NGF level in said patient has changed with, for example, a treatment regimen.

The invention is also directed to a method of in vivo imaging which detects the presence of cells which express NGF comprising administering a diagnostically effective amount of a diagnostic composition. Said in vivo imaging is useful for the detection or imaging of NGF expressing tumors or metastases, for example, and can be useful as part of a planning regimen for the design of an effective cancer treatment protocol. The treatment protocol may include, for example, one or more of radiation, chemotherapy, cytokine therapy, gene therapy, and antibody therapy, as well as an anti-NGF antibody or fragment thereof.

The present invention further provides for a kit for detecting binding of an anti-NGF antibody of the invention to NGF. In particular, the kit may be used to detect the presence of a NGF specifically reactive with an anti-NGF antibody of the invention or an immunoreactive fragment thereof. The kit may also include an antibody bound to a substrate, a secondary antibody reactive with the antigen and a reagent for detecting a reaction of the secondary antibody with the antigen. Such a kit may be an ELISA kit and can comprise the substrate, primary and secondary antibodies when appropriate, and any other necessary reagents such as detectable moieties, enzyme substrates, and color reagents, for example as described herein. The diagnostic kit may also be in the form of an immunoblot kit.

A skilled clinician would understand that a biological sample includes, but is not limited to, sera, plasma, urine, saliva, mucous, pleural fluid, synovial fluid and spinal fluid.

Methods of Ameliorating or Reducing Symptoms of, or Treating, or Preventing, Diseases and Disorders Associated with, NGF In another embodiment of the invention, anti-NGF antibodies described herein, or fragments thereof, i.e., those which inhibit the association of NGF with TrkA without appreciably inhibiting the association of NGF with p75, are useful for ameliorating or reducing the symptoms of, or treating, or preventing, diseases and disorders associated with NGF. Anti-NGF antibodies described herein, or fragments thereof, as well as combinations, can also be administered in a therapeutically effective amount to patients in need of treatment of diseases and disorders associated with NGF in the form of a pharmaceutical composition as described in greater detail below.

In a preferred embodiment of the invention, the antibodies described herein or fragments thereof, including Fab fragments, are utilized in methods for the treatment of pain in a patient via administration of said antibodies and/or fragments thereof.

In one embodiment of the invention, anti-NGF antibodies and/or fragments thereof described herein which inhibit the association of NGF with TrkA without appreciably inhibiting the association of NGF with p75, in conjunction with a second agent, are useful for ameliorating or reducing the symptoms of, or treating, or preventing, the following non-limiting listing of diseases and disorders: inflammatory pain, post-operative incision pain, complex regional pain syndrome, cancer pain (particularly primary or metastatic bone cancer pain), fracture pain, osteoporotic fracture pain, pain resulting from burn, osteoporosis, gout joint pain, pain associated with sickle cell crises, and other nociceptive pain, as well as hepatocellular carcinoma, breast cancer, liver cirrhosis.

In another embodiment of the invention, anti-NGF antibodies and/or fragments thereof described herein, which inhibit the association of NGF with TrkA without appreciably inhibiting the association of NGF with p75, in conjunction with a second agent, are useful for ameliorating or reducing the symptoms of, or treating, or preventing, the following non-limiting listing of diseases and disorders: neurogenic, neuropathic or nociceptive pain. Neuropathic pain may include, but is not limited to, trigeminal neuralgia, post-herpetic neuralgia, phantom limb pain, fibromyalgia, menstrual pain, ovarialgia, reflex sympathetic dystrophy and neurogenic pain. In other preferred embodiments, osteoarthritis or rheumatoid arthritis pain, lower back pain, diabetic neuropathy, sciatica, migraine, and other neuropathic pain.

Administration

In one embodiment of the invention, the anti-NGF antibodies described herein, or NGF binding fragments thereof, which inhibit the association of NGF with TrkA without appreciably inhibiting the association of NGF with p'75, as well as combinations of said antibodies or antibody fragments, and other anti-NGF antibodies or other actives are administered to a subject at a concentration of between about 0.01 and 100.0 mg/kg of body weight of recipient subject. In a preferred embodiment of the invention, the anti-NGF antibodies described herein, or NGF binding fragments thereof, as well as combinations of said antibodies or antibody fragments, are administered to a subject at a concentration of about 0.4 mg/kg of body weight of recipient subject. In a preferred embodiment of the invention, the anti-NGF antibodies described herein, or NGF binding fragments thereof, as well as combinations of said antibodies or antibody fragments, are administered to a recipient subject with a frequency of once every twenty-six weeks or less, such as once every sixteen weeks or less, once every eight weeks or less, once every four weeks or less, once every two weeks or less, once every week or less, or once daily or less.

Fab fragments may be administered every two weeks or less, every week or less, once daily or less, multiple times per day, and/or every few hours. In one embodiment of the invention, a patient receives Fab fragments of 0.01 mg/kg to 40 mg/kg per day given in divided doses of 1 to 6 times a day, or in a sustained release form, effective to obtain desired results.

It is to be understood that the concentration of the antibody or Fab administered to a given patient may be greater or lower than the exemplary administration concentrations set forth above.

A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins.

In another embodiment of the invention, the anti-NGF antibodies described herein, or NGF binding fragments thereof, as well as combinations of said antibodies or antibody fragments, are administered to a subject for treatment or prevention of pain and pain associated conditions in a pharmaceutical formulation.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

In one embodiment of the invention, the anti-NGF antibodies described herein, or NGF binding fragments thereof, which inhibit the association of NGF with TrkA without appreciably inhibiting the association of NGF with p75, optionally in association with other antibodies and fragments thereof which inhibit the association of NGF with TrkA as well as inhibiting the association of NGF with p75, and combinations of said antibodies or antibody fragments, may be optionally administered in combination with one or more active agents including other analgesic agents. Such active agents include analgesic, anti-histamine, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include but are not limited to 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lornoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Nerve Growth Factor (NGF), Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib.

An anti-histamine can be any compound that opposes the action of histamine or its release from cells (e.g., mast cells). Anti-histamines include but are not limited to acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast.

Antibiotics include but are not limited to Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Timidazole, Tobramycin, Trimethoprim, Trimethoprim-Sulfamethoxazole, Troleandomycin, Trovafloxacin, and Vancomycin.

Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a chimeric or humanized antibody for treatment or prevention of pain and pain associated conditions described herein, or one or more fragments thereof. The excipient generally does not provide any pharmacological activity to the formulation, though it may provide chemical and/or biological stability, and release characteristics. Exemplary formulations can be found, for example, in Remington's Pharmaceutical Sciences, 19th Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the alkaline polypeptide can be formulated in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B cells were disclosed in U.S. Provisional patent application No. 60/801,412, filed May 19, 2006, the disclosure of which is herein incorporated by reference in its entirety.

Certain teachings related to humanization of rabbit-derived monoclonal antibodies and preferred sequence modifications to maintain antigen binding affinity were disclosed in International Application No. PCT/US2008/064421, corresponding to International Publication No. WO/2008/144757, entitled "Novel Rabbit Antibody Humanization Methods and Humanized Rabbit Antibodies", filed May 21, 2008, the disclosure of which is herein incorporated by reference in its entirety.

Certain teachings related to producing antibodies or fragments thereof using mating competent yeast and corresponding methods were disclosed in U.S. patent application Ser. No. 11/429,053, filed May 8, 2006, (U.S. Patent Application Publication No. US2006/0270045), the disclosure of which is herein incorporated by reference in its entirety.

Certain teachings related to anti-NGF compositions and uses thereof were disclosed in U.S. provisional patent application No. 61/418,832, filed Dec. 1, 2010, the disclosure of which is herein incorporated by reference in its entirety.

Certain NGF antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1

Preparation of Antibodies that Bind NGF

By using the antibody selection protocol described herein, one can generate an extensive panel of antibodies.
Immunization Strategy Rabbits were immunized with huNGF (R&D Systems, Minneapolis, Minn.). Immunization consisted of a first subcutaneous (sc) injection of 100 µg in complete Freund's adjuvant (CFA) (Sigma) followed by two boosts, two weeks apart, of 50 µg each in incomplete Freund's adjuvant (IFA) (Sigma). Animals were bled on day 55, and serum titers were determined by ELISA (antigen recognition) and by non-radioactive proliferation assay (Promega) using the T1165 cell line.
Antibody Selection Titer Assessment To identify and characterize antibodies that bind to human NGF, antibody containing solutions were tested by ELISA. Briefly, neutravidin coated plates (Thermo Scientific), were blocked with ELISA buffer (0.1 mg/mL BSA, 1×PBS pH 7.4, 0.002% Tween 20 and 0.005% sodium azide) for 1 hr at room temperature. The plates were then coated with a 1 µg/mL biotinylated B-NGF solution in ELISA buffer for 1 hour at room temperature. This was followed by a wash step (3× using PBS plus 0.05% Tween 20) and a second block with ELISA buffer. The recombinant antibodies were then added onto the plates and incubated for 1 hour at room temperature and then washed 3× with PBS/Tween solution. For development, an anti-rabbit Fc-HRP (1:5000 dilution in ELISA buffer) was added onto the wells and incubated for 45 min at RT. After a 3× wash step with PBS/Tween solution, the plate was developed using TMB substrate for 3 minutes, stopped using 0.5M HCl and read at 450 nm.

Functional Titer Assessment

To test for the ability of NGF antibodies to block NGF-dependent cell proliferation, we used TF-1 cells (Chevalier et al. Expression and functionality of the trkA proto-oncogene product/NGF receptor in undifferentiated hematopoietic cells. Blood (1994) vol. 83 (6) pp. 1479-85). Briefly, TF-1 cells were maintained in 10% FBS cRPMI media ("complete media") supplemented with rhuGM-CSF. On the day of the assay, the antibodies were serially diluted in complete media in a round bottom 96 well plate. B-NGF (R&D systems) was concomitantly added and the resultant antibody/B-NGF mixture was incubated at 37° C. for 1 hr. While the Ab and B-NGF mixture was incubating, TF-1 cells were washed 3× with complete media, counted and plated in a flat bottom 96 well plate using 25,000 cells per well in a 50 µL volume. After 1 hour incubation the NGF-Antibody mixtures were added onto the cells and the plates were incubated for 48 hrs at 37° C. in a humidified 5% CO2 incubator. Cell proliferation was measured using the "CellTiter" aqueous one solution cell proliferation assay (Promega) according to the manufacturer's instructions. The dependency of the signals on the concentration of antibody was analyzed, and IC50 values were calculated using the GraphPad Prism program.

Tissue Harvesting

Once acceptable titers were established, the rabbit(s) were sacrificed. Spleen, lymph nodes, and whole blood were harvested and processed as follows:

Spleen and lymph nodes were processed into a single cell suspension by disassociating the tissue and pushing through sterile wire mesh at 70 µm (Fisher) with a plunger of a 20 cc syringe. Cells were collected in PBS. Cells were washed twice by centrifugation. After the last wash, cell density was determined by trypan blue. Cells were centrifuged at 1500 rpm for 10 minutes; the supernatant was discarded. Cells were resuspended in the appropriate volume of 10% dimethyl sulfoxide (DMSO, Sigma) in FBS (Hyclone) and dispensed at 1 ml/vial. Vials were stored at −70° C. in a slow freezing chamber for 24 hours and stored in liquid nitrogen.

Peripheral blood mononuclear cells (PBMCs) were isolated by mixing whole blood with equal parts of the low glucose medium described above without FBS. 35 ml of the whole blood mixture was carefully layered onto 8 ml of Lympholyte Rabbit (Cedarlane) into a 45 ml conical tube (Corning) and centrifuged 30 minutes at 2500 rpm at room temperature without brakes. After centrifugation, the PBMC layers were carefully removed using a glass Pasteur pipette (VWR), combined, and placed into a clean 50 ml vial. Cells were washed twice with the modified medium described above by centrifugation at 1500 rpm for 10 minutes at room temperature, and cell density was determined by trypan blue staining. After the last wash, cells were resuspended in an appropriate volume of 10% DMSO/FBS medium and frozen as described above.

B Cell Culture

On the day of setting up B cell culture, PBMC, splenocyte, or lymph node vials were thawed for use. Vials were removed from LN2 tank and placed in a 37° C. water bath until thawed. Contents of vials were transferred into 15 ml conical centrifuge tube (Corning) and 10 ml of modified RPMI described above was slowly added to the tube. Cells were centrifuged for 5 minutes at 1.5K rpm, and the supernatant was discarded. Cells were resuspended in 10 ml of fresh media. Cell density and viability was determined by trypan blue. Cells were washed again and resuspended at 1E07 cells/80 µL medium. Biotinylated huNGF (B huNGF) was added to the cell suspension at the final concentration of 3 ug/mL and incubated for 30 minutes at 4° C. Unbound B huNGF was removed with two 10 ml washes of phosphate-buffered (PBF):Ca/Mg free PBS (Hyclone), 2 mM ethylenediamine tetraacetic acid (EDTA), 0.5% bovine serum albumin (BSA) (Sigma-biotin free). After the second wash, cells were resuspended at 1E07 cells/80 µl PBF. 20 µl of MACS® streptavidin beads (Milteni)/10E7 cells were added to the cell suspension. Cells were incubated at 4° C. for 15 minutes. Cells were washed once with 2 ml of PBF/10E7 cells. After washing, the cells were resuspended at 1E08 cells/500 µl of PBF and set aside. A MACS® MS column (Milteni) was pre-rinsed with 500 ml of PBF on a magnetic stand (Milteni). Cell suspension was applied to the column through a pre-filter, and unbound fraction was collected. The column was washed with 1.5 ml of PBF buffer. The column was removed from the magnet stand and placed onto a clean, sterile 5 ml Polypropylene Falcon tube. 1 ml of PBF buffer was added to the top of the column, and positive selected cells were collected. The yield and viability of positive and negative cell fraction was determined by trypan blue staining. Positive selection yielded an average of 1% of the starting cell concentration.

A pilot cell screen was established to provide information on seeding levels for the culture. Plates were seeded at 10, 25, 50, 100, or 200 enriched B cells/well. In addition, each well contained 50K cells/well of irradiated EL-4.B5 cells (5,000 Rads) and an appropriate level of activated rabbit T cell supernatant (See U.S. Patent Application Publication No. 20070269868)(ranging from 1-5% depending on preparation) in high glucose modified RPMI medium at a final volume of 250 µl/well. Cultures were incubated for 5 to 7 days at 37° C. in 4% CO2.

Identification of Selective Antibody Secreting B Cells

Cultures were tested for antigen recognition and functional activity between days 5 and 7.

Antigen Recognition Screening

The ELISA format used is as described above except 50 µl of supernatant from the B cell cultures (BCC) wells was used as the source of the antibody. The conditioned medium was transferred to antigen-coated plates. After positive wells were identified, the supernatant was removed and transferred to a 96-well master plate(s). The original culture plates were then frozen by removing all the supernatant except 40 µl/well and adding 60 µl/well of 16% DMSO in FBS. Plates were wrapped in paper towels to slow freezing and frozen after the addition of 10% DMSO at −70° C.

Functional Activity Screening

To test for the ability of NGF antibodies to block NGF-dependent cell proliferation, we used TF-1 cells (Chevalier et al. Expression and functionality of the trkA proto-oncogene product/NGF receptor in undifferentiated hematopoietic cells. Blood (1994) vol. 83 (6) pp. 1479-85). Briefly, TF-1 cells were maintained in 10% FBS cRPMI media ("complete media") supplemented with rhuGM-CSF. On the day of the assay, the antibodies were serially diluted in complete media in a round bottom 96 well plate. B-NGF (R&D systems) was concomitantly added and the resultant antibody/B-NGF mixture was incubated at 37° C. for 1 hr. While the Ab and B-NGF mixture was incubating, TF-1 cells were washed 3× with complete media, counted and plated in a flat bottom 96 well plate using 25,000 cells per well in a 50 µL volume. After 1 hour incubation the NGF-Antibody mixtures were added onto the cells and the plates were incubated for 48 hrs at 37° C. in a humidified 5% CO2 incubator. Cell proliferation was measured using the "CellTiter" aqueous one solution cell proliferation assay (Promega) according to the manufacturer's instructions. The dependency of the signals on the concentration of antibody was analyzed, and IC50 values were calculated using the GraphPad Prism program.

B Cell Recovery

Plates containing wells of interest were removed from −70° C., and the cells from each well were recovered with 5-200 µl washes of medium/well. The washes were pooled in a 1.5 ml sterile centrifuge tube, and cells were pelleted for 2 minutes at 1500 rpm.

The tube was inverted, the spin repeated, and the supernatant carefully removed. Cells were resuspended in 100 µl/tube of medium. 100 µl biotinylated NGF coated streptavidin M280 dynabeads (Invitrogen) and 16 µl of goat anti-rabbit H&L IgG-FITC diluted 1:100 in medium was added to the cell suspension.

20 µl cell/beads/FITC suspension was removed, and 5 µl droplets were prepared on a glass slide (Corning) previously treated with Sigmacote (Sigma), 35 to 40 droplets/slide. An impermeable barrier of paraffin oil (JT Baker) was added to submerge the droplets, and the slide was incubated for 90 minutes at 37° C., 4% CO2 in the dark.

Specific B cells that produce antibody can be identified by the fluorescent ring around them due to antibody secretion, recognition of the bead-associated biotinylated antigen, and subsequent detection by the fluorescent-IgG detection reagent. Once a cell of interest was identified, the cell in the center of the fluorescent ring was recovered via a micromanipulator (Eppendorf). The single cell synthesizing and exporting the antibody was transferred into a 250 µl microcentrifuge tube and placed in dry ice. After recovering all cells of interest, these were transferred to −70° C. for long-term storage.

Isolation of Antibody Sequences from Antigen-Specific B Cell

Antibody sequences were recovered using a combined RT-PCR based method from a single isolated B-cell or an antigenic specific B cell isolated from the clonal B cell population. Primers are designed to anneal in conserved and constant regions of the target immunoglobulin genes (heavy and light), such as rabbit immunoglobulin sequences, and a two-step nested PCR recovery step is used to obtain the antibody sequence. Amplicons from each well are analyzed for recovery and size integrity. The resulting fragments are then digested with AluI to fingerprint the sequence clonality. Identical sequences display a common fragmentation pattern in their electrophoretic analysis. The original heavy and light chain amplicon fragments are then restriction enzyme digested with HindIII and XhoI or HindIII and BsiwI to prepare the respective pieces of DNA for cloning. The resulting digestions are then ligated into an expression vector and transformed into bacteria for plasmid propagation and production. Colonies are selected for sequence characterization.

Recombinant Production of Monoclonal Antibody of Desired Antigen Specificity and/or Functional Properties Correct full-length antibody sequences for each well containing a single monoclonal antibody are established and miniprep DNA is prepared using Qiagen solid-phase methodology. This DNA is then used to transfect mammalian cells to produce recombinant full-length antibody. Either antibody containing supernatants or protein-A affinity purified antibodies are tested for antigen recognition and functional properties to confirm the original characteristics are found in the recombinant antibody protein.

Antigen Specific ELISA

To identify and characterize antibodies and Fab fragments that bind to human NGF, antibody- and Fab-containing solutions were tested by ELISA. Briefly, neutravidin coated plates (Thermo Scientific), were blocked with ELISA buffer (0.1 mg/mL BSA, 1×PBS pH 7.4, 0.002% Tween 20 and 0.005% sodium azide) for 1 hr at room temperature. The plates were then coated with a 1 µg/mL biotinylated B-NGF solution in ELISA buffer for 1 hour at room temperature. This was followed by a wash step (3× using PBS plus 0.05% Tween 20) and a second block with ELISA buffer. The recombinant antibodies or Fabs were then added onto the plates and incubated for 1 hour at room temperature and then washed 3× with PBS/Tween solution. For development, an anti-human Fc-HRP or an anti-human Fab-fragment HRP (1:5000 dilution in ELISA buffer) was added onto the wells and incubated for 45 min at RT. After a 3× wash step with PBS/Tween solution, the plate was developed using TMB substrate for 3 minutes, stopped using 0.5M HCl, and read at 450 nm.

Figure 28:
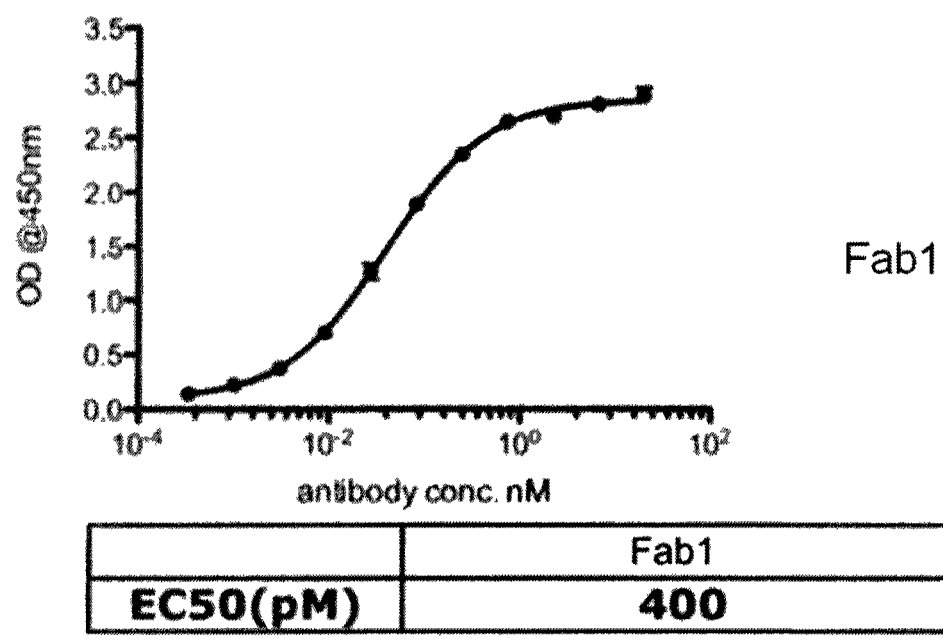
FIG. 28 provides the NGF ELISA binding data obtained following the protocol described infra for Fab1.
Figure 29:
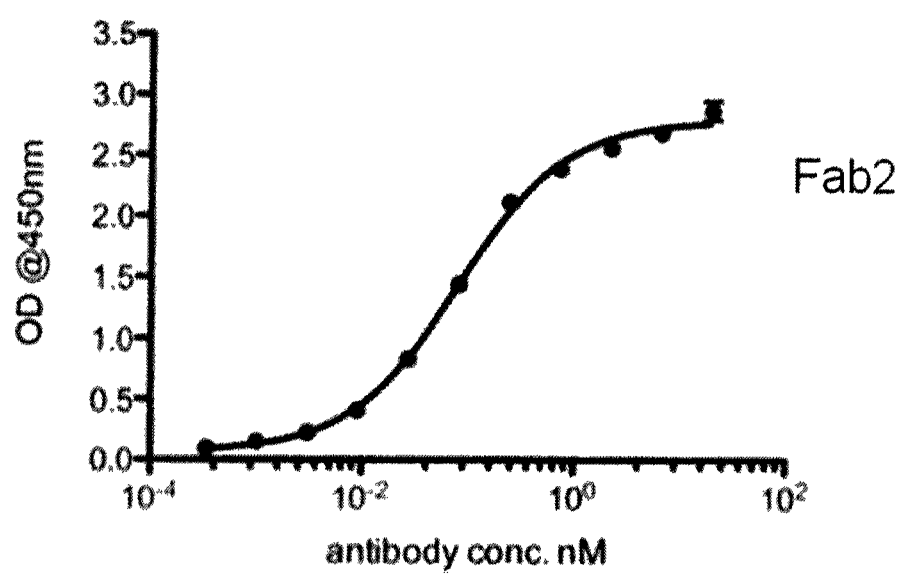
FIG. 29 provides the NGF ELISA binding data obtained following the protocol described infra for Fab2.
Figure 30:
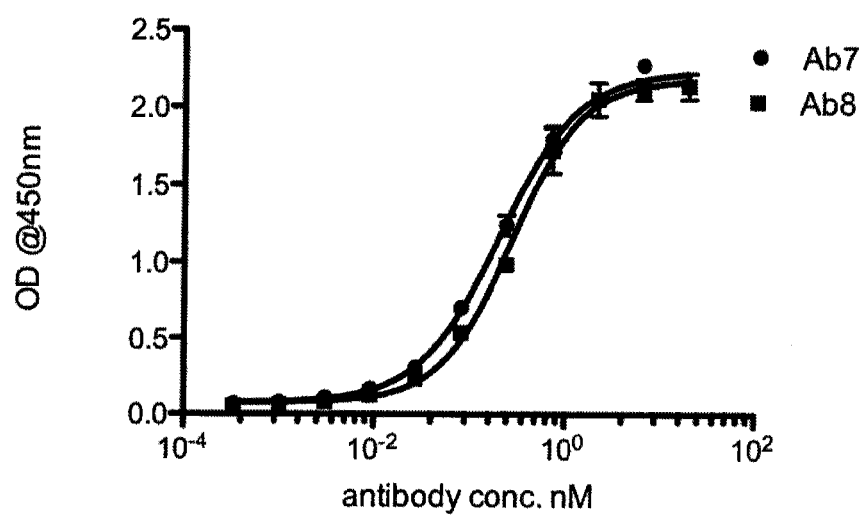
FIG. 30 provides the NGF ELISA binding data obtained following the protocol described infra for antibodies Ab7 and Ab8.
Figure 31:
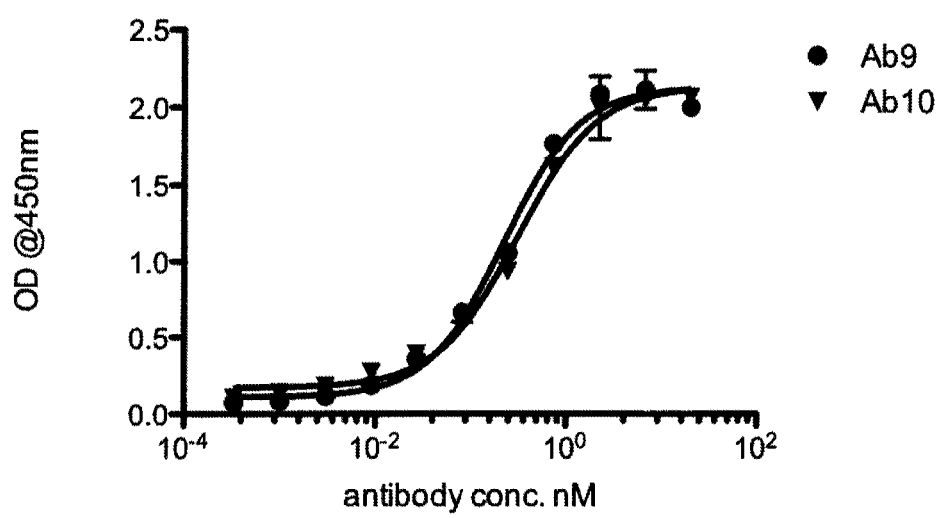
FIG. 31 provides the NGF ELISA binding data obtained following the protocol described infra for antibodies Ab9 and Ab10.
Figure 32:
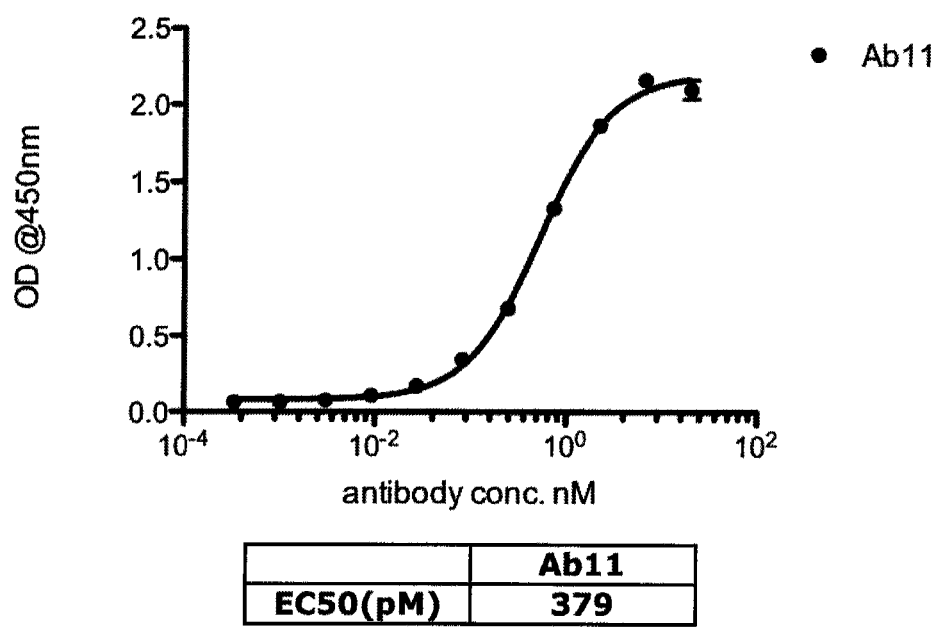
FIG. 32 provides the NGF ELISA binding data obtained following the protocol described infra for antibody Ab11.
Figure 33:
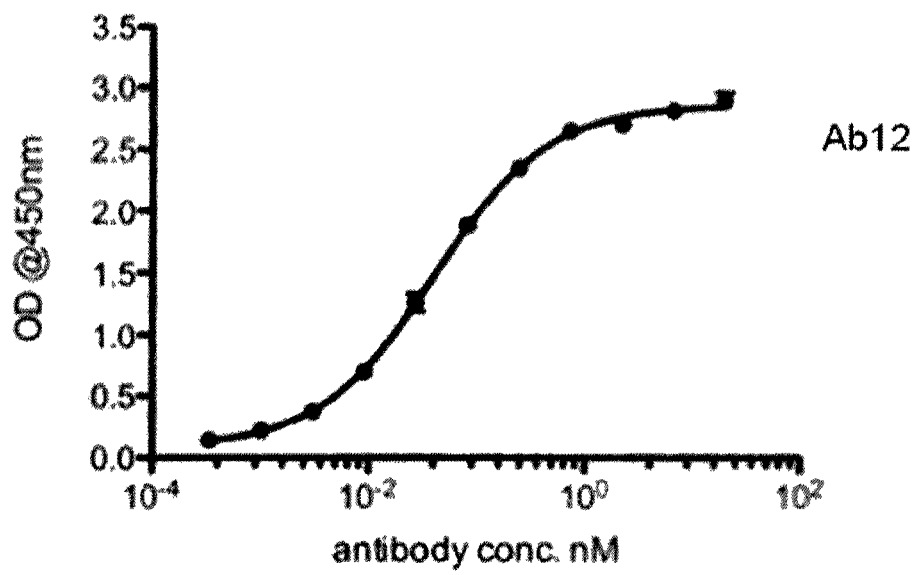
FIG. 33 provides the NGF ELISA binding data obtained following the protocol described infra for antibody Ab12.
Figure 34:
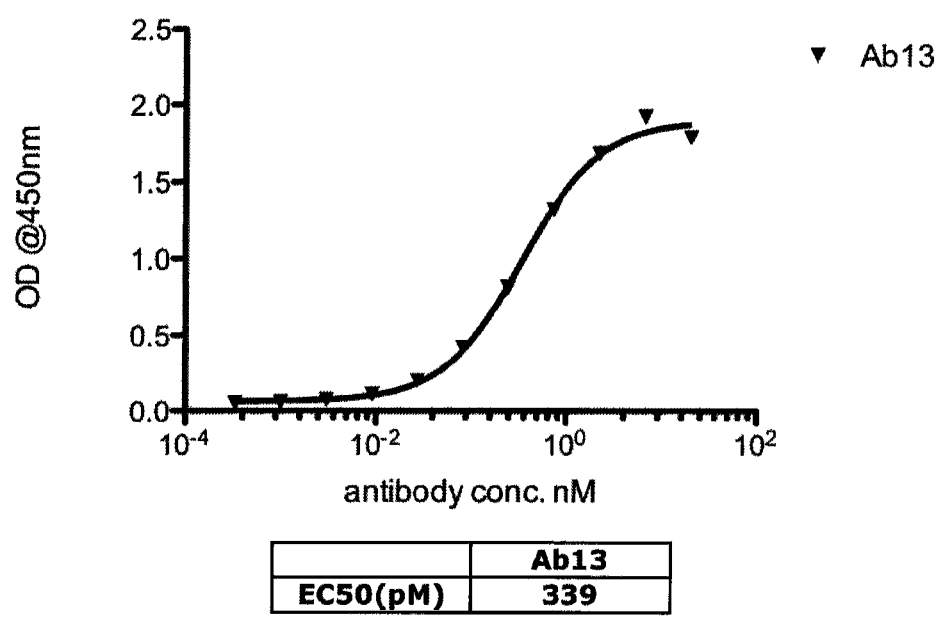
FIG. 34 provides the NGF ELISA binding data obtained following the protocol described infra for antibody Ab13.
Figure 35:
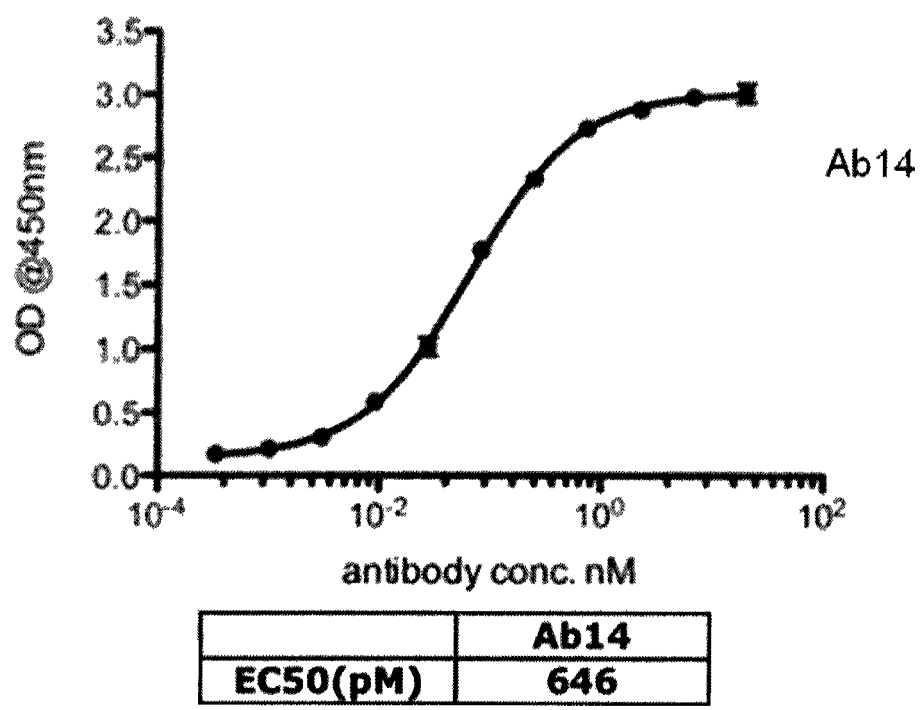
FIG. 35 provides the NGF ELISA binding data obtained following the protocol described infra for antibody Ab14.
Figure 36:
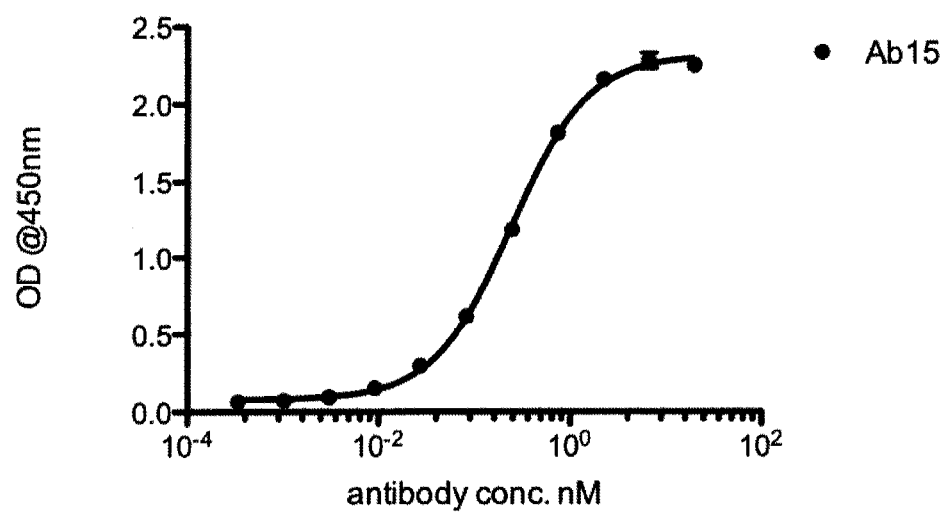
FIG. 36 provides the NGF ELISA binding data obtained following the protocol described infra for antibody Ab15.
Figure 37:
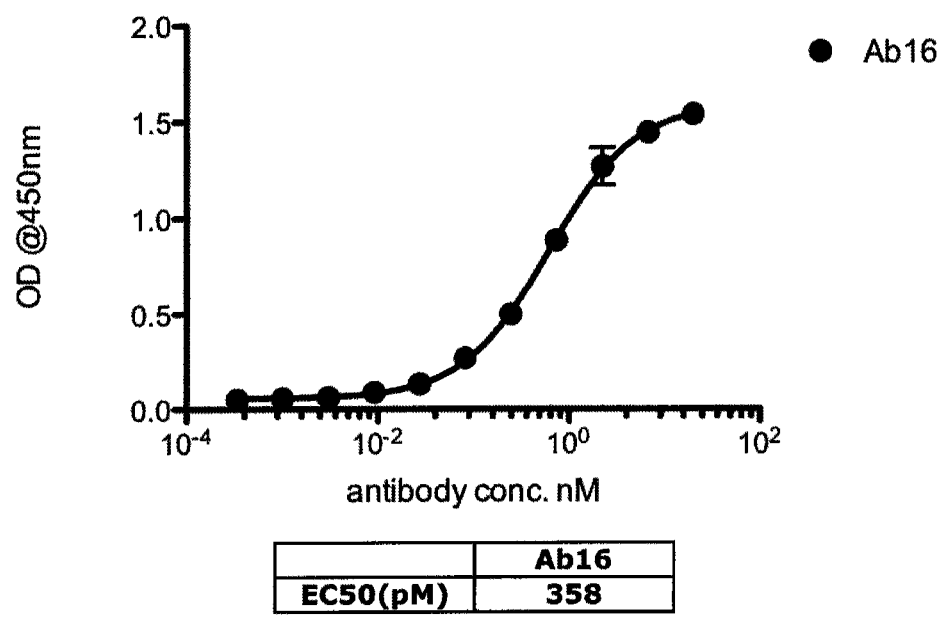
FIG. 37 provides the NGF ELISA binding data obtained following the protocol described infra for antibody Ab16.
Figure 38:
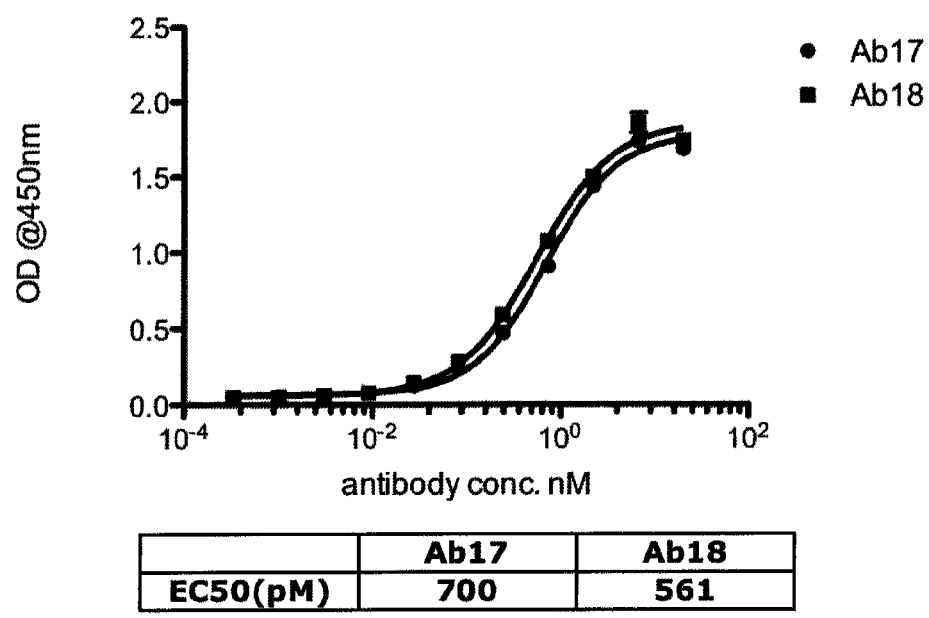
FIG. 38 provides the NGF ELISA binding data obtained following the protocol described infra for antibodies Ab17 and Ab18.
Figure 39:
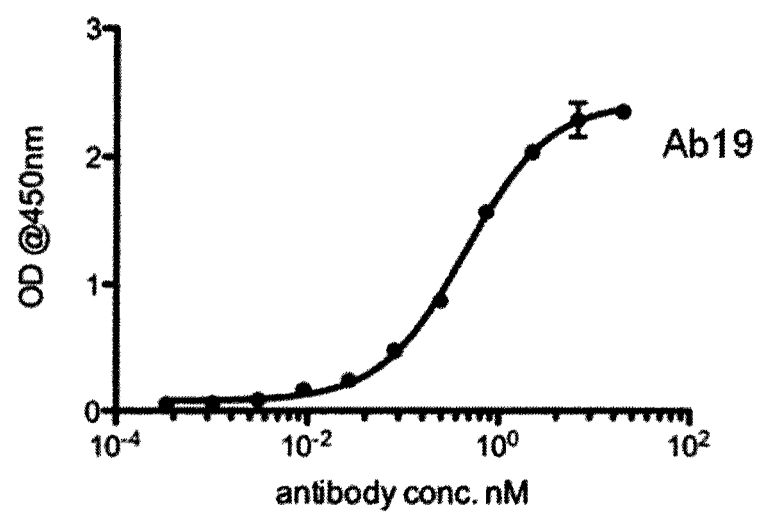
FIG. 39 provides the NGF ELISA binding data obtained following the protocol described infra for antibody Ab19.
Figure 40:
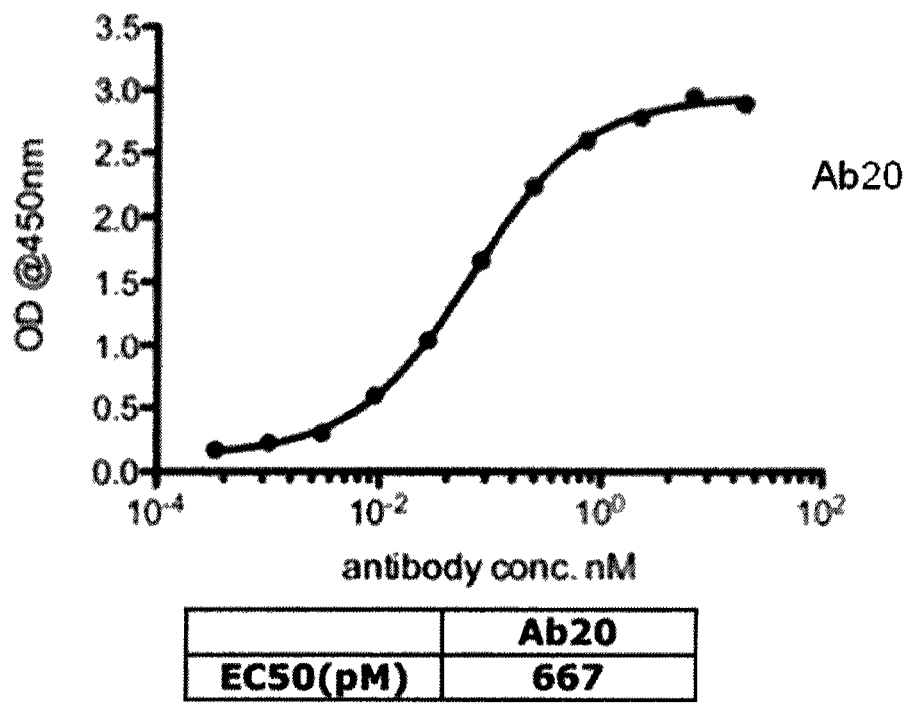
FIG. 40 provides the NGF ELISA binding data obtained following the protocol described infra for antibody Ab20.
Figure 41:
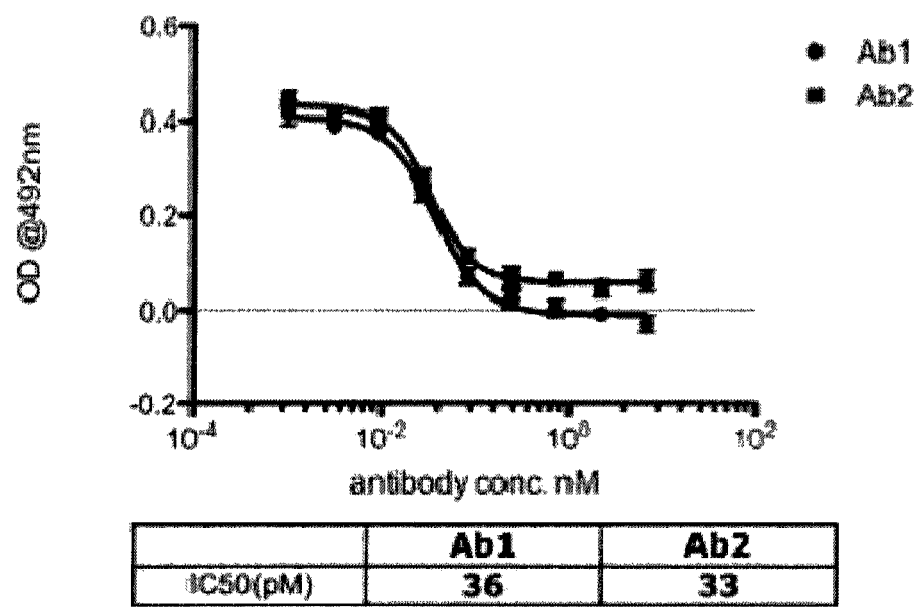
FIG. 41 provides the TF1 cell proliferation data obtained following example 1 for antibodies Ab1 and Ab2.
Figure 42:
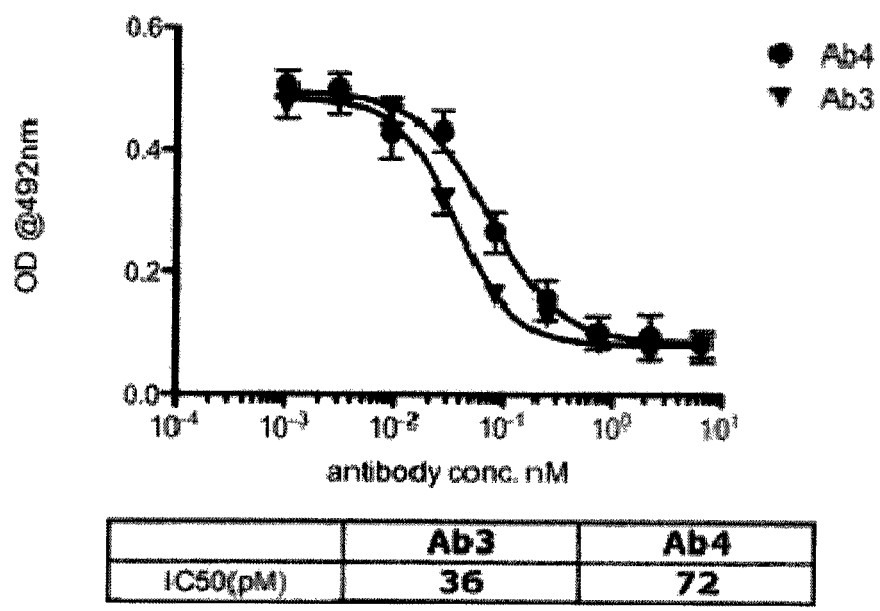
FIG. 42 provides the TF1 cell proliferation data obtained following example 1 for antibodies Ab3 and Ab4.
Figure 43:
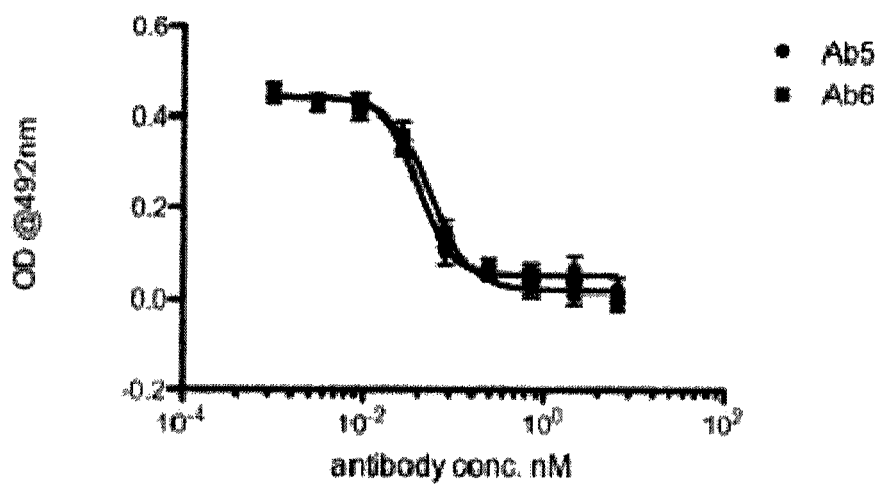
FIG. 43 provides the TF1 cell proliferation data obtained following example 1 for antibodies Ab5 and Ab6.
Figure 44:
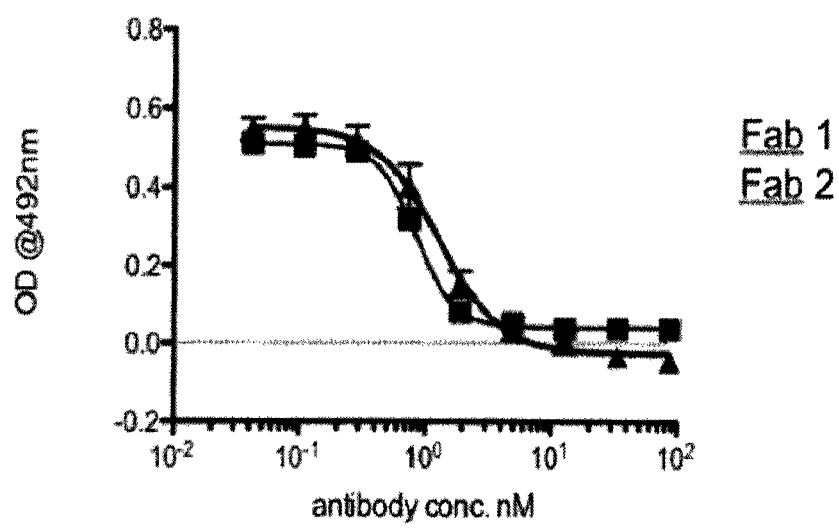
FIG. 44 provides the TF1 cell proliferation data obtained following example 1 for the Fab1 and Fab2 antibody fragments.
Figure 45:
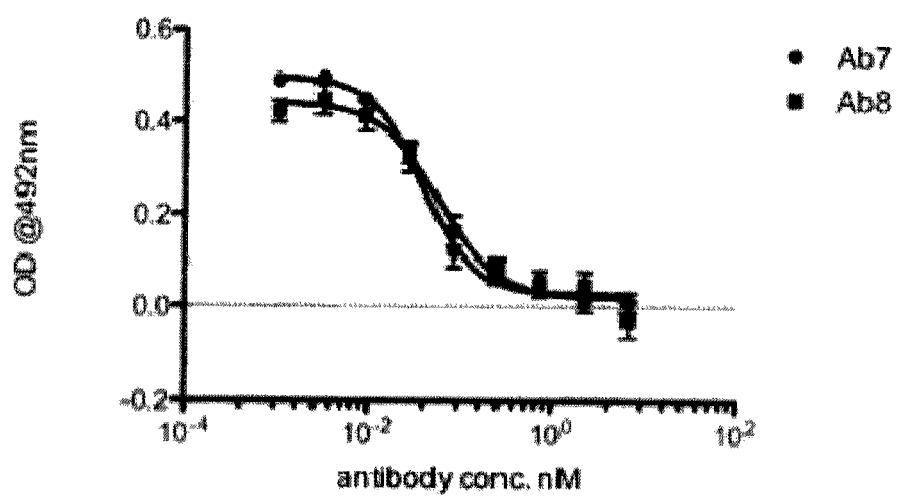
FIG. 45 provides the TF1 cell proliferation data obtained following example 1 for antibodies Ab7 and Ab8.
Figure 46:
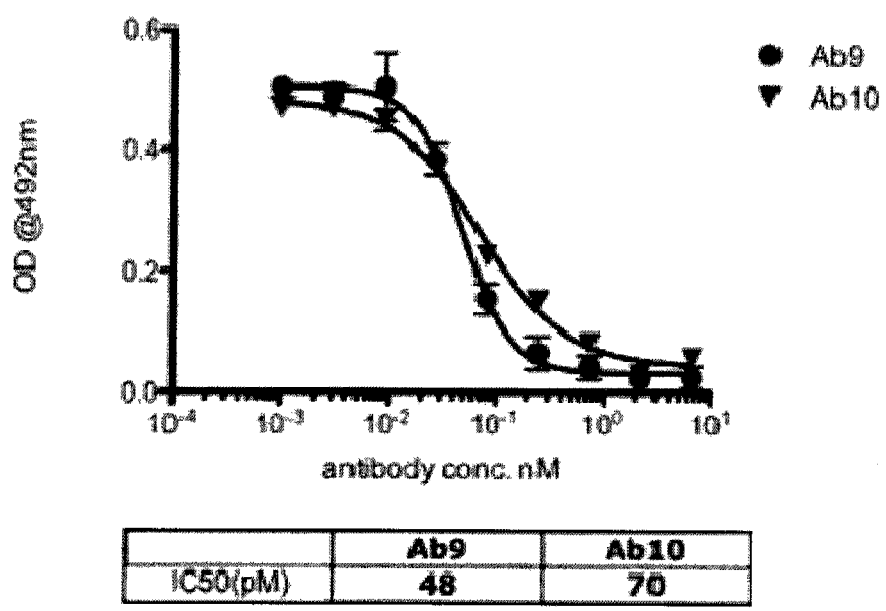
FIG. 46 provides the TF1 cell proliferation data obtained following example 1 for antibodies Ab9 and Ab10.
Figure 47:
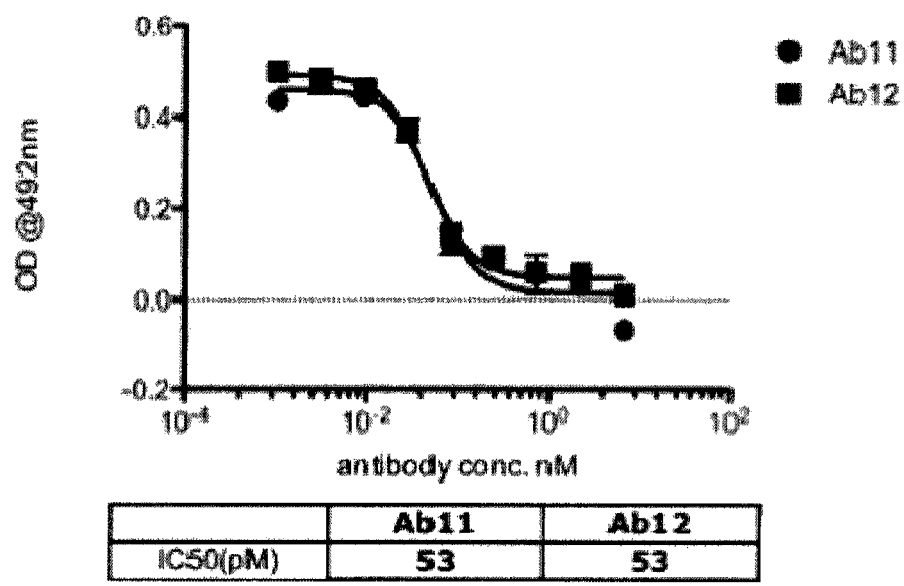
FIG. 47 provides the TF1 cell proliferation data obtained following example 1 for antibodies Ab11 and Ab12.
Figure 48:
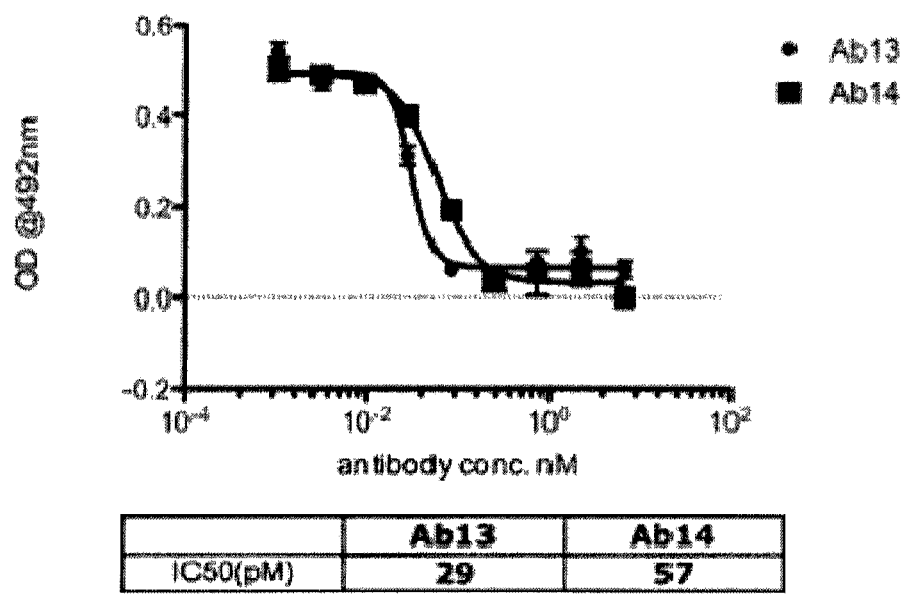
FIG. 48 provides the TF1 cell proliferation data obtained following example 1 for antibodies Ab13 and Ab14.
Figure 49:
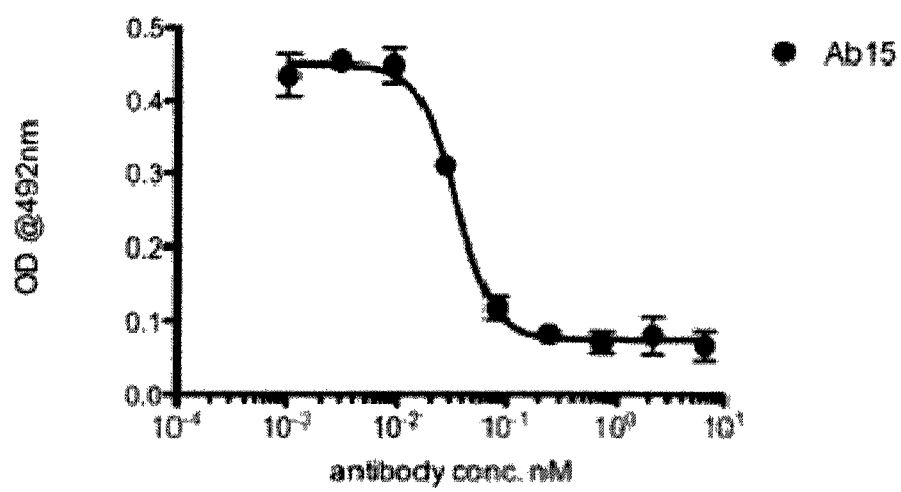
FIG. 49 provides the TF1 cell proliferation data obtained following example 1 for antibody Ab15.
Figure 50:
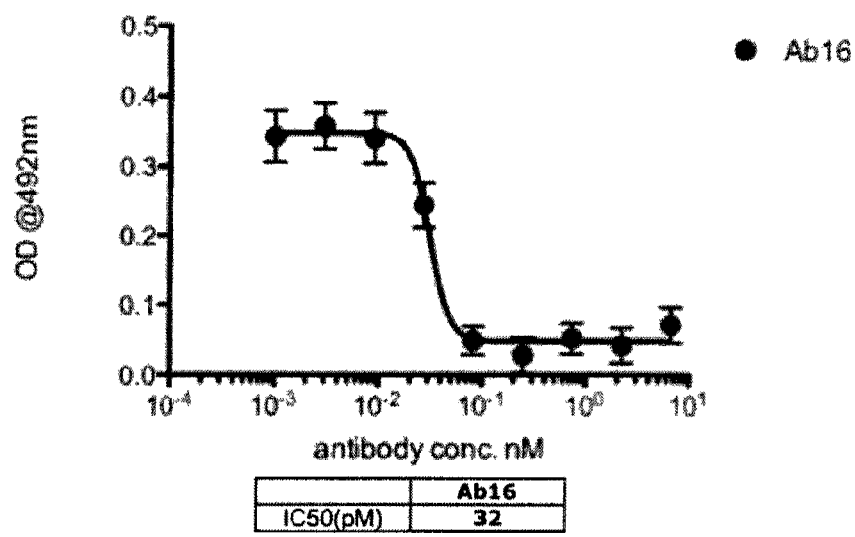
FIG. 50 provides the TF1 cell proliferation data obtained following example 1 for antibody Ab16.
Figure 51:
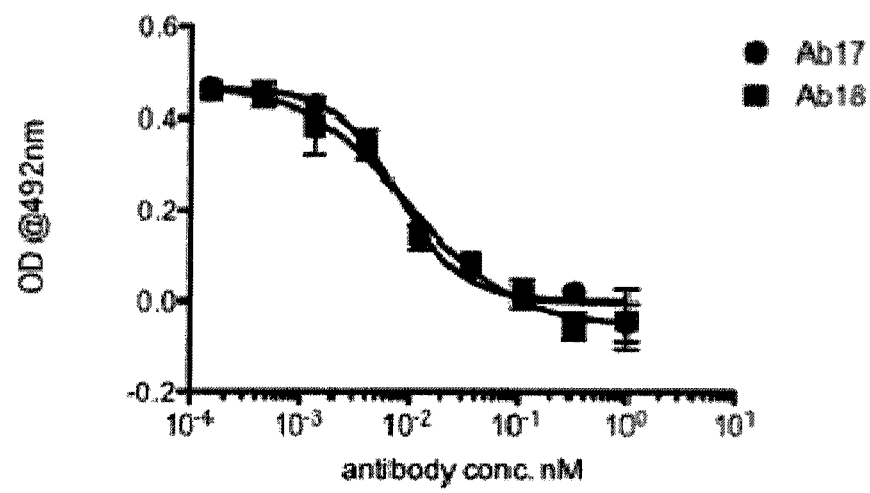
FIG. 51 provides the TF1 cell proliferation data obtained following example 1 for antibodies Ab17 and Ab18.
Figure 52:
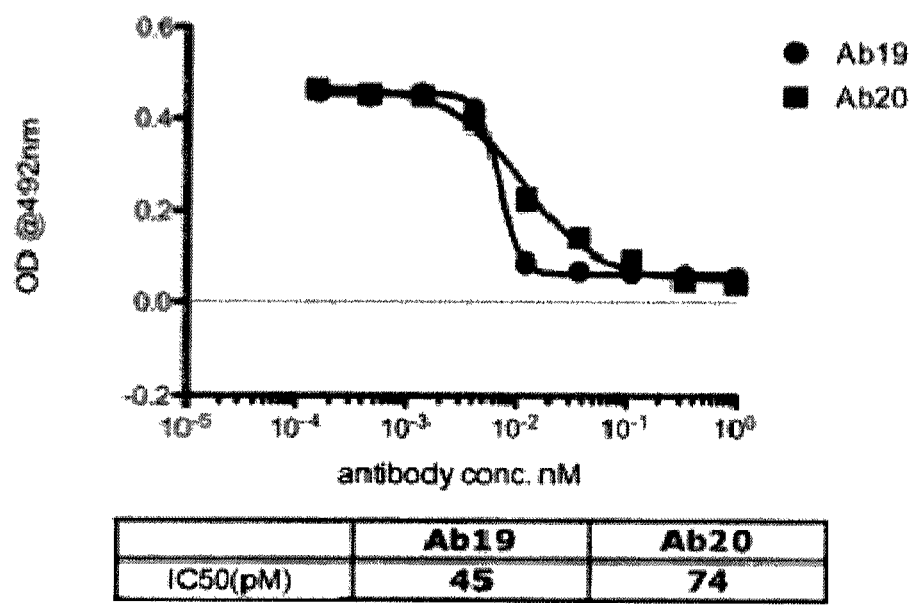
FIG. 52 provides the TF1 cell proliferation data obtained following example 1 for antibodies Ab19 and Ab20.

Results: FIGS. 24-40 demonstrate that anti-NGF antibodies Ab1-Ab21 bind to NGF. Furthermore, FIGS. 28 and 29 demonstrate that Fab antibody fragments Fab1 and Fab2 bind to NGF.

Functional Activity Screening

To test for the ability of NGF antibodies to block NGF-dependent and TrkA receptor-mediated cell proliferation activity, we used TF-1 cells (Chevalier et al. Expression and functionality of the trkA proto-oncogene product/NGF receptor in undifferentiated hematopoietic cells. Blood (1994) vol. 83 (6) pp. 1479-85). Briefly, TF-1 cells were maintained in 10% FBS cRPMI media ("complete media") supplemented with rhuGM-CSF. On the day of the assay, the antibodies were serially diluted in complete media in a round bottom 96 well plate. B-NGF (R&D systems) was concomitantly added and the resultant antibody/B-NGF mixture was incubated at 37° C. for 1 hr. While the Ab and B-NGF mixture was incubating, TF-1 cells were washed 3× with complete media, counted and plated in a flat bottom 96 well plate using 25,000 cells per well in a 50 µL volume. After 1 hour incubation the NGF-Antibody mixtures were added onto the cells and the plates were incubated for 48 hrs at 37° C. in a humidified 5% CO2 incubator. Cell proliferation was measured using the "CellTiter" aqueous one solution cell proliferation assay (Promega) according to the manufacturer's instructions. The dependency of the signals on the concentration of antibody was analyzed, and IC50 values were calculated using the GraphPad Prism program.

Results: FIGS. 41-52 demonstrate that anti-NGF antibodies Ab1-Ab20 inhibit the proliferation of TF-1 cells. Furthermore, FIG. 44 demonstrates that Fab antibody fragments also inhibit the proliferation of TF-1 cells. These Fab antibody fragments were produced by: 1.) *Pichia pastoris* expression of Fab2; and 2.) enzymatic digestion of Ab21 produced in *Pichia pastoris* (Fab1).

Example 2

Enzymatic Production of Fab Fragments

Papain digestions were conducted using immobilized papain (Thermo/Pierce) as per manufacturer's instructions. Briefly, purified antibodies were incubated in a cystein/HCl-containing buffer with immobilized papain at 37° C. with gentle rocking. The digestion was monitored by taking an aliquot and analyzing using SDS-PAGE for cleavage of the heavy chain. To stop the reaction, the immobilized papain was spun out and washed using 50 mM Tris pH 7.5 and filtered. Undigested full length antibody and Fc fragments were removed by using a MabSelectSure (GE) column.

Example 3

Yeast Cell Expression

Antibody genes: Genes were cloned and constructed that directed the synthesis of a chimeric or humanized rabbit monoclonal antibody.
Methods
Construction of *Pichia pastoris* Expression Vectors for Heavy and Light Chain Antibodies.

The light and heavy chain fragments (chimera or humanized) were commercially synthesized and subcloned into a pGAP expression vector. The pGAP expression vector uses the GAP promoter to drive expression of the immunoglobulin chain and the human serum albumin (HAS) leader sequence for export. In addition, this vector contains common elements such as a bacterial origin of replication, and a copy of the Sh ble gene which confers resistance to the antibiotic Zeocin™ (phleomycin). Zeocin™ provides a means of selection for strains that contain the desired expression vector integrated into their genome.
Transformation of Expression Vectors into Haploid met1 and Lys3 Host Strains of *Pichia pastoris*

All methods used for transformation of haploid *P. pastoris* strains and manipulation of the *P. pastoris* sexual cycle were done as described in *Pichia* Protocols (Methods in Molecular Biology Higgings, D R, and Cregg, J M, Eds. 1998. Humana Press, Totowa, N.J.). Prior to transformation each vector was linearized within the GAP promoter sequences to direct the integration of the vector into the GAP promoter locus of the *P. pastoris* genome. Haploid strains were transfected using electroporation and successful transformants were selected on YPD Zeocin™ plates and then cultured in 96-well plates for two days. Haploid strains were mated and selected for their ability to grow in the absence of the auxotroph markers (i.e., Lys and Met). Diploid strains were then selected for their ability to express either full length or Fab antibody fragments using a ForteBio Octet system fitted with Protein A biosensors to monitor expression.

Example 4

Expression of Ab21 and Fab2 in *Pichia pastoris*

Two *Pichia* strains for expression of either full length Ab21 or Fab2 antibody fragment were made. For both the full length or the Fab expressing strains, haploids strains were created and subsequently mated. One haploid strain expressed full length light sequences for Ab21 and another haploid strain expressed either the full length Ab21 or a truncated form of heavy chain to express an Fab fragment (e.g., Fab2). Each diploid strain was used to generate a research cell bank and used for expression in a bioreactor.

First an inoculum was expanded using the research cell bank using medium comprised of the following nutrients (% w/v): yeast extract 3%, anhydrous dextrose 4%, YNB 1.34%, 0.004% Biotin with 100 mM potassium phosphate. The culture was expanded for approximately 24 hours in a shaking incubator at 30° C. and 300 rpm to generate the inoculum for the fermenters. A 10% inoculum was then added to Labfors 2.5 L working volume vessels containing sterile growth medium. The growth medium for the full length Ab21 was comprised of the following nutrients: potassium sulfate 18.2 g/L, ammonium phosphate monobasic 36.4 g/L, potassium phosphate dibasic 12.8 g/L, magnesium sulfate heptahydrate 3.72 g/L, sodium citrate dihydrate 10 g/L, glycerol 40 g/L, yeast extract 30 g/L, PTM1 trace metals 4.35 mL/L, and antifoam 204 1.67 mL/L. The PTM1 trace metal solution was comprised of the following components: cupric sulfate pentahydrate 6 g/L, sodium iodide 0.08 g/L, manganese sulfate hydrate 3 g/L, sodium molybdate dihyrate 0.2 g/L, boric acid 0.02 g/L, cobalt chloride 0.5 g/L, zinc chloride 20 g/L, ferrous sulfate heptahydrate 65 g/L, biotin 0.2 g/L, and sulfuric acid 5 mL/L.

The growth medium for the Fab2 fragment was comprised of the following nutrients: potassium sulfate 10.92 g/L, ammonium phosphate monobasic 21.84 g/L, potassium phosphate dibasic 7.68 g/L, magnesium sulfate heptahydrate 3.72 g/L, sodium citrate dihydrate 10 g/L, glycerol 40 g/L, yeast extract 30 g/L, PTM1 trace metal solution 2.61 mL/L, and antifoam 204 1.67 mL/L. The PTM1 trace metal solution was comprised of the following components: cupric sulfate pentahydrate 6 g/L, sodium iodide 0.08 g/L, manganese sulfate hydrate 3 g/L, sodium molybdate dihyrate 0.2 g/L, boric acid 0.02 g/L, cobalt chloride 0.5 g/L, zinc chloride 20 g/L, ferrous sulfate heptahydrate 65 g/L, biotin 0.2 g/L, and sulfuric acid 5 mL/L. Both proteins were expressed under similar conditions. Briefly, the bioreactor process control parameters were set as follows: Agitation 1000 rpm, airflow 1.35 standard liter per minute, temperature 28° C. and pH was controlled at six using ammonium hydroxide. No oxygen supplementation was provided.

The fermentation cultures were grown for approximately 12 to 16 hours until the initial glycerol was consumed as denoted by a dissolved oxygen spike. The cultures were starved for approximately three hours after the dissolved oxygen spike. After this starvation period, a bolus addition of ethanol was added to the reactor to reach 1% ethanol (w/v). The fermentation cultures were allowed to equilibrate for 15 to 30 minutes. Feed addition was initiated 30 minutes post-ethanol bolus and set at a constant rate of 1 mL/min for 40 minutes, then the feed pump was controlled by an ethanol sensor keeping the concentration of ethanol at 1% for the remainder of the run. The feed was comprised of the following components: yeast extract 50 g/L, dextrose 500 g/L, magnesium sulfate heptahydrate 3 g/L, and PTM1 trace metals 12 mL/L. For fermentation of the full length Ab21, sodium citrate dihydrate (0.5 g/L) was also added to the feed. The total fermentation time was approximately 90 hours.

Example 5

Inhibition of NGF-p75 Interactions

NGF is reported to interact with two receptors on the cell surface: TrkA and p75. A biolayer interferometry assay via the "Octet" was used to characterize the ability of anti-NGF antibodies to inhibit NGF-p75 interactions. Briefly, streptavidin (SA) sensors were pre-wetted in 1× kinetics buffer (1×PBS pH 7.4, 0.002% Tween 20, 0.005% sodium azide and 0.1 mg/mL BSA). A baseline was obtained using again 1× kinetics buffer, followed by binding of the biotinylated antibody being tested and another short baseline in 1× kinetics buffer. NGF (1 µg/mL) was loaded next and the sensor was then transferred onto 1× kinetics buffer. After loading of NGF onto the antibody, on one sensor, all possible sites of NGF were blocked using an un-labeled solution of the biotinylated antibody at 5 µg/mL. As control, a parallel sensor was submerged into 1× kinetics buffer during this second blocking step. Both sensors were then exposed to a solution containing p75 (1.2 μg/mL). The ability of an antibody to block NGF-p75 interactions was then characterized by monitoring the increase in signal when antibody-immobilized NGF was exposed to soluble p75.

Figure 54:
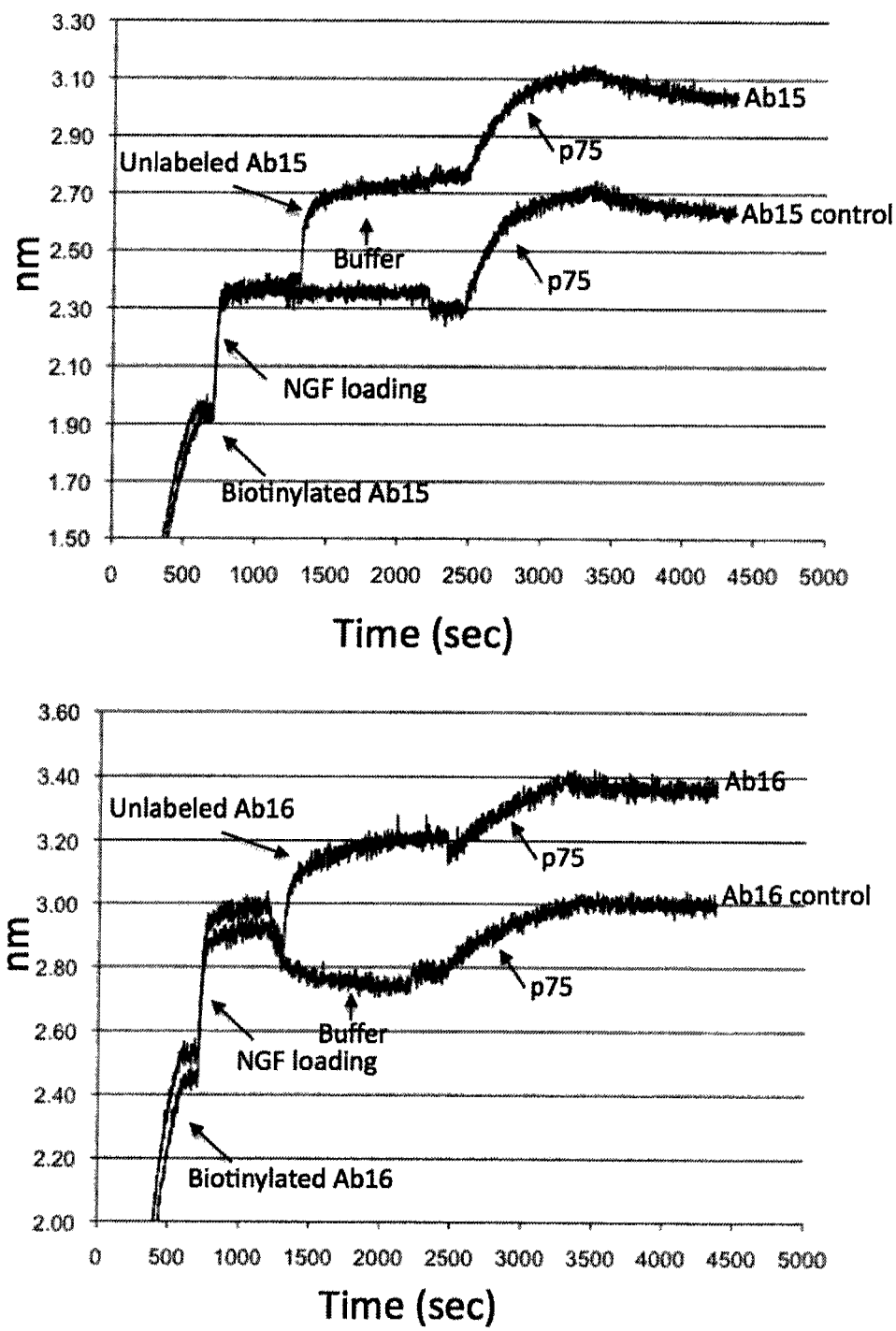
FIG. 54 provides the inhibition of NGF-p75 interaction data obtained following example 5 for antibodies Ab15 and Ab16. Antibodies Ab15 and Ab16 do not demonstrate the ability to inhibit the interaction of NGF and p75.
Figure 55:
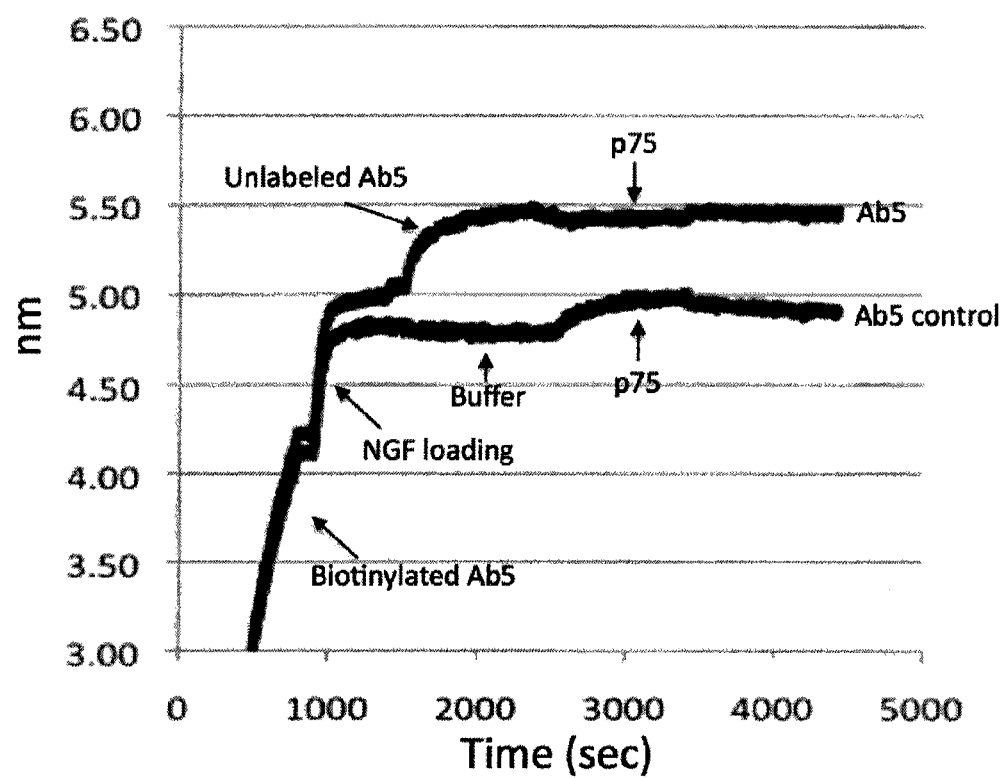
FIG. 55 provides the inhibition of NGF-p75 interaction data obtained following example 5 for antibody Ab5. Antibody Ab5 demonstrates the ability to inhibit the interaction of NGF and p75.
Figure 56:
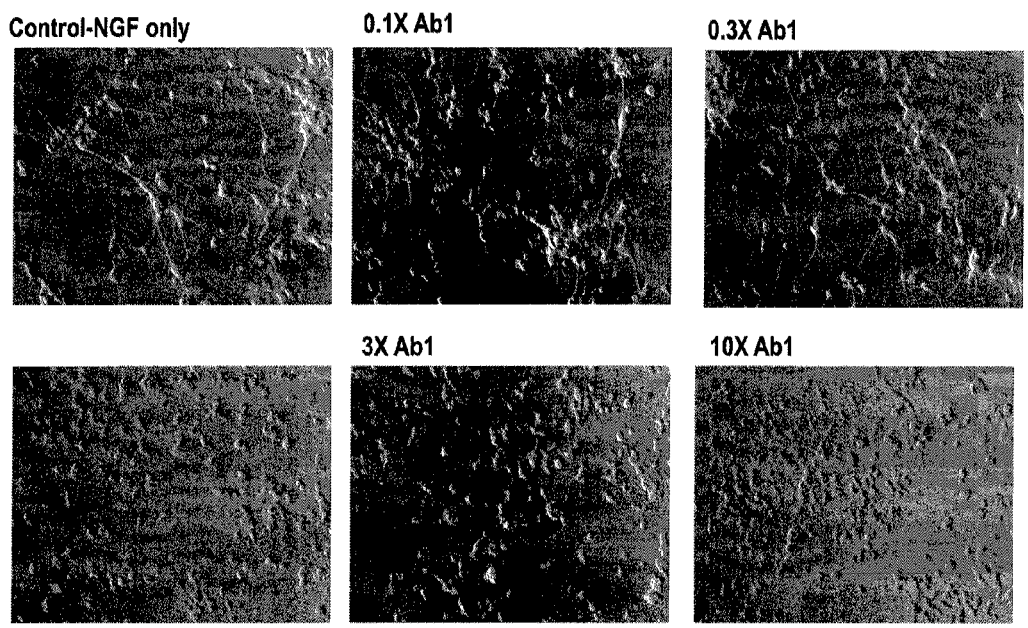
FIG. 56 demonstrates the inhibition of PC-12 neurite outgrowth in the presence of increasing concentrations of antibody Ab1 obtained following example 6.
Figure 58:
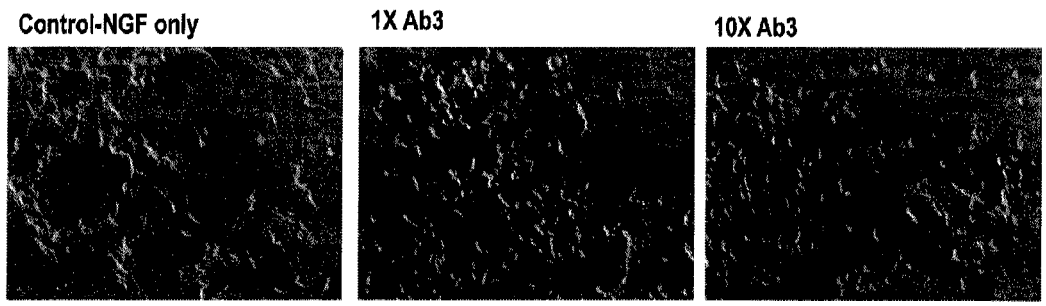
FIG. 58 demonstrates the inhibition of PC-12 neurite outgrowth in the presence of increasing concentrations of antibody Ab3 obtained following example 6. The results further demonstrate that the inhibition of PC-12 neurite outgrowth at the same concentrations of antibody is less than that seen with anti-NGF antibodies which exhibit different NGF binding selectivity.
Figure 59:
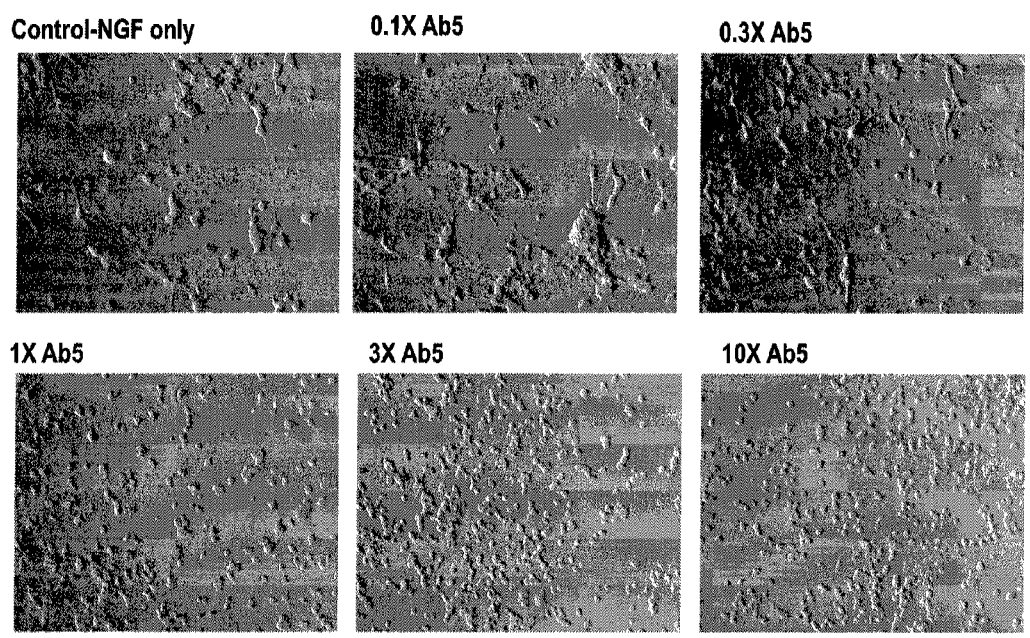
FIG. 59 demonstrates the inhibition of PC-12 neurite outgrowth in the presence of increasing concentrations of antibody Ab5 obtained following example 6.
Figure 60:
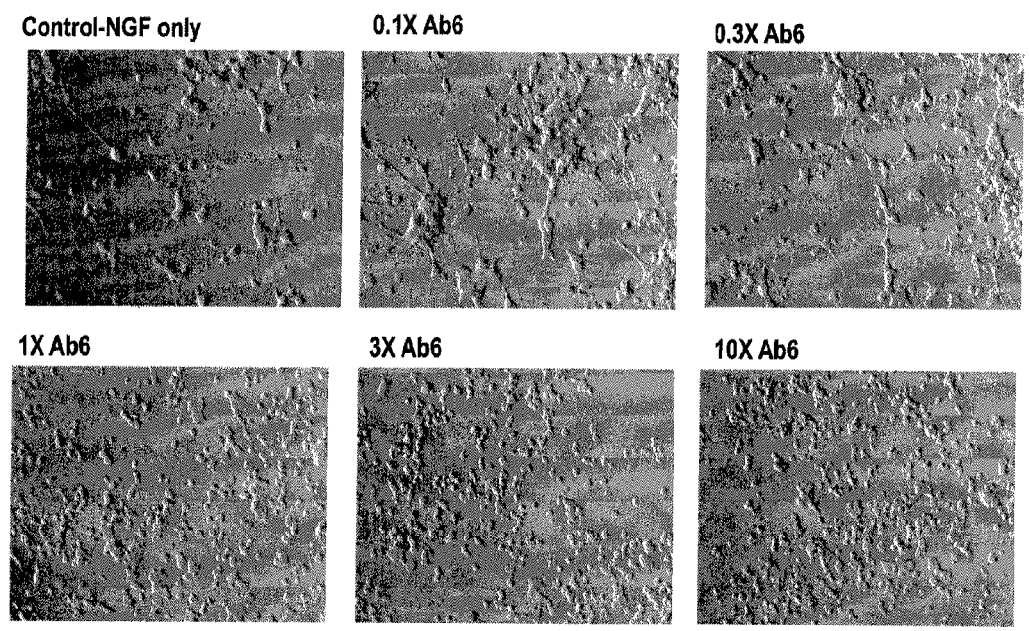
FIG. 60 demonstrates the inhibition of PC-12 neurite outgrowth in the presence of increasing concentrations of antibody Ab6 obtained following example 6.
Figure 61:
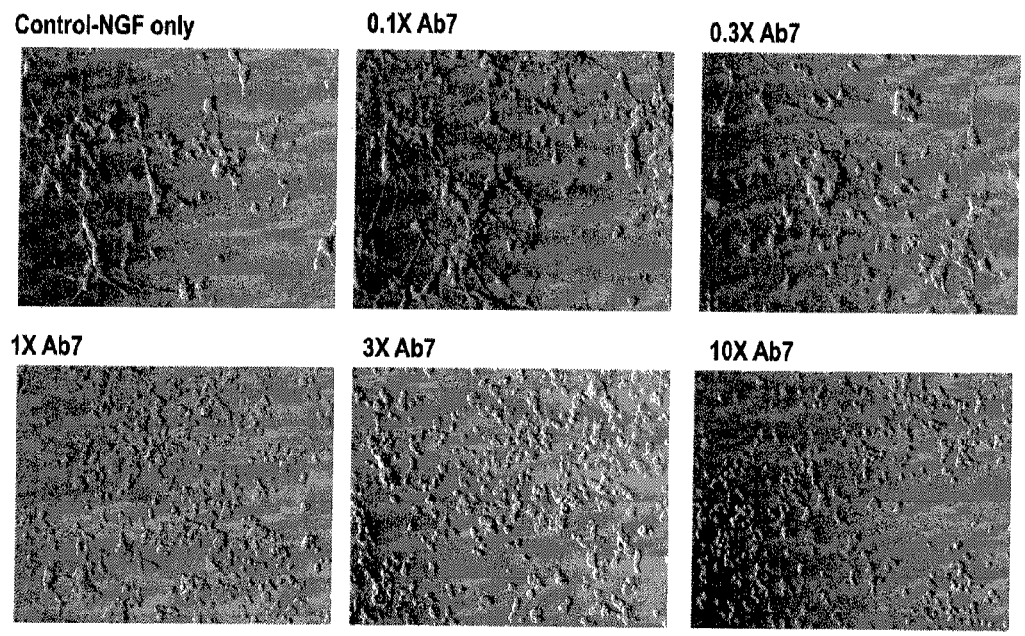
FIG. 61 demonstrates the inhibition of PC-12 neurite outgrowth in the presence of increasing concentrations of antibody Ab7 obtained following example 6.
Figure 62:
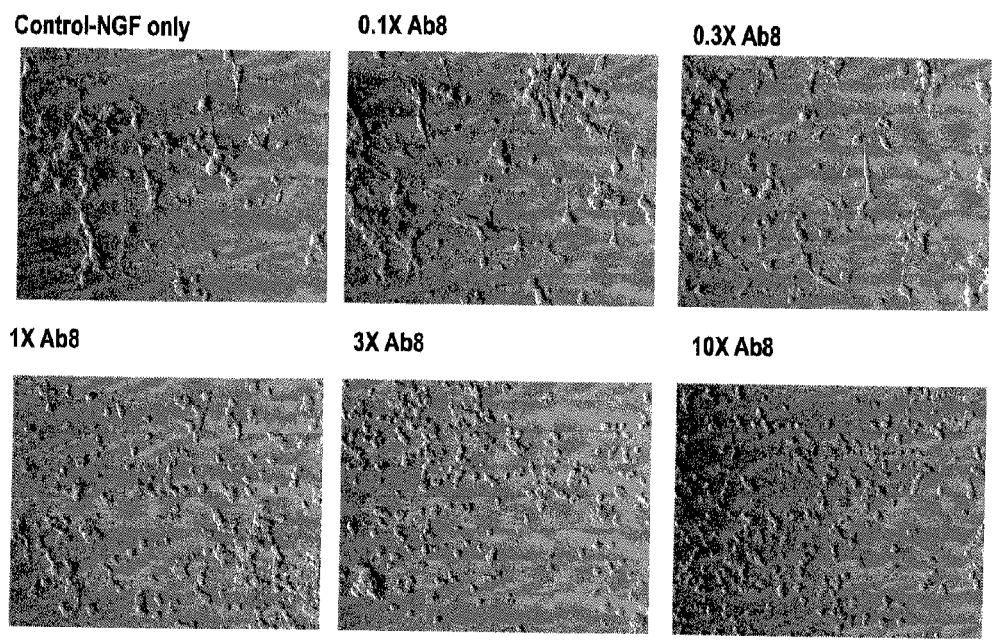
FIG. 62 demonstrates the inhibition of PC-12 neurite outgrowth in the presence of increasing concentrations of antibody Ab8 obtained following example 6.
Figure 63:
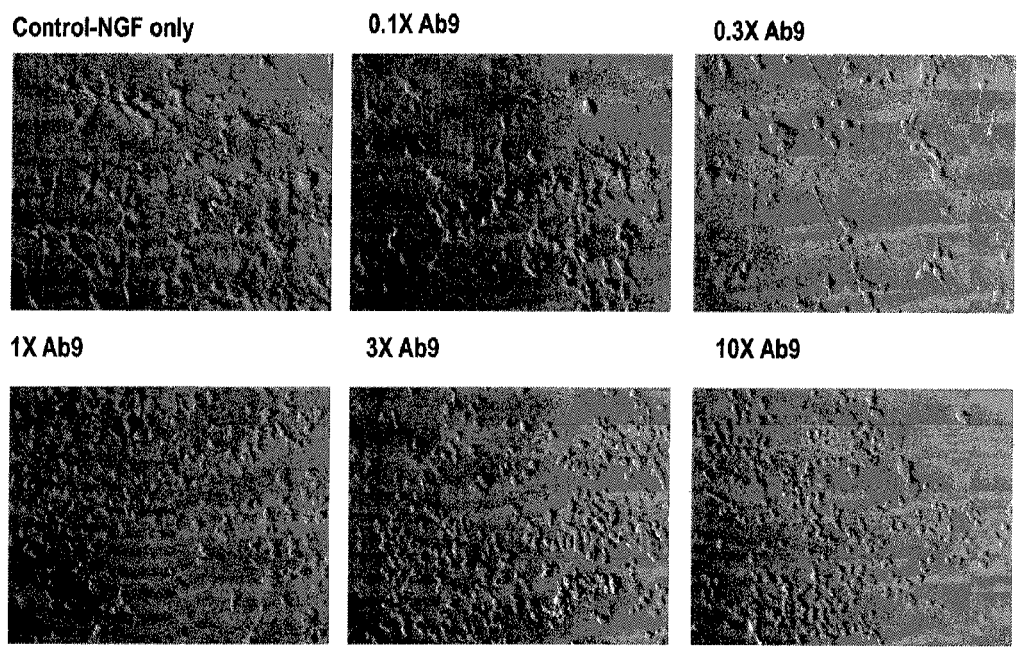
FIG. 63 demonstrates the inhibition of PC-12 neurite outgrowth in the presence of increasing concentrations of antibody Ab9 obtained following example 6.
Figure 64:
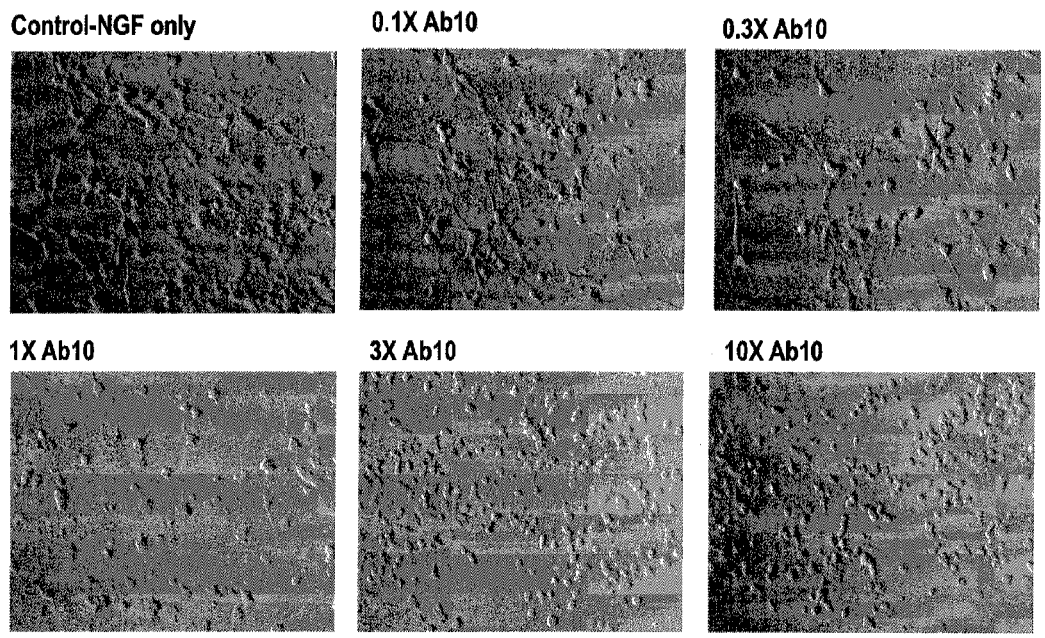
FIG. 64 demonstrates the inhibition of PC-12 neurite outgrowth in the presence of increasing concentrations of antibody Ab10 obtained following example 6.
Figure 65:
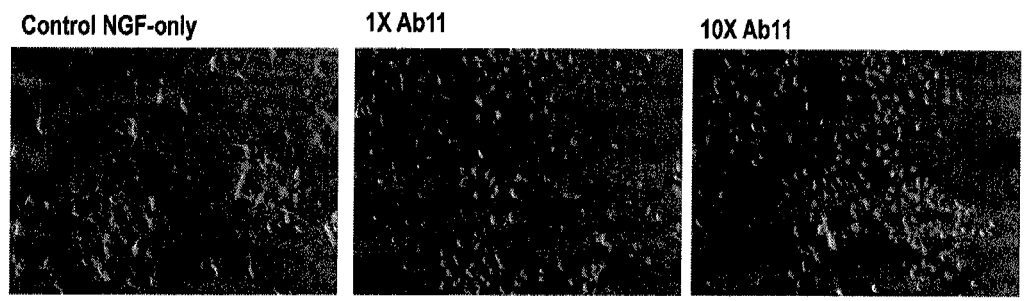
FIG. 65 demonstrates the inhibition of PC-12 neurite outgrowth in the presence of increasing concentrations of antibody Ab11 obtained following example 6.
Figure 67:
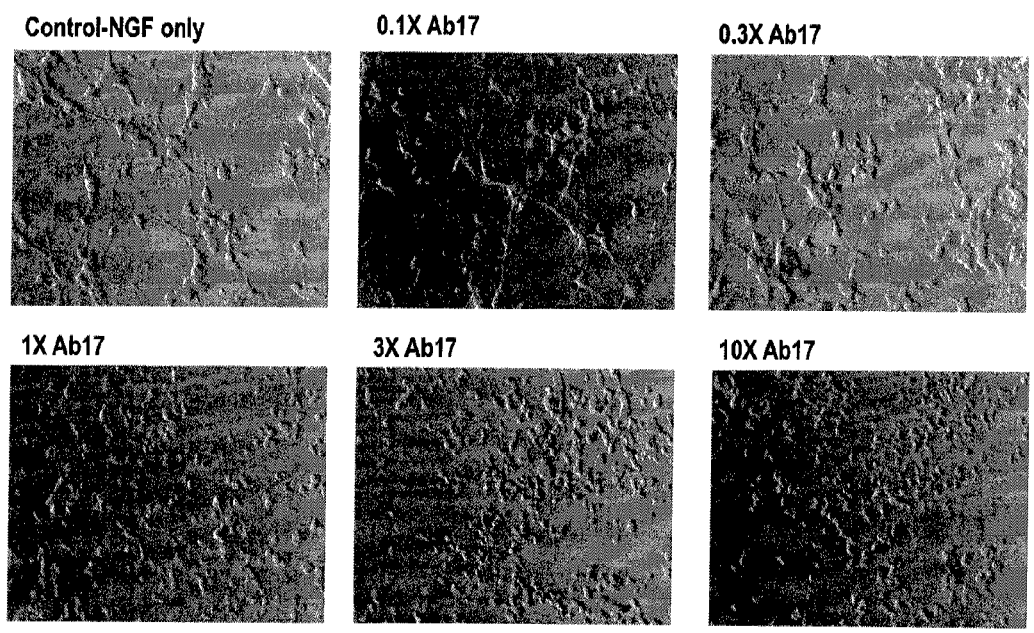
FIG. 67 demonstrates the inhibition of PC-12 neurite outgrowth in the presence of increasing concentrations of antibody Ab17 obtained following example 6.
Figure 68:
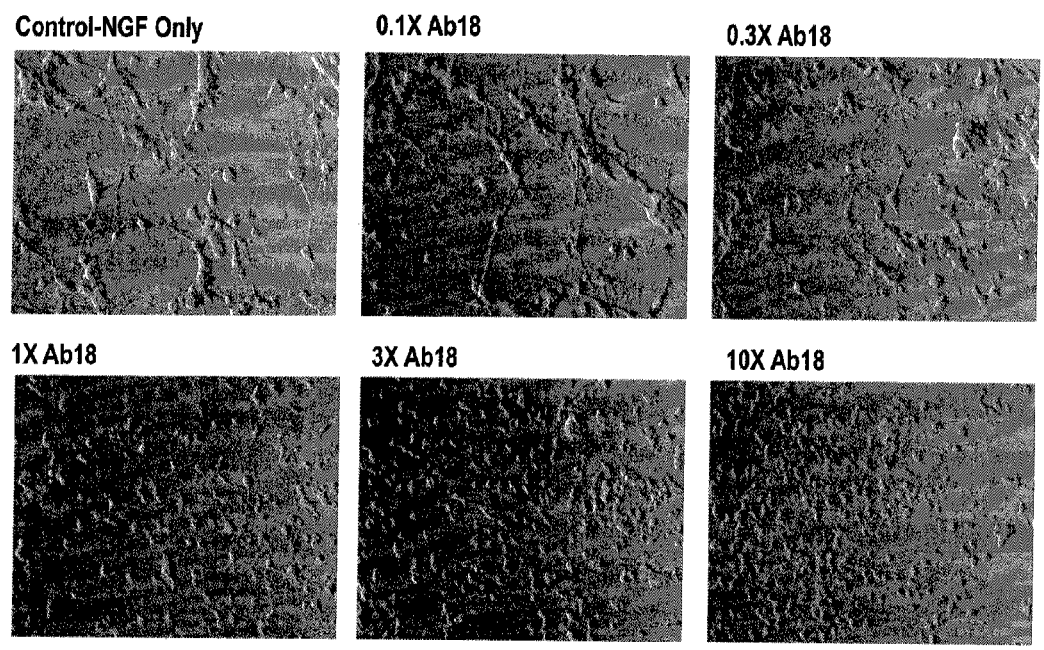
FIG. 68 demonstrates the inhibition of PC-12 neurite outgrowth in the presence of increasing concentrations of antibody Ab18 obtained following example 6.

Results: FIGS. 53 and 54 demonstrates that anti-NGF antibodies Ab3, Ab4, Ab15, and Ab16 do not inhibit binding of NGF to p75, while FIG. 55 demonstrates that antibody Ab5 inhibits binding of NGF to p75.

Example 6

Neurite PC12 Assay

The ability of anti-NGF antibodies to block NGF signaling mediated through the p75 and TrkA receptors was measured in vitro using a rat adrenal medulla cell line, PC12. PC12 cells express both p75 and TrkA receptors on their cell surface (Urdiales et al. Cell cycle phase-specific surface expression of nerve growth factor receptors TrkA and p75(NTR). J Neurosci (1998) vol. 18 (17) pp. 6767-75); (Greene and Tischler. Establishment of a noradrenergic clonal line of rat adrenal pheochromocytoma cells which respond to nerve growth factor. Proc Natl Acad Sci USA (1976) vol. 73 (7) pp. 2424-8). Briefly, PC12 cells were maintained in culture using 15% FBS RPMI and grown on a collagen I-coated flask for 48 hours before priming. The cells were then 'primed' for 72 hours by exposing them to 100 ng/mL NGF in differentiation media (1% horse serum RPMI). On the day of the assay, the cells were harvested with a cell scraper, resuspended, rinsed in differentiation media (without NGF) and plated onto a collagen I-coated 24-well plate. The final concentration of NGF in the assay was 100 ng/mL. The antibodies being tested were pre-incubated with the NGF at different molar ratios (from 10× to 0.1×) for 1 hour in differentiation media prior to adding them onto the PC-12 cells. On day 3, the media was gently removed and antibody-NGF mixtures were replaced. On day 10, the wells were observed under a microscope and representative fields were digitized using a 10× magnification lens.

Results: FIGS. 56-69 and FIGS. 78 and 79 demonstrate that anti-NGF antibodies Ab1-Ab3, Ab5-Ab11, Ab13, Ab15, Ab16, and Ab17-Ab19 inhibit the outgrowth of PC-12 neurite cells at increasing concentrations. It can be seen that antibodies Ab3, Ab15 and Ab16, when assayed at the same antibody concentrations as the other tested anti-NGF antibodies (those than antagonize the interaction of NGF with both Trka and p75), showed significantly less inhibition of the outgrowth of PC-12 neurite cells. This difference is believed to be attributable to the fact that Ab3, Ab15 and Ab16, all inhibit TrkA/NGF interactions and not NGF/p75 interactions, whereas the remaining tested antibodies inhibit the interaction of NGF with both TrkA and p75.

Example 7

Modulation of Pain Assessed by Gait Analysis

To assess the effect of anti-NGF agents (full length and Fab fragments) in their ability to modulate pain, a PGPS (peptidoglycan polysaccharide)-induced arthritis model was used. Briefly, male Lewis rats were injected with a solution of PGPS into their right ankle on day (−)17. One day later, ankles were evaluated for an inflammatory response to the PGPS injection and non-responders were eliminated. Responders were allowed to recover for seventeen days before an IV tail vein reactivation with PGPS.

Full-length antibodies were dosed once, either 2 hours or the night before reactivation. Fab fragments were administered once a day with the first dose administered two hours prior to reactivation. Gait analysis was performed by applying ink to the ventral surface of the foot and documenting weight bearing during movement (footprints) across paper. The rear feet of the rats were placed in blue colored ink, and black ink was applied to the dorsal side of the foot on the suspected painful leg. Rats were placed on paper and allowed to walk. Gaits were scored as follows: 0=normal, equal ink staining on both feet; 1=slight limp, toe staining evident and some heel staining; 2=limping, toes only staining; 3=dragging/carrying leg, black drag marks from dorsal side of foot present; 4=carrying leg, no staining from painful leg.

Figure 70:
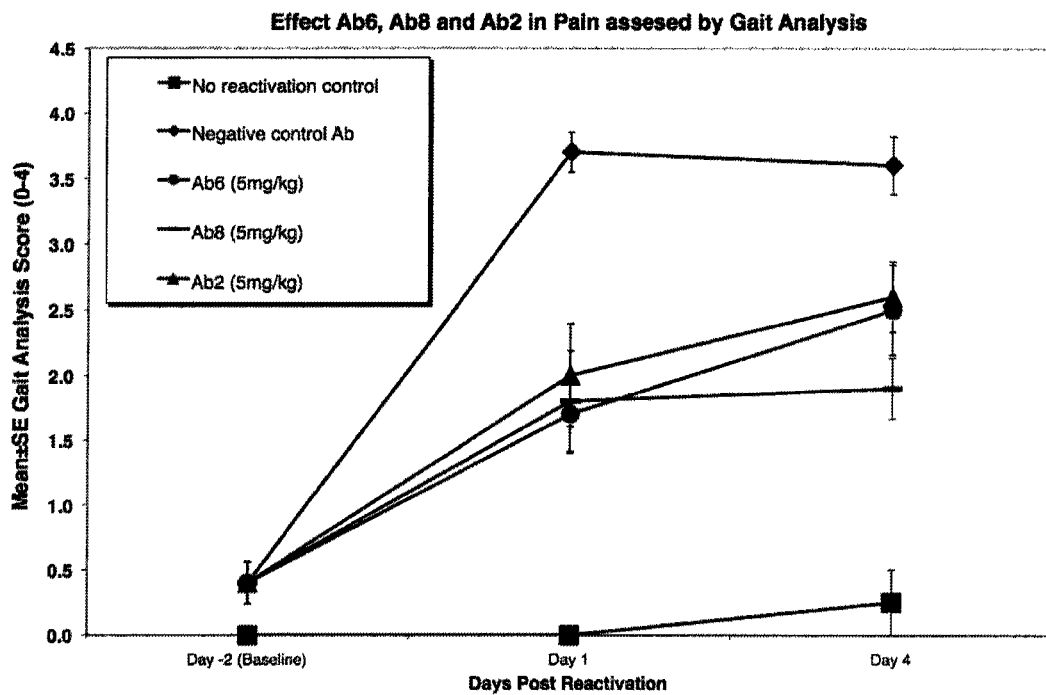
FIG. 70 demonstrates a statistically significant reduction in pain as assessed by Gait analysis following administration of antibodies Ab2, Ab6, and Ab8, when compared with results obtained with the controls following example 7.

Results: FIG. 70 demonstrates a statistically significant reduction in pain as assessed by Gait analysis following administration of antibodies Ab2, Ab6, and Ab8, when compared with results obtained with the controls.

Figure 71:
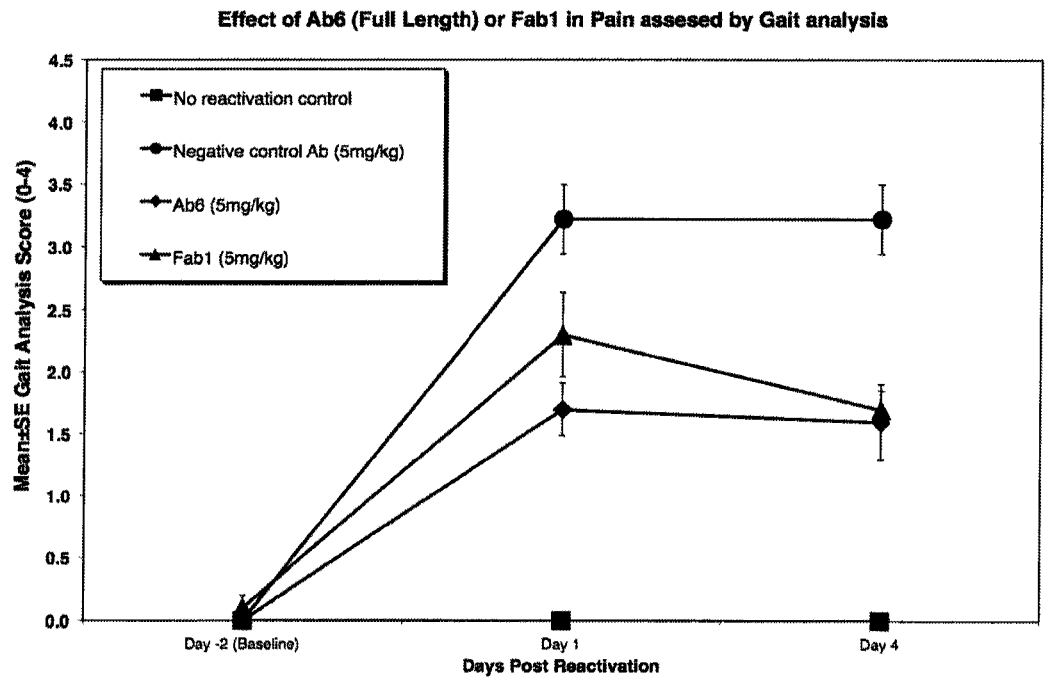
FIG. 71 demonstrates a statistically significant reduction in pain as assessed by Gait analysis following administration of antibody Ab6 and Fab1, when compared with results obtained with the controls following example 7.

FIG. 71 demonstrates a statistically significant reduction in pain as assessed by Gait analysis following administration of antibody Ab6 and Fab1, when compared with results obtained with the controls.

Figure 72:
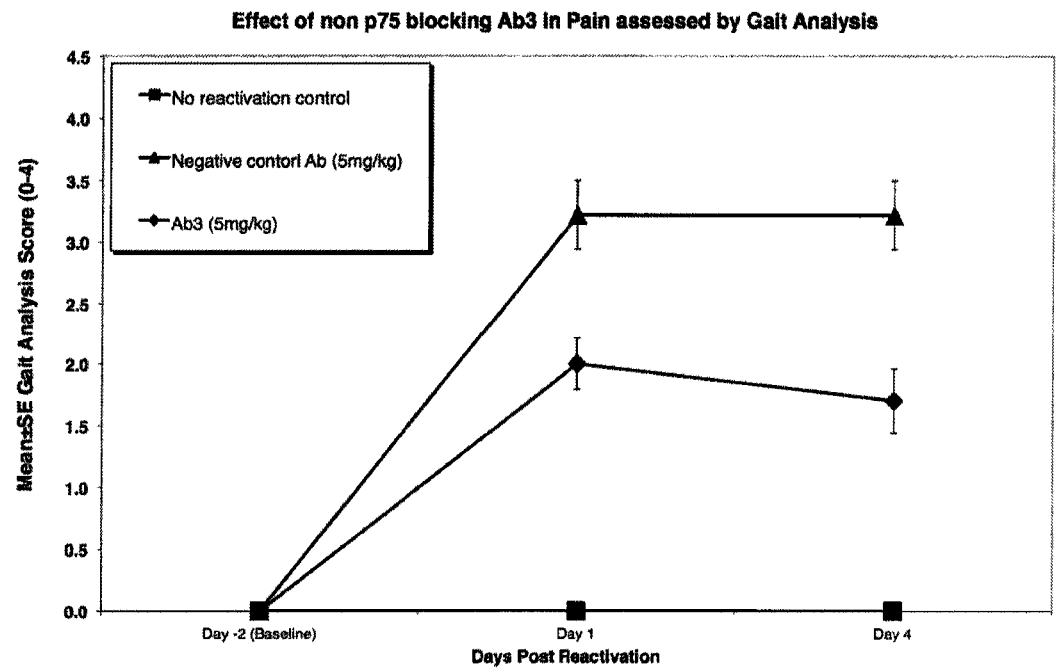
FIG. 72 demonstrates a statistically significant reduction in pain as assessed by Gait analysis following administration of antibody Ab3, when compared with results obtained with the controls following example 7.

FIG. 72 demonstrates a statistically significant reduction in pain as assessed by Gait analysis following administration of antibody Ab3, when compared with results obtained with the controls.

Figure 73:
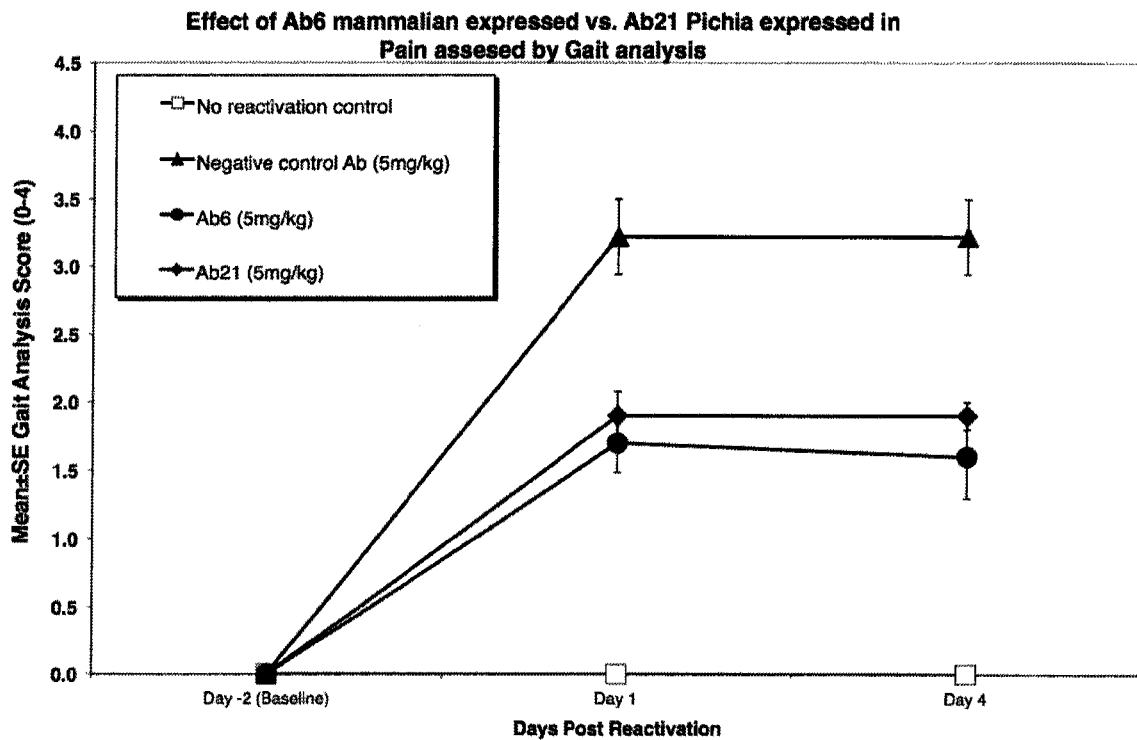
FIG. 73 demonstrates a statistically significant reduction in pain as assessed by Gait analysis following administration of antibody Ab6 and antibody Ab21, when compared with results obtained with the controls following example 7.

FIG. 73 demonstrates a statistically significant reduction in pain as assessed by Gait analysis following administration of antibody Ab6 and antibody Ab21, when compared with results obtained with the controls.

Example 8

Inflammation in PGPS-Induced Arthritis

The PGPS (peptidoglycan polysaccharide) induced arthritis model used to assess pain (Example 7) also has an associated inflammation response. To assess inflammation, all animals had caliper measurements taken of their ankles prior to reactivation on day 0, and then on days 1, 2, 3 and 4 to determine any anti-inflammatory or pro-inflammatory effects present in treated rats.

Figure 74:
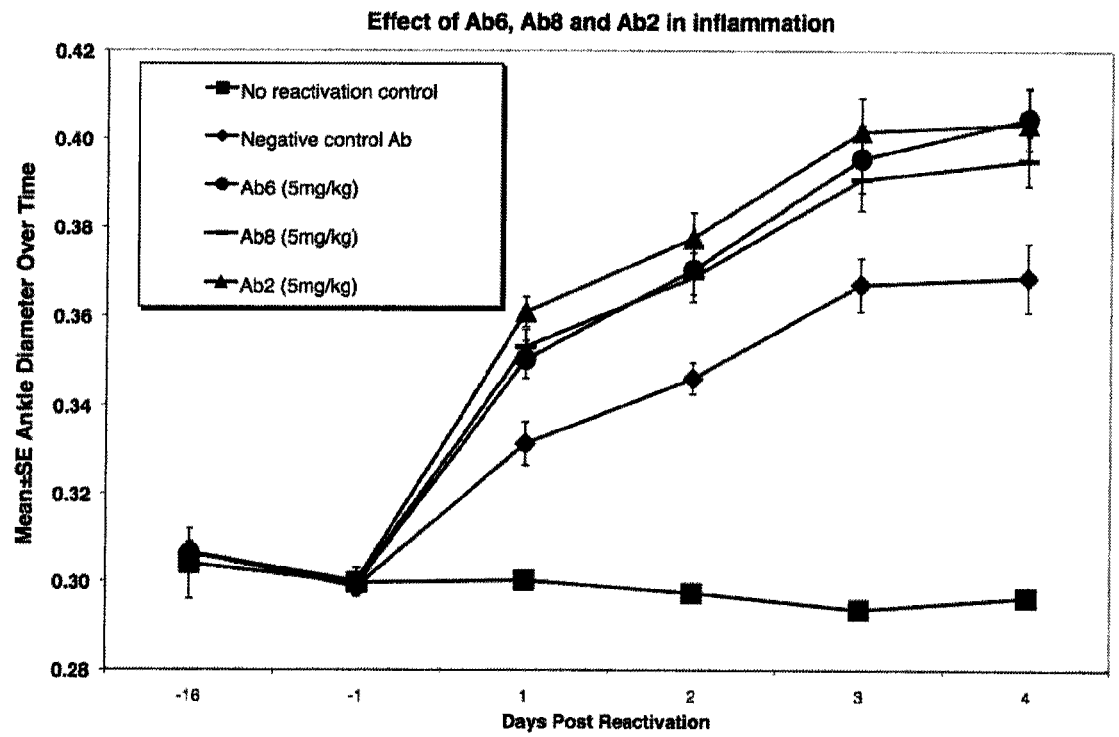
FIG. 74 demonstrates an increase in inflammation following administration of each of antibodies Ab2, Ab6, and Ab8, when compared with inflammation results for the controls.

Results: FIG. 74 demonstrates an increase in inflammation following administration of each of antibodies Ab2, Ab6, and Ab8, when compared with inflammation results for the controls.

Figure 75:
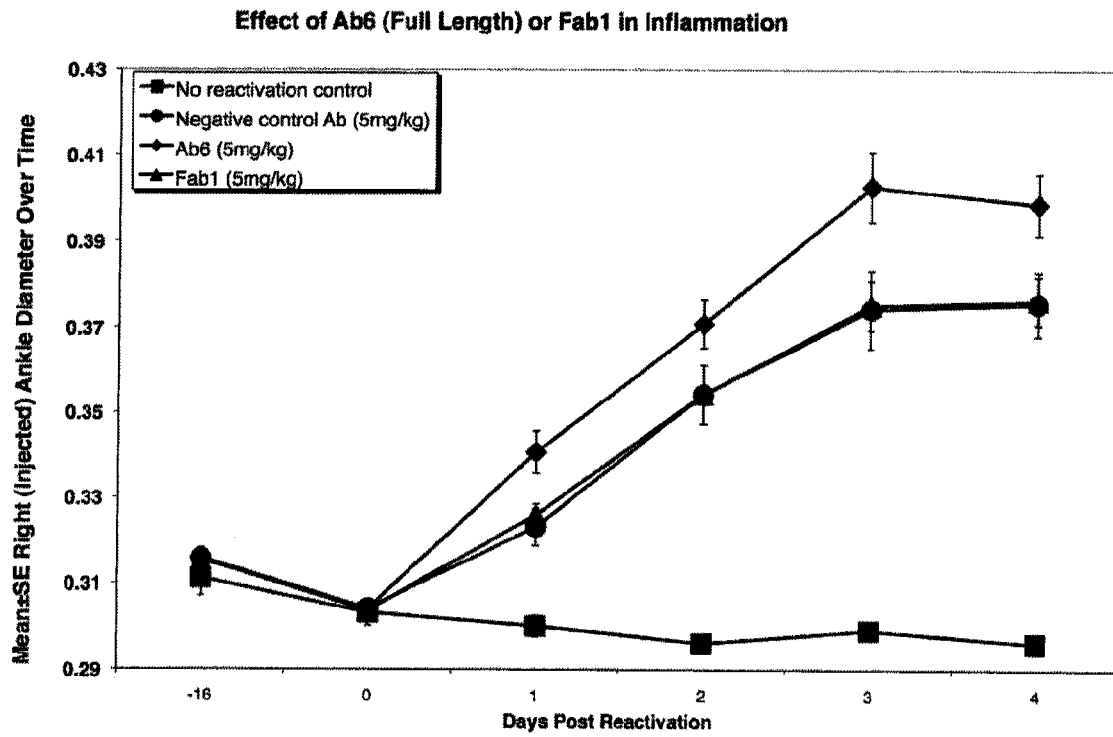
FIG. 75 demonstrates no significant increase in inflammation following administration of the Fab1 antibody fragment, when compared with inflammation results for the control. In contrast, administration of antibody Ab6 resulted in increased inflammation, when compared with inflammation results for the controls following example 8.

FIG. 75 demonstrates no significant increase in inflammation following administration of the Fab1 antibody fragment, when compared with inflammation results for the control. In contrast, administration of antibody Ab6 resulted in increased inflammation, when compared with inflammation results for the controls.

Figure 76:
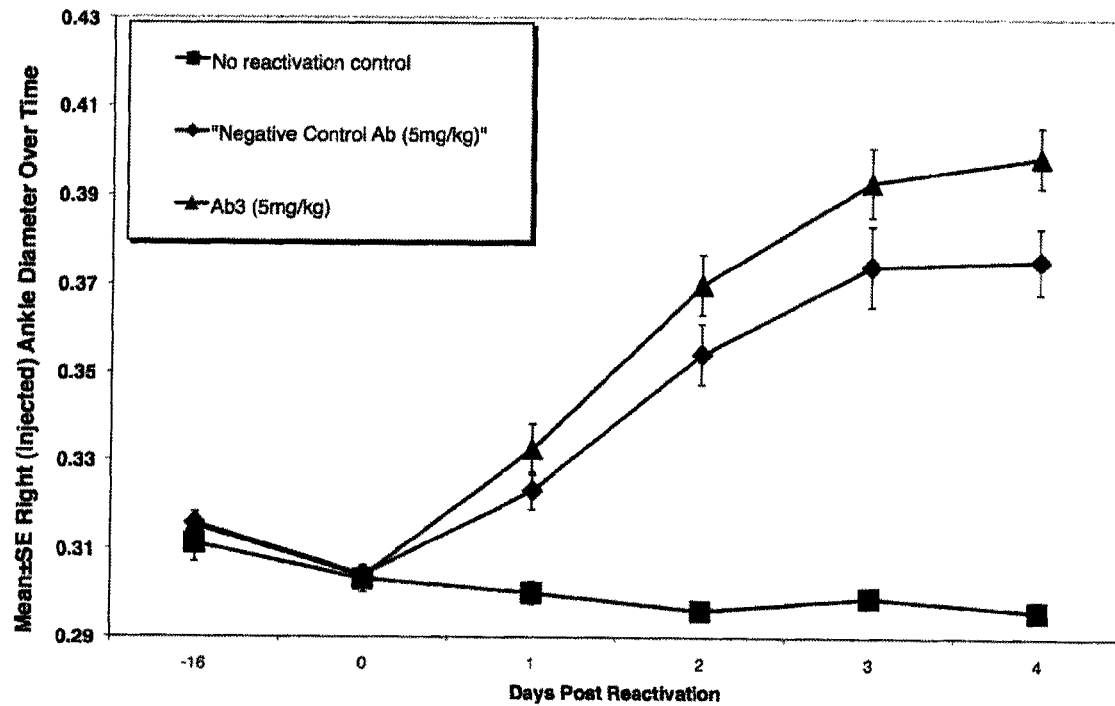
FIG. 76 demonstrates an increase in inflammation following administration of antibody Ab3, when compared with inflammation results for the controls following example 8.

FIG. 76 demonstrates an increase in inflammation following administration of antibody Ab3, when compared with inflammation results for the controls.

Figure 77:
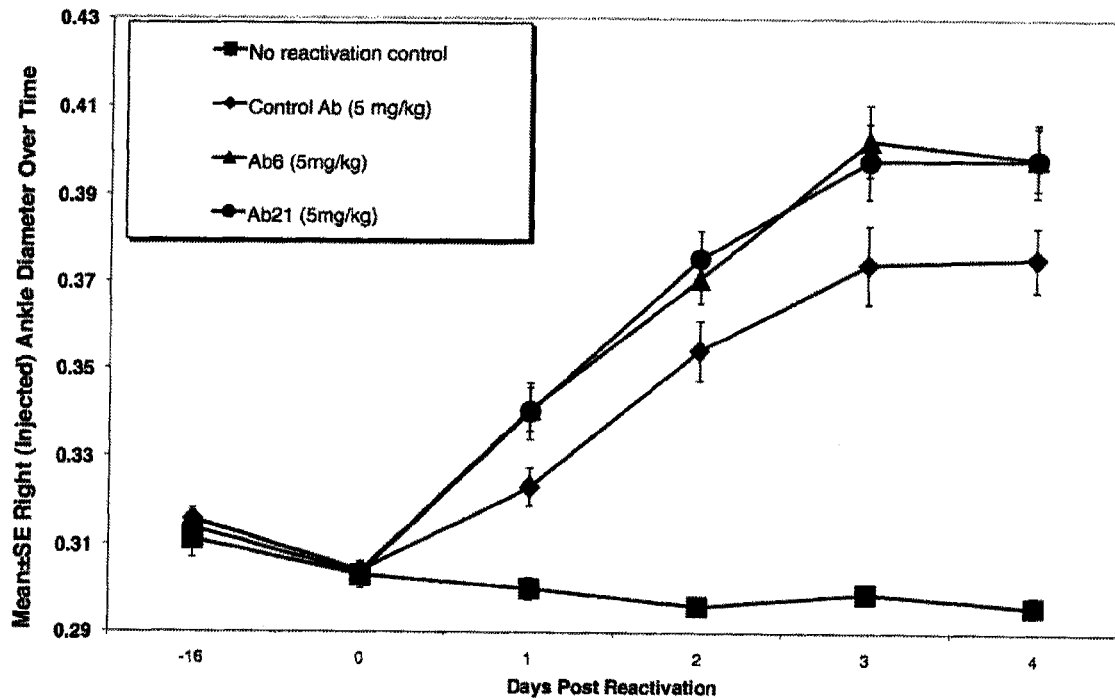
FIG. 77 also demonstrates an increase in inflammation following administration of antibody Ab6 and antibody Ab21, when compared with inflammation results for the controls following example 8.

FIG. 77 also demonstrates an increase in inflammation following administration of antibody Ab6 and antibody Ab21, when compared with inflammation results for the controls.

SEQUENCE LISTING

<160> NUMBER OF SEQ ID NOS: 413

<210> SEQ ID NO 1
<211> LENGTH: 111
<212> TYPE: PRT
<213> ORGANISM: Oryctolagus cuniculus

<400> SEQUENCE: 1

```
Ala Leu Val Met Thr Gln Thr Pro Ser Ser Val Ser Ala Ala Val Gly
 1               5                  10                  15

Gly Thr Val Thr Ile Asn Cys Gln Ala Ser Gln Asn Ile Tyr Ser Asn
            20                  25                  30

Leu Ala Trp Tyr Gln Gln Arg Pro Gly Gln Arg Pro Lys Leu Leu Ile
        35                  40                  45

Tyr Gly Ala Ser Asn Leu Asp Ala Gly Val Pro Ser Arg Phe Arg Gly
    50                  55                  60

Ser Gly Ser Gly Thr Glu Tyr Thr Leu Thr Ile Ser Asp Leu Glu Cys
65                  70                  75                  80

Asp Asp Val Gly Thr Tyr Tyr Cys Gln Ser Ala Phe Asp Ser Asp Ser
                85                  90                  95

Thr Glu Asn Thr Phe Gly Gly Gly Thr Glu Val Val Val Lys Arg
                100                 105                 110
```

<210> SEQ ID NO 2
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 2

```
Ala Leu Val Met Thr Gln Thr Pro Ser Ser Val Ser Ala Ala Val Gly
 1               5                  10                  15

Gly Thr Val Thr Ile Asn Cys Gln Ala Ser Gln Asn Ile Tyr Ser Asn
            20                  25                  30

Leu Ala Trp Tyr Gln Gln Arg Pro Gly Gln Arg Pro Lys Leu Leu Ile
        35                  40                  45

Tyr Gly Ala Ser Asn Leu Asp Ala Gly Val Pro Ser Arg Phe Arg Gly
    50                  55                  60

Ser Gly Ser Gly Thr Glu Tyr Thr Leu Thr Ile Ser Asp Leu Glu Cys
65                  70                  75                  80

Asp Asp Val Gly Thr Tyr Tyr Cys Gln Ser Ala Phe Asp Ser Asp Ser
                85                  90                  95

Thr Glu Asn Thr Phe Gly Gly Gly Thr Glu Val Val Val Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205
```

```
Thr Lys Ser Phe Asn Arg Gly Glu Cys
    210                 215

<210> SEQ ID NO 3
<211> LENGTH: 118
<212> TYPE: PRT
<213> ORGANISM: Oryctolagus cuniculus

<400> SEQUENCE: 3

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Val Ile Thr Ser Ile Gly Ser Thr Val Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Tyr
                85                  90                  95

Asp Asp Tyr Asp Glu Met Thr Tyr Phe Asn Ile Trp Gly Gln Gly Thr
            100                 105                 110

Leu Val Thr Val Ser Ser
            115

<210> SEQ ID NO 4
<211> LENGTH: 448
<212> TYPE: PRT
<213> ORGANISM: Artificial Sequence
<220> FEATURE:
<223> OTHER INFORMATION: Chemically Synthesized

<400> SEQUENCE: 4

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Val Ile Thr Ser Ile Gly Ser Thr Val Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Tyr
                85                  90                  95

Asp Asp Tyr Asp Glu Met Thr Tyr Phe Asn Ile Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 5
<211> LENGTH: 11
<212> TYPE: PRT
<213> ORGANISM: Oryctolagus cuniculus

<400> SEQUENCE: 5

Gln Ala Ser Gln Asn Ile Tyr Ser Asn Leu Ala
1               5                   10

<210> SEQ ID NO 6
<211> LENGTH: 7
<212> TYPE: PRT
<213> ORGANISM: Oryctolagus cuniculus

<400> SEQUENCE: 6

Gly Ala Ser Asn Leu Asp Ala
1               5

<210> SEQ ID NO 7
<211> LENGTH: 12
<212> TYPE: PRT
<213> ORGANISM: Oryctolagus cuniculus
```

```
<400> SEQUENCE: 7

Gln Ser Ala Phe Asp Ser Asp Ser Thr Glu Asn Thr
1               5                   10

<210> SEQ ID NO 8
<211> LENGTH: 5
<212> TYPE: PRT
<213> ORGANISM: Oryctolagus cuniculus

<400> SEQUENCE: 8

Ser Tyr Ala Met Ser
1               5

<210> SEQ ID NO 9
<211> LENGTH: 16
<212> TYPE: PRT
<213> ORGANISM: Oryctolagus cuniculus

<400> SEQUENCE: 9

Val Ile Thr Ser Ile Gly Ser Thr Val Tyr Ala Ser Trp Ala Lys Gly
1               5                   10                  15

<210> SEQ ID NO 10
<211> LENGTH: 13
<212> TYPE: PRT
<213> ORGANISM: Oryctolagus cuniculus

<400> SEQUENCE: 10

Gly Tyr Asp Asp Tyr Asp Glu Met Thr Tyr Phe Asn Ile
1               5                   10

<210> SEQ ID NO 11
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Gly Ala Ser Asn Leu Asp Ala Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Ser Ala Phe Asp Ser Asp Ser
                85                  90                  95

Thr Glu Asn Thr Phe Gly Gly Gly Thr Lys Val Glu Ile Lys Arg
            100                 105                 110

<210> SEQ ID NO 12
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 12
```

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Gly Ala Ser Asn Leu Asp Ala Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Ser Ala Phe Asp Ser Asp Ser
                85                  90                  95

Thr Glu Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 13
<211> LENGTH: 121
<212> TYPE: PRT
<213> ORGANISM: Artificial Sequence
<220> FEATURE:
<223> OTHER INFORMATION: Chemically Synthesized

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Ala Met Ser Trp Val Arg Gln Ala Pro Gly Lys Gly Leu Glu Trp Val
        35                  40                  45

Gly Val Ile Thr Ser Ile Gly Ser Thr Val Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Asp Asp Tyr Asp Glu Met Thr Tyr Phe Asn Ile Trp Gly
            100                 105                 110

Gln Gly Thr Leu Val Thr Val Ser Ser
        115                 120

<210> SEQ ID NO 14
<211> LENGTH: 451
```

```
<212> TYPE: PRT
<213> ORGANISM: Artificial Sequence
<220> FEATURE:
<223> OTHER INFORMATION: Chemically Synthesized

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Ala Met Ser Trp Val Arg Gln Ala Pro Gly Lys Gly Leu Glu Trp Val
        35                  40                  45

Gly Val Ile Thr Ser Ile Gly Ser Thr Val Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Tyr Asp Asp Tyr Asp Glu Met Thr Tyr Phe Asn Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380
```

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro Gly Lys
    450

<210> SEQ ID NO 15
<211> LENGTH: 11
<212> TYPE: PRT
<213> ORGANISM: Oryctolagus cuniculus

<400> SEQUENCE: 15

Gln Ala Ser Gln Asn Ile Tyr Ser Asn Leu Ala
1               5                   10

<210> SEQ ID NO 16
<211> LENGTH: 7
<212> TYPE: PRT
<213> ORGANISM: Oryctolagus cuniculus

<400> SEQUENCE: 16

Gly Ala Ser Asn Leu Asp Ala
1               5

<210> SEQ ID NO 17
<211> LENGTH: 12
<212> TYPE: PRT
<213> ORGANISM: Oryctolagus cuniculus

<400> SEQUENCE: 17

Gln Ser Ala Phe Asp Ser Asp Ser Thr Glu Asn Thr
1               5                   10

<210> SEQ ID NO 18
<211> LENGTH: 5
<212> TYPE: PRT
<213> ORGANISM: Oryctolagus cuniculus

<400> SEQUENCE: 18

Ser Tyr Ala Met Ser
1               5

<210> SEQ ID NO 19
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 19

Val Ile Thr Ser Ile Gly Ser Thr Val Tyr Ala Ser Ser Ala Lys Gly
1               5                   10                  15

<210> SEQ ID NO 20
<211> LENGTH: 13
<212> TYPE: PRT
<213> ORGANISM: Oryctolagus cuniculus

<400> SEQUENCE: 20

```
Gly Tyr Asp Asp Tyr Asp Glu Met Thr Tyr Phe Asn Ile
1               5                   10

<210> SEQ ID NO 21
<211> LENGTH: 111
<212> TYPE: PRT
<213> ORGANISM: Oryctolagus cuniculus

<400> SEQUENCE: 21

Ala Val Leu Thr Gln Thr Pro Ser Pro Val Ser Ala Ala Met Gly Asp
1               5                   10                  15

Thr Val Thr Ile Lys Cys Gln Ser Ser Gln Ser Val Tyr Lys Asn Asn
            20                  25                  30

Tyr Leu Ser Trp Tyr Gln Gln Lys Pro Gly Gln Pro Arg Leu Leu
        35                  40                  45

Ile Tyr Asp Ala Ser Asn Leu Pro Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Asp Tyr Asp Asp
                85                  90                  95

Ala Asp Asn Ala Phe Gly Gly Gly Thr Glu Val Val Val Lys Arg
            100                 105                 110

<210> SEQ ID NO 22
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 22

Ala Val Leu Thr Gln Thr Pro Ser Pro Val Ser Ala Ala Met Gly Asp
1               5                   10                  15

Thr Val Thr Ile Lys Cys Gln Ser Ser Gln Ser Val Tyr Lys Asn Asn
            20                  25                  30

Tyr Leu Ser Trp Tyr Gln Gln Lys Pro Gly Gln Pro Arg Leu Leu
        35                  40                  45

Ile Tyr Asp Ala Ser Asn Leu Pro Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Asp Tyr Asp Asp Asp
                85                  90                  95

Ala Asp Asn Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190
```

```
Lys Val Tyr Ala Cys Glu Val Thr His Gln Gly Leu Ser Ser Pro Val
            195                 200                 205

Thr Lys Ser Phe Asn Arg Gly Glu Cys
    210                 215

<210> SEQ ID NO 23
<211> LENGTH: 113
<212> TYPE: PRT
<213> ORGANISM: Oryctolagus cuniculus

<400> SEQUENCE: 23

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Val
            20                  25                  30

Met Ile Trp Val Arg Gln Ala Pro Gly Lys Gly Leu Glu Tyr Ile Gly
        35                  40                  45

Ile Thr Trp Ser Ala Gly Thr Tyr Tyr Ala Ser Trp Ala Lys Gly Arg
    50                  55                  60

Phe Thr Ile Ser Lys Thr Ser Ser Thr Thr Val Asp Leu Lys Ile Thr
65                  70                  75                  80

Ser Pro Thr Thr Glu Asp Thr Ala Thr Tyr Phe Cys Ala Gly Gly Gly
                85                  90                  95

Gly Ser Ile Tyr Asp Ile Trp Gly Pro Gly Thr Leu Val Thr Val Ser
            100                 105                 110

Ser

<210> SEQ ID NO 24
<211> LENGTH: 443
<212> TYPE: PRT
<213> ORGANISM: Artificial Sequence
<220> FEATURE:
<223> OTHER INFORMATION: Chemically Synthesized

<400> SEQUENCE: 24

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Val
            20                  25                  30

Met Ile Trp Val Arg Gln Ala Pro Gly Lys Gly Leu Glu Tyr Ile Gly
        35                  40                  45

Ile Thr Trp Ser Ala Gly Thr Tyr Tyr Ala Ser Trp Ala Lys Gly Arg
    50                  55                  60

Phe Thr Ile Ser Lys Thr Ser Ser Thr Thr Val Asp Leu Lys Ile Thr
65                  70                  75                  80

Ser Pro Thr Thr Glu Asp Thr Ala Thr Tyr Phe Cys Ala Gly Gly Gly
                85                  90                  95

Gly Ser Ile Tyr Asp Ile Trp Gly Pro Gly Thr Leu Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175
```

```
Ser Leu Ser Ser Val Val Thr Val Pro Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 25
<211> LENGTH: 13
<212> TYPE: PRT
<213> ORGANISM: Oryctolagus cuniculus

<400> SEQUENCE: 25

Gln Ser Ser Gln Ser Val Tyr Lys Asn Asn Tyr Leu Ser
1               5                   10

<210> SEQ ID NO 26
<211> LENGTH: 7
<212> TYPE: PRT
<213> ORGANISM: Oryctolagus cuniculus

<400> SEQUENCE: 26

Asp Ala Ser Asn Leu Pro Ser
1               5

<210> SEQ ID NO 27
<211> LENGTH: 11
<212> TYPE: PRT
<213> ORGANISM: Oryctolagus cuniculus
```

```
<400> SEQUENCE: 27

Leu Gly Asp Tyr Asp Asp Asp Ala Asp Asn Ala
1               5                   10

<210> SEQ ID NO 28
<211> LENGTH: 5
<212> TYPE: PRT
<213> ORGANISM: Oryctolagus cuniculus

<400> SEQUENCE: 28

Ser Tyr Val Met Ile
1               5

<210> SEQ ID NO 29
<211> LENGTH: 15
<212> TYPE: PRT
<213> ORGANISM: Oryctolagus cuniculus

<400> SEQUENCE: 29

Ile Thr Trp Ser Ala Gly Thr Tyr Tyr Ala Ser Trp Ala Lys Gly
1               5                   10                  15

<210> SEQ ID NO 30
<211> LENGTH: 8
<212> TYPE: PRT
<213> ORGANISM: Oryctolagus cuniculus

<400> SEQUENCE: 30

Gly Gly Gly Ser Ile Tyr Asp Ile
1               5

<210> SEQ ID NO 31
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Lys Asn
            20                  25                  30

Asn Tyr Leu Ser Trp Tyr Gln Gln Lys Pro Gly Lys Ala Pro Lys Leu
        35                  40                  45

Leu Ile Tyr Asp Ala Ser Asn Leu Pro Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Leu Gly Asp Tyr Asp Asp
                85                  90                  95

Asp Ala Asp Asn Ala Phe Gly Gly Gly Thr Lys Val Glu Ile Lys Arg
            100                 105                 110

<210> SEQ ID NO 32
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 32
```

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Lys Asn
            20                  25                  30

Asn Tyr Leu Ser Trp Tyr Gln Gln Lys Pro Gly Lys Ala Pro Lys Leu
        35                  40                  45

Leu Ile Tyr Asp Ala Ser Asn Leu Pro Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Leu Gly Tyr Asp Asp
                85                  90                  95

Asp Ala Asp Asn Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 33
<211> LENGTH: 115
<212> TYPE: PRT
<213> ORGANISM: Artificial Sequence
<220> FEATURE:
<223> OTHER INFORMATION: Chemically Synthesized

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Val Met Ile Trp Val Arg Gln Ala Pro Gly Lys Gly Leu Glu Tyr Ile
        35                  40                  45

Gly Ile Thr Trp Ser Ala Gly Thr Tyr Tyr Ala Ser Ser Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Gly
            85                  90                  95

Gly Gly Gly Ser Ile Tyr Asp Ile Trp Gly Gln Gly Thr Leu Val Thr
            100                 105                 110

Val Ser Ser
    115

<210> SEQ ID NO 34

```
<211> LENGTH: 445
<212> TYPE: PRT
<213> ORGANISM: Artificial Sequence
<220> FEATURE:
<223> OTHER INFORMATION: Chemically Synthesized

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Val Met Ile Trp Val Arg Gln Ala Pro Gly Lys Gly Leu Glu Tyr Ile
        35                  40                  45

Gly Ile Thr Trp Ser Ala Gly Thr Tyr Tyr Ala Ser Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Gly
                85                  90                  95

Gly Gly Gly Ser Ile Tyr Asp Ile Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ala Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

```
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 35
<211> LENGTH: 13
<212> TYPE: PRT
<213> ORGANISM: Oryctolagus cuniculus

<400> SEQUENCE: 35

Gln Ser Ser Gln Ser Val Tyr Lys Asn Asn Tyr Leu Ser
1               5                   10

<210> SEQ ID NO 36
<211> LENGTH: 7
<212> TYPE: PRT
<213> ORGANISM: Oryctolagus cuniculus

<400> SEQUENCE: 36

Asp Ala Ser Asn Leu Pro Ser
1               5

<210> SEQ ID NO 37
<211> LENGTH: 11
<212> TYPE: PRT
<213> ORGANISM: Oryctolagus cuniculus

<400> SEQUENCE: 37

Leu Gly Asp Tyr Asp Asp Asp Ala Asp Asn Ala
1               5                   10

<210> SEQ ID NO 38
<211> LENGTH: 5
<212> TYPE: PRT
<213> ORGANISM: Oryctolagus cuniculus

<400> SEQUENCE: 38

Ser Tyr Val Met Ile
1               5

<210> SEQ ID NO 39
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 39

Ile Thr Trp Ser Ala Gly Thr Tyr Tyr Ala Ser Ser Ala Lys Gly
1               5                   10                  15

<210> SEQ ID NO 40
<211> LENGTH: 8
<212> TYPE: PRT
<213> ORGANISM: Oryctolagus cuniculus

<400> SEQUENCE: 40

Gly Gly Gly Ser Ile Tyr Asp Ile
```

<210> SEQ ID NO 41
<211> LENGTH: 111
<212> TYPE: PRT
<213> ORGANISM: Oryctolagus cuniculus

<400> SEQUENCE: 41

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Ser Asn
            20                  25                  30

Leu Ala Trp Tyr Gln Gln Arg Pro Gly Gln Pro Pro Lys Leu Leu Ile
        35                  40                  45

Tyr Asp Ala Ser Thr Leu Glu Ser Gly Val Pro Ser Arg Phe Lys Gly
50                  55                  60

Ser Gly Ser Gly Thr Glu Tyr Thr Leu Thr Ile Ser Gly Val Glu Cys
65                  70                  75                  80

Ala Asp Ala Ala Ser Tyr Tyr Cys Gln Gln Gly Phe Thr Val Ser Asp
                85                  90                  95

Ile Asp Asn Ala Phe Gly Gly Gly Thr Glu Val Val Val Lys Arg
            100                 105                 110
```

<210> SEQ ID NO 42
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 42

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Ser Asn
            20                  25                  30

Leu Ala Trp Tyr Gln Gln Arg Pro Gly Gln Pro Pro Lys Leu Leu Ile
        35                  40                  45

Tyr Asp Ala Ser Thr Leu Glu Ser Gly Val Pro Ser Arg Phe Lys Gly
50                  55                  60

Ser Gly Ser Gly Thr Glu Tyr Thr Leu Thr Ile Ser Gly Val Glu Cys
65                  70                  75                  80

Ala Asp Ala Ala Ser Tyr Tyr Cys Gln Gln Gly Phe Thr Val Ser Asp
                85                  90                  95

Ile Asp Asn Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205
```

```
Thr Lys Ser Phe Asn Arg Gly Glu Cys
    210                 215
```

<210> SEQ ID NO 43
<211> LENGTH: 118
<212> TYPE: PRT
<213> ORGANISM: Oryctolagus cuniculus

<400> SEQUENCE: 43

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Val Gly Trp Val Arg Gln Ala Pro Gly Lys Gly Leu Glu Trp Ile Gly
        35                  40                  45

Ile Ile Gly Arg Asn Gly Asn Thr Trp Tyr Ala Ser Trp Ala Arg Gly
    50                  55                  60

Arg Phe Thr Ile Ser Lys Thr Ser Thr Thr Val Asp Leu Lys Ile Thr
65                  70                  75                  80

Ser Pro Thr Ser Glu Asp Thr Ala Thr Tyr Phe Cys Ala Arg Gly Tyr
                85                  90                  95

Gly Arg Ser Val Ala Tyr Tyr Val Phe Asn Ile Trp Gly Pro Gly Thr
            100                 105                 110

Leu Val Thr Val Ser Ser
            115
```

<210> SEQ ID NO 44
<211> LENGTH: 448
<212> TYPE: PRT
<213> ORGANISM: Artificial Sequence
<220> FEATURE:
<223> OTHER INFORMATION: Chemically Synthesized

<400> SEQUENCE: 44

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Val Gly Trp Val Arg Gln Ala Pro Gly Lys Gly Leu Glu Trp Ile Gly
        35                  40                  45

Ile Ile Gly Arg Asn Gly Asn Thr Trp Tyr Ala Ser Trp Ala Arg Gly
    50                  55                  60

Arg Phe Thr Ile Ser Lys Thr Ser Thr Thr Val Asp Leu Lys Ile Thr
65                  70                  75                  80

Ser Pro Thr Ser Glu Asp Thr Ala Thr Tyr Phe Cys Ala Arg Gly Tyr
                85                  90                  95

Gly Arg Ser Val Ala Tyr Tyr Val Phe Asn Ile Trp Gly Pro Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 45
<211> LENGTH: 11
<212> TYPE: PRT
<213> ORGANISM: Oryctolagus cuniculus

<400> SEQUENCE: 45

Gln Ala Ser Gln Ser Ile Tyr Ser Asn Leu Ala
1               5                   10

<210> SEQ ID NO 46
<211> LENGTH: 7
<212> TYPE: PRT
<213> ORGANISM: Oryctolagus cuniculus

<400> SEQUENCE: 46

Asp Ala Ser Thr Leu Glu Ser
1               5

<210> SEQ ID NO 47
<211> LENGTH: 12
<212> TYPE: PRT
<213> ORGANISM: Oryctolagus cuniculus

```
<400> SEQUENCE: 47

Gln Gln Gly Phe Thr Val Ser Asp Ile Asp Asn Ala
1               5                   10

<210> SEQ ID NO 48
<211> LENGTH: 5
<212> TYPE: PRT
<213> ORGANISM: Oryctolagus cuniculus

<400> SEQUENCE: 48

Asn Tyr Ala Val Gly
1               5

<210> SEQ ID NO 49
<211> LENGTH: 16
<212> TYPE: PRT
<213> ORGANISM: Oryctolagus cuniculus

<400> SEQUENCE: 49

Ile Ile Gly Arg Asn Gly Asn Thr Trp Tyr Ala Ser Trp Ala Arg Gly
1               5                   10                  15

<210> SEQ ID NO 50
<211> LENGTH: 13
<212> TYPE: PRT
<213> ORGANISM: Oryctolagus cuniculus

<400> SEQUENCE: 50

Gly Tyr Gly Arg Ser Val Ala Tyr Tyr Val Phe Asn Ile
1               5                   10

<210> SEQ ID NO 51
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 51

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Gly Phe Thr Val Ser Asp
                85                  90                  95

Ile Asp Asn Ala Phe Gly Gly Gly Thr Lys Val Glu Ile Lys Arg
            100                 105                 110

<210> SEQ ID NO 52
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 52
```

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Gly Phe Thr Val Ser Asp
                85                  90                  95

Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 53
<211> LENGTH: 121
<212> TYPE: PRT
<213> ORGANISM: Artificial Sequence
<220> FEATURE:
<223> OTHER INFORMATION: Chemically Synthesized

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Val Gly Trp Val Arg Gln Ala Pro Gly Lys Gly Leu Glu Trp Val
        35                  40                  45

Gly Ile Ile Gly Arg Asn Gly Asn Thr Trp Tyr Ala Ser Ser Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Arg Ser Val Ala Tyr Tyr Val Phe Asn Ile Trp Gly
            100                 105                 110

Pro Gly Thr Leu Val Thr Val Ser Ser
        115                 120

<210> SEQ ID NO 54
<211> LENGTH: 451
```

```
<212> TYPE: PRT
<213> ORGANISM: Artificial Sequence
<220> FEATURE:
<223> OTHER INFORMATION: Chemically Synthesized

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Val Gly Trp Val Arg Gln Ala Pro Gly Lys Gly Leu Glu Trp Val
        35                  40                  45

Gly Ile Ile Gly Arg Asn Gly Asn Thr Trp Tyr Ala Ser Ser Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Arg Ser Val Ala Tyr Tyr Val Phe Asn Ile Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 55
<211> LENGTH: 11
<212> TYPE: PRT
<213> ORGANISM: Oryctolagus cuniculus

<400> SEQUENCE: 55

Gln Ala Ser Gln Ser Ile Tyr Ser Asn Leu Ala
1               5                   10

<210> SEQ ID NO 56
<211> LENGTH: 7
<212> TYPE: PRT
<213> ORGANISM: Oryctolagus cuniculus

<400> SEQUENCE: 56

Asp Ala Ser Thr Leu Glu Ser
1               5

<210> SEQ ID NO 57
<211> LENGTH: 12
<212> TYPE: PRT
<213> ORGANISM: Oryctolagus cuniculus

<400> SEQUENCE: 57

Gln Gln Gly Phe Thr Val Ser Asp Ile Asp Asn Ala
1               5                   10

<210> SEQ ID NO 58
<211> LENGTH: 5
<212> TYPE: PRT
<213> ORGANISM: Oryctolagus cuniculus

<400> SEQUENCE: 58

Asn Tyr Ala Val Gly
1               5

<210> SEQ ID NO 59
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 59

Ile Ile Gly Arg Asn Gly Asn Thr Trp Tyr Ala Ser Ser Ala Arg Gly
1               5                   10                  15

<210> SEQ ID NO 60
<211> LENGTH: 13
<212> TYPE: PRT
<213> ORGANISM: Oryctolagus cuniculus

<400> SEQUENCE: 60
```

```
Gly Tyr Gly Arg Ser Val Ala Tyr Tyr Val Phe Asn Ile
1               5                   10
```

<210> SEQ ID NO 61
<211> LENGTH: 112
<212> TYPE: PRT
<213> ORGANISM: Oryctolagus cuniculus

<400> SEQUENCE: 61

```
Ala Asp Val Val Met Thr Gln Thr Pro Ala Ser Val Ser Gln Pro Val
1               5                   10                  15

Gly Gly Thr Val Thr Ile Lys Cys Gln Ala Ser Glu Asp Ile Tyr Asn
            20                  25                  30

Leu Leu Ala Trp Tyr Gln Gln Lys Pro Gly Gln Pro Pro Lys Leu Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Glu Tyr Thr Leu Thr Ile Ser Gly Leu Glu
65                  70                  75                  80

Cys Ala Asp Ala Ala Thr Tyr Tyr Cys Gln Asn Asn Tyr Leu Val Thr
                85                  90                  95

Thr Tyr Gly Val Ala Phe Gly Gly Gly Thr Glu Val Val Val Lys Arg
            100                 105                 110
```

<210> SEQ ID NO 62
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 62

```
Ala Asp Val Val Met Thr Gln Thr Pro Ala Ser Val Ser Gln Pro Val
1               5                   10                  15

Gly Gly Thr Val Thr Ile Lys Cys Gln Ala Ser Glu Asp Ile Tyr Asn
            20                  25                  30

Leu Leu Ala Trp Tyr Gln Gln Lys Pro Gly Gln Pro Pro Lys Leu Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Glu Tyr Thr Leu Thr Ile Ser Gly Leu Glu
65                  70                  75                  80

Cys Ala Asp Ala Ala Thr Tyr Tyr Cys Gln Asn Asn Tyr Leu Val Thr
                85                  90                  95

Thr Tyr Gly Val Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 63
<211> LENGTH: 120
<212> TYPE: PRT
<213> ORGANISM: Oryctolagus cuniculus

<400> SEQUENCE: 63

Gln Glu Gln Leu Lys Glu Ser Gly Gly Arg Leu Val Thr Pro Gly Thr
1               5                   10                  15

Pro Leu Thr Leu Thr Cys Thr Val Ser Gly Phe Ser Leu Ser Ser Tyr
            20                  25                  30

Ala Met Ile Trp Val Arg Gln Ala Pro Gly Lys Gly Leu Glu Tyr Ile
            35                  40                  45

Gly Tyr Ile Asp Thr Asp Thr Ser Ala Tyr Tyr Ala Ser Trp Val Lys
    50                  55                  60

Gly Arg Phe Thr Ile Ser Arg Thr Ser Thr Thr Val Asp Leu Lys Ile
65                  70                  75                  80

Thr Ser Pro Thr Thr Glu Asp Thr Ala Thr Tyr Phe Cys Ala Arg Ser
                85                  90                  95

Tyr Ala Ala Tyr Gly Gly Tyr Pro Ala Thr Phe Asp Pro Trp Gly Pro
            100                 105                 110

Gly Thr Leu Val Thr Val Ser Ser
        115                 120

<210> SEQ ID NO 64
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 64

Gln Glu Gln Leu Lys Glu Ser Gly Gly Arg Leu Val Thr Pro Gly Thr
1               5                   10                  15

Pro Leu Thr Leu Thr Cys Thr Val Ser Gly Phe Ser Leu Ser Ser Tyr
            20                  25                  30

Ala Met Ile Trp Val Arg Gln Ala Pro Gly Lys Gly Leu Glu Tyr Ile
            35                  40                  45

Gly Tyr Ile Asp Thr Asp Thr Ser Ala Tyr Tyr Ala Ser Trp Val Lys
    50                  55                  60

Gly Arg Phe Thr Ile Ser Arg Thr Ser Thr Thr Val Asp Leu Lys Ile
65                  70                  75                  80

Thr Ser Pro Thr Thr Glu Asp Thr Ala Thr Tyr Phe Cys Ala Arg Ser
                85                  90                  95

Tyr Ala Ala Tyr Gly Gly Tyr Pro Ala Thr Phe Asp Pro Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val

```
                165                 170                 175
Leu Gln Ser Ser Gly Leu Tyr Ser Leu Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
    275                 280                 285
Asn Ala Lys Thr Lys Pro Arg Glu Glu Gln Tyr Ala Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Glu Glu Met Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly Lys
    450

<210> SEQ ID NO 65
<211> LENGTH: 11
<212> TYPE: PRT
<213> ORGANISM: Oryctolagus cuniculus

<400> SEQUENCE: 65

Gln Ala Ser Glu Asp Ile Tyr Asn Leu Leu Ala
1               5                   10

<210> SEQ ID NO 66
<211> LENGTH: 7
<212> TYPE: PRT
<213> ORGANISM: Oryctolagus cuniculus

<400> SEQUENCE: 66

Ser Ala Ser Thr Leu Ala Ser
1               5
```

<210> SEQ ID NO 67
<211> LENGTH: 12
<212> TYPE: PRT
<213> ORGANISM: Oryctolagus cuniculus

<400> SEQUENCE: 67

Gln Asn Asn Tyr Leu Val Thr Thr Tyr Gly Val Ala
1               5                   10

<210> SEQ ID NO 68
<211> LENGTH: 5
<212> TYPE: PRT
<213> ORGANISM: Oryctolagus cuniculus

<400> SEQUENCE: 68

Ser Tyr Ala Met Ile
1               5

<210> SEQ ID NO 69
<211> LENGTH: 16
<212> TYPE: PRT
<213> ORGANISM: Oryctolagus cuniculus

<400> SEQUENCE: 69

Tyr Ile Asp Thr Asp Thr Ser Ala Tyr Tyr Ala Ser Trp Val Lys Gly
1               5                   10                  15

<210> SEQ ID NO 70
<211> LENGTH: 14
<212> TYPE: PRT
<213> ORGANISM: Oryctolagus cuniculus

<400> SEQUENCE: 70

Ser Tyr Ala Ala Tyr Gly Gly Tyr Pro Ala Thr Phe Asp Pro
1               5                   10

<210> SEQ ID NO 71
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Asn Leu
            20                  25                  30

Leu Ala Trp Tyr Gln Gln Lys Pro Gly Lys Val Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Asn Asn Tyr Leu Val Thr Thr
                85                  90                  95

Tyr Gly Val Ala Phe Gly Gly Gly Thr Lys Val Glu Ile Lys Arg
            100                 105                 110

<210> SEQ ID NO 72
<211> LENGTH: 217
<212> TYPE: PRT
<213> ORGANISM: Artificial Sequence

```
<220> FEATURE:
<223> OTHER INFORMATION: Chemically Synthesized

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Asn Leu
            20                  25                  30

Leu Ala Trp Tyr Gln Gln Lys Pro Gly Lys Val Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Asn Asn Tyr Leu Val Thr Thr
                85                  90                  95

Tyr Gly Val Ala Phe Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 73
<211> LENGTH: 122
<212> TYPE: PRT
<213> ORGANISM: Artificial Sequence
<220> FEATURE:
<223> OTHER INFORMATION: Chemically Synthesized

<400> SEQUENCE: 73

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ile Trp Val Arg Gln Ala Pro Gly Lys Gly Leu Glu Tyr Ile
        35                  40                  45

Gly Tyr Ile Asp Thr Asp Thr Ser Ala Tyr Tyr Ala Ser Ser Val Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Ser Tyr Ala Ala Tyr Gly Gly Tyr Pro Ala Thr Phe Asp Pro Trp
            100                 105                 110

Gly Gln Gly Thr Leu Val Thr Val Ser Ser
        115                 120
```

115                 120

<210> SEQ ID NO 74
<211> LENGTH: 452
<212> TYPE: PRT
<213> ORGANISM: Artificial Sequence
<220> FEATURE:
<223> OTHER INFORMATION: Chemically Synthesized

<400> SEQUENCE: 74

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met Ile Trp Val Arg Gln Ala Pro Gly Lys Gly Leu Glu Tyr Ile
            35                  40                  45

Gly Tyr Ile Asp Thr Asp Thr Ser Ala Tyr Tyr Ala Ser Ser Val Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Ser Tyr Ala Ala Tyr Gly Gly Tyr Pro Ala Thr Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val

```
                355                 360                 365
Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Cys Ser Val
        420                 425                 430

Met His Glu Ala Leu His Asn His Tyr Thr Gln Lys Ser Leu Ser Leu
                435                 440                 445

Ser Pro Gly Lys
    450

<210> SEQ ID NO 75
<211> LENGTH: 11
<212> TYPE: PRT
<213> ORGANISM: Oryctolagus cuniculus

<400> SEQUENCE: 75

Gln Ala Ser Glu Asp Ile Tyr Asn Leu Leu Ala
1               5                   10

<210> SEQ ID NO 76
<211> LENGTH: 7
<212> TYPE: PRT
<213> ORGANISM: Oryctolagus cuniculus

<400> SEQUENCE: 76

Ser Ala Ser Thr Leu Ala Ser
1               5

<210> SEQ ID NO 77
<211> LENGTH: 12
<212> TYPE: PRT
<213> ORGANISM: Oryctolagus cuniculus

<400> SEQUENCE: 77

Gln Asn Asn Tyr Leu Val Thr Thr Tyr Gly Val Ala
1               5                   10

<210> SEQ ID NO 78
<211> LENGTH: 5
<212> TYPE: PRT
<213> ORGANISM: Oryctolagus cuniculus

<400> SEQUENCE: 78

Ser Tyr Ala Met Ile
1               5

<210> SEQ ID NO 79
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 79

Tyr Ile Asp Thr Asp Thr Ser Ala Tyr Tyr Ala Ser Ser Val Lys Gly
1               5                   10                  15

<210> SEQ ID NO 80
```

```
<211> LENGTH: 14
<212> TYPE: PRT
<213> ORGANISM: Oryctolagus cuniculus

<400> SEQUENCE: 80

Ser Tyr Ala Ala Tyr Gly Gly Tyr Pro Ala Thr Phe Asp Pro
1               5                   10

<210> SEQ ID NO 81
<211> LENGTH: 111
<212> TYPE: PRT
<213> ORGANISM: Oryctolagus cuniculus

<400> SEQUENCE: 81

Ala Tyr Asp Met Thr Gln Thr Pro Ala Ser Val Ser Ala Ala Val Gly
1               5                   10                  15

Gly Thr Val Thr Ile Lys Cys Gln Ala Ser Glu Asn Ile Gly Ser Tyr
                20                  25                  30

Leu Ala Trp Tyr Gln Gln Lys Pro Gly Gln Pro Pro Glu Leu Leu Ile
            35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Asn Ser Glu Asn
                85                  90                  95

Leu Asp Asn Ala Phe Gly Gly Gly Thr Glu Val Val Val Lys Arg
                100                 105                 110

<210> SEQ ID NO 82
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 82

Ala Tyr Asp Met Thr Gln Thr Pro Ala Ser Val Ser Ala Ala Val Gly
1               5                   10                  15

Gly Thr Val Thr Ile Lys Cys Gln Ala Ser Glu Asn Ile Gly Ser Tyr
                20                  25                  30

Leu Ala Trp Tyr Gln Gln Lys Pro Gly Gln Pro Pro Glu Leu Leu Ile
            35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Asn Ser Glu Asn
                85                  90                  95

Leu Asp Asn Ala Phe Gly Gly Gly Thr Glu Val Val Val Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
```

```
                    165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 83
<211> LENGTH: 115
<212> TYPE: PRT
<213> ORGANISM: Oryctolagus cuniculus

<400> SEQUENCE: 83

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Met Tyr Ser
            20                  25                  30

Met Gly Trp Val Arg Gln Ala Pro Gly Lys Gly Leu Glu Tyr Ile Gly
        35                  40                  45

Trp Ile Ser Tyr Gly Gly Thr Ala Tyr Tyr Ala Ser Trp Ala Lys Gly
    50                  55                  60

Arg Phe Thr Ile Ser Lys Thr Ser Thr Val Glu Leu Lys Ile Thr
65                  70                  75                  80

Ser Pro Thr Ile Glu Asp Thr Ala Thr Tyr Phe Cys Ala Arg Glu Thr
                85                  90                  95

Pro Val Asn Tyr Tyr Leu Asp Ile Trp Gly Gln Gly Thr Leu Val Thr
            100                 105                 110

Val Ser Ser
        115

<210> SEQ ID NO 84
<211> LENGTH: 445
<212> TYPE: PRT
<213> ORGANISM: Artificial Sequence
<220> FEATURE:
<223> OTHER INFORMATION: Chemically Synthesized

<400> SEQUENCE: 84

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Met Tyr Ser
            20                  25                  30

Met Gly Trp Val Arg Gln Ala Pro Gly Lys Gly Leu Glu Tyr Ile Gly
        35                  40                  45

Trp Ile Ser Tyr Gly Gly Thr Ala Tyr Tyr Ala Ser Trp Ala Lys Gly
    50                  55                  60

Arg Phe Thr Ile Ser Lys Thr Ser Thr Val Glu Leu Lys Ile Thr
65                  70                  75                  80

Ser Pro Thr Ile Glu Asp Thr Ala Thr Tyr Phe Cys Ala Arg Glu Thr
                85                  90                  95

Pro Val Asn Tyr Tyr Leu Asp Ile Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Ala Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 85
<211> LENGTH: 11
<212> TYPE: PRT
<213> ORGANISM: Oryctolagus cuniculus

<400> SEQUENCE: 85

Gln Ala Ser Glu Asn Ile Gly Ser Tyr Leu Ala
1               5                   10

<210> SEQ ID NO 86
<211> LENGTH: 7
<212> TYPE: PRT
<213> ORGANISM: Oryctolagus cuniculus

<400> SEQUENCE: 86

Arg Ala Ser Thr Leu Ala Ser
1               5
```

-continued

```
<210> SEQ ID NO 87
<211> LENGTH: 12
<212> TYPE: PRT
<213> ORGANISM: Oryctolagus cuniculus

<400> SEQUENCE: 87

Gln Gln Gly Tyr Asn Ser Glu Asn Leu Asp Asn Ala
1               5                   10

<210> SEQ ID NO 88
<211> LENGTH: 5
<212> TYPE: PRT
<213> ORGANISM: Oryctolagus cuniculus

<400> SEQUENCE: 88

Met Tyr Ser Met Gly
1               5

<210> SEQ ID NO 89
<211> LENGTH: 16
<212> TYPE: PRT
<213> ORGANISM: Oryctolagus cuniculus

<400> SEQUENCE: 89

Trp Ile Ser Tyr Gly Gly Thr Ala Tyr Tyr Ala Ser Trp Ala Lys Gly
1               5                   10                  15

<210> SEQ ID NO 90
<211> LENGTH: 10
<212> TYPE: PRT
<213> ORGANISM: Oryctolagus cuniculus

<400> SEQUENCE: 90

Glu Thr Pro Val Asn Tyr Tyr Leu Asp Ile
1               5                   10

<210> SEQ ID NO 91
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 91

Ala Tyr Asp Met Thr Gln Ser Pro Ser Ser Leu Ser Ala Ser Val Gly
1               5                   10                  15

Asp Arg Val Thr Ile Thr Cys Gln Ala Ser Glu Asn Ile Gly Ser Tyr
            20                  25                  30

Leu Ala Trp Tyr Gln Gln Lys Pro Gly Lys Val Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Tyr Asn Ser Glu Asn
                85                  90                  95

Leu Asp Asn Ala Phe Gly Gly Gly Thr Lys Val Glu Ile Lys Arg
            100                 105                 110

<210> SEQ ID NO 92
<211> LENGTH: 217
```

```
<212> TYPE: PRT
<213> ORGANISM: Artificial Sequence
<220> FEATURE:
<223> OTHER INFORMATION: Chemically Synthesized

<400> SEQUENCE: 92

Ala Tyr Asp Met Thr Gln Ser Pro Ser Ser Leu Ser Ala Ser Val Gly
1               5                   10                  15

Asp Arg Val Thr Ile Thr Cys Gln Ala Ser Glu Asn Ile Gly Ser Tyr
            20                  25                  30

Leu Ala Trp Tyr Gln Gln Lys Pro Gly Lys Val Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Tyr Asn Ser Glu Asn
                85                  90                  95

Leu Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
210                 215

<210> SEQ ID NO 93
<211> LENGTH: 118
<212> TYPE: PRT
<213> ORGANISM: Artificial Sequence
<220> FEATURE:
<223> OTHER INFORMATION: Chemically Synthesized

<400> SEQUENCE: 93

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Met Tyr
            20                  25                  30

Ser Met Gly Trp Val Arg Gln Ala Pro Gly Lys Gly Leu Glu Tyr Ile
        35                  40                  45

Gly Trp Ile Ser Tyr Gly Gly Thr Ala Tyr Tyr Ala Ser Ser Ala Lys
50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Glu Thr Pro Val Asn Tyr Tyr Leu Asp Ile Trp Gly Gln Gly Thr
            100                 105                 110
```

```
Leu Val Thr Val Ser Ser
        115

<210> SEQ ID NO 94
<211> LENGTH: 448
<212> TYPE: PRT
<213> ORGANISM: Artificial Sequence
<220> FEATURE:
<223> OTHER INFORMATION: Chemically Synthesized

<400> SEQUENCE: 94

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Met Tyr
                20                  25                  30

Ser Met Gly Trp Val Arg Gln Ala Pro Gly Lys Gly Leu Glu Tyr Ile
            35                  40                  45

Gly Trp Ile Ser Tyr Gly Gly Thr Ala Tyr Tyr Ala Ser Ser Ala Lys
        50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Glu Thr Pro Val Asn Tyr Tyr Leu Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445

<210> SEQ ID NO 95
<211> LENGTH: 11
<212> TYPE: PRT
<213> ORGANISM: Oryctolagus cuniculus

<400> SEQUENCE: 95

Gln Ala Ser Glu Asn Ile Gly Ser Tyr Leu Ala
1               5                   10

<210> SEQ ID NO 96
<211> LENGTH: 7
<212> TYPE: PRT
<213> ORGANISM: Oryctolagus cuniculus

<400> SEQUENCE: 96

Arg Ala Ser Thr Leu Ala Ser
1               5

<210> SEQ ID NO 97
<211> LENGTH: 12
<212> TYPE: PRT
<213> ORGANISM: Oryctolagus cuniculus

<400> SEQUENCE: 97

Gln Gln Gly Tyr Asn Ser Glu Asn Leu Asp Asn Ala
1               5                   10

<210> SEQ ID NO 98
<211> LENGTH: 5
<212> TYPE: PRT
<213> ORGANISM: Oryctolagus cuniculus

<400> SEQUENCE: 98

Met Tyr Ser Met Gly
1               5

<210> SEQ ID NO 99
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 99

Trp Ile Ser Tyr Gly Gly Thr Ala Tyr Tyr Ala Ser Ser Ala Lys Gly
1               5                   10                  15

<210> SEQ ID NO 100
<211> LENGTH: 10
```

```
<212> TYPE: PRT
<213> ORGANISM: Oryctolagus cuniculus

<400> SEQUENCE: 100

Glu Thr Pro Val Asn Tyr Tyr Leu Asp Ile
1               5                   10

<210> SEQ ID NO 101
<211> LENGTH: 109
<212> TYPE: PRT
<213> ORGANISM: Oryctolagus cuniculus

<400> SEQUENCE: 101

Ala Phe Glu Leu Thr Gln Thr Pro Ser Ser Val Glu Ala Ala Val Gly
1               5                   10                  15

Gly Thr Val Thr Ile Lys Cys Gln Ala Ser Gln Asn Ile Val Thr Asn
            20                  25                  30

Leu Ala Trp Tyr Gln Gln Lys Pro Gly Gln Pro Pro Lys Leu Leu Ile
        35                  40                  45

Tyr Gly Ala Ser Thr Leu Ala Ser Gly Val Ser Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Phe Cys Gln Ser Tyr Asp Gly Phe Asn Ser
                85                  90                  95

Ala Gly Phe Gly Gly Gly Thr Glu Val Val Val Lys Arg
            100                 105

<210> SEQ ID NO 102
<211> LENGTH: 215
<212> TYPE: PRT
<213> ORGANISM: Artificial Sequence
<220> FEATURE:
<223> OTHER INFORMATION: Chemically Synthesized

<400> SEQUENCE: 102

Ala Phe Glu Leu Thr Gln Thr Pro Ser Ser Val Glu Ala Ala Val Gly
1               5                   10                  15

Gly Thr Val Thr Ile Lys Cys Gln Ala Ser Gln Asn Ile Val Thr Asn
            20                  25                  30

Leu Ala Trp Tyr Gln Gln Lys Pro Gly Gln Pro Pro Lys Leu Leu Ile
        35                  40                  45

Tyr Gly Ala Ser Thr Leu Ala Ser Gly Val Ser Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Phe Cys Gln Ser Tyr Asp Gly Phe Asn Ser
                85                  90                  95

Ala Gly Phe Gly Gly Gly Thr Glu Val Val Val Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

-continued

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 103
<211> LENGTH: 120
<212> TYPE: PRT
<213> ORGANISM: Oryctolagus cuniculus

<400> SEQUENCE: 103

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Gly Tyr Asp
            20                  25                  30

Met Ser Trp Val Arg Gln Ala Pro Gly Lys Gly Leu Glu Tyr Ile Gly
        35                  40                  45

Leu Ile Ser Tyr Asp Gly Asn Thr Tyr Tyr Ala Thr Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ser Leu
                85                  90                  95

Tyr Ala Gly Pro Asn Ala Gly Ile Gly Pro Phe Asn Ile Trp Gly Gln
            100                 105                 110

Gly Thr Leu Val Thr Val Ser Ser
        115                 120

<210> SEQ ID NO 104
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 104

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Gly Tyr Asp
            20                  25                  30

Met Ser Trp Val Arg Gln Ala Pro Gly Lys Gly Leu Glu Tyr Ile Gly
        35                  40                  45

Leu Ile Ser Tyr Asp Gly Asn Thr Tyr Tyr Ala Thr Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ser Leu
                85                  90                  95

Tyr Ala Gly Pro Asn Ala Gly Ile Gly Pro Phe Asn Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 105
<211> LENGTH: 11
<212> TYPE: PRT
<213> ORGANISM: Oryctolagus cuniculus

<400> SEQUENCE: 105

Gln Ala Ser Gln Asn Ile Val Thr Asn Leu Ala
1               5                   10

<210> SEQ ID NO 106
<211> LENGTH: 7
<212> TYPE: PRT
<213> ORGANISM: Oryctolagus cuniculus

<400> SEQUENCE: 106
```

```
Gly Ala Ser Thr Leu Ala Ser
1               5
```

<210> SEQ ID NO 107
<211> LENGTH: 10
<212> TYPE: PRT
<213> ORGANISM: Oryctolagus cuniculus

<400> SEQUENCE: 107

```
Gln Ser Tyr Asp Gly Phe Asn Ser Ala Gly
1               5                   10
```

<210> SEQ ID NO 108
<211> LENGTH: 5
<212> TYPE: PRT
<213> ORGANISM: Oryctolagus cuniculus

<400> SEQUENCE: 108

```
Gly Tyr Asp Met Ser
1               5
```

<210> SEQ ID NO 109
<211> LENGTH: 16
<212> TYPE: PRT
<213> ORGANISM: Oryctolagus cuniculus

<400> SEQUENCE: 109

```
Leu Ile Ser Tyr Asp Gly Asn Thr Tyr Tyr Ala Thr Trp Ala Lys Gly
1               5                   10                  15
```

<210> SEQ ID NO 110
<211> LENGTH: 15
<212> TYPE: PRT
<213> ORGANISM: Oryctolagus cuniculus

<400> SEQUENCE: 110

```
Ser Leu Tyr Ala Gly Pro Asn Ala Gly Ile Gly Pro Phe Asn Ile
1               5                   10                  15
```

<210> SEQ ID NO 111
<211> LENGTH: 109
<212> TYPE: PRT
<213> ORGANISM: Artificial Sequence
<220> FEATURE:
<223> OTHER INFORMATION: Chemically Synthesized

<400> SEQUENCE: 111

```
Ala Phe Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Val Thr Asn
            20                  25                  30

Leu Ala Trp Tyr Gln Gln Lys Pro Gly Lys Val Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Tyr Asp Gly Phe Asn Ser
                85                  90                  95

Ala Gly Phe Gly Gly Gly Thr Lys Val Glu Ile Lys Arg
                100                 105
```

```
<210> SEQ ID NO 112
<211> LENGTH: 215
<212> TYPE: PRT
<213> ORGANISM: Artificial Sequence
<220> FEATURE:
<223> OTHER INFORMATION: Chemically Synthesized

<400> SEQUENCE: 112
```

Ala Phe Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Val Thr Asn
            20                  25                  30

Leu Ala Trp Tyr Gln Gln Lys Pro Gly Lys Val Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Tyr Asp Gly Phe Asn Ser
                85                  90                  95

Ala Gly Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

```
<210> SEQ ID NO 113
<211> LENGTH: 123
<212> TYPE: PRT
<213> ORGANISM: Artificial Sequence
<220> FEATURE:
<223> OTHER INFORMATION: Chemically Synthesized

<400> SEQUENCE: 113
```

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Leu Ser Gly Tyr
            20                  25                  30

Asp Met Ser Trp Val Arg Gln Ala Pro Gly Lys Gly Leu Glu Trp Val
        35                  40                  45

Gly Leu Ile Ser Tyr Asp Gly Asn Thr Tyr Tyr Ala Thr Ser Ala Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

```
Arg Ser Leu Tyr Ala Gly Pro Asn Ala Gly Ile Gly Pro Phe Asn Ile
            100                 105                 110

Trp Gly Gln Gly Thr Leu Val Thr Val Ser Ser
        115                 120
```

<210> SEQ ID NO 114
<211> LENGTH: 453
<212> TYPE: PRT
<213> ORGANISM: Artificial Sequence
<220> FEATURE:
<223> OTHER INFORMATION: Chemically Synthesized

<400> SEQUENCE: 114

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Ser Gly Tyr
            20                  25                  30

Asp Met Ser Trp Val Arg Gln Ala Pro Gly Lys Gly Leu Glu Trp Val
        35                  40                  45

Gly Leu Ile Ser Tyr Asp Gly Asn Thr Tyr Tyr Ala Thr Ser Ala Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Ser Leu Tyr Ala Gly Pro Asn Ala Gly Ile Gly Pro Phe Asn Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Ala Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 115
<211> LENGTH: 11
<212> TYPE: PRT
<213> ORGANISM: Oryctolagus cuniculus

<400> SEQUENCE: 115

Gln Ala Ser Gln Asn Ile Val Thr Asn Leu Ala
1               5                   10

<210> SEQ ID NO 116
<211> LENGTH: 7
<212> TYPE: PRT
<213> ORGANISM: Oryctolagus cuniculus

<400> SEQUENCE: 116

Gly Ala Ser Thr Leu Ala Ser
1               5

<210> SEQ ID NO 117
<211> LENGTH: 10
<212> TYPE: PRT
<213> ORGANISM: Oryctolagus cuniculus

<400> SEQUENCE: 117

Gln Ser Tyr Asp Gly Phe Asn Ser Ala Gly
1               5                   10

<210> SEQ ID NO 118
<211> LENGTH: 5
<212> TYPE: PRT
<213> ORGANISM: Oryctolagus cuniculus

<400> SEQUENCE: 118

Gly Tyr Asp Met Ser
1               5

<210> SEQ ID NO 119
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 119

Leu Ile Ser Tyr Asp Gly Asn Thr Tyr Tyr Ala Thr Ser Ala Lys Gly
```

<210> SEQ ID NO 120
<211> LENGTH: 15
<212> TYPE: PRT
<213> ORGANISM: Oryctolagus cuniculus

<400> SEQUENCE: 120

Ser Leu Tyr Ala Gly Pro Asn Ala Gly Ile Gly Pro Phe Asn Ile
1               5                   10                  15

<210> SEQ ID NO 121
<211> LENGTH: 112
<212> TYPE: PRT
<213> ORGANISM: Oryctolagus cuniculus

<400> SEQUENCE: 121

Ala Ala Val Leu Thr Gln Thr Pro Ser Pro Val Ser Ala Ala Val Gly
1               5                   10                  15

Gly Thr Val Ser Ile Ser Cys Gln Ser Ser Gln Asn Val Tyr Lys Asn
            20                  25                  30

Asn Tyr Leu Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Gly Gly Ser Gly Thr Asp Phe Thr Leu Thr Ile Ser Asp Val
65                  70                  75                  80

Gln Cys Asp Ala Ala Thr Tyr Tyr Cys Ala Gly Gly Tyr Thr Ser
            85                  90                  95

Ser Ser Asp Asn Ala Phe Gly Gly Gly Thr Glu Val Val Val Lys Arg
            100                 105                 110

<210> SEQ ID NO 122
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 122

Ala Ala Val Leu Thr Gln Thr Pro Ser Pro Val Ser Ala Ala Val Gly
1               5                   10                  15

Gly Thr Val Ser Ile Ser Cys Gln Ser Ser Gln Asn Val Tyr Lys Asn
            20                  25                  30

Asn Tyr Leu Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Gly Gly Ser Gly Thr Asp Phe Thr Leu Thr Ile Ser Asp Val
65                  70                  75                  80

Gln Cys Asp Ala Ala Thr Tyr Tyr Cys Ala Gly Gly Tyr Thr Ser
            85                  90                  95

Ser Ser Asp Asn Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 123
<211> LENGTH: 117
<212> TYPE: PRT
<213> ORGANISM: Oryctolagus cuniculus

<400> SEQUENCE: 123

Gln Ser Val Glu Ala Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Trp
            20                  25                  30

Met Ser Trp Val Arg Gln Ala Pro Gly Lys Gly Leu Glu Trp Ile Gly
        35                  40                  45

Asp Ile Tyr Phe Ser Asn Glu Glu Thr Asn Tyr Ala Ser Trp Ala Lys
50                  55                  60

Gly Arg Phe Thr Ile Ser Lys Thr Ser Thr Thr Val Asp Leu Asn Val
65                  70                  75                  80

Ile Ser Pro Thr Thr Glu Asp Thr Ala Thr Tyr Phe Cys Ala Arg Gly
                85                  90                  95

Ser Pro Asp Val Asp Ile Gly Ile Asp Met Trp Gly Pro Gly Thr Leu
            100                 105                 110

Val Thr Val Ser Ser
            115

<210> SEQ ID NO 124
<211> LENGTH: 447
<212> TYPE: PRT
<213> ORGANISM: Artificial Sequence
<220> FEATURE:
<223> OTHER INFORMATION: Chemically Synthesized

<400> SEQUENCE: 124

Gln Ser Val Glu Ala Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Trp
            20                  25                  30

Met Ser Trp Val Arg Gln Ala Pro Gly Lys Gly Leu Glu Trp Ile Gly
        35                  40                  45

Asp Ile Tyr Phe Ser Asn Glu Glu Thr Asn Tyr Ala Ser Trp Ala Lys
50                  55                  60

Gly Arg Phe Thr Ile Ser Lys Thr Ser Thr Thr Val Asp Leu Asn Val
65                  70                  75                  80

Ile Ser Pro Thr Thr Glu Asp Thr Ala Thr Tyr Phe Cys Ala Arg Gly
                85                  90                  95

Ser Pro Asp Val Asp Ile Gly Ile Asp Met Trp Gly Pro Gly Thr Leu
            100                 105                 110

Val Thr Val Ser Ser Ala Ser Thr Lys Gly Pro Ser Val Phe Pro Leu

```
                 115                 120                 125
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Ala Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445

<210> SEQ ID NO 125
<211> LENGTH: 13
<212> TYPE: PRT
<213> ORGANISM: Oryctolagus cuniculus

<400> SEQUENCE: 125

Gln Ser Ser Gln Asn Val Tyr Lys Asn Asn Tyr Leu Ser
1               5                   10

<210> SEQ ID NO 126
<211> LENGTH: 7
<212> TYPE: PRT
<213> ORGANISM: Oryctolagus cuniculus
```

<400> SEQUENCE: 126

Lys Ala Ser Thr Leu Ala Ser
1               5

<210> SEQ ID NO 127
<211> LENGTH: 11
<212> TYPE: PRT
<213> ORGANISM: Oryctolagus cuniculus

<400> SEQUENCE: 127

Ala Gly Gly Tyr Thr Ser Ser Ser Asp Asn Ala
1               5                   10

<210> SEQ ID NO 128
<211> LENGTH: 5
<212> TYPE: PRT
<213> ORGANISM: Oryctolagus cuniculus

<400> SEQUENCE: 128

Thr Tyr Trp Met Ser
1               5

<210> SEQ ID NO 129
<211> LENGTH: 17
<212> TYPE: PRT
<213> ORGANISM: Oryctolagus cuniculus

<400> SEQUENCE: 129

Asp Ile Tyr Phe Ser Asn Glu Glu Thr Asn Tyr Ala Ser Trp Ala Lys
1               5                   10                  15

Gly

<210> SEQ ID NO 130
<211> LENGTH: 11
<212> TYPE: PRT
<213> ORGANISM: Oryctolagus cuniculus

<400> SEQUENCE: 130

Gly Ser Pro Asp Val Asp Ile Gly Ile Asp Met
1               5                   10

<210> SEQ ID NO 131
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Asn Val Tyr Lys Asn
                20                  25                  30

Asn Tyr Leu Ser Trp Tyr Gln Gln Lys Pro Gly Lys Val Pro Lys Leu
            35                  40                  45

Leu Ile Tyr Lys Ala Ser Thr Leu Ala Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Thr Ser
                85                  90                  95

Ser Ser Asp Asn Ala Phe Gly Gly Gly Thr Lys Val Glu Ile Lys Arg
            100                 105                 110

<210> SEQ ID NO 132
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Asn Val Tyr Lys Asn
            20                  25                  30

Asn Tyr Leu Ser Trp Tyr Gln Gln Lys Pro Gly Lys Val Pro Lys Leu
        35                  40                  45

Leu Ile Tyr Lys Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Thr Ser
                85                  90                  95

Ser Ser Asp Asn Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 133
<211> LENGTH: 120
<212> TYPE: PRT
<213> ORGANISM: Artificial Sequence
<220> FEATURE:
<223> OTHER INFORMATION: Chemically Synthesized

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Trp Met Ser Trp Val Arg Gln Ala Pro Gly Lys Gly Leu Glu Trp Val
        35                  40                  45

Gly Asp Ile Tyr Phe Ser Asn Glu Glu Thr Asn Tyr Ala Ser Ser Ala
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Gly Ser Pro Asp Val Asp Ile Gly Ile Asp Met Trp Gly Pro
            100                 105                 110

Gly Thr Leu Val Thr Val Ser Ser
        115                 120

<210> SEQ ID NO 134
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Trp Met Ser Trp Val Arg Gln Ala Pro Gly Lys Gly Leu Glu Trp Val
        35                  40                  45

Gly Asp Ile Tyr Phe Ser Asn Glu Glu Thr Asn Tyr Ala Ser Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Pro Asp Val Asp Ile Gly Ile Asp Met Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 135
<211> LENGTH: 13
<212> TYPE: PRT
<213> ORGANISM: Oryctolagus cuniculus

<400> SEQUENCE: 135

Gln Ser Ser Gln Asn Val Tyr Lys Asn Asn Tyr Leu Ser
1               5                   10

<210> SEQ ID NO 136
<211> LENGTH: 7
<212> TYPE: PRT
<213> ORGANISM: Oryctolagus cuniculus

<400> SEQUENCE: 136

Lys Ala Ser Thr Leu Ala Ser
1               5

<210> SEQ ID NO 137
<211> LENGTH: 11
<212> TYPE: PRT
<213> ORGANISM: Oryctolagus cuniculus

<400> SEQUENCE: 137

Ala Gly Gly Tyr Thr Ser Ser Ser Asp Asn Ala
1               5                   10

<210> SEQ ID NO 138
<211> LENGTH: 5
<212> TYPE: PRT
<213> ORGANISM: Oryctolagus cuniculus

<400> SEQUENCE: 138

Thr Tyr Trp Met Ser
1               5

<210> SEQ ID NO 139
<211> LENGTH: 17
<212> TYPE: PRT
<213> ORGANISM: Artificial Sequence
<220> FEATURE:
<223> OTHER INFORMATION: Chemically Synthesized
```

```
<400> SEQUENCE: 139

Asp Ile Tyr Phe Ser Asn Glu Glu Thr Asn Tyr Ala Ser Ser Ala Lys
1               5                   10                  15
Gly

<210> SEQ ID NO 140
<211> LENGTH: 11
<212> TYPE: PRT
<213> ORGANISM: Oryctolagus cuniculus

<400> SEQUENCE: 140

Gly Ser Pro Asp Val Asp Ile Gly Ile Asp Met
1               5                   10

<210> SEQ ID NO 141
<211> LENGTH: 112
<212> TYPE: PRT
<213> ORGANISM: Oryctolagus cuniculus

<400> SEQUENCE: 141

Ala Ala Val Leu Thr Gln Thr Pro Ser Pro Val Ser Ala Ala Val Gly
1               5                   10                  15

Asp Thr Val Thr Ile Lys Cys Gln Ser Ser Gln Ser Val Tyr Lys Asn
            20                  25                  30

Asn Tyr Leu Ser Trp Tyr Gln Gln Lys Pro Gly Gln Pro Pro Lys Leu
        35                  40                  45

Leu Ile Tyr Asp Ala Ser Asn Leu Pro Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Asp Tyr Asp Asp
                85                  90                  95

Asp Thr Asp Asn Gly Phe Gly Gly Thr Glu Val Val Val Lys Arg
            100                 105                 110

<210> SEQ ID NO 142
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 142

Ala Ala Val Leu Thr Gln Thr Pro Ser Pro Val Ser Ala Ala Val Gly
1               5                   10                  15

Asp Thr Val Thr Ile Lys Cys Gln Ser Ser Gln Ser Val Tyr Lys Asn
            20                  25                  30

Asn Tyr Leu Ser Trp Tyr Gln Gln Lys Pro Gly Gln Pro Pro Lys Leu
        35                  40                  45

Leu Ile Tyr Asp Ala Ser Asn Leu Pro Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Asp Tyr Asp Asp
                85                  90                  95

Asp Thr Asp Asn Gly Phe Gly Gly Thr Glu Val Val Val Lys Arg
            100                 105                 110
```

```
Thr Val Ala Ala Pro Ser Val Phe Ile Phe Pro Ser Asp Glu Gln
            115                 120                 125
Leu Lys Ser Gly Thr Ala Ser Val Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 143
<211> LENGTH: 112
<212> TYPE: PRT
<213> ORGANISM: Oryctolagus cuniculus

<400> SEQUENCE: 143

```
Gln Ser Val Glu Glu Ser Gly Gly Arg Leu Val Thr Pro Gly Thr Pro
1               5                   10                  15
Leu Thr Leu Thr Cys Thr Val Ser Gly Ile Asp Leu Ser Ser Tyr Ala
            20                  25                  30
Met Ile Trp Val Arg Gln Ala Pro Gly Lys Gly Leu Glu Tyr Ile Gly
        35                  40                  45
Ile Ile Trp Ser Gly Gly Thr Tyr Tyr Ala Thr Trp Ala Lys Gly Arg
    50                  55                  60
Phe Thr Ile Ser Lys Thr Ser Thr Thr Val Asp Leu Gln Ile Thr Ser
65                  70                  75                  80
Pro Thr Thr Glu Asp Ala Ala Thr Tyr Phe Cys Ala Ala Gly Gly Gly
                85                  90                  95
Ser Ile Tyr Asp Val Trp Gly Pro Gly Thr Leu Val Thr Val Ser Ser
            100                 105                 110
```

<210> SEQ ID NO 144
<211> LENGTH: 442
<212> TYPE: PRT
<213> ORGANISM: Artificial Sequence
<220> FEATURE:
<223> OTHER INFORMATION: Chemically Synthesized

<400> SEQUENCE: 144

```
Gln Ser Val Glu Glu Ser Gly Gly Arg Leu Val Thr Pro Gly Thr Pro
1               5                   10                  15
Leu Thr Leu Thr Cys Thr Val Ser Gly Ile Asp Leu Ser Ser Tyr Ala
            20                  25                  30
Met Ile Trp Val Arg Gln Ala Pro Gly Lys Gly Leu Glu Tyr Ile Gly
        35                  40                  45
Ile Ile Trp Ser Gly Gly Thr Tyr Tyr Ala Thr Trp Ala Lys Gly Arg
    50                  55                  60
Phe Thr Ile Ser Lys Thr Ser Thr Thr Val Asp Leu Gln Ile Thr Ser
65                  70                  75                  80
Pro Thr Thr Glu Asp Ala Ala Thr Tyr Phe Cys Ala Ala Gly Gly Gly
                85                  90                  95
Ser Ile Tyr Asp Val Trp Gly Pro Gly Thr Leu Val Thr Val Ser Ser
```

```
                100             105             110
Ala Ser Thr Lys Gly Pro Ser Val Phe Pro Leu Ala Pro Ser Ser Lys
            115                 120                 125
Ser Thr Ser Gly Gly Thr Ala Ala Leu Gly Cys Leu Val Lys Asp Tyr
            130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Gln Thr
                180                 185                 190
Tyr Ile Cys Asn Val Asn His Lys Pro Ser Asn Thr Lys Val Asp Lys
                195                 200                 205
Arg Val Glu Pro Lys Ser Cys Asp Lys Thr His Thr Cys Pro Pro Cys
            210                 215                 220
Pro Ala Pro Glu Leu Leu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Lys Phe Asn Trp
                260                 265                 270
Tyr Val Asp Gly Val Glu Val His Asn Ala Lys Thr Lys Pro Arg Glu
                275                 280                 285
Glu Gln Tyr Ala Ser Thr Tyr Arg Val Val Ser Val Leu Thr Val Leu
            290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Glu Glu
                340                 345                 350
Met Thr Lys Asn Gln Val Ser Leu Thr Cys Leu Val Lys Gly Phe Tyr
            355                 360                 365
Pro Ser Asp Ile Ala Val Glu Trp Glu Ser Asn Gly Gln Pro Glu Asn
            370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
                420                 425                 430
Gln Lys Ser Leu Ser Leu Ser Pro Gly Lys
            435                 440

<210> SEQ ID NO 145
<211> LENGTH: 13
<212> TYPE: PRT
<213> ORGANISM: Oryctolagus cuniculus

<400> SEQUENCE: 145

Gln Ser Ser Gln Ser Val Tyr Lys Asn Asn Tyr Leu Ser
1               5                   10

<210> SEQ ID NO 146
<211> LENGTH: 7
```

```
<212> TYPE: PRT
<213> ORGANISM: Oryctolagus cuniculus

<400> SEQUENCE: 146

Asp Ala Ser Asn Leu Pro Ser
1               5

<210> SEQ ID NO 147
<211> LENGTH: 11
<212> TYPE: PRT
<213> ORGANISM: Oryctolagus cuniculus

<400> SEQUENCE: 147

Leu Gly Asp Tyr Asp Asp Thr Asp Asn Gly
1               5                   10

<210> SEQ ID NO 148
<211> LENGTH: 5
<212> TYPE: PRT
<213> ORGANISM: Oryctolagus cuniculus

<400> SEQUENCE: 148

Ser Tyr Ala Met Ile
1               5

<210> SEQ ID NO 149
<211> LENGTH: 15
<212> TYPE: PRT
<213> ORGANISM: Oryctolagus cuniculus

<400> SEQUENCE: 149

Ile Ile Trp Ser Gly Gly Thr Tyr Tyr Ala Thr Trp Ala Lys Gly
1               5                   10                  15

<210> SEQ ID NO 150
<211> LENGTH: 8
<212> TYPE: PRT
<213> ORGANISM: Oryctolagus cuniculus

<400> SEQUENCE: 150

Gly Gly Gly Ser Ile Tyr Asp Val
1               5

<210> SEQ ID NO 151
<211> LENGTH: 112
<212> TYPE: PRT
<213> ORGANISM: Oryctolagus cuniculus

<400> SEQUENCE: 151

Ala Leu Val Met Thr Gln Thr Pro Ser Ser Thr Ser Glu Pro Val Gly
1               5                   10                  15

Gly Thr Val Thr Ile Asn Cys Gln Ala Ser Gln Asn Ile Gly Asn Asp
                20                  25                  30

Leu Ser Trp Tyr Gln Gln Lys Pro Gly Gln Pro Pro Glu Leu Leu Ile
        35                  40                  45

Tyr Ser Thr Ser Lys Leu Ala Thr Gly Val Pro Lys Arg Phe Ser Gly
    50                  55                  60

Ser Arg Ser Gly Thr Gln Phe Thr Leu Thr Ile Ser Asp Leu Glu Cys
65                  70                  75                  80

Asp Asp Ala Ala Thr Tyr Tyr Cys Leu Gly Val Tyr Ser Tyr Ile Ser
                85                  90                  95

Asp Asp Gly Asn Ala Phe Gly Gly Gly Thr Glu Val Val Val Lys Arg
```

```
                100                 105                 110

<210> SEQ ID NO 152
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 152

Ala Leu Val Met Thr Gln Thr Pro Ser Ser Thr Ser Glu Pro Val Gly
1               5                   10                  15

Gly Thr Val Thr Ile Asn Cys Gln Ala Ser Gln Asn Ile Gly Asn Asp
            20                  25                  30

Leu Ser Trp Tyr Gln Gln Lys Pro Gly Gln Pro Pro Glu Leu Leu Ile
        35                  40                  45

Tyr Ser Thr Ser Lys Leu Ala Thr Gly Val Pro Lys Arg Phe Ser Gly
    50                  55                  60

Ser Arg Ser Gly Thr Gln Phe Thr Leu Thr Ile Ser Asp Leu Glu Cys
65                  70                  75                  80

Asp Asp Ala Ala Thr Tyr Tyr Cys Leu Gly Val Tyr Ser Tyr Ile Ser
                85                  90                  95

Asp Asp Gly Asn Ala Phe Gly Gly Thr Glu Val Val Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 153
<211> LENGTH: 120
<212> TYPE: PRT
<213> ORGANISM: Oryctolagus cuniculus

<400> SEQUENCE: 153

Gln Ser Val Glu Glu Phe Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Thr Trp Val Arg Gln Ala Pro Gly Lys Gly Leu Glu Trp Ile Gly
        35                  40                  45

Ile Ile Gly Ser Ile Gly Thr Thr Tyr Tyr Ala Ser Trp Ala Lys Gly
    50                  55                  60

Arg Phe Phe Ile Ser Lys Thr Ser Thr Thr Val Asp Leu Lys Ile Ile
65                  70                  75                  80

Ser Pro Thr Thr Glu Asp Thr Ala Thr Tyr Phe Cys Ala Arg Asp Ala
                85                  90                  95
```

Gly Val Thr Val Asp Gly Tyr Gly Tyr Tyr Phe Asn Ile Trp Gly Pro
              100                 105                 110

Gly Thr Leu Val Thr Val Ser Ser
        115                 120

<210> SEQ ID NO 154
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 154

Gln Ser Val Glu Glu Phe Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Thr Trp Val Arg Gln Ala Pro Gly Lys Gly Leu Glu Trp Ile Gly
        35                  40                  45

Ile Ile Gly Ser Ile Gly Thr Thr Tyr Tyr Ala Ser Trp Ala Lys Gly
50                  55                  60

Arg Phe Phe Ile Ser Lys Thr Ser Thr Thr Val Asp Leu Lys Ile Ile
65                  70                  75                  80

Ser Pro Thr Thr Glu Asp Thr Ala Thr Tyr Phe Cys Ala Arg Asp Ala
                85                  90                  95

Gly Val Thr Val Asp Gly Tyr Gly Tyr Tyr Phe Asn Ile Trp Gly Pro
              100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 155
<211> LENGTH: 11
<212> TYPE: PRT
<213> ORGANISM: Oryctolagus cuniculus

<400> SEQUENCE: 155

Gln Ala Ser Gln Asn Ile Gly Asn Asp Leu Ser
1               5                   10

<210> SEQ ID NO 156
<211> LENGTH: 7
<212> TYPE: PRT
<213> ORGANISM: Oryctolagus cuniculus

<400> SEQUENCE: 156

Ser Thr Ser Lys Leu Ala Thr
1               5

<210> SEQ ID NO 157
<211> LENGTH: 13
<212> TYPE: PRT
<213> ORGANISM: Oryctolagus cuniculus

<400> SEQUENCE: 157

Leu Gly Val Tyr Ser Tyr Ile Ser Asp Asp Gly Asn Ala
1               5                   10

<210> SEQ ID NO 158
<211> LENGTH: 5
<212> TYPE: PRT
<213> ORGANISM: Oryctolagus cuniculus

<400> SEQUENCE: 158

Asn Tyr Ala Met Thr
1               5

<210> SEQ ID NO 159
<211> LENGTH: 16
<212> TYPE: PRT
<213> ORGANISM: Oryctolagus cuniculus

<400> SEQUENCE: 159

Ile Ile Gly Ser Ile Gly Thr Thr Tyr Tyr Ala Ser Trp Ala Lys Gly
1               5                   10                  15
```

<210> SEQ ID NO 160
<211> LENGTH: 15
<212> TYPE: PRT
<213> ORGANISM: Oryctolagus cuniculus

<400> SEQUENCE: 160

Asp Ala Gly Val Thr Val Asp Gly Tyr Gly Tyr Tyr Phe Asn Ile
1               5                   10                  15

<210> SEQ ID NO 161
<211> LENGTH: 112
<212> TYPE: PRT
<213> ORGANISM: Oryctolagus cuniculus

<400> SEQUENCE: 161

Ala Ile Glu Met Thr Gln Thr Pro Phe Ser Val Ser Ala Ala Val Gly
1               5                   10                  15

Gly Thr Val Thr Ile Lys Cys Gln Ala Ser Gln Thr Ile Ser Asn Tyr
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Asp Asp Ala Ala Thr Tyr Tyr Cys Gln Gln Gly Tyr Thr Ile Ser Asn
                85                  90                  95

Val Asp Asn Asn Val Phe Gly Gly Gly Thr Glu Val Val Val Lys Arg
            100                 105                 110

<210> SEQ ID NO 162
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 162

Ala Ile Glu Met Thr Gln Thr Pro Phe Ser Val Ser Ala Ala Val Gly
1               5                   10                  15

Gly Thr Val Thr Ile Lys Cys Gln Ala Ser Gln Thr Ile Ser Asn Tyr
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Asp Asp Ala Ala Thr Tyr Tyr Cys Gln Gln Gly Tyr Thr Ile Ser Asn
                85                  90                  95

Val Asp Asn Asn Val Phe Gly Gly Gly Thr Glu Val Val Val Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser

```
                  145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
                180                 185                 190
His Lys Val Tyr Ala Cys Glu Val Thr His Gln Gly Leu Ser Ser Pro
                195                 200                 205
Val Thr Lys Ser Phe Asn Arg Gly Glu Cys
                210                 215

<210> SEQ ID NO 163
<211> LENGTH: 115
<212> TYPE: PRT
<213> ORGANISM: Oryctolagus cuniculus

<400> SEQUENCE: 163

Gln Ser Leu Glu Glu Ser Gly Gly Arg Leu Val Thr Pro Gly Gly Ser
1               5                   10                  15
Leu Thr Leu Thr Cys Ala Ala Ser Gly Phe Ser Leu Thr Gly Tyr Asn
                20                  25                  30
Leu Val Trp Val Arg Gln Ala Pro Gly Lys Gly Leu Glu Trp Ile Gly
                35                  40                  45
Phe Ile Ser Tyr Gly Asp Thr Thr Tyr Ala Ser Trp Ala Lys Gly
 50                  55                  60
Arg Phe Thr Ile Ser Lys Thr Ser Thr Val Thr Leu Thr Ile Thr
65                  70                  75                  80
Asp Leu Gln Pro Ser Asp Thr Gly Thr Tyr Phe Cys Ala Arg Glu Thr
                85                  90                  95
Ala Asn Thr Tyr Asp Tyr Gly Ile Trp Gly Pro Gly Thr Leu Val Thr
                100                 105                 110
Val Ser Ser
        115

<210> SEQ ID NO 164
<211> LENGTH: 445
<212> TYPE: PRT
<213> ORGANISM: Artificial Sequence
<220> FEATURE:
<223> OTHER INFORMATION: Chemically Synthesized

<400> SEQUENCE: 164

Gln Ser Leu Glu Glu Ser Gly Gly Arg Leu Val Thr Pro Gly Gly Ser
1               5                   10                  15
Leu Thr Leu Thr Cys Ala Ala Ser Gly Phe Ser Leu Thr Gly Tyr Asn
                20                  25                  30
Leu Val Trp Val Arg Gln Ala Pro Gly Lys Gly Leu Glu Trp Ile Gly
                35                  40                  45
Phe Ile Ser Tyr Gly Asp Thr Thr Tyr Ala Ser Trp Ala Lys Gly
 50                  55                  60
Arg Phe Thr Ile Ser Lys Thr Ser Thr Val Thr Leu Thr Ile Thr
65                  70                  75                  80
Asp Leu Gln Pro Ser Asp Thr Gly Thr Tyr Phe Cys Ala Arg Glu Thr
                85                  90                  95
Ala Asn Thr Tyr Asp Tyr Gly Ile Trp Gly Pro Gly Thr Leu Val Thr
                100                 105                 110
Val Ser Ser Ala Ser Thr Lys Gly Pro Ser Val Phe Pro Leu Ala Pro
                115                 120                 125
```

-continued

```
Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Ala Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 165
<211> LENGTH: 11
<212> TYPE: PRT
<213> ORGANISM: Oryctolagus cuniculus

<400> SEQUENCE: 165

Gln Ala Ser Gln Thr Ile Ser Asn Tyr Leu Ala
1               5                   10

<210> SEQ ID NO 166
<211> LENGTH: 7
<212> TYPE: PRT
<213> ORGANISM: Oryctolagus cuniculus

<400> SEQUENCE: 166
```

```
Gly Ala Ser Asn Leu Glu Ser
1               5
```

<210> SEQ ID NO 167
<211> LENGTH: 13
<212> TYPE: PRT
<213> ORGANISM: Oryctolagus cuniculus

<400> SEQUENCE: 167

```
Gln Gln Gly Tyr Thr Ile Ser Asn Val Asp Asn Asn Val
1               5                   10
```

<210> SEQ ID NO 168
<211> LENGTH: 5
<212> TYPE: PRT
<213> ORGANISM: Oryctolagus cuniculus

<400> SEQUENCE: 168

```
Gly Tyr Asn Leu Val
1               5
```

<210> SEQ ID NO 169
<211> LENGTH: 16
<212> TYPE: PRT
<213> ORGANISM: Oryctolagus cuniculus

<400> SEQUENCE: 169

```
Phe Ile Ser Tyr Gly Asp Thr Thr Tyr Tyr Ala Ser Trp Ala Lys Gly
1               5                   10                  15
```

<210> SEQ ID NO 170
<211> LENGTH: 10
<212> TYPE: PRT
<213> ORGANISM: Oryctolagus cuniculus

<400> SEQUENCE: 170

```
Glu Thr Ala Asn Thr Tyr Asp Tyr Gly Ile
1               5                   10
```

<210> SEQ ID NO 171
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 171

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Thr Ile Ser Asn Tyr
            20                  25                  30

Leu Ala Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Thr Ile Ser Asn
                85                  90                  95

Val Asp Asn Asn Val Phe Gly Gly Gly Thr Lys Val Glu Ile Lys Arg
            100                 105                 110
```

```
<210> SEQ ID NO 172
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 172

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Thr Ile Ser Asn Tyr
            20                  25                  30

Leu Ala Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Thr Ile Ser Asn
                85                  90                  95

Val Asp Asn Asn Val Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 173
<211> LENGTH: 118
<212> TYPE: PRT
<213> ORGANISM: Artificial Sequence
<220> FEATURE:
<223> OTHER INFORMATION: Chemically Synthesized

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Gly Tyr
            20                  25                  30

Asn Leu Val Trp Val Arg Gln Ala Pro Gly Lys Gly Leu Glu Trp Val
        35                  40                  45

Gly Phe Ile Ser Tyr Gly Asp Thr Thr Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

Arg Glu Thr Ala Asn Thr Tyr Asp Tyr Gly Ile Trp Gly Gln Gly Thr
                100                 105                 110

Leu Val Thr Val Ser Ser
        115

<210> SEQ ID NO 174
<211> LENGTH: 448
<212> TYPE: PRT
<213> ORGANISM: Artificial Sequence
<220> FEATURE:
<223> OTHER INFORMATION: Chemically Synthesized

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Gly Tyr
            20                  25                  30

Asn Leu Val Trp Val Arg Gln Ala Pro Gly Lys Gly Leu Glu Trp Val
        35                  40                  45

Gly Phe Ile Ser Tyr Gly Asp Thr Thr Tyr Tyr Ala Ser Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Ala Asn Thr Tyr Asp Tyr Gly Ile Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 175
<211> LENGTH: 11
<212> TYPE: PRT
<213> ORGANISM: Oryctolagus cuniculus

<400> SEQUENCE: 175

Gln Ala Ser Gln Thr Ile Ser Asn Tyr Leu Ala
1               5                   10

<210> SEQ ID NO 176
<211> LENGTH: 7
<212> TYPE: PRT
<213> ORGANISM: Oryctolagus cuniculus

<400> SEQUENCE: 176

Gly Ala Ser Asn Leu Glu Ser
1               5

<210> SEQ ID NO 177
<211> LENGTH: 13
<212> TYPE: PRT
<213> ORGANISM: Oryctolagus cuniculus

<400> SEQUENCE: 177

Gln Gln Gly Tyr Thr Ile Ser Asn Val Asp Asn Asn Val
1               5                   10

<210> SEQ ID NO 178
<211> LENGTH: 5
<212> TYPE: PRT
<213> ORGANISM: Oryctolagus cuniculus

<400> SEQUENCE: 178

Gly Tyr Asn Leu Val
1               5

<210> SEQ ID NO 179
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 179

Phe Ile Ser Tyr Gly Asp Thr Thr Tyr Tyr Ala Ser Ser Ala Lys Gly
1               5                   10                  15

<210> SEQ ID NO 180
<211> LENGTH: 10
<212> TYPE: PRT
<213> ORGANISM: Oryctolagus cuniculus

<400> SEQUENCE: 180

Glu Thr Ala Asn Thr Tyr Asp Tyr Gly Ile
1               5                   10

<210> SEQ ID NO 181
<211> LENGTH: 112
<212> TYPE: PRT
<213> ORGANISM: Oryctolagus cuniculus

<400> SEQUENCE: 181

Ala Ala Val Leu Thr Gln Thr Pro Ser Pro Val Ser Ala Ala Val Gly
1               5                   10                  15

Gly Thr Val Ser Ile Ser Cys Gln Ser Ser Gln Asn Val Tyr Lys Asn
            20                  25                  30

Asn Tyr Leu Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Ser Gly Ser Gly Thr Asp Phe Thr Leu Thr Ile Ser Asp Val
65                  70                  75                  80

Gln Cys Asp Ala Ala Ala Thr Tyr Tyr Cys Ala Gly Gly Tyr Ser Ser
                85                  90                  95

Ser Ser Asp Asn Ala Phe Gly Gly Gly Thr Glu Val Val Val Lys Arg
            100                 105                 110

<210> SEQ ID NO 182
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 182

Ala Ala Val Leu Thr Gln Thr Pro Ser Pro Val Ser Ala Ala Val Gly
1               5                   10                  15

Gly Thr Val Ser Ile Ser Cys Gln Ser Ser Gln Asn Val Tyr Lys Asn
            20                  25                  30

Asn Tyr Leu Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Ser Gly Ser Gly Thr Asp Phe Thr Leu Thr Ile Ser Asp Val
65                  70                  75                  80

Gln Cys Asp Ala Ala Ala Thr Tyr Tyr Cys Ala Gly Gly Tyr Ser Ser
                85                  90                  95

Ser Ser Asp Asn Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 183
<211> LENGTH: 117
<212> TYPE: PRT
<213> ORGANISM: Oryctolagus cuniculus

<400> SEQUENCE: 183

Gln Ser Val Glu Ala Ser Gly Gly Arg Leu Val Met Pro Gly Gly Ser
1               5                   10                  15

Leu Thr Leu Thr Cys Thr Ala Ser Gly Phe Ser Leu Ser Thr Tyr Trp
            20                  25                  30

Met Ser Trp Val Arg Gln Ala Pro Gly Lys Gly Leu Glu Trp Ile Gly
        35                  40                  45

Asp Ile Tyr Phe Ser Asn Glu Glu Thr Asn Tyr Ala Thr Trp Ala Lys
    50                  55                  60

Gly Arg Phe Thr Ile Ser Lys Thr Ser Thr Thr Val Asp Leu Asn Val
65                  70                  75                  80

Ile Ser Pro Thr Thr Glu Asp Thr Ala Thr Tyr Phe Cys Ala Arg Gly
                85                  90                  95

Ser Pro Asp Val Glu Ile Ala Ile Asp Met Trp Gly Gln Gly Thr Leu
            100                 105                 110

Val Thr Val Ser Ser
        115

<210> SEQ ID NO 184
<211> LENGTH: 447
<212> TYPE: PRT
<213> ORGANISM: Artificial Sequence
<220> FEATURE:
<223> OTHER INFORMATION: Chemically Synthesized

<400> SEQUENCE: 184

Gln Ser Val Glu Ala Ser Gly Gly Arg Leu Val Met Pro Gly Gly Ser
1               5                   10                  15

Leu Thr Leu Thr Cys Thr Ala Ser Gly Phe Ser Leu Ser Thr Tyr Trp
            20                  25                  30

Met Ser Trp Val Arg Gln Ala Pro Gly Lys Gly Leu Glu Trp Ile Gly
        35                  40                  45

Asp Ile Tyr Phe Ser Asn Glu Glu Thr Asn Tyr Ala Thr Trp Ala Lys
    50                  55                  60

Gly Arg Phe Thr Ile Ser Lys Thr Ser Thr Thr Val Asp Leu Asn Val
65                  70                  75                  80

Ile Ser Pro Thr Thr Glu Asp Thr Ala Thr Tyr Phe Cys Ala Arg Gly
                85                  90                  95

Ser Pro Asp Val Glu Ile Ala Ile Asp Met Trp Gly Gln Gly Thr Leu
            100                 105                 110

Val Thr Val Ser Ser Ala Ser Thr Lys Gly Pro Ser Val Phe Pro Leu
        115                 120                 125
```

```
Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 185
<211> LENGTH: 13
<212> TYPE: PRT
<213> ORGANISM: Oryctolagus cuniculus

<400> SEQUENCE: 185

Gln Ser Ser Gln Asn Val Tyr Lys Asn Asn Tyr Leu Ser
1               5                   10

<210> SEQ ID NO 186
<211> LENGTH: 7
<212> TYPE: PRT
<213> ORGANISM: Oryctolagus cuniculus

<400> SEQUENCE: 186
```

```
Lys Ala Ser Thr Leu Ala Ser
1               5
```

<210> SEQ ID NO 187
<211> LENGTH: 11
<212> TYPE: PRT
<213> ORGANISM: Oryctolagus cuniculus

<400> SEQUENCE: 187

```
Ala Gly Gly Tyr Ser Ser Ser Asp Asn Ala
1               5                   10
```

<210> SEQ ID NO 188
<211> LENGTH: 5
<212> TYPE: PRT
<213> ORGANISM: Oryctolagus cuniculus

<400> SEQUENCE: 188

```
Thr Tyr Trp Met Ser
1               5
```

<210> SEQ ID NO 189
<211> LENGTH: 17
<212> TYPE: PRT
<213> ORGANISM: Oryctolagus cuniculus

<400> SEQUENCE: 189

```
Asp Ile Tyr Phe Ser Asn Glu Glu Thr Asn Tyr Ala Thr Trp Ala Lys
1               5                   10                  15

Gly
```

<210> SEQ ID NO 190
<211> LENGTH: 11
<212> TYPE: PRT
<213> ORGANISM: Oryctolagus cuniculus

<400> SEQUENCE: 190

```
Gly Ser Pro Asp Val Glu Ile Ala Ile Asp Met
1               5                   10
```

<210> SEQ ID NO 191
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 191

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Asn Val Tyr Lys Asn
            20                  25                  30

Asn Tyr Leu Ser Trp Tyr Gln Gln Lys Pro Gly Lys Val Pro Lys Leu
        35                  40                  45

Leu Ile Tyr Lys Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Thr Ser
                85                  90                  95

Ser Ser Asp Asn Ala Phe Gly Gly Gly Thr Lys Val Glu Ile Lys Arg
                100                 105                 110
```

<210> SEQ ID NO 192
<211> LENGTH: 218
<212> TYPE: PRT
<213> ORGANISM: Artificial Sequence
<220> FEATURE:
<223> OTHER INFORMATION: Chemically Synthesized

<400> SEQUENCE: 192

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Asn Val Tyr Lys Asn
            20                  25                  30

Asn Tyr Leu Ser Trp Tyr Gln Gln Lys Pro Gly Lys Val Pro Lys Leu
        35                  40                  45

Leu Ile Tyr Lys Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Thr Ser
                85                  90                  95

Ser Ser Asp Asn Ala Phe Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 193
<211> LENGTH: 120
<212> TYPE: PRT
<213> ORGANISM: Artificial Sequence
<220> FEATURE:
<223> OTHER INFORMATION: Chemically Synthesized

<400> SEQUENCE: 193

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Tyr
            20                  25                  30

Trp Met Ser Trp Val Arg Gln Ala Pro Gly Lys Gly Leu Glu Trp Val
        35                  40                  45

Gly Asp Ile Tyr Phe Ser Asn Glu Glu Thr Asn Tyr Ala Thr Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Arg Gly Ser Pro Asp Val Glu Ile Ala Ile Asp Met Trp Gly Gln
            100                 105                 110

Gly Thr Leu Val Thr Val Ser Ser
        115                 120

<210> SEQ ID NO 194
<211> LENGTH: 450
<212> TYPE: PRT
<213> ORGANISM: Artificial Sequence
<220> FEATURE:
<223> OTHER INFORMATION: Chemically Synthesized

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Trp Met Ser Trp Val Arg Gln Ala Pro Gly Lys Gly Leu Glu Trp Val
        35                  40                  45

Gly Asp Ile Tyr Phe Ser Asn Glu Glu Thr Asn Tyr Ala Thr Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Pro Asp Val Glu Ile Ala Ile Asp Met Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                    325                 330                 335
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 195
<211> LENGTH: 13
<212> TYPE: PRT
<213> ORGANISM: Oryctolagus cuniculus

<400> SEQUENCE: 195

Gln Ser Ser Gln Asn Val Tyr Lys Asn Asn Tyr Leu Ser
1               5                   10

<210> SEQ ID NO 196
<211> LENGTH: 7
<212> TYPE: PRT
<213> ORGANISM: Oryctolagus cuniculus

<400> SEQUENCE: 196

Lys Ala Ser Thr Leu Ala Ser
1               5

<210> SEQ ID NO 197
<211> LENGTH: 11
<212> TYPE: PRT
<213> ORGANISM: Oryctolagus cuniculus

<400> SEQUENCE: 197

Ala Gly Gly Tyr Thr Ser Ser Ser Asp Asn Ala
1               5                   10

<210> SEQ ID NO 198
<211> LENGTH: 5
<212> TYPE: PRT
<213> ORGANISM: Oryctolagus cuniculus

<400> SEQUENCE: 198

Thr Tyr Trp Met Ser
1               5

<210> SEQ ID NO 199
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 199
```

```
Asp Ile Tyr Phe Ser Asn Glu Glu Thr Asn Tyr Ala Thr Ser Ala Lys
1               5                   10                  15
Gly

<210> SEQ ID NO 200
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 200

Gly Ser Pro Asp Val Glu Ile Ala Ile Asp Met
1               5                   10

<210> SEQ ID NO 201
<211> LENGTH: 333
<212> TYPE: DNA
<213> ORGANISM: Oryctolagus cuniculus

<400> SEQUENCE: 201
gcccttgtga tgacccagac tccatcctcc gtgtctgcag ctgtgggagg cacagtcacc      60
atcaattgcc aggccagtca gaacatttac agcaatttag cctggtatca acagagacca     120
gggcagcgtc ccaagctcct gatctatggt gcatccaatc tggatgctgg ggtcccatcg     180
cggttcagag gcagtggatc tgggacagag tacactctca ccatcagcga cctggagtgt     240
gacgatgttg gcacttacta ctgtcaaagt gcttttgata gtgatagtac tgaaaatact     300
ttcggcggag ggaccgaggt ggtggtcaaa cgt                                  333

<210> SEQ ID NO 202
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 202
gcccttgtga tgacccagac tccatcctcc gtgtctgcag ctgtgggagg cacagtcacc      60
atcaattgcc aggccagtca gaacatttac agcaatttag cctggtatca acagagacca     120
gggcagcgtc ccaagctcct gatctatggt gcatccaatc tggatgctgg ggtcccatcg     180
cggttcagag gcagtggatc tgggacagag tacactctca ccatcagcga cctggagtgt     240
gacgatgttg gcacttacta ctgtcaaagt gcttttgata gtgatagtac tgaaaatact     300
ttcggcggag ggaccgaggt ggtggtcaaa cgtacggtag cggccccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg ttag           654

<210> SEQ ID NO 203
<211> LENGTH: 354
<212> TYPE: DNA
<213> ORGANISM: Oryctolagus cuniculus

<400> SEQUENCE: 203
```

| | |
|---|---:|
| cagtcgctgg aggagtccgg gggtcgcctg gtcacgcctg ggacacccct gacactcacc | 60 |
| tgcacagtct ctggcttctc cctcagtagc tatgcaatga gctgggtccg ccaggctcca | 120 |
| gggaagggc tggaatggat cggagtcatt actagtattg gtagcacagt ctacgcgagc | 180 |
| tgggcgaaag gccgattcac catctccaaa acctcgacca cggtggatct gaaaatcacc | 240 |
| agtccgacaa ccgaggacac ggccacctat ttctgtgcca gaggctacga tgactatgat | 300 |
| gagatgacct actttaacat ctggggccag gggaccctcg tcaccgtctc gagc | 354 |

```
<210> SEQ ID NO 204
<211> LENGTH: 1347
<212> TYPE: DNA
<213> ORGANISM: Artificial Sequence
<220> FEATURE:
<223> OTHER INFORMATION: Chemically Synthesized

<400> SEQUENCE: 204
```

| | |
|---|---:|
| cagtcgctgg aggagtccgg gggtcgcctg gtcacgcctg ggacacccct gacactcacc | 60 |
| tgcacagtct ctggcttctc cctcagtagc tatgcaatga gctgggtccg ccaggctcca | 120 |
| gggaagggc tggaatggat cggagtcatt actagtattg gtagcacagt ctacgcgagc | 180 |
| tgggcgaaag gccgattcac catctccaaa acctcgacca cggtggatct gaaaatcacc | 240 |
| agtccgacaa ccgaggacac ggccacctat ttctgtgcca gaggctacga tgactatgat | 300 |
| gagatgacct actttaacat ctggggccag gggaccctcg tcaccgtctc gagcgcctcc | 360 |
| accaagggcc catcggtctt ccccctggca ccctcctcca agagcacctc tgggggcaca | 420 |
| gcggccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctca gcagcgtggt gaccgtgccc tccagcagct gggcacccca gacctacatc | 600 |
| tgcaacgtga atcacaagcc cagcaacacc aaggtggaca gagagttga gcccaaatct | 660 |
| tgtgacaaaa ctcacacatg cccaccgtgc ccagcacctg aactcctggg gggaccgtca | 720 |
| gtcttcctct tccccccaaa acccaaggac accctcatga tctcccggac ccctgaggtc | 780 |
| acatgcgtgt ggtggacgt gagccacgaa gaccctgagg tcaagttcaa ctggtacgtg | 840 |
| gacggcgtgg aggtgcataa tgccaagaca aagccgcggg aggagcagta cgccagcacg | 900 |
| taccgtgtgt cagcgtcct caccgtcctg caccaggact ggctgaatgg caaggagtac | 960 |
| aagtgcaagg tctccaacaa agccctccca gcccccatcg agaaaaccat ctccaaagcc | 1020 |
| aaagggcagc cccgagaacc acaggtgtac accctgcccc catcccggga ggagatgacc | 1080 |
| aagaaccagg tcagcctgac ctgcctggtc aaaggcttct atcccagcga catcgccgtg | 1140 |
| gagtgggaga gcaatgggca gccggagaac aactacaaga ccacgcctcc cgtgctggac | 1200 |
| tccgacggct ccttcttcct ctacagcaag ctcaccgtgg acaagagcag gtggcagcag | 1260 |
| gggaacgtct tctcatgctc cgtgatgcat gaggctctgc acaaccacta cacgcagaag | 1320 |
| agcctctccc tgtctccggg taaatga | 1347 |

```
<210> SEQ ID NO 205
<211> LENGTH: 33
<212> TYPE: DNA
<213> ORGANISM: Oryctolagus cuniculus

<400> SEQUENCE: 205
```

| | |
|---|---:|
| caggccagtc agaacattta cagcaattta gcc | 33 |

<210> SEQ ID NO 206
<211> LENGTH: 21
<212> TYPE: DNA
<213> ORGANISM: Oryctolagus cuniculus

<400> SEQUENCE: 206
ggtgcatcca atctggatgc t                                              21

<210> SEQ ID NO 207
<211> LENGTH: 36
<212> TYPE: DNA
<213> ORGANISM: Oryctolagus cuniculus

<400> SEQUENCE: 207
caaagtgctt ttgatagtga tagtactgaa aatact                              36

<210> SEQ ID NO 208
<211> LENGTH: 15
<212> TYPE: DNA
<213> ORGANISM: Oryctolagus cuniculus

<400> SEQUENCE: 208
agctatgcaa tgagc                                                     15

<210> SEQ ID NO 209
<211> LENGTH: 48
<212> TYPE: DNA
<213> ORGANISM: Oryctolagus cuniculus

<400> SEQUENCE: 209
gtcattacta gtattggtag cacagtctac gcgagctggg cgaaaggc                 48

<210> SEQ ID NO 210
<211> LENGTH: 39
<212> TYPE: DNA
<213> ORGANISM: Oryctolagus cuniculus

<400> SEQUENCE: 210
ggctacgatg actatgatga gatgacctac tttaacatc                           39

<210> SEQ ID NO 211
<211> LENGTH: 333
<212> TYPE: DNA
<213> ORGANISM: Artificial Sequence
<220> FEATURE:
<223> OTHER INFORMATION: Chemically Synthesized

<400> SEQUENCE: 211
gacatccaga tgacccagtc tccttccacc ctgtctgcat ctgtaggaga cagagtcacc    60
atcacttgcc aggccagtca gaacatttac agcaacttag cctggtatca gcagaaacca   120
ggaaaagccc ctaagctcct gatctatggt gcatccaatc tggatgctgg agtcccatca   180
aggttctctg gcagtggatc tgggacagag tacactctca ccatcagcag cctgcagcct   240
gatgattttg caacttacta ctgccaaagt gcttttgata gtgatagtac tgaaaacact   300
ttcggcggag gaaccaaggt ggaaatcaaa cgt                                333

<210> SEQ ID NO 212
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 212

```
gacatccaga tgacccagtc tccttccacc ctgtctgcat ctgtaggaga cagagtcacc      60
atcacttgcc aggccagtca gaacatttac agcaacttag cctggtatca gcagaaacca     120
ggaaaagccc ctaagctcct gatctatggt gcatccaatc tggatgctgg agtcccatca     180
aggttctctg gcagtggatc tgggacagag tacactctca ccatcagcag cctgcagcct     240
gatgattttg caacttacta ctgccaaagt gcttttgata gtgatagtac tgaaaacact     300
ttcggcggag gaaccaaggt ggaaatcaaa cgtacggtag cggccccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg ttag           654
```

<210> SEQ ID NO 213
<211> LENGTH: 363
<212> TYPE: DNA
<213> ORGANISM: Artificial Sequence
<220> FEATURE:
<223> OTHER INFORMATION: Chemically Synthesized

<400> SEQUENCE: 213

```
gaggtgcagc tggtggagtc tgggggaggc ttggtccagc ctggggggtc cctgagactc      60
tcctgtgcag cctctggatt caccgtcagt agctatgcaa tgagctgggt ccgtcaggct     120
ccagggaagg ggctggagtg ggtcggagtc attactagta ttggtagcac agtctacgcg     180
agcagcgcga aaggccgatt caccatctcc agagacaatt ccaagaacac cctgtatctt     240
caaatgaaca gcctgagagc tgaggacact gctgtgtatt actgtgctag aggctacgat     300
gactatgatg agatgaccta ctttaacatc tggggccaag ggaccctcgt caccgtctcg     360
agc                                                                    363
```

<210> SEQ ID NO 214
<211> LENGTH: 1356
<212> TYPE: DNA
<213> ORGANISM: Artificial Sequence
<220> FEATURE:
<223> OTHER INFORMATION: Chemically Synthesized

<400> SEQUENCE: 214

```
gaggtgcagc tggtggagtc tgggggaggc ttggtccagc ctggggggtc cctgagactc      60
tcctgtgcag cctctggatt caccgtcagt agctatgcaa tgagctgggt ccgtcaggct     120
ccagggaagg ggctggagtg ggtcggagtc attactagta ttggtagcac agtctacgcg     180
agcagcgcga aaggccgatt caccatctcc agagacaatt ccaagaacac cctgtatctt     240
caaatgaaca gcctgagagc tgaggacact gctgtgtatt actgtgctag aggctacgat     300
gactatgatg agatgaccta ctttaacatc tggggccaag ggaccctcgt caccgtctcg     360
agcgcctcca caagggccc atcggtcttc cccctggcac cctcctccaa gagcacctct     420
gggggcacag cggccctggg ctgcctggtc aaggactact ccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
```

```
cccaaatctt gtgacaaaac tcacacatgc ccaccgtgcc cagcacctga actcctgggg    720
ggaccgtcag tcttcctctt cccccaaaa cccaaggaca ccctcatgat ctcccggacc     780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
gccagcacgt accgtgtggt cagcgtcctc accgtcctgc accaggactg gctgaatggc    960
aaggagtaca agtgcaaggt ctccaacaaa gccctcccag cccccatcga aaaaccatc    1020 tccaaagcca agggcagcc ccgagaacca caggtgtaca ccctgccccc atcccgggag   1080
gagatgacca gaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaatga                             1356

<210> SEQ ID NO 215
<211> LENGTH: 33
<212> TYPE: DNA
<213> ORGANISM: Oryctolagus cuniculus

<400> SEQUENCE: 215
caggccagtc agaacattta cagcaactta gcc                                 33

<210> SEQ ID NO 216
<211> LENGTH: 21
<212> TYPE: DNA
<213> ORGANISM: Oryctolagus cuniculus

<400> SEQUENCE: 216
ggtgcatcca atctggatgc t                                              21

<210> SEQ ID NO 217
<211> LENGTH: 36
<212> TYPE: DNA
<213> ORGANISM: Oryctolagus cuniculus

<400> SEQUENCE: 217
caaagtgctt ttgatagtga tagtactgaa aacact                              36

<210> SEQ ID NO 218
<211> LENGTH: 15
<212> TYPE: DNA
<213> ORGANISM: Oryctolagus cuniculus

<400> SEQUENCE: 218
agctatgcaa tgagc                                                     15

<210> SEQ ID NO 219
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 219
gtcattacta gtattggtag cacagtctac gcgagcagcg cgaaaggc                 48

<210> SEQ ID NO 220
```

```
<211> LENGTH: 39
<212> TYPE: DNA
<213> ORGANISM: Oryctolagus cuniculus

<400> SEQUENCE: 220
ggctacgatg actatgatga gatgacctac tttaacatc                           39

<210> SEQ ID NO 221
<211> LENGTH: 336
<212> TYPE: DNA
<213> ORGANISM: Oryctolagus cuniculus

<400> SEQUENCE: 221
gcagccgtgc tgacccagac accatcgccc gtgtctgcag ctatgggaga cacagtcacc    60
atcaagtgcc agtccagtca gagtgtttat aagaacaact acttatcctg gtatcagcag   120
aaaccagggc agcctcccag gctcctgatc tatgatgcat ccaatctgcc atctggggtc   180
ccatcacggt tcagcggcag tggatctggg acacagttca ctctcaccat cagcggcgtg   240
cagtgtgacg atgctgccac ttactactgt ctaggcgatt atgatgatga tgctgataat   300
gctttcggcg agggaccga ggtggtggtc aaacgt                              336

<210> SEQ ID NO 222
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 222
gcagccgtgc tgacccagac accatcgccc gtgtctgcag ctatgggaga cacagtcacc    60
atcaagtgcc agtccagtca gagtgtttat aagaacaact acttatcctg gtatcagcag   120
aaaccagggc agcctcccag gctcctgatc tatgatgcat ccaatctgcc atctggggtc   180
ccatcacggt tcagcggcag tggatctggg acacagttca ctctcaccat cagcggcgtg   240
cagtgtgacg atgctgccac ttactactgt ctaggcgatt atgatgatga tgctgataat   300
gctttcggcg agggaccga ggtggtggtc aaacgtacgg tagcggcccc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600 acccatcagg gcctgagctc gcccgtcaca aagagcttca caggggaga gtgttag      657

<210> SEQ ID NO 223
<211> LENGTH: 339
<212> TYPE: DNA
<213> ORGANISM: Oryctolagus cuniculus

<400> SEQUENCE: 223
cagtcggtgg aggagtccgg gggtcgcctg gtcacgcctg gacacccct gacactcacc     60 tgcacagtct ctggattctc cctcagtagc tatgtaatga tctgggtccg ccaggctcca   120
gggaaggggc tggaatacat cggaatcact tggagtgctg gtacatacta cgcgagctgg   180
gcgaaaggcc gattcaccat ctccaaaacc tcgtcgacca cggtggatct gaaaatcacc   240
agtccgacaa ccgaggacac ggccacctat ttctgtgccg gaggtggtgg tagtatttat   300
gatatttggg gcccgggcac cctggtcacc gtctcgagc                          339
```

<210> SEQ ID NO 224
<211> LENGTH: 1332
<212> TYPE: DNA
<213> ORGANISM: Artificial Sequence
<220> FEATURE:
<223> OTHER INFORMATION: Chemically Synthesized

<400> SEQUENCE: 224

```
cagtcggtgg aggagtccgg gggtcgcctg gtcacgcctg ggacacccct gacactcacc      60
tgcacagtct ctggattctc cctcagtagc tatgtaatga tctgggtccg ccaggctcca     120
gggaaggggc tggaatacat cggaatcact tggagtgctg gtacatacta cgcgagctgg     180
gcgaaaggcc gattcaccat ctccaaaacc tcgtcgacca cggtggatct gaaaatcacc     240
agtccgacaa ccgaggacac ggccacctat ttctgtgccg gaggtggtgg tagtatttat     300
gatatttggg gcccgggcac cctggtcacc gtctcgagcg cctccaccaa gggcccatcg     360
gtcttccccc tggcaccctc ctccaagagc acctctgggg cacagcggc cctgggctgc      420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acccagacct acatctgcaa cgtgaatcac     600
aagcccagca acaccaaggt ggacaagaga gttgagccca aatcttgtga caaaactcac     660
acatgcccac cgtgcccagc acctgaactc ctggggggac cgtcagtctt cctcttcccc     720
ccaaaaccca aggacaccct catgatctcc cggacccctg aggtcacatg cgtggtggtg     780
gacgtgagcc acgaagaccc tgaggtcaag ttcaactggt acgtggacgg cgtggaggtg     840
cataatgcca agacaaagcc gcgggaggag cagtacgcca gcacgtaccg tgtggtcagc     900
gtcctcaccg tcctgcacca ggactggctg aatggcaagg agtacaagtg caaggtctcc     960
aacaaagccc tcccagcccc catcgagaaa accatctcca aagccaaagg gcagccccga    1020
gaaccacagg tgtacaccct gcccccatcc cgggaggaga tgaccaagaa ccaggtcagc    1080
ctgacctgcc tggtcaaagg cttctatccc agcgacatcg ccgtggagtg ggagagcaat    1140
gggcagccgg agaacaacta caagaccacg cctcccgtgc tggactccga cggctccttc    1200
ttcctctaca gcaagctcac cgtggacaag agcaggtggc agcaggggaa cgtcttctca    1260
tgctccgtga tgcatgaggc tctgcacaac cactacacgc agaagagcct ctccctgtct    1320
ccgggtaaat ga                                                        1332
```

<210> SEQ ID NO 225
<211> LENGTH: 39
<212> TYPE: DNA
<213> ORGANISM: Oryctolagus cuniculus

<400> SEQUENCE: 225

```
cagtccagtc agagtgttta taagaacaac tacttatcc                             39
```

<210> SEQ ID NO 226
<211> LENGTH: 21
<212> TYPE: DNA
<213> ORGANISM: Oryctolagus cuniculus

<400> SEQUENCE: 226

```
gatgcatcca atctgccatc t                                                21
```

<210> SEQ ID NO 227

```
<211> LENGTH: 33
<212> TYPE: DNA
<213> ORGANISM: Oryctolagus cuniculus

<400> SEQUENCE: 227
ctaggcgatt atgatgatga tgctgataat gct                              33

<210> SEQ ID NO 228
<211> LENGTH: 15
<212> TYPE: DNA
<213> ORGANISM: Oryctolagus cuniculus

<400> SEQUENCE: 228
agctatgtaa tgatc                                                  15

<210> SEQ ID NO 229
<211> LENGTH: 45
<212> TYPE: DNA
<213> ORGANISM: Oryctolagus cuniculus

<400> SEQUENCE: 229
atcacttgga gtgctggtac atactacgcg agctgggcga aaggc                 45

<210> SEQ ID NO 230
<211> LENGTH: 24
<212> TYPE: DNA
<213> ORGANISM: Oryctolagus cuniculus

<400> SEQUENCE: 230
ggtggtggta gtatttatga tatt                                        24

<210> SEQ ID NO 231
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 231
gacatccaga tgacccagtc tccttccacc ctgtctgcat ctgtaggaga cagagtcacc   60
atcacttgcc agtccagtca gagtgtctat aagaacaact acttatcctg gtatcagcag  120
aaaccaggaa aagcccctaa gctcctgatc tatgatgcat ccaatctgcc atctggagtc  180
ccatcaaggt tcagcggcag tggatctgga acagaattca ctctcaccat cagcagcctg  240
cagcctgatg attttgcaac ttattactgc ctaggcgatt atgatgatga tgctgataat  300
gctttcggcg gaggaaccaa ggtggaaatc aaacgt                            336

<210> SEQ ID NO 232
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 232
gacatccaga tgacccagtc tccttccacc ctgtctgcat ctgtaggaga cagagtcacc   60
atcacttgcc agtccagtca gagtgtctat aagaacaact acttatcctg gtatcagcag  120
aaaccaggaa aagcccctaa gctcctgatc tatgatgcat ccaatctgcc atctggagtc  180
ccatcaaggt tcagcggcag tggatctgga acagaattca ctctcaccat cagcagcctg  240
cagcctgatg attttgcaac ttattactgc ctaggcgatt atgatgatga tgctgataat  300
```

```
gctttcggcg gaggaaccaa ggtggaaatc aaacgtacgg tagcggcccc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca caggggaga gtgttag      657

<210> SEQ ID NO 233
<211> LENGTH: 345
<212> TYPE: DNA
<213> ORGANISM: Artificial Sequence
<220> FEATURE:
<223> OTHER INFORMATION: Chemically Synthesized

<400> SEQUENCE: 233
gaggtgcagc tggtggagtc tgggggaggc ttggtccagc ctgggggtc cctgagactc      60 tcctgtgcag cctctggatt caccgtcagt agctatgtaa tgatctgggt ccgtcaggct    120
ccagggaagg ggctggagta catcggaatc acttggagtg ctggtacata ctacgcgagc    180
agtgcgaaag gccgattcac catctccaga gacaattcca agaacaccct gtatcttcaa    240
atgaacagcc tgagagctga ggacactgct gtgtattact gtgctggagg tggtggtagt    300
atctatgata tttggggcca agggaccctc gtcaccgtct cgagc                    345

<210> SEQ ID NO 234
<211> LENGTH: 1338
<212> TYPE: DNA
<213> ORGANISM: Artificial Sequence
<220> FEATURE:
<223> OTHER INFORMATION: Chemically Synthesized

<400> SEQUENCE: 234
gaggtgcagc tggtggagtc tgggggaggc ttggtccagc ctgggggtc cctgagactc      60 tcctgtgcag cctctggatt caccgtcagt agctatgtaa tgatctgggt ccgtcaggct    120
ccagggaagg ggctggagta catcggaatc acttggagtg ctggtacata ctacgcgagc    180
agtgcgaaag gccgattcac catctccaga gacaattcca agaacaccct gtatcttcaa    240
atgaacagcc tgagagctga ggacactgct gtgtattact gtgctggagg tggtggtagt    300
atctatgata tttggggcca agggaccctc gtcaccgtct cgagcgcctc caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaactcctgg ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acgccagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag   1020
```

-continued

```
cccgagaac cacaggtgta caccctgccc ccatcccggg aggagatgac caagaaccag      1080
gtcagcctga cctgcctggt caaaggcttc tatcccagcg acatcgccgt ggagtgggag      1140
agcaatgggc agccggagaa caactacaag accacgcctc ccgtgctgga ctccgacggc      1200
tccttcttcc tctacagcaa gctcaccgtg gacaagagca ggtggcagca ggggaacgtc      1260
ttctcatgct ccgtgatgca tgaggctctg cacaaccact acacgcagaa gagcctctcc      1320
ctgtctccgg gtaaatga                                                   1338
```

<210> SEQ ID NO 235
<211> LENGTH: 39
<212> TYPE: DNA
<213> ORGANISM: Oryctolagus cuniculus

<400> SEQUENCE: 235

```
cagtccagtc agaatgttta taagaacaac tacttatcc                              39
```

<210> SEQ ID NO 236
<211> LENGTH: 21
<212> TYPE: DNA
<213> ORGANISM: Oryctolagus cuniculus

<400> SEQUENCE: 236

```
aaggcatcca ctctggcatc t                                                 21
```

<210> SEQ ID NO 237
<211> LENGTH: 32
<212> TYPE: DNA
<213> ORGANISM: Oryctolagus cuniculus

<400> SEQUENCE: 237

```
gcaggcggtt ataccagtag tagtgataat gc                                     32
```

<210> SEQ ID NO 238
<211> LENGTH: 15
<212> TYPE: DNA
<213> ORGANISM: Oryctolagus cuniculus

<400> SEQUENCE: 238

```
agctatgtaa tgatc                                                        15
```

<210> SEQ ID NO 239
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 239

```
atcacttgga gtgctggtac atactacgcg agcagtgcga aaggc                       45
```

<210> SEQ ID NO 240
<211> LENGTH: 24
<212> TYPE: DNA
<213> ORGANISM: Oryctolagus cuniculus

<400> SEQUENCE: 240

```
ggtggtggta gtatctatga tatt                                              24
```

<210> SEQ ID NO 241
<211> LENGTH: 333
<212> TYPE: DNA
<213> ORGANISM: Oryctolagus cuniculus

<400> SEQUENCE: 241

```
gcctatgata tgacccagac tccagcctct gtggaggtag ctgtgggagg cacagtcacc      60
atcaagtgcc aggccagtca gagcatttac agcaatttag cctggtatca gcagagacca     120
gggcagcctc ccaagctcct gatctatgat gcatccactc tggaatctgg ggtcccatcg     180
cggttcaaag gcagtggatc tgggacagag tacactctca ccatcagcgg cgtggagtgt     240
gccgatgctg cctcttacta ctgtcaacag ggttttactg ttagtgatat tgataatgct     300
ttcggcggag ggaccgaggt ggtggtcaaa cgt                                  333
```

<210> SEQ ID NO 242
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 242

```
gcctatgata tgacccagac tccagcctct gtggaggtag ctgtgggagg cacagtcacc      60
atcaagtgcc aggccagtca gagcatttac agcaatttag cctggtatca gcagagacca     120
gggcagcctc ccaagctcct gatctatgat gcatccactc tggaatctgg ggtcccatcg     180
cggttcaaag gcagtggatc tgggacagag tacactctca ccatcagcgg cgtggagtgt     240
gccgatgctg cctcttacta ctgtcaacag ggttttactg ttagtgatat tgataatgct     300
ttcggcggag ggaccgaggt ggtggtcaaa cgtacggtag cggccccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg ttag           654
```

<210> SEQ ID NO 243
<211> LENGTH: 354
<212> TYPE: DNA
<213> ORGANISM: Oryctolagus cuniculus

<400> SEQUENCE: 243

```
cagtcggtgg aggagtccgg gggtcgcctg gtcacgcctg gacacccct gacactcacc       60
tgcacagtct ctggattctc cctcagtaac tatgcagtgg gctgggtccg ccaggctcca     120
gggaaggggc tggaatggat cggaatcatt ggtcgtaatg gtaacacatg gtacgcgagc     180
tgggcaagag gccgattcac catctccaaa acctcgacca cggtggatct gaaaatcacc     240
agtccgacaa gcgaggacac ggccacatat ttctgtgcca gaggatatgg ccgtagtgtt     300
gcttattacg tctttaacat ctggggccca ggcacccctcg tcaccgtctc gagc          354
```

<210> SEQ ID NO 244
<211> LENGTH: 1347
<212> TYPE: DNA
<213> ORGANISM: Artificial Sequence
<220> FEATURE:
<223> OTHER INFORMATION: Chemically Synthesized

<400> SEQUENCE: 244

```
cagtcggtgg aggagtccgg gggtcgcctg gtcacgcctg gacacccct gacactcacc       60
```

-continued

```
tgcacagtct ctggattctc cctcagtaac tatgcagtgg gctgggtccg ccaggctcca    120
gggaaggggc tggaatggat cggaatcatt ggtcgtaatg gtaacacatg gtacgcgagc    180
tgggcaagag gccgattcac catctccaaa acctcgacca cggtggatct gaaaatcacc    240
agtccgacaa gcgaggacac ggccacatat ttctgtgcca gaggatatgg ccgtagtgtt    300
gcttattacg tctttaacat ctggggccca ggcaccctcg tcaccgtctc gagcgcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc    600
tgcaacgtga atcacaagcc cagcaacacc aaggtggaca gagagttga gcccaaatct    660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta cgccagcacg    900
taccgtgtgg tcagcgtcct caccgtcctg caccaggact ggctgaatgg caaggagtac    960
aagtgcaagg tctccaacaa agccctccca gccccatcg agaaaaccat ctccaaagcc   1020
aaagggcagc cccgagaacc acaggtgtac accctgcccc catcccggga ggagatgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaatga                                       1347
```

<210> SEQ ID NO 245
<211> LENGTH: 33
<212> TYPE: DNA
<213> ORGANISM: Oryctolagus cuniculus

<400> SEQUENCE: 245

```
caggccagtc agagcattta cagcaattta gcc                                 33
```

<210> SEQ ID NO 246
<211> LENGTH: 21
<212> TYPE: DNA
<213> ORGANISM: Oryctolagus cuniculus

<400> SEQUENCE: 246

```
gatgcatcca ctctggaatc t                                              21
```

<210> SEQ ID NO 247
<211> LENGTH: 36
<212> TYPE: DNA
<213> ORGANISM: Oryctolagus cuniculus

<400> SEQUENCE: 247

```
caacagggtt ttactgttag tgatattgat aatgct                              36
```

<210> SEQ ID NO 248
<211> LENGTH: 15
<212> TYPE: DNA
<213> ORGANISM: Oryctolagus cuniculus

<400> SEQUENCE: 248
aactatgcag tgggc                                                  15

<210> SEQ ID NO 249
<211> LENGTH: 48
<212> TYPE: DNA
<213> ORGANISM: Oryctolagus cuniculus

<400> SEQUENCE: 249
atcattggtc gtaatggtaa cacatggtac gcgagctggg caagaggc              48

<210> SEQ ID NO 250
<211> LENGTH: 39
<212> TYPE: DNA
<213> ORGANISM: Oryctolagus cuniculus

<400> SEQUENCE: 250
ggatatggcc gtagtgttgc ttattacgtc tttaacatc                        39

<210> SEQ ID NO 251
<211> LENGTH: 333
<212> TYPE: DNA
<213> ORGANISM: Artificial Sequence
<220> FEATURE:
<223> OTHER INFORMATION: Chemically Synthesized

<400> SEQUENCE: 251
gacatccaga tgacccagtc tccttccacc ctgtctgcat ctgtaggaga cagagtcacc    60
atcacttgcc aggccagtca gagcatttac agcaatcttg cctggtatca gcagaaacca   120
ggaaaagccc ctaagctcct gatctatgat gcatccactc tggaatctgg agtcccatca   180
aggttcagcg gcagtggatc tgggacagag tacactctca ccatcagcag cctgcagcct   240
gatgattttg caacttacta ctgccaacag ggttttactg ttagtgatat tgataatgct   300
ttcggcggag gaaccaaggt ggaaatcaaa cgt                               333

<210> SEQ ID NO 252
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 252
gacatccaga tgacccagtc tccttccacc ctgtctgcat ctgtaggaga cagagtcacc    60
atcacttgcc aggccagtca gagcatttac agcaatcttg cctggtatca gcagaaacca   120
ggaaaagccc ctaagctcct gatctatgat gcatccactc tggaatctgg agtcccatca   180
aggttcagcg gcagtggatc tgggacagag tacactctca ccatcagcag cctgcagcct   240
gatgattttg caacttacta ctgccaacag ggttttactg ttagtgatat tgataatgct   300
ttcggcggag gaaccaaggt ggaaatcaaa cgtacggtag cggccccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
accctgacgc tgagcaaagc agactacgag aaacacaaag tctacgcctg cgaagtcacc   600
catcagggcc tgagctcgcc cgtcacaaag agcttcaaca ggggagagtg ttag         654

<210> SEQ ID NO 253
<211> LENGTH: 363
<212> TYPE: DNA
<213> ORGANISM: Artificial Sequence
<220> FEATURE:
<223> OTHER INFORMATION: Chemically Synthesized

<400> SEQUENCE: 253

```
gaggtgcagc tggtggagtc tgggggaggc ttggtccagc ctgggggtc cctgagactc      60
tcctgtgcag cctctggatt caccgtcagt aactatgcag tgggctgggt ccgtcaggct    120
ccagggaagg ggctggagtg ggtcggaatc attggtcgta atggtaacac atggtacgcg    180
agctctgcaa gaggccgatt caccatctcc agagacaatt ccaagaacac cctgtatctt    240
caaatgaaca gcctgagagc tgaggacact gctgtgtatt actgtgctag aggatatggc    300
cgtagtgttg cttattacgt ctttaacatc tggggcccag ggaccctcgt caccgtctcg    360
agc                                                                  363
```

<210> SEQ ID NO 254
<211> LENGTH: 1356
<212> TYPE: DNA
<213> ORGANISM: Artificial Sequence
<220> FEATURE:
<223> OTHER INFORMATION: Chemically Synthesized

<400> SEQUENCE: 254

```
gaggtgcagc tggtggagtc tgggggaggc ttggtccagc ctgggggtc cctgagactc      60
tcctgtgcag cctctggatt caccgtcagt aactatgcag tgggctgggt ccgtcaggct    120
ccagggaagg ggctggagtg ggtcggaatc attggtcgta atggtaacac atggtacgcg    180
agctctgcaa gaggccgatt caccatctcc agagacaatt ccaagaacac cctgtatctt    240
caaatgaaca gcctgagagc tgaggacact gctgtgtatt actgtgctag aggatatggc    300
cgtagtgttg cttattacgt ctttaacatc tggggcccag ggaccctcgt caccgtctcg    360
agcgcctcca caagggccc atcggtcttc cccctggcac cctcctccaa gagcacctct    420
gggggcacag cggccctggg ctgcctggtc aaggactact ccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga actcctgggg    720
ggaccgtcag tcttcctctt ccccccaaaa cccaaggaca cctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
gccagcacgt accgtgtggt cagcgtcctc accgtcctgc accaggactg gctgaatggc    960
aaggagtaca agtgcaaggt ctccaacaaa gccctcccag cccccatcga gaaaaccatc    1020
tccaaagcca agggcagcc ccgagaacca caggtgtaca ccctgccccc atcccgggag    1080
gagatgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatga                              1356
```

<210> SEQ ID NO 255
<211> LENGTH: 33
<212> TYPE: DNA
<213> ORGANISM: Oryctolagus cuniculus

<400> SEQUENCE: 255
caggccagtc agagcattta cagcaatctt gcc                          33

<210> SEQ ID NO 256
<211> LENGTH: 21
<212> TYPE: DNA
<213> ORGANISM: Oryctolagus cuniculus

<400> SEQUENCE: 256
gatgcatcca ctctggaatc t                                      21

<210> SEQ ID NO 257
<211> LENGTH: 36
<212> TYPE: DNA
<213> ORGANISM: Oryctolagus cuniculus

<400> SEQUENCE: 257
caacagggtt ttactgttag tgatattgat aatgct                      36

<210> SEQ ID NO 258
<211> LENGTH: 15
<212> TYPE: DNA
<213> ORGANISM: Oryctolagus cuniculus

<400> SEQUENCE: 258
aactatgcag tgggc                                             15

<210> SEQ ID NO 259
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 259
atcattggtc gtaatggtaa cacatggtac gcgagctctg caagaggc          48

<210> SEQ ID NO 260
<211> LENGTH: 39
<212> TYPE: DNA
<213> ORGANISM: Oryctolagus cuniculus

<400> SEQUENCE: 260
ggatatggcc gtagtgttgc ttattacgtc tttaacatc                    39

<210> SEQ ID NO 261
<211> LENGTH: 336
<212> TYPE: DNA
<213> ORGANISM: Oryctolagus cuniculus

<400> SEQUENCE: 261
gccgatgttg tgatgaccca gactccagcc tccgtgtctc aacctgtggg aggcacagtc      60
accatcaagt gccaggccag tgaggacatt tataacttat tggcctggta tcagcagaaa     120
ccagggcagc ctcccaagct cctgatctat tctgcatcca ctctggcatc tggggtccca     180
tcgcggttca aaggcagtgg atctgggaca gagtacactc tcaccatcag cggcctggag     240

```
tgtgccgatg ctgccactta ctactgtcaa acaattatc ttgttactac ttatggtgtt      300
gctttcggcg agggaccga ggtggtggtc aaacgt                               336

<210> SEQ ID NO 262
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 262
gccgatgttg tgatgaccca gactccagcc tccgtgtctc aacctgtggg aggcacagtc      60
accatcaagt gccaggccag tgaggacatt tataacttat tggcctggta tcagcagaaa     120
ccagggcagc ctcccaagct cctgatctat tctgcatcca ctctggcatc tggggtccca     180
tcgcggttca aggcagtgg atctgggaca gagtacactc tcaccatcag cggcctggag     240
tgtgccgatg ctgccactta ctactgtcaa acaattatc ttgttactac ttatggtgtt     300
gctttcggcg agggaccga ggtggtggtc aaacgtacgg tagcggcccc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc     600 acccatcagg gcctgagctc gcccgtcaca aagagcttca caggggaga gtgttag       657

<210> SEQ ID NO 263
<211> LENGTH: 360
<212> TYPE: DNA
<213> ORGANISM: Oryctolagus cuniculus

<400> SEQUENCE: 263
caggagcagc tgaaggagtc cggggggtcgc ctggtcacgc ctgggacacc cctgacactc      60
acctgtacag tctctggatt ctccctcagt agctatgcaa tgatctgggt ccgccaggct     120
ccagggaagg ggctggaata catcggatac attgatactg atactagcgc atactacgcg     180
agctgggtga aaggccgatt caccatctcc agaacctcga ccacggtgga tctcaaaatc     240
actagtccga caaccgagga cacggccacc tatttctgtg ccagatctta tgctgcttat     300
ggtggttatc ctgctacttt tgatccctgg ggcccaggca cctggtcac cgtctcgagc     360

<210> SEQ ID NO 264
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 264
caggagcagc tgaaggagtc cggggggtcgc ctggtcacgc ctgggacacc cctgacactc      60
acctgtacag tctctggatt ctccctcagt agctatgcaa tgatctgggt ccgccaggct     120
ccagggaagg ggctggaata catcggatac attgatactg atactagcgc atactacgcg     180
agctgggtga aaggccgatt caccatctcc agaacctcga ccacggtgga tctcaaaatc     240
actagtccga caaccgagga cacggccacc tatttctgtg ccagatctta tgctgcttat     300
ggtggttatc ctgctacttt tgatccctgg ggcccaggca cctggtcac cgtctcgagc     360 gcctccacca agggcccatc ggtcttcccc ctggcaccct cctccaagag cacctctggg     420
```

```
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagag agttgagccc      660
aaatcttgtg acaaaactca cacatgccca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacgcc      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggaggag     1080
atgaccaaga accaggtcag cctgacctgc ctggtcaaag gcttctatcc agcgacatc      1140 gccgtggagt gggagagcaa tgggcagccg gagaacaact acaagaccac gcctcccgtg     1200
ctggactccg acggctcctt cttcctctac agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa tga                                 1353

<210> SEQ ID NO 265
<211> LENGTH: 33
<212> TYPE: DNA
<213> ORGANISM: Oryctolagus cuniculus

<400> SEQUENCE: 265
caggccagtg aggacattta aacttattg gcc                                   33

<210> SEQ ID NO 266
<211> LENGTH: 21
<212> TYPE: DNA
<213> ORGANISM: Oryctolagus cuniculus

<400> SEQUENCE: 266
tctgcatcca ctctggcatc t                                               21

<210> SEQ ID NO 267
<211> LENGTH: 36
<212> TYPE: DNA
<213> ORGANISM: Oryctolagus cuniculus

<400> SEQUENCE: 267
caaaacaatt atcttgttac tacttatggt gttgct                               36

<210> SEQ ID NO 268
<211> LENGTH: 15
<212> TYPE: DNA
<213> ORGANISM: Oryctolagus cuniculus

<400> SEQUENCE: 268
agctatgcaa tgatc                                                      15

<210> SEQ ID NO 269
<211> LENGTH: 48
<212> TYPE: DNA
<213> ORGANISM: Oryctolagus cuniculus
```

<400> SEQUENCE: 269
tacattgata ctgatactag cgcatactac gcgagctggg tgaaaggc                48

<210> SEQ ID NO 270
<211> LENGTH: 36
<212> TYPE: DNA
<213> ORGANISM: Oryctolagus cuniculus

<400> SEQUENCE: 270
tcttatgctg cttatggtgg ttatcctgct actttt                              36

<210> SEQ ID NO 271
<211> LENGTH: 333
<212> TYPE: DNA
<213> ORGANISM: Artificial Sequence
<220> FEATURE:
<223> OTHER INFORMATION: Chemically Synthesized

<400> SEQUENCE: 271
gacatccaga tgacccagtc tccatcctcc ctgtctgcat ctgtaggaga cagagtcacc    60
atcacttgcc aggccagtga ggacatttac aacttattgg cctggtatca gcagaaacca   120
gggaaagtcc ctaagctcct gatctattct gcatccactc tggcatctgg ggtcccatct   180
cgtttcagtg gcagtggatc tgggacagat tacactctca ccatcagcag cctgcagcct   240
gaagatgttg caacttatta ctgtcaaaac aactatcttg ttactactta tggtgttgct   300
ttcggcggag gaaccaaggt ggaaatcaaa cgt                                333

<210> SEQ ID NO 272
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 272
gacatccaga tgacccagtc tccatcctcc ctgtctgcat ctgtaggaga cagagtcacc    60
atcacttgcc aggccagtga ggacatttac aacttattgg cctggtatca gcagaaacca   120
gggaaagtcc ctaagctcct gatctattct gcatccactc tggcatctgg ggtcccatct   180
cgtttcagtg gcagtggatc tgggacagat tacactctca ccatcagcag cctgcagcct   240
gaagatgttg caacttatta ctgtcaaaac aactatcttg ttactactta tggtgttgct   300
ttcggcggag gaaccaaggt ggaaatcaaa cgtacggtag cggccccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
accctgacgc tgagcaaagc agactacgag aaacacaaag tctacgcctg cgaagtcacc   600
catcagggcc tgagctcgcc cgtcacaaag agcttcaaca ggggagagtg ttag          654

<210> SEQ ID NO 273
<211> LENGTH: 366
<212> TYPE: DNA
<213> ORGANISM: Artificial Sequence
<220> FEATURE:
<223> OTHER INFORMATION: Chemically Synthesized

<400> SEQUENCE: 273
caggtacagc tggtggagtc tggtggaggc gtggtccagc ctgggaggtc cctgagactc    60

```
tcctgtgcag cttctggatt caccttcagt agctatgcaa tgatctgggt ccgccaggct    120
ccagggaagg ggctggaata catcggatac attgatactg atactagcgc atactacgca    180
agcagtgtga aaggccgatt caccatctcc agagacaatt ccaagaacac gctgtacctg    240
caaatgtcta gcctgagagc cgaggacacg gctgtgtatt actgtgctag atcttatgct    300
gcttatggtg gttatcctgc tactttgat ccctggggcc aaggtaccct cgtcaccgtc    360
tcgagc                                                              366
```

<210> SEQ ID NO 274
<211> LENGTH: 1359
<212> TYPE: DNA
<213> ORGANISM: Artificial Sequence
<220> FEATURE:
<223> OTHER INFORMATION: Chemically Synthesized

<400> SEQUENCE: 274

```
caggtacagc tggtggagtc tggtggaggc gtggtccagc ctgggaggtc cctgagactc     60
tcctgtgcag cttctggatt caccttcagt agctatgcaa tgatctgggt ccgccaggct    120
ccagggaagg ggctggaata catcggatac attgatactg atactagcgc atactacgca    180
agcagtgtga aaggccgatt caccatctcc agagacaatt ccaagaacac gctgtacctg    240
caaatgtcta gcctgagagc cgaggacacg gctgtgtatt actgtgctag atcttatgct    300
gcttatggtg gttatcctgc tactttgat ccctggggcc aaggtaccct cgtcaccgtc    360
tcgagcgcct ccaccaaggg cccatcggtc ttccccctgg cacctctc caagagcacc    420 tctgggggca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaactcctg    720
gggggaccgt cagtcttcct cttccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacgccagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga acaactacaa gaccacgcct   1200
cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaatga                          1359
```

<210> SEQ ID NO 275
<211> LENGTH: 33
<212> TYPE: DNA
<213> ORGANISM: Oryctolagus cuniculus

<400> SEQUENCE: 275

```
caggccagtg aggacattta caacttattg gcc                                 33
```

<210> SEQ ID NO 276
<211> LENGTH: 21
<212> TYPE: DNA
<213> ORGANISM: Oryctolagus cuniculus

<400> SEQUENCE: 276
tctgcatcca ctctggcatc t                                              21

<210> SEQ ID NO 277
<211> LENGTH: 36
<212> TYPE: DNA
<213> ORGANISM: Oryctolagus cuniculus

<400> SEQUENCE: 277
caaaacaact atcttgttac tacttatggt gttgct                              36

<210> SEQ ID NO 278
<211> LENGTH: 15
<212> TYPE: DNA
<213> ORGANISM: Oryctolagus cuniculus

<400> SEQUENCE: 278
agctatgcaa tgatc                                                     15

<210> SEQ ID NO 279
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 279
tacattgata ctgatactag cgcatactac gcaagcagtg tgaaaggc                 48

<210> SEQ ID NO 280
<211> LENGTH: 42
<212> TYPE: DNA
<213> ORGANISM: Oryctolagus cuniculus

<400> SEQUENCE: 280
tcttatgctg cttatggtgg ttatcctgct acttttgatc cc                       42

<210> SEQ ID NO 281
<211> LENGTH: 333
<212> TYPE: DNA
<213> ORGANISM: Oryctolagus cuniculus

<400> SEQUENCE: 281
gcctatgata tgacccagac tccagcctcc gtgtctgcag ctgtgggagg cacagtcacc    60
atcaagtgcc aggccagtga aacattggt agctacttag cctggtatca gcagaaacca   120
gggcagcctc ccgaactcct gatctacagg gcgtccactc tggcatctgg ggtcccatcg   180
cggttcaaag gcagtggatc tgggacacag ttcactctca ccatcagcgg cgtggagtgt   240
gccgatgctg ccacttacta ctgtcaacag ggttataata gtgagaatct tgataatgct   300
ttcggcggag ggaccgaggt ggtggtcaaa cgt                                333

<210> SEQ ID NO 282
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 282

```
gcctatgata tgacccagac tccagcctcc gtgtctgcag ctgtgggagg cacagtcacc      60
atcaagtgcc aggccagtga aacattggt agctacttag cctggtatca gcagaaacca     120
gggcagcctc ccgaactcct gatctacagg gcgtccactc tggcatctgg ggtcccatcg    180
cggttcaaag gcagtggatc tgggacacag ttcactctca ccatcagcgg cgtggagtgt    240
gccgatgctg ccacttacta ctgtcaacag ggttataata gtgagaatct tgataatgct    300
ttcggcggag ggaccgaggt ggtggtcaaa cgtacggtag cggccccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg ttag          654
```

<210> SEQ ID NO 283
<211> LENGTH: 345
<212> TYPE: DNA
<213> ORGANISM: Oryctolagus cuniculus

<400> SEQUENCE: 283

```
cagtcggtgg aggagtccgg gggtcgcctg gtcacgcctg gacacccct gacactcacc      60
tgcacagtct ctggaatcga cctcagtatg tattcaatgg gctgggtccg ccaggctcca    120
gggaagggc tggaatacat cggatggatt agttatggtg gtactgcata ttacgcgagc    180
tgggcgaagg gccgattcac catctccaaa acctcgacca cggtggagct gaagatcacc    240
agtccgacaa tcgaggacac ggccacctat ttctgtgcca gagagactcc tgttaattat    300
tatttggaca tttggggcca ggggaccctc gtcaccgtct cgagc                    345
```

<210> SEQ ID NO 284
<211> LENGTH: 1338
<212> TYPE: DNA
<213> ORGANISM: Artificial Sequence
<220> FEATURE:
<223> OTHER INFORMATION: Chemically Synthesized

<400> SEQUENCE: 284

```
cagtcggtgg aggagtccgg gggtcgcctg gtcacgcctg gacacccct gacactcacc      60
tgcacagtct ctggaatcga cctcagtatg tattcaatgg gctgggtccg ccaggctcca    120
gggaagggc tggaatacat cggatggatt agttatggtg gtactgcata ttacgcgagc    180
tgggcgaagg gccgattcac catctccaaa acctcgacca cggtggagct gaagatcacc    240
agtccgacaa tcgaggacac ggccacctat ttctgtgcca gagagactcc tgttaattat    300
tatttggaca tttggggcca ggggaccctc gtcaccgtct cgagcgcctc caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaactcctgg ggggaccgtc agtcttcctc    720
```

-continued

```
ttcccccccaa aacccaagga cacccctcatg atctcccgga ccccctgaggt cacatgcgtg    780 gtggtggacg tgagccacga agaccctgag gtcaagttca actggtacgt ggacggcgtg    840
gaggtgcata atgccaagac aaagccgcgg gaggagcagt acgccagcac gtaccgtgtg    900
gtcagcgtcc tcaccgtcct gcaccaggac tggctgaatg gcaaggagta caagtgcaag    960
gtctccaaca aagccctccc agccccatc gagaaaacca tctccaaagc caaagggcag    1020
ccccgagaac cacaggtgta caccctgccc ccatcccggg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaatga                                                   1338
```

<210> SEQ ID NO 285
<211> LENGTH: 33
<212> TYPE: DNA
<213> ORGANISM: Oryctolagus cuniculus

<400> SEQUENCE: 285

```
caggccagtg agaacattgg tagctactta gcc                                    33
```

<210> SEQ ID NO 286
<211> LENGTH: 21
<212> TYPE: DNA
<213> ORGANISM: Oryctolagus cuniculus

<400> SEQUENCE: 286

```
agggcgtcca ctctggcatc t                                                 21
```

<210> SEQ ID NO 287
<211> LENGTH: 36
<212> TYPE: DNA
<213> ORGANISM: Oryctolagus cuniculus

<400> SEQUENCE: 287

```
caacagggtt ataatagtga gaatcttgat aatgct                                 36
```

<210> SEQ ID NO 288
<211> LENGTH: 15
<212> TYPE: DNA
<213> ORGANISM: Oryctolagus cuniculus

<400> SEQUENCE: 288

```
atgtattcaa tgggc                                                        15
```

<210> SEQ ID NO 289
<211> LENGTH: 48
<212> TYPE: DNA
<213> ORGANISM: Oryctolagus cuniculus

<400> SEQUENCE: 289

```
tggattagtt atggtggtac tgcatattac gcgagctggg cgaagggc                    48
```

<210> SEQ ID NO 290
<211> LENGTH: 30
<212> TYPE: DNA
<213> ORGANISM: Oryctolagus cuniculus

<400> SEQUENCE: 290
```
gagactcctg ttaattatta tttggacatt                                           30

<210> SEQ ID NO 291
<211> LENGTH: 333
<212> TYPE: DNA
<213> ORGANISM: Artificial Sequence
<220> FEATURE:
<223> OTHER INFORMATION: Chemically Synthesized

<400> SEQUENCE: 291
gcctatgata tgacccagtc tccatcctcc ctgtctgcat ctgtaggaga cagagtcacc         60
atcacttgcc aggccagtga aacattggt agctacttag cctggtatca gcagaaacca        120
gggaaagtcc ctaagctcct gatctatagg gcttccactc tggcatctgg ggtcccatct       180
cgtttcagtg gcagtggatc tgggacagat ttcactctca ccatcagcag cctgcagcct       240
gaagatgttg caacttatta ctgtcaacag ggttacaata gtgagaatct tgataatgct       300
ttcggcggag gaaccaaggt ggaaatcaaa cgt                                    333

<210> SEQ ID NO 292
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 292
gcctatgata tgacccagtc tccatcctcc ctgtctgcat ctgtaggaga cagagtcacc         60
atcacttgcc aggccagtga aacattggt agctacttag cctggtatca gcagaaacca        120
gggaaagtcc ctaagctcct gatctatagg gcttccactc tggcatctgg ggtcccatct       180
cgtttcagtg gcagtggatc tgggacagat ttcactctca ccatcagcag cctgcagcct       240
gaagatgttg caacttatta ctgtcaacag ggttacaata gtgagaatct tgataatgct       300
ttcggcggag gaaccaaggt ggaaatcaaa cgtacggtag cggccccatc tgtcttcatc       360
ttcccgccat ctgatgagca gttgaaatct ggaactgcct ctgttgtgtg cctgctgaat       420
aacttctatc ccagagaggc caaagtacag tggaaggtgg ataacgccct ccaatcgggt       480
aactcccagg agagtgtcac agagcaggac agcaaggaca gcacctacag cctcagcagc       540
accctgacgc tgagcaaagc agactacgag aaacacaaag tctacgcctg cgaagtcacc       600
catcagggcc tgagctcgcc cgtcacaaag agcttcaaca ggggagagtg ttag             654

<210> SEQ ID NO 293
<211> LENGTH: 354
<212> TYPE: DNA
<213> ORGANISM: Artificial Sequence
<220> FEATURE:
<223> OTHER INFORMATION: Chemically Synthesized

<400> SEQUENCE: 293
caggtacagc tggtggagtc tggtggaggc gtggtccagc ctgggaggtc cctgagactc         60
tcctgtgcag cttctggatt caccttcagt atgtattcaa tgggctgggt ccgccaggct       120
ccagggaagg ggctggaata catcggatgg attagttatg gtggtactgc atactacgct       180
agcagcgcta agggccgatt caccatctcc agagacaatt ccaagaacac gctgtacctg       240
caaatgtcta gcctgagagc cgaggacacg gctgtgtatt actgtgctag agagactcct       300
gttaattact acttggacat ttggggccaa ggtaccctcg tcaccgtctc gagc             354

<210> SEQ ID NO 294
<211> LENGTH: 1347
<212> TYPE: DNA
<213> ORGANISM: Artificial Sequence
<220> FEATURE:
<223> OTHER INFORMATION: Chemically Synthesized

<400> SEQUENCE: 294

```
caggtacagc tggtggagtc tggtggaggc gtggtccagc ctgggaggtc cctgagactc      60
tcctgtgcag cttctggatt caccttcagt atgtattcaa tgggctgggt ccgccaggct     120
ccagggaagg gctgaaata catcggatgg attagttatg gtggtactgc atactacgct     180
agcagcgcta agggccgatt caccatctcc agagacaatt ccaagaacac gctgtacctg     240
caaatgtcta gcctgagagc cgaggacacg gctgtgtatt actgtgctag agagactcct     300
gttaattact acttggacat ttggggccaa ggtaccctcg tcaccgtctc gagcgcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc     600
tgcaacgtga atcacaagcc cagcaacacc aaggtggaca gagagttga gcccaaatct     660
tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta cgccagcacg     900
taccgtgtgt cagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaatga                                         1347
```

<210> SEQ ID NO 295
<211> LENGTH: 33
<212> TYPE: DNA
<213> ORGANISM: Oryctolagus cuniculus

<400> SEQUENCE: 295

```
caggccagtg agaacattgg tagctactta gcc                                    33
```

<210> SEQ ID NO 296
<211> LENGTH: 21
<212> TYPE: DNA
<213> ORGANISM: Oryctolagus cuniculus

<400> SEQUENCE: 296

```
agggcttcca ctctggcatc t                                                 21
```

<210> SEQ ID NO 297
<211> LENGTH: 36

```
<212> TYPE: DNA
<213> ORGANISM: Oryctolagus cuniculus

<400> SEQUENCE: 297
caacagggtt acaatagtga gaatcttgat aatgct                              36

<210> SEQ ID NO 298
<211> LENGTH: 15
<212> TYPE: DNA
<213> ORGANISM: Oryctolagus cuniculus

<400> SEQUENCE: 298
atgtattcaa tgggc                                                     15

<210> SEQ ID NO 299
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 299
tggattagtt atggtggtac tgcatactac gctagcagcg ctaagggc                 48

<210> SEQ ID NO 300
<211> LENGTH: 30
<212> TYPE: DNA
<213> ORGANISM: Oryctolagus cuniculus

<400> SEQUENCE: 300
gagactcctg ttaattacta cttggacatt                                     30

<210> SEQ ID NO 301
<211> LENGTH: 327
<212> TYPE: DNA
<213> ORGANISM: Oryctolagus cuniculus

<400> SEQUENCE: 301
gcattcgaat tgacccagac tccatcctcc gtggaggcag ctgtgggagg cacagtcacc    60
atcaagtgcc aggccagtca gaacattgtt accaatttag cctggtatca acagaaacca   120
gggcagcctc ccaagctcct gatctatggt gcatccactc tggcatctgg ggtctcatcg   180
cggttcaaag gcagtggatc tgggacacag ttcactctca ccatcagcga cctggagtgt   240
gccgatgctg ccacttattt ctgtcagagc tatgatggtt taatagtgc tgggttcggc    300 ggagggaccg aggtggtggt caaacgt                                       327

<210> SEQ ID NO 302
<211> LENGTH: 648
<212> TYPE: DNA
<213> ORGANISM: Artificial Sequence
<220> FEATURE:
<223> OTHER INFORMATION: Chemically Synthesized

<400> SEQUENCE: 302
gcattcgaat tgacccagac tccatcctcc gtggaggcag ctgtgggagg cacagtcacc    60
atcaagtgcc aggccagtca gaacattgtt accaatttag cctggtatca acagaaacca   120
gggcagcctc ccaagctcct gatctatggt gcatccactc tggcatctgg ggtctcatcg   180
cggttcaaag gcagtggatc tgggacacag ttcactctca ccatcagcga cctggagtgt   240
gccgatgctg ccacttattt ctgtcagagc tatgatggtt taatagtgc tgggttcggc    300
```

```
ggagggaccg aggtggtggt caaacgtacg gtagcggccc catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag acagcacct acagcctcag cagcaccctg        540
acgctgagca aagcagacta cgagaaacac aaagtctacg cctgcgaagt cacccatcag      600
ggcctgagct cgcccgtcac aaagagcttc aacaggggag agtgttag                   648

<210> SEQ ID NO 303
<211> LENGTH: 360
<212> TYPE: DNA
<213> ORGANISM: Oryctolagus cuniculus

<400> SEQUENCE: 303
cagtcgctgg aggagtccgg gggtcgcctg gtcacgcctg gacacccct gacactcacc       60
tgcacagcct ctggattctc cctcagtggc tacgacatga gctgggtccg ccaggctcca     120
ggaaaggggc tggaatacat cggactcatt agttatgatg gtaacacata ctacgcgacc     180
tgggcgaaag gccgattcac catctccaaa acctcgacca cggtggatct gaaaatcacc     240
agtccgacaa ccgaggacac ggccacctat ttctgtgcca gaagtcttta tgctggtcct     300
aatgctggta tcggaccgtt taacatctgg ggccagggga ccctcgtcac cgtctcgagc     360

<210> SEQ ID NO 304
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 304
cagtcgctgg aggagtccgg gggtcgcctg gtcacgcctg gacacccct gacactcacc       60
tgcacagcct ctggattctc cctcagtggc tacgacatga gctgggtccg ccaggctcca     120
ggaaaggggc tggaatacat cggactcatt agttatgatg gtaacacata ctacgcgacc     180
tgggcgaaag gccgattcac catctccaaa acctcgacca cggtggatct gaaaatcacc     240
agtccgacaa ccgaggacac ggccacctat ttctgtgcca gaagtcttta tgctggtcct     300
aatgctggta tcggaccgtt taacatctgg ggccagggga ccctcgtcac cgtctcgagc     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacgcc     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagcccg agaaccacag gtgtacaccc tgcccccatc ccgggaggag     1080
atgaccaaga accaggtcag cctgacctgc ctggtcaaag gcttctatcc cagcgacatc    1140
```

```
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                  1353
```

<210> SEQ ID NO 305
<211> LENGTH: 33
<212> TYPE: DNA
<213> ORGANISM: Oryctolagus cuniculus

<400> SEQUENCE: 305

```
caggccagtc agaacattgt taccaattta gcc                                    33
```

<210> SEQ ID NO 306
<211> LENGTH: 21
<212> TYPE: DNA
<213> ORGANISM: Oryctolagus cuniculus

<400> SEQUENCE: 306

```
ggtgcatcca ctctggcatc t                                                 21
```

<210> SEQ ID NO 307
<211> LENGTH: 30
<212> TYPE: DNA
<213> ORGANISM: Oryctolagus cuniculus

<400> SEQUENCE: 307

```
cagagctatg atggttttaa tagtgctggg                                        30
```

<210> SEQ ID NO 308
<211> LENGTH: 15
<212> TYPE: DNA
<213> ORGANISM: Oryctolagus cuniculus

<400> SEQUENCE: 308

```
ggctacgaca tgagc                                                        15
```

<210> SEQ ID NO 309
<211> LENGTH: 48
<212> TYPE: DNA
<213> ORGANISM: Oryctolagus cuniculus

<400> SEQUENCE: 309

```
ctcattagtt atgatggtaa cacatactac gcgacctggg cgaaaggc                    48
```

<210> SEQ ID NO 310
<211> LENGTH: 45
<212> TYPE: DNA
<213> ORGANISM: Oryctolagus cuniculus

<400> SEQUENCE: 310

```
agtctttatg ctggtcctaa tgctggtatc ggaccgttta acatc                       45
```

<210> SEQ ID NO 311
<211> LENGTH: 327
<212> TYPE: DNA
<213> ORGANISM: Artificial Sequence
<220> FEATURE:
<223> OTHER INFORMATION: Chemically Synthesized

<400> SEQUENCE: 311

```
gcattccaga tgacccagtc tccatcctcc ctgtctgcat ctgtaggaga cagagtcacc      60
atcacttgcc aggccagtca gaacattgtt accaacttag cctggtatca gcagaaacca     120
gggaaagtcc ctaagctcct gatctatggt gcatccactc tggcatctgg ggtcccatct     180
cgtttcagtg gcagtggatc tgggacagat ttcactctca ccatcagcag cctgcagcct     240
gaagatgttg caacttatta ctgtcagagc tatgatggtt caatagtgc tggtttcggc      300 ggaggaacca aggtggaaat caaacgt                                         327

<210> SEQ ID NO 312
<211> LENGTH: 648
<212> TYPE: DNA
<213> ORGANISM: Artificial Sequence
<220> FEATURE:
<223> OTHER INFORMATION: Chemically Synthesized

<400> SEQUENCE: 312
gcattccaga tgacccagtc tccatcctcc ctgtctgcat ctgtaggaga cagagtcacc      60
atcacttgcc aggccagtca gaacattgtt accaacttag cctggtatca gcagaaacca    120
gggaaagtcc ctaagctcct gatctatggt gcatccactc tggcatctgg ggtcccatct    180
cgtttcagtg gcagtggatc tgggacagat ttcactctca ccatcagcag cctgcagcct    240
gaagatgttg caacttatta ctgtcagagc tatgatggtt caatagtgc tggtttcggc     300 ggaggaacca aggtggaaat caaacgtacg gtagcggccc catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttag                648

<210> SEQ ID NO 313
<211> LENGTH: 369
<212> TYPE: DNA
<213> ORGANISM: Artificial Sequence
<220> FEATURE:
<223> OTHER INFORMATION: Chemically Synthesized

<400> SEQUENCE: 313
caggtacagc tggtggagtc tggtggaggc gtggtccagc ctgggaggtc cctgagactc      60
tcctgtgcag cttctggatt ctccctcagt ggctacgaca tgagctgggt ccgtcaggct    120
ccaggcaagg gactggagtg ggtgggactc attagttatg atggtaacac atactacgcg    180
acctccgcga aaggccgatt caccatctcc agagacaatt ccaagaacac gctgtacctg    240
caaatgtcta gcctgagagc cgaggacacg gctgtgtatt actgtgctag aagtctttat    300
gctggtccta atgctggtat cggaccgttt aacatctggg gccaaggtac cctcgtcacc    360
gtctcgagc                                                            369

<210> SEQ ID NO 314
<211> LENGTH: 1362
<212> TYPE: DNA
<213> ORGANISM: Artificial Sequence
<220> FEATURE:
<223> OTHER INFORMATION: Chemically Synthesized

<400> SEQUENCE: 314
caggtacagc tggtggagtc tggtggaggc gtggtccagc ctgggaggtc cctgagactc      60
```

```
tcctgtgcag cttctggatt ctccctcagt ggctacgaca tgagctgggt ccgtcaggct    120
ccaggcaagg gactggagtg ggtgggactc attagttatg atggtaacac atactacgcg    180
acctccgcga aaggccgatt caccatctcc agagacaatt ccaagaacac gctgtacctg    240
caaatgtcta gcctgagagc cgaggacacg gctgtgtatt actgtgctag aagtctttat    300
gctggtccta atgctggtat cggaccgttt aacatctggg gccaaggtac cctcgtcacc    360
gtctcgagcg cctccaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgcctccag cagcttgggc    600 acccagacct acatctgcaa cgtgaatcac aagcccagca acaccaaggt ggacaagaga    660
gttgagccca atcttgtgac aaaactcaca catgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcggaggag    900 cagtacgcca gcacgtaccg tgtggtcagc gtcctcaccg tcctgcacca ggactggctg    960
aatggcaagg agtacaagtg caaggtctcc aacaaagccc tcccagcccc catcgagaaa    1020
accatctcca aagccaaagg gcagccccga gaaccacagg tgtacaccct gcccccatcc    1080
cgggaggaga tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaat ga                      1362
```

<210> SEQ ID NO 315
<211> LENGTH: 33
<212> TYPE: DNA
<213> ORGANISM: Oryctolagus cuniculus

<400> SEQUENCE: 315

```
caggccagtc agaacattgt taccaactta gcc                                 33
```

<210> SEQ ID NO 316
<211> LENGTH: 21
<212> TYPE: DNA
<213> ORGANISM: Oryctolagus cuniculus

<400> SEQUENCE: 316

```
ggtgcatcca ctctggcatc t                                              21
```

<210> SEQ ID NO 317
<211> LENGTH: 29
<212> TYPE: DNA
<213> ORGANISM: Oryctolagus cuniculus

<400> SEQUENCE: 317

```
cagagctatg atggtttcaa tagtgctgg                                      29
```

<210> SEQ ID NO 318
<211> LENGTH: 15
<212> TYPE: DNA

<213> ORGANISM: Oryctolagus cuniculus

<400> SEQUENCE: 318
ggctacgaca tgagc                                                      15

<210> SEQ ID NO 319
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 319
ctcattagtt atgatggtaa cacatactac gcgacctccg cgaaaggc                  48

<210> SEQ ID NO 320
<211> LENGTH: 45
<212> TYPE: DNA
<213> ORGANISM: Oryctolagus cuniculus

<400> SEQUENCE: 320
agtctttatg ctggtcctaa tgctggtatc ggaccgttta acatc                    45

<210> SEQ ID NO 321
<211> LENGTH: 336
<212> TYPE: DNA
<213> ORGANISM: Oryctolagus cuniculus

<400> SEQUENCE: 321
gccgccgtgc tgacccagac tccatctccc gtgtctgcag ctgtgggagg cacagtcagc    60
atcagttgcc agtccagtca gaatgtttat aagaacaact acttatcctg gtatcagcag   120
aaaccagggc agcctcccaa gctcctgatc tacaaggcat ccactctggc atctggggtc   180
ccatcgcggt tcaaaggcgg tggatctggg acagatttca ctctcaccat cagcgacgtg   240
cagtgtgacg ctgctgccac ttactactgt gcaggcggtt ataccagtag tagtgataat   300
gctttcggcg agggaccga ggtggtggtc aaacgt                              336

<210> SEQ ID NO 322
<211> LENGTH: 656
<212> TYPE: DNA
<213> ORGANISM: Artificial Sequence
<220> FEATURE:
<223> OTHER INFORMATION: Chemically Synthesized

<400> SEQUENCE: 322
gccgccgtgc tgacccagac tccatctccc gtgtctgcag ctgtgggagg cacagtcagc    60
atcagttgcc agtccagtca gaatgtttat aagaacaact acttatcctg gtatcagcag   120
aaaccagggc agcctcccaa gctcctgatc tacaaggcat ccactctggc atctggggtc   180
ccatcgcggt tcaaaggcgg tggatctggg acagatttca ctctcaccat cagcgacgtg   240
cagtgtgacg ctgctgccac ttactactgt gcaggcggtt ataccagtag tagtgataat   300
gctttcggcg agggaccga ggtggtggtc aaacgtacgg tagcggcccc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca cagggggaga gtgtta       656

<210> SEQ ID NO 323
<211> LENGTH: 351
<212> TYPE: DNA
<213> ORGANISM: Oryctolagus cuniculus

<400> SEQUENCE: 323

| | | | | | | |
|---|---|---|---|---|---|---|
| cagtcggtgg | aggcgtccgg | gggtcgcctg | gtcacgcctg | ggacacccct | gacactcacc | 60 |
| tgcacagcct | ctggattctc | cctcagtacc | tactggatga | gctgggtccg | ccaggctcca | 120 |
| gggaaggggc | tggaatggat | cggagacatt | tattttagta | atgaagaaac | aaactacgcg | 180 |
| agctgggcga | aggccgatt | taccatctcc | aaaacctcga | ccacggtgga | tctgaatgtc | 240 |
| atcagtccga | caaccgagga | cacggccacc | tatttctgtg | ccagaggttc | tcctgatgtt | 300 |
| gatattggta | tagatatgtg | gggcccgggc | accctcgtca | ccgtctcgag | c | 351 |

<210> SEQ ID NO 324
<211> LENGTH: 1344
<212> TYPE: DNA
<213> ORGANISM: Artificial Sequence
<220> FEATURE:
<223> OTHER INFORMATION: Chemically Synthesized

<400> SEQUENCE: 324

| | | | | | | |
|---|---|---|---|---|---|---|
| cagtcggtgg | aggcgtccgg | gggtcgcctg | gtcacgcctg | ggacacccct | gacactcacc | 60 |
| tgcacagcct | ctggattctc | cctcagtacc | tactggatga | gctgggtccg | ccaggctcca | 120 |
| gggaaggggc | tggaatggat | cggagacatt | tattttagta | atgaagaaac | aaactacgcg | 180 |
| agctgggcga | aggccgatt | taccatctcc | aaaacctcga | ccacggtgga | tctgaatgtc | 240 |
| atcagtccga | caaccgagga | cacggccacc | tatttctgtg | ccagaggttc | tcctgatgtt | 300 |
| gatattggta | tagatatgtg | gggcccgggc | accctcgtca | ccgtctcgag | cgcctccacc | 360 |
| aagggcccat | cggtcttccc | cctggcaccc | tcctccaaga | gcacctctgg | ggcacagcg | 420 |
| gccctgggct | gcctggtcaa | ggactacttc | cccgaaccgg | tgacggtgtc | gtggaactca | 480 |
| ggcgccctga | ccagcggcgt | gcacaccttc | ccggctgtcc | tacagtcctc | aggactctac | 540 |
| tccctcagca | gcgtggtgac | cgtgccctcc | agcagcttgg | gcacccagac | ctacatctgc | 600 |
| aacgtgaatc | acaagcccag | caacaccaag | gtggacaaga | gagttgagcc | caaatcttgt | 660 |
| gacaaaactc | acacatgccc | accgtgccca | gcacctgaac | tcctgggggg | accgtcagtc | 720 |
| ttcctcttcc | ccccaaaacc | caaggacacc | ctcatgatct | cccggacccc | tgaggtcaca | 780 |
| tgcgtggtgg | tggacgtgag | ccacgaagac | cctgaggtca | agttcaactg | gtacgtggac | 840 |
| ggcgtggagg | tgcataatgc | caagacaaag | ccgcgggagg | agcagtacgc | cagcacgtac | 900 |
| cgtgtggtca | gcgtcctcac | cgtcctgcac | caggactggc | tgaatggcaa | ggagtacaag | 960 |
| tgcaaggtct | ccaacaaagc | cctcccagcc | cccatcgaga | aaaccatctc | caaagccaaa | 1020 |
| gggcagcccc | gagaaccaca | ggtgtacacc | ctgcccccat | cccgggagga | gatgaccaag | 1080 |
| aaccaggtca | gcctgacctg | cctggtcaaa | ggcttctatc | ccagcgacat | cgccgtggag | 1140 |
| tgggagagca | atgggcagcc | ggagaacaac | tacaagacca | cgcctcccgt | gctggactcc | 1200 |
| gacggctcct | tcttcctcta | cagcaagctc | accgtggaca | agagcaggtg | gcagcagggg | 1260 |
| aacgtcttct | catgctccgt | gatgcatgag | gctctgcaca | accactacac | gcagaagagc | 1320 |
| ctctccctgt | ctccgggtaa | atga | | | | 1344 |

<210> SEQ ID NO 325

```
<211> LENGTH: 39
<212> TYPE: DNA
<213> ORGANISM: Oryctolagus cuniculus

<400> SEQUENCE: 325
cagtccagtc agaatgttta taagaacaac tacttatcc                           39

<210> SEQ ID NO 326
<211> LENGTH: 21
<212> TYPE: DNA
<213> ORGANISM: Oryctolagus cuniculus

<400> SEQUENCE: 326
aaggcatcca ctctggcatc t                                              21

<210> SEQ ID NO 327
<211> LENGTH: 33
<212> TYPE: DNA
<213> ORGANISM: Oryctolagus cuniculus

<400> SEQUENCE: 327
gcaggcggtt ataccagtag tagtgataat gct                                 33

<210> SEQ ID NO 328
<211> LENGTH: 15
<212> TYPE: DNA
<213> ORGANISM: Oryctolagus cuniculus

<400> SEQUENCE: 328
acctactgga tgagc                                                     15

<210> SEQ ID NO 329
<211> LENGTH: 51
<212> TYPE: DNA
<213> ORGANISM: Oryctolagus cuniculus

<400> SEQUENCE: 329
gacatttatt ttagtaatga agaaacaaac tacgcgagct gggcgaaagg c             51

<210> SEQ ID NO 330
<211> LENGTH: 33
<212> TYPE: DNA
<213> ORGANISM: Oryctolagus cuniculus

<400> SEQUENCE: 330
ggttctcctg atgttgatat tggtatagat atg                                 33

<210> SEQ ID NO 331
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 331
gacatccaga tgacccagtc tccatcctcc ctgtctgcat ctgtaggaga cagagtcacc    60
atcacttgcc agtccagtca gaatgtttat aagaacaact acttatctg gtatcagcag   120 aaaccaggga agtccctaa gctcctgatc tataaggcat ccactctggc atctggggtc   180
ccatctcgtt tcagtggcag tggatctggg acagatttca ctctcaccat cagcagcctg   240
cagcctgaag atgttgcaac ttattactgt gcaggcggtt ataccagtag tagtgataat   300
gctttcggcg gaggaaccaa ggtggaaatc aaacgt                             336
```

<210> SEQ ID NO 332
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 332

```
gacatccaga tgacccagtc tccatcctcc ctgtctgcat ctgtaggaga cagagtcacc      60
atcacttgcc agtccagtca gaatgtttat aagaacaact acttatcctg gtatcagcag     120
aaaccaggga aagtccctaa gctcctgatc tataaggcat ccactctggc atctggggtc     180
ccatctcgtt tcagtggcag tggatctggg acagatttca ctctcaccat cagcagcctg     240
cagcctgaag atgttgcaac ttattactgt gcaggcggtt ataccagtag tagtgataat     300
gctttcggcg gaggaaccaa ggtggaaatc aaacgtacgg tagcggcccc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc tgcgaagtc      600
acccatcagg gcctgagctc gcccgtcaca aagagcttca caggggaga gtgttag        657
```

<210> SEQ ID NO 333
<211> LENGTH: 360
<212> TYPE: DNA
<213> ORGANISM: Artificial Sequence
<220> FEATURE:
<223> OTHER INFORMATION: Chemically Synthesized

<400> SEQUENCE: 333

```
gaggtgcagc tggtggagtc tgggggaggc ttggtccagc ctgggggtc cctgagactc      60
tcctgtgcag cctctggatt caccgtcagt acctactgga tgagctgggt ccgtcaggct     120
ccagggaagg ggctggagtg ggtcggagac atttacttta gtaatgaaga aacaaactac     180
gcgagcagcg cgaaaggccg attcaccatc tccagagaca attccaagaa caccctgtat     240
cttcaaatga acagcctgag agctgaggac actgctgtgt attactgtgc tagaggttct     300
cctgatgttg atattggtat agatatgtgg ggcccaggga ccctcgtcac cgtctcgagc     360
```

<210> SEQ ID NO 334
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 334

```
gaggtgcagc tggtggagtc tgggggaggc ttggtccagc ctgggggtc cctgagactc      60
tcctgtgcag cctctggatt caccgtcagt acctactgga tgagctgggt ccgtcaggct     120
ccagggaagg ggctggagtg ggtcggagac atttacttta gtaatgaaga aacaaactac     180
gcgagcagcg cgaaaggccg attcaccatc tccagagaca attccaagaa caccctgtat     240
cttcaaatga acagcctgag agctgaggac actgctgtgt attactgtgc tagaggttct     300
cctgatgttg atattggtat agatatgtgg ggcccaggga ccctcgtcac cgtctcgagc     360
gcctccacca agggcccatc ggtcttcccc ctggcaccct cctccaagag cacctctggg     420
```

```
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagag agttgagccc      660
aaatcttgtg acaaaactca cacatgccca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcggaggga gcagtacgcc      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggaggag     1080
atgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctac agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa tga                                  1353

<210> SEQ ID NO 335
<211> LENGTH: 39
<212> TYPE: DNA
<213> ORGANISM: Oryctolagus cuniculus

<400> SEQUENCE: 335
cagtccagtc agaatgttta taagaacaac tacttatcc                             39

<210> SEQ ID NO 336
<211> LENGTH: 21
<212> TYPE: DNA
<213> ORGANISM: Oryctolagus cuniculus

<400> SEQUENCE: 336
aaggcatcca ctctggcatc t                                                21

<210> SEQ ID NO 337
<211> LENGTH: 33
<212> TYPE: DNA
<213> ORGANISM: Oryctolagus cuniculus

<400> SEQUENCE: 337
gcaggcggtt ataccagtag tagtgataat gct                                   33

<210> SEQ ID NO 338
<211> LENGTH: 15
<212> TYPE: DNA
<213> ORGANISM: Oryctolagus cuniculus

<400> SEQUENCE: 338
acctactgga tgagc                                                       15

<210> SEQ ID NO 339
<211> LENGTH: 51
<212> TYPE: DNA
<213> ORGANISM: Artificial Sequence
<220> FEATURE:
<223> OTHER INFORMATION: Chemically Synthesized
```

<400> SEQUENCE: 339
gacatttact ttagtaatga agaaacaaac tacgcgagca gcgcgaaagg c                51

<210> SEQ ID NO 340
<211> LENGTH: 33
<212> TYPE: DNA
<213> ORGANISM: Oryctolagus cuniculus

<400> SEQUENCE: 340
ggttctcctg atgttgatat tggtatagat atg                                   33

<210> SEQ ID NO 341
<211> LENGTH: 336
<212> TYPE: DNA
<213> ORGANISM: Oryctolagus cuniculus

<400> SEQUENCE: 341
gcagccgtgc tgacccagac accatcgccc gtgtctgcag ctgtgggaga cacagtcacc      60
atcaagtgcc agtccagtca gagtgtttat aagaacaact acttatcctg gtatcagcag    120
aaaccagggc agcctcccaa gctcctgatc tatgatgcat ccaatctgcc atctggggtc    180
ccatcacggt tcagcggcag tggatctggg acacagttca ctctcaccat cagcggcgtg    240
cagtgtgacg atgctgccac ttactactgt ctaggcgatt atgatgatga tactgataat    300
ggtttcggcg agggaccga ggtggtggtc aaacgt                                336

<210> SEQ ID NO 342
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 342
gcagccgtgc tgacccagac accatcgccc gtgtctgcag ctgtgggaga cacagtcacc      60
atcaagtgcc agtccagtca gagtgtttat aagaacaact acttatcctg gtatcagcag    120
aaaccagggc agcctcccaa gctcctgatc tatgatgcat ccaatctgcc atctggggtc    180
ccatcacggt tcagcggcag tggatctggg acacagttca ctctcaccat cagcggcgtg    240
cagtgtgacg atgctgccac ttactactgt ctaggcgatt atgatgatga tactgataat    300
ggtttcggcg agggaccga ggtggtggtc aaacgtacgg tagcggcccc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600
acccatcagg gcctgagctc gcccgtcaca aagagcttca caggggaga gtgttag       657

<210> SEQ ID NO 343
<211> LENGTH: 336
<212> TYPE: DNA
<213> ORGANISM: Oryctolagus cuniculus

<400> SEQUENCE: 343
cagtcggtgg aggagtccgg gggtcgcctg gtcacgcctg gacaccccct gacactcacc      60
tgcacagtct ctggaatcga cctcagtagc tatgcaatga tctgggtccg ccaggctcca    120

```
gggaaggggc tggaatacat cggaatcatt tggagtggtg gcacctacta cgcgacctgg      180
gcgaaaggcc gattcaccat ctccaaaacc tcgaccacgg tggatctgca aatcaccagt      240
ccgacaaccg aggacgcggc cacctatttc tgtgccgcag gtggtggtag tatttatgat      300
gtttggggcc cgggcaccct ggtcaccgtc tcgagc                                336
```

<210> SEQ ID NO 344
<211> LENGTH: 1329
<212> TYPE: DNA
<213> ORGANISM: Artificial Sequence
<220> FEATURE:
<223> OTHER INFORMATION: Chemically Synthesized

<400> SEQUENCE: 344

```
cagtcggtgg aggagtccgg gggtcgcctg gtcacgcctg ggacacccct gacactcacc       60
tgcacagtct ctggaatcga cctcagtagc tatgcaatga tctgggtccg ccaggctcca      120
gggaaggggc tggaatacat cggaatcatt tggagtggtg gcacctacta cgcgacctgg      180
gcgaaaggcc gattcaccat ctccaaaacc tcgaccacgg tggatctgca aatcaccagt      240
ccgacaaccg aggacgcggc cacctatttc tgtgccgcag gtggtggtag tatttatgat      300
gtttggggcc cgggcaccct ggtcaccgtc tcgagcgcct ccaccaaggg cccatcggtc      360
ttccccctgg cacccctcct caagagcacc tctgggggca gcggccct gggctgcctg       420 gtcaaggact acttccccga accggtgacg gtgtcgtgga actcaggcgc cctgaccagc      480
ggcgtgcaca ccttcccggc tgtcctacag tcctcaggac tctactccct cagcagcgtg      540
gtgaccgtgc cctccagcag cttgggcacc cagacctaca tctgcaacgt gaatcacaag      600
cccagcaaca ccaaggtgga caagagagtt gagcccaaat cttgtgacaa aactcacaca      660
tgcccaccgt gcccagcacc tgaactcctg ggggaccgt cagtcttcct cttccccca       720 aaacccaagg acaccctcat gatctcccgg acccctgagg tcacatgcgt ggtggtggac      780
gtgagccacg aagaccctga ggtcaagttc aactggtacg tggacggcgt ggaggtgcat      840
aatgccaaga caaagccgcg ggaggagcag tacgccagca cgtaccgtgt ggtcagcgtc      900
ctcaccgtcc tgcaccagga ctggctgaat ggcaaggagt acaagtgcaa ggtctccaac      960
aaagccctcc cagcccccat cgagaaaacc atctccaaag ccaaagggca gccccgagaa     1020
ccacaggtgt acaccctgcc cccatcccgg gaggagatga ccaagaacca ggtcagcctg     1080
acctgcctgg tcaaaggctt ctatcccagc gacatcgccg tggagtggga gagcaatggg     1140
cagccggaga acaactacaa gaccacgcct cccgtgctgg actccgacgg ctccttcttc     1200
ctctacagca agctcaccgt ggacaagagc aggtggcagc aggggaacgt cttctcatgc     1260
tccgtgatgc atgaggctct gcacaaccac tacacgcaga agagcctctc cctgtctccg     1320
ggtaaatga                                                            1329
```

<210> SEQ ID NO 345
<211> LENGTH: 39
<212> TYPE: DNA
<213> ORGANISM: Oryctolagus cuniculus

<400> SEQUENCE: 345

```
cagtccagtc agagtgttta taagaacaac tacttatcc                              39
```

<210> SEQ ID NO 346
<211> LENGTH: 21
<212> TYPE: DNA
<213> ORGANISM: Oryctolagus cuniculus
<210> SEQ ID NO 347
<211> LENGTH: 33
<212> TYPE: DNA
<213> ORGANISM: Oryctolagus cuniculus

<400> SEQUENCE: 347
ctaggcgatt atgatgatga tactgataat ggt           33

<210> SEQ ID NO 348
<211> LENGTH: 15
<212> TYPE: DNA
<213> ORGANISM: Oryctolagus cuniculus

<400> SEQUENCE: 348
agctatgcaa tgatc           15

<210> SEQ ID NO 349
<211> LENGTH: 45
<212> TYPE: DNA
<213> ORGANISM: Oryctolagus cuniculus

<400> SEQUENCE: 349
atcatttgga gtggtggcac ctactacgcg acctgggcga aaggc           45

<210> SEQ ID NO 350
<211> LENGTH: 24
<212> TYPE: DNA
<213> ORGANISM: Oryctolagus cuniculus

<400> SEQUENCE: 350
ggtggtggta gtatttatga tgtt           24

<210> SEQ ID NO 351
<211> LENGTH: 336
<212> TYPE: DNA
<213> ORGANISM: Oryctolagus cuniculus

<400> SEQUENCE: 351
gccctggtga tgacccagac tccatcctcc acgtctgaac cagtgggagg cacagtcacc      60
atcaattgcc aggctagtca gaatattggt aacgacctat cctggtatca gcagaaacca     120
gggcagcctc ccgagctcct aatctattct acatccaaac tggcaactgg ggtcccaaag     180
cggttcagtg gcagcagatc tgggacacag ttcactctca ccatcagcga cctggagtgt     240
gacgatgctg ccacttacta ctgtctaggt gtttatagtt atattagtga tgatggtaat     300
gctttcggcg gagggaccga ggtggtggtc aaacgt                               336

<210> SEQ ID NO 352
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 352
gccctggtga tgacccagac tccatcctcc acgtctgaac cagtgggagg cacagtcacc      60
atcaattgcc aggctagtca gaatattggt aacgacctat cctggtatca gcagaaacca     120

```
gggcagcctc ccgagctcct aatctattct acatccaaac tggcaactgg ggtcccaaag      180
cggttcagtg gcagcagatc tgggacacag ttcactctca ccatcagcga cctggagtgt      240
gacgatgctg ccacttacta ctgtctaggt gtttatagtt atattagtga tgatggtaat      300
gctttcggcg gagggaccga ggtggtggtc aaacgtacgg tagcggcccc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcacCctga cgctgagcaa agcagactac gagaaacaca agtctacgc ctgcgaagtc      600 acccatcagg gcctgagctc gcccgtcaca aagagcttca caggggaga gtgttag        657
```

<210> SEQ ID NO 353
<211> LENGTH: 360
<212> TYPE: DNA
<213> ORGANISM: Oryctolagus cuniculus

<400> SEQUENCE: 353

```
cagtcggtgg aggagttcgg gggtcgcctg tcacgcctg gacacccct gacactcacc        60 tgcaccgtct ctggattctc cctcaataac tatgcaatga cctgggtccg ccaggctcca     120
gggaaggggc tggagtggat cgggatcatt ggtagtattg gtaccacata ctacgcgagc     180
tgggcgaaag gccgattctt catctccaaa acctcgacca ctgtggatct gaaaatcatt     240
agtccgacaa ccgaggacac ggccacctat ttctgtgcca gagatgctgg cgttactgtt     300
gatggttatg ctactacttt taacatctgg ggcccaggca ccctcgtcac cgtctcgagc     360
```

<210> SEQ ID NO 354
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 354

```
cagtcggtgg aggagttcgg gggtcgcctg tcacgcctg gacacccct gacactcacc        60 tgcaccgtct ctggattctc cctcaataac tatgcaatga cctgggtccg ccaggctcca     120
gggaaggggc tggagtggat cgggatcatt ggtagtattg gtaccacata ctacgcgagc     180
tgggcgaaag gccgattctt catctccaaa acctcgacca ctgtggatct gaaaatcatt     240
agtccgacaa ccgaggacac ggccacctat ttctgtgcca gagatgctgg cgttactgtt     300
gatggttatg ctactacttt taacatctgg ggcccaggca ccctcgtcac cgtctcgagc     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacgcc     900
agcacgtacc gtgtggtcag cgtcctcacc gtcctgcacc aggactggct gaatggcaag     960
```

```
gagtacaagt gcaaggtctc caacaaagcc ctcccagccc ccatcgagaa aaccatctcc    1020
aaagccaaag ggcagccccg agaaccacag gtgtacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                 1353
```

<210> SEQ ID NO 355
<211> LENGTH: 33
<212> TYPE: DNA
<213> ORGANISM: Oryctolagus cuniculus

<400> SEQUENCE: 355

```
caggctagtc agaatattgg taacgaccta tcc                                 33
```

<210> SEQ ID NO 356
<211> LENGTH: 21
<212> TYPE: DNA
<213> ORGANISM: Oryctolagus cuniculus

<400> SEQUENCE: 356

```
tctacatcca aactggcaac t                                              21
```

<210> SEQ ID NO 357
<211> LENGTH: 39
<212> TYPE: DNA
<213> ORGANISM: Oryctolagus cuniculus

<400> SEQUENCE: 357

```
ctaggtgttt atagttatat tagtgatgat ggtaatgct                           39
```

<210> SEQ ID NO 358
<211> LENGTH: 15
<212> TYPE: DNA
<213> ORGANISM: Oryctolagus cuniculus

<400> SEQUENCE: 358

```
aactatgcaa tgacc                                                     15
```

<210> SEQ ID NO 359
<211> LENGTH: 48
<212> TYPE: DNA
<213> ORGANISM: Oryctolagus cuniculus

<400> SEQUENCE: 359

```
atcattggta gtattggtac cacatactac gcgagctggg cgaaaggc                 48
```

<210> SEQ ID NO 360
<211> LENGTH: 45
<212> TYPE: DNA
<213> ORGANISM: Oryctolagus cuniculus

<400> SEQUENCE: 360

```
gatgctggcg ttactgttga tggttatggc tactacttta acatc                    45
```

<210> SEQ ID NO 361
<211> LENGTH: 336
<212> TYPE: DNA

<213> ORGANISM: Oryctolagus cuniculus

<400> SEQUENCE: 361

```
gccatcgaaa tgacccagac tccattctcc gtgtctgcag ctgtgggagg cacagtcacc    60
atcaagtgcc aggccagtca gaccattagc aactacttag cctggtatca gcagaaacca   120
gggcagcctc ccaagctcct gatctatggt gcatccaatc tggaatctgg ggtcccatcg   180
cggttcaaag gcagtggatc tgggacacag ttcactctca ccatcagcga cctggagtgt   240
gacgatgctg ccacttacta ctgtcaacag ggttatacta tcagtaatgt tgataacaat   300
gttttcggcg agggaccgga ggtggtggtc aaacgt                             336
```

<210> SEQ ID NO 362
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 362

```
gccatcgaaa tgacccagac tccattctcc gtgtctgcag ctgtgggagg cacagtcacc    60
atcaagtgcc aggccagtca gaccattagc aactacttag cctggtatca gcagaaacca   120
gggcagcctc ccaagctcct gatctatggt gcatccaatc tggaatctgg ggtcccatcg   180
cggttcaaag gcagtggatc tgggacacag ttcactctca ccatcagcga cctggagtgt   240
gacgatgctg ccacttacta ctgtcaacag ggttatacta tcagtaatgt tgataacaat   300
gttttcggcg agggaccgga ggtggtggtc aaacgtacgg tagcggcccc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca caggggaga gtgttag      657
```

<210> SEQ ID NO 363
<211> LENGTH: 345
<212> TYPE: DNA
<213> ORGANISM: Oryctolagus cuniculus

<400> SEQUENCE: 363

```
cagtcgctgg aggagtccgg gggtcgcctg gtcacgcctg ggggatccct gacactcacc    60
tgcgcagcct ctggattctc cctcactggc tacaacttgg tctgggtccg ccaggctcca   120
gggaaggggc tggagtggat cggattcatt agttatggtg ataccacata ctacgcgagc   180
tgggcgaaag gccgattcac catctccaaa acctcgacca cggtgactct gacgatcacc   240
gatctgcaac cttcagacac gggcacctat ttctgtgcca gagagactgc taatactat    300
gattatggca tctgggccc aggcacctc gtcaccgtct cgagc                     345
```

<210> SEQ ID NO 364
<211> LENGTH: 1338
<212> TYPE: DNA
<213> ORGANISM: Artificial Sequence
<220> FEATURE:
<223> OTHER INFORMATION: Chemically Synthesized

<400> SEQUENCE: 364

```
cagtcgctgg aggagtccgg gggtcgcctg gtcacgcctg ggggatccct gacactcacc    60
```

```
tgcgcagcct ctggattctc cctcactggc tacaacttgg tctgggtccg ccaggctcca    120
gggaaggggc tggagtggat cggattcatt agttatggtg ataccacata ctacgcgagc    180
tgggcgaaag gccgattcac catctccaaa acctcgacca cggtgactct gacgatcacc    240
gatctgcaac cttcagacac gggcacctat ttctgtgcca gagagactgc taatacttat    300
gattatggca tctggggccc aggcacccte gtcaccgtet cgagcgccte caccaagggc    360 ccatcggtct tccccctggc accctcctcc aagagcacct ctggggggcac agcggccctg    420 ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaactcctgg ggggaccgtc agtcttcctc    720
ttccccccaa acccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acgccagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag   1020
ccccgagaac acaggtgta caccctgccc ccatcccggg aggagatgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                 1338
```

<210> SEQ ID NO 365
<211> LENGTH: 33
<212> TYPE: DNA
<213> ORGANISM: Oryctolagus cuniculus

<400> SEQUENCE: 365

```
caggccagtc agaccattag caactactta gcc                                  33
```

<210> SEQ ID NO 366
<211> LENGTH: 21
<212> TYPE: DNA
<213> ORGANISM: Oryctolagus cuniculus

<400> SEQUENCE: 366

```
ggtgcatcca atctggaatc t                                               21
```

<210> SEQ ID NO 367
<211> LENGTH: 39
<212> TYPE: DNA
<213> ORGANISM: Oryctolagus cuniculus

<400> SEQUENCE: 367

```
caacagggtt atactatcag taatgttgat aacaatgtt                            39
```

<210> SEQ ID NO 368
<211> LENGTH: 15
<212> TYPE: DNA

<213> ORGANISM: Oryctolagus cuniculus

<400> SEQUENCE: 368
ggctacaact tggtc                                                          15

<210> SEQ ID NO 369
<211> LENGTH: 48
<212> TYPE: DNA
<213> ORGANISM: Oryctolagus cuniculus

<400> SEQUENCE: 369
ttcattagtt atggtgatac cacatactac gcgagctggg cgaaaggc                      48

<210> SEQ ID NO 370
<211> LENGTH: 30
<212> TYPE: DNA
<213> ORGANISM: Oryctolagus cuniculus

<400> SEQUENCE: 370
gagactgcta atacttatga ttatggcatc                                          30

<210> SEQ ID NO 371
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 371
gacatccaga tgacccagtc tccttccacc ctgtctgcat ctgtaggaga cagagtcacc         60
atcacttgtc aggctagtca gaccattagc aactacttag cctggtatca gcagaaacca        120
ggaaaagccc ctaagctcct gatctatggt gcatccaatc tggaatctgg agtcccatca        180
aggttcagcg gcagtggatc tgggacagaa ttcactctca ccatcagcag cctgcagcct        240
gatgattttg caacttacta ctgtcaacag ggttatacta tcagtaatgt tgataacaat        300
gttttcggcg gaggaaccaa ggtggaaatc aaacgt                                  336

<210> SEQ ID NO 372
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 372
gacatccaga tgacccagtc tccttccacc ctgtctgcat ctgtaggaga cagagtcacc         60
atcacttgtc aggctagtca gaccattagc aactacttag cctggtatca gcagaaacca        120
ggaaaagccc ctaagctcct gatctatggt gcatccaatc tggaatctgg agtcccatca        180
aggttcagcg gcagtggatc tgggacagaa ttcactctca ccatcagcag cctgcagcct        240
gatgattttg caacttacta ctgtcaacag ggttatacta tcagtaatgt tgataacaat        300
gttttcggcg gaggaaccaa ggtggaaatc aaacgtacgg tagcggcccc atctgtcttc        360
atcttcccgc catctgatga gcagttgaaa tctggaactg cctctgttgt gtgcctgctg        420
aataacttct atcccagaga ggccaaagta cagtggaagg tggataacgc cctccaatcg        480
ggtaactccc aggagagtgt cacagagcag gacagcaagg acagcaccta cagcctcagc        540
agcaccctga cgctgagcaa agcagactac gagaaacaca agtctacgc ctgcgaagtc        600
acccatcagg gcctgagctc gcccgtcaca aagagcttca caggggaga gtgttag            657

<210> SEQ ID NO 373
<211> LENGTH: 354
<212> TYPE: DNA
<213> ORGANISM: Artificial Sequence
<220> FEATURE:
<223> OTHER INFORMATION: Chemically Synthesized

<400> SEQUENCE: 373

| | | | | | |
|---|---|---|---|---|---|
| gaggtgcagc | tggtggagtc | tgggggaggc | ttggtccagc | ctggggggtc | cctgagactc | 60 |
| tcctgtgcag | cctctggatt | caccgtcagt | ggctacaact | tggtctgggt | ccgtcaggct | 120 |
| ccagggaagg | ggctggagtg | ggtcggattc | attagttatg | gtgataccac | atactacgct | 180 |
| agctctgcta | aaggccgatt | caccatctcc | agagacaatt | ccaagaacac | cctgtatctt | 240 |
| caaatgaaca | gcctgagagc | tgaggacact | gctgtgtatt | actgtgctag | agagactgct | 300 |
| aatacttatg | attatggcat | ctggggccaa | gggaccctcg | tcaccgtctc | gagc | 354 |

<210> SEQ ID NO 374
<211> LENGTH: 1347
<212> TYPE: DNA
<213> ORGANISM: Artificial Sequence
<220> FEATURE:
<223> OTHER INFORMATION: Chemically Synthesized

<400> SEQUENCE: 374

| | | | | | |
|---|---|---|---|---|---|
| gaggtgcagc | tggtggagtc | tgggggaggc | ttggtccagc | ctggggggtc | cctgagactc | 60 |
| tcctgtgcag | cctctggatt | caccgtcagt | ggctacaact | tggtctgggt | ccgtcaggct | 120 |
| ccagggaagg | ggctggagtg | ggtcggattc | attagttatg | gtgataccac | atactacgct | 180 |
| agctctgcta | aaggccgatt | caccatctcc | agagacaatt | ccaagaacac | cctgtatctt | 240 |
| caaatgaaca | gcctgagagc | tgaggacact | gctgtgtatt | actgtgctag | agagactgct | 300 |
| aatacttatg | attatggcat | ctggggccaa | gggaccctcg | tcaccgtctc | gagcgcctcc | 360 |
| accaagggcc | catcggtctt | ccccctggca | ccctcctcca | agagcacctc | tgggggcaca | 420 |
| gcggccctgg | gctgcctggt | caaggactac | ttccccgaac | cggtgacggt | gtcgtggaac | 480 |
| tcaggcgccc | tgaccagcgg | cgtgcacacc | ttcccggctg | tcctacagtc | ctcaggactc | 540 |
| tactccctca | gcagcgtggt | gaccgtgccc | tccagcagct | tgggcaccca | gacctacatc | 600 |
| tgcaacgtga | atcacaagcc | cagcaacacc | aaggtggaca | agagagttga | gcccaaatct | 660 |
| tgtgacaaaa | ctcacacatg | cccaccgtgc | ccagcacctg | aactcctggg | gggaccgtca | 720 |
| gtcttcctct | tccccccaaa | acccaaggac | accctcatga | tctcccggac | ccctgaggtc | 780 |
| acatgcgtgg | tggtggacgt | gagccacgaa | gaccctgagg | tcaagttcaa | ctggtacgtg | 840 |
| gacggcgtgg | aggtgcataa | tgccaagaca | aagccgcggg | aggagcagta | cgccagcacg | 900 |
| taccgtgtgg | tcagcgtcct | caccgtcctg | caccaggact | ggctgaatgg | caaggagtac | 960 |
| aagtgcaagg | tctccaacaa | agccctccca | gcccccatcg | agaaaaccat | ctccaaagcc | 1020 |
| aaagggcagc | cccgagaacc | acaggtgtac | accctgcccc | catcccggga | ggagatgacc | 1080 |
| aagaaccagg | tcagcctgac | ctgcctggtc | aaaggcttct | atcccagcga | catcgccgtg | 1140 |
| gagtgggaga | gcaatgggca | gccggagaac | aactacaaga | ccacgcctcc | cgtgctggac | 1200 |
| tccgacggct | ccttcttcct | ctacagcaag | ctcaccgtgg | acaagagcag | gtggcagcag | 1260 |
| gggaacgtct | tctcatgctc | cgtgatgcat | gaggctctgc | acaaccacta | cacgcagaag | 1320 |
| agcctctccc | tgtctccggg | taaatga | | | | 1347 |

<210> SEQ ID NO 375
<211> LENGTH: 33
<212> TYPE: DNA
<213> ORGANISM: Oryctolagus cuniculus

<400> SEQUENCE: 375
caggctagtc agaccattag caactactta gcc                          33

<210> SEQ ID NO 376
<211> LENGTH: 21
<212> TYPE: DNA
<213> ORGANISM: Oryctolagus cuniculus

<400> SEQUENCE: 376
ggtgcatcca atctggaatc t                                       21

<210> SEQ ID NO 377
<211> LENGTH: 39
<212> TYPE: DNA
<213> ORGANISM: Oryctolagus cuniculus

<400> SEQUENCE: 377
caacagggtt atactatcag taatgttgat aacaatgtt                    39

<210> SEQ ID NO 378
<211> LENGTH: 15
<212> TYPE: DNA
<213> ORGANISM: Oryctolagus cuniculus

<400> SEQUENCE: 378
ggctacaact tggtc                                              15

<210> SEQ ID NO 379
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 379
ttcattagtt atggtgatac cacatactac gctagctctg ctaaaggc          48

<210> SEQ ID NO 380
<211> LENGTH: 30
<212> TYPE: DNA
<213> ORGANISM: Oryctolagus cuniculus

<400> SEQUENCE: 380
gagactgcta atacttatga ttatggcatc                              30

<210> SEQ ID NO 381
<211> LENGTH: 336
<212> TYPE: DNA
<213> ORGANISM: Oryctolagus cuniculus

<400> SEQUENCE: 381
gccgccgtgc tgacccagac tccatctccc gtgtctgcag ctgtgggagg cacagtcagc    60
atcagttgcc agtccagtca gaatgtttat aagaacaact atttatcctg gtatcagcag   120
aaaccagggc agcctcccaa gctcctgatc tacaaggctt ccactctggc atctgggtc    180 ccatcgcggt tcaaaggcag tggatctggg acagatttca ctctcaccat cagcgacgtg   240
cagtgtgacg ctgctgccac ttactactgt gcaggcggtt atagtagtag tagtgataat   300

```
gctttcggcg agggaccga ggtggtggtc aaacgt                                  336
```

<210> SEQ ID NO 382
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 382

```
gccgccgtgc tgacccagac tccatctccc gtgtctgcag ctgtgggagg cacagtcagc      60
atcagttgcc agtccagtca gaatgtttat aagaacaact atttatcctg gtatcagcag     120
aaaccagggc agcctcccaa gctcctgatc tacaaggctt ccactctggc atctggggtc     180
ccatcgcggt tcaaaggcag tggatctggg acagatttca ctctcaccat cagcgacgtg     240
cagtgtgacg ctgctgccac ttactactgt gcaggcggtt atagtagtag tagtgataat     300
gctttcggcg agggaccga ggtggtggtc aaacgtacgg tagcggcccc atctgtcttc      360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag acagcaagg acagcaccta cagcctcagc      540
agcaccctga cgctgagcaa agcagactac gagaaacaca agtctacgc ctgcgaagtc      600
acccatcagg gcctgagctc gcccgtcaca aagagcttca caggggaga gtgttag         657
```

<210> SEQ ID NO 383
<211> LENGTH: 351
<212> TYPE: DNA
<213> ORGANISM: Oryctolagus cuniculus

<400> SEQUENCE: 383

```
cagtcggtgg aggcgtccgg gggtcgtctg tcatgcctg gaggatccct gacactcacc       60
tgcacagcct ctggattctc cctcagtacc tactggatgt cctgggtccg ccaggctcca     120
gggaaggggc tggaatggat cggagacatt tattttagta atgaggaaac aaactacgcg     180
acctgggcga aaggccgatt taccatctcc aaaacctcga ccacggtgga tctgaatgtc     240
atcagtccga caaccgagga cacggccacc tatttctgtg caagaggttc tcctgatgtt     300
gagattgcta tagatatgtg gggccagggc accctcgtca ccgtctcgag c              351
```

<210> SEQ ID NO 384
<211> LENGTH: 1344
<212> TYPE: DNA
<213> ORGANISM: Artificial Sequence
<220> FEATURE:
<223> OTHER INFORMATION: Chemically Synthesized

<400> SEQUENCE: 384

```
cagtcggtgg aggcgtccgg gggtcgtctg tcatgcctg gaggatccct gacactcacc       60
tgcacagcct ctggattctc cctcagtacc tactggatgt cctgggtccg ccaggctcca     120
gggaaggggc tggaatggat cggagacatt tattttagta atgaggaaac aaactacgcg     180
acctgggcga aaggccgatt taccatctcc aaaacctcga ccacggtgga tctgaatgtc     240
atcagtccga caaccgagga cacggccacc tatttctgtg caagaggttc tcctgatgtt     300
gagattgcta tagatatgtg gggccagggc accctcgtca ccgtctcgag cgcctccacc     360
aagggcccat cggtcttccc cctggcaccc tcctccaaga gcacctctgg gggcacagcg     420
```

```
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacgc cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca gagcaggtg gcagcagggg    1260
aacgtcttct catgctccgt gatgcatgag gctctgcaca ccactacac gcagaagagc    1320
ctctccctgt ctccgggtaa atga                                          1344
```

```
<210> SEQ ID NO 385
<211> LENGTH: 39
<212> TYPE: DNA
<213> ORGANISM: Oryctolagus cuniculus

<400> SEQUENCE: 385
cagtccagtc agaatgttta taagaacaac tatttatcc                           39

<210> SEQ ID NO 386
<211> LENGTH: 21
<212> TYPE: DNA
<213> ORGANISM: Oryctolagus cuniculus

<400> SEQUENCE: 386
aaggcttcca ctctggcatc t                                              21

<210> SEQ ID NO 387
<211> LENGTH: 33
<212> TYPE: DNA
<213> ORGANISM: Oryctolagus cuniculus

<400> SEQUENCE: 387
gcaggcggtt atagtagtag tagtgataat gct                                 33

<210> SEQ ID NO 388
<211> LENGTH: 15
<212> TYPE: DNA
<213> ORGANISM: Oryctolagus cuniculus

<400> SEQUENCE: 388
acctactgga tgtcc                                                     15

<210> SEQ ID NO 389
<211> LENGTH: 51
<212> TYPE: DNA
<213> ORGANISM: Oryctolagus cuniculus

<400> SEQUENCE: 389
```

```
gacatttatt ttagtaatga ggaaacaaac tacgcgacct gggcgaaagg c           51
```

<210> SEQ ID NO 390
<211> LENGTH: 33
<212> TYPE: DNA
<213> ORGANISM: Oryctolagus cuniculus

<400> SEQUENCE: 390

```
ggttctcctg atgttgagat tgctatagat atg                              33
```

<210> SEQ ID NO 391
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 391

```
gacatccaga tgacccagtc tccatcctcc ctgtctgcat ctgtaggaga cagagtcacc   60
atcacttgcc agtccagtca gaatgtttat aagaacaact acttatcctg gtatcagcag  120
aaaccaggga agtccctaa gctcctgatc tataaggcat ccactctggc atctggggtc  180
ccatctcgtt tcagtggcag tggatctggg acagatttca ctctcaccat cagcagcctg  240
cagcctgaag atgttgcaac ttattactgt gcaggcggtt ataccagtag tagtgataat  300
gctttcggcg gaggaaccaa ggtggaaatc aaacgt                             336
```

<210> SEQ ID NO 392
<211> LENGTH: 657
<212> TYPE: DNA
<213> ORGANISM: Artificial Sequence
<220> FEATURE:
<223> OTHER INFORMATION: Chemically Synthesized

<400> SEQUENCE: 392

```
gacatccaga tgacccagtc tccatcctcc ctgtctgcat ctgtaggaga cagagtcacc   60
atcacttgcc agtccagtca gaatgtttat aagaacaact acttatcctg gtatcagcag  120
aaaccaggga agtccctaa gctcctgatc tataaggcat ccactctggc atctggggtc  180
ccatctcgtt tcagtggcag tggatctggg acagatttca ctctcaccat cagcagcctg  240
cagcctgaag atgttgcaac ttattactgt gcaggcggtt ataccagtag tagtgataat  300
gctttcggcg gaggaaccaa ggtggaaatc aaacgtacgg tagcggcccc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca agtctacgc ctgcgaagtc  600
acccatcagg gcctgagctc gcccgtcaca aagagcttca caggggaga gtgttag     657
```

<210> SEQ ID NO 393
<211> LENGTH: 360
<212> TYPE: DNA
<213> ORGANISM: Artificial Sequence
<220> FEATURE:
<223> OTHER INFORMATION: Chemically Synthesized

<400> SEQUENCE: 393

```
gaggtgcagc tggtggagtc tgggggaggc ttggtccagc ctggggggtc cctgagactc   60
```

| tcctgtgcag cctctggatt caccgtcagt acctactgga tgagctgggt ccgtcaggct | 120 |
| ccagggaagg ggctggagtg ggtcggagac atttacttta gtaatgaaga aacaaactac | 180 |
| gcgaccagcg cgaaaggccg attcaccatc tccagagaca attccaagaa caccctgtat | 240 |
| cttcaaatga acagcctgag agctgaggac actgctgtgt attactgtgc tagaggttct | 300 |
| cctgatgttg agattgctat agatatgtgg ggccaaggga ccctcgtcac cgtctcgagc | 360 |

<210> SEQ ID NO 394
<211> LENGTH: 1353
<212> TYPE: DNA
<213> ORGANISM: Artificial Sequence
<220> FEATURE:
<223> OTHER INFORMATION: Chemically Synthesized

<400> SEQUENCE: 394

| gaggtgcagc tggtggagtc tgggggaggc ttggtccagc ctggggggtc cctgagactc | 60 |
| tcctgtgcag cctctggatt caccgtcagt acctactgga tgagctgggt ccgtcaggct | 120 |
| ccagggaagg ggctggagtg ggtcggagac atttacttta gtaatgaaga aacaaactac | 180 |
| gcgaccagcg cgaaaggccg attcaccatc tccagagaca attccaagaa caccctgtat | 240 |
| cttcaaatga acagcctgag agctgaggac actgctgtgt attactgtgc tagaggttct | 300 |
| cctgatgttg agattgctat agatatgtgg ggccaaggga ccctcgtcac cgtctcgagc | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagag agttgagccc | 660 |
| aaatcttgtg acaaaactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacgcc | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggaggag | 1080 |
| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctac agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa tga | 1353 |

<210> SEQ ID NO 395
<211> LENGTH: 39
<212> TYPE: DNA
<213> ORGANISM: Oryctolagus cuniculus

<400> SEQUENCE: 395

| cagtccagtc agaatgttta taagaacaac tacttatcc | 39 |

<210> SEQ ID NO 396
<211> LENGTH: 21

```
<212> TYPE: DNA
<213> ORGANISM: Oryctolagus cuniculus

<400> SEQUENCE: 396
aaggcatcca ctctggcatc t                                              21

<210> SEQ ID NO 397
<211> LENGTH: 33
<212> TYPE: DNA
<213> ORGANISM: Oryctolagus cuniculus

<400> SEQUENCE: 397
gcaggcggtt ataccagtag tagtgataat gct                                 33

<210> SEQ ID NO 398
<211> LENGTH: 15
<212> TYPE: DNA
<213> ORGANISM: Oryctolagus cuniculus

<400> SEQUENCE: 398
acctactgga tgagc                                                     15

<210> SEQ ID NO 399
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 399
gacatttact ttagtaatga agaaacaaac tacgcgacca gcgcgaaagg c              51

<210> SEQ ID NO 400
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 400
ggttctcctg atgttgagat tgctatagat atg                                 33

<210> SEQ ID NO 401
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 401

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Gly Phe Thr Val Ser Asp
                85                  90                  95
```

```
Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

```
<210> SEQ ID NO 402
<211> LENGTH: 451
<212> TYPE: PRT
<213> ORGANISM: Artificial Sequence
<220> FEATURE:
<223> OTHER INFORMATION: Chemically Synthesized

<400> SEQUENCE: 402

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Val Gly Trp Val Arg Gln Ala Pro Gly Lys Gly Leu Glu Trp Val
        35                  40                  45

Gly Ile Ile Gly Arg Asn Gly Asn Thr Trp Tyr Ala Ser Ser Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Arg Ser Val Ala Tyr Tyr Val Phe Asn Ile Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Ala Arg Val Glu Pro Lys Ser Cys
    210                 215                 220

Asp Lys Thr His Thr Cys Pro Pro Cys Pro Ala Pro Glu Leu Leu Gly
225                 230                 235                 240
```

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 403
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 403
gacatccaga tgacccagtc tccttccacc ctgtctgcat ctgtaggaga cagagtcacc      60
atcacttgcc aggccagtca gagcatttac agcaatcttg cctggtatca gcagaaacca     120
ggaaaagccc ctaagctcct gatctatgat gcatccactc tggaatctgg agtcccatca     180
aggttcagcg gcagtggatc tgggacagag tacactctca ccatcagcag cctgcagcct     240
gatgattttg caacttacta ctgccaacag ggttttactg ttagtgatat tgataatgct     300
ttcggcggag gaaccaaggt ggaaatcaaa cgtacggtag cggccccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg ttag           654

<210> SEQ ID NO 404
<211> LENGTH: 1356
<212> TYPE: DNA
<213> ORGANISM: Artificial Sequence

```
<220> FEATURE:
<223> OTHER INFORMATION: Chemically Synthesized

<400> SEQUENCE: 404
gaggtgcagc tggtggagtc tgggggaggc ttggtccagc ctgggggtc cctgagactc      60
tcctgtgcag cctctggatt caccgtcagt aactatgcag tgggctgggt ccgtcaggct     120
ccagggaagg ggctggagtg ggtcggaatc attggtcgta atggtaacac atggtacgcg     180
agctctgcaa gaggccgatt caccatctcc agagacaatt ccaagaacac cctgtatctt     240
caaatgaaca gcctgagagc tgaggacact gctgtgtatt actgtgctag aggatatggc     300
cgtagtgttg cttactacgt ctttaacatc tggggcccag ggaccctcgt caccgtctcg     360
agcgcctcca ccaagggccc atcggtcttc cccctggcac cctcctccaa gagcacctct     420
gggggcacag cggccctggg ctgcctggtc aaggactact ccccgaacc ggtgacggtg      480
tcgtggaact caggcgccct gaccagcggc gtgcacacct cccggctgt cctacagtcc      540
tcaggactct actccctcag cagcgtggtg accgtgccct ccagcagctt gggcacccag     600
acctacatct gcaacgtgaa tcacaagccc agcaacacca aggtggacgc gagagttgag     660
cccaaatctt gtgacaaaac tcacacatgc ccaccgtgcc cagcacctga actcctgggg     720
ggaccgtcag tcttcctctt ccccccaaaa cccaaggaca ccctcatgat ctcccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
gccagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggag    1080
gagatgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatga                              1356

<210> SEQ ID NO 405
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 405

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Gly Phe Thr Val Ser Asp
                85                  90                  95
```

```
Ile Asp Asn Ala Phe Gly Gly Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 406
<211> LENGTH: 228
<212> TYPE: PRT
<213> ORGANISM: Artificial Sequence
<220> FEATURE:
<223> OTHER INFORMATION: Chemically Synthesized

<400> SEQUENCE: 406

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Val Gly Trp Val Arg Gln Ala Pro Gly Lys Gly Leu Glu Trp Val
        35                  40                  45

Gly Ile Ile Gly Arg Asn Gly Asn Thr Trp Tyr Ala Ser Ser Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Arg Ser Val Ala Tyr Tyr Val Phe Asn Ile Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Ala Arg Val Glu Pro Lys Ser Cys
    210                 215                 220

Asp Lys Thr His
225
```

```
<210> SEQ ID NO 407
<211> LENGTH: 217
<212> TYPE: PRT
<213> ORGANISM: Artificial Sequence
<220> FEATURE:
<223> OTHER INFORMATION: Chemically Synthesized

<400> SEQUENCE: 407

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Gly Phe Thr Val Ser Asp
                85                  90                  95

Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 408
<211> LENGTH: 228
<212> TYPE: PRT
<213> ORGANISM: Artificial Sequence
<220> FEATURE:
<223> OTHER INFORMATION: Chemically Synthesized

<400> SEQUENCE: 408

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Val Gly Trp Val Arg Gln Ala Pro Gly Lys Gly Leu Glu Trp Val
        35                  40                  45

Gly Ile Ile Gly Arg Asn Gly Asn Thr Trp Tyr Ala Ser Ser Ala Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Arg Gly Tyr Gly Arg Ser Val Ala Tyr Tyr Val Phe Asn Ile Trp Gly
                100                 105                 110
Pro Gly Thr Leu Val Thr Val Ser Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Ala Arg Val Glu Pro Lys Ser Cys
            210                 215                 220
Asp Lys Thr His
225
```

```
<210> SEQ ID NO 409
<211> LENGTH: 654
<212> TYPE: DNA
<213> ORGANISM: Artificial Sequence
<220> FEATURE:
<223> OTHER INFORMATION: Chemically Synthesized

<400> SEQUENCE: 409
gacatccaga tgacccagtc tccttccacc ctgtctgcat ctgtaggaga cagagtcacc      60
atcacttgcc aggccagtca gagcatttac agcaatcttg cctggtatca gcagaaacca     120
ggaaaagccc ctaagctcct gatctatgat gcatccactc tggaatctgg agtcccatca     180
aggttcagcg gcagtggatc tgggacagag tacactctca ccatcagcag cctgcagcct     240
gatgattttg caacttacta ctgccaacag ggttttactg ttagtgatat tgataatgct     300
ttcggcggag gaaccaaggt ggaaatcaaa cgtacggtag cggccccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg ttag           654
```

```
<210> SEQ ID NO 410
<211> LENGTH: 687
<212> TYPE: DNA
<213> ORGANISM: Artificial Sequence
<220> FEATURE:
<223> OTHER INFORMATION: Chemically Synthesized

<400> SEQUENCE: 410
gaggtgcagc tggtggagtc tgggggaggc ttggtccagc ctgggggtc cctgagactc       60
tcctgtgcag cctctggatt caccgtcagt aactatgcag tgggctgggt ccgtcaggct     120
ccagggaagg ggctggagtg ggtcggaatc attggtcgta atggtaacac atggtacgcg     180
agctctgcaa aggccgatt caccatctcc agagacaatt ccaagaacac cctgtatctt     240
caaatgaaca gcctgagagc tgaggacact gctgtgtatt actgtgctag aggatatggc     300
```

```
cgtagtgttg cttactacgt ctttaacatc tggggcccag ggaccctcgt caccgtctcg    360
agcgcctcca ccaagggccc atcggtcttc ccctggcac cctcctccaa gagcacctct     420 ggggcacag cggccctggg ctgcctggtc aaggactact ccccgaacc ggtgacggtg      480 tcgtggaact caggcgccct gaccagcggc gtgcacacct ccccggctgt cctacagtcc    540
tcaggactct actccctcag cagcgtggtg accgtgccct ccagcagctt gggcacccag    600
acctacatct gcaacgtgaa tcacaagccc agcaacacca aggtggacgc gagagttgag    660
cccaaatctt gtgacaaaac tcactag                                        687
```

```
<210> SEQ ID NO 411
<211> LENGTH: 120
<212> TYPE: PRT
<213> ORGANISM: Homo sapiens

<400> SEQUENCE: 411
```

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
                20                  25                  30

Gly Lys Glu Val Met Val Leu Gly Glu Val Asn Ile Asn Asn Ser Val
            35                  40                  45

Phe Lys Gln Tyr Phe Phe Glu Thr Lys Cys Arg Asp Pro Asn Pro Val
        50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

```
<210> SEQ ID NO 412
<211> LENGTH: 105
<212> TYPE: PRT
<213> ORGANISM: Homo sapiens

<400> SEQUENCE: 412
```

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
                20                  25                  30

Arg Glu Ala Lys Val Gln Trp Lys Val Asp Asn Ala Leu Gln Ser Gly
            35                  40                  45

Asn Ser Gln Glu Ser Val Thr Glu Gln Asp Ser Lys Asp Ser Thr Tyr
        50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

```
<210> SEQ ID NO 413
<211> LENGTH: 330
```

```
<212> TYPE: PRT
<213> ORGANISM: Homo sapiens

<400> SEQUENCE: 413
```

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Arg | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| | 130 | | | | | 135 | | | | | 140 | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Ala | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | 195 | | | | | 200 | | | | | 205 | | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

What is claimed is:

1. A method of treating pain or eliciting an analgesic effect in an individual, comprising administering to the individual an effective amount of an NGF antagonist which comprises an anti-human NGF antibody or antibody fragment which inhibits the association of NGF with TrkA, without appreciably inhibiting the association of NGF with p75.

2. The method of claim 1, wherein NGF antagonist is an intact anti-human NGF antibody which inhibits the association of NGF with TrkA, without appreciably inhibiting the association of NGF with p75.

3. The method of claim 1, wherein the NGF antagonist is an anti-human NGF antibody fragment which inhibits the association of NGF with TrkA, without appreciably inhibiting the association of NGF with p75.

4. The method of claim 3, wherein the antibody fragment is a monovalent antibody fragment selected from a Fab, Fab', Fv, scFv fragments, SMIPs (small molecule immunopharmaceuticals), camelbody, nanobody, IgNAR, or a monovalent antibody molecule analogous to MetMab.

5. The method of claim 1, wherein said pain is associated with pre- or post-operative surgery, or pain associated with trauma or injury to the musculoskeletal system, or the prevention or treatment of chronic visceral pain.

6. The method of claim 5, wherein said chronic visceral pain is due to a physiological disorder selected from dysmenorrhoea, dyspepsia, gastrooesophageal reflux, pancreatitis, visceralgia and irritable bowel syndrome.

7. The method of claim 5, wherein the post-surgical pain comprises resting pain and mechanically-induced pain, and wherein the resting pain and mechanically-induced pain are ameliorated.

8. The method of claim 5, wherein the post-surgical pain comprises thermally-induced pain, and wherein the thermally-induced pain is ameliorated.

9. The method of claim 5, wherein the post-surgical pain comprises resting pain, mechanically-induced pain, and/or thermally-induced pain, and wherein the resting pain, mechanically-induced pain, and/or thermally-induced pain are ameliorated.

10. The method of claim 5, wherein wound healing is not significantly inhibited.

11. The method of claim 1, wherein said pain is selected from pain associated with a cancer, neuropathic pain, and neurogenic pain.

12. The method of claim 1, wherein said treatment comprises treatment of an acute pain or a chronic pain.

13. The method of claim 1, wherein the pain is a craniofacial pain or a head pain.

14. The method of claim 13, wherein the craniofacial pain or the head pain is caused by temporomandibular joint disorder (TMJ), migraine or trigeminal neuralgia.

15. The method of claim 1, wherein the pain treated is acute pain, dental pain, pain from trauma, surgical pain, pain resulting from amputation or abscess, causalgia, demyelinating diseases, trigeminal neuralgia, cancer, chronic alcoholism, stroke, thalamic pain syndrome, diabetes, acquired immune deficiency syndrome ("AIDS"), toxins, chemotherapy, general headache, migraine, cluster headache, mixed-vascular or non-vascular syndromes, tension headache, general inflammation, arthritis, rheumatic diseases, lupus, osteoarthritis, fibromyalgia, inflammatory bowel disorders, irritable bowel syndrome, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia or allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritic, vitiligo, general gastrointestinal disorders, colitis, gastric ulceration, duodenal ulcers, vasomotor or allergic rhinitis, or bronchial disorders, dysmenorrhoea, dyspepsia, gastroesophageal reflux, pancreatitis, or visceralgia.

16. The method of claim 1, wherein the administration is effected via craniofacial mucosal administration comprises intranasal administration, buccal administration, sublingual administration or conjunctival administration.

17. The method of claim 1, which further includes administration of at least one NSAID.

18. The method of claim 17, wherein the NSAID is selected from the group consisting of ibuprofen, naproxen, naprosyn, diclofenac, ketoprofen, tolmetin, sulindac, mefanamic acid, meclofenamic acid, diflunisal, flufenisal, piroxicam, sudoxicam, isoxicam, celecoxib, fofecoxib, DUP-697, flosulide, meloxicam, 6-methoxy-2-naphthylacetic acid, MK-966, nabumetone, nimesulide, NS-398, SC-5766, SC-58215 and T-614.

19. The method of claim 1, which is used or treating bone cancer pain.

20. The method of claim 19, wherein the bone cancer pain is from cancer originated in bone, osteosarcoma, cancer metastasized to bone, prostate cancer metastasized to bone, breast cancer metastasized to bone, lung cancer metastasized to bone, sarcoma metastasized to bone, renal cancer metastasized to bone, or cancer metastasized to bone from an undetermined tissue.

21. The method of claim 1, which is used for treating back or neck pain with or without radiculopathy comprising providing an effective amount of said antibody or fragment to a disc region comprising a disc, wherein the disc is a degenerated disc.

22. The method of claim 1, which is used to treat or prevent pain and/or a lower urinary tract symptom associated with chronic prostatitis and/or chronic pelvic pain syndrome in a subject.

23. The method of claim 22, wherein pain associated with chronic prostatitis and/or chronic pelvic pain syndrome is selected from the group comprising lower abdominal (pelvic) pain; lower stomach pain; bladder pain; suprapubic pain; pain in the penis, testicles, scrotum and perineum; urethral pain; dyspareunia; pain, pressure or discomfort that may increase as the bladder fills; dysuria and ejaculatory pain.

24. The method of claim 1, wherein the antibody or fragment comprises a $V_L$ polypeptide and a $V_H$ polypeptide respectively selected from (i) the $V_L$ polypeptide in SEQ ID NO:22 and the $V_H$ polypeptide in SEQ ID NO:24; (ii) the $V_L$ polypeptide in SEQ ID NO:32 and the $V_H$ polypeptide in SEQ ID NO:34; (ii) the $V_L$ polypeptide in SEQ ID NO:142 and the $V_H$ polypeptide in SEQ ID NO:144; and (iv) the $V_L$ polypeptide in SEQ ID NO:152 and the $V_H$ polypeptide in SEQ ID NO:154 or a fragment thereof containing the identical 6 CDRs as any of said antibodies (i) (ii), (iii), or (iv).

25. The method of claim 1, wherein the antibody specifically binds the same or overlapping epitope as an anti-human NGF antibody comprising a $V_L$ polypeptide and a $V_H$ polypeptide selected from the group consisting of: (i) the $V_L$ polypeptide in SEQ ID NO:22 and the $V_H$ polypeptide in SEQ ID NO:24; (ii) the $V_L$ polypeptide in SEQ ID NO:32 and the $V_H$ polypeptide in SEQ ID NO:34; (iii) the $V_L$ polypeptide in SEQ ID NO:142 and the V$_H$ polypeptide in SEQ ID NO:144; (iv) the V$_L$ polypeptide in SEQ ID NO:152 and the V$_H$ polypeptide in SEQ ID NO:154; and/or competes for binding to the same or overlapping epitope on an intact NGF polypeptide or fragment thereof as an anti-human NGF antibody comprising a V$_L$ polypeptide and a V$_H$ polypeptide selected from the group consisting of (i) the polypeptide in SEQ ID NO:22 and the polypeptide in SEQ ID NO:24; (ii) the polypeptide in SEQ ID NO:32 and the polypeptide in SEQ ID NO:34 (iii) the polypeptide in SEQ ID NO:142 and the polypeptide in SEQ ID NO:144; and (iv) the polypeptide in SEQ ID NO:152 and the polypeptide in SEQ ID NO:154.

26. The method claim 1, wherein said antibody fragment is selected from a Fab fragment, and Fab' fragment, a MetMab like monovalent agent, or an F(ab')$_2$ fragment.

27. The method of claim 26, wherein said fragment is a Fab fragment.

28. The method of claim 1, wherein said anti-human NGF antibody binds the same NGF epitope or competes for binding to NGF with an antibody or antibody fragment comprising a V$_L$ polypeptide sequence and a V$_H$ polypeptide sequence respectively selected from the group consisting of:
(i) the polypeptides in SEQ ID NO:25, 26 and 27 and the polypeptides in SEQ ID NO:28, 29 and 30;
(ii) the polypeptides in SEQ ID NO:35, 36 and 37 and the polypeptides in SEQ ID NO:38, 39 and 40;
(iii) the polypeptides in SEQ ID NO:145, 146 and 147 and the polypeptides in SEQ ID NO:148, 149 and 150; and
(iv) the polypeptides in SEQ ID NO:155, 156 and 157 and the polypeptides in SEQ ID NO:158, 159 and 160.

29. The method of claim 28, wherein said anti-human NGF antibody or fragment thereof is aglycosylated.

30. The method of claim 28, wherein said antibody contains an Fc region that has been modified to alter effector function, half-life, proteolysis, and/or glycosylation.

31. The method of claim 28, wherein said anti-human NGF antibody or fragment thereof comprises a V$_L$ or V$_H$ polypeptide sequence having at least 90% or greater homology to any one of the polypeptide sequences selected from the V$_L$ polypeptide in SEQ ID NO:22 and the V$_H$ polypeptide in SEQ ID NO:24; (ii) the V$_L$ polypeptide in SEQ ID NO:32 and the V$_H$ polypeptide in SEQ ID NO:34 (iii) the V$_L$ polypeptide in SEQ ID NO:142 and the V$_H$ polypeptide in SEQ ID NO:144 and (iv) the V$_L$ polypeptide in SEQ ID NO:152 and the V$_H$ polypeptide in SEQ ID NO:154.

32. The method of claim 1, wherein said anti-human NGF antibody is human, humanized, single chain, or chimeric.

33. The method of claim 1, wherein said anti-human NGF antibody or fragment thereof specifically binds to NGF expressing human cells and/or to circulating soluble NGF molecules in vivo.

34. The method of claim 1, wherein said anti-human NGF antibody or fragment thereof is directly or indirectly attached to a detectable label or therapeutic agent or is attached to a moiety that increases half-life.

35. The method of claim 1, wherein said anti-human NGF antibody or fragment thereof further comprises an effector moiety or a water soluble polymer.

36. The method of claim 35, wherein said effector moiety is a detectable moiety or a functional moiety.

37. The method of claim 36, wherein said detectable moiety is a fluorescent dye, an enzyme, a substrate, a bioluminescent material, a radioactive material, or a chemiluminescent material.

38. The method of claim 36, wherein said functional moiety is streptavidin, avidin, biotin, a cytotoxin, a cytotoxic agent, or a radioactive material.

39. The method of claim 1, further comprising the administration of another therapeutic agent or regimen selected from anti-histamines, anti-inflammatory agents, or antibiotics.

40. The method of claim 1, wherein said anti-human NGF antibody or fragment thereof is contained in a pharmaceutical or diagnostic composition comprising a pharmaceutically acceptable carrier.

41. The method of claim 1, wherein the antibody is administered via injection or intranasal administration.

42. The method claim 1, wherein the NGF antagonist binds to NGF with a dissociation constant (K$_D$) of less than or equal to $5\times10^{-7}$ M, $10^{-7}$ M, $5\times10^{-8}$ M, $10^{-8}$ M, $5\times10^{-9}$ M, $10^{-9}$M, $5\times10^{-10}$ M, $10^{-10}$ M, $5\times10^{-11}$ M, $10^{-11}$ M, $5\times10^{-12}$ M, $10^{-12}$ M, $5\times10^{-13}$M, or $10^{-13}$ M.

43. The method of claim 1, wherein the NGF antagonist binds to NGF with a dissociation constant of less than or equal to $5\times10^{-10}$ M.

44. The method of claim 1, wherein the antibody is or antibody fragment is one comprising the light chain polypeptide in SEQ ID NO:22 and the heavy chain polypeptide in SEQ ID NO:24.

45. The method of claim 44, wherein said antibody contains a human constant region.

* * * * *